(12) United States Patent
Kinpara et al.

(10) Patent No.: US 11,993,578 B2
(45) Date of Patent: May 28, 2024

(54) PYRAZOLE-3-CARBOXYLIC ACID AMIDE DERIVATIVE AND PEST CONTROL AGENT

(71) Applicant: KUMIAI CHEMICAL INDUSTRY CO., LTD., Tokyo (JP)

(72) Inventors: Akira Kinpara, Tokyo (JP); Ryo Ishikawa, Tokyo (JP); Keiji Toriyabe, Tokyo (JP); Katsuya Kato, Tokyo (JP); Masao Nakatani, Tokyo (JP); Akira Takanezawa, Tokyo (JP); Takeshi Matsuda, Tokyo (JP)

(73) Assignee: KUMIAI CHEMICAL INDUSTRY CO., LTD. (JP)

( * ) Notice: Subject to any disclaimer, the term of this patent is extended or adjusted under 35 U.S.C. 154(b) by 0 days.

(21) Appl. No.: 16/613,078

(22) PCT Filed: May 9, 2018

(86) PCT No.: PCT/JP2018/018016
§ 371 (c)(1),
(2) Date: Nov. 12, 2019

(87) PCT Pub. No.: WO2018/207847
PCT Pub. Date: Nov. 15, 2018

(65) Prior Publication Data
US 2020/0199096 A1    Jun. 25, 2020

(30) Foreign Application Priority Data

May 11, 2017    (JP) .................. 2017-094998

(51) Int. Cl.
| | | |
|---|---|---|
| A61K 9/20 | (2006.01) | |
| A01N 43/56 | (2006.01) | |
| A61K 9/00 | (2006.01) | |
| A61K 9/06 | (2006.01) | |
| A61K 31/138 | (2006.01) | |
| A61K 31/337 | (2006.01) | |
| A61K 31/439 | (2006.01) | |
| A61K 31/4545 | (2006.01) | |
| A61K 31/4748 | (2006.01) | |
| A61K 31/502 | (2006.01) | |
| A61K 31/513 | (2006.01) | |
| A61K 31/519 | (2006.01) | |
| A61K 31/5377 | (2006.01) | |
| A61K 31/675 | (2006.01) | |
| A61K 31/704 | (2006.01) | |
| A61K 31/7068 | (2006.01) | |
| A61K 31/728 | (2006.01) | |
| A61K 33/243 | (2019.01) | |
| A61K 38/05 | (2006.01) | |
| A61K 38/06 | (2006.01) | |
| A61K 38/07 | (2006.01) | |
| A61K 38/08 | (2019.01) | |

(Continued)

(52) U.S. Cl.
CPC ........... C07D 401/04 (2013.01); A01N 43/56 (2013.01)

(58) Field of Classification Search
CPC .. C07D 401/04; A01N 43/56; A61K 31/4439; A61P 33/00; A61P 33/10; A61P 33/14
See application file for complete search history.

(56) References Cited

U.S. PATENT DOCUMENTS 8,802,713 B2 *  8/2014  Ohata ................. C07D 231/22
                                                            514/407
8,999,982 B2    4/2015  Schultz-Fademrecht et al.
2017/0260199 A1  9/2017  Hayashi et al.

FOREIGN PATENT DOCUMENTS

EP    2674423 A1    12/2013
WO    WO-9408991 A1 *  4/1994  ............. A01N 43/56

(Continued)

OTHER PUBLICATIONS

Patani et al. Chem. Rev. 1996, 96, 3147-3176. (Year: 1996).*

(Continued)

*Primary Examiner* — Mina Haghighatian
*Assistant Examiner* — Janice Y Silverman
(74) *Attorney, Agent, or Firm* — Bracewell LLP; Brad Y. Chin

(57) ABSTRACT

Embodiments provide a harmful organism control agent containing a pyrazole-3-carboxylic acid amide derivative or a salt thereof as an active ingredient, having an excellent harmful organism controlling effect. A pyrazole-3-carboxylic acid amide derivative represented by general formula [I]:

[Chemical formula 1]

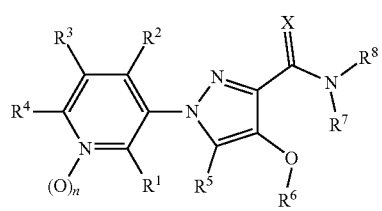

(wherein, $R^1$, $R^2$, $R^3$, $R^4$, and $R^5$ represent a hydrogen atom, halogen atom, $C_1$-$C_6$ alkyl group or the like, $R^6$ represents a $C_1$-$C_{12}$ alkyl group, $C_1$-$C_{12}$ haloalkyl group or the like, $R^7$ and $R^8$ represent a hydrogen atom, $C_1$-$C_{12}$ alkyl group or the like) or an agriculturally acceptable salt thereof, and a harmful organism control agent containing the pyrazole-3-carboxylic acid amide derivative or an agriculturally acceptable salt thereof as an active ingredient.

5 Claims, No Drawings

(51) Int. Cl.
| | |
|---|---|
| *A61K 38/39* | (2006.01) |
| *A61L 27/26* | (2006.01) |
| *A61L 27/54* | (2006.01) |
| *A61L 27/58* | (2006.01) |
| *A61P 35/00* | (2006.01) |
| *C07D 401/04* | (2006.01) |
| *C12M 1/12* | (2006.01) |
| *C12N 5/0775* | (2010.01) |
| *C12N 5/09* | (2010.01) |
| *G01N 33/50* | (2006.01) |

(56) References Cited

FOREIGN PATENT DOCUMENTS

| WO | WO-2012007500 A2 * | 1/2012 | ............. A01N 43/40 |
|---|---|---|---|
| WO | 2012028332 A1 | 3/2012 | |
| WO | WO-2016027790 A1 * | 2/2016 | ........... C07D 498/04 |
| WO | 2016166250 A1 | 10/2016 | |
| WO | 2016027790 A1 | 6/2017 | |

OTHER PUBLICATIONS

PCT/JP2018/018016 International Search Report dated Jul. 3, 2018; 4 pgs.
EP18798155.0 Extented European Search Report dated Nov. 27, 2020, 6 pgs.
JP2019-517679 Office Action dated Feb. 1, 2022, 8 pgs.

\* cited by examiner

PYRAZOLE-3-CARBOXYLIC ACID AMIDE DERIVATIVE AND PEST CONTROL AGENT

CROSS REFERENCE TO RELATED APPLICATIONS

This application claims the benefit of and priority to PCT/JP2018/018016, filed on May 9, 2018, entitled (translation), "PYRAZOLE-3-CARBOXYLIC ACID AMIDE DERIVATIVE AND PEST CONTROL AGENT," which claims the benefit of and priority to Japanese Patent Application No. 2017-094998, filed on May 11, 2017, which are hereby incorporated by reference in their entirety into this application.

FIELD

The present invention relates to a novel pyrazole-3-carboxylic acid amide derivative or an agriculturally acceptable salt thereof, and a harmful organism control agent containing the derivative as an active ingredient.

DESCRIPTION OF THE RELATED ART

Patent Document 1 discloses a pyrazole-3-carboxylic acid amide derivative having a harmful organism controlling effect, however, the compound disclosed in Patent Document 1 is limited to an oxazepine derivative in which the benzene ring substituting for the nitrogen atom of the carboxamide group at position 3 of the pyrazole ring, and the hydroxy group at position 4 form a ring.

Patent Documents 2 and 3 disclose a pyrazole-3-carboxylic acid amide derivative having an anticancer effect, however, the compounds disclosed in Patent Documents 2 and 3 are limited to derivatives in which a benzene ring and a pyridine ring substitute for the nitrogen atom of the carboxylic acid amide at position 3 of the pyrazole ring.

CITATION LIST

Patent Documents

[Patent Document 1] WO 2016/027790 A
[Patent Document 2] WO 2012/028332 A
[Patent Document 3] WO 2016/166250 A However, Patent Document 1 lacks description regarding a pyrazole-3-carboxylic acid amide derivative having a (substituted)alkoxy group at position 4 of the pyrazole ring. On the other hand, Patent Documents 2, 3 lack description regarding a pyrazole-3-carboxylic acid amide derivative in which a nitrogen atom in the carboxylic acid amide moiety at position 3 of the pyrazole ring is unsubstituted or has a (substituted)alkyl group. A harmful organism control agent used for useful crops are requested to be an agent that is applied to soil or foliage, and exhibits sufficient harmful organism controlling effect with a low dose. Also, increased demands for the safety and the influence on environment of chemicals lead to the request for developing a safer harmful organism control agent. Furthermore, in recent years, as a result of long-term use of a harmful organism control agent such as an insecticide or a miticide, harmful organisms having acquired the resistance to the harmful organism control agent have emerged, so that it becomes difficult to completely control harmful organisms. Also, use of harmful organism control agents having high mammalian toxicity is problematic in terms of the safety and the like for operators.

SUMMARY

In light of the aforementioned circumstance, it is an object of the present invention to solve the problems faced by the conventional harmful organism control agents, and to further provide a harmful organism control agent that is excellent in safety, control effect, residual activity, and the like.

In order to develop a harmful organism control agent having desirable characteristics as described above, the present inventors synthesized a variety of pyrazole-3-carboxylic acid amide derivatives, and diligently examined the physiological activity of the pyrazole-3-carboxylic acid amide derivatives. As a result, the present inventors found that a pyrazole-3-carboxylic acid amide derivative represented by the following general formula [I] (hereinafter, referred to as the present compound) shows outstanding effectiveness on various harmful organisms, and further continued the research to finally accomplish the present invention.

That is, the present invention has the subject matter having the following features.

(1) A pyrazole-3-carboxylic acid amide derivative represented by general formula [I] or an agriculturally acceptable salt thereof

[Chemical formula 1]

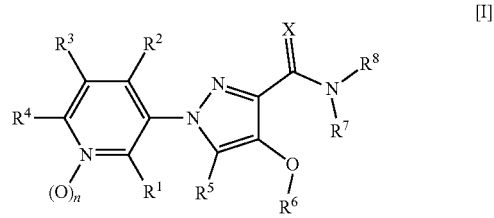

wherein,
n represents an integer of 0 or 1,
X represents an oxygen atom or a sulfur atom,
$R^1$, $R^2$, $R^3$, $R^4$, and $R^5$ each independently represent a hydrogen atom, halogen atom, $C_1$-$C_6$ alkyl group, $C_1$-$C_6$ haloalkyl group, $C_1$-$C_6$ alkoxy group, $C_1$-$C_6$ haloalkoxy group, $C_3$-$C_6$ cycloalkyl group, $C_1$-$C_6$ alkylthio group, $C_1$-$C_6$ alkylsulfinyl group, $C_1$-$C_6$ alkylsulfonyl group, amino group, mono($C_1$-$C_6$ alkyl)amino group, di($C_1$-$C_6$ alkyl)amino group, cyano group, or nitro group,
$R^6$ represents a hydrogen atom, $C_1$-$C_{12}$ alkyl group, $C_1$-$C_6$ alkoxy $C_1$-$C_6$ alkyl group, $C_1$-$C_{12}$ haloalkyl group, $C_1$-$C_6$ alkoxy $C_1$-$C_6$ haloalkyl group, $C_1$-$C_6$ haloalkoxy $C_1$-$C_6$ alkyl group, $C_1$-$C_6$ haloalkoxy $C_1$-$C_6$ haloalkyl group, $C_2$-$C_7$ alkynyl group, $C_3$-$C_6$ cycloalkyl $C_2$-$C_6$ alkynyl group, $C_2$-$C_6$ haloalkynyl group, $C_2$-$C_6$ alkenyl group, $C_2$-$C_6$ haloalkenyl group, $C_3$-$C_6$ cycloalkyl group, $C_3$-$C_6$ halocycloalkyl group, $C_1$-$C_6$ haloalkyl $C_3$-$C_6$ cycloalkyl group, $C_3$-$C_6$ cycloalkyl $C_1$-$C_6$ alkyl group, $C_3$-$C_6$ halocycloalkyl $C_1$-$C_6$ alkyl group, $C_1$-$C_6$ alkylthio $C_1$-$C_6$ alkyl group, $C_1$-$C_6$ alkylsulfinyl $C_1$-$C_6$ alkyl group, $C_1$-$C_6$ alkylsulfonyl $C_1$-$C_6$ alkyl group, $C_1$-$C_6$ haloalkylthio $C_1$-$C_6$ alkyl group, $C_1$-$C_6$ haloalkylsulfinyl $C_1$-$C_6$ alkyl group, $C_1$-$C_6$ haloalkylsulfonyl $C_1$-$C_6$ alkyl group, $C_1$-$C_6$ alkylcarbonyl $C_1$-$C_6$ alkyl group, $C_1$-$C_6$ haloalkylcarbonyl $C_1$-$C_6$ alkyl group, $C_1$-$C_6$ alkoxycarbonyl $C_1$-$C_6$ alkyl group, aminocarbonyl $C_1$-$C_6$ alkyl group, mono($C_1$-$C_6$ alkyl)aminocarbonyl $C_1$-$C_6$ alkyl group, mono($C_3$-$C_6$ cycloalkyl)aminocarbonyl $C_1$-$C_6$ alkyl group, mono($C_1$-$C_6$ haloalkyl)aminocarbonyl $C_1$-$C_6$ alkyl group, di($C_1$-$C_6$ alkyl)aminocarbonyl $C_1$-$C_6$ alkyl group, mono($C_1$-$C_6$ alkylcarbonyl)amino $C_1$-$C_6$ alkyl group, mono($C_1$-$C_6$ alkoxycarbonyl)amino $C_1$-$C_6$ alkyl group, mono($C_1$-$C_6$ alkyl)sulfonylamino $C_1$-$C_6$ alkyl group, mono($C_1$-$C_6$ haloalkylsulfonyl)amino $C_1$-$C_6$ alkyl group, hydroxy $C_1$-$C_6$ alkyl group, hydroxyimino $C_1$-$C_6$ alkyl group, $C_1$-$C_6$ alkoxyimino $C_1$-$C_6$ alkyl group, $C_1$-$C_6$ haloalkoxyimino $C_1$-$C_6$ alkyl group, or $C_7$-$C_{13}$ aralkyl group that is unsubstituted or substituted with $R^9$, $R^7$ and $R^8$ each independently represent a hydrogen atom, $C_1$-$C_6$ alkyl group, $C_3$-$C_6$ cycloalkyl group, $C_3$-$C_6$ cycloalkyl $C_1$-$C_6$ alkyl group, $C_2$-$C_7$ alkynyl group, $C_2$-$C_6$ alkenyl group, hydroxy group, $C_1$-$C_6$ alkoxy group, $C_1$-$C_6$ alkoxy $C_1$-$C_6$ alkyl group, $C_1$-$C_6$ haloalkyl group, 2-tetrahydrofuranyl group, 3-tetrahydrofuranyl group, 2-tetrahydropyranyl group, 4-tetrahydropyranyl group, cyano $C_1$-$C_6$ alkyl group, cyano $C_3$-$C_6$ cycloalkyl group, hydroxy $C_1$-$C_6$ alkyl group, formyl group, amino group, mono($C_1$-$C_6$ alkyl)amino group, di($C_1$-$C_6$ alkyl)amino group, $C_1$-$C_6$ alkylcarbonyl group, $C_1$-$C_6$ alkoxy $C_1$-$C_6$ alkylcarbonyl group, $C_3$-$C_6$ cycloalkyl carbonyl group, $C_3$-$C_6$ cycloalkyl $C_1$-$C_6$ alkylcarbonyl group, $C_1$-$C_6$ alkoxycarbonyl group, carbamoyl group, mono($C_1$-$C_6$ alkyl)aminocarbonyl group, di($C_1$-$C_6$ alkyl)aminocarbonyl group, phenylcarbonyl group that is unsubstituted or substituted with $R^9$, $C_7$-$C_{13}$ aralkylcarbonyl group that is unsubstituted or substituted with $R^9$, pyridylcarbonyl group that is unsubstituted or substituted with $R^9$, pyrazolylcarbonyl group that is unsubstituted or substituted with $R^9$, ($C_1$-$C_6$ alkyl)thiocarbonyl group, ($C_1$-$C_6$ alkoxy)thiocarbonyl group, thiocarbamoyl group, mono($C_1$-$C_6$ alkyl)aminothiocarbonyl group, di($C_1$-$C_6$ alkyl)aminothiocarbonyl group, $C_1$-$C_6$ alkylsulfonyl group, sulfamoyl group, mono($C_1$-$C_6$ alkyl)aminosulfonyl group, di($C_1$-$C_6$ alkyl)aminosulfonyl group, $R^{10}R^{11}N$—$C_1$-$C_6$ alkyl group, $C_1$-$C_6$ alkoxycarbonyl $C_1$-$C_6$ alkyl group, aminocarbonyl $C_1$-$C_6$ alkyl group, mono($C_1$-$C_6$ alkyl)aminocarbonyl $C_1$-$C_6$ alkyl group, mono($C_3$-$C_6$ cycloalkyl)aminocarbonyl $C_1$-$C_6$ alkyl group, mono($C_1$-$C_6$ haloalkyl)aminocarbonyl $C_1$-$C_6$ alkyl group, di($C_1$-$C_6$ alkyl)aminocarbonyl $C_1$-$C_6$ alkyl group, hydroxyimino group, $C_1$-$C_6$ alkoxyimino group, hydroxyimino $C_1$-$C_6$ alkyl group, or $C_1$-$C_6$ alkoxyimino $C_1$-$C_6$ alkyl group, and $R^7$ and $R^8$ may together form $=CR^{12}N(R^{13})R^{14}$ or $=CR^{12}OR^{15}$, and $R^7$ and $R^8$ may form, together with a carbon atom bound thereto, a 3 to 6-membered carbon ring, or a 3 to 6-membered hetero ring having 1 to 4 heteroatoms selected from an oxygen atom, a sulfur atom, and a nitrogen atom, and the hetero ring may be substituted with a halogen atom, cyano group, nitro group, $C_1$-$C_6$ alkyl group, $C_1$-$C_6$ alkoxy group, $C_1$-$C_6$ haloalkyl group, or oxo group, $R^9$ represents a halogen atom, $C_1$-$C_6$ alkyl group, $C_1$-$C_6$ haloalkyl group, $C_1$-$C_6$ alkoxy group, $C_1$-$C_6$ haloalkoxy group, $C_1$-$C_6$ alkylthio group, $C_1$-$C_6$ alkylsulfinyl group, $C_1$-$C_6$ alkylsulfonyl group, $C_1$-$C_6$ haloalkylthio group, $C_1$-$C_6$ haloalkylsulfinyl group, $C_1$-$C_6$ haloalkylsulfonyl group, amino group, mono ($C_1$-$C_6$ alkyl)amino group, di($C_1$-$C_6$ alkyl)amino group, cyano group, or nitro group, $R^{10}$ and $R^{11}$ each independently represent a hydrogen atom, $C_1$-$C_6$ alkyl group, $C_1$-$C_6$ haloalkyl group, or $C_3$-$C_6$ cycloalkyl group, and $R^{10}$ and $R^{11}$ may form, together with a carbon atom bound thereto, a 3 to 6-membered ring, $R^{12}$ represents a hydrogen atom, $C_1$-$C_6$ alkyl group, or $C_3$-$C_6$ cycloalkyl group, $R^{13}$ and $R^{14}$ each independently represent a hydrogen atom, $C_1$-$C_6$ alkyl group, $C_1$-$C_6$ haloalkyl group, $C_3$-$C_6$ cycloalkyl group, or $C_1$-$C_6$ alkoxy group, and $R^{13}$ and $R^{14}$ may form, together with a carbon atom bound thereto, a 3 to 6-membered carbon ring, or a 3 to 6-membered hetero ring having 1 to 4 heteroatoms selected from an oxygen atom, a sulfur atom, and a nitrogen atom, and $R^{15}$ represents a $C_1$-$C_6$ alkyl group.

(2) A pyrazole-3-carboxylic acid derivative represented by general formula [II] or a salt thereof

[Chemical formula 2]

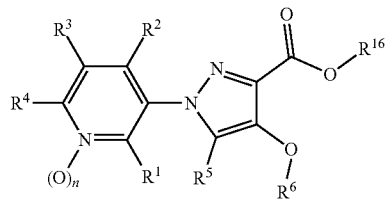

[II]

wherein, n represents an integer of 0 or 1, $R^1$, $R^2$, $R^3$, $R^4$, and $R^5$ each independently represent a hydrogen atom, halogen atom, $C_1$-$C_6$ alkyl group, $C_1$-$C_6$ haloalkyl group, $C_1$-$C_6$ alkoxy group, $C_1$-$C_6$ haloalkoxy group, $C_3$-$C_6$ cycloalkyl group, $C_1$-$C_6$ alkylthio group, $C_1$-$C_6$ alkylsulfinyl group, $C_1$-$C_6$ alkylsulfonyl group, amino group, mono($C_1$-$C_6$ alkyl)amino group, di($C_1$-$C_6$ alkyl)amino group, cyano group, or nitro group, $R^6$ represents a hydrogen atom, $C_1$-$C_{12}$ alkyl group, $C_1$-$C_6$ alkoxy $C_1$-$C_6$ alkyl group, $C_1$-$C_{12}$ haloalkyl group, $C_1$-$C_6$ alkoxy $C_1$-$C_6$ haloalkyl group, $C_1$-$C_6$ haloalkoxy $C_1$-$C_6$ alkyl group, $C_1$-$C_6$ haloalkoxy $C_1$-$C_6$ haloalkyl group, $C_2$-$C_7$ alkynyl group, $C_3$-$C_6$ cycloalkyl $C_2$-$C_6$ alkynyl group, $C_2$-$C_6$ haloalkynyl group, $C_2$-$C_6$ alkenyl group, $C_2$-$C_6$ haloalkenyl group, $C_3$-$C_6$ cycloalkyl group, $C_3$-$C_6$ halocycloalkyl group, $C_1$-$C_6$ haloalkyl $C_3$-$C_6$ cycloalkyl group, $C_3$-$C_6$ cycloalkyl $C_1$-$C_6$ alkyl group, $C_3$-$C_6$ halocycloalkyl $C_1$-$C_6$ alkyl group, $C_1$-$C_6$ alkylthio $C_1$-$C_6$ alkyl group, $C_1$-$C_6$ alkylsulfinyl $C_1$-$C_6$ alkyl group, $C_1$-$C_6$ alkylsulfonyl $C_1$-$C_6$ alkyl group, $C_1$-$C_6$ haloalkylthio $C_1$-$C_6$ alkyl group, $C_1$-$C_6$ haloalkylsulfinyl $C_1$-$C_6$ alkyl group, $C_1$-$C_6$ haloalkylsulfonyl $C_1$-$C_6$ alkyl group, $C_1$-$C_6$ alkylcarbonyl $C_1$-$C_6$ alkyl group, $C_1$-$C_6$ haloalkylcarbonyl $C_1$-$C_6$ alkyl group, $C_1$-$C_6$ alkoxycarbonyl $C_1$-$C_6$ alkyl group, aminocarbonyl $C_1$-$C_6$ alkyl group, mono($C_1$-$C_6$ alkyl)aminocarbonyl $C_1$-$C_6$ alkyl group, mono($C_3$-$C_6$ cycloalkyl)aminocarbonyl $C_1$-$C_6$ alkyl group, mono($C_1$-$C_6$ haloalkyl)aminocarbonyl $C_1$-$C_6$ alkyl group, di($C_1$-$C_6$ alkyl)aminocarbonyl $C_1$-$C_6$ alkyl group, mono($C_1$-$C_6$ alkyl)carbonylamino $C_1$-$C_6$ alkyl group, mono($C_1$-$C_6$ alkoxy)carbonylamino $C_1$-$C_6$ alkyl group, mono($C_1$-$C_6$ alkylsulfonyl)amino $C_1$-$C_6$ alkyl group, mono($C_1$-$C_6$ haloalkyl sulfonyl)amino $C_1$-$C_6$ alkyl group, hydroxy $C_1$-$C_6$ alkyl group, hydroxyimino $C_1$-$C_6$ alkyl group, $C_1$-$C_6$ alkoxyimino $C_1$-$C_6$ alkyl group, $C_1$-$C_6$ haloalkoxyimino $C_1$-$C_6$ alkyl group, or $C_7$-$C_{13}$ aralkyl group that is unsubstituted or substituted with $R^9$, and $R^{16}$ represents a hydrogen atom or $C_1$-$C_6$ alkyl group.

(3) The pyrazole-3-carboxylic acid amide derivative or an agriculturally acceptable salt thereof according to (1), wherein $R^6$ represents a $C_1$-$C_{12}$ alkyl group, $C_1$-$C_6$ alkoxy $C_1$-$C_6$ alkyl group, $C_1$-$C_{12}$ haloalkyl group, $C_1$-$C_6$ alkoxy $C_1$-$C_6$ haloalkyl group, $C_1$-$C_6$ haloalkoxy $C_1$-$C_6$ alkyl group, $C_1$-$C_6$ haloalkoxy $C_1$-$C_6$ haloalkyl group, $C_2$-$C_7$ alkynyl group, $C_3$-$C_6$ cycloalkyl $C_2$-$C_6$ alkynyl group, $C_2$-$C_6$ haloalkynyl group, $C_2$-$C_6$ alkenyl group, $C_2$-$C_6$ haloalkenyl group, $C_3$-$C_6$ cycloalkyl group, $C_3$-$C_6$ halocycloalkyl group, $C_1$-$C_6$ haloalkyl $C_3$-$C_6$ cycloalkyl group, $C_3$-$C_6$ cycloalkyl $C_1$-$C_6$ alkyl group, $C_3$-$C_6$ halocycloalkyl $C_1$-$C_6$ alkyl group, $C_1$-$C_6$ alkylthio $C_1$-$C_6$ alkyl group, $C_1$-$C_6$ alkylsulfinyl $C_1$-$C_6$ alkyl group, $C_1$-$C_6$ alkylsulfonyl $C_1$-$C_6$ alkyl group, $C_1$-$C_6$ haloalkylthio $C_1$-$C_6$ alkyl group, $C_1$-$C_6$ haloalkylsulfinyl $C_1$-$C_6$ alkyl group, $C_1$-$C_6$ haloalkylsulfonyl $C_1$-$C_6$ alkyl group, $C_1$-$C_6$ alkylcarbonyl $C_1$-$C_6$ alkyl group, $C_1$-$C_6$ haloalkylcarbonyl $C_1$-$C_6$ alkyl group, $C_1$-$C_6$ alkoxycarbonyl $C_1$-$C_6$ alkyl group, aminocarbonyl $C_1$-$C_6$ alkyl group, mono($C_1$-$C_6$ alkyl)aminocarbonyl $C_1$-$C_6$ alkyl group, mono($C_3$-$C_6$ cycloalkyl)aminocarbonyl $C_1$-$C_6$ alkyl group, mono($C_1$-$C_6$ haloalkyl)aminocarbonyl $C_1$-$C_6$ alkyl group, di($C_1$-$C_6$ alkyl)aminocarbonyl $C_1$-$C_6$ alkyl group, mono($C_1$-$C_6$ alkyl)carbonylamino $C_1$-$C_6$ alkyl group, mono($C_1$-$C_6$ alkoxy)carbonylamino $C_1$-$C_6$ alkyl group, mono($C_1$-$C_6$ alkyl)sulfonylamino $C_1$-$C_6$ alkyl group, mono($C_1$-$C_6$ haloalkyl)sulfonylamino $C_1$-$C_6$ alkyl group, hydroxy $C_1$-$C_6$ alkyl group, hydroxyimino $C_1$-$C_6$ alkyl group, $C_1$-$C_6$ alkoxyimino $C_1$-$C_6$ alkyl group, $C_1$-$C_6$ haloalkoxyimino $C_1$-$C_6$ alkyl group, or $C_7$-$C_{13}$ aralkyl group that is unsubstituted or substituted with $R^9$.

(4) The pyrazole-3-carboxylic acid derivative or a salt thereof according to (2), wherein $R^6$ represents a $C_1$-$C_{12}$ alkyl group, $C_1$-$C_6$ alkoxy $C_1$-$C_6$ alkyl group, $C_1$-$C_{12}$ haloalkyl group, $C_1$-$C_6$ alkoxy $C_1$-$C_6$ haloalkyl group, $C_1$-$C_6$ haloalkoxy $C_1$-$C_6$ alkyl group, $C_1$-$C_6$ haloalkoxy $C_1$-$C_6$ haloalkyl group, $C_2$-$C_7$ alkynyl group, $C_3$-$C_6$ cycloalkyl $C_2$-$C_6$ alkynyl group, $C_2$-$C_6$ haloalkynyl group, $C_2$-$C_6$ alkenyl group, $C_2$-$C_6$ haloalkenyl group, $C_3$-$C_6$ cycloalkyl group, $C_3$-$C_6$ halocycloalkyl group, $C_1$-$C_6$ haloalkyl $C_3$-$C_6$ cycloalkyl group, $C_3$-$C_6$ cycloalkyl $C_1$-$C_6$ alkyl group, $C_3$-$C_6$ halocycloalkyl $C_1$-$C_6$ alkyl group, $C_1$-$C_6$ alkylthio $C_1$-$C_6$ alkyl group, $C_1$-$C_6$ alkylsulfinyl $C_1$-$C_6$ alkyl group, $C_1$-$C_6$ alkylsulfonyl $C_1$-$C_6$ alkyl group, $C_1$-$C_6$ haloalkylthio $C_1$-$C_6$ alkyl group, $C_1$-$C_6$ haloalkylsulfinyl $C_1$-$C_6$ alkyl group, $C_1$-$C_6$ haloalkylsulfonyl $C_1$-$C_6$ alkyl group, $C_1$-$C_6$ alkylcarbonyl $C_1$-$C_6$ alkyl group, $C_1$-$C_6$ haloalkylcarbonyl $C_1$-$C_6$ alkyl group, $C_1$-$C_6$ alkoxycarbonyl $C_1$-$C_6$ alkyl group, aminocarbonyl $C_1$-$C_6$ alkyl group, mono($C_1$-$C_6$ alkyl)aminocarbonyl $C_1$-$C_6$ alkyl group, mono($C_3$-$C_6$ cycloalkyl)aminocarbonyl $C_1$-$C_6$ alkyl group, mono($C_1$-$C_6$ haloalkyl)aminocarbonyl $C_1$-$C_6$ alkyl group, di($C_1$-$C_6$ alkyl)aminocarbonyl $C_1$-$C_6$ alkyl group, mono($C_1$-$C_6$ alkyl)carbonylamino $C_1$-$C_6$ alkyl group, mono($C_1$-$C_6$ alkoxy)carbonylamino $C_1$-$C_6$ alkyl group, mono($C_1$-$C_6$ alkylsulfonyl)amino $C_1$-$C_6$ alkyl group, mono($C_1$-$C_6$ haloalkylsulfonyl)amino $C_1$-$C_6$ alkyl group, hydroxy $C_1$-$C_6$ alkyl group, hydroxyimino $C_1$-$C_6$ alkyl group, $C_1$-$C_6$ alkoxyimino $C_1$-$C_6$ alkyl group, $C_1$-$C_6$ haloalkoxyimino $C_1$-$C_6$ alkyl group, or a $C_7$-$C_{13}$ aralkyl group that is unsubstituted or substituted with $R^9$.

(5) A pesticide composition containing the pyrazole-3-carboxylic acid amide derivative or an agriculturally acceptable salt thereof according to (1) or (3), or the pyrazole-3-carboxylic acid derivative or an agriculturally acceptable salt thereof according to (2) or (4) as an active ingredient.

(6) The pesticide composition according to (5), wherein the pesticide composition further contains a surfactant.

(7) A harmful organism control agent containing the pyrazole-3-carboxylic acid amide derivative or an agriculturally acceptable salt thereof according to (1) or (3), or the pyrazole-3-carboxylic acid derivative or an agriculturally acceptable salt thereof according to (2) or (4) as an active ingredient.

(8) The harmful organism control agent according to (7) that is an insecticide.

(9) The harmful organism control agent according to (7) having a control effect on a harmful organism in a dry field or a paddy field where a farming or gardening plant is cultured.

(10) The harmful organism control agent according to (9), wherein the farming or gardening plant is a plant provided with tolerance by a breeding method or a gene recombination technique.

(11) A method for controlling a harmful organism using an active ingredient amount of the pyrazole-3-carboxylic acid amide derivative or an agriculturally acceptable salt thereof according to (1) or (3), or the pyrazole-3-carboxylic acid derivative or an agriculturally acceptable salt thereof according to (2) or (4).

(12) A method for controlling a harmful organism by letting a pesticide composition containing the pyrazole-3-carboxylic acid amide derivative or an agriculturally acceptable salt thereof according to (1) or (3), or the pyrazole-3-carboxylic acid derivative or an agriculturally acceptable salt thereof according to (2) or (4) as an active ingredient act on a farming or gardening crop or a place where the farming or gardening crop is to be grown or being grown, at once or in batch.

(13) The method for controlling a harmful organism according to (11) or (12), wherein the place where the harmful organism control agent is to be applied is a paddy field, a dry field, a lawn, an orchard, a non-crop land, a greenhouse, a raising seeding facility, or a plant factory.

(14) The method for controlling a harmful organism according to any one of (11) to (13), wherein the pyrazole-3-carboxylic acid amide derivative or an agriculturally acceptable salt thereof is used as an insecticide.

(15) A use method of a harmful organism control agent, using the harmful organism control agent according to any one of (7) to (10) for controlling a harmful organism for a farming or gardening crop.

The harmful organism control agent containing the present compound shows excellent controlling effect on a wide range of harmful organisms including Hemiptera pests, Lepidoptera pests, Coleoptera pests, Diptera pests, Hymenoptera pests, Orthoptera pests, Isoptera pests, Thysanoptera pests, Acari pests, and plant parasitic nematoda, and is capable of controlling a harmful organism having acquired drug resistance.

DETAILED DESCRIPTION

Symbols and terms used in this specification are described.

In the present invention, "harmful organism control agent" means insecticides, miticides, nematicides, and the like in farming and gardening fields, for animals such as domestic animals and pets, for household use or for prevention of epidemics.

In the present invention, "halogen atom" refers to a fluorine atom, a chlorine atom, a bromine atom, or an iodine atom.

In the present invention, the notation "$C_1$-$C_6$" and the like indicates that the number of carbons in the substituent following the notation is 1 to 6, in this case.

In the present invention, unless otherwise specified, "$C_1$-$C_6$ alkyl group" refers to a linear or branched alkyl group having 1 to 6 carbon atoms, and examples of the $C_1$-$C_6$ alkyl group include a methyl, ethyl, n-propyl, isopropyl, n-butyl, s-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, or 1-ethyl-2-methylpropyl group.

In the present invention, unless otherwise specified, "$C_1$-$C_{12}$ alkyl group" refers to a linear or branched alkyl group having 1 to 12 carbon atoms, and examples of the $C_1$-$C_{12}$ alkyl group include, in addition to those exemplified in the "$C_1$-$C_6$ alkyl group", a n-heptyl, n-octyl, n-nonyl, n-decyl, n-undecyl, n-dodecyl, 4,4-dimethylpentyl, 5-methylhexyl, 5,5-dimethylhexyl, 3,5,5-trimethylhexyl, 6-methylheptyl, 6,6-dimethylheptyl, 3,6,6-trimethylheptyl, 7-methyloctyl, 7,7-dimethyloctyl, 8-methylnonyl, 8,8-dimethylnonyl, 9-methyldecyl, 9,9-dimethyldecyl or 10-methylundecyl group.

In the present invention, unless otherwise specified, "$C_2$-$C_6$ alkenyl group" refers to a linear or branched alkenyl group having 2 to 6 carbon atoms, and examples of the $C_2$-$C_6$ alkenyl group include a vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 1-vinyl-2-propenyl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-(isobutyl)vinyl, 1-ethyl-1-methyl-2-propenyl, 1-ethyl-2-methyl-2-propenyl, 1-(isopropyl)-2-propenyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1-vinyl-3-butenyl, or 2,4-hexadienyl group.

In the present invention, unless otherwise specified, "$C_2$-$C_7$ alkynyl group" refers to a linear or branched alkynyl group having 2 to 7 carbon atoms, and examples of the $C_2$-$C_7$ alkynyl group include an ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 1,1-dimethyl-2-butynyl or 2,2-dimethyl-3-butynyl, 1-heptynyl, 1-(n-butyl)-2-propynyl, 1-(s-butyl)-2-propynyl, 1-isobutyl-2-propynyl, 2-heptynyl, 3-heptynyl, 1-methyl-2-hexynyl, 4-methyl-2-hexynyl, 5-methyl-2-hexynyl, 6-heptynyl, 1,1-diethyl-2-propynyl, 1-methyl-1-propyl-2-propynyl, 1-isopropyl-1-methyl-2-propynyl, 1,1-dimethyl-2-pentynyl, 1,4-dimethyl-2-pentynyl, or 4,4-dimethyl-2-pentynyl group.

In the present invention, unless otherwise specified, "$C_1$-$C_6$ haloalkyl group" refers to a linear or branched alkynyl group having 1 to 6 carbon atoms, substituted with the same or different 1 to 13 halogen atoms, for example, a haloalkyl group, and examples of the $C_1$-$C_6$ haloalkyl group include a fluoromethyl, difluoromethyl, trifluoromethyl, chloromethyl, dichloromethyl, trichloromethyl, bromomethyl, dibromomethyl, tribromomethyl, iodomethyl, chlorodifluoromethyl, dichlorofluoromethyl, 1-fluoroethyl, 2-fluoroethyl, 1,1-difluoroethyl, 2,2-difluoroethyl, 2,2,2-trifluoroethyl, 1,1,2,2-tetrafluoroethyl, pentafluoroethyl, 1-chloroethyl, 2-chloroethyl, 1,1-dichloroethyl, 2,2-dichloroethyl, 2,2,2-trichloroethyl, 1,1,2,2-tetrachloroethyl, pentachloroethyl, 1-bromoethyl, 2-bromoethyl, 2,2,2-tribromoethyl, 1-iodoethyl, 2-iodoethyl, 2-chloro-2,2-difluoroethyl, 2,2-dichloro-2-fluoroethyl, 1-fluoropropyl, 2-fluoropropyl, 3-fluoropropyl, 1,1-difluoropropyl, 2,2-difluoropropyl, 3,3-difluoropropyl, 3,3,3-trifluoropropyl, 2,2,3,3,3-pentafluoropropyl, 1,1,2,3,3,3-hexafluoropropyl, heptafluoropropyl, 1-fluoropropane-2-yl, 2-fluoropropane-2-yl, 1,1-difluoropropane-2-yl, 1,2-difluoropropane-2-yl, 1,3-difluoropropane-2-yl, 1,2,3-trifluoropropane-2-yl, 1,1,3,3-tetrafluoropropane-2-yl, 1,1,1,3,3,3-hexafluoropropane-2-yl, heptafluoropropane-2-yl, 1-chloropropyl, 2-chloropropyl, 3-chloropropyl, 1,1-dichloropropyl, 2,2-dichloropropyl, 3,3-dichloropropyl, 3,3,3-trichloropropyl, 2,2,3,3,3-pentachloropropyl, heptachloropropyl, 1-chloropropane-2-yl, 2-chloropropane-2-yl, 1,1-dichloropropane-2-yl, 1,2-dichloropropane-2-yl, 1,3-dichloropropane-2-yl, 1,2,3-trichloropropane-2-yl, 1,1,3,3-tetrachloropropane-2-yl, 1,1,1,3,3,3-hexachloropropane-2-yl, heptachloropropane-2-yl, 1-bromopropyl, 2-bromopropyl, 3-bromopropyl, 1-bromopropane-2-yl, 2-bromopropane-2-yl, 1-iodopropyl, 2-iodopropyl, 3-iodopropyl, 1-iodopropane-2-yl, 2-iodopropane-2-yl, 1-fluorobutyl, 2-fluorobutyl, 3-fluorobutyl, 4-fluorobutyl, 4,4-difluorobutyl, 4,4,4-trifluorobutyl, 4,4,4-trifluoro-3-methylbutyl, 3,3,4,4,4-pentafluorobutyl, 2,2,3,4,4,4-hexafluorobutyl, 2,2,3,3,4,4,4-heptafluorobutyl, nonafluorobutyl, 1,1,1-trifluorobutane-2-yl, 4,4,4-trifluorobutane-2-yl, 3,3,4,4,4-pentafluorobutane-2-yl, nonafluorobutane-2-yl, 1,1,1,3,3,3-hexafluoro-2-(trifluoromethyl)propane-2-yl, 1-chlorobutyl, 2-chlorobutyl, 3-chlorobutyl, 4-chlorobutyl, 4,4-dichlorobutyl, 4,4,4-trichlorobutyl, nonachlorobutyl, 1,1,1-trichlorobutane-2-yl, 4,4,4-trichlorobutane-2-yl, nonachlorobutane-2-yl, 1-bromobutyl, 2-bromobutyl, 3-bromobutyl, 4-bromobutyl, 1-iodobutyl, 2-iodobutyl, 3-iodobutyl, 4-iodobutyl, 4-chloro-1,1,2,2,3,3,4,4-octafluorobutyl, 4-bromo-1,1,2,2,3,3,4,4-octafluorobutyl, 1-fluoropentyl, 2-fluoropentyl, 3-fluoropentyl, 4-fluoropentyl, 5-fluoropentyl, 5,5,5-trifluoropentyl, 4,4,5,5,5-pentafluoropentyl, 3,3,4,4,5,5,5-heptafluoropentyl, 2,2,3,3,4,4,5,5-octafluoropentyl, 2,2,3,3,4,4,5,5,5-nonafluoropentyl, undecafluoropentyl, 1-chloropentyl, 2-chloropentyl, 3-chloropentyl, 4-chloropentyl, 5-chloropentyl, 5,5,5-trichloropentyl, 4,4,5,5,5-pentachloropentyl, 3,3,4,4,5,5,5-heptachloropentyl, 2,2,3,3,4,4,5,5,5-nonachloropentyl, undecachloropentyl, 1-bromopentyl, 2-bromopentyl, 3-bromopentyl, 4-bromopentyl, 5-bromopentyl, 5-iodopentyl, 1-fluorohexyl, 2-fluorohexyl, 3-fluorohexyl, 4-fluorohexyl, 5-fluorohexyl, 6-fluorohexyl, 6,6,6-trifluorohexyl, 5,5,6,6,6-pentafluorohexyl, 4,4,5,5,6,6,6-heptafluorohexyl, 3,3,4,4,5,5,6,6,6-nonafluorohexyl, 2,2,3,3,4,4,5,5,6,6,6-undecafluorohexyl, 2,2,3,3,4,4,5,5,6,6-decafluorohexyl, tridecafluorohexyl, 1-chlorohexyl, 2-chlorohexyl, 3-chlorohexyl, 4-chlorohexyl, 5-chlorohexyl, 6-chlorohexyl, 5-bromohexyl, 6-bromohexyl, 5-iodohexyl, or 6-iodohexyl group.

In the present invention, unless otherwise specified, "$C_1$-$C_{12}$ haloalkyl group" refers to a linear or branched alkyl group having 1 to 12 carbon atoms, substituted with the same or different 1 to 25 halogen atoms, and examples of the $C_1$-$C_{12}$ haloalkyl group include, in addition to those exemplified in the "$C_1$-$C_6$ haloalkyl group", a 2,2,3,4,4,6,6,6-octafluoro-3,5,5-tris(trifluoromethyl)hexyl, 7,7,7-trifluoroheptyl, 1H,1H-perfluoroheptyl, 1H,1H,2H,2H-perfluoroheptyl, 1H, 1H,2H,2H,3H,3H-perfluoroheptyl, 1H,1H,7H-perfluoroheptyl, perfluoroheptyl,2-(perfluoro-3-methylbutyl)ethyl, 1H,1H-perfluorooctyl, 1H,1H,2H,2H-perfluorooctyl, 1H,1H,2H,2H,3H,3H-perfluorooctyl, 6-(perfluorohexyl)ethyl, 1H,1H,8H-perfluorooctyl, perfluorooctyl, 1H,1H-perfluorononyl, 1H,1H,2H,2H-perfluorononyl, 1H,1H,2H,2H,3H,3H-perfluorononyl, 6-(perfluoro-1-methylethyl)hexyl, 1H,1H,9H-perfluorononyl, perfluorononyl, 1H,1H-perfluorodecyl, 1H,1H,2H,2H-perfluorodecyl, 1H,1H,2H,2H,3H,3H-perfluorodecyl, 6-(perfluorobutyl)hexyl, 1H,1H,9H-perfluorodecyl, or perfluorodecyl group.

In the present invention, unless otherwise specified, "$C_1$-$C_6$ alkoxy group" refers to a ($C_1$-$C_6$ alkyl)-O— group in which the alkyl moiety is as defined above, and examples of the $C_1$-$C_6$ alkoxy group include a methoxy, ethoxy, n-propoxy, isopropoxy, n-butoxy, isobutoxy, sec-butoxy, tert-butoxy, n-pentoxy, 1-methylbutoxy, 2-methylbutoxy, 3-methylbutoxy, 1-ethylpropoxy, 1,1-dimethylpropoxy, 1,2-dimethylpropoxy, or n-hexyloxy group.

In the present invention, unless otherwise specified, "$C_1$-$C_6$ haloalkoxy group" refers to a ($C_1$-$C_6$ haloalkyl)-O— group in which the haloalkyl moiety is as defined above, and examples of the $C_1$-$C_6$ haloalkoxy group include a difluoromethoxy, dichloromethoxy, trifluoromethoxy, trichloromethoxy, tribromomethoxy, chlorodifluoromethoxy, bromodifluoromethoxy, 2-fluoroethoxy, 1-chloroethoxy, 2-chloroethoxy, 1-bromoethoxy, 2-bromoethoxy, 2,2-difluoroethoxy, 1,2-dichloroethoxy, 2,2-dichloroethoxy, 2,2,2-trifluoroethoxy, 2,2,2-trichloroethoxy, 1,1,2,2-tetrafluoroethoxy, pentafluoroethoxy, 2-bromo-2-chloroethoxy, 2-chloro-1,1,2,2-tetrafluoroethoxy, 1-chloro-1,2,2,2-tetrafluoroethoxy, 1-chloropropoxy, 2-chloropropoxy, 3-chloropropoxy, 2-bromopropoxy, 3-bromopropoxy, 2-bromo-1-methylethoxy, 3-iodopropoxy, 2,3-dichloropropoxy, 2,3-dibromopropoxy, 3,3,3-trifluoropropoxy, 3,3,3-trifluoro-2-propoxy, 3,3,3-trichloropropoxy, 3-bromo-3,3-difluoropropoxy, 2,2-difluoropropoxy, 3,3-dichloro-3-fluoropropoxy, 2,2,3,3-tetrafluoropropoxy, 1-bromo-3,3,3-trifluoropropoxy, 2,2,3,3,3-pentafluoropropoxy, 2,2,2-trifluoro-1-trifluoromethylethoxy, heptafluoropropoxy, heptafluoro-2-propoxy, 1,2,2,2-tetrafluoro-1-trifluoromethylethoxy, 1,1,2,3,3,3-hexafluoropropoxy, 2-chlorobutoxy, 3-chlorobutoxy, 4-chlorobutoxy, 2-chloro-1,1-dimethylethoxy, 4-bromobutoxy, 3-bromo-2-methylpropoxy, 2-bromo-1,1-dimethylethoxy, 2,2-dichloro-1,1-dimethylethoxy, 2-chloro-1-chloromethyl-2-methylethoxy, 4,4,4-trifluorobutoxy, 3,3,3-trifluoro-1-methylpropoxy, 3,3,3-trifluoro-2-methylpropoxy, 2,3,4-trichlorobutoxy, 2,2,2-trichloro-1,1-dimethylethoxy, 4-chloro-4,4-difluorobutoxy, 4,4-dichloro-4-fluorobutoxy, 4-bromo-4,4-difluorobutoxy, 2,4-dibromo-4,4-difluorobutoxy, 3,4-dichloro-3,4,4-trifluorobutoxy, 3,3-dichloro-4,4,4-trifluorobutoxy, 4-bromo-3,3,4,4-tetrafluorobutoxy, 4-bromo-3-chloro-3,4,4-trifluorobutoxy, 2,2,3,3,4,4-hexafluorobutoxy, 2,2,3,4,4,4-hexafluorobutoxy, 2,2,2-trifluoro-1-methyl-1-trifluoromethylethoxy, 3,3,3-trifluoro-2-trifluoromethylpropoxy, 2,2,3,3,4,4,4-heptafluorobutoxy, 3,3,4,4,4-pentafluoro-2-butoxy, 2,3,3,3-tetrafluoro-2-trifluoromethylpropoxy, 1,1,2,2,3,3,4,4-octafluorobutoxy, nonafluorobutoxy, perfluoro-tert-butoxy, 4-chloro-1,1,2,2,3,3,4,4-octafluorobutoxy, 5,5,5-trifluoropentoxy, 4,4,5,5,5-pentafluoropentoxy, 3,3,4,4,5,5,5-heptafluoropentoxy, 3,3,4,4,5,5,5-heptafluoro-2-pentoxy, 2,2,3,3,4,4,5,5,5-nonafluoropentoxy, 2,2,3,3,4,4,5,5-octafluoropentoxy, perfluoropentoxy, 4,4,5,5,5-pentafluoro-2-butoxy, 2,2-bis(trifluoromethyl)propoxy, 2,2,3,3,4,4,5,5,6,6,6-undecafluorohexyloxy, 3,3,4,4,5,5,6,6,6-nonafluorohexyloxy, 4,4,5,5,6,6,6-heptafluorohexyloxy, 2,2,3,3,4,4,5,5,6,6-decafluorohexyloxy, 4,4,4-trifluoro-3,3-bis(trifluoromethyl)butyloxy, or perfluorohexyloxy group.

In the present invention, unless otherwise specified, "$C_3$-$C_6$ cycloalkyl group" refers to a cycloalkyl group having 3 to 6 carbon atoms, and examples of the $C_3$-$C_6$ cycloalkyl group include a cyclopropyl, cyclobutyl, cyclopentyl, or cyclohexyl group.

In the present invention, unless otherwise specified, "$C_3$-$C_6$ cycloalkyl $C_2$-$C_6$ alkynyl group" refers to a ($C_3$-$C_6$ cycloalkyl)-($C_2$-$C_6$ alkynyl)- group in which the cycloalkyl moiety is as defined above, and examples of the $C_3$-$C_6$ cycloalkyl $C_2$-$C_6$ alkynyl group include a 3-cyclopropyl-2-propynyl, 3-cyclobutyl-2-propynyl, 3-cyclopentyl-2-propynyl, 3-cyclohexyl-2-propynyl, 3-cyclopropyl-1-methyl-2-propynyl, 3-cyclobutyl-1-methyl-2-propynyl, 3-cyclopentyl-1-methyl-2-propynyl or 3-cyclohexyl-1-methyl-2-propynyl group.

In the present invention, "$C_1$-$C_6$ alkylthio group" refers to a ($C_1$-$C_6$ alkyl)-S— group in which the alkyl moiety is as defined above, and examples of the $C_1$-$C_6$ alkylthio group include a methylthio, ethylthio, n-propylthio, isopropylthio, n-butylthio, isobutylthio, sec-butylthio, or tert-butylthio group.

In the present invention, "$C_1$-$C_6$ alkylsulfinyl group" refers to a ($C_1$-$C_6$ alkyl)-SO— group in which the alkyl moiety is as defined above, and examples of the $C_1$-$C_6$ alkylsulfinyl group include a methylsulfinyl, ethylsulfinyl, n-propylsulfinyl, isopropylsulfinyl, n-butylsulfinyl, isobutylsulfinyl, sec-butylsulfinyl, or tert-butylsulfinyl group.

In the present invention, "$C_1$-$C_6$ alkylsulfonyl group" refers to a ($C_1$-$C_6$ alkyl)-SO$_2$— group in which the alkyl moiety is as defined above, and examples of the $C_1$-$C_6$ alkylsulfonyl group include a methylsulfonyl, ethylsulfonyl, n-propylsulfonyl, isopropylsulfonyl, n-butylsulfonyl, isobutylsulfonyl, sec-butylsulfonyl, or tert-butylsulfonyl group.

In the present invention, "mono($C_1$-$C_6$ alkyl)amino group" refers to a ($C_1$-$C_6$ alkyl)-NH— group in which the alkyl moiety is as defined above, and examples of the mono($C_1$-$C_6$ alkyl)amino group include a methylamino, ethylamino, n-propylamino, or isopropyl amino group.

In the present invention, "di($C_1$-$C_6$ alkyl)amino group" refers to a ($C_1$-$C_6$ alkyl)$_2$-N— group in which the alkyl moiety is as defined above, and examples of the di($C_1$-$C_6$ alkyl)amino group include a dimethylamino, diethylamino, or N-ethyl-N-methylamino group.

In the present invention, "$C_1$-$C_6$ alkoxy $C_1$-$C_6$ alkyl group" refers to a ($C_1$-$C_6$ alkoxy)-($C_1$-$C_6$ alkyl)- group in which the alkoxy moiety is as defined above, and examples of the $C_1$-$C_6$ alkoxy $C_1$-$C_6$ alkyl group include a methoxymethyl, 1-methoxyethyl, 2-methoxyethyl, 2-ethoxyethyl, 2-methoxypropyl, 3-methoxypropyl, 2-ethoxypropyl, 3-ethoxypropyl, 1-methyl-3-methoxybutyl, or 3-butoxybutyl group.

In the present invention, "$C_1$-$C_6$ alkoxy $C_1$-$C_6$ haloalkyl group" refers to a ($C_1$-$C_6$ alkoxy)-($C_1$-$C_6$ haloalkyl)- group in which the alkoxy moiety is as defined above, and examples of the $C_1$-$C_6$ alkoxy $C_1$-$C_6$ haloalkyl group include a 2-methoxy-1,1,2-trifluoroethyl or 2-ethoxy-1,1,2-trifluoroethyl group.

In the present invention, "$C_1$-$C_6$ haloalkoxy $C_1$-$C_6$ alkyl group" refers to a ($C_1$-$C_6$ haloalkoxy)-($C_1$-$C_6$ alkyl)- group in which the haloalkoxy moiety is as defined above, and examples of the $C_1$-$C_6$ haloalkoxy $C_1$-$C_6$ alkyl group include a 2-(difluoromethoxy)ethyl, 2-(trifluoromethoxy)ethyl, 2-(2, 2-difluoroethoxy)ethyl, or 2-(2,2,2-trifluoroethoxy)ethyl group.

In the present invention, "$C_1$-$C_6$ haloalkoxy $C_1$-$C_6$ haloalkyl group" refers to a ($C_1$-$C_6$ haloalkoxy)-($C_1$-$C_6$ haloalkyl)- group in which the haloalkoxy moiety is as defined above, and examples of the $C_1$-$C_6$ haloalkoxy $C_1$-$C_6$ haloalkyl group include a 1,1,2-trifluoro-2-(trifluoromethoxy)ethyl, 1,1,2-trifluoro-2-(pentafluoroethoxy)ethyl, or 1,1,2-trifluoro-2-(heptafluoropropoxy)ethyl group.

In the present invention, unless otherwise specified, "$C_2$-$C_6$ haloalkynyl group" refers to a linear or branched alkynyl group having 2 to 6 carbon atoms, substituted with the same or different 1 to 9 halogen atoms, and examples of the $C_2$-$C_6$ haloalkynyl group include a fluoroethynyl, chloroethynyl, bromoethynyl, iodoethynyl, 3-fluoro-2-propynyl, 3-chloro-2-propynyl, 3-bromo-2-propynyl, 3-iodo-2-propynyl, 4-fluoro-3-butynyl, 4-chloro-3-butynyl, 4-bromo-3-butynyl, 4-iodo-3-butynyl, 4,4-difluoro-2-butynyl, 4,4-dichloro-2-butynyl, 4,4,4-trifluoro-2-butynyl, 4,4,4-trichloro-2-butynyl, 3-fluoro-1-methyl-2-propynyl, 3-chloro-1-methyl-2-propynyl, 5-fluoro-4-pentynyl, 5-chloro-4-pentynyl, 5,5,5-trifluoro-3-pentynyl, 5,5,5-trichloro-3-pentynyl, 4-fluoro-2-methyl-3-butynyl, 4-chloro-2-methyl-3-butynyl, 6-fluoro-5-hexynyl, 6-chloro-5-hexynyl, 6,6,6-trifluoro-4-hexynyl, 6,6,6-trichloro-4-hexynyl, 5-fluoro-3-methyl-4-pentynyl, or 5-chloro-3-methyl-4-pentynyl group.

In the present invention, unless otherwise specified, "$C_2$-$C_6$ haloalkenyl group" refers to a linear or branched alkenyl group having 2 to 6 carbon atoms, substituted with the same or different 1 to 11 halogen atoms, and examples of the $C_2$-$C_6$ haloalkenyl group include a 1-fluorovinyl, 2-fluorovinyl, 1,2-difluorovinyl, 2,2-difluorovinyl, trifluorovinyl, 1-chlorovinyl, 2-chlorovinyl, 1,2-dichlorovinyl, 2,2-dichlorovinyl, trichlorovinyl, 1,2-dibromovinyl, 2,2-dibromovinyl, tribromovinyl, 1,2-diiodovinyl, 2,2-diiodovinyl, triodovinyl, 1-fluoro-2-propenyl, 2-fluoro-2-propenyl, 3-fluoro-2-propenyl, 2,3-difluoro-2-propenyl, 3,3-difluoro-2-propenyl, 3,3-difluoro-1-propenyl, 2,3,3-trifluoro-2-propenyl, 3,3,3-trifluoro-1-propenyl, 2-chloro-3,3,3-trifluoro-1-propenyl, 1,2,3,3,3-pentafluoro-1-propenyl, 1-chloro-2-propenyl, 2-chloro-2-propenyl, 3-chloro-2-propenyl, 2,3-dichloro-2-propenyl, 3,3-dichloro-2-propenyl, 3,3-dichloro-1-propenyl, 2,3,3-trichloro-2-propenyl, 3,3,3-trichloro-1-propenyl, 3-bromo-2-propenyl, 3,3-dibromo-2-propenyl, 3,3-diiodo-2-propenyl, 2,2-difluoro-1-propene-2-yl, 3,3,3-trifluoro-1-propene-2-yl, 3,3,3-trichloro-1-propene-2-yl, 4-fluoro-3-butenyl, 4,4-difluoro-3-butenyl, 4,4-difluoro-3-butene-2-yl, 4,4,4-trifluoro-2-butenyl, 3,4,4-trifluoro-3-butenyl, 2-trifluoromethyl-2-propenyl, 2-trifluoromethyl-3,3-difluoro-2-propenyl, 4,4,4-trifluoro-3-chloro-2-butenyl, 4,4-dichloro-3-butenyl, 4,4,4-trichloro-2-butenyl, 2-trichloromethyl-2-propenyl, 5,5-difluoro-4-pentenyl, 4,5,5-trifluoro-4-pentenyl, 5,5,5-trifluoro-3-pentenyl, 4,4,4-trifluoro-3-methyl-2-butenyl, 4,4,4-trifluoro-3-trifluoromethyl-2-butenyl, 5,5-dichloro-4-pentenyl, 4,4,3-methyl-2-butenyl, 6,6-difluoro-5-hexenyl, 5,6,6-trifluoro-5-pentenyl, 6,6,6-trifluoro-4-pentenyl, 5,5,5-trifluoro-4-methyl-3-pentenyl, 5,5,5-trifluoro-4-trifluoromethyl-3-pentenyl, 6,6-dichloro-5-hexenyl, or 5,5,5-trichloro-4-methyl-3-pentenyl group.

In the present invention, unless otherwise specified, "$C_3$-$C_6$ halocycloalkyl group" refers to a cycloalkyl group having 3 to 6 carbon atoms, substituted by the same or different 1 to 11 halogen atoms, and examples of the $C_3$-$C_6$ halocycloalkyl group include a 1-fluorocyclopropyl, 2-fluorocyclopropyl, 2,2-difluorocyclopropyl, 2,2,3,3-tetrafluorocyclopropyl, 1-chlorocyclopropyl, 2-chlorocyclopropyl, 2,2-dichlorocyclopropyl, 2,2,3,3-tetrachlorocyclopropyl, 2,2-dibromocyclopropyl, 2,2-diiodocyclopropyl, 1-fluorocyclobutyl, 2-fluorocyclobutyl, 3-fluorocyclobutyl, 3,3-difluorocyclobutyl, heptafluorocyclobutyl, 2-chlorocyclobutyl, 3-chlorocyclobutyl, 3,3-dichlorocyclobutyl, 3,3-dibromocyclobutyl, 3,3-diiodocyclobutyl, 1-fluorocyclopentyl, 2-fluorocyclopentyl, 3-fluorocyclopentyl, 2,2-difluorocyclopentyl, 3,3-difluorocyclopentyl, nonafluorocyclopentyl, 2,2-dichlorocyclopentyl, 3,3-dichlorocyclopentyl, 2,2-dibromocyclopentyl, 3,3-dibromocyclopentyl, 2,2-diiodocyclopentyl, 3,3-diiodocyclopentyl, 1-fluorocyclohexyl, 2-fluorocyclohexyl, 3-fluorocyclohexyl, 4-fluorocyclohexyl, 2,2-difluorocyclohexyl, 3,3-difluorocyclohexyl, 4,4-difluorocyclohexyl, 1-chlorocyclohexyl, 2-chlorocyclohexyl, 3-chlorocyclohexyl, 4-chlorocyclohexyl, 2,2-dichlorocyclohexyl, 3,3-dichlorocyclohexyl, 4,4-dichlorocyclohexyl, 3,3-dibromocyclohexyl, 4,4-dibromocyclohexyl, 3,3-diiodocyclohexyl, or 4,4-diiodocyclohexyl group.

In the present invention, unless otherwise specified, "$C_1$-$C_6$ haloalkyl $C_3$-$C_6$ cycloalkyl group" refers to a ($C_1$-$C_6$ haloalkyl)-($C_3$-$C_6$ cyclo alkyl) group in which the haloalkyl moiety and the cycloalkyl moiety are as defined above, and examples of the "$C_1$-$C_6$ haloalkyl $C_3$-$C_6$ cycloalkyl group" include a 2-trifluoromethylcyclopropyl, 2-trifluoromethylcyclobutyl, 3-trifluoromethylcyclobutyl, 2-trifluoromethylcyclopentyl, 3-trifluoromethylcyclopentyl, 2-trifluoromethylcyclohexyl, 3-trifluoromethylcyclohexyl, or 4-trifluoromethylcyclohexyl group.

In the present invention, unless otherwise specified, "$C_3$-$C_6$ cycloalkyl $C_1$-$C_6$ alkyl group" refers to a ($C_3$-$C_6$ cycloalkyl)-($C_1$-$C_6$ alkyl) group in which the cycloalkyl moiety and the alkyl moiety are as defined above, and examples of the $C_3$-$C_6$ cycloalkyl $C_1$-$C_6$ alkyl group include a cyclopropylmethyl, cyclobutylmethyl, cyclopentylmethyl, cyclohexylmethyl, 1-cyclopropylethyl, 2-cyclopropylethyl, 2-cyclobutylethyl, 2-cyclopentylethyl, or 2-cyclohexylethyl group.

In the present invention, unless otherwise specified, "$C_3$-$C_6$ halocycloalkyl $C_1$-$C_6$ alkyl group" refers to a ($C_3$-$C_6$ halocycloalkyl)-($C_1$-$C_6$ alkyl)- group in which the halocycloalkyl moiety is as defined above, and examples of the "$C_3$-$C_6$ halocycloalkyl $C_1$-$C_6$ alkyl group" include a 2,2-difluorocyclopropylmethyl, 2,2-dichlorocyclopropylmethyl, 1-(2,2-difluorocyclopropyl)ethyl, 2-(2,2-difluorocyclopropyl)ethyl, 1-(2,2-dichlorocyclopropyl)ethyl, 2-(2,2-dichlorocyclopropyl)ethyl, 2-(2,2-difluorocyclopropyl)propyl, 3,3-difluorocyclobutylmethyl, 2,2,3,3-tetrafluorocyclobutylmethyl, 2-(2,2,3,3-tetrafluorocyclobutyl)ethyl, 2-(3,3-difluorocyclobutyl)ethyl, 2-(3,3-difluorocyclobutyl)propyl, 3,3-difluorocyclopentylmethyl or 2-(3,3-difluorocyclopentyl)propyl group.

In the present invention, unless otherwise specified, "$C_1$-$C_6$ alkylthio $C_1$-$C_6$ alkyl group" refers to a ($C_1$-$C_6$ alkyl)-S—($C_1$-$C_6$ alkyl)- group in which the alkyl moiety is as defined above, and examples of the $C_1$-$C_6$ alkylthio $C_1$-$C_6$ alkyl group include a methylthiomethyl, ethylthiomethyl, n-propylthiomethyl, isopropylthiomethyl, 1-(methylthio)ethyl, 2-(methylthio)ethyl, 2-(ethylthio)ethyl, 1-(n-propylthio)ethyl, 2-(n-propylthio)ethyl, 1-(isopropylthio)ethyl, 2-(isopropylthio)ethyl, 1-(methylthio)propyl, 2-(methylthio)propyl, 3-(methylthio)propyl, 1-(ethylthio)propyl, 2-(ethylthio)propyl, 3-(ethylthio)propyl, 1-(n-propylthio)propyl, 2-(n-propylthio)propyl, 3-(n-propylthio)propyl, 1-(methylthio)butyl, 2-(methylthio)butyl, 3-(methylthio)butyl, 4-(methylthio)butyl, 1-(methylthio)pentyl, 2-(methylthio)pentyl, 3-(methylthio)pentyl, 4-(methylthio)pentyl, 5-(methylthio)pentyl, 2-(n-butylthio)ethyl, 2-(isobutylthio)ethyl, sec-butylthioethyl, 2-(tert-butylthio)ethyl, pentylthiomethyl, or hexylthiomethyl group.

In the present invention, unless otherwise specified, "$C_1$-$C_6$ alkylsulfinyl $C_1$-$C_6$ alkyl group" refers to a ($C_1$-$C_6$ alkyl)-S(=O)—($C_1$-$C_6$ alkyl)- group in which the alkyl moiety is as defined above, and examples of the $C_1$-$C_6$ alkylsulfinyl $C_1$-$C_6$ alkyl group include a methylsulfinylmethyl, ethylsulfinylmethyl, n-propylsulfinylmethyl, isopropylsulfinylmethyl, 1-(methylsulfinyl)ethyl, 2-(methylsulfinyl)ethyl, 2-(ethylsulfinyl)ethyl, 1-(n-propylsulfinyl)ethyl, 2-(n-propylsulfinyl)ethyl, 1-(isopropylsulfinyl)ethyl, 2-(isopropylsulfinyl)ethyl, 1-(methylsulfinyl)propyl, 2-(methylsulfinyl)propyl, 3-(methylsulfinyl)propyl, 1-(ethylsulfinyl)propyl, 2-(ethylsulfinyl)propyl, 3-(ethylsulfinyl)propyl, 1-(n-propylsulfinyl)propyl, 2-(n-propylsulfinyl)propyl, 3-(n-propylsulfinyl)propyl, 1-(methylsulfinyl)butyl, 2-(methylsulfinyl)butyl, 3-(methylsulfinyl)butyl, 4-(methylsulfinyl)butyl, 1-(methylsulfinyl)pentyl, 2-(methylsulfinyl)pentyl, 3-(methylsulfinyl)pentyl, 4-(methylsulfinyl)pentyl, 5-(methylsulfinyl)pentyl, 2-(n-butylsulfinyl)ethyl, 2-(isobutylsulfinyl)ethyl, sec-butylsulfinylethyl, 2-(tert-butylsulfinyl)ethyl, pentylsulfinylmethyl, or hexylsulfinylmethyl group.

In the present invention, unless otherwise specified, "$C_1$-$C_6$ alkylsulfonyl $C_1$-$C_6$ alkyl group" refers to a ($C_1$-$C_6$ alkyl)-S(=O)$_2$—($C_1$-$C_6$ alkyl)- group in which the alkyl moiety is as defined above, and examples of the $C_1$-$C_6$ alkylsulfonyl $C_1$-$C_6$ alkyl group include a methylsulfonylmethyl, ethylsulfonylmethyl, n-propylsulfonylmethyl, isopropylsulfonylmethyl, 1-(methylsulfonyl)ethyl, 2-(methylsulfonyl)ethyl, 2-(ethylsulfonyl)ethyl, 1-(n-propylsulfonyl)ethyl, 2-(n-propylsulfonyl)ethyl, 1-(isopropylsulfonyl)ethyl, 2-(isopropylsulfonyl)ethyl, 1-(methylsulfonyl)propyl, 2-(methylsulfonyl)propyl, 3-(methylsulfonyl)propyl, 1-(ethylsulfonyl)propyl, 2-(ethylsulfonyl)propyl, 3-(ethylsulfonyl)propyl, 1-(n-propylsulfonyl)propyl, 2-(n-propylsulfonyl)propyl, 3-(n-propylsulfonyl)propyl, 1-(methylsulfonyl)butyl, 2-(methylsulfonyl)butyl, 3-(methylsulfonyl)butyl, 4-(methylsulfonyl)butyl, 1-(methylsulfonyl)pentyl, 2-(methylsulfonyl)pentyl, 3-(methylsulfonyl)pentyl, 4-(methylsulfonyl)pentyl, 5-(methylsulfonyl)pentyl, 2-(n-butylsulfonyl)ethyl, 2-(isobutylsulfonyl)ethyl, sec-butylsulfonylethyl, 2-(tert-butylsulfonyl)ethyl, pentylsulfonylmethyl, or hexylsulfonylmethyl group.

In the present invention, "$C_1$-$C_6$ haloalkylthio $C_1$-$C_6$ alkyl group" refers to a ($C_1$-$C_6$ haloalkyl)-S—($C_1$-$C_6$ alkyl)- group in which the haloalkyl moiety is as defined above, and examples of the $C_1$-$C_6$ haloalkylthio $C_1$-$C_6$ alkyl group include a 2-(difluoromethylthio)ethyl, 2-(trifluoromethylthio)ethyl, 2-(2,2-difluoroethylthio)ethyl, 2-(2,2,2-trifluoroethylthio)ethyl, 2-(3,3-difluoropropylthio)ethyl, 2-(3,3,3-trifluoropropylthio)ethyl, 3-(difluoromethylthio)propyl, 3-(trifluoromethylthio)propyl, 3-(2,2-difluoroethylthio)propyl, 3-(2,2,2-trifluoroethylthio)propyl, 3-(3,3-difluoropropylthio)propyl, 3-(3,3,3-trifluoropropylthio)propyl, 4-(trifluoromethylthio)butyl, or 5-(trifluoromethylthio)pentyl group.

In the present invention, "$C_1$-$C_6$ haloalkylsulfinyl $C_1$-$C_6$ alkyl group" refers to a ($C_1$-$C_6$ haloalkyl)-S(=O)—($C_1$-$C_6$ alkyl)- group in which the haloalkyl moiety is as defined above, and examples of the $C_1$-$C_6$ haloalkylsulfinyl $C_1$-$C_6$ alkyl group include a 2-(difluoromethylsulfinyl)ethyl, 2-(trifluoromethylsulfinyl)ethyl, 2-(2,2-difluoroethylsulfinyl)ethyl, 2-(2,2,2-trifluoroethylsulfinyl)ethyl, 2-(3,3-difluoropropylsulfinyl)ethyl, 2-(3,3,3-trifluoroethylsulfinyl)ethyl, 3-(difluoromethylsulfinyl)propyl, 3-(trifluoromethylsulfinyl)propyl, 3-(2,2-difluoroethylsulfinyl)propyl, 3-(2,2,2-trifluoroethylsulfinyl)propyl, 3-(3,3-difluoropropylsulfinyl)propyl, 3-(3,3,3-trifluoropropylsulfinyl)propyl, 4-(trifluoromethylsulfinyl)butyl, or 5-(trifluoromethylsulfinyl)pentyl group.

In the present invention, "$C_1$-$C_6$ haloalkylsulfonyl $C_1$-$C_6$ alkyl group" refers to a ($C_1$-$C_6$ haloalkyl)-S(=O)$_2$—($C_1$-$C_6$ alkyl)- group in which the haloalkyl moiety is as defined above, and examples of the $C_1$-$C_6$ haloalkylsulfonyl $C_1$-$C_6$ alkyl group include a 2-(difluoromethylsulfonyl)ethyl, 2-(trifluoromethylsulfonyl)ethyl, 2-(2,2-difluoroethylsulfonyl)ethyl, 2-(2,2,2-trifluoroethylsulfonyl)ethyl, 2-(3,3-difluoroethylsulfonyl)ethyl, 2-(3,3,3-trifluoroethylsulfonyl)ethyl, 3-(difluoromethylsulfonyl)propyl, 3-(trifluoromethylsulfonyl)propyl, 3-(2,2-difluoroethylsulfonyl)propyl, 3-(2,2,2-trifluoroethylsulfonyl)propyl, 3-(3,3-difluoropropylsulfonyl)propyl, 3-(3,3,3-trifluoropropylsulfonyl)propyl, 4-(trifluoromethylsulfonyl)butyl, or 5-(trifluoromethylsulfonyl)pentyl group.

In the present invention, "mono($C_1$-$C_6$ alkyl)aminocarbonyl group" refers to a ($C_1$-$C_6$ alkyl)-NH—C(=O)— group in which the alkyl moiety is as defined above, and examples of the mono($C_1$-$C_6$ alkyl)aminocarbonyl group include a methylaminocarbonyl, ethylaminocarbonyl, n-propylaminocarbonyl, isopropylaminocarbonyl, n-butylaminocarbonyl, isobutylaminocarbonyl, sec-butylaminocarbonyl, tert-butylaminocarbonyl, n-pentylaminocarbonyl, 1-methylbutylaminocarbonyl, 2-methylbutylaminocarbonyl, 3-methylbutylaminocarbonyl, 1-ethylpropylaminocarbonyl, 1,1-dimethylpropylaminocarbonyl, 1,2-dimethylpropylaminocarbonyl, 2,2-dimethylpropylaminocarbonyl, or n-hexylaminocarbonyl group.

In the present invention, "di($C_1$-$C_6$ alkyl)aminocarbonyl group" refers to a ($C_1$-$C_6$ alkyl)$_2$N—C(=O)— group in which the alkyl moiety is as defined above, and the two alkyl groups may be different from each other, and examples of the di($C_1$-$C_6$ alkyl)aminocarbonyl group include a dimethylaminocarbonyl, diethylaminocarbonyl, di(n-propyl)aminocarbonyl, diisopropylaminocarbonyl, dibutylaminocarbonyl, N-ethyl-N-methylaminocarbonyl, N-methyl-N-propylaminocarbonyl, N-isopropyl-N-methylaminocarbonyl, N-butyl-N-methylaminocarbonyl, N-(s-butyl)-N-methylaminocarbonyl, N-isobutyl-N-methylaminocarbonyl, N-pentyl-N-methylaminocarbonyl, N-ethyl-N-propylaminocarbonyl, N-ethyl-N-isopropylaminocarbonyl, or N-ethyl-N-butylaminocarbonyl group.

In the present invention, "mono($C_1$-$C_6$ alkyl)aminothiocarbonyl group" refers to a ($C_1$-$C_6$ alkyl)-NH—C(=S)— group in which the alkyl moiety is as defined above, and examples of the mono($C_1$-$C_6$ alkyl)aminothiocarbonyl group include a methylaminothiocarbonyl, ethylaminothiocarbonyl, n-propylaminothiocarbonyl, isopropylaminothiocarbonyl, n-butylaminothiocarbonyl, isobutylaminothiocarbonyl, sec-butylaminothiocarbonyl, tert-butylaminothiocarbonyl, n-pentylaminothiocarbonyl, 1-methylbutylaminothiocarbonyl, 2-methylbutylaminothiocarbonyl, 3-methylbutylaminothiocarbonyl, 1-ethylpropylaminothiocarbonyl, 1,1-dimethylpropylaminothiocarbonyl, 1,2-dimethylpropylaminothiocarbonyl, 2,2-dimethylpropylaminothiocarbonyl, or n-hexylaminothiocarbonyl group.

In the present invention, "di($C_1$-$C_6$ alkyl)aminothiocarbonyl group" refers to a ($C_1$-$C_6$ alkyl)$_2$-N—C(=S)— group in which the alkyl moiety is as defined above, and the two alkyl groups may be different from each other, and examples of the di($C_1$-$C_6$ alkyl)aminothiocarbonyl group include a dimethylaminothiocarbonyl, diethylaminothiocarbonyl, di(n-propyl)aminothiocarbonyl, diisopropylaminothiocarbonyl, dibutylaminothiocarbonyl, N-ethyl-N-methylaminothiocarbonyl, N-methyl-N-propylaminothiocarbonyl, N-isopropyl-N-methylaminothiocarbonyl, N-butyl-N-methylaminothiocarbonyl, N-(s-butyl)-N-methylaminothiocarbonyl, N-isobutyl-N-methylaminothiocarbonyl, N-pentyl-N-methylaminothiocarbonyl, N-ethyl-N-propylaminothiocarbonyl, N-ethyl-N-isopropylaminothiocarbonyl, or N-ethyl-N-butylaminothiocarbonyl group.

In the present invention, "$C_1$-$C_6$ alkylcarbonyl $C_1$-$C_6$ alkyl group" refers to a ($C_1$-$C_6$ alkyl)-C(=O)—($C_1$-$C_6$ alkyl) group in which the alkyl moiety is as defined above, and examples of the $C_1$-$C_6$ alkylcarbonyl $C_1$-$C_6$ alkyl group include an acetonitrile, propionylmethyl, 2-methylpropionylmethyl, pivaloylmethyl, 2-acetylethyl, 2-propionylethyl, 2(2-methylpropionyl)ethyl, 2-pivaloylethyl, 3-acetylpropyl, 3-propionylpropyl, 3(2-methylpropionyl)propyl, or 3-pivaloylpropyl group.

In the present invention, "$C_1$-$C_6$ haloalkylcarbonyl $C_1$-$C_6$ alkyl group" refers to a ($C_1$-$C_6$ haloalkyl)-C(=O)—($C_1$-$C_6$ alkyl) group in which the alkyl moiety is as defined above, and examples of the $C_1$-$C_6$ haloalkylcarbonyl $C_1$-$C_6$ alkyl group include a 2-oxo-3,3-difluoropropyl, 3-chloro-2-oxo-3,3-difluoropropyl, 2-oxo-3,3,3-trifluoropropyl, 3-oxo-4,4-difluorobutyl, 4-chloro-3-oxo-4,4-difluorobutyl, 3-oxo-4,4,4-trifluorobutyl, 3-oxo-4,4,5,5,5-pentafluoropentyl, 4-oxo-5,5,5-trifluoropentyl, or 4-oxo-5,5,6,6,6-pentafluorohexyl group.

In the present invention, "$C_1$-$C_6$ alkoxycarbonyl $C_1$-$C_6$ alkyl group" refers to a ($C_1$-$C_6$ alkoxy)-C(=O)—($C_1$-$C_6$ alkyl)- group in which the alkoxy moiety is as defined above, and examples of the $C_1$-$C_6$ alkoxycarbonyl $C_1$-$C_6$ alkyl group include a methoxy carbonylmethyl, ethoxy carbonylmethyl, n-propoxy carbonylmethyl, isopropoxycarbonylmethyl, tert-butoxycarbonylmethyl, 1-(methoxycarbonyl)ethyl, 2-(methoxy carbonyl)ethyl, 1-(ethoxycarbonyl)ethyl, 2-(ethoxy carbonyl)ethyl, 1-(methoxy carbonyl)-1-methylethyl, 1-(ethoxy carbonyl)-1-methylethyl, or 2-(tert-butoxycarbonyl)ethyl group.

In the present invention, "aminocarbonyl $C_1$-$C_6$ alkyl group" refers to a $H_2N$—C(=O)—($C_1$-$C_6$ alkyl)- group in which the alkyl moiety is as defined above, and examples of the aminocarbonyl $C_1$-$C_6$ alkyl group include a carbamoylmethyl, 1-carbamoylethyl, or 2-carbamoylethyl group.

In the present invention, "mono($C_1$-$C_6$ alkyl)aminocarbonyl $C_1$-$C_6$ alkyl group" refers to a ($C_1$-$C_6$ alkyl)-NH—C(=O)—($C_1$-$C_6$ alkyl)- group in which the alkyl moiety is as defined above, and examples of the mono($C_1$-$C_6$ alkyl) aminocarbonyl $C_1$-$C_6$ alkyl group include a N-methylcarbamoylmethyl, N-ethylcarbamoylmethyl, or N-(tert-butyl)carbamoylmethyl group.

In the present invention, "mono($C_1$-$C_6$ haloalkyl)aminocarbonyl $C_1$-$C_6$ alkyl group" refers to a ($C_1$-$C_6$ haloalkyl)-NH—C(=O)—($C_1$-$C_6$ alkyl)- group in which the haloalkyl moiety is as defined above, and examples of the mono($C_1$-$C_6$ haloalkyl)aminocarbonyl $C_1$-$C_6$ alkyl group include a N-(2,2-difluoroethyl)carbamoylmethyl, N-(2,2,2-trifluoroethyl)carbamoylmethyl, 1-{N-(2,2-difluoroethyl)carbamoyl}ethyl, 1-{N-(2,2-trifluoroethyl)carbamoyl}}ethyl, 1-{N-(2,2-difluoroethyl)carbamoyl}-1-methylethyl, or 1-{N-(2,2-trifluoroethyl)carbamoyl}-1-methylethyl group.

In the present invention, "mono($C_3$-$C_6$ cycloalkyl)aminocarbonyl $C_1$-$C_6$ alkyl group" refers to a ($C_3$-$C_6$ cycloalkyl)-NH—C(=O)—($C_1$-$C_6$ alkyl)- group in which the cycloalkyl moiety is as defined above, and examples of the mono($C_3$-$C_6$ cycloalkyl)aminocarbonyl $C_1$-$C_6$ alkyl group include a N-cyclopropylcarbamoylmethyl, N-cyclobutylcarbamoylmethyl, N-cyclopentylcarbamoylmethyl, or N-cyclohexylcarbamoylmethyl group.

In the present invention, "di($C_1$-$C_6$ alkyl)aminocarbonyl $C_1$-$C_6$ alkyl group" refers to a ($C_1$-$C_6$ alkyl)$_2$-N—C(=O)—($C_1$-$C_6$ alkyl)- group in which the alkyl moiety is as defined above, and examples of the di($C_1$-$C_6$ alkyl)aminocarbonyl $C_1$-$C_6$ alkyl group include a N,N-dimethylcarbamoylmethyl, N,N-diethylcarbamoylmethyl, N,N-dipropylcarbamoylmethyl, N-ethyl-N-methylcarbamoylmethyl, or N-methyl-N-propylcarbamoylmethyl group.

In the present invention, "mono($C_1$-$C_6$ alkylcarbonyl)amino $C_1$-$C_6$ alkyl group" refers to a ($C_1$-$C_6$ alkyl)-C(=O)—NH—($C_1$-$C_6$ alkyl)- group in which the alkyl moiety is as defined above, and examples of the mono($C_1$-$C_6$ alkylcarbonyl)amino $C_1$-$C_6$ alkyl group include a 2-(acetylamino)ethyl, 2-(propanoylamino)ethyl, 2-(isopropanoylamino)ethyl, or 3-(acetylamino)propyl, 3-(acetylamino)butyl group.

In the present invention, "mono($C_1$-$C_6$ alkoxycarbonyl)amino $C_1$-$C_6$ alkyl group" refers to a ($C_1$-$C_6$ alkoxy)-C(=O)—NH—($C_1$-$C_6$ alkyl)- group in which the alkoxy moiety is as defined above, and examples of the mono($C_1$-$C_6$ alkoxycarbonyl)amino $C_1$-$C_6$ alkyl group include a 2-(methoxycarbonylamino)ethyl, 2-(ethoxycarbonylamino)ethyl, or 2-(tert-butylcarbonylamino)ethyl group.

In the present invention, "mono($C_1$-$C_6$ alkylsulfonyl)amino $C_1$-$C_6$ alkyl group" refers to a ($C_1$-$C_6$ alkyl)-S(=O)$_2$—NH—($C_1$-$C_6$ alkyl)- group in which the alkyl moiety is as defined above, and examples of the mono($C_1$-$C_6$ alkylsulfonyl)amino $C_1$-$C_6$ alkyl group include a 2-(methylsulfonylamino)ethyl, 2-(ethylsulfonylamino)ethyl, 2-(isopropylsulfonylamino)ethyl, 3-(methylsulfonylamino)propyl, or 4-(methylsulfonylamino)butyl group.

In the present invention, "mono($C_1$-$C_6$ haloalkylsulfonyl)amino $C_1$-$C_6$ alkyl group" refers to a ($C_1$-$C_6$ haloalkyl)-S(=O)$_2$—NH—($C_1$-$C_6$ alkyl)- group in which the alkyl moiety is as defined above, and examples of the mono($C_1$-$C_6$ haloalkylsulfonyl)amino $C_1$-$C_6$ alkyl group include a 2-(difluoromethylsulfonylamino)ethyl, 2-(trifluoromethylsulfonylamino)ethyl, 3-(difluoromethylsulfonylamino)propyl, or 3-(trifluoromethylsulfonylamino)propyl group.

In the present invention, "mono($C_1$-$C_6$ alkyl)aminosulfonyl group" refers to a ($C_1$-$C_6$ alkyl)-NH—S(=O)— group in which the alkyl moiety is as defined above, and examples of the mono($C_1$-$C_6$ alkyl)aminosulfonyl group include a methylaminosulfonyl, ethylaminosulfonyl, n-propylaminosulfonyl, isopropylaminosulfonyl, n-butylaminosulfonyl, isobutylaminosulfonyl, sec-butylaminosulfonyl, tert-butylaminosulfonyl, n-pentylaminosulfonyl, 1-methylbutylaminosulfonyl, 2-methylbutylaminosulfonyl, 3-methylbutylaminosulfonyl, 1-ethylpropylaminosulfonyl, 1,1-dimethylpropylaminosulfonyl, 1,2-dimethylpropylaminosulfonyl, 2,2-dimethylpropylaminosulfonyl, or n-hexylaminosulfonyl group.

In the present invention, "di($C_1$-$C_6$ alkyl)aminosulfonyl group" refers to a ($C_1$-$C_6$ alkyl)$_2$-N—S(=O)$_2$— group in which the alkyl moiety is as defined above, and the two alkyl groups may be different from each other, and examples of the di($C_1$-$C_6$ alkyl)aminosulfonyl group include a dimethylaminosulfonyl, diethylaminosulfonyl, di(n-propyl)aminosulfonyl, diisopropylaminosulfonyl, dibutylaminosulfonyl, N-ethyl-N-methylaminosulfonyl, N-methyl-N-propylaminosulfonyl, N-isopropyl-N-methylaminosulfonyl, N-butyl-N-methylaminosulfonyl, N-(s-butyl)-N-methylaminosulfonyl, N-isobutyl-N-methylaminosulfonyl, N-pentyl-N-methylaminosulfonyl, N-ethyl-N-propylaminosu- lfocarbonyl, N-ethyl-N-isopropylaminosulfocarbonyl, or N-ethyl-N-butylaminosulfonyl group.

In the present invention, unless otherwise specified, "hydroxy $C_1$-$C_6$ alkyl group" refers to a (hydroxy)-($C_1$-$C_6$ alkyl) group in which the alkyl moiety is as defined above, and examples of the hydroxy $C_1$-$C_6$ alkyl group include a hydroxymethyl, 1-hydroxyethyl, 2-hydroxyethyl, 1-hydroxypropyl, 2-hydroxypropyl, 3-hydroxypropyl, 1-hydroxybutyl or 4-hydroxybutyl group.

In the present invention, unless otherwise specified, "hydroxyimino $C_1$-$C_6$ alkyl group" refers to a HO—N=($C_1$-$C_6$ alkyl) group in which the alkyl moiety is as defined above, and examples of the hydroxyimino $C_1$-$C_6$ alkyl group include a 1-(hydroxyimino)ethyl, 2-(hydroxyimino)ethyl, 1-(hydroxyimino)propyl, 2-(hydroxyimino)propyl, or 3-(hydroxyimino)propyl group.

In the present invention, unless otherwise specified, "$C_1$-$C_6$ alkoxyimino group" refers to a ($C_1$-$C_6$ alkyl)-O—N=C— group in which the alkyl moiety is as defined above, and examples of the $C_1$-$C_6$ alkoxyimino group include a methoxyimino, ethoxyimino, or isopropoxyimino group.

In the present invention, unless otherwise specified, "$C_1$-$C_6$ alkoxyimino $C_1$-$C_6$ alkyl group" refers to a ($C_1$-$C_6$ alkyl)-O—N=($C_1$-$C_6$ alkyl) group in which the alkyl moiety is as defined above, and examples of the $C_1$-$C_6$ alkoxyimino $C_1$-$C_6$ alkyl group include a 1-(methoxyimino)ethyl, 2-(methoxyimino)ethyl, 1-(methoxyimino)propyl, 2-(methoxyimino)propyl, 3-(methoxyimino)propyl, 1-(ethoxyimino)ethyl, 2-(ethoxyimino)ethyl, 1-(ethoxyimino)propyl, 2-(ethoxyimino)propyl, 3-(ethoxyimino)propyl, 1-(isopropoxyimino)ethyl, or 2-(isopropoxyimino)ethyl group.

In the present invention, unless otherwise specified, "$C_1$-$C_6$ haloalkoxyimino $C_1$-$C_6$ alkyl group" refers to a ($C_1$-$C_6$ haloalkyl)-O—N=($C_1$-$C_6$ alkyl) group in which the alkyl moiety is as defined above, and examples of the $C_1$-$C_6$ haloalkoxyimino $C_1$-$C_6$ alkyl group include a 2-(2,2-difluoroethoxyimino)ethyl, 2-(2,2,2-trifluoroethoxyimino)ethyl, 2-(2,2,2-trifluoroethoxyimino)propyl, or 3-(2,2,2-trifluoroethoxyimino)propyl group.

In the present invention, unless otherwise specified, examples of the "$C_7$-$C_{13}$ aralkyl group" include a benzyl, 1-phenylethyl, 2-phenylethyl, 2-phenylpropyl, (naphthalene-1-yl)methyl, or (naphthalene-2-yl)methyl group.

In the present invention, unless otherwise specified, "cyano $C_1$-$C_6$ alkyl group" refers to a (cyano)-($C_1$-$C_6$ alkyl) group in which the alkyl moiety is as defined above, and examples of the cyano $C_1$-$C_6$ alkyl group include a cyanomethyl, 1-cyanoethyl, 2-cyanoethyl, 1-cyanopropyl, 3-cyanopropyl, 2-cyanopropane-2-yl, 1-cyanobutyl, 4-cyanobutyl, 5-cyanopentyl, or 6-cyanohexyl group.

In the present invention, unless otherwise specified, "cyano $C_3$-$C_6$ cycloalkyl group" refers to a (cyano)-($C_3$-$C_6$ cycloalkyl) group in which the cycloalkyl moiety is as defined above, and examples of the cyano $C_3$-$C_6$ cycloalkyl group include a 1-cyanocyclopropyl, 2-cyanocyclopropyl, 1-cyanocyclobutyl, 3-cyanocyclobutyl, or 1-cyanocyclopentyl group.

In the present invention, unless otherwise specified, "$C_1$-$C_6$ alkylsulfonyloxy group" refers to a ($C_1$-$C_6$ alkyl)-S(=O)$_2$—O— group in which the alkyl moiety is as defined above, and examples of the $C_1$-$C_6$ alkylsulfonyloxy group include a methylsulfonyloxy, ethylsulfonyloxy, or isopropylsulfonyloxy group.

In the present invention, unless otherwise specified, "$C_1$-$C_6$ alkylcarbonyl group" refers to a ($C_1$-$C_6$ alkyl)-C(=O)— group in which the alkyl moiety is as defined above, and examples of the $C_1$-$C_6$ alkylcarbonyl group include an acetyl, propionyl, 2-methylpropionyl, 2,2-dimethylpropionyl, butanoyl, 2-methylbutanoyl, 3-methylbutanoyl, 2-ethylbutanoyl, 2,2-dimethylbutanoyl, 2,3-dimethylbutanoyl, 3,3-dimethylbutanoyl, pentanoyl, 2-methylpentanoyl, 3-methylpentanoyl, 4-methylpentanoyl, or hexanoyl group.

In the present invention, unless otherwise specified, "$C_1$-$C_6$ alkoxy $C_1$-$C_6$ alkylcarbonyl group" refers to a ($C_1$-$C_6$ alkyl)-O—($C_1$-$C_6$ alkyl)-C(=O)— group in which the alkyl moiety is as defined above, and examples of the $C_1$-$C_6$ alkoxy $C_1$-$C_6$ alkylcarbonyl group include a methoxyacetyl, ethoxyacetyl, propoxyacetyl, isopropoxyacetyl, butoxyacetyl, 2-methoxypropionyl, 3-methoxypropionyl, 2-ethoxypropionyl, 3-ethoxypropionyl, 2-methoxybutanoyl, 4-methoxybutanoyl, 2-methoxypentanoyl, or 5-methoxypentanoyl group.

In the present invention, unless otherwise specified, "$C_3$-$C_6$ cycloalkylcarbonyl group" refers to a ($C_3$-$C_6$ cycloalkyl)-C(=O)— group in which the cycloalkyl moiety is as defined above, and examples of the $C_3$-$C_6$ cycloalkylcarbonyl group include a cyclopropanecarbonyl, cyclobutanecarbonyl, cyclopentanecarbonyl, or cyclohexanecamyl group.

In the present invention, "$C_1$-$C_6$ alkoxycarbonyl group" refers to a ($C_1$-$C_6$ alkoxy)-C(=O)— group in which the alkoxy moiety is as defined above, and examples of the $C_1$-$C_6$ alkoxycarbonyl group include a methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentoxycarbonyl, 1-methylbutoxycarbonyl, 2-methylbutoxy carbonyl, 3-methylbutoxy carbonyl, 1-ethylpropoxycarbonyl, 1,1-dimethylpropoxycarbonyl, 1,2-dimethylpropoxycarbonyl, or 2,2-dimethylpropoxycarbonyl group.

In the present invention, unless otherwise specified, "$C_7$-$C_{13}$ aralkylcarbonyl group" refers to a ($C_7$-$C_{13}$ aralkyl)-C(=O)— group in which the aralkyl moiety is as defined above, and examples of the $C_7$-$C_{13}$ aralkylcarbonyl group include a phenylethanoyl, 1-phenylpropanoyl, or 2-phenylpropanoyl group.

In the present invention, unless otherwise specified, "($C_1$-$C_6$ alkyl)thiocarbonyl group" refers to a ($C_1$-$C_6$ alkyl)-C(=S)— group in which the alkyl moiety is as defined above, and examples of the ($C_1$-$C_6$ alkyl)thiocarbonyl group include a methylthiocarbonyl, ethylthiocarbonyl, n-propylthiocarbonyl, isopropylthiocarbonyl, n-butylthiocarbonyl, isobutylthiocarbonyl, sec-butylthiocarbonyl, tert-butylthiocarbonyl, or n-pentylthiocarbonyl group.

In the present invention, unless otherwise specified, "($C_1$-$C_6$ alkoxy)thiocarbonyl group" refers to a ($C_1$-$C_6$ alkyl)-O—C(=S)— group in which the alkyl moiety is as defined above, and examples of the ($C_1$-$C_6$ alkoxy)thiocarbonyl group include a methoxythiocarbonyl, ethoxythiocarbonyl, n-propoxythiocarbonyl, isopropoxythiocarbonyl, n-butoxythiocarbonyl, isobutoxythiocarbonyl, sec-butoxythiocarbonyl, tert-butoxythiocarbonyl, n-pentoxythiocarbonyl, 1-methyl butoxythiocarbonyl, 2-methyl butoxythiocarbonyl, 3-methyl butoxythiocarbonyl, 1-ethylpropoxythiocarbonyl, 1,1-dimethylpropoxythiocarbonyl, 1,2-dimethylpropoxythiocarbonyl, or 2,2-dimethylpropoxythiocarbonyl group.

In the present invention, "$C_3$-$C_6$ cycloalkyl $C_1$-$C_6$ alkylcarbonyl group" refers to a ($C_3$-$C_6$ cycloalkyl $C_1$-$C_6$ alkyl)-C(=O)— group in which the cycloalkyl alkyl moiety is as defined above, and examples of the $C_3$-$C_6$ cycloalkyl $C_1$-$C_6$ alkylcarbonyl group include a 2-cyclopropylacetyl, 2-cyclobutylacetyl, 2-cyclopentylacetyl, 2-cyclohexylacetyl, 2-cyclopropylpropanoyl, or 2-cyclopropylbutanoyl group.

In the present invention, unless otherwise specified, "$C_1$-$C_6$ haloalkylthio group" refers to a ($C_1$-$C_6$ haloalkyl)-S— group in which the haloalkyl moiety is as defined above, and examples of the $C_1$-$C_6$ haloalkylthio group include a fluoromethylthio, difluoromethylthio, trifluoromethylthio, trichloromethylthio, 2,2,2-trifluoroethylthio, pentafluoroethylthio, 2,2,2-trichloroethylthio, 3,3,3-trifluoropropylthio, 1,1,2,3,3,3-hexafluoropropyl, heptafluoropropylthio, 1,1,1,3,3,3-hexafluoropropane-2-ylthio, heptafluoropropane-2-ylthio, or 4,4,4-trifluorobutylthio group.

In the present invention, unless otherwise specified, "$C_1$-$C_6$ haloalkylsulfinyl group" refers to a ($C_1$-$C_6$ haloalkyl)-S(=O)— group in which the haloalkyl moiety is as defined above, and examples of the $C_1$-$C_6$ haloalkylsulfinyl group include a difluoromethylsulfinyl, trifluoromethylsulfinyl, trichloromethylsulfinyl, 2,2,2-trifluoroethylsulfinyl, 2,2,2-trichloroethylsulfinyl, pentafluoroethylsulfinyl, 3,3,3-trifluoropropylsulfinyl, heptafluoropropylsulfinyl, or heptafluoro-2-propylsulfinyl group.

In the present invention, unless otherwise specified, "$C_1$-$C_6$ haloalkylsulfonyl group" refers to a ($C_1$-$C_6$ haloalkyl)-S(=O)$_2$— group in which the haloalkyl moiety is as defined above, and examples of the $C_1$-$C_6$ haloalkylsulfonyl group include a difluoromethylsulfonyl, trifluoromethylsulfonyl, trichloromethylsulfonyl, 2,2,2-trifluoroethylsulfonyl, pentafluoroethylsulfonyl, 3,3,3-trifluoropropylsulfonyl, heptafluoropropylsulfonyl, or heptafluoro-2-propylsulfonyl group.

In the present invention, the wording "agriculturally acceptable salt" refers to a salt of a hydroxyl group, a carboxyl group, an amino group or the like when such a group exists in the structure of the present compound represented by general formula [I] or [II], or a nitrogen atom in a pyridine ring, with metal or an organic base, or a salt with a mineral acid or an organic acid, and examples of the metal include alkali metal such as sodium or potassium, and alkali earth metal such as magnesium or calcium, examples of the organic base include triethylamine or diisopropylamine, examples of the mineral acid include phosphoric acid, hydrochloric acid, hydrobromic acid, hydroiodic acid, boric acid, or sulfuric acid, and examples of the organic acid include formic acid, acetic acid, lactic acid, ascorbic acid, succinic acid, fumaric acid, maleic acid, oxalic acid, citric acid, benzoic acid, salicylic acid, tartaric acid, methanesulfonic acid, 4-toluenesulfonic acid, or trifluoromethanesulfonic acid.

Next, representative compound examples of compounds included in the pyrazole-3-carboxylic acid amide derivative of the present invention represented by general formula [I] are shown in Table 1 to Table 93, and representative compound examples of compounds included in the pyrazole-3-carboxylic acid derivative of the present invention represented by general formula [II] are shown in Table 94 to Table 149. However, the compounds included in the derivatives of the present invention are not limited to these. The compound numbers in Tables are referred to in the following description.

The compounds included in the pyrazole-3-carboxylic acid amide derivative or pyrazole-3-carboxylic acid derivative of the present invention can have geometrical isomers of E-body and Z-body depending on the kind of the substituent, and the present invention encompasses such E-body, Z-body, or a mixture containing E-body and Z-body in any ratio. The compounds encompassed in the present invention can have optical isomers caused by the existence of one or two or more asymmetric carbon atoms and asymmetric sulfur atoms, and the present invention encompasses any optically active substances, racemic bodies, or diastereomers.

In the present specification, the following signs in tables respectively represent the corresponding groups as shown below.

$CF_3$: trifluoromethyl
(4-$CF_3$)Ph: 4-trifluoromethylphenyl
(2-F-4-$CF_3$)Ph: 2-fluoro-4-trifluoromethylphenyl

TABLE 1

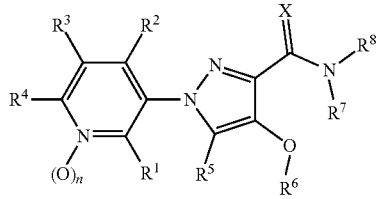

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-0001 | H | H | H | H | H | H | H | H | O | 0 |
| A-0002 | H | H | H | H | H | $CH_3$ | H | H | O | 0 |
| A-0003 | H | H | H | H | H | $CH_2CH_3$ | H | H | O | 0 |
| A-0004 | H | H | H | H | H | $CH(CH_3)_2$ | H | H | O | 0 |
| A-0005 | H | H | H | H | H | $C(CH_3)_3$ | H | H | O | 0 |
| A-0006 | H | H | H | H | H | $CH_2CH_2CH_3$ | H | H | O | 0 |
| A-0007 | H | H | H | H | H | $CH_2CH(CH_3)_2$ | H | H | O | 0 |
| A-0008 | H | H | H | H | H | $CH(CH_3)CH_2CH_3$ | H | H | O | 0 |
| A-0009 | H | H | H | H | H | $CH(CH_2CH_3)CH_2CH_3$ | H | H | O | 0 |
| A-0010 | H | H | H | H | H | $CH_2C(CH_3)_3$ | H | H | O | 0 |
| A-0011 | H | H | H | H | H | $CH_2(CH_2)_2CH_3$ | H | H | O | 0 |
| A-0012 | H | H | H | H | H | $CH_2CH_2CH(CH_3)_2$ | H | H | O | 0 |
| A-0013 | H | H | H | H | H | $CH_2CH(CH_3)CH_2CH_3$ | H | H | O | 0 |

TABLE 1-continued

| Compound | R¹ | R² | R³ | R⁴ | R⁵ | R⁶ | R⁷ | R⁸ | X | n |
|---|---|---|---|---|---|---|---|---|---|---|
| A-0014 | H | H | H | H | H | $CH(CH_3)CH_2CH_2CH_3$ | H | H | O | 0 |
| A-0015 | H | H | H | H | H | $CH_2CH(CH_2CH_3)CH_2CH_3$ | H | H | O | 0 |
| A-0016 | H | H | H | H | H | $CH(CH_2CH_3)CH_2CH_2CH_3$ | H | H | O | 0 |
| A-0017 | H | H | H | H | H | $CH_2CH_2C(CH_3)_3$ | H | H | O | 0 |
| A-0018 | H | H | H | H | H | $CH_2(CH_2)_3CH_3$ | H | H | O | 0 |
| A-0019 | H | H | H | H | H | $CH_2CH_2CH_2CH(CH_3)_2$ | H | H | O | 0 |
| A-0020 | H | H | H | H | H | $CH_2(CH_2)_4CH_3$ | H | H | O | 0 |
| A-0021 | H | H | H | H | H | $CH_2CH_2CH_2CH_2CH(CH_3)_2$ | H | H | O | 0 |
| A-0022 | H | H | H | H | H | $CH_2(CH_2)_5CH_3$ | H | H | O | 0 |
| A-0023 | H | H | H | H | H | $CH_2(CH_2)_6CH_3$ | H | H | O | 0 |
| A-0024 | H | H | H | H | H | $CH_2OCH_3$ | H | H | O | 0 |
| A-0025 | H | H | H | H | H | $CH_2OCH_2CH_3$ | H | H | O | 0 |
| A-0026 | H | H | H | H | H | $CH_2CH_2OCH_3$ | H | H | O | 0 |
| A-0027 | H | H | H | H | H | $CH_2CH_2OCH_2CH_3$ | H | H | O | 0 |
| A-0028 | H | H | H | H | H | $CH_2CH_2CH_2OCH_3$ | H | H | O | 0 |
| A-0029 | H | H | H | H | H | $CH_2CH_2CH_2OCH_2CH_3$ | H | H | O | 0 |
| A-0030 | H | H | H | H | H | $CF_3$ | H | H | O | 0 |
| A-0031 | H | H | H | H | H | $CHF_2$ | H | H | O | 0 |
| A-0032 | H | H | H | H | H | $CH_2CF_3$ | H | H | O | 0 |
| A-0033 | H | H | H | H | H | $CH_2CHF_2$ | H | H | O | 0 |
| A-0034 | H | H | H | H | H | $CH_2CClF_2$ | H | H | O | 0 |
| A-0035 | H | H | H | H | H | $CF_2CHCl_2$ | H | H | O | 0 |
| A-0036 | H | H | H | H | H | $CF_2CCl_3$ | H | H | O | 0 |
| A-0037 | H | H | H | H | H | $CH_2CH_2Cl$ | H | H | O | 0 |
| A-0038 | H | H | H | H | H | $CHClCHCl_2$ | H | H | O | 0 |
| A-0039 | H | H | H | H | H | $CH_2CCl_3$ | H | H | O | 0 |
| A-0040 | H | H | H | H | H | $CH_2CBrF_2$ | H | H | O | 0 |
| A-0041 | H | H | H | H | H | $CF_2CF_3$ | H | H | O | 0 |
| A-0042 | H | H | H | H | H | $CF_2CHF_2$ | H | H | O | 0 |
| A-0043 | H | H | H | H | H | $CH_2CH_2CF_3$ | H | H | O | 0 |
| A-0044 | H | H | H | H | H | $CH_2CF_2CF_3$ | H | H | O | 0 |
| A-0045 | H | H | H | H | H | $CH_2CF_2CHF_2$ | H | H | O | 0 |
| A-0046 | H | H | H | H | H | $CF_2CHFCF_3$ | H | H | O | 0 |
| A-0047 | H | H | H | H | H | $CF_2CF_2CF_3$ | H | H | O | 0 |
| A-0048 | H | H | H | H | H | $CH_2CH_2CH_2Cl$ | H | H | O | 0 |
| A-0049 | H | H | H | H | H | $CH_2CHClCH_2Cl$ | H | H | O | 0 |
| A-0050 | H | H | H | H | H | $CH_2CF_2CF_2CF_3$ | H | H | O | 0 |
| A-0051 | H | H | H | H | H | $CH_2CF_2CHFCF_3$ | H | H | O | 0 |
| A-0052 | H | H | H | H | H | $CH_2CH_2CH_2CF_3$ | H | H | O | 0 |
| A-0053 | H | H | H | H | H | $CH_2CH_2CF_2CF_3$ | H | H | O | 0 |
| A-0054 | H | H | H | H | H | $CF_2CF_2CF_2CF_3$ | H | H | O | 0 |
| A-0055 | H | H | H | H | H | $CH_2CH_2CH(CF_3)_2$ | H | H | O | 0 |
| A-0056 | H | H | H | H | H | $CH_2CH_2CH(CH_3)CF_3$ | H | H | O | 0 |

TABLE 2

| Compound | R¹ | R² | R³ | R⁴ | R⁵ | R⁶ | R⁷ | R⁸ | X | n |
|---|---|---|---|---|---|---|---|---|---|---|
| A-0057 | H | H | H | H | H | $CF_2CF_2CF_2CF_2CF_3$ | H | H | O | 0 |
| A-0058 | H | H | H | H | H | $CH_2CF_2CF_2CF_2CF_3$ | H | H | O | 0 |
| A-0059 | H | H | H | H | H | $CH_2CH_2CH_2CH_2CF_3$ | H | H | O | 0 |
| A-0060 | H | H | H | H | H | $CH_2CF_2CF_2CF_2CHF_2$ | H | H | O | 0 |
| A-0061 | H | H | H | H | H | $CH_2CF_2CF(CF_3)CF_2C(CF_3)_3$ | H | H | O | 0 |
| A-0062 | H | H | H | H | H | $CF_2CF_2CF_2CF_2CF_3$ | H | H | O | 0 |
| A-0063 | H | H | H | H | H | $CH_2CH_2CH_2CH_2CH_2CF_3$ | H | H | O | 0 |
| A-0064 | H | H | H | H | H | $CF_2CF_2CF_2CF_2CHF_2$ | H | H | O | 0 |
| A-0065 | H | H | H | H | H | $CF_2CF_2CF_2CF_2CF_2CF_3$ | H | H | O | 0 |
| A-0066 | H | H | H | H | H | $CH_2CH_2CH_2CH_2CH_2CH_2CF_3$ | H | H | O | 0 |
| A-0067 | H | H | H | H | H | $CF_2CF_2CF_2CF_2CF_2CF_2CHF_2$ | H | H | O | 0 |
| A-0068 | H | H | H | H | H | $CF_2CHFOCH_3$ | H | H | O | 0 |
| A-0069 | H | H | H | H | H | $CF_2CHFOCH_2CH_3$ | H | H | O | 0 |
| A-0070 | H | H | H | H | H | $CH_2CH_2OCH_2CF_3$ | H | H | O | 0 |
| A-0071 | H | H | H | H | H | $CF_2CHFOCF_3$ | H | H | O | 0 |
| A-0072 | H | H | H | H | H | $CF_2CHFOCF_2CF_3$ | H | H | O | 0 |
| A-0073 | H | H | H | H | H | $CF_2CHFOCF_2CF_2CF_3$ | H | H | O | 0 |

TABLE 2-continued

| Compound | R¹ | R² | R³ | R⁴ | R⁵ | R⁶ | R⁷ | R⁸ | X | n |
|---|---|---|---|---|---|---|---|---|---|---|
| A-0074 | H | H | H | H | H | CH$_2$CH=CH$_2$ | H | H | O | 0 |
| A-0075 | H | H | H | H | H | CH$_2$CH=CHCl | H | H | O | 0 |
| A-0076 | H | H | H | H | H | CH$_2$CH=CCl$_2$ | H | H | O | 0 |
| A-0077 | H | H | H | H | H | CH$_2$CH=C(CH$_3$)CF$_3$ | H | H | O | 0 |
| A-0078 | H | H | H | H | H | CH$_2$CH$_2$CF=CF$_2$ | H | H | O | 0 |
| A-0079 | H | H | H | H | H | CH$_2$CH$_2$CH=CF$_2$ | H | H | O | 0 |
| A-0080 | H | H | H | H | H | CH$_2$C≡CH | H | H | O | 0 |
| A-0081 | H | H | H | H | H | CH$_2$C≡CCH$_3$ | H | H | O | 0 |
| A-0082 | H | H | H | H | H | CH$_2$C≡CC(CH$_3$)$_3$ | H | H | O | 0 |
| A-0083 | H | H | H | H | H | CH$_2$C≡C(cyclopropyl) | H | H | O | 0 |
| A-0084 | H | H | H | H | H | CH$_2$C≡Cl | H | H | O | 0 |
| A-0085 | H | H | H | H | H | CH$_2$C≡CCF$_3$ | H | H | O | 0 |
| A-0086 | H | H | H | H | H | cyclopropyl | H | H | O | 0 |
| A-0087 | H | H | H | H | H | cyclobutyl | H | H | O | 0 |
| A-0088 | H | H | H | H | H | cyclopentyl | H | H | O | 0 |
| A-0089 | H | H | H | H | H | cyclohexyl | H | H | O | 0 |
| A-0090 | H | H | H | H | H | 4,4-difluorocyclohexyl | H | H | O | 0 |
| A-0091 | H | H | H | H | H | 4-trifluoromethylcyclohexyl | H | H | O | 0 |
| A-0092 | H | H | H | H | H | CH$_2$(cyclopropyl) | H | H | O | 0 |
| A-0093 | H | H | H | H | H | CH$_2$(cyclobutyl) | H | H | O | 0 |
| A-0094 | H | H | H | H | H | CH$_2$(cyclopentyl) | H | H | O | 0 |
| A-0095 | H | H | H | H | H | CH$_2$(cyclohexyl) | H | H | O | 0 |
| A-0096 | H | H | H | H | H | CH$_2$CH$_2$(cyclopropyl) | H | H | O | 0 |
| A-0097 | H | H | H | H | H | CH$_2$(2,2-difluorocyclopropyl) | H | H | O | 0 |
| A-0098 | H | H | H | H | H | CH$_2$(2,2-dichlorocyclopropyl) | H | H | O | 0 |
| A-0099 | H | H | H | H | H | CH$_2$(4,4-difluorocyclohexyl) | H | H | O | 0 |
| A-0100 | H | H | H | H | H | CH$_2$CH$_2$(2,2-difluorocyclopropyl) | H | H | O | 0 |
| A-0101 | H | H | H | H | H | CH$_2$CH$_2$(2,2-dichlorocyclopropyl) | H | H | O | 0 |
| A-0102 | H | H | H | H | H | CH$_2$CH$_2$(4,4-difluorocyclohexyl) | H | H | O | 0 |
| A-0103 | H | H | H | H | H | CH$_2$SCH$_3$ | H | H | O | 0 |
| A-0104 | H | H | H | H | H | CH$_2$SCH$_2$CH$_3$ | H | H | O | 0 |
| A-0105 | H | H | H | H | H | CH$_2$CH$_2$SCH$_3$ | H | H | O | 0 |
| A-0106 | H | H | H | H | H | CH$_2$CH$_2$SCH$_2$CH$_3$ | H | H | O | 0 |
| A-0107 | H | H | H | H | H | CH$_2$CH$_2$CH$_2$SCH$_3$ | H | H | O | 0 |
| A-0108 | H | H | H | H | H | CH$_2$CH$_2$CH$_2$SCH$_2$CH$_3$ | H | H | O | 0 |
| A-0109 | H | H | H | H | H | CH(CH$_3$)SCH$_3$ | H | H | O | 0 |
| A-0110 | H | H | H | H | H | CH(CH$_3$)SCH$_2$CH$_3$ | H | H | O | 0 |
| A-0111 | H | H | H | H | H | CH$_2$CH(CH$_3$)SCH$_3$ | H | H | O | 0 |
| A-0112 | H | H | H | H | H | CH$_2$CH(CH$_3$)SCH$_2$CH$_3$ | H | H | O | 0 |
| A-0113 | H | H | H | H | H | CH$_2$CH$_2$SCH(CH$_3$)$_2$ | H | H | O | 0 |
| A-0114 | H | H | H | H | H | CH(CH$_3$)CH$_2$CH$_2$SCH$_3$ | H | H | O | 0 |
| A-0115 | H | H | H | H | H | CH(CH$_3$)CH$_2$CH$_2$SCH$_2$CH$_3$ | H | H | O | 0 |
| A-0116 | H | H | H | H | H | CH$_2$CH(CH$_3$)CH$_2$SCH$_3$ | H | H | O | 0 |
| A-0117 | H | H | H | H | H | CH$_2$CH(CH$_3$)CH$_2$SCH$_2$CH$_3$ | H | H | O | 0 |

TABLE 3

| Compound | R¹ | R² | R³ | R⁴ | R⁵ | R⁶ | R⁷ | R⁸ | X | n |
|---|---|---|---|---|---|---|---|---|---|---|
| A-0118 | H | H | H | H | H | CH$_2$CH$_2$CH(CH$_3$)SCH$_3$ | H | H | O | 0 |
| A-0119 | H | H | H | H | H | CH$_2$CH$_2$CH(CH$_3$)SCH$_2$CH$_3$ | H | H | O | 0 |
| A-0120 | H | H | H | H | H | CH$_2$CH$_2$CH$_2$CH$_2$SCH$_3$ | H | H | O | 0 |
| A-0121 | H | H | H | H | H | CH$_2$CH$_2$CH$_2$CH$_2$CH$_2$SCH$_3$ | H | H | O | 0 |
| A-0122 | H | H | H | H | H | CH$_2$SOCH$_3$ | H | H | O | 0 |
| A-0123 | H | H | H | H | H | CH$_2$CH$_2$SOCH$_3$ | H | H | O | 0 |
| A-0124 | H | H | H | H | H | CH$_2$CH$_2$SOCH$_2$CH$_3$ | H | H | O | 0 |
| A-0125 | H | H | H | H | H | CH$_2$CH$_2$SOCH(CH$_3$)$_2$ | H | H | O | 0 |
| A-0126 | H | H | H | H | H | CH$_2$CH$_2$CH$_2$SOCH$_3$ | H | H | O | 0 |
| A-0127 | H | H | H | H | H | CH(CH$_3$)SOCH$_3$ | H | H | O | 0 |
| A-0128 | H | H | H | H | H | CH$_2$CH(CH$_3$)SOCH$_3$ | H | H | O | 0 |
| A-0129 | H | H | H | H | H | CH(CH$_3$)CH$_2$CH$_2$SOCH$_3$ | H | H | O | 0 |
| A-0130 | H | H | H | H | H | CH$_2$CH(CH$_3$)CH$_2$SOCH$_3$ | H | H | O | 0 |
| A-0131 | H | H | H | H | H | CH$_2$CH$_2$CH(CH$_3$)SOCH$_3$ | H | H | O | 0 |
| A-0132 | H | H | H | H | H | CH$_2$CH$_2$CH$_2$CH$_2$SOCH$_3$ | H | H | O | 0 |
| A-0133 | H | H | H | H | H | CH$_2$CH$_2$CH$_2$CH$_2$CH$_2$SOCH$_3$ | H | H | O | 0 |
| A-0134 | H | H | H | H | H | CH$_2$SO$_2$CH$_3$ | H | H | O | 0 |
| A-0135 | H | H | H | H | H | CH$_2$CH$_2$SO$_2$CH$_3$ | H | H | O | 0 |
| A-0136 | H | H | H | H | H | CH$_2$CH$_2$SO$_2$CH$_2$CH$_3$ | H | H | O | 0 |
| A-0137 | H | H | H | H | H | CH$_2$CH$_2$SO$_2$CH(CH$_3$)$_2$ | H | H | O | 0 |
| A-0138 | H | H | H | H | H | CH$_2$CH$_2$CH$_2$SO$_2$CH$_3$ | H | H | O | 0 |
| A-0139 | H | H | H | H | H | CH(CH$_3$)SO$_2$CH$_3$ | H | H | O | 0 |
| A-0140 | H | H | H | H | H | CH$_2$CH(CH$_3$)SO$_2$CH$_3$ | H | H | O | 0 |
| A-0141 | H | H | H | H | H | CH(CH$_3$)CH$_2$CH$_2$SO$_2$CH$_3$ | H | H | O | 0 |
| A-0142 | H | H | H | H | H | CH$_2$CH(CH$_3$)CH$_2$SO$_2$CH$_3$ | H | H | O | 0 |
| A-0143 | H | H | H | H | H | CH$_2$CH$_2$CH(CH$_3$)SO$_2$CH$_3$ | H | H | O | 0 |

TABLE 3-continued

| Compound | R¹ | R² | R³ | R⁴ | R⁵ | R⁶ | R⁷ | R⁸ | X | n |
|---|---|---|---|---|---|---|---|---|---|---|
| A-0144 | H | H | H | H | H | $CH_2CH_2CH_2CH_2SO_2CH_3$ | H | H | O | 0 |
| A-0145 | H | H | H | H | H | $CH_2CH_2CH_2CH_2CH_2SO_2CH_3$ | H | H | O | 0 |
| A-0146 | H | H | H | H | H | $CH_2SCF_3$ | H | H | O | 0 |
| A-0147 | H | H | H | H | H | $CH_2SCHF_2$ | H | H | O | 0 |
| A-0148 | H | H | H | H | H | $CH_2SCH_2CF_3$ | H | H | O | 0 |
| A-0149 | H | H | H | H | H | $CH_2SCH_2CHF_2$ | H | H | O | 0 |
| A-0150 | H | H | H | H | H | $CH_2SCF_2CF_3$ | H | H | O | 0 |
| A-0151 | H | H | H | H | H | $CH_2CH_2SCF_3$ | H | H | O | 0 |
| A-0152 | H | H | H | H | H | $CH_2CH_2SCH_2CF_3$ | H | H | O | 0 |
| A-0153 | H | H | H | H | H | $CH_2CH_2CH_2SCF_3$ | H | H | O | 0 |
| A-0154 | H | H | H | H | H | $CH_2CH_2CH_2SCH_2CF_3$ | H | H | O | 0 |
| A-0155 | H | H | H | H | H | $CH(CH_3)SCF_3$ | H | H | O | 0 |
| A-0156 | H | H | H | H | H | $CH(CH_3)SCH_2CF_3$ | H | H | O | 0 |
| A-0157 | H | H | H | H | H | $CH_2CH(CH_3)SCF_3$ | H | H | O | 0 |
| A-0158 | H | H | H | H | H | $CH_2CH(CH_3)SCH_2CF_3$ | H | H | O | 0 |
| A-0159 | H | H | H | H | H | $CH(CH_3)CH_2SCF_3$ | H | H | O | 0 |
| A-0160 | H | H | H | H | H | $CH(CH_3)CH_2CH_2SCH_2CF_3$ | H | H | O | 0 |
| A-0161 | H | H | H | H | H | $CH_2CH(CH_3)CH_2SCF_3$ | H | H | O | 0 |
| A-0162 | H | H | H | H | H | $CH_2CH(CH_3)CH_2SCH_2CF_3$ | H | H | O | 0 |
| A-0163 | H | H | H | H | H | $CH_2CH_2CH(CH_3)SCF_3$ | H | H | O | 0 |
| A-0164 | H | H | H | H | H | $CH_2CH_2CH(CH_3)SCH_2CF_3$ | H | H | O | 0 |
| A-0165 | H | H | H | H | H | $CH_2CH_2CH_2CH_2SCF_3$ | H | H | O | 0 |
| A-0166 | H | H | H | H | H | $CH_2CH_2CH_2CH_2CH_2SCF_3$ | H | H | O | 0 |
| A-0167 | H | H | H | H | H | $CH_2SOCF_3$ | H | H | O | 0 |
| A-0168 | H | H | H | H | H | $CH_2CH_2SOCF_3$ | H | H | O | 0 |
| A-0169 | H | H | H | H | H | $CH_2CH_2CH_2SOCF_3$ | H | H | O | 0 |
| A-0170 | H | H | H | H | H | $CH(CH_3)SOCF_3$ | H | H | O | 0 |
| A-0171 | H | H | H | H | H | $CH_2CH(CH_3)SOCF_3$ | H | H | O | 0 |
| A-0172 | H | H | H | H | H | $CH(CH_3)CH_2CH_2SOCF_3$ | H | H | O | 0 |
| A-0173 | H | H | H | H | H | $CH(CH_3)CH_2SOCF_3$ | H | H | O | 0 |
| A-0174 | H | H | H | H | H | $CH_2CH_2CH(CH_3)SOCF_3$ | H | H | O | 0 |
| A-0175 | H | H | H | H | H | $CH_2SO_2CF_3$ | H | H | O | 0 |
| A-0176 | H | H | H | H | H | $CH_2CH_2SO_2CF_3$ | H | H | O | 0 |
| A-0177 | H | H | H | H | H | $CH_2SO_2CH_2CF_3$ | H | H | O | 0 |
| A-0178 | H | H | H | H | H | $CH_2CH_2CH_2SO_2CF_3$ | H | H | O | 0 |

TABLE 4

| Compound | R¹ | R² | R³ | R⁴ | R⁵ | R⁶ | R⁷ | R⁸ | X | n |
|---|---|---|---|---|---|---|---|---|---|---|
| A-0179 | H | H | H | H | H | $CH(CH_3)SO_2CF_3$ | H | H | O | 0 |
| A-0180 | H | H | H | H | H | $CH_2CH(CH_3)SO_2CF_3$ | H | H | O | 0 |
| A-0181 | H | H | H | H | H | $CH(CH_3)CH_2CH_2SO_2CF_3$ | H | H | O | 0 |
| A-0182 | H | H | H | H | H | $CH_2CH(CH_3)CH_2SO_2CF_3$ | H | H | O | 0 |
| A-0183 | H | H | H | H | H | $CH_2CH_2CH(CH_3)SO_2CF_3$ | H | H | O | 0 |
| A-0184 | H | H | H | H | H | $CH_2C(=O)CH_3$ | H | H | O | 0 |
| A-0185 | H | H | H | H | H | $CH_2C(=O)CH_2CH_3$ | H | H | O | 0 |
| A-0186 | H | H | H | H | H | $CH_2C(=O)C(CH_3)_3$ | H | H | O | 0 |
| A-0187 | H | H | H | H | H | $CH_2CH_2C(=O)CH_3$ | H | H | O | 0 |
| A-0188 | H | H | H | H | H | $CH_2CH_2C(=O)C(CH_3)_3$ | H | H | O | 0 |
| A-0189 | H | H | H | H | H | $CH_2C(=O)CF_3$ | H | H | O | 0 |
| A-0190 | H | H | H | H | H | $CH_2CH_2C(=O)CF_3$ | H | H | O | 0 |
| A-0191 | H | H | H | H | H | $CH_2C(=O)OCH_3$ | H | H | O | 0 |
| A-0192 | H | H | H | H | H | $CH_2C(=O)OCH_2CH_3$ | H | H | O | 0 |
| A-0193 | H | H | H | H | H | $CH_2C(=O)OC(CH_3)_3$ | H | H | O | 0 |
| A-0194 | H | H | H | H | H | $CH_2CH_2C(=O)OCH_3$ | H | H | O | 0 |
| A-0195 | H | H | H | H | H | $CH_2CH_2C(=O)OCH_2CH_3$ | H | H | O | 0 |
| A-0196 | H | H | H | H | H | $CH_2CH_2C(=O)OC(CH_3)_3$ | H | H | O | 0 |
| A-0197 | H | H | H | H | H | $CH_2C(=O)NH_2$ | H | H | O | 0 |
| A-0198 | H | H | H | H | H | $CH_2CH_2C(=O)NH_2$ | H | H | O | 0 |
| A-0199 | H | H | H | H | H | $CH_2C(=O)NHCH_3$ | H | H | O | 0 |
| A-0200 | H | H | H | H | H | $CH_2C(=O)NHCH(CH_3)_2$ | H | H | O | 0 |
| A-0201 | H | H | H | H | H | $CH_2CH_2C(=O)NHCH_3$ | H | H | O | 0 |
| A-0202 | H | H | H | H | H | $CH_2CH_2C(=O)NHCH(CH_3)_2$ | H | H | O | 0 |
| A-0203 | H | H | H | H | H | $CH_2C(=O)NH(cyclopropyl)$ | H | H | O | 0 |
| A-0204 | H | H | H | H | H | $CH_2C(=O)NHCH_2CHF_2$ | H | H | O | 0 |
| A-0205 | H | H | H | H | H | $CH_2C(=O)NHCH_2CF_3$ | H | H | O | 0 |
| A-0206 | H | H | H | H | H | $CH_2CH_2C(=O)NHCH_2CHF_2$ | H | H | O | 0 |
| A-0207 | H | H | H | H | H | $CH_2CH_2C(=O)NHCH_2CF_3$ | H | H | O | 0 |
| A-0208 | H | H | H | H | H | $CH(CH_3)C(=O)NHCH_2CHF_2$ | H | H | O | 0 |
| A-0209 | H | H | H | H | H | $CH(CH_3)C(=O)NHCH_2CF_3$ | H | H | O | 0 |
| A-0210 | H | H | H | H | H | $C(CH_3)_2C(=O)NHCH_2CHF_2$ | H | H | O | 0 |
| A-0211 | H | H | H | H | H | $C(CH_3)_2C(=O)NHCH_2CF_3$ | H | H | O | 0 |
| A-0212 | H | H | H | H | H | $CH_2C(=O)N(CH_3)_2$ | H | H | O | 0 |
| A-0213 | H | H | H | H | H | $CH_2C(=O)N(CH_2CH_3)_2$ | H | H | O | 0 |

TABLE 4-continued

| Compound | R¹ | R² | R³ | R⁴ | R⁵ | R⁶ | R⁷ | R⁸ | X | n |
|---|---|---|---|---|---|---|---|---|---|---|
| A-0214 | H | H | H | H | H | CH₂CH₂C(=O)N(CH₃)₂ | H | H | O | 0 |
| A-0215 | H | H | H | H | H | CH₂CH₂C(=O)N(CH₂CH₃)₂ | H | H | O | 0 |
| A-0216 | H | H | H | H | H | CH₂CH₂NHC(=O)OCH₃ | H | H | O | 0 |
| A-0217 | H | H | H | H | H | CH₂CH₂NHC(=O)OC(CH₃)₃ | H | H | O | 0 |
| A-0218 | H | H | H | H | H | CH₂CH₂CH₂NHC(=O)OCH₃ | H | H | O | 0 |
| A-0219 | H | H | H | H | H | CH₂CH₂CH₂NHC(=O)OC(CH₃)₃ | H | H | O | 0 |
| A-0220 | H | H | H | H | H | CH₂CH₂NHSO₂CHF₂ | H | H | O | 0 |
| A-0221 | H | H | H | H | H | CH₂CH₂NHSO₂CF₃ | H | H | O | 0 |
| A-0222 | H | H | H | H | H | CH₂CH₂CH₂NHSO₂CHF₂ | H | H | O | 0 |
| A-0223 | H | H | H | H | H | CH₂CH₂CH₂NHSO₂CF₃ | H | H | O | 0 |
| A-0224 | H | H | H | H | H | CH₂CH₂OH | H | H | O | 0 |
| A-0225 | H | H | H | H | H | CH₂CH(OH)CH₃ | H | H | O | 0 |
| A-0226 | H | H | H | H | H | CH₂CH₂CH₂OH | H | H | O | 0 |
| A-0227 | H | H | H | H | H | CH₂CH(OH)CH₂CH₃ | H | H | O | 0 |
| A-0228 | H | H | H | H | H | CH₂CH(OH)C(CH₃)₃ | H | H | O | 0 |
| A-0229 | H | H | H | H | H | CH₂CH₂CH(OH)CH₃ | H | H | O | 0 |
| A-0230 | H | H | H | H | H | CH₂CH₂CH(OH)C(CH₃)₃ | H | H | O | 0 |
| A-0231 | H | H | H | H | H | CH₂C(=NOH)CH₃ | H | H | O | 0 |
| A-0232 | H | H | H | H | H | CH₂C(=NOH)CH₂CH₃ | H | H | O | 0 |
| A-0233 | H | H | H | H | H | CH₂C(=NOH)C(CH₃)₃ | H | H | O | 0 |
| A-0234 | H | H | H | H | H | CH₂C(=NOCH₃)CH₃ | H | H | O | 0 |
| A-0235 | H | H | H | H | H | CH₂C(=NOCH₃)CH₂CH₃ | H | H | O | 0 |
| A-0236 | H | H | H | H | H | CH₂C(=NOCH₂CH₃)CH₃ | H | H | O | 0 |
| A-0237 | H | H | H | H | H | CH₂C(=NOCH₂CH₃)CH₂CH₃ | H | H | O | 0 |
| A-0238 | H | H | H | H | H | CH₂C(=NOCH₂CF₃)CH₃ | H | H | O | 0 |
| A-0239 | H | H | H | H | H | CH₂C(=NOCH₂CF₃)CH₂CH₃ | H | H | O | 0 |

TABLE 5

| Compound | R¹ | R² | R³ | R⁴ | R⁵ | R⁶ | R⁷ | R⁸ | X | n |
|---|---|---|---|---|---|---|---|---|---|---|
| A-0240 | H | H | H | H | H | CH₂Ph | H | H | O | 0 |
| A-0241 | H | H | H | H | H | CH₂(2-F)Ph | H | H | O | 0 |
| A-0242 | H | H | H | H | H | CH₂(3-F)Ph | H | H | O | 0 |
| A-0243 | H | H | H | H | H | CH₂(4-F)Ph | H | H | O | 0 |
| A-0244 | H | H | H | H | H | CH₂(2-Cl)Ph | H | H | O | 0 |
| A-0245 | H | H | H | H | H | CH₂(3-Cl)Ph | H | H | O | 0 |
| A-0246 | H | H | H | H | H | CH₂(4-Cl)Ph | H | H | O | 0 |
| A-0247 | H | H | H | H | H | CH₂(2-CF₃)Ph | H | H | O | 0 |
| A-0248 | H | H | H | H | H | CH₂(3-CF₃)Ph | H | H | O | 0 |
| A-0249 | H | H | H | H | H | CH₂(4-CF₃)Ph | H | H | O | 0 |
| A-0250 | H | H | H | H | H | CH₂(2-F—4-CF₃)Ph | H | H | O | 0 |
| A-0251 | H | H | H | H | H | CH₂(naphthalen-1-yl) | H | H | O | 0 |
| A-0252 | H | H | H | H | H | CH₂(naphthalen-2-yl) | H | H | O | 0 |
| A-0253 | H | H | H | H | H | CH(CH₃)Ph | H | H | O | 0 |
| A-0254 | H | H | H | H | H | CH₂CH₂Ph | H | H | O | 0 |
| A-0255 | H | H | H | H | H | H | CH₃ | H | O | 0 |
| A-0256 | H | H | H | H | H | CH₃ | CH₃ | H | O | 0 |
| A-0257 | H | H | H | H | H | CH₂CH₃ | CH₃ | H | O | 0 |
| A-0258 | H | H | H | H | H | CH(CH₃)2 | CH₃ | H | O | 0 |
| A-0259 | H | H | H | H | H | CH₂CH(CH₃)₂ | CH₃ | H | O | 0 |
| A-0260 | H | H | H | H | H | CH(CH₃)CH₂CH₃ | CH₃ | H | O | 0 |
| A-0261 | H | H | H | H | H | CH₂C(CH₃)₃ | CH₃ | H | O | 0 |
| A-0262 | H | H | H | H | H | CH₂(CH₂)₂CH₃ | CH₃ | H | O | 0 |
| A-0263 | H | H | H | H | H | CH₂(CH₂)₃CH₃ | CH₃ | H | O | 0 |
| A-0264 | H | H | H | H | H | CH₂(CH₂)₄CH₃ | CH₃ | H | O | 0 |
| A-0265 | H | H | H | H | H | CH₂(CH₂)₆CH₃ | CH₃ | H | O | 0 |
| A-0266 | H | H | H | H | H | CH₂OCH₃ | CH₃ | H | O | 0 |
| A-0267 | H | H | H | H | H | CH₂OCH₂CH₃ | CH₃ | H | O | 0 |
| A-0268 | H | H | H | H | H | CH₂CH₂OCH₃ | CH₃ | H | O | 0 |
| A-0269 | H | H | H | H | H | CH₂CH₂OCH₂CH₃ | CH₃ | H | O | 0 |
| A-0270 | H | H | H | H | H | CF₃ | CH₃ | H | O | 0 |
| A-0271 | H | H | H | H | H | CHF₂ | CH₃ | H | O | 0 |
| A-0272 | H | H | H | H | H | CH₂CF₃ | CH₃ | H | O | 0 |
| A-0273 | H | H | H | H | H | CH₂CHF₂ | CH₃ | H | O | 0 |
| A-0274 | H | H | H | H | H | CH₂CClF₂ | CH₃ | H | O | 0 |
| A-0275 | H | H | H | H | H | CH₂CBrF₂ | CH₃ | H | O | 0 |
| A-0276 | H | H | H | H | H | CF₂CF₃ | CH₃ | H | O | 0 |
| A-0277 | H | H | H | H | H | CF₂CHF₂ | CH₃ | H | O | 0 |
| A-0278 | H | H | H | H | H | CH₂CH₂CF₃ | CH₃ | H | O | 0 |
| A-0279 | H | H | H | H | H | CH₂CF₂CF₃ | CH₃ | H | O | 0 |
| A-0280 | H | H | H | H | H | CH₂CF₂CHF₂ | CH₃ | H | O | 0 |
| A-0281 | H | H | H | H | H | CF₂CHFCF₃ | CH₃ | H | O | 0 |
| A-0282 | H | H | H | H | H | CF₂CF₂CF₃ | CH₃ | H | O | 0 |
| A-0283 | H | H | H | H | H | CH₂CF₂CF₂CF₂ | CH₃ | H | O | 0 |

TABLE 5-continued

| Compound | R¹ | R² | R³ | R⁴ | R⁵ | R⁶ | R⁷ | R⁸ | X | n |
|---|---|---|---|---|---|---|---|---|---|---|
| A-0284 | H | H | H | H | H | CH$_2$CF$_2$CHFCF$_3$ | CH$_3$ | H | O | 0 |
| A-0285 | H | H | H | H | H | CH$_2$CH$_2$CH$_2$CF$_3$ | CH$_3$ | H | O | 0 |
| A-0286 | H | H | H | H | H | CH$_2$CH$_2$CF$_2$CF$_3$ | CH$_3$ | H | O | 0 |
| A-0287 | H | H | H | H | H | CF$_2$CF$_2$CF$_2$CF$_3$ | CH$_3$ | H | O | 0 |
| A-0288 | H | H | H | H | H | CH$_2$CH$_2$CH(CF$_3$)$_2$ | CH$_3$ | H | O | 0 |
| A-0289 | H | H | H | H | H | CF$_2$CF$_2$CF$_2$CF$_2$CF$_3$ | CH$_3$ | H | O | 0 |
| A-0290 | H | H | H | H | H | CH$_2$CF$_2$CF$_2$CF$_2$CF$_3$ | CH$_3$ | H | O | 0 |
| A-0291 | H | H | H | H | H | CH$_2$CH$_2$CH$_2$CH$_2$CF$_3$ | CH$_3$ | H | O | 0 |
| A-0292 | H | H | H | H | H | CH$_2$CF$_2$CF$_2$CF$_2$CHF$_2$ | CH$_3$ | H | O | 0 |
| A-0293 | H | H | H | H | H | CH$_2$CF$_2$CF(CF$_3$)CF$_2$C(CF$_3$)$_3$ | CH$_3$ | H | O | 0 |
| A-0294 | H | H | H | H | H | CH$_2$CH=CH$_2$ | CH$_3$ | H | O | 0 |
| A-0295 | H | H | H | H | H | CH$_2$CH=CHCl | CH$_3$ | H | O | 0 |
| A-0296 | H | H | H | H | H | CH$_2$CH=CCl$_2$ | CH$_3$ | H | O | 0 |
| A-0297 | H | H | H | H | H | CH$_2$CH$_2$CF=CF$_2$ | CH$_3$ | H | O | 0 |
| A-0298 | H | H | H | H | H | CH$_2$CH$_2$CH=CF$_2$ | CH$_3$ | H | O | 0 |
| A-0299 | H | H | H | H | H | CH$_2$C≡CH | CH$_3$ | H | O | 0 |
| A-0300 | H | H | H | H | H | CH$_2$C≡CCH$_3$ | CH$_3$ | H | O | 0 |

TABLE 6

| Compound | R¹ | R² | R³ | R⁴ | R⁵ | R⁶ | R⁷ | R⁸ | X | n |
|---|---|---|---|---|---|---|---|---|---|---|
| A-0301 | H | H | H | H | H | CH$_2$C≡CI | CH$_3$ | H | O | 0 |
| A-0302 | H | H | H | H | H | CH$_2$C≡CCF$_3$ | CH$_3$ | H | O | 0 |
| A-0303 | H | H | H | H | H | cyclobutyl | CH$_3$ | H | O | 0 |
| A-0304 | H | H | H | H | H | cyclopentyl | CH$_3$ | H | O | 0 |
| A-0305 | H | H | H | H | H | cyclohexyl | CH$_3$ | H | O | 0 |
| A-0306 | H | H | H | H | H | 4,4-difluorocyclohexyl | CH$_3$ | H | O | 0 |
| A-0307 | H | H | H | H | H | CH$_2$(cyclopropyl) | CH$_3$ | H | O | 0 |
| A-0308 | H | H | H | H | H | CH$_2$(cyclobutyl) | CH$_3$ | H | O | 0 |
| A-0309 | H | H | H | H | H | CH$_2$(cyclopentyl) | CH$_3$ | H | O | 0 |
| A-0310 | H | H | H | H | H | CH$_2$CH$_2$(cyclopropyl) | CH$_3$ | H | O | 0 |
| A-0311 | H | H | H | H | H | CH$_2$(2,2-difluorocyclopropyl) | CH$_3$ | H | O | 0 |
| A-0312 | H | H | H | H | H | CH$_2$(2,2-dichlorocyclopropyl) | CH$_3$ | H | O | 0 |
| A-0313 | H | H | H | H | H | CH$_2$(4,4-difluorocyclohexyl) | CH$_3$ | H | O | 0 |
| A-0314 | H | H | H | H | H | CH$_2$CH$_2$(2,2-difluorocyclopropyl) | CH$_3$ | H | O | 0 |
| A-0315 | H | H | H | H | H | CH$_2$CH$_2$(2,2-dichlorocyclopropyl) | CH$_3$ | H | O | 0 |
| A-0316 | H | H | H | H | H | CH$_2$SCH$_3$ | CH$_3$ | H | O | 0 |
| A-0317 | H | H | H | H | H | CH$_2$SCH$_2$CH$_3$ | CH$_3$ | H | O | 0 |
| A-0318 | H | H | H | H | H | CH$_2$CH$_2$SCH$_3$ | CH$_3$ | H | O | 0 |
| A-0319 | H | H | H | H | H | CH$_2$CH$_2$SCH$_2$CH$_3$ | CH$_3$ | H | O | 0 |
| A-0320 | H | H | H | H | H | CH$_2$CH$_2$CH$_2$SCH$_3$ | CH$_3$ | H | O | 0 |
| A-0321 | H | H | H | H | H | CH$_2$CH$_2$CH$_2$SCH$_2$CH$_3$ | CH$_3$ | H | O | 0 |
| A-0322 | H | H | H | H | H | CH(CH$_3$)SCH$_3$ | CH$_3$ | H | O | 0 |
| A-0323 | H | H | H | H | H | CH(CH$_3$)SCH$_2$CH$_3$ | CH$_3$ | H | O | 0 |
| A-0324 | H | H | H | H | H | CH$_2$CH(CH$_3$)SCH$_3$ | CH$_3$ | H | O | 0 |
| A-0325 | H | H | H | H | H | CH$_2$CH(CH$_3$)SCH$_2$CH$_3$ | CH$_3$ | H | O | 0 |
| A-0326 | H | H | H | H | H | CH(CH$_3$)CH$_2$CH$_2$SCH$_3$ | CH$_3$ | H | O | 0 |
| A-0327 | H | H | H | H | H | CH(CH$_3$)CH$_2$CH$_2$SCH$_2$CH$_3$ | CH$_3$ | H | O | 0 |
| A-0328 | H | H | H | H | H | CH(CH$_3$)CH$_2$SCH$_3$ | CH$_3$ | H | O | 0 |
| A-0329 | H | H | H | H | H | CH$_2$CH(CH$_3$)CH$_2$SCH$_2$CH$_3$ | CH$_3$ | H | O | 0 |
| A-0330 | H | H | H | H | H | CH$_2$CH$_2$CH(CH$_3$)SCH$_3$ | CH$_3$ | H | O | 0 |
| A-0331 | H | H | H | H | H | CH$_2$CH$_2$CH(CH$_3$)SCH$_3$CH$_3$ | CH$_3$ | H | O | 0 |
| A-0332 | H | H | H | H | H | CH$_2$SOCH$_3$ | CH$_3$ | H | O | 0 |
| A-0333 | H | H | H | H | H | CH$_2$CH$_2$SOCH$_3$ | CH$_3$ | H | O | 0 |
| A-0334 | H | H | H | H | H | CH$_2$CH$_2$CH$_2$SOCH$_3$ | CH$_3$ | H | O | 0 |
| A-0335 | H | H | H | H | H | CH(CH$_3$)SOCH$_3$ | CH$_3$ | H | O | 0 |
| A-0336 | H | H | H | H | H | CH$_2$CH(CH$_3$)SOCH$_3$ | CH$_3$ | H | O | 0 |
| A-0337 | H | H | H | H | H | CH(CH$_3$)CH$_2$CH$_2$SOCH$_3$ | CH$_3$ | H | O | 0 |
| A-0338 | H | H | H | H | H | CH(CH$_3$)CH$_2$SOCH$_3$ | CH$_3$ | H | O | 0 |
| A-0339 | H | H | H | H | H | CH$_2$CH$_2$CH(CH$_3$)SOCH$_3$ | CH$_3$ | H | O | 0 |
| A-0340 | H | H | H | H | H | CH$_2$SO$_2$CH$_3$ | CH$_3$ | H | O | 0 |
| A-0341 | H | H | H | H | H | CH$_2$CH$_2$SO$_2$CH$_3$ | CH$_3$ | H | O | 0 |
| A-0342 | H | H | H | H | H | CH$_2$CH$_2$CH$_2$SO$_2$CH$_3$ | CH$_3$ | H | O | 0 |
| A-0343 | H | H | H | H | H | CH(CH$_3$)SO$_2$CH$_3$ | CH$_3$ | H | O | 0 |
| A-0344 | H | H | H | H | H | CH$_2$CH(CH$_3$)SO$_2$CH$_3$ | CH$_3$ | H | O | 0 |
| A-0345 | H | H | H | H | H | CH(CH$_3$)CH$_2$CH$_2$SO$_2$CH$_3$ | CH$_3$ | H | O | 0 |
| A-0346 | H | H | H | H | H | CH(CH$_3$)CH$_2$SO$_2$CH$_3$ | CH$_3$ | H | O | 0 |
| A-0347 | H | H | H | H | H | CH$_2$CH$_2$CH(CH$_3$)SO$_2$CH$_3$ | CH$_3$ | H | O | 0 |
| A-0348 | H | H | H | H | H | CH$_2$SCF$_3$ | CH$_3$ | H | O | 0 |
| A-0349 | H | H | H | H | H | CH$_2$SCHF$_2$ | CH$_3$ | H | O | 0 |
| A-0350 | H | H | H | H | H | CH$_2$SCH$_2$CF$_3$ | CH$_3$ | H | O | 0 |
| A-0351 | H | H | H | H | H | CH$_2$SCH$_2$CHF$_2$ | CH$_3$ | H | O | 0 |
| A-0352 | H | H | H | H | H | CH$_2$SCF$_2$CF$_3$ | CH$_3$ | H | O | 0 |
| A-0353 | H | H | H | H | H | CH$_2$CH$_2$SCF$_3$ | CH$_3$ | H | O | 0 |

TABLE 6-continued

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-0354 | H | H | H | H | H | $CH_2CH_2SCH_2CF_3$ | $CH_3$ | H | O | 0 |
| A-0355 | H | H | H | H | H | $CH_2CH_2CH_2SCF_3$ | $CH_3$ | H | O | 0 |
| A-0356 | H | H | H | H | H | $CH_2CH_2CH_2SCH_2CF_3$ | $CH_3$ | H | O | 0 |
| A-0357 | H | H | H | H | H | $CH(CH_3)SCF_3$ | $CH_3$ | H | O | 0 |
| A-0358 | H | H | H | H | H | $CH(CH_3)SCH_2CF_3$ | $CH_3$ | H | O | 0 |
| A-0359 | H | H | H | H | H | $CH_2CH(CH_3)SCF_3$ | $CH_3$ | H | O | 0 |
| A-0360 | H | H | H | H | H | $CH_2CH(CH_3)SCH_2CF_3$ | $CH_3$ | H | O | 0 |
| A-0361 | H | H | H | H | H | $CH(CH_3)CH_2CH_2SCF_3$ | $CH_3$ | H | O | 0 |

TABLE 7

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-0362 | H | H | H | H | H | $CH(CH_3)CH_2CH_2SCH_2CF_3$ | $CH_3$ | H | O | 0 |
| A-0363 | H | H | H | H | H | $CH_2CH(CH_3)CH_2SCF_3$ | $CH_3$ | H | O | 0 |
| A-0364 | H | H | H | H | H | $CH_2CH(CH_3)CH_2SCH_2CF_3$ | $CH_3$ | H | O | 0 |
| A-0365 | H | H | H | H | H | $CH_2CH_2CH(CH_3)SCF_3$ | $CH_3$ | H | O | 0 |
| A-0366 | H | H | H | H | H | $CH_2CH_2CH(CH_3)SCH_2CF_3$ | $CH_3$ | H | O | 0 |
| A-0367 | H | H | H | H | H | $CH_2SOCF_3$ | $CH_3$ | H | O | 0 |
| A-0368 | H | H | H | H | H | $CH_2CH_2SOCF_3$ | $CH_3$ | H | O | 0 |
| A-0369 | H | H | H | H | H | $CH_2CH_2CH_2SOCF_3$ | $CH_3$ | H | O | 0 |
| A-0370 | H | H | H | H | H | $CH(CH_3)SOCF_3$ | $CH_3$ | H | O | 0 |
| A-0371 | H | H | H | H | H | $CH_2CH(CH_3)SOCF_3$ | $CH_3$ | H | O | 0 |
| A-0372 | H | H | H | H | H | $CH(CH_3)CH_2CH_2SOCF_3$ | $CH_3$ | H | O | 0 |
| A-0373 | H | H | H | H | H | $CH(CH_3)CH_2SOCF_3$ | $CH_3$ | H | O | 0 |
| A-0374 | H | H | H | H | H | $CH_2CH_2CH(CH_3)SOCF_3$ | $CH_3$ | H | O | 0 |
| A-0375 | H | H | H | H | H | $CH_2SO_2CF_3$ | $CH_3$ | H | O | 0 |
| A-0376 | H | H | H | H | H | $CH_2CH_2SO_2CF_3$ | $CH_3$ | H | O | 0 |
| A-0377 | H | H | H | H | H | $CH_2CH_2CH_2SO_2CF_3$ | $CH_3$ | H | O | 0 |
| A-0378 | H | H | H | H | H | $CH(CH_3)SO_2CF_3$ | $CH_3$ | H | O | 0 |
| A-0379 | H | H | H | H | H | $CH_2CH(CH_3)SO_2CF_3$ | $CH_3$ | H | O | 0 |
| A-0380 | H | H | H | H | H | $CH(CH_3)CH_2CH_2SO_2CF_3$ | $CH_3$ | H | O | 0 |
| A-0381 | H | H | H | H | H | $CH(CH_3)CH_2SO_2CF_3$ | $CH_3$ | H | O | 0 |
| A-0382 | H | H | H | H | H | $CH_2CH_2CH(CH_3)SO_2CF_3$ | $CH_3$ | H | O | 0 |
| A-0383 | H | H | H | H | H | $CH_2C(=O)CH_3$ | $CH_3$ | H | O | 0 |
| A-0384 | H | H | H | H | H | $CH_2C(=O)CH_2CH_3$ | $CH_3$ | H | O | 0 |
| A-0385 | H | H | H | H | H | $CH_2C(=O)C(CH_3)_3$ | $CH_3$ | H | O | 0 |
| A-0386 | H | H | H | H | H | $CH_2CH_2C(=O)CH_3$ | $CH_3$ | H | O | 0 |
| A-0387 | H | H | H | H | H | $CH_2CH_2C(=O)C(CH_3)_3$ | $CH_3$ | H | O | 0 |
| A-0388 | H | H | H | H | H | $CH_2C(=O)CF_3$ | $CH_3$ | H | O | 0 |
| A-0389 | H | H | H | H | H | $CH_2CH_2C(=O)CF_3$ | $CH_3$ | H | O | 0 |
| A-0390 | H | H | H | H | H | $CH_2C(=O)OCH_3$ | $CH_3$ | H | O | 0 |
| A-0391 | H | H | H | H | H | $CH_2C(=O)OCH_2CH_3$ | $CH_3$ | H | O | 0 |
| A-0392 | H | H | H | H | H | $CH_2C(=O)OC(CH_3)_3$ | $CH_3$ | H | O | 0 |
| A-0393 | H | H | H | H | H | $CH_2CH_2C(=O)OCH_3$ | $CH_3$ | H | O | 0 |
| A-0394 | H | H | H | H | H | $CH_2CH_2C(=O)OCH_2CH_3$ | $CH_3$ | H | O | 0 |
| A-0395 | H | H | H | H | H | $CH_2CH_2C(=O)OC(CH_3)_3$ | $CH_3$ | H | O | 0 |
| A-0396 | H | H | H | H | H | $CH_2C(=O)NH_2$ | $CH_3$ | H | O | 0 |
| A-0397 | H | H | H | H | H | $CH_2CH_2C(=O)NH_2$ | $CH_3$ | H | O | 0 |
| A-0398 | H | H | H | H | H | $CH_2C(=O)NCH_3$ | $CH_3$ | H | O | 0 |
| A-0399 | H | H | H | H | H | $CH_2C(=O)NHCH(CH_3)_2$ | $CH_3$ | H | O | 0 |
| A-0400 | H | H | H | H | H | $CH_2CH_2C(=O)NHCH_3$ | $CH_3$ | H | O | 0 |
| A-0401 | H | H | H | H | H | $CH_2CH_2C(=O)NHCH(CH_3)_2$ | $CH_3$ | H | O | 0 |
| A-0402 | H | H | H | H | H | $CH_2C(=O)NHCH_2CHF_2$ | $CH_3$ | H | O | 0 |
| A-0403 | H | H | H | H | H | $CH_2C(=O)NHCH_2CF_3$ | $CH_3$ | H | O | 0 |
| A-0404 | H | H | H | H | H | $CH_2CH_2C(=O)NHCH_2CHF_2$ | $CH_3$ | H | O | 0 |
| A-0405 | H | H | H | H | H | $CH_2CH_2C(=O)NHCH_2CF_3$ | $CH_3$ | H | O | 0 |
| A-0406 | H | H | H | H | H | $CH_2C(=O)N(CH_3)_2$ | $CH_3$ | H | O | 0 |
| A-0407 | H | H | H | H | H | $CH_2C(=O)N(CH_2CH_3)_2$ | $CH_3$ | H | O | 0 |
| A-0408 | H | H | H | H | H | $CH_2CH_2C(=O)N(CH_3)_2$ | $CH_3$ | H | O | 0 |
| A-0409 | H | H | H | H | H | $CH_2CH_2C(=O)N(CH_2CH_3)_2$ | $CH_3$ | H | O | 0 |
| A-0410 | H | H | H | H | H | $CH_2CH_2OH$ | $CH_3$ | H | O | 0 |
| A-0411 | H | H | H | H | H | $CH_2CH(OH)CH_3$ | $CH_3$ | H | O | 0 |
| A-0412 | H | H | H | H | H | $CH_2CH_2CH_2OH$ | $CH_3$ | H | O | 0 |
| A-0413 | H | H | H | H | H | $CH_2CH(OH)CH_2CH_3$ | $CH_3$ | H | O | 0 |
| A-0414 | H | H | H | H | H | $CH_2CH(OH)C(CH_3)_3$ | $CH_3$ | H | O | 0 |
| A-0415 | H | H | H | H | H | $CH_2CH_2CH(OH)CH_3$ | $CH_3$ | H | O | 0 |
| A-0416 | H | H | H | H | H | $CH_2CH_2CH(OH)C(CH_3)_3$ | $CH_3$ | H | O | 0 |
| A-0417 | H | H | H | H | H | $CH_2C(=NOH)CH_3$ | $CH_3$ | H | O | 0 |
| A-0418 | H | H | H | H | H | $CH_2C(=NOH)CH_2CH_3$ | $CH_3$ | H | O | 0 |
| A-0419 | H | H | H | H | H | $CH_2C(=NOH)C(CH_3)_3$ | $CH_3$ | H | O | 0 |
| A-0420 | H | H | H | H | H | $CH_2C(=NOCH_3)CH_3$ | $CH_3$ | H | O | 0 |
| A-0421 | H | H | H | H | H | $CH_2C(=NOCH_3)CH_2CH_3$ | $CH_3$ | H | O | 0 |
| A-0422 | H | H | H | H | H | $CH_2C(=NOCH_2CH_3)CH_3$ | $CH_3$ | H | O | 0 |

TABLE 8

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-0423 | H | H | H | H | H | CH$_2$C(=NOCH$_2$CH$_3$)CH$_2$CH$_3$ | CH$_3$ | H | O | 0 |
| A-0424 | H | H | H | H | H | CH$_2$C(=NOCH$_2$CF$_3$)CH$_3$ | CH$_3$ | H | O | 0 |
| A-0425 | H | H | H | H | H | CH$_2$C(=NOCH$_2$CF$_3$)CH$_2$CH$_3$ | CH$_3$ | H | O | 0 |
| A-0426 | H | H | H | H | H | CH$_2$Ph | CH$_3$ | H | O | 0 |
| A-0427 | H | H | H | H | H | CH$_2$(2-F)Ph | CH$_3$ | H | O | 0 |
| A-0428 | H | H | H | H | H | CH$_2$(3-F)Ph | CH$_3$ | H | O | 0 |
| A-0429 | H | H | H | H | H | CH$_2$(4-F)Ph | CH$_3$ | H | O | 0 |
| A-0430 | H | H | H | H | H | CH$_2$(2-Cl)Ph | CH$_3$ | H | O | 0 |
| A-0431 | H | H | H | H | H | CH$_2$(3-Cl)Ph | CH$_3$ | H | O | 0 |
| A-0432 | H | H | H | H | H | CH$_2$(4-Cl)Ph | CH$_3$ | H | O | 0 |
| A-0433 | H | H | H | H | H | CH$_2$(2-CF$_3$)Ph | CH$_3$ | H | O | 0 |
| A-0434 | H | H | H | H | H | CH$_2$(3-CF$_3$)Ph | CH$_3$ | H | O | 0 |
| A-0435 | H | H | H | H | H | CH$_2$(4-CF$_3$)Ph | CH$_3$ | H | O | 0 |
| A-0436 | H | H | H | H | H | CH$_2$(naphthalen-1-yl) | CH$_3$ | H | O | 0 |
| A-0437 | H | H | H | H | H | CH$_2$(naphthalen-2-yl) | CH$_3$ | H | O | 0 |
| A-0438 | H | H | H | H | H | CH$_2$CH$_2$Ph | CH$_3$ | H | O | 0 |
| A-0439 | H | H | H | H | H | H | CH$_2$CH$_3$ | H | O | 0 |
| A-0440 | H | H | H | H | H | CH$_3$ | CH$_2$CH$_3$ | H | O | 0 |
| A-0441 | H | H | H | H | H | CH$_2$CH$_3$ | CH$_2$CH$_3$ | H | O | 0 |
| A-0442 | H | H | H | H | H | CH(CH$_3$)$_2$ | CH$_2$CH$_3$ | H | O | 0 |
| A-0443 | H | H | H | H | H | CH$_2$CH$_2$CH$_3$ | CH$_2$CH$_3$ | H | O | 0 |
| A-0444 | H | H | H | H | H | CH$_2$CH(CH$_3$)$_2$ | CH$_2$CH$_3$ | H | O | 0 |
| A-0445 | H | H | H | H | H | CH(CH$_3$)CH$_2$CH$_3$ | CH$_2$CH$_3$ | H | O | 0 |
| A-0446 | H | H | H | H | H | CH$_2$C(CH$_3$)$_3$ | CH$_2$CH$_3$ | H | O | 0 |
| A-0447 | H | H | H | H | H | CH$_2$(CH$_2$)$_2$CH$_3$ | CH$_2$CH$_3$ | H | O | 0 |
| A-0448 | H | H | H | H | H | CH$_2$(CH$_2$)$_3$CH$_3$ | CH$_2$CH$_3$ | H | O | 0 |
| A-0449 | H | H | H | H | H | CH$_2$(CH$_2$)$_4$CH$_3$ | CH$_2$CH$_3$ | H | O | 0 |
| A-0450 | H | H | H | H | H | CH$_2$(CH$_2$)$_6$CH$_3$ | CH$_2$CH$_3$ | H | O | 0 |
| A-0451 | H | H | H | H | H | CH$_2$OCH$_3$ | CH$_2$CH$_3$ | H | O | 0 |
| A-0452 | H | H | H | H | H | CH$_2$OCH$_2$CH$_3$ | CH$_2$CH$_3$ | H | O | 0 |
| A-0453 | H | H | H | H | H | CH$_2$CH$_2$OCH$_3$ | CH$_2$CH$_3$ | H | O | 0 |
| A-0454 | H | H | H | H | H | CH$_2$CH$_2$OCH$_2$CH$_3$ | CH$_2$CH$_3$ | H | O | 0 |
| A-0455 | H | H | H | H | H | CF$_3$ | CH$_2$CH$_3$ | H | O | 0 |
| A-0456 | H | H | H | H | H | CHF$_2$ | CH$_2$CH$_3$ | H | O | 0 |
| A-0457 | H | H | H | H | H | CH$_2$CF$_3$ | CH$_2$CH$_3$ | H | O | 0 |
| A-0458 | H | H | H | H | H | CH$_2$CHF$_2$ | CH$_2$CH$_3$ | H | O | 0 |
| A-0459 | H | H | H | H | H | CH$_2$CClF$_2$ | CH$_2$CH$_3$ | H | O | 0 |
| A-0460 | H | H | H | H | H | CH$_2$CBrF$_2$ | CH$_2$CH$_3$ | H | O | 0 |
| A-0461 | H | H | H | H | H | CF$_2$CF$_3$ | CH$_2$CH$_3$ | H | O | 0 |
| A-0462 | H | H | H | H | H | CF$_2$CHF$_2$ | CH$_2$CH$_3$ | H | O | 0 |
| A-0463 | H | H | H | H | H | CH$_2$CH$_2$CF$_3$ | CH$_2$CH$_3$ | H | O | 0 |
| A-0464 | H | H | H | H | H | CH$_2$CF$_2$CF$_3$ | CH$_2$CH$_3$ | H | O | 0 |
| A-0465 | H | H | H | H | H | CH$_2$CF$_2$CHF$_2$ | CH$_2$CH$_3$ | H | O | 0 |
| A-0466 | H | H | H | H | H | CF$_2$CHFCF$_3$ | CH$_2$CH$_3$ | H | O | 0 |
| A-0467 | H | H | H | H | H | CF$_2$CF$_2$CF$_3$ | CH$_2$CH$_3$ | H | O | 0 |
| A-0468 | H | H | H | H | H | CH$_2$CF$_2$CF$_2$CF$_3$ | CH$_2$CH$_3$ | H | O | 0 |
| A-0469 | H | H | H | H | H | CH$_2$CF$_2$CHFCF$_3$ | CH$_2$CH$_3$ | H | O | 0 |
| A-0470 | H | H | H | H | H | CH$_2$CH$_2$CH$_2$CF$_3$ | CH$_2$CH$_3$ | H | O | 0 |
| A-0471 | H | H | H | H | H | CH$_2$CH$_2$CF$_2$CF$_3$ | CH$_2$CH$_3$ | H | O | 0 |
| A-0472 | H | H | H | H | H | CF$_2$CF$_2$CF$_2$CF$_3$ | CH$_2$CH$_3$ | H | O | 0 |
| A-0473 | H | H | H | H | H | CH$_2$CH$_2$CH(CF$_3$)$_2$ | CH$_2$CH$_3$ | H | O | 0 |
| A-0474 | H | H | H | H | H | CF$_2$CF$_2$CF$_2$CF$_2$CF$_3$ | CH$_2$CH$_3$ | H | O | 0 |
| A-0475 | H | H | H | H | H | CH$_2$CF$_2$CF$_2$CF$_2$CF$_3$ | CH$_2$CH$_3$ | H | O | 0 |
| A-0476 | H | H | H | H | H | CH$_2$CH$_2$CH$_2$CH$_2$CF$_3$ | CH$_2$CH$_3$ | H | O | 0 |
| A-0477 | H | H | H | H | H | CH$_2$CF$_2$CF$_2$CF$_2$CHF$_2$ | CH$_2$CH$_3$ | H | O | 0 |
| A-0478 | H | H | H | H | H | CH$_2$CF$_2$CF(CF$_3$)CF$_2$C(CF$_3$)$_3$ | CH$_2$CH$_3$ | H | O | 0 |
| A-0479 | H | H | H | H | H | CF$_2$CHFOCH$_3$ | CH$_2$CH$_3$ | H | O | 0 |
| A-0480 | H | H | H | H | H | CF$_2$CHFOCH$_2$CH$_3$ | CH$_2$CH$_3$ | H | O | 0 |
| A-0481 | H | H | H | H | H | CH$_2$CH$_2$OCH$_2$CF$_3$ | CH$_2$CH$_3$ | H | O | 0 |
| A-0482 | H | H | H | H | H | CF$_2$CHFOCF$_3$ | CH$_2$CH$_3$ | H | O | 0 |
| A-0483 | H | H | H | H | H | CF$_2$CHFOCF$_2$CF$_3$ | CH$_2$CH$_3$ | H | O | 0 |

TABLE 9

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-0484 | H | H | H | H | H | CF$_2$CHFOCF$_2$CF$_2$CF$_3$ | CH$_2$CH$_3$ | H | O | 0 |
| A-0485 | H | H | H | H | H | CH$_2$CH=CH$_2$ | CH$_2$CH$_3$ | H | O | 0 |
| A-0486 | H | H | H | H | H | CH$_2$CH=CHCl | CH$_2$CH$_3$ | H | O | 0 |
| A-0487 | H | H | H | H | H | CH$_2$CH=CCl$_2$ | CH$_2$CH$_3$ | H | O | 0 |
| A-0488 | H | H | H | H | H | CH$_2$CH$_2$CF=CF$_2$ | CH$_2$CH$_3$ | H | O | 0 |
| A-0489 | H | H | H | H | H | CH$_2$CH$_2$CH=CF$_2$ | CH$_2$CH$_3$ | H | O | 0 |
| A-0490 | H | H | H | H | H | CH$_2$C≡CH | CH$_2$CH$_3$ | H | O | 0 |
| A-0491 | H | H | H | H | H | CH$_2$C≡CCH$_3$ | CH$_2$CH$_3$ | H | O | 0 |
| A-0492 | H | H | H | H | H | CH$_2$C≡CI | CH$_2$CH$_3$ | H | O | 0 |

TABLE 9-continued

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-0493 | H | H | H | H | H | CH$_2$C≡CCF$_3$ | CH$_2$CH$_3$ | H | O | 0 |
| A-0494 | H | H | H | H | H | cyclobutyl | CH$_2$CH$_3$ | H | O | 0 |
| A-0495 | H | H | H | H | H | cyclopentyl | CH$_2$CH$_3$ | H | O | 0 |
| A-0496 | H | H | H | H | H | cyclohexyl | CH$_2$CH$_3$ | H | O | 0 |
| A-0497 | H | H | H | H | H | 4,4-difluorocyclohexyl | CH$_2$CH$_3$ | H | O | 0 |
| A-0498 | H | H | H | H | H | CH$_2$(cyclopropyl) | CH$_2$CH$_3$ | H | O | 0 |
| A-0499 | H | H | H | H | H | CH$_2$(cyclobutyl) | CH$_2$CH$_3$ | H | O | 0 |
| A-0500 | H | H | H | H | H | CH$_2$(cyclopentyl) | CH$_2$CH$_3$ | H | O | 0 |
| A-0501 | H | H | H | H | H | CH$_2$CH$_2$(cyclopropyl) | CH$_2$CH$_3$ | H | O | 0 |
| A-0502 | H | H | H | H | H | CH$_2$(2,2-difluorocyclopropyl) | CH$_2$CH$_3$ | H | O | 0 |
| A-0503 | H | H | H | H | H | CH$_2$(2,2-dichlorocyclopropyl) | CH$_2$CH$_3$ | H | O | 0 |
| A-0504 | H | H | H | H | H | CH$_2$(4,4-difluorocyclohexyl) | CH$_2$CH$_3$ | H | O | 0 |
| A-0505 | H | H | H | H | H | CH$_2$CH$_2$(2,2-difluorocyclopropyl) | CH$_2$CH$_3$ | H | O | 0 |
| A-0506 | H | H | H | H | H | CH$_2$CH$_2$(2,2-dichlorocyclopropyl) | CH$_2$CH$_3$ | H | O | 0 |
| A-0507 | H | H | H | H | H | CH$_2$SCH$_3$ | CH$_2$CH$_3$ | H | O | 0 |
| A-0508 | H | H | H | H | H | CH$_2$SCH$_2$CH$_3$ | CH$_2$CH$_3$ | H | O | 0 |
| A-0509 | H | H | H | H | H | CH$_2$CH$_2$SCH$_3$ | CH$_2$CH$_3$ | H | O | 0 |
| A-0510 | H | H | H | H | H | CH$_2$CH$_2$SCH$_2$CH$_3$ | CH$_2$CH$_3$ | H | O | 0 |
| A-0511 | H | H | H | H | H | CH$_2$CH$_2$CH$_2$SCH$_3$ | CH$_2$CH$_3$ | H | O | 0 |
| A-0512 | H | H | H | H | H | CH$_2$CH$_2$CH$_2$SCH$_2$CH$_3$ | CH$_2$CH$_3$ | H | O | 0 |
| A-0513 | H | H | H | H | H | CH(CH$_3$)SCH$_3$ | CH$_2$CH$_3$ | H | O | 0 |
| A-0514 | H | H | H | H | H | CH(CH$_3$)SCH$_2$CH$_3$ | CH$_2$CH$_3$ | H | O | 0 |
| A-0515 | H | H | H | H | H | CH$_2$CH(CH$_3$)SCH$_3$ | CH$_2$CH$_3$ | H | O | 0 |
| A-0516 | H | H | H | H | H | CH$_2$CH(CH$_3$)SCH$_2$CH$_3$ | CH$_2$CH$_3$ | H | O | 0 |
| A-0517 | H | H | H | H | H | CH(CH$_3$)CH$_2$CH$_2$SCH$_3$ | CH$_2$CH$_3$ | H | O | 0 |
| A-0518 | H | H | H | H | H | CH(CH$_3$)CH$_2$CH$_2$SCH$_2$CH$_3$ | CH$_2$CH$_3$ | H | O | 0 |
| A-0519 | H | H | H | H | H | CH(CH$_3$)CH$_2$SCH$_3$ | CH$_2$CH$_3$ | H | O | 0 |
| A-0520 | H | H | H | H | H | CH(CH$_3$)CH$_2$SCH$_2$CH$_3$ | CH$_2$CH$_3$ | H | O | 0 |
| A-0521 | H | H | H | H | H | CH$_2$CH$_2$CH(CH$_3$)SCH$_3$ | CH$_2$CH$_3$ | H | O | 0 |
| A-0522 | H | H | H | H | H | CH$_2$CH$_2$CH(CH$_3$)SCH$_2$CH$_3$ | CH$_2$CH$_3$ | H | O | 0 |
| A-0523 | H | H | H | H | H | CH$_2$SOCH$_3$ | CH$_2$CH$_3$ | H | O | 0 |
| A-0524 | H | H | H | H | H | CH$_2$CH$_2$SOCH$_3$ | CH$_2$CH$_3$ | H | O | 0 |
| A-0525 | H | H | H | H | H | CH$_2$CH$_2$CH$_2$SOCH$_3$ | CH$_2$CH$_3$ | H | O | 0 |
| A-0526 | H | H | H | H | H | CH(CH$_3$)SOCH$_3$ | CH$_2$CH$_3$ | H | O | 0 |
| A-0527 | H | H | H | H | H | CH$_2$CH(CH$_3$)SOCH$_3$ | CH$_2$CH$_3$ | H | O | 0 |
| A-0528 | H | H | H | H | H | CH(CH$_3$)CH$_2$CH$_2$SOCH$_3$ | CH$_2$CH$_3$ | H | O | 0 |
| A-0529 | H | H | H | H | H | CH(CH$_3$)CH$_2$SOCH$_3$ | CH$_2$CH$_3$ | H | O | 0 |
| A-0530 | H | H | H | H | H | CH$_2$CH$_2$CH(CH$_3$)SOCH$_3$ | CH$_2$CH$_3$ | H | O | 0 |
| A-0531 | H | H | H | H | H | CH$_2$SO$_2$CH$_3$ | CH$_2$CH$_3$ | H | O | 0 |
| A-0532 | H | H | H | H | H | CH$_2$CH$_2$SO$_2$CH$_3$ | CH$_2$CH$_3$ | H | O | 0 |
| A-0533 | H | H | H | H | H | CH$_2$CH$_2$CH$_2$SO$_2$CH$_3$ | CH$_2$CH$_3$ | H | O | 0 |
| A-0534 | H | H | H | H | H | CH(CH$_3$)SO$_2$CH$_3$ | CH$_2$CH$_3$ | H | O | 0 |
| A-0535 | H | H | H | H | H | CH$_2$CH(CH$_3$)SO$_2$CH$_3$ | CH$_2$CH$_3$ | H | O | 0 |
| A-0536 | H | H | H | H | H | CH(CH$_3$)CH$_2$CH$_2$SO$_2$CH$_3$ | CH$_2$CH$_3$ | H | O | 0 |
| A-0537 | H | H | H | H | H | CH(CH$_3$)CH$_2$SO$_2$CH$_3$ | CH$_2$CH$_3$ | H | O | 0 |
| A-0538 | H | H | H | H | H | CH$_2$CH$_2$CH(CH$_3$)SO$_2$CH$_3$ | CH$_2$CH$_3$ | H | O | 0 |
| A-0539 | H | H | H | H | H | CH$_2$SCF$_3$ | CH$_2$CH$_3$ | H | O | 0 |
| A-0540 | H | H | H | H | H | CH$_2$SCHF$_2$ | CH$_2$CH$_3$ | H | O | 0 |
| A-0541 | H | H | H | H | H | CH$_2$SCH$_2$CF$_3$ | CH$_2$CH$_3$ | H | O | 0 |
| A-0542 | H | H | H | H | H | CH$_2$SCH$_2$CHF$_2$ | CH$_2$CH$_3$ | H | O | 0 |
| A-0543 | H | H | H | H | H | CH$_2$SCF$_2$CF$_3$ | CH$_2$CH$_3$ | H | O | 0 |
| A-0544 | H | H | H | H | H | CH$_2$CH$_2$SCF$_3$ | CH$_2$CH$_3$ | H | O | 0 |

TABLE 10

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-0545 | H | H | H | H | H | CH$_2$CH$_2$SCH$_2$CF$_3$ | CH$_2$CH$_3$ | H | O | 0 |
| A-0546 | H | H | H | H | H | CH$_2$CH$_2$CH$_2$SCF$_3$ | CH$_2$CH$_3$ | H | O | 0 |
| A-0547 | H | H | H | H | H | CH$_2$CH$_2$CH$_2$SCH$_2$CF$_3$ | CH$_2$CH$_3$ | H | O | 0 |
| A-0548 | H | H | H | H | H | CH(CH$_3$)SCF$_3$ | CH$_2$CH$_3$ | H | O | 0 |
| A-0549 | H | H | H | H | H | CH(CH$_3$)SCH$_2$CF$_3$ | CH$_2$CH$_3$ | H | O | 0 |
| A-0550 | H | H | H | H | H | CH$_2$CH(CH$_3$)SCF$_3$ | CH$_2$CH$_3$ | H | O | 0 |
| A-0551 | H | H | H | H | H | CH$_2$CH(CH$_3$)SCH$_2$CF$_3$ | CH$_2$CH$_3$ | H | O | 0 |
| A-0552 | H | H | H | H | H | CH(CH$_3$)CH$_2$CH$_2$SCF$_3$ | CH$_2$CH$_3$ | H | O | 0 |
| A-0553 | H | H | H | H | H | CH(CH$_3$)CH$_2$CH$_2$SCH$_2$CF$_3$ | CH$_2$CH$_3$ | H | O | 0 |
| A-0554 | H | H | H | H | H | CH(CH$_3$)CH$_2$SCF$_3$ | CH$_2$CH$_3$ | H | O | 0 |
| A-0555 | H | H | H | H | H | CH(CH$_3$)CH$_2$SCH$_2$CF$_3$ | CH$_2$CH$_3$ | H | O | 0 |
| A-0556 | H | H | H | H | H | CH$_2$CH$_2$CH(CH$_3$)SCF$_3$ | CH$_2$CH$_3$ | H | O | 0 |
| A-0557 | H | H | H | H | H | CH$_2$CH$_2$CH(CH$_3$)SCH$_2$CF$_3$ | CH$_2$CH$_3$ | H | O | 0 |
| A-0558 | H | H | H | H | H | CH$_2$SOCF$_3$ | CH$_2$CH$_3$ | H | O | 0 |
| A-0559 | H | H | H | H | H | CH$_2$CH$_2$SOCF$_3$ | CH$_2$CH$_3$ | H | O | 0 |
| A-0560 | H | H | H | H | H | CH$_2$CH$_2$CH$_2$SOCF$_3$ | CH$_2$CH$_3$ | H | O | 0 |
| A-0561 | H | H | H | H | H | CH(CH$_3$)SOCF$_3$ | CH$_2$CH$_3$ | H | O | 0 |
| A-0562 | H | H | H | H | H | CH$_2$CH(CH$_3$)SOCF$_3$ | CH$_2$CH$_3$ | H | O | 0 |

TABLE 10-continued

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-0563 | H | H | H | H | H | CH(CH$_3$)CH$_2$CH$_2$SOCF$_3$ | CH$_2$CH$_3$ | H | O | 0 |
| A-0564 | H | H | H | H | H | CH$_2$CH(CH$_3$)CH$_2$SOCF$_3$ | CH$_2$CH$_3$ | H | O | 0 |
| A-0565 | H | H | H | H | H | CH$_2$CH$_2$CH(CH$_3$)SOCF$_3$ | CH$_2$CH$_3$ | H | O | 0 |
| A-0566 | H | H | H | H | H | CH$_2$SO$_2$CF$_3$ | CH$_2$CH$_3$ | H | O | 0 |
| A-0567 | H | H | H | H | H | CH$_2$CH$_2$SO$_2$CF$_3$ | CH$_2$CH$_3$ | H | O | 0 |
| A-0568 | H | H | H | H | H | CH$_2$CH$_2$CH$_2$SO$_2$CF$_3$ | CH$_2$CH$_3$ | H | O | 0 |
| A-0569 | H | H | H | H | H | CH(CH$_3$)SO$_2$CF$_3$ | CH$_2$CH$_3$ | H | O | 0 |
| A-0570 | H | H | H | H | H | CH$_2$CH(CH$_3$)SO$_2$CF$_3$ | CH$_2$CH$_3$ | H | O | 0 |
| A-0571 | H | H | H | H | H | CH(CH$_3$)CH$_2$CH$_2$SO$_2$CF$_3$ | CH$_2$CH$_3$ | H | O | 0 |
| A-0572 | H | H | H | H | H | CH$_2$CH(CH$_3$)CH$_2$SO$_2$CF$_3$ | CH$_2$CH$_3$ | H | O | 0 |
| A-0573 | H | H | H | H | H | CH$_2$CH$_2$CH(CH$_3$)SO$_2$CF$_3$ | CH$_2$CH$_3$ | H | O | 0 |
| A-0574 | H | H | H | H | H | CH$_2$C(=O)CH$_3$ | CH$_2$CH$_3$ | H | O | 0 |
| A-0575 | H | H | H | H | H | CH$_2$C(=O)CH$_2$CH$_3$ | CH$_2$CH$_3$ | H | O | 0 |
| A-0576 | H | H | H | H | H | CH$_2$C(=O)C(CH$_3$)$_3$ | CH$_2$CH$_3$ | H | O | 0 |
| A-0577 | H | H | H | H | H | CH$_2$CH$_2$C(=O)CH$_3$ | CH$_2$CH$_3$ | H | O | 0 |
| A-0578 | H | H | H | H | H | CH$_2$CH$_2$C(=O)C(CH$_3$)$_3$ | CH$_2$CH$_3$ | H | O | 0 |
| A-0579 | H | H | H | H | H | CH$_2$C(=O)CF$_3$ | CH$_2$CH$_3$ | H | O | 0 |
| A-0580 | H | H | H | H | H | CH$_2$CH$_2$C(=O)CF$_3$ | CH$_2$CH$_3$ | H | O | 0 |
| A-0581 | H | H | H | H | H | CH$_2$C(=O)OCH$_3$ | CH$_2$CH$_3$ | H | O | 0 |
| A-0582 | H | H | H | H | H | CH$_2$C(=O)OCH$_2$CH$_3$ | CH$_2$CH$_3$ | H | O | 0 |
| A-0583 | H | H | H | H | H | CH$_2$C(=O)OC(CH$_3$)$_3$ | CH$_2$CH$_3$ | H | O | 0 |
| A-0584 | H | H | H | H | H | CH$_2$CH$_2$C(=O)OCH$_3$ | CH$_2$CH$_3$ | H | O | 0 |
| A-0585 | H | H | H | H | H | CH$_2$CH$_2$C(=O)OCH$_2$CH$_3$ | CH$_2$CH$_3$ | H | O | 0 |
| A-0586 | H | H | H | H | H | CH$_2$CH$_2$C(=O)OC(CH$_3$)$_3$ | CH$_2$CH$_3$ | H | O | 0 |
| A-0587 | H | H | H | H | H | CH$_2$C(=O)NH$_2$ | CH$_2$CH$_3$ | H | O | 0 |
| A-0588 | H | H | H | H | H | CH$_2$CH$_2$C(=O)NH$_2$ | CH$_2$CH$_3$ | H | O | 0 |
| A-0589 | H | H | H | H | H | CH$_2$C(=O)NHCH$_3$ | CH$_2$CH$_3$ | H | O | 0 |
| A-0590 | H | H | H | H | H | CH$_2$C(=O)NHCH(CH$_3$)$_2$ | CH$_2$CH$_3$ | H | O | 0 |
| A-0591 | H | H | H | H | H | CH$_2$CH$_2$C(=O)NHCH$_3$ | CH$_2$CH$_3$ | H | O | 0 |
| A-0592 | H | H | H | H | H | CH$_2$CH$_2$C(=O)NHCH(CH$_3$)$_2$ | CH$_2$CH$_3$ | H | O | 0 |
| A-0593 | H | H | H | H | H | CH$_2$C(=O)NHCH$_2$CHF$_2$ | CH$_2$CH$_3$ | H | O | 0 |
| A-0594 | H | H | H | H | H | CH$_2$C(=O)NHCH$_2$CF$_3$ | CH$_2$CH$_3$ | H | O | 0 |
| A-0595 | H | H | H | H | H | CH$_2$CH$_2$C(=O)NHCH$_2$CHF$_2$ | CH$_2$CH$_3$ | H | O | 0 |
| A-0596 | H | H | H | H | H | CH$_2$CH$_2$C(=O)NHCH$_2$CF$_3$ | CH$_2$CH$_3$ | H | O | 0 |
| A-0597 | H | H | H | H | H | CH$_2$C(=O)N(CH$_3$)$_2$ | CH$_2$CH$_3$ | H | O | 0 |
| A-0598 | H | H | H | H | H | CH$_2$C(=O)N(CH$_2$CH$_3$)$_2$ | CH$_2$CH$_3$ | H | O | 0 |
| A-0599 | H | H | H | H | H | CH$_2$CH$_2$C(=O)N(CH$_3$)$_2$ | CH$_2$CH$_3$ | H | O | 0 |
| A-0600 | H | H | H | H | H | CH$_2$CH$_2$C(=O)N(CH$_2$CH$_3$)$_2$ | CH$_2$CH$_3$ | H | O | 0 |
| A-0601 | H | H | H | H | H | CH$_2$CH$_2$OH | CH$_2$CH$_3$ | H | O | 0 |
| A-0602 | H | H | H | H | H | CH$_2$CH(OH)CH$_3$ | CH$_2$CH$_3$ | H | O | 0 |
| A-0603 | H | H | H | H | H | CH$_2$CH$_2$CH$_2$OH | CH$_2$CH$_3$ | H | O | 0 |
| A-0604 | H | H | H | H | H | CH$_2$CH(OH)CH$_2$CH$_3$ | CH$_2$CH$_3$ | H | O | 0 |
| A-0605 | H | H | H | H | H | CH$_2$CH(OH)C(CH$_3$)$_3$ | CH$_2$CH$_3$ | H | O | 0 |

TABLE 11

| Compund | R$^1$ | R$^2$ | R$^3$ | R$^4$ | R$^5$ | R$^6$ | R$^7$ | R$^8$ | X | n |
|---|---|---|---|---|---|---|---|---|---|---|
| A-0606 | H | H | H | H | H | CH$_2$CH$_2$CH(OH)CH$_3$ | CH$_2$CH$_3$ | H | O | 0 |
| A-0607 | H | H | H | H | H | CH$_2$CH$_2$CH(OH)C(CH$_3$)$_3$ | CH$_2$CH$_3$ | H | O | 0 |
| A-0608 | H | H | H | H | H | CH$_2$C(=NOH)CH$_3$ | CH$_2$CH$_3$ | H | O | 0 |
| A-0609 | H | H | H | H | H | CH$_2$C(=NOH)CH$_2$CH$_3$ | CH$_2$CH$_3$ | H | O | 0 |
| A-0610 | H | H | H | H | H | CH$_2$C(=NOH)C(CH$_3$)$_3$ | CH$_2$CH$_3$ | H | O | 0 |
| A-0611 | H | H | H | H | H | CH$_2$C(=NOCH$_3$)CH$_3$ | CH$_2$CH$_3$ | H | O | 0 |
| A-0612 | H | H | H | H | H | CH$_2$C(=NOCH$_3$)CH$_2$CH$_3$ | CH$_2$CH$_3$ | H | O | 0 |
| A-0613 | H | H | H | H | H | CH$_2$C(=NOCH$_2$CH$_3$)CH$_3$ | CH$_2$CH$_3$ | H | O | 0 |
| A-0614 | H | H | H | H | H | CH$_2$C(=NOCH$_2$CH$_3$)CH$_2$CH$_3$ | CH$_2$CH$_3$ | H | O | 0 |
| A-0615 | H | H | H | H | H | CH$_2$C(=NOCH$_2$CF$_3$)CH$_3$ | CH$_2$CH$_3$ | H | O | 0 |
| A-0616 | H | H | H | H | H | CH$_2$C(=NOCH$_2$CF$_3$)CH$_2$CH$_3$ | CH$_2$CH$_3$ | H | O | 0 |
| A-0617 | H | H | H | H | H | CH$_2$Ph | CH$_2$CH$_3$ | H | O | 0 |
| A-0618 | H | H | H | H | H | CH$_2$(2-F)Ph | CH$_2$CH$_3$ | H | O | 0 |
| A-0619 | H | H | H | H | H | CH$_2$(3-F)Ph | CH$_2$CH$_3$ | H | O | 0 |
| A-0620 | H | H | H | H | H | CH$_2$(4-F)Ph | CH$_2$CH$_3$ | H | O | 0 |
| A-0621 | H | H | H | H | H | CH$_2$(2-Cl)Ph | CH$_2$CH$_3$ | H | O | 0 |
| A-0622 | H | H | H | H | H | CH$_2$(3-Cl)Ph | CH$_2$CH$_3$ | H | O | 0 |
| A-0623 | H | H | H | H | H | CH$_2$(4-Cl)Ph | CH$_2$CH$_3$ | H | O | 0 |
| A-0624 | H | H | H | H | H | CH$_2$(2-CF$_3$)Ph | CH$_2$CH$_3$ | H | O | 0 |
| A-0625 | H | H | H | H | H | CH$_2$(3-CF$_3$)Ph | CH$_2$CH$_3$ | H | O | 0 |
| A-0626 | H | H | H | H | H | CH$_2$(4-CF$_3$)Ph | CH$_2$CH$_3$ | H | O | 0 |
| A-0627 | H | H | H | H | H | CH$_2$(naphthalen-1-yl) | CH$_2$CH$_3$ | H | O | 0 |
| A-0628 | H | H | H | H | H | CH$_2$(naphthalen-2-yl) | CH$_2$CH$_3$ | H | O | 0 |
| A-0629 | H | H | H | H | H | CH$_2$CH$_2$Ph | CH$_2$CH$_3$ | H | O | 0 |
| A-0630 | H | H | H | H | H | H | CH(CH$_3$)$_2$ | H | O | 0 |
| A-0631 | H | H | H | H | H | CH$_3$ | CH(CH$_3$)$_2$ | H | O | 0 |
| A-0632 | H | H | H | H | H | CH$_2$CH$_3$ | CH(CH$_3$)$_2$ | H | O | 0 |

TABLE 11-continued

| Compund | R$^1$ | R$^2$ | R$^3$ | R$^4$ | R$^5$ | R$^6$ | R$^7$ | R$^8$ | X | n |
|---|---|---|---|---|---|---|---|---|---|---|
| A-0633 | H | H | H | H | H | CH(CH$_3$)$_2$ | CH(CH$_3$)$_3$ | H | O | 0 |
| A-0634 | H | H | H | H | H | CH$_2$CH$_2$CH$_3$ | CH(CH$_3$)$_2$ | H | O | 0 |
| A-0635 | H | H | H | H | H | CH$_2$CH(CH$_3$)$_2$ | CH(CH$_3$)$_2$ | H | O | 0 |
| A-0636 | H | H | H | H | H | CH(CH$_3$)CH$_3$CH$_3$ | CH(CH$_3$)$_2$ | H | O | 0 |
| A-0637 | H | H | H | H | H | CH$_2$C(CH$_3$)3 | CH(CH$_3$)$_2$ | H | O | 0 |
| A-0638 | H | H | H | H | H | CH$_2$(CH$_2$)$_2$CH$_3$ | CH(CH$_3$)$_2$ | H | O | 0 |
| A-0639 | H | H | H | H | H | CH$_2$(CH$_2$)$_3$CH$_3$ | CH(CH$_3$)$_2$ | H | O | 0 |
| A-0640 | H | H | H | H | H | CH$_2$(CH$_2$)$_4$CH$_3$ | CH(CH$_3$)$_2$ | H | O | 0 |
| A-0641 | H | H | H | H | H | CH$_2$OCH$_3$ | CH(CH$_3$)$_2$ | H | O | 0 |
| A-0642 | H | H | H | H | H | CH$_2$OCH$_2$CH$_3$ | CH(CH$_3$)$_2$ | H | O | 0 |
| A-0643 | H | H | H | H | H | CH$_2$CH$_2$OCH$_3$ | CH(CH$_3$)$_2$ | H | O | 0 |
| A-0644 | H | H | H | H | H | CH$_2$CH$_2$OCH$_2$CH$_3$ | CH(CH$_3$)$_2$ | H | O | 0 |
| A-0645 | H | H | H | H | H | CF$_3$ | CH(CH$_3$)$_2$ | H | O | 0 |
| A-0646 | H | H | H | H | H | CHF$_2$ | CH(CH$_3$)$_2$ | H | O | 0 |
| A-0647 | H | H | H | H | H | CH$_2$CF$_3$ | CH(CH$_3$)$_2$ | H | O | 0 |
| A-0648 | H | H | H | H | H | CH$_2$CHF$_2$ | CH(CH$_3$)$_2$ | H | O | 0 |
| A-0649 | H | H | H | H | H | CH$_2$CClF$_2$ | CH(CH$_3$)$_2$ | H | O | 0 |
| A-0650 | H | H | H | H | H | CH$_2$CBrF$_2$ | CH(CH$_3$)$_2$ | H | O | 0 |
| A-0651 | H | H | H | H | H | CF$_2$CF$_3$ | CH(CH$_3$)$_2$ | H | O | 0 |
| A-0652 | H | H | H | H | H | CF$_2$CHF$_2$ | CH(CH$_3$)$_2$ | H | O | 0 |
| A-0653 | H | H | H | H | H | CH$_2$CH$_2$CF$_3$ | CH(CH$_3$)$_2$ | H | O | 0 |
| A-0654 | H | H | H | H | H | CH$_2$CF$_2$CF$_3$ | CH(CH$_3$)$_2$ | H | O | 0 |
| A-0655 | H | H | H | H | H | CH$_2$CF$_2$CHF$_2$ | CH(CH$_3$)$_2$ | H | O | 0 |
| A-0656 | H | H | H | H | H | CF$_2$CHFCF$_3$ | CH(CH$_3$)$_2$ | H | O | 0 |
| A-0657 | H | H | H | H | H | CF$_2$CF$_2$CF$_3$ | CH(CH$_3$)$_2$ | H | O | 0 |
| A-0658 | H | H | H | H | H | CH$_2$CF$_2$CF$_2$CF$_3$ | CH(CH$_3$)$_2$ | H | O | 0 |
| A-0659 | H | H | H | H | H | CH$_2$CF$_2$CHFCF$_3$ | CH(CH$_3$)$_2$ | H | O | 0 |
| A-0660 | H | H | H | H | H | CH$_2$CH$_2$CH$_2$CF$_3$ | CH(CH$_3$)$_2$ | H | O | 0 |
| A-0661 | H | H | H | H | H | CH$_2$CF$_2$CF$_2$CF$_3$ | CH(CH$_3$)$_2$ | H | O | 0 |
| A-0662 | H | H | H | H | H | CF$_2$CF$_2$CF$_2$CF$_3$ | CH(CH$_3$)$_2$ | H | O | 0 |
| A-0663 | H | H | H | H | H | CH$_2$CH$_2$CH(CF$_3$)2 | CH(CH$_3$)$_2$ | H | O | 0 |
| A-0664 | H | H | H | H | H | CF$_2$CF$_2$CF$_2$CF$_2$CF$_3$ | CH(CH$_3$)$_2$ | H | O | 0 |
| A-0665 | H | H | H | H | H | CH$_2$CF$_2$CF$_2$CF$_2$CF$_3$ | CH(CH$_3$)$_2$ | H | O | 0 |
| A-0666 | H | H | H | H | H | CH$_2$CH$_2$CH$_2$CH$_2$CF$_3$ | CH(CH$_3$)$_2$ | H | O | 0 |

TABLE 12

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-0667 | H | H | H | H | H | CH$_2$CF$_2$CF$_2$CF$_2$CHF$_2$ | CH(CH$_3$)$_2$ | H | O | 0 |
| A-0668 | H | H | H | H | H | CH$_2$CF$_2$CF(CF$_3$)CF$_2$C(CF$_3$)$_3$ | CH(CH$_3$)$_2$ | H | O | 0 |
| A-0669 | H | H | H | H | H | CF$_2$CHFOCH$_3$ | CH(CH$_3$)$_2$ | H | O | 0 |
| A-0670 | H | H | H | H | H | CF$_2$CHFOCH$_2$CH$_3$ | CH(CH$_3$)$_2$ | H | O | 0 |
| A-0671 | H | H | H | H | H | CH$_2$CH$_2$OCH$_2$CF$_3$ | CH(CH$_3$)$_2$ | H | O | 0 |
| A-0672 | H | H | H | H | H | CF$_2$CHFOCF$_3$ | CH(CH$_3$)$_2$ | H | O | 0 |
| A-0673 | H | H | H | H | H | CF$_2$CHFOCF$_2$CF$_3$ | CH(CH$_3$)$_2$ | H | O | 0 |
| A-0674 | H | H | H | H | H | CF$_2$CHFOCF$_2$CF$_2$CF$_3$ | CH(CH$_3$)$_2$ | H | O | 0 |
| A-0675 | H | H | H | H | H | CH$_2$CH=CH$_2$ | CH(CH$_3$)$_2$ | H | O | 0 |
| A-0676 | H | H | H | H | H | CH$_2$CH=CHCl | CH(CH$_3$)$_2$ | H | O | 0 |
| A-0677 | H | H | H | H | H | CH$_2$CH=CCl$_2$ | CH(CH$_3$)$_2$ | H | O | 0 |
| A-0678 | H | H | H | H | H | CH$_2$CH$_2$CF=CF$_2$ | CH(CH$_3$)$_2$ | H | O | 0 |
| A-0679 | H | H | H | H | H | CH$_2$CH$_2$CH=CF$_2$ | CH(CH$_3$)$_2$ | H | O | 0 |
| A-0680 | H | H | H | H | H | CH$_2$C≡CH | CH(CH$_3$)$_2$ | H | O | 0 |
| A-0681 | H | H | H | H | H | CH$_2$C≡CCH$_3$ | CH(CH$_3$)$_2$ | H | O | 0 |
| A-0682 | H | H | H | H | H | CH$_2$C≡Cl | CH(CH$_3$)$_2$ | H | O | 0 |
| A-0683 | H | H | H | H | H | CH$_2$C≡CCF$_3$ | CH(CH$_3$)$_2$ | H | O | 0 |
| A-0684 | H | H | H | H | H | cydobutyl | CH(CH$_3$)$_2$ | H | O | 0 |
| A-0685 | H | H | H | H | H | cyclopentyl | CH(CH$_3$)$_2$ | H | O | 0 |
| A-0686 | H | H | H | H | H | cyclohexyl | CH(CH$_3$)$_2$ | H | O | 0 |
| A-0687 | H | H | H | H | H | 4,4-difluorocyclohexyl | CH(CH$_3$)$_2$ | H | O | 0 |
| A-0688 | H | H | H | H | H | CH$_2$(cyclopropyl) | CH(CH$_3$)$_2$ | H | O | 0 |
| A-0689 | H | H | H | H | H | CH$_2$(cyclobutyl) | CH(CH$_3$)$_2$ | H | O | 0 |
| A-0690 | H | H | H | H | H | CH$_2$(cyclopentyl) | CH(CH$_3$)$_2$ | H | O | 0 |
| A-0691 | H | H | H | H | H | CH$_2$CH$_2$(cyclopropyl) | CH(CH$_3$)$_2$ | H | O | 0 |
| A-0692 | H | H | H | H | H | CH$_2$(2,2-difluorocyclopropyl) | CH(CH$_3$)$_2$ | H | O | 0 |
| A-0693 | H | H | H | H | H | CH$_2$(2,2-dichlorocyclopropyl) | CH(CH$_3$)$_2$ | H | O | 0 |
| A-0694 | H | H | H | H | H | CH$_2$(4,4-difluorocyclohexyl) | CH(CH$_3$)$_2$ | H | O | 0 |
| A-0695 | H | H | H | H | H | CH$_2$CH$_2$(2,2-difluorocyclopropyl) | CH(CH$_3$)$_2$ | H | O | 0 |
| A-0696 | H | H | H | H | H | CH$_2$CH$_2$(2,2-dichlorocyclopropyl) | CH(CH$_3$)$_2$ | H | O | 0 |
| A-0697 | H | H | H | H | H | CH$_2$SCH$_3$ | CH(CH$_3$)$_2$ | H | O | 0 |
| A-0698 | H | H | H | H | H | CH$_2$SCH$_2$CH$_3$ | CH(CH$_3$)$_2$ | H | O | 0 |
| A-0699 | H | H | H | H | H | CH$_2$CH$_2$SCH$_3$ | CH(CH$_3$)$_2$ | H | O | 0 |
| A-0700 | H | H | H | H | H | CH$_2$CH$_2$SCH$_2$CH$_3$ | CH(CH$_3$)$_2$ | H | O | 0 |
| A-0701 | H | H | H | H | H | CH$_2$CH$_2$CH$_2$SCH$_3$ | CH(CH$_3$)$_2$ | H | O | 0 |
| A-0702 | H | H | H | H | H | CH$_2$CH$_2$CH$_2$SCH$_2$CH$_3$ | CH(CH$_3$)$_2$ | H | O | 0 |

TABLE 12-continued

| Compound | R¹ | R² | R³ | R⁴ | R⁵ | R⁶ | R⁷ | R⁸ | X | n |
|---|---|---|---|---|---|---|---|---|---|---|
| A-0703 | H | H | H | H | H | CH(CH₃)SCH₃ | CH(CH₃)₂ | H | O | 0 |
| A-0704 | H | H | H | H | H | CH(CH₃)SCH₂CH₃ | CH(CH₃)₂ | H | O | 0 |
| A-0705 | H | H | H | H | H | CH₂CH(CH₃)SCH₃ | CH(CH₃)₂ | H | O | 0 |
| A-0706 | H | H | H | H | H | CH₂CH(CH₃)SCH₂CH₃ | CH(CH₃)₂ | H | O | 0 |
| A-0707 | H | H | H | H | H | CH(CH₃)CH₂CH₂SCH₃ | CH(CH₃)₂ | H | O | 0 |
| A-0708 | H | H | H | H | H | CH(CH₃)CH₂CH₂SCH₂CH₃ | CH(CH₃)₂ | H | O | 0 |
| A-0709 | H | H | H | H | H | CH₂CH(CH₃)CH₂SCH₃ | CH(CH₃)₂ | H | O | 0 |
| A-0710 | H | H | H | H | H | CH₂CH(CH₃)CH₂SCH₂CH₃ | CH(CH₃)₂ | H | O | 0 |
| A-0711 | H | H | H | H | H | CH₂CH₂CH(CH₃)SCH₃ | CH(CH₃)₂ | H | O | 0 |
| A-0712 | H | H | H | H | H | CH₂CH₂CH(CH₃)SCH₂CH₃ | CH(CH₃)₂ | H | O | 0 |
| A-0713 | H | H | H | H | H | CH₂SOCH₃ | CH(CH₃)₂ | H | O | 0 |
| A-0714 | H | H | H | H | H | CH₂CH₂SOCH₃ | CH(CH₃)₂ | H | O | 0 |
| A-0715 | H | H | H | H | H | CH₂CH₂CH₂SOCH₃ | CH(CH₃)₂ | H | O | 0 |
| A-0716 | H | H | H | H | H | CH(CH₃)SOCH₃ | CH(CH₃)₂ | H | O | 0 |
| A-0717 | H | H | H | H | H | CH₂CH(CH₃)SOCH₃ | CH(CH₃)₂ | H | O | 0 |
| A-0718 | H | H | H | H | H | CH(CH₃)CH₂CH₂SOCH₃ | CH(CH₃)₂ | H | O | 0 |
| A-0719 | H | H | H | H | H | CH₂CH(CH₃)CH₂SOCH₃ | CH(CH₃)₂ | H | O | 0 |
| A-0720 | H | H | H | H | H | CH₂CH₂CH(CH₃)SOCH₃ | CH(CH₃)₂ | H | O | 0 |
| A-0721 | H | H | H | H | H | CH₂SO2CH₃ | CH(CH₃)₂ | H | O | 0 |
| A-0722 | H | H | H | H | H | CH₂CH₂SO2CH₃ | CH(CH₃)₂ | H | O | 0 |
| A-0723 | H | H | H | H | H | CH₂CH₂CH₂SO2CH₃ | CH(CH₃)₂ | H | O | 0 |
| A-0724 | H | H | H | H | H | CH(CH₃)SO2CH₃ | CH(CH₃)₂ | H | O | 0 |
| A-0725 | H | H | H | H | H | CH₂CH(CH₃)SO2CH₃ | CH(CH₃)₂ | H | O | 0 |
| A-0726 | H | H | H | H | H | CH(CH₃)CH₂CH₂SO2CH₃ | CH(CH₃)₂ | H | O | 0 |
| A-0727 | H | H | H | H | H | CH₂CH(CH₃)CH₂SO2CH₃ | CH(CH₃)₂ | H | O | 0 |

TABLE 13

| Compound | R¹ | R² | R³ | R⁴ | R⁵ | R⁶ | R⁷ | R⁸ | X | n |
|---|---|---|---|---|---|---|---|---|---|---|
| A-0728 | H | H | H | H | H | CH₂CH₂CH(CH₃)SO₂CH₃ | CH(CH₃)₂ | H | O | 0 |
| A-0729 | H | H | H | H | H | CH₂SOF₃ | CH(CH₃)₂ | H | O | 0 |
| A-0730 | H | H | H | H | H | CH₂SCHF₂ | CH(CH₃)₂ | H | O | 0 |
| A-0731 | H | H | H | H | H | CH₂SCH₂CF₃ | CH(CH₃)₂ | H | O | 0 |
| A-0732 | H | H | H | H | H | CH₂SCH₂CHF₂ | CH(CH₃)₂ | H | O | 0 |
| A-0733 | H | H | H | H | H | CH₂SCF₂CF₃ | CH(CH₃)₂ | H | O | 0 |
| A-0734 | H | H | H | H | H | CH₂CH₂SCF₃ | CH(CH₃)₂ | H | O | 0 |
| A-0735 | H | H | H | H | H | CH₂CH₂SCH₂CF₃ | CH(CH₃)₂ | H | O | 0 |
| A-0736 | H | H | H | H | H | CH₂CH₂CH₂SCF₃ | CH(CH₃)₂ | H | O | 0 |
| A-0737 | H | H | H | H | H | CH₂CH₂CH₂SCH₂CF₃ | CH(CH₃)₂ | H | O | 0 |
| A-0738 | H | H | H | H | H | CH(CH₃)SCF₃ | CH(CH₃)₂ | H | O | 0 |
| A-0739 | H | H | H | H | H | CH(CH₃)SCH₂CF₃ | CH(CH₃)₂ | H | O | 0 |
| A-0740 | H | H | H | H | H | CH₂CH(CH₃)SCF₃ | CH(CH₃)₂ | H | O | 0 |
| A-0741 | H | H | H | H | H | CH₂CH(CH₃)SCH₂CF₃ | CH(CH₃)₂ | H | O | 0 |
| A-0742 | H | H | H | H | H | CH(CH₃)CH₂CH₂SCF₃ | CH(CH₃)₂ | H | O | 0 |
| A-0743 | H | H | H | H | H | CH(CH₃)CH₂CH₂SCH₂CF₃ | CH(CH₃)₂ | H | O | 0 |
| A-0744 | H | H | H | H | H | CH₂CH(CH₃)CH₂SCF₃ | CH(CH₃)₂ | H | O | 0 |
| A-0745 | H | H | H | H | H | CH₂CH(CH₃)CH₂SCH₂CF₃ | CH(CH₃)₂ | H | O | 0 |
| A-0746 | H | H | H | H | H | CH₂CH₂CH(CH₃)SCF₃ | CH(CH₃)₂ | H | O | 0 |
| A-0747 | H | H | H | H | H | CH₂CH₂CH(CH₃)SCH₂CF₃ | CH(CH₃)₂ | H | O | 0 |
| A-0748 | H | H | H | H | H | CH₂SOCF₃ | CH(CH₃)₂ | H | O | 0 |
| A-0749 | H | H | H | H | H | CH₂CH₂SOCF₃ | CH(CH₃)₂ | H | O | 0 |
| A-0750 | H | H | H | H | H | CH₂CH₂CH₂SOCF₃ | CH(CH₃)₂ | H | O | 0 |
| A-0751 | H | H | H | H | H | CH(CH₃)SOCF₃ | CH(CH₃)₂ | H | O | 0 |
| A-0752 | H | H | H | H | H | CH₂CH(CH₃)SOCF₃ | CH(CH₃)₂ | H | O | 0 |
| A-0753 | H | H | H | H | H | CH(CH₃)CH₂CH₂SOCF₃ | CH(CH₃)₂ | H | O | 0 |
| A-0754 | H | H | H | H | H | CH₂CH(CH₃)CH₂SOCF₃ | CH(CH₃)₂ | H | O | 0 |
| A-0755 | H | H | H | H | H | CH₂CH₂CH(CH₃)SOCF₃ | CH(CH₃)₂ | H | O | 0 |
| A-0756 | H | H | H | H | H | CH₂SO₂CF₃ | CH(CH₃)₂ | H | O | 0 |
| A-0757 | H | H | H | H | H | CH₂CH₂SO₂CF₃ | CH(CH₃)₂ | H | O | 0 |
| A-0758 | H | H | H | H | H | CH₂CH₂CH₂SO₂CF₃ | CH(CH₃)₂ | H | O | 0 |
| A-0759 | H | H | H | H | H | CH(CH₃)SO₂CF₃ | CH(CH₃)₂ | H | O | 0 |
| A-0760 | H | H | H | H | H | CH₂CH(CH₃)SO₂CF₃ | CH(CH₃)₂ | H | O | 0 |
| A-0761 | H | H | H | H | H | CH(CH₃)CH₂CH₂SO₂CF₃ | CH(CH₃)₂ | H | O | 0 |
| A-0762 | H | H | H | H | H | CH₂CH(CH₃)CH₂SO₂CF₃ | CH(CH₃)₂ | H | O | 0 |
| A-0763 | H | H | H | H | H | CH₂CH₂CH(CH₃)SO₂CF₃ | CH(CH₃)₂ | H | O | 0 |
| A-0764 | H | H | H | H | H | CH₂C(=O)CH₃ | CH(CH₃)₂ | H | O | 0 |
| A-0765 | H | H | H | H | H | CH₂C(=O)CH₂CH₃ | CH(CH₃)₂ | H | O | 0 |
| A-0766 | H | H | H | H | H | CH₂C(=O)C(CH₃)₃ | CH(CH₃)₂ | H | O | 0 |
| A-0767 | H | H | H | H | H | CH₂CH₂C(=O)CH₃ | CH(CH₃)₂ | H | O | 0 |
| A-0768 | H | H | H | H | H | CH₂CH₂C(=O)C(CH₃)₃ | CH(CH₃)₂ | H | O | 0 |
| A-0769 | H | H | H | H | H | CH₂C(=O)CF₃ | CH(CH₃)₂ | H | O | 0 |
| A-0770 | H | H | H | H | H | CH₂CH₂C(=O)CF₃ | CH(CH₃)₂ | H | O | 0 |
| A-0771 | H | H | H | H | H | CH₂C(=O)OCH₃ | CH(CH₃)₂ | H | O | 0 |
| A-0772 | H | H | H | H | H | CH₂C(=O)OCH₂CH₃ | CH(CH₃)₂ | H | O | 0 |

TABLE 13-continued

| Compound | R¹ | R² | R³ | R⁴ | R⁵ | R⁶ | R⁷ | R⁸ | X | n |
|---|---|---|---|---|---|---|---|---|---|---|
| A-0773 | H | H | H | H | H | $CH_2C(=O)OC(CH_3)_3$ | $CH(CH_3)_2$ | H | O | 0 |
| A-0774 | H | H | H | H | H | $CH_2CH_2C(=O)OCH_3$ | $CH(CH_3)_2$ | H | O | 0 |
| A-0775 | H | H | H | H | H | $CH_2CH_2C(=O)OCH_2CH_3$ | $CH(CH_3)_2$ | H | O | 0 |
| A-0776 | H | H | H | H | H | $CH_2CH_2C(=O)OC(CH_3)_3$ | $CH(CH_3)_2$ | H | O | 0 |
| A-0777 | H | H | H | H | H | $CH_2C(=O)NH_2$ | $CH(CH_3)_2$ | H | O | 0 |
| A-0778 | H | H | H | H | H | $CH_2CH_2C(=O)NH_2$ | $CH(CH_3)_2$ | H | O | 0 |
| A-0779 | H | H | H | H | H | $CH_2C(=O)NHCH_3$ | $CH(CH_3)_2$ | H | O | 0 |
| A-0780 | H | H | H | H | H | $CH_2C(=O)NHCH(CH_3)_2$ | $CH(CH_3)_2$ | H | O | 0 |
| A-0781 | H | H | H | H | H | $CH_2CH_2C(=O)NHCH_3$ | $CH(CH_3)_2$ | H | O | 0 |
| A-0782 | H | H | H | H | H | $CH_2CH_2C(=O)NHCH(CH_3)_2$ | $CH(CH_3)_2$ | H | O | 0 |
| A-0783 | H | H | H | H | H | $CH_2C(=O)NHCH_2CHF_2$ | $CH(CH_3)_2$ | H | O | 0 |
| A-0784 | H | H | H | H | H | $CH_2C(=O)NHCH_2CF_3$ | $CH(CH_3)_2$ | H | O | 0 |
| A-0785 | H | H | H | H | H | $CH_2CH_2C(=O)NHCH_2CHF_2$ | $CH(CH_3)_2$ | H | O | 0 |
| A-0786 | H | H | H | H | H | $CH_2CH_2C(=O)NHCH_2CF_3$ | $CH(CH_3)_2$ | H | O | 0 |
| A-0787 | H | H | H | H | H | $CH_2C(=O)N(CH_3)_2$ | $CH(CH_3)_2$ | H | O | 0 |
| A-0788 | H | H | H | H | H | $CH_2C(=O)N(CH_2CH_3)_2$ | $CH(CH_3)_2$ | H | O | 0 |

TABLE 14

| Compound | R¹ | R² | R³ | R⁴ | R⁵ | R⁶ | R⁷ | R⁸ | X | n |
|---|---|---|---|---|---|---|---|---|---|---|
| A-0789 | H | H | H | H | H | $CH_2CH_2C(=O)N(CH_3)_2$ | $CH(CH_3)_2$ | H | O | 0 |
| A-0790 | H | H | H | H | H | $CH_2CH_2C(=O)N(CH_2CH_3)_2$ | $CH(CH_3)_2$ | H | O | 0 |
| A-0791 | H | H | H | H | H | $CH_2CH_2OH$ | $CH(CH_3)_2$ | H | O | 0 |
| A-0792 | H | H | H | H | H | $CH_2CH(OH)CH_3$ | $CH(CH_3)_2$ | H | O | 0 |
| A-0793 | H | H | H | H | H | $CH_2CH_2CH_2OH$ | $CH(CH_3)_2$ | H | O | 0 |
| A-0794 | H | H | H | H | H | $CH_2CH(OH)CH_2CH_3$ | $CH(CH_3)_2$ | H | O | 0 |
| A-0795 | H | H | H | H | H | $CH_2CH(OH)C(CH_3)_3$ | $CH(CH_3)_2$ | H | O | 0 |
| A-0796 | H | H | H | H | H | $CH_2CH_2CH(OH)CH_3$ | $CH(CH_3)_2$ | H | O | 0 |
| A-0797 | H | H | H | H | H | $CH_2CH_2CH(OH)C(CH_3)_3$ | $CH(CH_3)_2$ | H | O | 0 |
| A-0798 | H | H | H | H | H | $CH_2C(=NOH)CH_3$ | $CH(CH_3)_2$ | H | O | 0 |
| A-0799 | H | H | H | H | H | $CH_2C(=NOH)CH_2CH_3$ | $CH(CH_3)_2$ | H | O | 0 |
| A-0800 | H | H | H | H | H | $CH_2C(=NOH)C(CH_3)_3$ | $CH(CH_3)_2$ | H | O | 0 |
| A-0801 | H | H | H | H | H | $CH_2C(=NOCH_3)CH_3$ | $CH(CH_3)_2$ | H | O | 0 |
| A-0802 | H | H | H | H | H | $CH_2C(=NOCH_3)CH_2CH_3$ | $CH(CH_3)_2$ | H | O | 0 |
| A-0803 | H | H | H | H | H | $CH_2C(=NOCH_2CH_3)CH_3$ | $CH(CH_3)_2$ | H | O | 0 |
| A-0804 | H | H | H | H | H | $CH_2C(=NOCH_2CH_3)CH_2CH_3$ | $CH(CH_3)_2$ | H | O | 0 |
| A-0805 | H | H | H | H | H | $CH_2C(=NOCH_2CF_3)CH_3$ | $CH(CH_3)_2$ | H | O | 0 |
| A-0806 | H | H | H | H | H | $CH_2C(=NOCH_2CF_3)CH_2CH_3$ | $CH(CH_3)_2$ | H | O | 0 |
| A-0807 | H | H | H | H | H | $CH_2Ph$ | $CH(CH_3)_2$ | H | O | 0 |
| A-0808 | H | H | H | H | H | $CH_2(2-F)Ph$ | $CH(CH_3)_2$ | H | O | 0 |
| A-0809 | H | H | H | H | H | $CH_2(3-F)Ph$ | $CH(CH_3)_2$ | H | O | 0 |
| A-0810 | H | H | H | H | H | $CH_2(4-F)Ph$ | $CH(CH_3)_2$ | H | O | 0 |
| A-0811 | H | H | H | H | H | $CH_2(2-Cl)Ph$ | $CH(CH_3)_2$ | H | O | 0 |
| A-0812 | H | H | H | H | H | $CH_2(3-Cl)Ph$ | $CH(CH_3)_2$ | H | O | 0 |
| A-0813 | H | H | H | H | H | $CH_2(4-Cl)Ph$ | $CH(CH_3)_2$ | H | O | 0 |
| A-0814 | H | H | H | H | H | $CH_2(2-CF_3)Ph$ | $CH(CH_3)_2$ | H | O | 0 |
| A-0815 | H | H | H | H | H | $CH_2(3-CF_3)Ph$ | $CH(CH_3)_2$ | H | O | 0 |
| A-0816 | H | H | H | H | H | $CH_2(4-CF_3)Ph$ | $CH(CH_3)_2$ | H | O | 0 |
| A-0817 | H | H | H | H | H | $CF_2(naphthalen-1-yl)$ | $CH(CH_3)_2$ | H | O | 0 |
| A-0818 | H | H | H | H | H | $CH_2(naphthalen-2-yl)$ | $CH(CH_3)_2$ | H | O | 0 |
| A-0819 | H | H | H | H | H | $CH_2CH_2Ph$ | $CH(CH_3)_2$ | H | O | 0 |
| A-0820 | H | H | H | H | H | H | $CH_2CH_2CH_3$ | H | O | 0 |
| A-0821 | H | H | H | H | H | $CH_3$ | $CH_2CH_2CH_3$ | H | O | 0 |
| A-0822 | H | H | H | H | H | $CH_2CH_3$ | $CH_2CH_2CH_3$ | H | O | 0 |
| A-0823 | H | H | H | H | H | $CH(CH_3)_2$ | $CH_2CH_2CH_3$ | H | O | 0 |
| A-0824 | H | H | H | H | H | $CH_2CH_2CH_3$ | $CH_2CH_2CH_3$ | H | O | 0 |
| A-0825 | H | H | H | H | H | $CH_2CH(CH_3)_2$ | $CH_2CH_2CH_3$ | H | O | 0 |
| A-0826 | H | H | H | H | H | $CH(CH_3)CH_2CH_3$ | $CH_2CH_2CH_3$ | H | O | 0 |
| A-0827 | H | H | H | H | H | $CH_2C(CH_3)_3$ | $CH_2CH_2CH_3$ | H | O | 0 |
| A-0828 | H | H | H | H | H | $CH_2(CH_2)_2CH_3$ | $CH_2CH_2CH_3$ | H | O | 0 |
| A-0829 | H | H | H | H | H | $CH_2(CH_2)_3CH_3$ | $CH_2CH_2CH_3$ | H | O | 0 |
| A-0830 | H | H | H | H | H | $CH_2(CH_2)_4CH_3$ | $CH_2CH_2CH_3$ | H | O | 0 |
| A-0831 | H | H | H | H | H | $CH_2(CH_2)_6CH_3$ | $CH_2CH_2CH_3$ | H | O | 0 |
| A-0832 | H | H | H | H | H | $CH_2OCH_3$ | $CH_2CH_2CH_3$ | H | O | 0 |
| A-0833 | H | H | H | H | H | $CH_2OCH_2CH_3$ | $CH_2CH_2CH_3$ | H | O | 0 |
| A-0834 | H | H | H | H | H | $CH_2CH_2OCH_3$ | $CH_2CH_2CH_3$ | H | O | 0 |
| A-0835 | H | H | H | H | H | $CH_2CH_2OCH_2CH_3$ | $CH_2CH_2CH_3$ | H | O | 0 |
| A-0836 | H | H | H | H | H | $CF_3$ | $CH_2CH_2CH_3$ | H | O | 0 |
| A-0837 | H | H | H | H | H | $CHF_2$ | $CH_2CH_2CH_3$ | H | O | 0 |
| A-0838 | H | H | H | H | H | $CH_2CF_3$ | $CH_2CH_2CH_3$ | H | O | 0 |
| A-0839 | H | H | H | H | H | $CH_2CHF_2$ | $CH_2CH_2CH_3$ | H | O | 0 |
| A-0840 | H | H | H | H | H | $CH_2CClF_2$ | $CH_2CH_2CH_3$ | H | O | 0 |
| A-0841 | H | H | H | H | H | $CH_2CBrF_2$ | $CH_2CH_2CH_3$ | H | O | 0 |
| A-0842 | H | H | H | H | H | $CF_2CF_3$ | $CH_2CH_2CH_3$ | H | O | 0 |

TABLE 14-continued

| Compound | R¹ | R² | R³ | R⁴ | R⁵ | R⁶ | R⁷ | R⁸ | X | n |
|---|---|---|---|---|---|---|---|---|---|---|
| A-0843 | H | H | H | H | H | $CF_2CHF_2$ | $CH_2CH_2CH_3$ | H | O | 0 |
| A-0844 | H | H | H | H | H | $CH_2CH_2CF_3$ | $CH_2CH_2CH_3$ | H | O | 0 |
| A-0845 | H | H | H | H | H | $CH_2CF_2CF_3$ | $CH_2CH_2CH_3$ | H | O | 0 |
| A-0846 | H | H | H | H | H | $CH_2CF_2CHF_2$ | $CH_2CH_2CH_3$ | H | O | 0 |
| A-0847 | H | H | H | H | H | $CF_2CHFCF_3$ | $CH_2CH_2CH_3$ | H | O | 0 |
| A-0848 | H | H | H | H | H | $CF_2CF_2CF_3$ | $CH_2CH_2CH_3$ | H | O | 0 |
| A-0849 | H | H | H | H | H | $CH_2CF_2CF_2CF_3$ | $CH_2CH_2CH_3$ | H | O | 0 |

TABLE 15

| Compound | R¹ | R² | R³ | R⁴ | R⁵ | R⁶ | R⁷ | R⁸ | X | n |
|---|---|---|---|---|---|---|---|---|---|---|
| A-0850 | H | H | H | H | H | $CH_2CF_2CHFCF_3$ | $CH_2CH_2CH_3$ | H | O | 0 |
| A-0851 | H | H | H | H | H | $CH_2CH_2CH_2CF_3$ | $CH_2CH_2CH_3$ | H | O | 0 |
| A-0852 | H | H | H | H | H | $CH_2CH_2CF_2CF_3$ | $CH_2CH_2CH_3$ | H | O | 0 |
| A-0853 | H | H | H | H | H | $CF_2CF_2CF_2CF_3$ | $CH_2CH_2CH_3$ | H | O | 0 |
| A-0854 | H | H | H | H | H | $CH_2CH_2CH(CF_3)_2$ | $CH_2CH_2CH_3$ | H | O | 0 |
| A-0855 | H | H | H | H | H | $CF_2CF_2CF_2CF_2CF_3$ | $CH_2CH_2CH_3$ | H | O | 0 |
| A-0856 | H | H | H | H | H | $CH_2CF_2CF_2CF_2CF_3$ | $CH_2CH_2CH_3$ | H | O | 0 |
| A-0857 | H | H | H | H | H | $CH_2CF_2CH_2CH_2CF_3$ | $CH_2CH_2CH_3$ | H | O | 0 |
| A-0858 | H | H | H | H | H | $CH_2CF_2CF_2CF_2CHF_2$ | $CH_2CH_2CH_3$ | H | O | 0 |
| A-0859 | H | H | H | H | H | $CH_2CF_2CF(CF_3)CF_2C(CF_3)_3$ | $CH_2CH_2CH_3$ | H | O | 0 |
| A-0860 | H | H | H | H | H | $CF_2CHFOCH_3$ | $CH_2CH_2CH_3$ | H | O | 0 |
| A-0861 | H | H | H | H | H | $CF_2CHFOCH_2CH_3$ | $CH_2CH_2CH_3$ | H | O | 0 |
| A-0862 | H | H | H | H | H | $CH_2CH_2OCH_2CF_3$ | $CH_2CH_2CH_3$ | H | O | 0 |
| A-0863 | H | H | H | H | H | $CF_2CHFOCF_3$ | $CH_2CH_2CH_3$ | H | O | 0 |
| A-0864 | H | H | H | H | H | $CF_2CHFOCF_2CF_3$ | $CH_2CH_2CH_3$ | H | O | 0 |
| A-0865 | H | H | H | H | H | $CF_2CHFOCF_2CF_2CF_3$ | $CH_2CH_2CH_3$ | H | O | 0 |
| A-0866 | H | H | H | H | H | $CH_2CH=CH_2$ | $CH_2CH_2CH_3$ | H | O | 0 |
| A-0867 | H | H | H | H | H | $CH_2CH=CHCl$ | $CH_2CH_2CH_3$ | H | O | 0 |
| A-0868 | H | H | H | H | H | $CH_2CH=CCl_2$ | $CH_2CH_2CH_3$ | H | O | 0 |
| A-0869 | H | H | H | H | H | $CH_2CH_2CF=CF_2$ | $CH_2CH_2CH_3$ | H | O | 0 |
| A-0870 | H | H | H | H | H | $CH_2CH_2CH=CF_2$ | $CH_2CH_2CH_3$ | H | O | 0 |
| A-0871 | H | H | H | H | H | $CH_2C\equiv CH$ | $CH_2CH_2CH_3$ | H | O | 0 |
| A-0872 | H | H | H | H | H | $CH_2C\equiv CCH_3$ | $CH_2CH_2CH_3$ | H | O | 0 |
| A-0873 | H | H | H | H | H | $CH_2C\equiv CI$ | $CH_2CH_2CH_3$ | H | O | 0 |
| A-0874 | H | H | H | H | H | $CH_2C\equiv CCF_3$ | $CH_2CH_2CH_3$ | H | O | 0 |
| A-0875 | H | H | H | H | H | cyclobutyl | $CH_2CH_2CH_3$ | H | O | 0 |
| A-0876 | H | H | H | H | H | cyclopentyl | $CH_2CH_2CH_3$ | H | O | 0 |
| A-0877 | H | H | H | H | H | cyclohexyl | $CH_2CH_2CH_3$ | H | O | 0 |
| A-0878 | H | H | H | H | H | 4,4-difluorocyclohexyl | $CH_2CH_2CH_3$ | H | O | 0 |
| A-0879 | H | H | H | H | H | $CH_2$(cyclopropyl) | $CH_2CH_2CH_3$ | H | O | 0 |
| A-0880 | H | H | H | H | H | $CH_2$(cyclobutyl) | $CH_2CH_2CH_3$ | H | O | 0 |
| A-0881 | H | H | H | H | H | $CH_2$(cyclopentyl) | $CH_2CH_2CH_3$ | H | O | 0 |
| A-0882 | H | H | H | H | H | $CH_2CH_2$(cyclopropyl) | $CH_2CH_2CH_3$ | H | O | 0 |
| A-0883 | H | H | H | H | H | $CH_2$(2,2-difluorocyclopropyl) | $CH_2CH_2CH_3$ | H | O | 0 |
| A-0884 | H | H | H | H | H | $CH_2$(2,2-dichlorocyclopropyl) | $CH_2CH_2CH_3$ | H | O | 0 |
| A-0885 | H | H | H | H | H | $CH_2$(4,4-difluorocyclohexyl) | $CH_2CH_2CH_3$ | H | O | 0 |
| A-0886 | H | H | H | H | H | $CH_2CH_2$(2,2-difluorocyclopropyl) | $CH_2CH_2CH_3$ | H | O | 0 |
| A-0887 | H | H | H | H | H | $CH_2CH_2$(2,2-dichlorocyclopropyl) | $CH_2CH_2CH_3$ | H | O | 0 |
| A-0888 | H | H | H | H | H | $CH_2SCH_3$ | $CH_2CH_2CH_3$ | H | O | 0 |
| A-0889 | H | H | H | H | H | $CH_2SCH_2CH_3$ | $CH_2CH_2CH_3$ | H | O | 0 |
| A-0890 | H | H | H | H | H | $CH_2CH_2SCH_3$ | $CH_2CH_2CH_3$ | H | O | 0 |
| A-0891 | H | H | H | H | H | $CH_2CH_2SCH_2CH_3$ | $CH_2CH_2CH_3$ | H | O | 0 |
| A-0892 | H | H | H | H | H | $CH_2CH_2CH_2SCH_3$ | $CH_2CH_2CH_3$ | H | O | 0 |
| A-0893 | H | H | H | H | H | $CH_2CH_2CH_2SCH_2CH_3$ | $CH_2CH_2CH_3$ | H | O | 0 |
| A-0894 | H | H | H | H | H | $CH(CH_3)SCH_3$ | $CH_2CH_2CH_3$ | H | O | 0 |
| A-0895 | H | H | H | H | H | $CH(CH_3)SCH_2CH_3$ | $CH_2CH_2CH_3$ | H | O | 0 |
| A-0896 | H | H | H | H | H | $CH_2CH(CH_3)SCH_3$ | $CH_2CH_2CH_3$ | H | O | 0 |
| A-0897 | H | H | H | H | H | $CH_2CH(CH_3)SCH_2CH_3$ | $CH_2CH_2CH_3$ | H | O | 0 |
| A-0898 | H | H | H | H | H | $CH(CH_3)CH_2SCH_3$ | $CH_2CH_2CH_3$ | H | O | 0 |
| A-0899 | H | H | H | H | H | $CH(CH_3)CH_2SCH_2CH_3$ | $CH_2CH_2CH_3$ | H | O | 0 |
| A-0900 | H | H | H | H | H | $CH_2CH(CH_3)CH_2SCH_3$ | $CH_2CH_2CH_3$ | H | O | 0 |
| A-0901 | H | H | H | H | H | $CH_2CH(CH_3)CH_2SCH_2CH_3$ | $CH_2CH_2CH_3$ | H | O | 0 |
| A-0902 | H | H | H | H | H | $CH_2CH_2CH(CH_3)SCH_3$ | $CH_2CH_2CH_3$ | H | O | 0 |
| A-0903 | H | H | H | H | H | $CH_2CH_2CH(CH_3)SCH_2CH_3$ | $CH_2CH_2CH_3$ | H | O | 0 |
| A-0904 | H | H | H | H | H | $CH_2SOCH_3$ | $CH_2CH_2CH_3$ | H | O | 0 |
| A-0905 | H | H | H | H | H | $CH_2CH_2SOCH_3$ | $CH_2CH_2CH_3$ | H | O | 0 |
| A-0906 | H | H | H | H | H | $CH_2CH_2CH_2SOCH_3$ | $CH_2CH_2CH_3$ | H | O | 0 |
| A-0907 | H | H | H | H | H | $CH(CH_3)SOCH_3$ | $CH_2CH_2CH_3$ | H | O | 0 |
| A-0908 | H | H | H | H | H | $CH_2CH(CH_3)SOCH_3$ | $CH_2CH_2CH_3$ | H | O | 0 |
| A-0909 | H | H | H | H | H | $CH(CH_3)CH_2CH_2SOCH_3$ | $CH_2CH_2CH_3$ | H | O | 0 |
| A-0910 | H | H | H | H | H | $CH_2CH(CH_3)CH_2SOCH_3$ | $CH_2CH_2CH_3$ | H | O | 0 |

TABLE 16

| Compound | R¹ | R² | R³ | R⁴ | R⁵ | R⁶ | R⁷ | R⁸ | X | n |
|---|---|---|---|---|---|---|---|---|---|---|
| A-0911 | H | H | H | H | H | $CH_2CH_2CH(CH_3)SOCH_3$ | $CH_2CH_2CH_3$ | H | O | 0 |
| A-0912 | H | H | H | H | H | $CH_2SO_2CH_3$ | $CH_2CH_2CH_3$ | H | O | 0 |
| A-0913 | H | H | H | H | H | $CH_2CH_2SO_2CH_3$ | $CH_2CH_2CH_3$ | H | O | 0 |
| A-0914 | H | H | H | H | H | $CH_2CH_2CH_2SO_2CH_3$ | $CH_2CH_2CH_3$ | H | O | 0 |
| A-0915 | H | H | H | H | H | $CH(CH_3)SO_2CH_3$ | $CH_2CH_2CH_3$ | H | O | 0 |
| A-0916 | H | H | H | H | H | $CH_2CH(CH_3)SO_2CH_3$ | $CH_2CH_2CH_3$ | H | O | 0 |
| A-0917 | H | H | H | H | H | $CH(CH_3)CH_2CH_2SO_2CH_3$ | $CH_2CH_2CH_3$ | H | O | 0 |
| A-0918 | H | H | H | H | H | $CH_2CH(CH_3)CH_2SO_2CH_3$ | $CH_2CH_2CH_3$ | H | O | 0 |
| A-0919 | H | H | H | H | H | $CH_2CH_2CH(CH_3)SO_2CH_3$ | $CH_2CH_2CH_3$ | H | O | 0 |
| A-0920 | H | H | H | H | H | $CH_2SCF_3$ | $CH_2CH_2CH_3$ | H | O | 0 |
| A-0921 | H | H | H | H | H | $CH_2SCHF_2$ | $CH_2CH_2CH_3$ | H | O | 0 |
| A-0922 | H | H | H | H | H | $CH_2SCH_2CF_3$ | $CH_2CH_2CH_3$ | H | O | 0 |
| A-0923 | H | H | H | H | H | $CH_2SCH_2CHF_2$ | $CH_2CH_2CH_3$ | H | O | 0 |
| A-0924 | H | H | H | H | H | $CH_2SCF_2CF_3$ | $CH_2CH_2CH_3$ | H | O | 0 |
| A-0925 | H | H | H | H | H | $CH_2CH_2SCF_3$ | $CH_2CH_2CH_3$ | H | O | 0 |
| A-0926 | H | H | H | H | H | $CH_2CH_2SCH_2CF_3$ | $CH_2CH_2CH_3$ | H | O | 0 |
| A-0927 | H | H | H | H | H | $CH_2CH_2CH_2SCF_3$ | $CH_2CH_2CH_3$ | H | O | 0 |
| A-0928 | H | H | H | H | H | $CH_2CH_2CH_2SCH_2CF_3$ | $CH_2CH_2CH_3$ | H | O | 0 |
| A-0929 | H | H | H | H | H | $CH(CH_3)SCF_3$ | $CH_2CH_2CH_3$ | H | O | 0 |
| A-0930 | H | H | H | H | H | $CH(CH_3)SCH_2CF_3$ | $CH_2CH_2CH_3$ | H | O | 0 |
| A-0931 | H | H | H | H | H | $CH_2CH(CH_3)SCF_3$ | $CH_2CH_2CH_3$ | H | O | 0 |
| A-0932 | H | H | H | H | H | $CH_2CH(CH_3)SCH_2CF_3$ | $CH_2CH_2CH_3$ | H | O | 0 |
| A-0933 | H | H | H | H | H | $CH(CH_3)CH_2CH_2SCF_3$ | $CH_2CH_2CH_3$ | H | O | 0 |
| A-0934 | H | H | H | H | H | $CH(CH_3)CH_2CH_2SCH_2CF_3$ | $CH_2CH_2CH_3$ | H | O | 0 |
| A-0935 | H | H | H | H | H | $CH_2CH(CH_3)CH_2SCF_3$ | $CH_2CH_2CH_3$ | H | O | 0 |
| A-0936 | H | H | H | H | H | $CH_2CH(CH_3)CH_2SCH_2CF_3$ | $CH_2CH_2CH_3$ | H | O | 0 |
| A-0937 | H | H | H | H | H | $CH_2CH_2CH(CH)SCF_3$ | $CH_2CH_2CH_3$ | H | O | 0 |
| A-0938 | H | H | H | H | H | $CH_2CH_2CH(CH_3)SCH_2CF_3$ | $CH_2CH_2CH_3$ | H | O | 0 |
| A-0939 | H | H | H | H | H | $CH_2SOCF_3$ | $CH_2CH_2CH_3$ | H | O | 0 |
| A-0940 | H | H | H | H | H | $CH_2CH_2SOCF_3$ | $CH_2CH_2CH_3$ | H | O | 0 |
| A-0941 | H | H | H | H | H | $CH_2CH_2CH_2SOCF_3$ | $CH_2CH_2CH_3$ | H | O | 0 |
| A-0942 | H | H | H | H | H | $CH(CH_3)SOCF_3$ | $CH_2CH_2CH_3$ | H | O | 0 |
| A-0943 | H | H | H | H | H | $CH_2CH(CH_3)SOCF_3$ | $CH_2CH_2CH_3$ | H | O | 0 |
| A-0944 | H | H | H | H | H | $CH(CH_3)CH_2CH_2SOCF_3$ | $CH_2CH_2CH_3$ | H | O | 0 |
| A-0945 | H | H | H | H | H | $CH_2CH(CH_3)CH_2SOCF_3$ | $CH_2CH_2CH_3$ | H | O | 0 |
| A-0946 | H | H | H | H | H | $CH_2CH_2CH(CH_3)SOCF_3$ | $CH_2CH_2CH_3$ | H | O | 0 |
| A-0947 | H | H | H | H | H | $CH_2SO_2CF_3$ | $CH_2CH_2CH_3$ | H | O | 0 |
| A-0948 | H | H | H | H | H | $CH_2CH_2SO_2CF_3$ | $CH_2CH_2CH_3$ | H | O | 0 |
| A-0949 | H | H | H | H | H | $CH_2CH_2CH_2SO_2CF_3$ | $CH_2CH_2CH_3$ | H | O | 0 |
| A-0950 | H | H | H | H | H | $CH(CH_3)SO_2CF_3$ | $CH_2CH_2CH_3$ | H | O | 0 |
| A-0951 | H | H | H | H | H | $CH_2CH(CH_3)SO_2CF_3$ | $CH_2CH_2CH_3$ | H | O | 0 |
| A-0952 | H | H | H | H | H | $CH(CH_3)CH_2CH_2SO_2CF_3$ | $CH_2CH_2CH_3$ | H | O | 0 |
| A-0953 | H | H | H | H | H | $CH_2CH(CH_3)CH_2SO_2CF_3$ | $CH_2CH_2CH_3$ | H | O | 0 |
| A-0954 | H | H | H | H | H | $CH_2CH_2CH(CH_3)SO_2CF_3$ | $CH_2CH_2CH_3$ | H | O | 0 |
| A-0955 | H | H | H | H | H | $CH_2C(=O)CH_3$ | $CH_2CH_2CH_3$ | H | O | 0 |
| A-0956 | H | H | H | H | H | $CH_2C(=O)CH_2CH_3$ | $CH_2CH_2CH_3$ | H | O | 0 |
| A-0957 | H | H | H | H | H | $CH_2C(=O)C(CH_3)_3$ | $CH_2CH_2CH_3$ | H | O | 0 |
| A-0958 | H | H | H | H | H | $CH_2CH_2C(=O)CH_3$ | $CH_2CH_2CH_3$ | H | O | 0 |
| A-0959 | H | H | H | H | H | $CH_2CH_2C(=O)C(CH_3)_3$ | $CH_2CH_2CH_3$ | H | O | 0 |
| A-0960 | H | H | H | H | H | $CH_2C(=O)CF_3$ | $CH_2CH_2CH_3$ | H | O | 0 |
| A-0961 | H | H | H | H | H | $CH_2CH_2C(=O)CF_3$ | $CH_2CH_2CH_3$ | H | O | 0 |
| A-0962 | H | H | H | H | H | $CH_2C(=O)OCH_3$ | $CH_2CH_2CH_3$ | H | O | 0 |
| A-0963 | H | H | H | H | H | $CH_2C(=O)OCH_2CH_3$ | $CH_2CH_2CH_3$ | H | O | 0 |
| A-0964 | H | H | H | H | H | $CH_2C(=O)OC(CH_3)_3$ | $CH_2CH_2CH_3$ | H | O | 0 |
| A-0965 | H | H | H | H | H | $CH_2CH_2C(=O)OCH_3$ | $CH_2CH_2CH_3$ | H | O | 0 |
| A-0966 | H | H | H | H | H | $CH_2CH_2C(=O)OCH_2CH_3$ | $CH_2CH_2CH_3$ | H | O | 0 |
| A-0967 | H | H | H | H | H | $CH_2CH_2C(=O)OC(CH_3)_3$ | $CH_2CH_2CH_3$ | H | O | 0 |
| A-0968 | H | H | H | H | H | $CH_2C(=O)NH_2$ | $CH_2CH_2CH_3$ | H | O | 0 |
| A-0969 | H | H | H | H | H | $CH_2CH_2C(=O)NH_2$ | $CH_2CH_2CH_3$ | H | O | 0 |
| A-0970 | H | H | H | H | H | $CH_2C(=O)NHCH_3$ | $CH_2CH_2CH_3$ | H | O | 0 |
| A-0971 | H | H | H | H | H | $CH_2C(=O)NHCH(CH_3)_2$ | $CH_2CH_2CH_3$ | H | O | 0 |

TABLE 17

| Compound | R¹ | R² | R³ | R⁴ | R⁵ | R⁶ | R⁷ | R⁸ | X | n |
|---|---|---|---|---|---|---|---|---|---|---|
| A-0972 | H | H | H | H | H | $CH_2CH_2C(=O)NHCH_3$ | $CH_2CH_2CH_3$ | H | O | 0 |
| A-0973 | H | H | H | H | H | $CH_2CH_2C(=O)NHCH(CH_3)_2$ | $CH_2CH_2CH_3$ | H | O | 0 |
| A-0974 | H | H | H | H | H | $CH_2C(=O)NHCH_2CHF_2$ | $CH_2CH_2CH_3$ | H | O | 0 |
| A-0975 | H | H | H | H | H | $CH_2C(=O)NHCH_2CF_3$ | $CH_2CH_2CH_3$ | H | O | 0 |
| A-0976 | H | H | H | H | H | $CH_2CH_2C(=O)NHCH_2CHF_2$ | $CH_2CH_2CH_3$ | H | O | 0 |
| A-0977 | H | H | H | H | H | $CH_2CH_2C(=O)NHCH_2CF_3$ | $CH_2CH_2CH_3$ | H | O | 0 |
| A-0978 | H | H | H | H | H | $CH_2C(=O)N(CH3)_2$ | $CH_2CH_2CH_3$ | H | O | 0 |
| A-0979 | H | H | H | H | H | $CH_2C(=O)N(CH_2CH_3)_2$ | $CH_2CH_2CH_3$ | H | O | 0 |
| A-0980 | H | H | H | H | H | $CH_2CH_2C(=O)N(CH_3)_2$ | $CH_2CH_2CH_3$ | H | O | 0 |

TABLE 17-continued

| Compound | R¹ | R² | R³ | R⁴ | R⁵ | R⁶ | R⁷ | R⁸ | X | n |
|---|---|---|---|---|---|---|---|---|---|---|
| A-0981 | H | H | H | H | H | CH₂CH₂C(=O)N(CH₂CH₃)₂ | CH₂CH₂CH₃ | H | O | 0 |
| A-0982 | H | H | H | H | H | CH₂CH₂OH | CH₂CH₂CH₃ | H | O | 0 |
| A-0983 | H | H | H | H | H | CH₂CH(OH)CH₃ | CH₂CH₂CH₃ | H | O | 0 |
| A-0984 | H | H | H | H | H | CH₂CH₂CH₂OH | CH₂CH₂CH₃ | H | O | 0 |
| A-0985 | H | H | H | H | H | CH₂CH(OH)CH₂CH₃ | CH₂CH₂CH₃ | H | O | 0 |
| A-0986 | H | H | H | H | H | CH₂CH(OH)C(CH₃)₃ | CH₂CH₂CH₃ | H | O | 0 |
| A-0987 | H | H | H | H | H | CH₂CH₂CH(OH)CH₃ | CH₂CH₂CH₃ | H | O | 0 |
| A-0988 | H | H | H | H | H | CH₂CH₂CH(OH)C(CH₃)₃ | CH₂CH₂CH₃ | H | O | 0 |
| A-0989 | H | H | H | H | H | CH₂C(=NOH)CH₃ | CH₂CH₂CH₃ | H | O | 0 |
| A-0990 | H | H | H | H | H | CH₂C(=NOH)CH₂CH₃ | CH₂CH₂CH₃ | H | O | 0 |
| A-0991 | H | H | H | H | H | CH₂C(=NOH)C(CH₃)₃ | CH₂CH₂CH₃ | H | O | 0 |
| A-0992 | H | H | H | H | H | CH₂C(=NOCH₃)CH₃ | CH₂CH₂CH₃ | H | O | 0 |
| A-0993 | H | H | H | H | H | CH₂C(=NOCH₃)CH₂CH₃ | CH₂CH₂CH₃ | H | O | 0 |
| A-0994 | H | H | H | H | H | CH₂C(=NOCH₂CH₃)CH₃ | CH₂CH₂CH₃ | H | O | 0 |
| A-0995 | H | H | H | H | H | CH₂C(=NOCH₂CH₃)CH₂CH₃ | CH₂CH₂CH₃ | H | O | 0 |
| A-0996 | H | H | H | H | H | CH₂C(=NOCH₂CF₃)CH₃ | CH₂CH₂CH₃ | H | O | 0 |
| A-0997 | H | H | H | H | H | CH₂C(=NOCH₂CF₃)CH₂CH₃ | CH₂CH₂CH₃ | H | O | 0 |
| A-0998 | H | H | H | H | H | CH₂Ph | CH₂CH₂CH₃ | H | O | 0 |
| A-0999 | H | H | H | H | H | CH₂(2-F)Ph | CH₂CH₂CH₃ | H | O | 0 |
| A-1000 | H | H | H | H | H | CH₂(3-F)Ph | CH₂CH₂CH₃ | H | O | 0 |
| A-1001 | H | H | H | H | H | CH₂(4-F)Ph | CH₂CH₂CH₃ | H | O | 0 |
| A-1002 | H | H | H | H | H | CH₂(2-Cl)Ph | CH₂CH₂CH₃ | H | O | 0 |
| A-1003 | H | H | H | H | H | CH₂(3-Cl)Ph | CH₂CH₂CH₃ | H | O | 0 |
| A-1004 | H | H | H | H | H | CH₂(4-O)Ph | CH₂CH₂CH₃ | H | O | 0 |
| A-1005 | H | H | H | H | H | CH₂(2-CF₃)Ph | CH₂CH₂CH₃ | H | O | 0 |
| A-1006 | H | H | H | H | H | CH₂(3-CF₃)Ph | CH₂CH₂CH₃ | H | O | 0 |
| A-1007 | H | H | H | H | H | CH₂(4-CF₃)Ph | CH₂CH₂CH₃ | H | O | 0 |
| A-1008 | H | H | H | H | H | CH₂(naphthalen-1-yl) | CH₂CH₂CH₃ | H | O | 0 |
| A-1009 | H | H | H | H | H | CH₂(naphthalen-2-yl) | CH₂CH₂CH₃ | H | O | 0 |
| A-1010 | H | H | H | H | H | CH₂CH₂Ph | CH₂CH₂CH₃ | H | O | 0 |
| A-1011 | H | H | H | H | H | H | cyclopropyl | H | O | 0 |
| A-1012 | H | H | H | H | H | CH₃ | cyclopropyl | H | O | 0 |
| A-1013 | H | H | H | H | H | CH₂CH₃ | cyclopropyl | H | O | 0 |
| A-1014 | H | H | H | H | H | CH(CH₃)₂ | cyclopropyl | H | O | 0 |
| A-1015 | H | H | H | H | H | CH₂CH₂CH₃ | cyclopropyl | H | O | 0 |
| A-1016 | H | H | H | H | H | CH₂CH(CH₃)₂ | cyclopropyl | H | O | 0 |
| A-1017 | H | H | H | H | H | CH(CH₃)CH₂CH₃ | cyclopropyl | H | O | 0 |
| A-1018 | H | H | H | H | H | CH₂C(CH₃)₃ | cyclopropyl | H | O | 0 |
| A-1019 | H | H | H | H | H | CH₂(CH₂)₂CH₃ | cyclopropyl | H | O | 0 |
| A-1020 | H | H | H | H | H | CH₂(CH₂)₃CH₃ | cyclopropyl | H | O | 0 |
| A-1021 | H | H | H | H | H | CF₃ | cyclopropyl | H | O | 0 |
| A-1022 | H | H | H | H | H | CHF₂ | cyclopropyl | H | O | 0 |
| A-1023 | H | H | H | H | H | CH₂CF₃ | cyclopropyl | H | O | 0 |
| A-1024 | H | H | H | H | H | CH₂CHF₂ | cyclopropyl | H | O | 0 |
| A-1025 | H | H | H | H | H | CH₂CClF₂ | cyclopropyl | H | O | 0 |
| A-1026 | H | H | H | H | H | CH₂CBrF₂ | cyclopropyl | H | O | 0 |
| A-1027 | H | H | H | H | H | CF₂CF₃ | cyclopropyl | H | O | 0 |
| A-1028 | H | H | H | H | H | CF₂CHF₂ | cyclopropyl | H | O | 0 |
| A-1029 | H | H | H | H | H | CH₂CH₂CF₃ | cyclopropyl | H | O | 0 |
| A-1030 | H | H | H | H | H | CH₂CF₂CF₃ | cyclopropyl | H | O | 0 |
| A-1031 | H | H | H | H | H | CH₂CF₂CHF₂ | cyclopropyl | H | O | 0 |
| A-1032 | H | H | H | H | H | CF₂CHFCF₃ | cyclopropyl | H | O | 0 |

TABLE 18

| Compound | R¹ | R² | R³ | R⁴ | R⁵ | R⁶ | R⁷ | R⁸ | X | n |
|---|---|---|---|---|---|---|---|---|---|---|
| A-1033 | H | H | H | H | H | CF₂CF₂CF₃ | cyclopropyl | H | O | 0 |
| A-1034 | H | H | H | H | H | CH₂CF₂CF₂CF₃ | cyclopropyl | H | O | 0 |
| A-1035 | H | H | H | H | H | CH₂CF₂CHFCF₃ | cyclopropyl | H | O | 0 |
| A-1036 | H | H | H | H | H | CH₂CH₂CH₂CF₃ | cyclopropyl | H | O | 0 |
| A-1037 | H | H | H | H | H | CH₂CH₂CF₂CF₃ | cyclopropyl | H | O | 0 |
| A-1038 | H | H | H | H | H | CF₂CF₂CF₂CF₃ | cyclopropyl | H | O | 0 |
| A-1039 | H | H | H | H | H | CH₂CH₂CH(CF₃)₂ | cyclopropyl | H | O | 0 |
| A-1040 | H | H | H | H | H | CF₂CF₂CF₂CF₂CF₃ | cyclopropyl | H | O | 0 |
| A-1041 | H | H | H | H | H | CH₂CF₂CF₂CF₂CF₃ | cyclopropyl | H | O | 0 |
| A-1042 | H | H | H | H | H | CH₂CH₂CH₂CH₂CF₃ | cyclopropyl | H | O | 0 |
| A-1043 | H | H | H | H | H | CH₂CF₂CF₂CF₂CHF₂ | cyclopropyl | H | O | 0 |
| A-1044 | H | H | H | H | H | CH₂CH₂OCH₂CF₃ | cyclopropyl | H | O | 0 |
| A-1045 | H | H | H | H | H | CF₂CHFOCF₃ | cyclopropyl | H | O | 0 |
| A-1046 | H | H | H | H | H | CF₂CHFOCF₂CF₃ | cyclopropyl | H | O | 0 |
| A-1047 | H | H | H | H | H | CH₂CH₂CF=CF₂ | cyclopropyl | H | O | 0 |
| A-1048 | H | H | H | H | H | CH₂CH₂CH=CF₂ | cyclopropyl | H | O | 0 |
| A-1049 | H | H | H | H | H | CH₂C≡CCH₃ | cyclopropyl | H | O | 0 |
| A-1050 | H | H | H | H | H | CH₂C≡CCF₃ | cyclopropyl | H | O | 0 |

TABLE 18-continued

| Compound | R¹ | R² | R³ | R⁴ | R⁵ | R⁶ | R⁷ | R⁸ | X | n |
|---|---|---|---|---|---|---|---|---|---|---|
| A-1051 | H | H | H | H | H | $CH_2C\equiv CI$ | cyclopropyl | H | O | 0 |
| A-1052 | H | H | H | H | H | $CH_2(2,2\text{-difluorocyclopropyl})$ | cyclopropyl | H | O | 0 |
| A-1053 | H | H | H | H | H | $CH_2(2,2\text{-dichlorocyclopropyl})$ | cyclopropyl | H | O | 0 |
| A-1054 | H | H | H | H | H | $CH_2CH_2(2,2\text{-difluorocyclopropyl})$ | cyclopropyl | H | O | 0 |
| A-1055 | H | H | H | H | H | $CH_2CH_2(2,2\text{-dichlorocyclopropyl})$ | cyclopropyl | H | O | 0 |
| A-1056 | H | H | H | H | H | $CH_2SCH_3$ | cyclopropyl | H | O | 0 |
| A-1057 | H | H | H | H | H | $CH_2SCH_2CH_3$ | cyclopropyl | H | O | 0 |
| A-1058 | H | H | H | H | H | $CH_2CH_2SCH_3$ | cyclopropyl | H | O | 0 |
| A-1059 | H | H | H | H | H | $CH_2SOCH_3$ | cyclopropyl | H | O | 0 |
| A-1060 | H | H | H | H | H | $CH_2CH_2SOCH_3$ | cyclopropyl | H | O | 0 |
| A-1061 | H | H | H | H | H | $CH_2SO_2CH_3$ | cyclopropyl | H | O | 0 |
| A-1062 | H | H | H | H | H | $CH_2CH_2SO_2CH_3$ | cyclopropyl | H | O | 0 |
| A-1063 | H | H | H | H | H | $CH_2SCF_3$ | cyclopropyl | H | O | 0 |
| A-1064 | H | H | H | H | H | $CH_2SCHF_2$ | cyclopropyl | H | O | 0 |
| A-1065 | H | H | H | H | H | $CH_2SCH_2CF_3$ | cyclopropyl | H | O | 0 |
| A-1066 | H | H | H | H | H | $CH_2SCH_2CHF_2$ | cyclopropyl | H | O | 0 |
| A-1067 | H | H | H | H | H | $CH_2SCF_2CF_3$ | cyclopropyl | H | O | 0 |
| A-1068 | H | H | H | H | H | $CH_2CH_2SCF_3$ | cyclopropyl | H | O | 0 |
| A-1069 | H | H | H | H | H | $CH_2SOCF_3$ | cyclopropyl | H | O | 0 |
| A-1070 | H | H | H | H | H | $CH_2CH_2SOCF_3$ | cyclopropyl | H | O | 0 |
| A-1071 | H | H | H | H | H | $CH_2CH_2CH_2SOCF_3$ | cyclopropyl | H | O | 0 |
| A-1072 | H | H | H | H | H | $CH_2SO_2CF_3$ | cyclopropyl | H | O | 0 |
| A-1073 | H | H | H | H | H | $CH_2CH_2SO_2CF_3$ | cyclopropyl | H | O | 0 |
| A-1074 | H | H | H | H | H | $CH_2CH_2CH_2SO_2CF_3$ | cyclopropyl | H | O | 0 |
| A-1075 | H | H | H | H | H | $CH_2C(=O)NHCH_2CHF_2$ | cyclopropyl | H | O | 0 |
| A-1076 | H | H | H | H | H | $CH_2C(=O)NHCH_2CF_3$ | cyclopropyl | H | O | 0 |
| A-1077 | H | H | H | H | H | H | $CH_2C\equiv CH$ | H | O | 0 |
| A-1078 | H | H | H | H | H | $CH_3$ | $CH_2C\equiv CH$ | H | O | 0 |
| A-1079 | H | H | H | H | H | $CH_2CH_3$ | $CH_2C\equiv CH$ | H | O | 0 |
| A-1080 | H | H | H | H | H | $CH(CH_3)_2$ | $CH_2C\equiv CH$ | H | O | 0 |
| A-1081 | H | H | H | H | H | $CH_2CH_2CH_3$ | $CH_2C\equiv CH$ | H | O | 0 |
| A-1082 | H | H | H | H | H | $CH_2CH(CH_3)_2$ | $CH_2C\equiv CH$ | H | O | 0 |
| A-1083 | H | H | H | H | H | $CH(CH_3)CH_2CH_3$ | $CH_2C\equiv CH$ | H | O | 0 |
| A-1084 | H | H | H | H | H | $CH_2C(CH_3)_3$ | $CH_2C\equiv CH$ | H | O | 0 |
| A-1085 | H | H | H | H | H | $CH_2(CH_2)_2CH_3$ | $CH_2C\equiv CH$ | H | O | 0 |
| A-1086 | H | H | H | H | H | $CH_2(CH_2)_3CH_3$ | $CH_2C\equiv CH$ | H | O | 0 |
| A-1087 | H | H | H | H | H | $CH_2(CH2)_4CH_3$ | $CH_2C\equiv CH$ | H | O | 0 |
| A-1088 | H | H | H | H | H | $CH_2(CH_2)_6CH_3$ | $CH_2C\equiv CH$ | H | O | 0 |
| A-1089 | H | H | H | H | H | $CH_2OCH_3$ | $CH_2C\equiv CH$ | H | O | 0 |
| A-1090 | H | H | H | H | H | $CH_2OCH_2CH_3$ | $CH_2C\equiv CH$ | H | O | 0 |
| A-1091 | H | H | H | H | H | $CH_2CH_2OCH_3$ | $CH_2C\equiv CH$ | H | O | 0 |
| A-1092 | H | H | H | H | H | $CH_2CH_2OCH_2CH_3$ | $CH_2C\equiv CH$ | H | O | 0 |
| A-1093 | H | H | H | H | H | $CF_3$ | $CH_2C\equiv CH$ | H | O | 0 |

TABLE 19

| Compound | R¹ | R² | R³ | R⁴ | R⁵ | R⁶ | R⁷ | R⁸ | X | n |
|---|---|---|---|---|---|---|---|---|---|---|
| A-1094 | H | H | H | H | H | $CHF_2$ | $CH_2C\equiv CH$ | H | O | 0 |
| A-1095 | H | H | H | H | H | $CH_2CF_3$ | $CH_2C\equiv CH$ | H | O | 0 |
| A-1096 | H | H | H | H | H | $CH_2CHF_2$ | $CH_2C\equiv CH$ | H | O | 0 |
| A-1097 | H | H | H | H | H | $CH_2CClF_2$ | $CH_2C\equiv CH$ | H | O | 0 |
| A-1098 | H | H | H | H | H | $CH_2CBrF_2$ | $CH_2C\equiv CH$ | H | O | 0 |
| A-1099 | H | H | H | H | H | $CF_2CF_3$ | $CH_2C\equiv CH$ | H | O | 0 |
| A-1100 | H | H | H | H | H | $CF_2CHF_2$ | $CH_2C\equiv CH$ | H | O | 0 |
| A-1101 | H | H | H | H | H | $CH_2CH_2CF_3$ | $CH_2C\equiv CH$ | H | O | 0 |
| A-1102 | H | H | H | H | H | $CH_2CF_2CF_3$ | $CH_2C\equiv CH$ | H | O | 0 |
| A-1103 | H | H | H | H | H | $CH_2CF_2CHF_2$ | $CH_2C\equiv CH$ | H | O | 0 |
| A-1104 | H | H | H | H | H | $CF_2CHFCF_3$ | $CH_2C\equiv CH$ | H | O | 0 |
| A-1105 | H | H | H | H | H | $CF_2CF_2CF_3$ | $CH_2C\equiv CH$ | H | O | 0 |
| A-1106 | H | H | H | H | H | $CH_2CF_2CF_2CF_3$ | $CH_2C\equiv CH$ | H | O | 0 |
| A-1107 | H | H | H | H | H | $CH_2CF_2CHFCF_3$ | $CH_2C\equiv CH$ | H | O | 0 |
| A-1108 | H | H | H | H | H | $CH_2CH_2CH_2CF_3$ | $CH_2C\equiv CH$ | H | O | 0 |
| A-1109 | H | H | H | H | H | $CH_2CH_2CF_2CF_3$ | $CH_2C\equiv CH$ | H | O | 0 |
| A-1110 | H | H | H | H | H | $CF_2CF_2CF_2CF_3$ | $CH_2C\equiv CH$ | H | O | 0 |
| A-1111 | H | H | H | H | H | $CH_2CH_2CH(CF_3)_2$ | $CH_2C\equiv CH$ | H | O | 0 |
| A-1112 | H | H | H | H | H | $CF_2CF_2CF_2CF_2CF_3$ | $CH_2C\equiv CH$ | H | O | 0 |
| A-1113 | H | H | H | H | H | $CH_2CF_2CF_2CF_2CF_3$ | $CH_2C\equiv CH$ | H | O | 0 |
| A-1114 | H | H | H | H | H | $CH_2CH_2CH_2CH_2CF_3$ | $CH_2C\equiv CH$ | H | O | 0 |
| A-1115 | H | H | H | H | H | $CF_2CF_2CF_2CF_2CHF_2$ | $CH_2C\equiv CH$ | H | O | 0 |
| A-1116 | H | H | H | H | H | $CH_2CF_2CF(CF_3)CF_2C(CF_3)_3$ | $CH_2C\equiv CH$ | H | O | 0 |
| A-1117 | H | H | H | H | H | $CF_2CHFOCH_3$ | $CH_2C\equiv CH$ | H | O | 0 |
| A-1118 | H | H | H | H | H | $CF_2CHFOCH_2CH_3$ | $CH_2C\equiv CH$ | H | O | 0 |
| A-1119 | H | H | H | H | H | $CH_2CH_2OCH_2CF_3$ | $CH_2C\equiv CH$ | H | O | 0 |
| A-1120 | H | H | H | H | H | $CF_2CHFOCF_3$ | $CH_2C\equiv CH$ | H | O | 0 |

TABLE 19-continued

| Compound | R¹ | R² | R³ | R⁴ | R⁵ | R⁶ | R⁷ | R⁸ | X | n |
|---|---|---|---|---|---|---|---|---|---|---|
| A-1121 | H | H | H | H | H | CF$_2$CHFOCF$_2$CF$_3$ | CH$_2$C≡CH | H | O | 0 |
| A-1122 | H | H | H | H | H | CF$_2$CHFOCF$_2$CF$_3$ | CH$_2$C≡CH | H | O | 0 |
| A-1123 | H | H | H | H | H | CH$_2$CH═CH$_2$ | CH$_2$C≡CH | H | O | 0 |
| A-1124 | H | H | H | H | H | CH$_2$CH═CHCl | CH$_2$C≡CH | H | O | 0 |
| A-1125 | H | H | H | H | H | CH$_2$CH═CCl$_2$ | CH$_2$C≡CH | H | O | 0 |
| A-1126 | H | H | H | H | H | CH$_2$CH$_2$CF═CF$_2$ | CH$_2$C≡CH | H | O | 0 |
| A-1127 | H | H | H | H | H | CH$_2$CH$_2$CH═CF$_2$ | CH$_2$C≡CH | H | O | 0 |
| A-1128 | H | H | H | H | H | CH$_2$C≡CH | CH$_2$C≡CH | H | O | 0 |
| A-1129 | H | H | H | H | H | CH$_2$C≡CCH$_3$ | CH$_2$C≡CH | H | O | 0 |
| A-1130 | H | H | H | H | H | CH$_2$C≡CCF$_3$ | CH$_2$C≡CH | H | O | 0 |
| A-1131 | H | H | H | H | H | CH$_2$C≡Cl | CH$_2$C≡CH | H | O | 0 |
| A-1132 | H | H | H | H | H | cyclobutyl | CH$_2$C≡CH | H | O | 0 |
| A-1133 | H | H | H | H | H | cyclopentyl | CH$_2$C≡CH | H | O | 0 |
| A-1134 | H | H | H | H | H | cyclohexyl | CH$_2$C≡CH | H | O | 0 |
| A-1135 | H | H | H | H | H | 4,4-difluorocyohexyl | CH$_2$C≡CH | H | O | 0 |
| A-1136 | H | H | H | H | H | CH$_2$(cyclopropyl) | CH$_2$C≡CH | H | O | 0 |
| A-1137 | H | H | H | H | H | CH$_2$(cyclobutyl) | CH$_2$C≡CH | H | O | 0 |
| A-1138 | H | H | H | H | H | CH$_2$(cyclopentyl) | CH$_2$C≡CH | H | O | 0 |
| A-1139 | H | H | H | H | H | CH$_2$CH$_2$(cyclopropyl) | CH$_2$C≡CH | H | O | 0 |
| A-1140 | H | H | H | H | H | CH$_2$(2,2-difluorocyclopropyl) | CH$_2$C≡CH | H | O | 0 |
| A-1141 | H | H | H | H | H | CH$_2$(2,2-dichlorocyclopropyl) | CH$_2$C≡CH | H | O | 0 |
| A-1142 | H | H | H | H | H | CH$_2$(4,4-difluorocyclohexyl) | CH$_2$C≡CH | H | O | 0 |
| A-1143 | H | H | H | H | H | CH$_2$CH$_2$(2,2-difluorocyclopropyl) | CH$_2$C≡CH | H | O | 0 |
| A-1144 | H | H | H | H | H | CH$_2$CH$_2$(2,2-dichlorocyclopropyl) | CH$_2$C≡CH | H | O | 0 |
| A-1145 | H | H | H | H | H | CH$_2$SCH$_3$ | CH$_2$C≡CH | H | O | 0 |
| A-1146 | H | H | H | H | H | CH$_2$SCH$_2$CH$_3$ | CH$_2$C≡CH | H | O | 0 |
| A-1147 | H | H | H | H | H | CH$_2$CH$_2$SCH$_3$ | CH$_2$C≡CH | H | O | 0 |
| A-1148 | H | H | H | H | H | CH$_2$CH$_2$SCH$_2$CH$_3$ | CH$_2$C≡CH | H | O | 0 |
| A-1149 | H | H | H | H | H | CH$_2$CH$_2$CH$_2$SCH$_3$ | CH$_2$C≡CH | H | O | 0 |
| A-1150 | H | H | H | H | H | CH$_2$CH$_2$CH$_2$SCH$_2$CH$_3$ | CH$_2$C≡CH | H | O | 0 |
| A-1151 | H | H | H | H | H | CH(CH$_3$)SCH$_3$ | CH$_2$C≡CH | H | O | 0 |
| A-1152 | H | H | H | H | H | CH(CH$_3$)SCH$_2$CH$_3$ | CH$_2$C≡CH | H | O | 0 |
| A-1153 | H | H | H | H | H | CH$_2$CH(CH$_3$)SCH$_3$ | CH$_2$C≡CH | H | O | 0 |
| A-1154 | H | H | H | H | H | CH$_2$CH(CH$_3$)SCH$_2$CH$_3$ | CH$_2$C≡CH | H | O | 0 |

TABLE 20

| Compound | R¹ | R² | R³ | R⁴ | R⁵ | R⁶ | R⁷ | R⁸ | X | n |
|---|---|---|---|---|---|---|---|---|---|---|
| A-1155 | H | H | H | H | H | CH(CH$_3$)CH$_2$CH$_2$SCH$_3$ | CH$_2$C≡CH | H | O | 0 |
| A-1156 | H | H | H | H | H | CH(CH$_3$)CH$_2$CH$_2$SCH$_2$CH$_3$ | CH$_2$C≡CH | H | O | 0 |
| A-1157 | H | H | H | H | H | CH$_2$CH(CH$_3$)CH$_2$SCH$_3$ | CH$_2$C≡CH | H | O | 0 |
| A-1158 | H | H | H | H | H | CH$_2$CH(CH$_3$)CH$_2$SCH$_2$CH$_3$ | CH$_2$C≡CH | H | O | 0 |
| A-1159 | H | H | H | H | H | CH$_2$CH$_2$CH(CH)SCH$_3$ | CH$_2$C≡CH | H | O | 0 |
| A-1160 | H | H | H | H | H | CH$_2$CH$_2$CH(CH$_3$)SCH$_2$CH$_3$ | CH$_2$C≡CH | H | O | 0 |
| A-1161 | H | H | H | H | H | CH$_2$SOCH$_3$ | CH$_2$C≡CH | H | O | 0 |
| A-1162 | H | H | H | H | H | CH$_2$CH$_2$SOCH$_3$ | CH$_2$C≡CH | H | O | 0 |
| A-1163 | H | H | H | H | H | CH$_2$CH$_2$CH$_2$SOCH$_3$ | CH$_2$C≡CH | H | O | 0 |
| A-1164 | H | H | H | H | H | CH(CH$_3$)SOCH$_3$ | CH$_2$C≡CH | H | O | 0 |
| A-1165 | H | H | H | H | H | CH$_2$CH(CH$_3$)SOCH$_3$ | CH$_2$C≡CH | H | O | 0 |
| A-1166 | H | H | H | H | H | CH(CH$_3$)CH$_2$CH$_2$SOCH$_3$ | CH$_2$C≡CH | H | O | 0 |
| A-1167 | H | H | H | H | H | CH$_2$CH(CH$_3$)CH$_2$SOCH$_3$ | CH$_2$C≡CH | H | O | 0 |
| A-1168 | H | H | H | H | H | CH$_2$CH$_2$CH(OH$_3$)SOCH$_3$ | CH$_2$C≡CH | H | O | 0 |
| A-1169 | H | H | H | H | H | CH$_2$SO$_2$CH$_3$ | CH$_2$C≡CH | H | O | 0 |
| A-1170 | H | H | H | H | H | CH$_2$CH$_2$SO$_2$CH$_3$ | CH$_2$C≡CH | H | O | 0 |
| A-1171 | H | H | H | H | H | CH$_2$CH$_2$CH$_2$SO$_2$CH$_3$ | CH$_2$C≡CH | H | O | 0 |
| A-1172 | H | H | H | H | H | CH(CH$_3$)SO$_2$CH$_3$ | CH$_2$C≡CH | H | O | 0 |
| A-1173 | H | H | H | H | H | CH$_2$CH(CH$_3$)SO$_2$CH$_3$ | CH$_2$C≡CH | H | O | 0 |
| A-1174 | H | H | H | H | H | CH(CH$_3$)CH$_2$CH$_2$SO$_2$CH$_3$ | CH$_2$C≡CH | H | O | 0 |
| A-1175 | H | H | H | H | H | CH$_2$CH(CH$_3$)CH$_2$SO$_2$CH$_3$ | CH$_2$C≡CH | H | O | 0 |
| A-1176 | H | H | H | H | H | CH$_2$CH$_2$CH(CH$_3$)SO$_2$CH$_3$ | CH$_2$C≡CH | H | O | 0 |
| A-1177 | H | H | H | H | H | CH$_2$SCF$_3$ | CH$_2$C≡CH | H | O | 0 |
| A-1178 | H | H | H | H | H | CH$_2$SCHF$_2$ | CH$_2$C≡CH | H | O | 0 |
| A-1179 | H | H | H | H | H | CH$_2$SCH$_2$CF$_3$ | CH$_2$C≡CH | H | O | 0 |
| A-1180 | H | H | H | H | H | CH$_2$SCH$_2$CHF$_2$ | CH$_2$C≡CH | H | O | 0 |
| A-1181 | H | H | H | H | H | CH$_2$SCF$_2$CF$_3$ | CH$_2$C≡CH | H | O | 0 |
| A-1182 | H | H | H | H | H | CH$_2$CH$_2$SCF$_3$ | CH$_2$C≡CH | H | O | 0 |
| A-1183 | H | H | H | H | H | CH$_2$CH$_2$SCH$_2$CF$_3$ | CH$_2$C≡CH | H | O | 0 |
| A-1184 | H | H | H | H | H | CH$_2$CH$_2$CH$_2$SCF$_3$ | CH$_2$C≡CH | H | O | 0 |
| A-1185 | H | H | H | H | H | CH$_2$CH$_2$CH$_2$SCH$_2$CF$_3$ | CH$_2$C≡CH | H | O | 0 |
| A-1186 | H | H | H | H | H | CH(CH$_3$)SCF$_3$ | CH$_2$C≡CH | H | O | 0 |
| A-1187 | H | H | H | H | H | CH(CH$_3$)SCH$_2$CF$_3$ | CH$_2$C≡CH | H | O | 0 |
| A-1188 | H | H | H | H | H | CH$_2$CH(CH$_3$)SCF$_3$ | CH$_2$C≡CH | H | O | 0 |

TABLE 20-continued

| Compound | R¹ | R² | R³ | R⁴ | R⁵ | R⁶ | R⁷ | R⁸ | X | n |
|---|---|---|---|---|---|---|---|---|---|---|
| A-1189 | H | H | H | H | H | $CH_2CH(CH_3)SCH_2CF_3$ | $CH_2C{\equiv}CH$ | H | O | 0 |
| A-1190 | H | H | H | H | H | $CH(CH_3)CH_2CH_2SCF_3$ | $CH_2C{\equiv}CH$ | H | O | 0 |
| A-1191 | H | H | H | H | H | $CH(CH_3)CH_2CH_2SCH_2CF_3$ | $CH_2C{\equiv}CH$ | H | O | 0 |
| A-1192 | H | H | H | H | H | $CH_2CH(CH_3)CH_2SCF_3$ | $CH_2C{\equiv}CH$ | H | O | 0 |
| A-1193 | H | H | H | H | H | $CH_2CH(CH_3)CH_2SCH_2CF_3$ | $CH_2C{\equiv}CH$ | H | O | 0 |
| A-1194 | H | H | H | H | H | $CH_2CH_2CH(CH_3)SCF_3$ | $CH_2C{\equiv}CH$ | H | O | 0 |
| A-1195 | H | H | H | H | H | $CH_2CH_2CH(CH_3)SCH_2CF_3$ | $CH_2C{\equiv}CH$ | H | O | 0 |
| A-1196 | H | H | H | H | H | $CH_2SOCF_3$ | $CH_2C{\equiv}CH$ | H | O | 0 |
| A-1197 | H | H | H | H | H | $CH_2CH_2SOCF_3$ | $CH_2C{\equiv}CH$ | H | O | 0 |
| A-1198 | H | H | H | H | H | $CH_2CH_2CH_2SOCF_3$ | $CH_2C{\equiv}CH$ | H | O | 0 |
| A-1199 | H | H | H | H | H | $CH(CH_3)SOCF_3$ | $CH_2C{\equiv}CH$ | H | O | 0 |
| A-1200 | H | H | H | H | H | $CH_2CH(CH_3)SOCF_3$ | $CH_2C{\equiv}CH$ | H | O | 0 |
| A-1201 | H | H | H | H | H | $CH(CH_3)CH_2CH_2SOCF_3$ | $CH_2C{\equiv}CH$ | H | O | 0 |
| A-1202 | H | H | H | H | H | $CH_2CH(CH_3)CH_2SOCF_3$ | $CH_2C{\equiv}CH$ | H | O | 0 |
| A-1203 | H | H | H | H | H | $CH_2CH2CH(CH_3)SOCF_3$ | $CH_2C{\equiv}CH$ | H | O | 0 |
| A-1204 | H | H | H | H | H | $CH_2SO_2CF_3$ | $CH_2C{\equiv}CH$ | H | O | 0 |
| A-1205 | H | H | H | H | H | $CH_2CH_2SO_2CF_3$ | $CH_2C{\equiv}CH$ | H | O | 0 |
| A-1206 | H | H | H | H | H | $CH_2CH_2CH_2SO_2CF_3$ | $CH_2C{\equiv}CH$ | H | O | 0 |
| A-1207 | H | H | H | H | H | $CH(CH_3)SO_2CF_3$ | $CH_2C{\equiv}CH$ | H | O | 0 |
| A-1208 | H | H | H | H | H | $CH_2CH(CH_3)SO_2CF_3$ | $CH_2C{\equiv}CH$ | H | O | 0 |
| A-1209 | H | H | H | H | H | $CH(CH_3)CH_2CH_2SO_2CF_3$ | $CH_2C{\equiv}CH$ | H | O | 0 |
| A-1210 | H | H | H | H | H | $CH_2CH(CH_3)CH_2SO_2CF_3$ | $CH_2C{\equiv}CH$ | H | O | 0 |
| A-1211 | H | H | H | H | H | $CH_2CH_2CH(CH_3)SO_2CF_3$ | $CH_2C{\equiv}CH$ | H | O | 0 |
| A-1212 | H | H | H | H | H | $CH_2C({=}O)CH_3$ | $CH_2C{\equiv}CH$ | H | O | 0 |
| A-1213 | H | H | H | H | H | $CH_2C({=}O)CH_2CH_3$ | $CH_2C{\equiv}CH$ | H | O | 0 |
| A-1214 | H | H | H | H | H | $CH_2C({=}O)C(CH_3)_3$ | $CH_2C{\equiv}CH$ | H | O | 0 |
| A-1215 | H | H | H | H | H | $CH_2CH_2C({=}O)CH_3$ | $CH_2C{\equiv}CH$ | H | O | 0 |

TABLE 21

| Compound | R¹ | R² | R³ | R⁴ | R⁵ | R⁶ | R⁷ | R⁸ | X | n |
|---|---|---|---|---|---|---|---|---|---|---|
| A-1216 | H | H | H | H | H | $CH_2CH_2C({=}O)C(CH_3)_3$ | $CH_2C{\equiv}CH$ | H | O | 0 |
| A-1217 | H | H | H | H | H | $CH_2C({=}O)CF_3$ | $CH_2C{\equiv}CH$ | H | O | 0 |
| A-1218 | H | H | H | H | H | $CH_2CH_2C({=}O)CF_3$ | $CH_2C{\equiv}CH$ | H | O | 0 |
| A-1219 | H | H | H | H | H | $CH_2C({=}O)OCH_3$ | $CH_2C{\equiv}CH$ | H | O | 0 |
| A-1220 | H | H | H | H | H | $CH_2C({=}O)OCH_2CH_3$ | $CH_2C{\equiv}CH$ | H | O | 0 |
| A-1221 | H | H | H | H | H | $CH_2C({=}O)OC(CH_3)_3$ | $CH_2C{\equiv}CH$ | H | O | 0 |
| A-1222 | H | H | H | H | H | $CH_2CH_2C({=}O)OCH_3$ | $CH_2C{\equiv}CH$ | H | O | 0 |
| A-1223 | H | H | H | H | H | $CH_2CH_2C({=}O)OCH_2CH_3$ | $CH_2C{\equiv}CH$ | H | O | 0 |
| A-1224 | H | H | H | H | H | $CH_2CH_2C({=}O)OC(CH_3)_3$ | $CH_2C{\equiv}CH$ | H | O | 0 |
| A-1225 | H | H | H | H | H | $CH_2C({=}O)NH_2$ | $CH_2C{\equiv}CH$ | H | O | 0 |
| A-1226 | H | H | H | H | H | $CH_2CH_2C({=}O)NH_2$ | $CH_2C{\equiv}CH$ | H | O | 0 |
| A-1227 | H | H | H | H | H | $CH_2C({=}O)NHCH_3$ | $CH_2C{\equiv}CH$ | H | O | 0 |
| A-1228 | H | H | H | H | H | $CH_2C({=}O)NHCH(CH_3)_2$ | $CH_2C{\equiv}CH$ | H | O | 0 |
| A-1229 | H | H | H | H | H | $CH_2CH_2C({=}O)NHCH_3$ | $CH_2C{\equiv}CH$ | H | O | 0 |
| A-1230 | H | H | H | H | H | $CH_2CH_2C({=}O)NHCH(CH_3)_2$ | $CH_2C{\equiv}CH$ | H | O | 0 |
| A-1231 | H | H | H | H | H | $CH_2C({=}O)NHCH_2CHF_2$ | $CH_2C{\equiv}CH$ | H | O | 0 |
| A-1232 | H | H | H | H | H | $CH_2C({=}O)NHCH_2CF_3$ | $CH_2C{\equiv}CH$ | H | O | 0 |
| A-1233 | H | H | H | H | H | $CH_2CH_2C({=}O)NHCH_2CHF_2$ | $CH_2C{\equiv}CH$ | H | O | 0 |
| A-1234 | H | H | H | H | H | $CH_2CH_2C({=}O)NHCH_2CF_3$ | $CH_2C{\equiv}CH$ | H | O | 0 |
| A-1235 | H | H | H | H | H | $CH_2C({=}O)N(CH_3)_2$ | $CH_2C{\equiv}CH$ | H | O | 0 |
| A-1236 | H | H | H | H | H | $CH_2C({=}O)N(CH_2CH_3)_2$ | $CH_2C{\equiv}CH$ | H | O | 0 |
| A-1237 | H | H | H | H | H | $CH_2CH_2C({=}O)N(CH3)_2$ | $CH_2C{\equiv}CH$ | H | O | 0 |
| A-1238 | H | H | H | H | H | $CH_2CH_2C({=}O)N(CH_2CH3)_2$ | $CH_2C{\equiv}CH$ | H | O | 0 |
| A-1239 | H | H | H | H | H | $CH_2CH_2OH$ | $CH_2C{\equiv}CH$ | H | O | 0 |
| A-1240 | H | H | H | H | H | $CH_2CH(OH)CH_3$ | $CH_2C{\equiv}CH$ | H | O | 0 |
| A-1241 | H | H | H | H | H | $CH_2CH2CH_2OH$ | $CH_2C{\equiv}CH$ | H | O | 0 |
| A-1242 | H | H | H | H | H | $CH_2CH(OH)CH_2CH_3$ | $CH_2C{\equiv}CH$ | H | O | 0 |
| A-1243 | H | H | H | H | H | $CH_2CH(OH)C(CH_3)_3$ | $CH_2C{\equiv}CH$ | H | O | 0 |
| A-1244 | H | H | H | H | H | $CH_2CH_2CH(OH)CH_3$ | $CH_2C{\equiv}CH$ | H | O | 0 |
| A-1245 | H | H | H | H | H | $CH_2CH_2CH(OH)C(CH3)_3$ | $CH_2C{\equiv}CH$ | H | O | 0 |
| A-1246 | H | H | H | H | H | $CH_2C({=}NOH)CH_3$ | $CH_2C{\equiv}CH$ | H | O | 0 |
| A-1247 | H | H | H | H | H | $CH_2C({=}NOH)CH_2CH_3$ | $CH_2C{\equiv}CH$ | H | O | 0 |
| A-1248 | H | H | H | H | H | $CH_2C({=}NOH)C(CH_2)_3$ | $CH_2C{\equiv}CH$ | H | O | 0 |
| A-1249 | H | H | H | H | H | $CH_2C({=}NOCH_3)CH_3$ | $CH_2C{\equiv}CH$ | H | O | 0 |
| A-1250 | H | H | H | H | H | $CH_2C({=}NOCH_3)CH_2CH_3$ | $CH_2C{\equiv}CH$ | H | O | 0 |
| A-1251 | H | H | H | H | H | $CH_2C({=}NOCH_2CH_3)CH3$ | $CH_2C{\equiv}CH$ | H | O | 0 |
| A-1252 | H | H | H | H | H | $CH_2C({=}NOCHXH_3)CH_2CH_3$ | $CH_2C{\equiv}CH$ | H | O | 0 |
| A-1253 | H | H | H | H | H | $CH_2C({=}NOCH_2CF_3)CH_3$ | $CH_2C{\equiv}CH$ | H | O | 0 |
| A-1254 | H | H | H | H | H | $CH_2C({=}NOCH_2CF_3)CH_2CH_3$ | $CH_2C{\equiv}CH$ | H | O | 0 |
| A-1255 | H | H | H | H | H | $CH_2Ph$ | $CH_2C{\equiv}CH$ | H | O | 0 |
| A-1256 | H | H | H | H | H | $CH_2(2\text{-}F)Ph$ | $CH_2C{\equiv}CH$ | H | O | 0 |
| A-1257 | H | H | H | H | H | $CH_2(3\text{-}F)Ph$ | $CH_2C{\equiv}CH$ | H | O | 0 |
| A-1258 | H | H | H | H | H | $CH_2(4\text{-}F)Ph$ | $CH_2C{\equiv}CH$ | H | O | 0 |

TABLE 21-continued

| Compound | R¹ | R² | R³ | R⁴ | R⁵ | R⁶ | R⁷ | R⁸ | X | n |
|---|---|---|---|---|---|---|---|---|---|---|
| A-1259 | H | H | H | H | H | CH$_2$(2-Cl)Ph | CH$_2$C≡CH | H | O | 0 |
| A-1260 | H | H | H | H | H | CH$_2$(3-Cl)Ph | CH$_2$C≡CH | H | O | 0 |
| A-1261 | H | H | H | H | H | CH$_2$(4-Cl)Ph | CH$_2$C≡CH | H | O | 0 |
| A-1262 | H | H | H | H | H | CH$_2$(2-CF$_3$)Ph | CH$_2$C≡CH | H | O | 0 |
| A-1263 | H | H | H | H | H | CH$_2$(3-CF$_3$)Ph | CH$_2$C≡CH | H | O | 0 |
| A-1264 | H | H | H | H | H | CH$_2$(4-CF$_3$)Ph | CH$_2$C≡CH | H | O | 0 |
| A-1265 | H | H | H | H | H | CH$_2$(naphthalen-1-yl) | CH$_2$C≡CH | H | O | 0 |
| A-1266 | H | H | H | H | H | CH$_2$(naplithalen-2-yl) | CH$_2$C≡CH | H | O | 0 |
| A-1267 | H | H | H | H | H | CH$_2$CH$_2$Ph | CH$_2$C≡CH | H | O | 0 |
| A-1268 | H | H | H | H | H | H | OH | H | O | 0 |
| A-1269 | H | H | H | H | H | CH$_3$ | OH | H | O | 0 |
| A-1270 | H | H | H | H | H | CH$_2$CH$_3$ | OH | H | O | 0 |
| A-1271 | H | H | H | H | H | CH(CH$_3$)$_2$ | OH | H | O | 0 |
| A-1272 | H | H | H | H | H | CH$_2$CH$_2$CH$_3$ | OH | H | O | 0 |
| A-1273 | H | H | H | H | H | CH$_2$CH(CH$_3$)$_2$ | OH | H | O | 0 |
| A-1274 | H | H | H | H | H | CH(CH$_3$)CH$_2$CH$_3$ | OH | H | O | 0 |
| A-1275 | H | H | H | H | H | CH$_2$C(CH$_3$)$_3$ | OH | H | O | 0 |
| A-1276 | H | H | H | H | H | CH$_2$(CH$_2$)$_2$CH$_2$ | OH | H | O | 0 |

TABLE 22

| Compound | R¹ | R² | R³ | R⁴ | R⁵ | R⁶ | R⁷ | R⁸ | X | n |
|---|---|---|---|---|---|---|---|---|---|---|
| A-1277 | H | H | H | H | H | CH$_2$(CH$_2$)$_3$CH$_3$ | OH | H | O | 0 |
| A-1278 | H | H | H | H | H | CF$_3$ | OH | H | O | 0 |
| A-1279 | H | H | H | H | H | CHF$_2$ | OH | H | O | 0 |
| A-1280 | H | H | H | H | H | CH$_2$CF$_3$ | OH | H | O | 0 |
| A-1281 | H | H | H | H | H | CH$_2$CHF$_2$ | OH | H | O | 0 |
| A-1282 | H | H | H | H | H | CH$_2$CClF$_2$ | OH | H | O | 0 |
| A-1283 | H | H | H | H | H | CH$_2$CBrF$_2$ | OH | H | O | 0 |
| A-1284 | H | H | H | H | H | CF$_2$CF$_3$ | OH | H | O | 0 |
| A-1285 | H | H | H | H | H | CF$_2$CHF$_2$ | OH | H | O | 0 |
| A-1286 | H | H | H | H | H | CH$_2$CH$_2$CF$_3$ | OH | H | O | 0 |
| A-1287 | H | H | H | H | H | CH$_2$CH$_2$CF$_3$ | OH | H | O | 0 |
| A-1288 | H | H | H | H | H | CH$_2$CF$_2$CHF$_2$ | OH | H | O | 0 |
| A-1289 | H | H | H | H | H | CF$_2$CHFCF$_3$ | OH | H | O | 0 |
| A-1290 | H | H | H | H | H | CF$_2$CF$_2$CF$_3$ | OH | H | O | 0 |
| A-1291 | H | H | H | H | H | CH$_2$CF$_2$CF$_2$CF$_3$ | OH | H | O | 0 |
| A-1292 | H | H | H | H | H | CH$_2$CF$_2$CHFCF$_3$ | OH | H | O | 0 |
| A-1293 | H | H | H | H | H | CH$_2$CH$_2$CH$_2$SF$_3$ | OH | H | O | 0 |
| A-1294 | H | H | H | H | H | CH$_2$CH$_2$CF$_2$CF$_3$ | OH | H | O | 0 |
| A-1295 | H | H | H | H | H | CF$_2$CF$_2$CF$_2$CF$_3$ | OH | H | O | 0 |
| A-1296 | H | H | H | H | H | CH$_2$CH$_2$CH(CF$_3$)$_2$ | OH | H | O | 0 |
| A-1297 | H | H | H | H | H | CF$_2$CFCF$_2$CF$_2$CF$_3$ | OH | H | O | 0 |
| A-1298 | H | H | H | H | H | CH$_2$CF$_2$CF$_2$CF$_2$CF$_3$ | OH | H | O | 0 |
| A-1299 | H | H | H | H | H | CH$_2$CH$_2$OH$_2$CH$_2$OF$_3$ | OH | H | O | 0 |
| A-1300 | H | H | H | H | H | CH$_2$CF$_2$CF$_2$CF$_2$CHF$_2$ | OH | H | O | 0 |
| A-1301 | H | H | H | H | H | CH$_2$CH$_2$OCH$_2$CF$_3$ | OH | H | O | 0 |
| A-1302 | H | H | H | H | H | CF$_2$CHFOOF$_3$ | OH | H | O | 0 |
| A-1303 | H | H | H | H | H | CF$_2$CHFOCF$_2$CF$_3$ | OH | H | O | 0 |
| A-1304 | H | H | H | H | H | CH$_2$CH$_2$CF═CF$_2$ | OH | H | O | 0 |
| A-1305 | H | H | H | H | H | CH$_2$CH$_2$CH═CF$_2$ | OH | H | O | 0 |
| A-1306 | H | H | H | H | H | CH$_2$C≡CCH$_3$ | OH | H | O | 0 |
| A-1307 | H | H | H | H | H | CH$_2$C≡CCF$_3$ | OH | H | O | 0 |
| A-1308 | H | H | H | H | H | CH$_2$C≡CI | OH | H | O | 0 |
| A-1309 | H | H | H | H | H | CH$_2$(2,2-difluorocyclopropyl) | OH | H | O | 0 |
| A-1310 | H | H | H | H | H | CH$_2$(2,2-dichlorocyclopropyl) | OH | H | O | 0 |
| A-1311 | H | H | H | H | H | CH$_2$CH$_2$(2,2-diftuorocyclopropyl) | OH | H | O | 0 |
| A-1312 | H | H | H | H | H | CH$_2$CH$_2$(2,2-dichlorocyclopropyl) | OH | H | O | 0 |
| A-1313 | H | H | H | H | H | CH$_2$SCH$_2$ | OH | H | O | 0 |
| A-1314 | H | H | H | H | H | CH$_2$SCH$_2$CH$_3$ | OH | H | O | 0 |
| A-1315 | H | H | H | H | H | CH$_2$CH$_2$SCH$_3$ | OH | H | O | 0 |
| A-1316 | H | H | H | H | H | CH$_2$SOCH$_3$ | OH | H | O | 0 |
| A-1317 | H | H | H | H | H | CH$_2$CH$_2$SOCH$_3$ | OH | H | O | 0 |
| A-1318 | H | H | H | H | H | CH$_2$SO$_2$CH$_3$ | OH | H | O | 0 |
| A-1319 | H | H | H | H | H | CH$_2$CH$_2$SO$_2$CH$_3$ | OH | H | O | 0 |
| A-1320 | H | H | H | H | H | CH$_2$SCF$_3$ | OH | H | O | 0 |
| A-1321 | H | H | H | H | H | CH$_2$SCHF$_2$ | OH | H | O | 0 |
| A-1322 | H | H | H | H | H | CH$_2$SCH$_2$CF$_2$ | OH | H | O | 0 |
| A-1323 | H | H | H | H | H | CH$_2$SCH$_2$CHF$_2$ | OH | H | O | 0 |
| A-1324 | H | H | H | H | H | CH$_2$SCF$_2$CF$_3$ | OH | H | O | 0 |

TABLE 22-continued

| Compound | R¹ | R² | R³ | R⁴ | R⁵ | R⁶ | R⁷ | R⁸ | X | n |
|---|---|---|---|---|---|---|---|---|---|---|
| A-1325 | H | H | H | H | H | CH₂CH₂SCF₂ | OH | H | O | 0 |
| A-1326 | H | H | H | H | H | CH₂SOCF₂ | OH | H | O | 0 |
| A-1327 | H | H | H | H | H | CH₂CH₂SOCF₃ | OH | H | O | 0 |
| A-1328 | H | H | H | H | H | CH₂CH₂CH₂SOCF₃ | OH | H | O | 0 |
| A-1329 | H | H | H | H | H | CH₂SO₂CF₃ | OH | H | O | 0 |
| A-1330 | H | H | H | H | H | CH₂CH₂SO₂CF₃ | OH | H | O | 0 |
| A-1331 | H | H | H | H | H | CH₂CH₂CH₂SO₂CF₃ | OH | H | O | 0 |
| A-1332 | H | H | H | H | H | CH₂C(=O)NNCH₂CHF₂ | OH | H | O | 0 |
| A-1333 | H | H | H | H | H | CH₂C(=O)NNCH₂CF₂ | OH | H | O | 0 |
| A-1334 | H | H | H | H | H | H | OH | H | O | 0 |
| A-1335 | H | H | H | H | H | CH₃ | OH | H | O | 0 |
| A-1336 | H | H | H | H | H | CH₂CH₃ | OH | H | O | 0 |
| A-1337 | H | H | H | H | H | CH(CH₃)₂ | OH | H | O | 0 |

TABLE 23

| Compound | R¹ | R² | R³ | R⁴ | R⁵ | R⁶ | R⁷ | R⁸ | X | n |
|---|---|---|---|---|---|---|---|---|---|---|
| A-1338 | H | H | H | H | H | CH₂CH₂CH₃ | OCH₃ | H | O | 0 |
| A-1339 | H | H | H | H | H | CH₂CH(CH₃)₂ | OCH₃ | H | O | 0 |
| A-1340 | H | H | H | H | H | CH(CH₃)CH₂CH₃ | OCH₃ | H | O | 0 |
| A-1341 | H | H | H | H | H | CH₂C(CH₃)₃ | OCH₃ | H | O | 0 |
| A-1342 | H | H | H | H | H | CH₂(CH₂)₂CH₃ | OCH₃ | H | O | 0 |
| A-1343 | H | H | H | H | H | CH₂(CH₂)₃CH₃ | OCH₃ | H | O | 0 |
| A-1344 | H | H | H | H | H | CF₃ | OCH₃ | H | O | 0 |
| A-1345 | H | H | H | H | H | CHF₂ | OCH₃ | H | O | 0 |
| A-1346 | H | H | H | H | H | CH₂CF₃ | OCH₃ | H | O | 0 |
| A-1347 | H | H | H | H | H | CH₂CHF₂ | OCH₃ | H | O | 0 |
| A-1348 | H | H | H | H | H | CH₂CClF₂ | OCH₃ | H | O | 0 |
| A-1349 | H | H | H | H | H | CH₂CBrF₂ | OCH₃ | H | O | 0 |
| A-1350 | H | H | H | H | H | CF₂CF₃ | OCH₃ | H | O | 0 |
| A-1351 | H | H | H | H | H | CF₂CHF₂ | OCH₃ | H | O | 0 |
| A-1352 | H | H | H | H | H | CH₂CH₂CF₃ | OCH₃ | H | O | 0 |
| A-1353 | H | H | H | H | H | CH₂CF₂CF₃ | OCH₃ | H | O | 0 |
| A-1354 | H | H | H | H | H | CH₂CF₂CHF₂ | OCH₃ | H | O | 0 |
| A-1355 | H | H | H | H | H | CF₂CHFCF₃ | OCH₃ | H | O | 0 |
| A-1356 | H | H | H | H | H | CF₂CF₂CF₃ | OCH₃ | H | O | 0 |
| A-1357 | H | H | H | H | H | CH₂CF₂CF₂CF₃ | OCH₃ | H | O | 0 |
| A-1358 | H | H | H | H | H | CH₂CF₂CHFCF₃ | OCH₃ | H | O | 0 |
| A-1359 | H | H | H | H | H | CH₂CH₂CH₂CF₃ | OCH₃ | H | O | 0 |
| A-1360 | H | H | H | H | H | CH₂CH₂CF₂CF₃ | OCH₃ | H | O | 0 |
| A-1361 | H | H | H | H | H | CF₂CF₂CF₂CF₃ | OCH₃ | H | O | 0 |
| A-1362 | H | H | H | H | H | CH₂CH₂CH(CF₃)₂ | OCH₃ | H | O | 0 |
| A-1363 | H | H | H | H | H | CF₂CF₂CF₂CF₂CF₃ | OCH₃ | H | O | 0 |
| A-1364 | H | H | H | H | H | CH₂CF₂CF₂CF₂CF₃ | OCH₃ | H | O | 0 |
| A-1365 | H | H | H | H | H | CH₂CH₂CH₂CH₂CF₃ | OCH₃ | H | O | 0 |
| A-1366 | H | H | H | H | H | CH₂CF₂CF₂CF₂CHF₂ | OCH₃ | H | O | 0 |
| A-1367 | H | H | H | H | H | CH₂CH₂OCH₂CF₃ | OCH₃ | H | O | 0 |
| A-1368 | H | H | H | H | H | CF₂CHFOCF₃ | OCH₃ | H | O | 0 |
| A-1369 | H | H | H | H | H | CF₂CHFOCF₂CF₃ | OCH₃ | H | O | 0 |
| A-1370 | H | H | H | H | H | CH₂CH₂CF=CF₂ | OCH₃ | H | O | 0 |
| A-1371 | H | H | H | H | H | CH₂CH₂CH=CF₂ | OCH₃ | H | O | 0 |
| A-1372 | H | H | H | H | H | CH₂C≡CCH₃ | OCH₃ | H | O | 0 |
| A-1373 | H | H | H | H | H | CH₂C≡CCF₃ | OCH₃ | H | O | 0 |
| A-1374 | H | H | H | H | H | CH₂C≡CI | OCH₃ | H | O | 0 |
| A-1375 | H | H | H | H | H | CH₂(2,2-difluorocyclopropyl) | OCH₃ | H | O | 0 |
| A-1376 | H | H | H | H | H | CH₂(2,2-dichlorocyclopropyl) | OCH₃ | H | O | 0 |
| A-1377 | H | H | H | H | H | CH₂CH₂(2,2-difluorocyclopropyl) | OCH₃ | H | O | 0 |
| A-1378 | H | H | H | H | H | CH₂CH₂(2,2-(dichlorocyclopropyl) | OCH₃ | H | O | 0 |
| A-1379 | H | H | H | H | H | CH₂SCH₃ | OCH₃ | H | O | 0 |
| A-1380 | H | H | H | H | H | CH₂SCH₂CH₃ | OCH₃ | H | O | 0 |
| A-1381 | H | H | H | H | H | CH₂CH₂SCH₃ | OCH₃ | H | O | 0 |
| A-1382 | H | H | H | H | H | CH₂SOCH₃ | OCH₃ | H | O | 0 |
| A-1383 | H | H | H | H | H | CH₂CH₂SOCH₃ | OCH₃ | H | O | 0 |
| A-1384 | H | H | H | H | H | CH₂SO₂CH₃ | OCH₃ | H | O | 0 |
| A-1385 | H | H | H | H | H | CH₂CH₂SO₂CH₃ | OCH₃ | H | O | 0 |
| A-1386 | H | H | H | H | H | CH₂SCF₃ | OCH₃ | H | O | 0 |
| A-1387 | H | H | H | H | H | CH₂SCHF₂ | OCH₃ | H | O | 0 |
| A-1388 | H | H | H | H | H | CH₂SCH₂CF₃ | OCH₃ | H | O | 0 |
| A-1389 | H | H | H | H | H | CH₂SCH₂CHF₂ | OCH₃ | H | O | 0 |
| A-1390 | H | H | H | H | H | CH₂SCF₂CF₃ | OCH₃ | H | O | 0 |
| A-1391 | H | H | H | H | H | CH₂CH₂SCF₃ | OCH₃ | H | O | 0 |
| A-1392 | H | H | H | H | H | CH₂SOCF₃ | OCH₃ | H | O | 0 |
| A-1393 | H | H | H | H | H | CH₂CH₂SOCF₃ | OCH₃ | H | O | 0 |
| A-1394 | H | H | H | H | H | CH₂CH₂CH₂SOCF₃ | OCH₃ | H | O | 0 |

TABLE 23-continued

| Compound | R¹ | R² | R³ | R⁴ | R⁵ | R⁶ | R⁷ | R⁸ | X | n |
|---|---|---|---|---|---|---|---|---|---|---|
| A-1395 | H | H | H | H | H | $CH_2SO_2CF_3$ | $OCH_3$ | H | O | 0 |
| A-1396 | H | H | H | H | H | $CH_2CH_2SO_2CF_3$ | $OCH_3$ | H | O | 0 |
| A-1397 | H | H | H | H | H | $CH_2CH_2CH_2SO_2CF_3$ | $OCH_3$ | H | O | 0 |
| A-1398 | H | H | H | H | H | $CH_2C(=O)NHCH_2CHF_2$ | $OCH_3$ | H | O | 0 |

TABLE 24

| Compound | R¹ | R² | R³ | R⁴ | R⁵ | R⁶ | R⁷ | R⁸ | X | n |
|---|---|---|---|---|---|---|---|---|---|---|
| A-1399 | H | H | H | H | H | $CH_2C(=O)NHCH_2CF_3$ | $OCH_3$ | H | O | 0 |
| A-1400 | H | H | H | H | H | H | $CH_2CF_3$ | H | O | 0 |
| A-1401 | H | H | H | H | H | $CH_3$ | $CH_2CF_3$ | H | O | 0 |
| A-1402 | H | H | H | H | H | $CH_2CH_3$ | $CH_2CF_3$ | H | O | 0 |
| A-1403 | H | H | H | H | H | $CH(CH3)_2$ | $CH_2CF_3$ | H | O | 0 |
| A-1404 | H | H | H | H | H | $CH_2CH_2CH_3$ | $CH_2CF_3$ | H | O | 0 |
| A-1405 | H | H | H | H | H | $CH_2CH(CH_3)_2$ | $CH_2CF_3$ | H | O | 0 |
| A-1406 | H | H | H | H | H | $CH_2C(CH_3)_3$ | $CH_2CF_3$ | H | O | 0 |
| A-1407 | H | H | H | H | H | $CH(CH3)CH_2CH_3$ | $CH_2CF_3$ | H | O | 0 |
| A-1408 | H | H | H | H | H | $CH_2(CH_2)_2CH_3$ | $CH_2CF_3$ | H | O | 0 |
| A-1409 | H | H | H | H | H | $CH_2(CH_2)_3CH_3$ | $CH_2CF_3$ | H | O | 0 |
| A-1410 | H | H | H | H | H | $CH_2(CH_2)_4CH_3$ | $CH_2CF_3$ | H | O | 0 |
| A-1411 | H | H | H | H | H | $CH_2(CH_2)_6CH_3$ | $CH_2CF_3$ | H | O | 0 |
| A-1412 | H | H | H | H | H | $CH_2OCH_3$ | $CH_2CF_3$ | H | O | 0 |
| A-1413 | H | H | H | H | H | $CH_2OCH_2CH_3$ | $CH_2CF_3$ | H | O | 0 |
| A-1414 | H | H | H | H | H | $CH_2CH_2OCH_3$ | $CH_2CF_3$ | H | O | 0 |
| A-1415 | H | H | H | H | H | $CH_2CH_2OCH_2CH_3$ | $CH_2CF_3$ | H | O | 0 |
| A-1416 | H | H | H | H | H | $CF_3$ | $CH_2CF_3$ | H | O | 0 |
| A-1417 | H | H | H | H | H | $CHF_2$ | $CH_2CF_3$ | H | O | 0 |
| A-1418 | H | H | H | H | H | $CH_2CF_3$ | $CH_2CF_3$ | H | O | 0 |
| A-1419 | H | H | H | H | H | $CH_2CHF_2$ | $CH_2CF_3$ | H | O | 0 |
| A-1420 | H | H | H | H | H | $CH_2CClF_2$ | $CH_2CF_3$ | H | O | 0 |
| A-1421 | H | H | H | H | H | $CH_2CBrF_2$ | $CH_2CF_3$ | H | O | 0 |
| A-1422 | H | H | H | H | H | $CF_2CF_3$ | $CH_2CF_3$ | H | O | 0 |
| A-1423 | H | H | H | H | H | $CF_2CHF_2$ | $CH_2CF_3$ | H | O | 0 |
| A-1424 | H | H | H | H | H | $CH_2CH_2CF_3$ | $CH_2CF_3$ | H | O | 0 |
| A-1425 | H | H | H | H | H | $CH_2CF_2CF_3$ | $CH_2CF_3$ | H | O | 0 |
| A-1426 | H | H | H | H | H | $CH_2CF_2CHF_2$ | $CH_2CF_3$ | H | O | 0 |
| A-1427 | H | H | H | H | H | $CF_2CHFCF_3$ | $CH_2CF_3$ | H | O | 0 |
| A-1428 | H | H | H | H | H | $CF_2CF_2CF_3$ | $CH_2CF_3$ | H | O | 0 |
| A-1429 | H | H | H | H | H | $CH_2CF_2CF_2CF_3$ | $CH_2CF_3$ | H | O | 0 |
| A-1430 | H | H | H | H | H | $CH_2CF_2CHFCF_3$ | $CH_2CF_3$ | H | O | 0 |
| A-1431 | H | H | H | H | H | $CH_2CH_2CH_2CF_3$ | $CH_2CF_3$ | H | O | 0 |
| A-1432 | H | H | H | H | H | $CH_2CH_2CF_2CF_3$ | $CH_2CF_3$ | H | O | 0 |
| A-1433 | H | H | H | H | H | $CF_2CF_2CF_2CF_3$ | $CH_2CF_3$ | H | O | 0 |
| A-1434 | H | H | H | H | H | $CH_2CH_2CH(CF_3)_2$ | $CH_2CF_3$ | H | O | 0 |
| A-1435 | H | H | H | H | H | $CF_2CF_2CF_2CF_2CF_3$ | $CH_2CF_3$ | H | O | 0 |
| A-1436 | H | H | H | H | H | $CH_2CF_2CF_2CF_2CF_3$ | $CH_2CF_3$ | H | O | 0 |
| A-1437 | H | H | H | H | H | $CH_2CH_2CH_2CH_2CF_3$ | $CH_2CF_3$ | H | O | 0 |
| A-1438 | H | H | H | H | H | $CH_2CF_2CF_2CF_2CHF_2$ | $CH_2CF_3$ | H | O | 0 |
| A-1439 | H | H | H | H | H | $CH_2CF_2CF(CF_3)CF_2C(CF_3)_3$ | $CH_2CF_3$ | H | O | 0 |
| A-1440 | H | H | H | H | H | $CF_2CHFOCH_3$ | $CH_2CF_3$ | H | O | 0 |
| A-1441 | H | H | H | H | H | $CF_2CHFOCH_2CH_3$ | $CH_2CF_3$ | H | O | 0 |
| A-1442 | H | H | H | H | H | $CH_2CH_2OCH_2CF_3$ | $CH_2CF_3$ | H | O | 0 |
| A-1443 | H | H | H | H | H | $CF_2CHFOCF_3$ | $CH_2CF_3$ | H | O | 0 |
| A-1444 | H | H | H | H | H | $CF_2CHFOCF_2CF_3$ | $CH_2CF_3$ | H | O | 0 |
| A-1445 | H | H | H | H | H | $CF_2CHFOCF_2CF_2CF_3$ | $CH_2CF_3$ | H | O | 0 |
| A-1446 | H | H | H | H | H | $CH_2CH=CH_2$ | $CH_2CF_3$ | H | O | 0 |
| A-1447 | H | H | H | H | H | $CH_2CH=CHCl$ | $CH_2CF_3$ | H | O | 0 |
| A-1448 | H | H | H | H | H | $CH_2CH=CCl_2$ | $CH_2CF_3$ | H | O | 0 |
| A-1449 | H | H | H | H | H | $CH_2CH_2CF=CF_2$ | $CH_2CF_3$ | H | O | 0 |
| A-1450 | H | H | H | H | H | $CH_2CH_2CH=CF_2$ | $CH_2CF_3$ | H | O | 0 |
| A-1451 | H | H | H | H | H | $CH_2CF=CH$ | $CH_2CF_3$ | H | O | 0 |
| A-1452 | H | H | H | H | H | $CH_2C≡CCH_3$ | $CH_2CF_3$ | H | O | 0 |
| A-1453 | H | H | H | H | H | $CH_2C≡Cl$ | $CH_2CF_3$ | H | O | 0 |
| A-1454 | H | H | H | H | H | $CH_2C≡CCF_3$ | $CH_2CF_3$ | H | O | 0 |
| A-1455 | H | H | H | H | H | cyclobutyl | $CH_2CF_3$ | H | O | 0 |
| A-1456 | H | H | H | H | H | cyclopentyl | $CH_2CF_3$ | H | O | 0 |
| A-1457 | H | H | H | H | H | cyclohexyl | $CH_2CF_3$ | H | O | 0 |
| A-1458 | H | H | H | H | H | 4,4-difluorocyclohexyl | $CH_2CF_3$ | H | O | 0 |
| A-1459 | H | H | H | H | H | CH2(cyclopropyl) | $CH_2CF_3$ | H | O | 0 |

TABLE 25

| Compound | R¹ | R² | R³ | R⁴ | R⁵ | R⁶ | R⁷ | R⁸ | X | n |
|---|---|---|---|---|---|---|---|---|---|---|
| A-1460 | H | H | H | H | H | CH$_2$(cyclobutyl) | CH$_2$CF$_3$ | H | O | 0 |
| A-1461 | H | H | H | H | H | CH$_2$(cyclopentyl) | CH$_2$CF$_3$ | H | O | 0 |
| A-1462 | H | H | H | H | H | CH$_2$CH$_2$(cyclopropyl) | CH$_2$CF$_3$ | H | O | 0 |
| A-1463 | H | H | H | H | H | CH$_2$(2,2-difluorocyclopropyl) | CH$_2$CF$_3$ | H | O | 0 |
| A-1464 | H | H | H | H | H | CH$_2$(2,2-dichlorocyclopropyl) | CH$_2$CF$_3$ | H | O | 0 |
| A-1465 | H | H | H | H | H | CH$_2$(4,4-difluorocyclohexyl) | CH$_2$CF$_3$ | H | O | 0 |
| A-1466 | H | H | H | H | H | CH$_2$CH$_2$(2,2-difluorocyclopropyl) | CH$_2$CF$_3$ | H | O | 0 |
| A-1467 | H | H | H | H | H | CH$_2$CH$_2$(2,2-dichlorocyclopropyl) | CH$_2$CF$_3$ | H | O | 0 |
| A-1468 | H | H | H | H | H | CH$_2$SCH$_3$ | CH$_2$CF$_3$ | H | O | 0 |
| A-1469 | H | H | H | H | H | CH$_2$SCH$_2$CH$_3$ | CH$_2$CF$_3$ | H | O | 0 |
| A-1470 | H | H | H | H | H | CH$_2$CH$_2$SCH$_3$ | CH$_2$CF$_3$ | H | O | 0 |
| A-1471 | H | H | H | H | H | CH$_2$CH$_2$SCH$_2$CH$_3$ | CH$_2$CF$_3$ | H | O | 0 |
| A-1472 | H | H | H | H | H | CH$_2$CH$_2$CH$_2$SCH$_3$ | CH$_2$CF$_3$ | H | O | 0 |
| A-1473 | H | H | H | H | H | CH$_2$CH$_2$CH$_2$SCH$_2$CH$_3$ | CH$_2$CF$_3$ | H | O | 0 |
| A-1474 | H | H | H | H | H | CH(CH$_3$)SCH$_3$ | CH$_2$CF$_3$ | H | O | 0 |
| A-1475 | H | H | H | H | H | CH(CH$_3$)SCH$_2$CH$_3$ | CH$_2$CF$_3$ | H | O | 0 |
| A-1476 | H | H | H | H | H | CH$_2$CH(CH$_3$)SCH$_3$ | CH$_2$CF$_3$ | H | O | 0 |
| A-1477 | H | H | H | H | H | CH$_2$CH(CH$_3$)SCH$_2$CH$_3$ | CH$_2$CF$_3$ | H | O | 0 |
| A-1478 | H | H | H | H | H | CH(CH$_3$)CH$_2$SCH$_3$ | CH$_2$CF$_3$ | H | O | 0 |
| A-1479 | H | H | H | H | H | CH(CH$_3$)CH$_2$CH$_2$SCH$_2$CH$_3$ | CH$_2$CF$_3$ | H | O | 0 |
| A-1480 | H | H | H | H | H | CH$_2$CH(CH$_3$)CH$_2$SCH$_3$ | CH$_2$CF$_3$ | H | O | 0 |
| A-1481 | H | H | H | H | H | CH$_2$CH(CH$_3$)CH$_2$SCH$_2$CH$_3$ | CH$_2$CF$_3$ | H | O | 0 |
| A-1482 | H | H | H | H | H | CH$_2$CH$_2$CH(CH$_3$)SCH$_3$ | CH$_2$CF$_3$ | H | O | 0 |
| A-1483 | H | H | H | H | H | CH$_2$CH$_2$CH(CH$_3$)SCH$_2$ | CH$_2$CF$_3$ | H | O | 0 |
| A-1484 | H | H | H | H | H | CH$_2$SOCH$_3$ | CH$_2$CF$_3$ | H | O | 0 |
| A-1485 | H | H | H | H | H | CH$_2$CH$_2$SOCH$_3$ | CH$_2$CF$_3$ | H | O | 0 |
| A-1486 | H | H | H | H | H | CH$_2$CH$_2$CH$_2$SOCH$_3$ | CH$_2$CF$_3$ | H | O | 0 |
| A-1487 | H | H | H | H | H | CH(CH$_3$)SOCH$_3$ | CH$_2$CF$_3$ | H | O | 0 |
| A-1488 | H | H | H | H | H | CH$_2$CH(CH$_3$)SOCH$_3$ | CH$_2$CF$_3$ | H | O | 0 |
| A-1489 | H | H | H | H | H | CH(CH$_3$)CH$_2$CH$_2$SOCH$_3$ | CH$_2$CF$_3$ | H | O | 0 |
| A-1490 | H | H | H | H | H | CH$_2$CH(CH$_3$)CH$_2$SOCH$_3$ | CH$_2$CF$_3$ | H | O | 0 |
| A-1491 | H | H | H | H | H | CH$_2$CH$_2$CH(CH$_3$)SOCH$_3$ | CH$_2$CF$_3$ | H | O | 0 |
| A-1492 | H | H | H | H | H | CH$_2$SO$_2$CH$_3$ | CH$_2$CF$_3$ | H | O | 0 |
| A-1493 | H | H | H | H | H | CH$_2$CH$_2$SO$_2$CH$_3$ | CH$_2$CF$_3$ | H | O | 0 |
| A-1494 | H | H | H | H | H | CH$_2$CH$_2$CH$_2$SO$_2$CH$_3$ | CH$_2$CF$_3$ | H | O | 0 |
| A-1495 | H | H | H | H | H | CH(CH$_3$)SO$_2$CH$_3$ | CH$_2$CF$_3$ | H | O | 0 |
| A-1496 | H | H | H | H | H | CH$_2$CH(CH$_3$)SO$_2$CH$_3$ | CH$_2$CF$_3$ | H | O | 0 |
| A-1497 | H | H | H | H | H | CH(CH$_3$)CH$_2$CH$_2$SO$_2$CH$_3$ | CH$_2$CF$_3$ | H | O | 0 |
| A-1498 | H | H | H | H | H | CH$_2$CH(CH$_3$)CH$_2$SO$_2$CH$_3$ | CH$_2$CF$_3$ | H | O | 0 |
| A-1499 | H | H | H | H | H | CH$_2$CH$_2$CH(CH$_3$)SO$_2$CH$_3$ | CH$_2$CF$_3$ | H | O | 0 |
| A-1500 | H | H | H | H | H | CH$_2$SCF$_3$ | CH$_2$CF$_3$ | H | O | 0 |
| A-1501 | H | H | H | H | H | CH$_2$SCHF$_2$ | CH$_2$CF$_3$ | H | O | 0 |
| A-1502 | H | H | H | H | H | CH$_2$SCH$_2$CF$_3$ | CH$_2$CF$_3$ | H | O | 0 |
| A-1503 | H | H | H | H | H | CH$_2$SCH$_2$CHF$_2$ | CH$_2$CF$_3$ | H | O | 0 |
| A-1504 | H | H | H | H | H | CH$_2$SCF$_2$CF$_3$ | CH$_2$CF$_3$ | H | O | 0 |
| A-1505 | H | H | H | H | H | CH$_2$CH$_2$SCF$_3$ | CH$_2$CF$_3$ | H | O | 0 |
| A-1506 | H | H | H | H | H | CH$_2$CH$_2$SCH$_2$CF$_3$ | CH$_2$CF$_3$ | H | O | 0 |
| A-1507 | H | H | H | H | H | CH$_2$CH$_2$CH$_2$SCF$_3$ | CH$_2$CF$_3$ | H | O | 0 |
| A-1508 | H | H | H | H | H | CH$_2$CH$_2$CH$_2$SCH$_2$CF$_3$ | CH$_2$CF$_3$ | H | O | 0 |
| A-1509 | H | H | H | H | H | CH(CH$_3$)SCF$_3$ | CH$_2$CF$_3$ | H | O | 0 |
| A-1510 | H | H | H | H | H | CH(CH$_3$)SCH$_2$CF$_3$ | CH$_2$CF$_3$ | H | O | 0 |
| A-1511 | H | H | H | H | H | CH$_2$CH(CH$_3$)SCF$_3$ | CH$_2$CF$_3$ | H | O | 0 |
| A-1512 | H | H | H | H | H | CH$_2$CH(CH$_3$)SCH$_2$CF$_3$ | CH$_2$CF$_3$ | H | O | 0 |
| A-1513 | H | H | H | H | H | CH(CH$_3$)CH$_2$CH$_2$SCF$_3$ | CH$_2$CF$_3$ | H | O | 0 |
| A-1514 | H | H | H | H | H | CH(CH$_3$)CH$_2$CH$_2$SCH$_2$CF$_3$ | CH$_2$CF$_3$ | H | O | 0 |
| A-1515 | H | H | H | H | H | CH$_2$CH(CH$_3$)CH$_2$SCF$_3$ | CH$_2$CF$_3$ | H | O | 0 |
| A-1516 | H | H | H | H | H | CH$_2$CH(CH$_3$)CH$_2$SCH$_2$CF$_3$ | CH$_2$CF$_3$ | H | O | 0 |
| A-1517 | H | H | H | H | H | CH$_2$CH$_2$CH(CH$_3$)SCF$_3$ | CH$_2$CF$_3$ | H | O | 0 |
| A-1518 | H | H | H | H | H | CH$_2$CH$_2$CH(CH$_3$)SCH$_2$CF$_3$ | CH$_2$CF$_3$ | H | O | 0 |
| A-1519 | H | H | H | H | H | CH$_2$SOCF$_3$ | CH$_2$CF$_3$ | H | O | 0 |
| A-1520 | H | H | H | H | H | CH$_2$CH$_2$SOCF$_3$ | CH$_2$CF$_3$ | H | O | 0 |

TABLE 26

| Compound | R¹ | R² | R³ | R⁴ | R⁵ | R⁶ | R⁷ | R⁸ | X | n |
|---|---|---|---|---|---|---|---|---|---|---|
| A-1521 | H | H | H | H | H | CH$_2$CH$_2$CH$_2$SOCF$_3$ | CH$_2$CF$_3$ | H | O | 0 |
| A-1522 | H | H | H | H | H | CH(CH$_3$)SOCF$_3$ | CH$_2$CF$_3$ | H | O | 0 |
| A-1523 | H | H | H | H | H | CH$_2$CH(CH$_3$)SOCF$_3$ | CH$_2$CF$_3$ | H | O | 0 |
| A-1524 | H | H | H | H | H | CH(CH$_3$)CH$_2$CH$_2$SOCF$_3$ | CH$_2$CF$_3$ | H | O | 0 |
| A-1525 | H | H | H | H | H | CH(CH$_3$)CH$_2$CH$_2$SOCF$_3$ | CH$_2$CF$_3$ | H | O | 0 |
| A-1526 | H | H | H | H | H | CH$_2$CH$_2$CH(CH$_3$)SOCF$_3$ | CH$_2$CF$_3$ | H | O | 0 |
| A-1527 | H | H | H | H | H | CH$_2$SO$_2$CF$_3$ | CH$_2$CF$_3$ | H | O | 0 |
| A-1528 | H | H | H | H | H | CH$_2$CH$_2$SO$_2$CF$_3$ | CH$_2$CF$_3$ | H | O | 0 |
| A-1529 | H | H | H | H | H | CH$_2$CH$_2$CH$_2$SO$_2$CF$_3$ | CH$_2$CF$_3$ | H | O | 0 |

TABLE 26-continued

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-1530 | H | H | H | H | H | CH(CH$_3$)SO$_2$CF$_3$ | CH$_2$CF$_3$ | H | O | 0 |
| A-1531 | H | H | H | H | H | CH$_2$CH(CH$_3$)SO$_2$CF$_3$ | CH$_2$CF$_3$ | H | O | 0 |
| A-1532 | H | H | H | H | H | CH(CH$_3$)CH$_2$CH$_2$SO$_2$CF$_3$ | CH$_2$CF$_3$ | H | O | 0 |
| A-1533 | H | H | H | H | H | CH$_2$CH(CH$_3$)CH$_2$SO$_2$CF$_3$ | CH$_2$CF$_3$ | H | O | 0 |
| A-1534 | H | H | H | H | H | CH$_2$CH$_2$CH(CH$_3$)SO$_2$CF$_3$ | CH$_2$CF$_3$ | H | O | 0 |
| A-1535 | H | H | H | H | H | CH$_2$C(=O)CH$_3$ | CH$_2$CF$_3$ | H | O | 0 |
| A-1536 | H | H | H | H | H | CH$_2$C(=O)CH$_2$CH$_3$ | CH$_2$CF$_3$ | H | O | 0 |
| A-1537 | H | H | H | H | H | CH$_2$C(=O)C(CH$_3$)$_3$ | CH$_2$CF$_3$ | H | O | 0 |
| A-1538 | H | H | H | H | H | CH$_2$CH$_2$C(=O)CH$_3$ | CH$_2$CF$_3$ | H | O | 0 |
| A-1539 | H | H | H | H | H | CH$_2$CH$_2$C(=O)C(CH$_3$)$_3$ | CH$_2$CF$_3$ | H | O | 0 |
| A-1540 | H | H | H | H | H | CH$_2$C(=O)CF$_3$ | CH$_2$CF$_3$ | H | O | 0 |
| A-1541 | H | H | H | H | H | CH$_2$CH$_2$C(=O)CF$_3$ | CH$_2$CF$_3$ | H | O | 0 |
| A-1542 | H | H | H | H | H | CH$_2$C(=O)OCH$_3$ | CH$_2$CF$_3$ | H | O | 0 |
| A-1543 | H | H | H | H | H | CH$_2$C(=O)OCH$_2$CH$_3$ | CH$_2$CF$_3$ | H | O | 0 |
| A-1544 | H | H | H | H | H | CH$_2$C(=O)OC(CH$_3$)$_3$ | CH$_2$CF$_3$ | H | O | 0 |
| A-1545 | H | H | H | H | H | CH$_2$CH$_2$C(=O)OCH$_3$ | CH$_2$CF$_3$ | H | O | 0 |
| A-1546 | H | H | H | H | H | CH$_2$CH$_2$C(=O)OCH$_2$CH$_3$ | CH$_2$CF$_3$ | H | O | 0 |
| A-1547 | H | H | H | H | H | CH$_2$CH$_2$C(=O)OC(CH$_3$)$_3$ | CH$_2$CF$_3$ | H | O | 0 |
| A-1548 | H | H | H | H | H | CH$_2$C(=O)NH$_2$ | CH$_2$CF$_3$ | H | O | 0 |
| A-1549 | H | H | H | H | H | CH$_2$CH$_2$C(=O)NH$_2$ | CH$_2$CF$_3$ | H | O | 0 |
| A-1550 | H | H | H | H | H | CH$_2$C(=O)NHCH$_3$ | CH$_2$CF$_3$ | H | O | 0 |
| A-1551 | H | H | H | H | H | CH$_2$C(H=O)NHCH(CH$_3$)$_2$ | CH$_2$CF$_3$ | H | O | 0 |
| A-1552 | H | H | H | H | H | CH$_2$CH$_2$C(=O)NHCH$_3$ | CH$_2$CF$_3$ | H | O | 0 |
| A-1553 | H | H | H | H | H | CH$_2$CH$_2$C(=O)NHCH(CH$_3$)$_2$ | CH$_2$CF$_3$ | H | O | 0 |
| A-1554 | H | H | H | H | H | CH$_2$C(=O)NHCH$_2$CHF$_2$ | CH$_2$CF$_3$ | H | O | 0 |
| A-1555 | H | H | H | H | H | CH$_2$C(=O)NHCH$_2$CF$_3$ | CH$_2$CF$_3$ | H | O | 0 |
| A-1556 | H | H | H | H | H | CH$_2$CH$_2$C(=O)NHCH$_2$CHF$_2$ | CH$_2$CF$_3$ | H | O | 0 |
| A-1557 | H | H | H | H | H | CH$_2$CH$_2$C(=O)NHCH$_2$CF$_3$ | CH$_2$CF$_3$ | H | O | 0 |
| A-1558 | H | H | H | H | H | CH$_2$C(=O)N(CH$_3$)$_2$ | CH$_2$CF$_3$ | H | O | 0 |
| A-1559 | H | H | H | H | H | CH$_2$C(=O)N(CH$_2$CH$_3$)$_2$ | CH$_2$CF$_3$ | H | O | 0 |
| A-1560 | H | H | H | H | H | CH$_2$CH$_2$C(=O)N(CH$_3$)$_2$ | CH$_2$CF$_3$ | H | O | 0 |
| A-1561 | H | H | H | H | H | CH$_2$CH$_2$C(=O)N(CH$_2$CH$_3$)$_2$ | CH$_2$CF$_3$ | H | O | 0 |
| A-1562 | H | H | H | H | H | CH$_2$CH$_2$OH | CH$_2$CF$_3$ | H | O | 0 |
| A-1563 | H | H | H | H | H | CH$_2$CH(OH)CH$_3$ | CH$_2$CF$_3$ | H | O | 0 |
| A-1564 | H | H | H | H | H | CH$_2$CH$_2$CH$_2$OH | CH$_2$CF$_3$ | H | O | 0 |
| A-1565 | H | H | H | H | H | CH$_2$CH(OH)CH$_2$CH$_3$ | CH$_2$CF$_3$ | H | O | 0 |
| A-1566 | H | H | H | H | H | CH$_2$CH(OH)C(CH$_3$)$_3$ | CH$_2$CF$_3$ | H | O | 0 |
| A-1567 | H | H | H | H | H | CH$_2$CH$_2$CH(OH)CH$_3$ | CH$_2$CF$_3$ | H | O | 0 |
| A-1568 | H | H | H | H | H | CH$_2$CH$_2$CH(OH)C(CH$_3$)$_3$ | CH$_2$CF$_3$ | H | O | 0 |
| A-1569 | H | H | H | H | H | CH$_2$C(=NOH)CH$_3$ | CH$_2$CF$_3$ | H | O | 0 |
| A-1570 | H | H | H | H | H | CH$_2$C(=NOH)CH$_2$CH$_3$ | CH$_2$CF$_3$ | H | O | 0 |
| A-1571 | H | H | H | H | H | CH$_2$C(=NOH)C(CH$_3$)$_3$ | CH$_2$CF$_3$ | H | O | 0 |
| A-1572 | H | H | H | H | H | CH$_2$C(=NOCH$_3$)CH$_3$ | CH$_2$CF$_3$ | H | O | 0 |
| A-1573 | H | H | H | H | H | CH$_2$C(=NOCH$_3$)CH$_2$CH$_3$ | CH$_2$CF$_3$ | H | O | 0 |
| A-1574 | H | H | H | H | H | CH$_2$C(=NOCH$_2$CH$_3$)CH$_3$ | CH$_2$CF$_3$ | H | O | 0 |
| A-1575 | H | H | H | H | H | CH$_2$C(=NOCH$_2$CH$_3$)CH$_2$CH$_3$ | CH$_2$CF$_3$ | H | O | 0 |
| A-1576 | H | H | H | H | H | CH$_2$C(=NOCH$_2$CF$_3$)CH$_3$ | CH$_2$CF$_3$ | H | O | 0 |
| A-1577 | H | H | H | H | H | CH$_2$C(=NOCH$_2$CF$_3$)CH$_2$CH$_3$ | CH$_2$CF$_3$ | H | O | 0 |
| A-1578 | H | H | H | H | H | CH$_2$Ph | CH$_2$CF$_3$ | H | O | 0 |
| A-1579 | H | H | H | H | H | CH$_2$(2-F)Ph | CH$_2$CF$_3$ | H | O | 0 |
| A-1580 | H | H | H | H | H | CH$_2$(3-F)Ph | CH$_2$CF$_3$ | H | O | 0 |
| A-1581 | H | H | H | H | H | CH$_2$(4-F)Ph | CH$_2$CF$_3$ | H | O | 0 |

TABLE 27

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-1582 | H | H | H | H | H | CH$_2$(2-Cl)Ph | CH$_2$CF$_3$ | H | O | 0 |
| A-1583 | H | H | H | H | H | CH$_2$(3-Cl)Ph | CH$_2$CF$_3$ | H | O | 0 |
| A-1584 | H | H | H | H | H | CH$_2$(4-Cl)Ph | CH$_2$CF$_3$ | H | O | 0 |
| A-1585 | H | H | H | H | H | CH$_2$(2-CF$_3$)Ph | CH$_2$CF$_3$ | H | O | 0 |
| A-1586 | H | H | H | H | H | CH$_2$(3-CF$_3$)Ph | CH$_2$CF$_3$ | H | O | 0 |
| A-1587 | H | H | H | H | H | CH$_2$(4-CF$_3$)Ph | CH$_2$CF$_3$ | H | O | 0 |
| A-1588 | H | H | H | H | H | CH$_2$(naphthalen-1-yl) | CH$_2$CF$_3$ | H | O | 0 |
| A-1589 | H | H | H | H | H | CH$_2$(naphthalen-2-yl) | CH$_2$CF$_3$ | H | O | 0 |
| A-1590 | H | H | H | H | H | CH$_2$CH$_2$Ph | CH$_2$CF$_3$ | H | O | 0 |
| A-1591 | H | H | H | H | H | H | 4-tetrahydropyranyl | H | O | 0 |
| A-1592 | H | H | H | H | H | CH$_3$ | 4-tetrahydropyranyl | H | O | 0 |
| A-1593 | H | H | H | H | H | CH$_2$CH$_3$ | 4-tetrahydropyranyl | H | O | 0 |
| A-1594 | H | H | H | H | H | CH(CH$_3$)$_2$ | 4-tetrahydropyranyl | H | O | 0 |
| A-1595 | H | H | H | H | H | CH$_2$CH$_2$CH$_3$ | 4-tetrahydropyranyl | H | O | 0 |
| A-1596 | H | H | H | H | H | CH$_2$CH(CH$_3$)$_2$ | 4-tetrahydropyranyl | H | O | 0 |
| A-1597 | H | H | H | H | H | CH(CH$_3$)CH$_2$CH$_3$ | 4-tetrahydropyranyl | H | O | 0 |
| A-1598 | H | H | H | H | H | CH$_2$C(CH$_3$)$_3$ | 4-tetrahydropyranyl | H | O | 0 |
| A-1599 | H | H | H | H | H | CH$_2$(CH$_2$)$_2$CH$_3$ | 4-tetrahydropyranyl | H | O | 0 |

TABLE 27-continued

| Compound | R¹ | R² | R³ | R⁴ | R⁵ | R⁶ | R⁷ | R⁸ | X | n |
|---|---|---|---|---|---|---|---|---|---|---|
| A-1600 | H | H | H | H | H | $CH_2(CH_2)_3CH_3$ | 4-tetrahydropyranyl | H | O | 0 |
| A-1601 | H | H | H | H | H | $CF_3$ | 4-tetrahydropyranyl | H | O | 0 |
| A-1602 | H | H | H | H | H | $CHF_2$ | 4-tetrahydropyranyl | H | O | 0 |
| A-1603 | H | H | H | H | H | $CH_2CF_3$ | 4-tetrahydropyranyl | H | O | 0 |
| A-1604 | H | H | H | H | H | $CH_2CHF_2$ | 4-tetrahydropyranyl | H | O | 0 |
| A-1605 | H | H | H | H | H | $CH_2CClF_2$ | 4-tetrahydropyranyl | H | O | 0 |
| A-1606 | H | H | H | H | H | $CH_2CBrF_2$ | 4-tetrahydropyranyl | H | O | 0 |
| A-1607 | H | H | H | H | H | $CF_2CF_3$ | 4-tetrahydropyranyl | H | O | 0 |
| A-1608 | H | H | H | H | H | $CF_2CHF_2$ | 4-tetrahydropyranyl | H | O | 0 |
| A-1609 | H | H | H | H | H | $CH_2CH_2CF_3$ | 4-tetrahydropyranyl | H | O | 0 |
| A-1610 | H | H | H | H | H | $CH_2CF_2CF_3$ | 4-tetrahydropyranyl | H | O | 0 |
| A-1611 | H | H | H | H | H | $CH_2CF_2CHF_2$ | 4-tetrahydropyranyl | H | O | 0 |
| A-1612 | H | H | H | H | H | $CF_2CHFCF_3$ | 4-tetrahydropyranyl | H | O | 0 |
| A-1613 | H | H | H | H | H | $CF_2CF_2CF_3$ | 4-tetrahydropyranyl | H | O | 0 |
| A-1614 | H | H | H | H | H | $CH_2CF_2CF_2CF_3$ | 4-tetrahydropyranyl | H | O | 0 |
| A-1615 | H | H | H | H | H | $CH_2CF_2CHFCF_3$ | 4-tetrahydropyranyl | H | O | 0 |
| A-1616 | H | H | H | H | H | $CH_2CH_2CH_2CF_3$ | 4-tetrahydropyranyl | H | O | 0 |
| A-1617 | H | H | H | H | H | $CH_2CH_2CF_2CF_3$ | 4-tetrahydropyranyl | H | O | 0 |
| A-1618 | H | H | H | H | H | $CF_2CF_2CF_2CF_3$ | 4-tetrahydropyranyl | H | O | 0 |
| A-1619 | H | H | H | H | H | $CH_2CH_2CH(CF_3)_2$ | 4-tetrahydropyranyl | H | O | 0 |
| A-1620 | H | H | H | H | H | $CF_2CF_2CF_2CF_2CF_3$ | 4-tetrahydropyranyl | H | O | 0 |
| A-1621 | H | H | H | H | H | $CH_2CF_2CF_2CF_2CF_3$ | 4-tetrahydropyranyl | H | O | 0 |
| A-1622 | H | H | H | H | H | $CH_2CH_2CH_2CH_2CF_3$ | 4-tetrahydropyranyl | H | O | 0 |
| A-1623 | H | H | H | H | H | $CH_2CF_2CF_2CF_2CHF_2$ | 4-tetrahydropyranyl | H | O | 0 |
| A-1624 | H | H | H | H | H | $CH_2CH_2OCH_2CF_3$ | 4-tetrahydropyranyl | H | O | 0 |
| A-1625 | H | H | H | H | H | $CF_2CHFOCF_3$ | 4-tetrahydropyranyl | H | O | 0 |
| A-1626 | H | H | H | H | H | $CF_2CHFOCF_2CF_3$ | 4-tetrahydropyranyl | H | O | 0 |
| A-1627 | H | H | H | H | H | $CH_2CH_2CF=CF_2$ | 4-tetrahydropyranyl | H | O | 0 |
| A-1628 | H | H | H | H | H | $CH_2CH_2CH=CF_2$ | 4-tetrahydropyranyl | H | O | 0 |
| A-1629 | H | H | H | H | H | $CH_2C\equiv CCH_3$ | 4-tetrahydropyranyl | H | O | 0 |
| A-1630 | H | H | H | H | H | $CH_2C\equiv CCF_3$ | 4-tetrahydropyranyl | H | O | 0 |
| A-1631 | H | H | H | H | H | $CH_2C\equiv CL$ | 4-tetrahydropyranyl | H | O | 0 |
| A-1632 | H | H | H | H | H | $CH_2$(2,2-difluorocyclopropyl) | 4-tetrahydropyranyl | H | O | 0 |
| A-1633 | H | H | H | H | H | $CH_2$(2,2-dichlorocyclopropyl) | 4-tetrahydropyranyl | H | O | 0 |
| A-1634 | H | H | H | H | H | $CH_2CH_2$(2,2-difluorocyclopropyl) | 4-tetrahydropyranyl | H | O | 0 |
| A-1635 | H | H | H | H | H | $CH_2CH_2$(2,2-dichlorocyclopropyl) | 4-tetrahydropyranyl | H | O | 0 |
| A-1636 | H | H | H | H | H | $CH_2SCH_3$ | 4-tetrahydropyranyl | H | O | 0 |
| A-1637 | H | H | H | H | H | $CH_2SCH_2CH_3$ | 4-tetrahydropyranyl | H | O | 0 |
| A-1638 | H | H | H | H | H | $CH_2CH_2SCH_3$ | 4-tetrahydropyranyl | H | O | 0 |
| A-1639 | H | H | H | H | H | $CH_2SOCH_3$ | 4-tetrahydropyranyl | H | O | 0 |
| A-1640 | H | H | H | H | H | $CH_2CH_2SOCH_3$ | 4-tetrahydropyranyl | H | O | 0 |
| A-1641 | H | H | H | H | H | $CH_2CH_2SO_2CH_3$ | 4-tetrahydropyranyl | H | O | 0 |
| A-1642 | H | H | H | H | H | $CH_2CH_2SO_2CH_3$ | 4-tetrahydropyranyl | H | O | 0 |

TABLE 28

| Compound | R¹ | R² | R³ | R⁴ | R⁵ | R⁶ | R⁷ | R⁸ | X | n |
|---|---|---|---|---|---|---|---|---|---|---|
| A-1643 | H | H | H | H | H | $CH_2SCF_3$ | 4-tetrahydropyranyl | H | O | 0 |
| A-1644 | H | H | H | H | H | $CH_2SCHF_2$ | 4-tetrahydropyranyl | H | O | 0 |
| A-1645 | H | H | H | H | H | $CH_2SCH_2CF_3$ | 4-tetrahydropyranyl | H | O | 0 |
| A-1646 | H | H | H | H | H | $CH_2SCH_2CHF_2$ | 4-tetrahydropyranyl | H | O | 0 |
| A-1647 | H | H | H | H | H | $CH_2SCF_2CF_2$ | 4-tetrahydropyranyl | H | O | 0 |
| A-1648 | H | H | H | H | H | $CH_2CH_2SCF_3$ | 4-tetrahydropyranyl | H | O | 0 |
| A-1649 | H | H | H | H | H | $CH_2SOCF_3$ | 4-tetrahydropyranyl | H | O | 0 |
| A-1650 | H | H | H | H | H | $CH_2CH_2SOCF_3$ | 4-tetrahydropyranyl | H | O | 0 |
| A-1651 | H | H | H | H | H | $CH_2CH_2CH_2SOCF_3$ | 4-tetrahydropyranyl | H | O | 0 |
| A-1652 | H | H | H | H | H | $CH_2SO_2CF_3$ | 4-tetrahydropyranyl | H | O | 0 |
| A-1653 | H | H | H | H | H | $CH_2CH_2SO_2CF_3$ | 4-tetrahydropyranyl | H | O | 0 |
| A-1654 | H | H | H | H | H | $CH_2CH_2CH_2SO_2CF_3$ | 4-tetrahydropyranyl | H | O | 0 |
| A-1655 | H | H | H | H | H | $CH_2C(=O)NHCH_2CHF_2$ | 4-tetrahydropyranyl | H | O | 0 |
| A-1656 | H | H | H | H | H | $CH_2C(=O)NHCH_2CF_3$ | 4-tetrahydropyranyl | H | O | 0 |
| A-1657 | H | H | H | H | H | H | $CH_2CN$ | H | O | 0 |
| A-1658 | H | H | H | H | H | $CH_3$ | $CH_2CN$ | H | O | 0 |
| A-1659 | H | H | H | H | H | $CH_2CH_3$ | $CH_2CN$ | H | O | 0 |
| A-1660 | H | H | H | H | H | $CH(CH_3)_2$ | $CH_2CN$ | H | O | 0 |
| A-1661 | H | H | H | H | H | $CH_2CH_2CH_3$ | $CH_2CN$ | H | O | 0 |
| A-1662 | H | H | H | H | H | $CH_2CH(CH_3)_2$ | $CH_2CN$ | H | O | 0 |
| A-1663 | H | H | H | H | H | $CH(CH_3)CH_2CH_3$ | $CH_2CN$ | H | O | 0 |
| A-1664 | H | H | H | H | H | $CH_2C(CH_3)_3$ | $CH_2CN$ | H | O | 0 |
| A-1665 | H | H | H | H | H | $CH_2(CH_2)_2CH_3$ | $CH_2CN$ | H | O | 0 |
| A-1666 | H | H | H | H | H | $CH_2(CH_2)_3CH_3$ | $CH_2CN$ | H | O | 0 |
| A-1667 | H | H | H | H | H | $CH_2(CH_2)_4CH_3$ | $CH_2CN$ | H | O | 0 |
| A-1668 | H | H | H | H | H | $CH_2(CH_2)_6CH_3$ | $CH_2CN$ | H | O | 0 |
| A-1669 | H | H | H | H | H | $CH_2OCH_3$ | $CH_2CN$ | H | O | 0 |

TABLE 28-continued

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-1670 | H | H | H | H | H | $CH_2OCH_2CH_3$ | $CH_2CN$ | H | O | 0 |
| A-1671 | H | H | H | H | H | $CH_2CH_2OCH_3$ | $CH_2CN$ | H | O | 0 |
| A-1672 | H | H | H | H | H | $CH_2CH_2OCH_2CH_3$ | $CH_2CN$ | H | O | 0 |
| A-1673 | H | H | H | H | H | $CF_3$ | $CH_2CN$ | H | O | 0 |
| A-1674 | H | H | H | H | H | $CHF_2$ | $CH_2CN$ | H | O | 0 |
| A-1675 | H | H | H | H | H | $CH_2CF_3$ | $CH_2CN$ | H | O | 0 |
| A-1676 | H | H | H | H | H | $CH_2CHF_2$ | $CH_2CN$ | H | O | 0 |
| A-1677 | H | H | H | H | H | $CH_2CClF_2$ | $CH_2CN$ | H | O | 0 |
| A-1678 | H | H | H | H | H | $CH_2CBrF_2$ | $CH_2CN$ | H | O | 0 |
| A-1679 | H | H | H | H | H | $CF_2CF_3$ | $CH_2CN$ | H | O | 0 |
| A-1680 | H | H | H | H | H | $CF_2CHF_2$ | $CH_2CN$ | H | O | 0 |
| A-1681 | H | H | H | H | H | $CH_2CH_2CF_3$ | $CH_2CN$ | H | O | 0 |
| A-1682 | H | H | H | H | H | $CH_2CF_2CF_3$ | $CH_2CN$ | H | O | 0 |
| A-1683 | H | H | H | H | H | $CH_2CF_2CHF_2$ | $CH_2CN$ | H | O | 0 |
| A-1684 | H | H | H | H | H | $CF_2CHFCF_3$ | $CH_2CN$ | H | O | 0 |
| A-1685 | H | H | H | H | H | $CF_2CF_2CF_3$ | $CH_2CN$ | H | O | 0 |
| A-1686 | H | H | H | H | H | $CH_2CF_2CF_2CF_3$ | $CH_2CN$ | H | O | 0 |
| A-1687 | H | H | H | H | H | $CH_2CF_2CHFCF_3$ | $CH_2CN$ | H | O | 0 |
| A-1688 | H | H | H | H | H | $CH_2CH_2CH_2CF_3$ | $CH_2CN$ | H | O | 0 |
| A-1689 | H | H | H | H | H | $CH_2CH_2CF_2CF_3$ | $CH_2CN$ | H | O | 0 |
| A-1690 | H | H | H | H | H | $CF_2CF_2CF_2CF_3$ | $CH_2CN$ | H | O | 0 |
| A-1691 | H | H | H | H | H | $CH_2CH_2CH(CF_3)_2$ | $CH_2CN$ | H | O | 0 |
| A-1692 | H | H | H | H | H | $CF_2CF_2CF_2CF_2CF_3$ | $CH_2CN$ | H | O | 0 |
| A-1693 | H | H | H | H | H | $CH_2CF_2CF_2CF_2CF_3$ | $CH_2CN$ | H | O | 0 |
| A-1694 | H | H | H | H | H | $CH_2CH_2CH_2CH_2CF_3$ | $CH_2CN$ | H | O | 0 |
| A-1695 | H | H | H | H | H | $CH_2CF_2CF_2CF_2CHF_2$ | $CH_2CN$ | H | O | 0 |
| A-1696 | H | H | H | H | H | $CH_2CF_2CF(CF_3)CF_2C(CF_3)_3$ | $CH_2CN$ | H | O | 0 |
| A-1697 | H | H | H | H | H | $CF_2CHFOCH_3$ | $CH_2CN$ | H | O | 0 |
| A-1698 | H | H | H | H | H | $CF_2CHFOCH_2CH_3$ | $CH_2CN$ | H | O | 0 |
| A-1699 | H | H | H | H | H | $CH_2CH_2OCH_2CF_3$ | $CH_2CN$ | H | O | 0 |
| A-1700 | H | H | H | H | H | $CF_2CHFOCF_3$ | $CH_2CN$ | H | O | 0 |
| A-1701 | H | H | H | H | H | $CF_2CHFOCF_2CF_3$ | $CH_2CN$ | H | O | 0 |
| A-1702 | H | H | H | H | H | $CF_2CHFOCF_2CF_2CF_3$ | $CH_2CN$ | H | O | 0 |
| A-1703 | H | H | H | H | H | $CH_2CH{=}CH_2$ | $CH_2CN$ | H | O | 0 |

TABLE 29

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-1704 | H | H | H | H | H | $CH_2CH{=}CHCl$ | $CH_2CN$ | H | O | 0 |
| A-1705 | H | H | H | H | H | $CH_2CH{=}CCl_2$ | $CH_2CN$ | H | O | 0 |
| A-1706 | H | H | H | H | H | $CH_2CH_2CF{=}CF_2$ | $CH_2CN$ | H | O | 0 |
| A-1707 | H | H | H | H | H | $CH_2CH_2CH{=}CF_2$ | $CH_2CN$ | H | O | 0 |
| A-1708 | H | H | H | H | H | $CH_2C{\equiv}CH$ | $CH_2CN$ | H | O | 0 |
| A-1709 | H | H | H | H | H | $CH_2C{\equiv}CCH_3$ | $CH_2CN$ | H | O | 0 |
| A-1710 | H | H | H | H | H | $CH_2C{\equiv}CCF_3$ | $CH_2CN$ | H | O | 0 |
| A-1711 | H | H | H | H | H | $CH_2C{\equiv}CI$ | $CH_2CN$ | H | O | 0 |
| A-1712 | H | H | H | H | H | cyclobutyl | $CH_2CN$ | H | O | 0 |
| A-1713 | H | H | H | H | H | cyclopentyl | $CH_2CN$ | H | O | 0 |
| A-1711 | H | H | H | H | H | cyclohexyl | $CH_2CN$ | H | O | 0 |
| A-1715 | H | H | H | H | H | 4,4-difluorocyclohexyl | $CH_2CN$ | H | O | 0 |
| A-1716 | H | H | H | H | H | $CH_2$(cyclopropyl) | $CH_2CN$ | H | O | 0 |
| A-1717 | H | H | H | H | H | $CH_2$(cyclobutyl) | $CH_2CN$ | H | O | 0 |
| A-1718 | H | H | H | H | H | $CH_2$(cyclopentyl) | $CH_2CN$ | H | O | 0 |
| A-1719 | H | H | H | H | H | $CH_2CH_2$(cyclopropyl) | $CH_2CN$ | H | O | 0 |
| A-1720 | H | H | H | H | H | $CH_2$(2,2-difluorocyclopropyl) | $CH_2CN$ | H | O | 0 |
| A-1721 | H | H | H | H | H | $CH_2$(2,2-dichlorocyclopropyl) | $CH_2CN$ | H | O | 0 |
| A-1722 | H | H | H | H | H | $CH_2$(4,4-difluorocyclohexyl) | $CH_2CN$ | H | O | 0 |
| A-1723 | H | H | H | H | H | $CH_2CH_2$(2,2-difluorocyclopropyl) | $CH_2CN$ | H | O | 0 |
| A-1724 | H | H | H | H | H | $CH_2CH_2$(2,2-dichlorocyclopropyl) | $CH_2CN$ | H | O | 0 |
| A-1725 | H | H | H | H | H | $CH_2SCH_3$ | $CH_2CN$ | H | O | 0 |
| A-1725 | H | H | H | H | H | $CH_2SCH_2CH_3$ | $CH_2CN$ | H | O | 0 |
| A-1727 | H | H | H | H | H | $CH_2CH_2SCH_3$ | $CH_2CN$ | H | O | 0 |
| A-1726 | H | H | H | H | H | $CH_2CH_2SCH_2CH_3$ | $CH_2CN$ | H | O | 0 |
| A-1729 | H | H | H | H | H | $CH_2CH_2CH_2SCH_3$ | $CH_2CN$ | H | O | 0 |
| A-1730 | H | H | H | H | H | $CH_2CH_2CH_2SCH_2CH_3$ | $CH_2CN$ | H | O | 0 |
| A-1731 | H | H | H | H | H | $CH(CH_3)SCH_3$ | $CH_2CN$ | H | O | 0 |
| A-1732 | H | H | H | H | H | $CH(CH_3)SCH_2CH_3$ | $CH_2CN$ | H | O | 0 |
| A-1733 | H | H | H | H | H | $CH_2CH(CH_3)SCH_3$ | $CH_2CN$ | H | O | 0 |
| A-1734 | H | H | H | H | H | $CH_2CH(CH_3)SCH_3$ | $CH_2CN$ | H | O | 0 |
| A-1735 | H | H | H | H | H | $CH(CH_3)CH_2CH_2SCH_2$ | $CH_2CN$ | H | O | 0 |
| A-1736 | H | H | H | H | H | $CH(CH_3)CH_2CH_2SCH_2CH_3$ | $CH_2CN$ | H | O | 0 |
| A-1737 | H | H | H | H | H | $CH_2CH(CH_3)CH_2SCH_3$ | $CH_2CN$ | H | O | 0 |
| A-1738 | H | H | H | H | H | $CH_2CH(CH_3)CH_2SCH_2CH_3$ | $CH_2CN$ | H | O | 0 |
| A-1739 | H | H | H | H | H | $CH_2CH_2CH(CH_3)SCH_3$ | $CH_2CN$ | H | O | 0 |

TABLE 29-continued

| Compound | R¹ | R² | R³ | R⁴ | R⁵ | R⁶ | R⁷ | R⁸ | X | n |
|---|---|---|---|---|---|---|---|---|---|---|
| A-1740 | H | H | H | H | H | $CH_2CH_2CH(CH_3)SCH_2CH_3$ | $CH_2CN$ | H | O | 0 |
| A-1741 | H | H | H | H | H | $CH_2SOCH_3$ | $CH_2CN$ | H | O | 0 |
| A-1742 | H | H | H | H | H | $CH_2CH_2SOCH_3$ | $CH_2CN$ | H | O | 0 |
| A-1743 | H | H | H | H | H | $CH_2CH_2CH_2SOCH_3$ | $CH_2CN$ | H | O | 0 |
| A-1744 | H | H | H | H | H | $CH(CH_3)SOCH_3$ | $CH_2CN$ | H | O | 0 |
| A-1745 | H | H | H | H | H | $CH_2CH(CH_3)SOCH_3$ | $CH_2CN$ | H | O | 0 |
| A-1746 | H | H | H | H | H | $CH(CH_3)CH_2CH_2SOCH_3$ | $CH_2CN$ | H | O | 0 |
| A-1747 | H | H | H | H | H | $CH_2CH(CH_3)CH_2SOCH_3$ | $CH_2CN$ | H | O | 0 |
| A-1748 | H | H | H | H | H | $CH_2CH_2CH(CH_3)SOCH_3$ | $CH_2CN$ | H | O | 0 |
| A-1749 | H | H | H | H | H | $CH_2SO_2CH_3$ | $CH_2CN$ | H | O | 0 |
| A-1750 | H | H | H | H | H | $CH_2CH_2SO_2CH_3$ | $CH_2CN$ | H | O | 0 |
| A-1751 | H | H | H | H | H | $CH_2CH_2CH_2SO_2CH_3$ | $CH_2CN$ | H | O | 0 |
| A-1752 | H | H | H | H | H | $CH(CH_3)SO_2CH_3$ | $CH_2CN$ | H | O | 0 |
| A-1753 | H | H | H | H | H | $CH_2CH(CH_3)SO_2CH_3$ | $CH_2CN$ | H | O | 0 |
| A-1754 | H | H | H | H | H | $CH(CH_3)CH_2CH_2SO_2CH_3$ | $CH_2CN$ | H | O | 0 |
| A-1755 | H | H | H | H | H | $CH_2CH(CH_3)CH_2SO_2CH_3$ | $CH_2CN$ | H | O | 0 |
| A-1756 | H | H | H | H | H | $CH_2CH_2CH(CH_3)SO_2CH_3$ | $CH_2CN$ | H | O | 0 |
| A-1757 | H | H | H | H | H | $CH_2SCF_3$ | $CH_2CN$ | H | O | 0 |
| A-1758 | H | H | H | H | H | $CH_2SCHF_2$ | $CH_2CN$ | H | O | 0 |
| A-1759 | H | H | H | H | H | $CH_2SCH_2CF_3$ | $CH_2CN$ | H | O | 0 |
| A-1760 | H | H | H | H | H | $CH_2SCH_2CHF_2$ | $CH_2CN$ | H | O | 0 |
| A-1761 | H | H | H | H | H | $CH_2SCF_2CF_3$ | $CH_2CN$ | H | O | 0 |
| A-1762 | H | H | H | H | H | $CH_2CH_2SCF_3$ | $CH_2CN$ | H | O | 0 |
| A-1763 | H | H | H | H | H | $CH_2CH_2SCH_2CF_3$ | $CH_2CN$ | H | O | 0 |
| A-1764 | H | H | H | H | H | $CH_2CH_2CH_2SCF_3$ | $CH_2CN$ | H | O | 0 |

TABLE 30

| Compound | R¹ | R² | R³ | R⁴ | R⁵ | R⁶ | R⁷ | R⁸ | X | n |
|---|---|---|---|---|---|---|---|---|---|---|
| A-1765 | H | H | H | H | H | $CH_2CH_2CH_2SCH_2CF_3$ | $CH_2CN$ | H | O | 0 |
| A-1766 | H | H | H | H | H | $CH(CH_3)SCF_3$ | $CH_2CN$ | H | O | 0 |
| A-1767 | H | H | H | H | H | $CH(CH_3)SCH_2CF_3$ | $CH_2CN$ | H | O | 0 |
| A-1768 | H | H | H | H | H | $CH_2CH(CH_3)SCF_3$ | $CH_2CN$ | H | O | 0 |
| A-1769 | H | H | H | H | H | $CH_2CH(CH_3)SCH_2CF_3$ | $CH_2CN$ | H | O | 0 |
| A-1770 | H | H | H | H | H | $CH(CH_3)CH_2CH_2SCF_3$ | $CH_2CN$ | H | O | 0 |
| A-1771 | H | H | H | H | H | $CH(CH_3)CH_2CH_2SCH_2CF_3$ | $CH_2CN$ | H | O | 0 |
| A-1772 | H | H | H | H | H | $CH_2CH(CH_3)CH_2SCF_3$ | $CH_2CN$ | H | O | 0 |
| A-1773 | H | H | H | H | H | $CH_2CH(CH_3)CH_2SCH_2CF_3$ | $CH_2CN$ | H | O | 0 |
| A-1774 | H | H | H | H | H | $CH_2CH_2CH(CH_3)SCF_3$ | $CH_2CN$ | H | O | 0 |
| A-1775 | H | H | H | H | H | $CH_2CH_2CH(CH_3)SCH_2CF_3$ | $CH_2CN$ | H | O | 0 |
| A-1776 | H | H | H | H | H | $CH_2SOCF_3$ | $CH_2CN$ | H | O | 0 |
| A-1777 | H | H | H | H | H | $CH_2CH_2SOCF_3$ | $CH_2CN$ | H | O | 0 |
| A-1778 | H | H | H | H | H | $CH_2CH_2CH_2SOCF_3$ | $CH_2CN$ | H | O | 0 |
| A-1779 | H | H | H | H | H | $CH(CH_3)SOCF_3$ | $CH_2CN$ | H | O | 0 |
| A-1780 | H | H | H | H | H | $CH_2CH(CH_3)SOCF_3$ | $CH_2CN$ | H | O | 0 |
| A-1781 | H | H | H | H | H | $CH(CH_3)CH_2CH_2SOCF_3$ | $CH_2CN$ | H | O | 0 |
| A-1782 | H | H | H | H | H | $CH_2CH(CH_3)CH_2SOCF_3$ | $CH_2CN$ | H | O | 0 |
| A-1783 | H | H | H | H | H | $CH_2CH_2CH(CH_3)SOCF_3$ | $CH_2CN$ | H | O | 0 |
| A-1784 | H | H | H | H | H | $CH_2SO_2CF_3$ | $CH_2CN$ | H | O | 0 |
| A-1785 | H | H | H | H | H | $CH_2CH_2SO_2CF_3$ | $CH_2CN$ | H | O | 0 |
| A-1786 | H | H | H | H | H | $CH_2CH_2CH_2SO_2CF_2$ | $CH_2CN$ | H | O | 0 |
| A-1787 | H | H | H | H | H | $CH(CH_3)SO_2CF_3$ | $CH_2CN$ | H | O | 0 |
| A-1788 | H | H | H | H | H | $CH_2CH(CH_3)SO_2CF_3$ | $CH_2CN$ | H | O | 0 |
| A-1789 | H | H | H | H | H | $CH(CH_3)CH_2CH_2SO_2CF_3$ | $CH_2CN$ | H | O | 0 |
| A-1790 | H | H | H | H | H | $CH_2CH(CH_3)CH_2SO_2CF_3$ | $CH_2CN$ | H | O | 0 |
| A-1791 | H | H | H | H | H | $CH_2CH_2CH(CH_3)SO_2CF_3$ | $CH_2CN$ | H | O | 0 |
| A-1792 | H | H | H | H | H | $CH_2C(=O)CH_3$ | $CH_2CN$ | H | O | 0 |
| A-1793 | H | H | H | H | H | $CH_2C(=O)CH_2CH_3$ | $CH_2CN$ | H | O | 0 |
| A-1794 | H | H | H | H | H | $CH_2C(=O)C(OH_3)_3$ | $CH_2CN$ | H | O | 0 |
| A-1795 | H | H | H | H | H | $CH_2CH_2C(=O)CH_3$ | $CH_2CN$ | H | O | 0 |
| A-1796 | H | H | H | H | H | $CH_2CH_2C(=O)C(CH_3)_3$ | $CH_2CN$ | H | O | 0 |
| A-1797 | H | H | H | H | H | $CH_2C(=O)CF_3$ | $CH_2CN$ | H | O | 0 |
| A-1798 | H | H | H | H | H | $CH_2CH_2C(=O)CF_3$ | $CH_2CN$ | H | O | 0 |
| A-1799 | H | H | H | H | H | $CH_2C(=O)OCH_3$ | $CH_2CN$ | H | O | 0 |
| A-1800 | H | H | H | H | H | $CH_2C(=O)OCH_2CH_3$ | $CH_2CN$ | H | O | 0 |
| A-1801 | H | H | H | H | H | $CH_2C(=O)OC(CH_3)_3$ | $CH_2CN$ | H | O | 0 |
| A-1802 | H | H | H | H | H | $CH_2CH_2C(=O)OCH_3$ | $CH_2CN$ | H | O | 0 |
| A-1803 | H | H | H | H | H | $CH_2CH_2C(=O)OCH_2CH_3$ | $CH_2CN$ | H | O | 0 |
| A-1804 | H | H | H | H | H | $CH_2CH_2C(=O)OC(CH_3)_3$ | $CH_2CN$ | H | O | 0 |
| A-1805 | H | H | H | H | H | $CH_2C(=O)NH_2$ | $CH_2CN$ | H | O | 0 |
| A-1806 | H | H | H | H | H | $CH_2CH_2C(=O)NH_2$ | $CH_2CN$ | H | O | 0 |
| A-1807 | H | H | H | H | H | $CH_2C(=O)NHCH_3$ | $CH_2CN$ | H | O | 0 |
| A-1808 | H | H | H | H | H | $CH_2C(=O)NHCH(CH_3)_2$ | $CH_2CN$ | H | O | 0 |
| A-1809 | H | H | H | H | H | $CH_2CH_2C(=O)NHCH_3$ | $CH_2CN$ | H | O | 0 |

TABLE 30-continued

| Compound | R¹ | R² | R³ | R⁴ | R⁵ | R⁶ | R⁷ | R⁸ | X | n |
|---|---|---|---|---|---|---|---|---|---|---|
| A-1810 | H | H | H | H | H | CH$_2$CH$_2$C(=O)NHCH(CH$_3$)$_2$ | CH$_2$CN | H | O | 0 |
| A-1811 | H | H | H | H | H | CH$_2$C(=O)NHCH$_2$CHF$_2$ | CH$_2$CN | H | O | 0 |
| A-1812 | H | H | H | H | H | CH$_2$C(=O)NHCH$_2$CF$_3$ | CH$_2$CN | H | O | 0 |
| A-1813 | H | H | H | H | H | CH$_2$CH$_2$C(=O)NHCH$_2$CHF$_2$ | CH$_2$CN | H | O | 0 |
| A-1814 | H | H | H | H | H | CH$_2$CH$_2$C(=O)NHCH$_2$CF$_3$ | CH$_2$CN | H | O | 0 |
| A-1815 | H | H | H | H | H | CH$_2$C(=O)N(CH$_3$)$_2$ | CH$_2$CN | H | O | 0 |
| A-1816 | H | H | H | H | H | CH$_2$C(=O)N(CH$_2$CH$_3$)$_2$ | CH$_2$CN | H | O | 0 |
| A-1817 | H | H | H | H | H | CH$_2$CH$_2$C(=O)N(CH$_3$)$_2$ | CH$_2$CN | H | O | 0 |
| A-1818 | H | H | H | H | H | CH$_2$CH$_2$C(=O)N(CH$_2$CH$_3$)$_2$ | CH$_2$CN | H | O | 0 |
| A-1819 | H | H | H | H | H | CH$_2$CH$_2$OH | CH$_2$CN | H | O | 0 |
| A-1820 | H | H | H | H | H | CH$_2$CH(OH)CH$_3$ | CH$_2$CN | H | O | 0 |
| A-1821 | H | H | H | H | H | CH$_2$CH$_2$CH$_2$OH | CH$_2$CN | H | O | 0 |
| A-1822 | H | H | H | H | H | CH$_2$CH(OH)CH$_2$CH$_3$ | CH$_2$CN | H | O | 0 |
| A-1823 | H | H | H | H | H | CH$_2$CH(OH)C(CH$_3$)$_3$ | CH$_2$CN | H | O | 0 |
| A-1824 | H | H | H | H | H | CH$_2$CH$_2$CH(OH)CH$_3$ | CH$_2$CN | H | O | 0 |
| A-1825 | H | H | H | H | H | CH$_2$CH$_2$CH(OH)C(CH$_3$)$_3$ | CH$_2$CN | H | O | 0 |

TABLE 31

| Compound | R¹ | R² | R³ | R⁴ | R⁵ | R⁶ | R⁷ | R⁸ | X | n |
|---|---|---|---|---|---|---|---|---|---|---|
| A-1826 | H | H | H | H | H | CH$_2$C(=NOH)CH$_3$ | CH$_2$CN | H | O | 0 |
| A-1827 | H | H | H | H | H | CH$_2$C(=NOH)CH$_2$CH$_3$ | CH$_2$CN | H | O | 0 |
| A-1828 | H | H | H | H | H | CH$_2$C(=NOH)C(CH$_3$)$_3$ | CH$_2$CN | H | O | 0 |
| A-1829 | H | H | H | H | H | CH$_2$C(=NOCH$_3$)CH$_3$ | CH$_2$CN | H | O | 0 |
| A-1830 | H | H | H | H | H | CH$_2$C(=NOCH$_3$)CH$_2$CH$_3$ | CH$_2$CN | H | O | 0 |
| A-1831 | H | H | H | H | H | CH$_2$C(=NOCH$_2$CH$_3$)CH$_3$ | CH$_2$CN | H | O | 0 |
| A-1832 | H | H | H | H | H | CH$_2$C(=NOCH$_2$CH$_3$)CH$_2$CH$_3$ | CH$_2$CN | H | O | 0 |
| A-1833 | H | H | H | H | H | CH$_2$C(=NOCH$_2$CF$_3$)CH$_3$ | CH$_2$CN | H | O | 0 |
| A-1834 | H | H | H | H | H | CH$_2$C(=NOCH$_2$CF$_3$)CH$_2$CH$_2$ | CH$_2$CN | H | O | 0 |
| A-1835 | H | H | H | H | H | CH$_2$Ph | CH$_2$CN | H | O | 0 |
| A-1836 | H | H | H | H | H | CH$_2$(2-F)Ph | CH$_2$CN | H | O | 0 |
| A-1837 | H | H | H | H | H | CH$_2$(3-F)Ph | CH$_2$CN | H | O | 0 |
| A-1838 | H | H | H | H | H | CH$_2$(4-F)Ph | CH$_2$CN | H | O | 0 |
| A-1839 | H | H | H | H | H | CH$_2$(2-Cl)Ph | CH$_2$CN | H | O | 0 |
| A-1840 | H | H | H | H | H | CH$_2$(3-Cl)Ph | CH$_2$CN | H | O | 0 |
| A-1841 | H | H | H | H | H | CH$_2$(4-Cl)Ph | CH$_2$CN | H | O | 0 |
| A-1842 | H | H | H | H | H | CH$_2$(2-CF$_3$)Ph | CH$_2$CN | H | O | 0 |
| A-1843 | H | H | H | H | H | CH$_2$(3-CF$_3$)Ph | CH$_2$CN | H | O | 0 |
| A-1844 | H | H | H | H | H | CH$_2$(4-CF$_3$)Ph | CH$_2$CN | H | O | 0 |
| A-1845 | H | H | H | H | H | CH$_2$(naphthalen-1-yl) | CH$_2$CN | H | O | 0 |
| A-1846 | H | H | H | H | H | CH$_2$(naphthalen-2-yl) | CH$_2$CN | H | O | 0 |
| A-1847 | H | H | H | H | H | CH$_2$CH$_2$Ph | CH$_2$CN | H | O | 0 |
| A-1848 | H | H | H | H | H | H | CH$_2$CH$_2$CN | H | O | 0 |
| A-1849 | H | H | H | H | H | CH$_3$ | CH$_2$CH$_2$CN | H | O | 0 |
| A-1850 | H | H | H | H | H | CH$_2$CH$_3$ | CH$_2$CH$_2$CN | H | O | 0 |
| A-1851 | H | H | H | H | H | CH(CH$_3$)$_2$ | CH$_2$CH$_2$CN | H | O | 0 |
| A-1852 | H | H | H | H | H | CH$_2$CH$_2$CH$_3$ | CH$_2$CH$_2$CN | H | O | 0 |
| A-1853 | H | H | H | H | H | CH$_2$CH(CH$_3$)$_2$ | CH$_2$CH$_2$CN | H | O | 0 |
| A-1854 | H | H | H | H | H | CH(CH$_3$)CH$_2$CH$_3$ | CH$_2$CH$_2$CN | H | O | 0 |
| A-1855 | H | H | H | H | H | CH$_2$C(CH$_3$)$_3$ | CH$_2$CH$_2$CN | H | O | 0 |
| A-1856 | H | H | H | H | H | CH$_2$(CH$_2$)$_2$CH$_3$ | CH$_2$CH$_2$CN | H | O | 0 |
| A-1857 | H | H | H | H | H | CH$_2$(CH$_2$)$_3$CH$_3$ | CH$_2$CH$_2$CN | H | O | 0 |
| A-1858 | H | H | H | H | H | CF$_3$ | CH$_2$CH$_2$CN | H | O | 0 |
| A-1859 | H | H | H | H | H | CHF$_2$ | CH$_2$CH$_2$CN | H | O | 0 |
| A-1860 | H | H | H | H | H | CH$_2$CF$_3$ | CH$_2$CH$_2$CN | H | O | 0 |
| A-1861 | H | H | H | H | H | CH$_2$CHF$_2$ | CH$_2$CH$_2$CN | H | O | 0 |
| A-1862 | H | H | H | H | H | CH$_2$CClF$_2$ | CH$_2$CH$_2$CN | H | O | 0 |
| A-1863 | H | H | H | H | H | CH$_2$CBrF$_2$ | CH$_2$CH$_2$CN | H | O | 0 |
| A-1864 | H | H | H | H | H | CF$_2$CF$_3$ | CH$_2$CH$_2$CN | H | O | 0 |
| A-1865 | H | H | H | H | H | CF$_2$CHF$_2$ | CH$_2$CH$_2$CN | H | O | 0 |
| A-1866 | H | H | H | H | H | CH$_2$CH$_2$CF$_3$ | CH$_2$CH$_2$CN | H | O | 0 |
| A-1867 | H | H | H | H | H | CH$_2$CF$_2$CF$_3$ | CH$_2$CH$_2$CN | H | O | 0 |
| A-1868 | H | H | H | H | H | CH$_2$CF$_2$CHF$_2$ | CH$_2$CH$_2$CN | H | O | 0 |
| A-1869 | H | H | H | H | H | CF$_2$CHFCF$_3$ | CH$_2$CH$_2$CN | H | O | 0 |
| A-1870 | H | H | H | H | H | CF$_2$CF$_2$CF$_3$ | CH$_2$CH$_2$CN | H | O | 0 |
| A-1871 | H | H | H | H | H | CH$_2$CF$_2$CF$_2$CF$_3$ | CH$_2$CH$_2$CN | H | O | 0 |
| A-1872 | H | H | H | H | H | CH$_2$CF$_2$CHFCF$_3$ | CH$_2$CH$_2$CN | H | O | 0 |
| A-1873 | H | H | H | H | H | CH$_2$CH$_2$CH$_2$CF$_3$ | CH$_2$CH$_2$CN | H | O | 0 |
| A-1874 | H | H | H | H | H | CH$_2$CH$_2$CF$_2$CF$_3$ | CH$_2$CH$_2$CN | H | O | 0 |
| A-1875 | H | H | H | H | H | CF$_2$CF$_2$CF$_2$CF$_3$ | CH$_2$CH$_2$CN | H | O | 0 |
| A-1876 | H | H | H | H | H | CH$_2$CH$_2$CH(CF$_3$)$_2$ | CH$_2$CH$_2$CN | H | O | 0 |
| A-1877 | H | H | H | H | H | CF$_2$CF$_2$CF$_2$CF$_2$CF$_3$ | CH$_2$CH$_2$CN | H | O | 0 |
| A-1878 | H | H | H | H | H | CH$_2$CF$_2$CF$_2$CF$_2$CF$_3$ | CH$_2$CH$_2$CN | H | O | 0 |
| A-1879 | H | H | H | H | H | CH$_2$CH$_2$CH$_2$CH$_2$CF$_3$ | CH$_2$CH$_2$CN | H | O | 0 |

TABLE 31-continued

| Compound | R¹ | R² | R³ | R⁴ | R⁵ | R⁶ | R⁷ | R⁸ | X | n |
|---|---|---|---|---|---|---|---|---|---|---|
| A-1880 | H | H | H | H | H | $CH_2CF_2CF_2CF_2CHF_2$ | $CH_2CH_2CN$ | H | O | 0 |
| A-1881 | H | H | H | H | H | $CH_2CH_2OCH_2CF_3$ | $CH_2CH_2CN$ | H | O | 0 |
| A-1882 | H | H | H | H | H | $CF_2CHFOCF_3$ | $CH_2CH_2CN$ | H | O | 0 |
| A-1883 | H | H | H | H | H | $CF_2CHFOCF_2CF_3$ | $CH_2CH_2CN$ | H | O | 0 |
| A-1884 | H | H | H | H | H | $CH_2CH_2CF=CF_2$ | $CH_2CH_2CN$ | H | O | 0 |
| A-1885 | H | H | H | H | H | $CH_2CH_2CH=CF_2$ | $CH_2CH_2CN$ | H | O | 0 |
| A-1886 | H | H | H | H | H | $CH_2C\equiv CCH_3$ | $CH_2CH_2CN$ | H | O | 0 |

TABLE 32

| Compound | R¹ | R² | R³ | R⁴ | R⁵ | R⁶ | R⁷ | R⁸ | X | n |
|---|---|---|---|---|---|---|---|---|---|---|
| A-1887 | H | H | H | H | H | $CH_2C\equiv CCF_3$ | $CH_2CH_2CN$ | H | O | 0 |
| A-1888 | H | H | H | H | H | $CH_2C\equiv CI$ | $CH_2CH_2CN$ | H | O | 0 |
| A-1889 | H | H | H | H | H | $CH_2$(2,2-difluorocyclopropyl) | $CH_2CH_2CN$ | H | O | 0 |
| A-1890 | H | H | H | H | H | $CH_2$(2,2-dichlorocyclopropyl) | $CH_2CH_2CN$ | H | O | 0 |
| A-1891 | H | H | H | H | H | $CH_2CH_2$(2,2-difluorocyclopropyl) | $CH_2CH_2CN$ | H | O | 0 |
| A-1892 | H | H | H | H | H | $CH_2CH_2$(2,2-dichlorocyclopropyl) | $CH_2CH_2CN$ | H | O | 0 |
| A-1893 | H | H | H | H | H | $CH_2SCH_3$ | $CH_2CH_2CN$ | H | O | 0 |
| A-1894 | H | H | H | H | H | $CH_2SCH_2CH_3$ | $CH_2CH_2CN$ | H | O | 0 |
| A-1895 | H | H | H | H | H | $CH_2CH_2SCH$ | $CH_2CH_2CN$ | H | O | 0 |
| A-1896 | H | H | H | H | H | $CH_2SOCH_3$ | $CH_2CH_2CN$ | H | O | 0 |
| A-1897 | H | H | H | H | H | $CH_2CH_2SOCH_3$ | $CH_2CH_2CN$ | H | O | 0 |
| A-1898 | H | H | H | H | H | $CH_2SO_2CH_3$ | $CH_2CH_2CN$ | H | O | 0 |
| A-1899 | H | H | H | H | H | $CH_2CH_2SO_2CH_3$ | $CH_2CH_2CN$ | H | O | 0 |
| A-1900 | H | H | H | H | H | $CH_2SCF_3$ | $CH_2CH_2CN$ | H | O | 0 |
| A-1901 | H | H | H | H | H | $CH_2SCHF_2$ | $CH_2CH_2CN$ | H | O | 0 |
| A-1902 | H | H | H | H | H | $CH_2SCH_2CF_3$ | $CH_2CH_2CN$ | H | O | 0 |
| A-1903 | H | H | H | H | H | $CH_2SCH_2CHF_2$ | $CH_2CH_2CN$ | H | O | 0 |
| A-1904 | H | H | H | H | H | $CH_2SCF_2CF_3$ | $CH_2CH_2CN$ | H | O | 0 |
| A-1905 | H | H | H | H | H | $CH_2CH_2SCF_3$ | $CH_2CH_2CN$ | H | O | 0 |
| A-1906 | H | H | H | H | H | $CH_2SOCF_3$ | $CH_2CH_2CN$ | H | O | 0 |
| A-1907 | H | H | H | H | H | $CH_2CH_2SOCF_3$ | $CH_2CH_2CN$ | H | O | 0 |
| A-1908 | H | H | H | H | H | $CH_2CH_2CH_2SOCF_3$ | $CH_2CH_2CN$ | H | O | 0 |
| A-1909 | H | H | H | H | H | $CH_2SO_2CF_3$ | $CH_2CH_2CN$ | H | O | 0 |
| A-1910 | H | H | H | H | H | $CH_2CH_2SO_2CF_3$ | $CH_2CH_2CN$ | H | O | 0 |
| A-1911 | H | H | H | H | H | $CH_2CH_2CH_2SO_2CF_3$ | $CH_2CH_2CN$ | H | O | 0 |
| A-1912 | H | H | H | H | H | $CH_2C(=O)NHCH_2CHF_2$ | $CH_2CH_2CN$ | H | O | 0 |
| A-1913 | H | H | H | H | H | $CH_2C(=O)NHCH_2CF_3$ | $CH_2CH_2CN$ | H | O | 0 |
| A-1914 | H | H | H | H | H | H | 1-CN-cyclopropyl | H | O | 0 |
| A-1915 | H | H | H | H | H | $CH_3$ | 1-CN-cyclopropyl | H | O | 0 |
| A-1916 | H | H | H | H | H | $CH_2CH_3$ | 1-CN-cyclopropyl | H | O | 0 |
| A-1917 | H | H | H | H | H | $CH(CH_3)_2$ | 1-CN-cyclopropyl | H | O | 0 |
| A-1918 | H | H | H | H | H | $CH_2CH_2CH_3$ | 1-CN-cyclopropyl | H | O | 0 |
| A-1919 | H | H | H | H | H | $CH_2CH(CH_3)_2$ | 1-CN-cyclopropyl | H | O | 0 |
| A-1920 | H | H | H | H | H | $CH(CH_3)CH_2CH_3$ | 1-CN-cyclopropyl | H | O | 0 |
| A-1921 | H | H | H | H | H | $CH_2C(CH_3)_3$ | 1-CN-cyclopropyl | H | O | 0 |
| A-1922 | H | H | H | H | H | $CH_2(CH_2)_2CH_3$ | 1-CN-cyclopropyl | H | O | 0 |
| A-1923 | H | H | H | H | H | $CH_2(CH_2)_3CH_3$ | 1-CN-cyclopropyl | H | O | 0 |
| A-1924 | H | H | H | H | H | $CF_3$ | 1-CN-cyclopropyl | H | O | 0 |
| A-1925 | H | H | H | H | H | $CHF_2$ | 1-CN-cyclopropyl | H | O | 0 |
| A-1926 | H | H | H | H | H | $CH_2CF_3$ | 1-CN-cyclopropyl | H | O | 0 |
| A-1927 | H | H | H | H | H | $CH_2CHF_2$ | 1-CN-cyclopropyl | H | O | 0 |
| A-1928 | H | H | H | H | H | $CH_2CClF_2$ | 1-CN-cyclopropyl | H | O | 0 |
| A-1929 | H | H | H | H | H | $CH_2CBrF_2$ | 1-CN-cyclopropyl | H | O | 0 |
| A-1930 | H | H | H | H | H | $CF_2CF_3$ | 1-CN-cyclopropyl | H | O | 0 |
| A-1931 | H | H | H | H | H | $CF_2CHF_2$ | 1-CN-cyclopropyl | H | O | 0 |
| A-1932 | H | H | H | H | H | $CH_2CH_2CF_3$ | 1-CN-cyclopropyl | H | O | 0 |
| A-1933 | H | H | H | H | H | $CH_2CF_2CF_3$ | 1-CN-cyclopropyl | H | O | 0 |
| A-1934 | H | H | H | H | H | $CH_2CF_2CHF_2$ | 1-CN-cyclopropyl | H | O | 0 |
| A-1935 | H | H | H | H | H | $CF_2CHFCF_3$ | 1-CN-cyclopropyl | H | O | 0 |
| A-1936 | H | H | H | H | H | $CF_2CF_2CF_3$ | 1-CN-cyclopropyl | H | O | 0 |
| A-1937 | H | H | H | H | H | $CH_2CF_2CF_2CF_3$ | 1-CN-cyclopropyl | H | O | 0 |
| A-1938 | H | H | H | H | H | $CH_2CF_3CHFCF_3$ | 1-CN-cyclopropyl | H | O | 0 |
| A-1939 | H | H | H | H | H | $CH_2CH_2CF_2CF_3$ | 1-CN-cyclopropyl | H | O | 0 |
| A-1940 | H | H | H | H | H | $CH_2CH_2CF_2CF_3$ | 1-CN-cyclopropyl | H | O | 0 |
| A-1941 | H | H | H | H | H | $CF_2CF_2CF_2CF_3$ | 1-CN-cyclopropyl | H | O | 0 |
| A-1942 | H | H | H | H | H | $CH_2CH_2CH(CF_3)_2$ | 1-CN-cyclopropyl | H | O | 0 |
| A-1943 | H | H | H | H | H | $CF_2CF_2CF_2CF_2CF_3$ | 1-CN-cyclopropyl | H | O | 0 |
| A-1944 | H | H | H | H | H | $CH_2CF_2CF_2CF_2CF_3$ | 1-CN-cyclopropyl | H | O | 0 |
| A-1945 | H | H | H | H | H | $CH_2CH_2CH_2CH_2CF_3$ | 1-CN-cyclopropyl | H | O | 0 |
| A-1946 | H | H | H | H | H | $CH_2CF_2CF_2CF_2CHF_2$ | 1-CN-cyclopropyl | H | O | 0 |
| A-1947 | H | H | H | H | H | $CF_2CH_2OCH_2CF_3$ | 1-CN-cyclopropyl | H | O | 0 |

TABLE 33

| Compound | R¹ | R² | R³ | R⁴ | R⁵ | R⁶ | R⁷ | R⁸ | X | n |
|---|---|---|---|---|---|---|---|---|---|---|
| A-1948 | H | H | H | H | H | CF$_2$CHFOCF$_3$ | 1-CN-cyclopropyl | H | O | 0 |
| A-1949 | H | H | H | H | H | CF$_2$CHFOCF$_2$CF$_3$ | 1-CN-cyclopropyl | H | O | 0 |
| A-1950 | H | H | H | H | H | CH$_2$CH$_2$CF=CF$_2$ | 1-CN-cyclopropyl | H | O | 0 |
| A-1951 | H | H | H | H | H | CH$_2$CH$_2$CH=CF$_2$ | 1-CN-cyclopropyl | H | O | 0 |
| A-1952 | H | H | H | H | H | CH$_2$C≡CCH$_3$ | 1-CN-cyclopropyl | H | O | 0 |
| A-1953 | H | H | H | H | H | CH$_2$C≡CCF$_3$ | 1-CN-cyclopropyl | H | O | 0 |
| A-1954 | H | H | H | H | H | CH$_2$C≡CI | 1-CN-cyclopropyl | H | O | 0 |
| A-1955 | H | H | H | H | H | CH$_2$(2,2-difluorocyclopropyl) | 1-CN-cyclopropyl | H | O | 0 |
| A-1956 | H | H | H | H | H | CH$_2$(2,2-dichlorocyclopropyl) | 1-CN-cyclopropyl | H | O | 0 |
| A-1957 | H | H | H | H | H | CH$_2$CH$_2$(2,2-difluorocyclopropyl) | 1-CN-cyclopropyl | H | O | 0 |
| A-1958 | H | H | H | H | H | CH$_2$CH$_2$(2,2-dichlorocyclopropyl) | 1-CN-cyclopropyl | H | O | 0 |
| A-1959 | H | H | H | H | H | CH$_2$SCH$_3$ | 1-CN-cyclopropyl | H | O | 0 |
| A-1960 | H | H | H | H | H | CH$_2$SCH$_2$CH$_3$ | 1-CN-cyclopropyl | H | O | 0 |
| A-1961 | H | H | H | H | H | CH$_2$CH$_2$SCH$_3$ | 1-CN-cyclopropyl | H | O | 0 |
| A-1962 | H | H | H | H | H | CH$_2$SOCH$_3$ | 1-CN-cyclopropyl | H | O | 0 |
| A-1963 | H | H | H | H | H | CH$_2$CH$_2$SOCH$_3$ | 1-CN-cyclopropyl | H | O | 0 |
| A-1964 | H | H | H | H | H | CH$_2$SO$_2$CH$_2$ | 1-CN-cyclopropyl | H | O | 0 |
| A-1965 | H | H | H | H | H | CH$_2$CH$_2$SO$_2$CH$_3$ | 1-CN-cyclopropyl | H | O | 0 |
| A-1966 | H | H | H | H | H | CH$_2$SCF$_3$ | 1-CN-cyclopropyl | H | O | 0 |
| A-1967 | H | H | H | H | H | CH$_2$SCHF$_2$ | 1-CN-cyclopropyl | H | O | 0 |
| A-1968 | H | H | H | H | H | CH$_2$SCH$_2$CF$_3$ | 1-CN-cyclopropyl | H | O | 0 |
| A-1969 | H | H | H | H | H | CH$_2$SCH$_2$CHF$_2$ | 1-CN-cyclopropyl | H | O | 0 |
| A-1970 | H | H | H | H | H | CH$_2$SCF$_2$CF$_3$ | 1-CN-cyclopropyl | H | O | 0 |
| A-1971 | H | H | H | H | H | CH$_2$CH$_2$SCF$_3$ | 1-CN-cyclopropyl | H | O | 0 |
| A-1972 | H | H | H | H | H | CH$_2$SOCF$_3$ | 1-CN-cyclopropyl | H | O | 0 |
| A-1973 | H | H | H | H | H | CH$_2$CH$_2$SOCF$_3$ | 1-CN-cyclopropyl | H | O | 0 |
| A-1974 | H | H | H | H | H | CH$_2$CH$_2$CH$_2$SOCF$_3$ | 1-CN-cyclopropyl | H | O | 0 |
| A-1975 | H | H | H | H | H | CH$_2$SO$_2$CF$_3$ | 1-CN-cyclopropyl | H | O | 0 |
| A-1976 | H | H | H | H | H | CH$_2$CH$_2$SO$_2$CF$_3$ | 1-CN-cyclopropyl | H | O | 0 |
| A-1977 | H | H | H | H | H | CH$_2$CH$_2$CH$_2$SO$_2$CF$_3$ | 1-CN-cyclopropyl | H | O | 0 |
| A-1978 | H | H | H | H | H | CH$_2$C(=O)NHCH$_2$CHF$_2$ | 1-CN-cyclopropyl | H | O | 0 |
| A-1979 | H | H | H | H | H | CH$_2$C(=O)NHCH$_2$CF$_3$ | 1-CN-cyclopropyl | H | O | 0 |
| A-1980 | H | H | H | H | H | H | CH$_2$OH | H | O | 0 |
| A-1981 | H | H | H | H | H | CH$_3$ | CH$_2$OH | H | O | 0 |
| A-1982 | H | H | H | H | H | CH$_2$CH$_3$ | CH$_2$OH | H | O | 0 |
| A-1983 | H | H | H | H | H | CH(CH$_3$)$_3$ | CH$_2$OH | H | O | 0 |
| A-1984 | H | H | H | H | H | CH$_2$CH$_2$CH$_3$ | CH$_2$OH | H | O | 0 |
| A-1985 | H | H | H | H | H | CH$_2$CH(CH$_3$)$_2$ | CH$_2$OH | H | O | 0 |
| A-1986 | H | H | H | H | H | CH(CH$_3$)CH$_2$CH$_3$ | CH$_2$OH | H | O | 0 |
| A-1987 | H | H | H | H | H | CH$_2$C(CH$_3$)$_3$ | CH$_2$OH | H | O | 0 |
| A-1988 | H | H | H | H | H | CH$_2$(CH$_2$)$_2$CH$_3$ | CH$_2$OH | H | O | 0 |
| A-1989 | H | H | H | H | H | CH$_2$(CH$_2$)$_3$CH$_3$ | CH$_2$OH | H | O | 0 |
| A-1990 | H | H | H | H | H | CF$_3$ | CH$_2$OH | H | O | 0 |
| A-1991 | H | H | H | H | H | CHF$_2$ | CH$_2$OH | H | O | 0 |
| A-1992 | H | H | H | H | H | CH$_2$CF$_3$ | CH$_2$OH | H | O | 0 |
| A-1993 | H | H | H | H | H | CH$_2$CHF$_2$ | CH$_2$OH | H | O | 0 |
| A-1994 | H | H | H | H | H | CH$_2$CClF$_2$ | CH$_2$OH | H | O | 0 |
| A-1995 | H | H | H | H | H | CH$_2$CBrF$_2$ | CH$_2$OH | H | O | 0 |
| A-1996 | H | H | H | H | H | CF$_2$CF$_3$ | CH$_2$OH | H | O | 0 |
| A-1997 | H | H | H | H | H | CH$_2$CHF$_2$ | CH$_2$OH | H | O | 0 |
| A-1998 | H | H | H | H | H | CH$_2$CH$_2$CF$_2$ | CH$_2$OH | H | O | 0 |
| A-1999 | H | H | H | H | H | CH$_2$CF$_2$CF$_3$ | CH$_2$OH | H | O | 0 |
| A-2000 | H | H | H | H | H | CH$_2$CF$_2$CHF$_2$ | CH$_2$OH | H | O | 0 |
| A-2001 | H | H | H | H | H | CF$_2$CHFCF$_2$ | CH$_2$OH | H | O | 0 |
| A-2002 | H | H | H | H | H | CF$_2$CF$_2$CF$_3$ | CH$_2$OH | H | O | 0 |
| A-2003 | H | H | H | H | H | CH$_2$CF$_2$CF$_2$CF$_3$ | CH$_2$OH | H | O | 0 |
| A-2004 | H | H | H | H | H | CH$_2$CF$_2$CHFCF$_3$ | CH$_2$OH | H | O | 0 |
| A-2005 | H | H | H | H | H | CH$_2$CH$_2$CH$_2$CF$_3$ | CH$_2$OH | H | O | 0 |
| A-2006 | H | H | H | H | H | CH$_2$CH$_2$CF$_2$CF$_3$ | CH$_2$OH | H | O | 0 |
| A-2007 | H | H | H | H | H | CF$_2$CF$_2$CF$_2$CF$_3$ | CH$_2$OH | H | O | 0 |
| A-2008 | H | H | H | H | H | CH$_2$CH$_2$CH(CF$_3$)$_2$ | CH$_2$OH | H | O | 0 |

TABLE 34

| Compound | R¹ | R² | R³ | R⁴ | R⁵ | R⁶ | R⁷ | R⁸ | X | n |
|---|---|---|---|---|---|---|---|---|---|---|
| A-2009 | H | H | H | H | H | CF$_2$CF$_2$CF$_2$CF$_2$CF$_3$ | CH$_2$OH | H | O | 0 |
| A-2010 | H | H | H | H | H | CH$_2$CF$_2$CF$_2$CF$_2$CF$_3$ | CH$_2$OH | H | O | 0 |
| A-2011 | H | H | H | H | H | CH$_2$CH$_2$CH$_2$CH$_2$CF$_3$ | CH$_2$OH | H | O | 0 |
| A-2012 | H | H | H | H | H | CH$_2$CF$_2$CF$_2$CF$_2$CHF$_2$ | CH$_2$OH | H | O | 0 |
| A-2013 | H | H | H | H | H | CH$_2$CH$_2$OCH$_2$CF$_3$ | CH$_2$OH | H | O | 0 |
| A-2014 | H | H | H | H | H | CF$_2$CHFOCF$_3$ | CH$_2$OH | H | O | 0 |
| A-2015 | H | H | H | H | H | CF$_2$CHFOCF$_2$CF$_3$ | CH$_2$OH | H | O | 0 |
| A-2016 | H | H | H | H | H | CH$_2$CH$_2$CF=CF$_2$ | CH$_2$OH | H | O | 0 |
| A-2017 | H | H | H | H | H | CH$_2$CH$_2$CH=CF$_2$ | CH$_2$OH | H | O | 0 |

TABLE 34-continued

| Compound | R¹ | R² | R³ | R⁴ | R⁵ | R⁶ | R⁷ | R⁸ | X | n |
|---|---|---|---|---|---|---|---|---|---|---|
| A-2018 | H | H | H | H | H | CH₂C≡CCH₃ | CH₂OH | H | O | 0 |
| A-2019 | H | H | H | H | H | CH₂C≡CCF₃ | CH₂OH | H | O | 0 |
| A-2020 | H | H | H | H | H | CH₂C≡CI | CH₂OH | H | O | 0 |
| A-2021 | H | H | H | H | H | CH₂(2,2-difluorocyclopropyl) | CH₂OH | H | O | 0 |
| A-2022 | H | H | H | H | H | CH₂(2,2-dichlorocyclopropyl) | CH₂OH | H | O | 0 |
| A-2023 | H | H | H | H | H | CH₂CH₂(2,2-difluorocyclopropyl) | CH₂OH | H | O | 0 |
| A-2024 | H | H | H | H | H | CH₂CH₂(2,2-dichlorocyclopropyl) | CH₂OH | H | O | 0 |
| A-2025 | H | H | H | H | H | CH₂SCH₃ | CH₂OH | H | O | 0 |
| A-2026 | H | H | H | H | H | CH₂SCH₂CH₃ | CH₂OH | H | O | 0 |
| A-2027 | H | H | H | H | H | CH₂CH₂SCH₃ | CH₂OH | H | O | 0 |
| A-2028 | H | H | H | H | H | CH₂SOCH₃ | CH₂OH | H | O | 0 |
| A-2029 | H | H | H | H | H | CH₂CH₂SOCH₃ | CH₂OH | H | O | 0 |
| A-2030 | H | H | H | H | H | CH₂SO₂CH₃ | CH₂OH | H | O | 0 |
| A-2031 | H | H | H | H | H | CH₂CH₂SO₂CH₃ | CH₂OH | H | O | 0 |
| A-2032 | H | H | H | H | H | CH₂SCF₃ | CH₂OH | H | O | 0 |
| A-2033 | H | H | H | H | H | CH₂SCHF₂ | CH₂OH | H | O | 0 |
| A-2034 | H | H | H | H | H | CH₂SCH₂CF₃ | CH₂OH | H | O | 0 |
| A-2035 | H | H | H | H | H | CH₂SCH₂CHF₂ | CH₂OH | H | O | 0 |
| A-2036 | H | H | H | H | H | CH₂SCF₂CF₃ | CH₂OH | H | O | 0 |
| A-2037 | H | H | H | H | H | CH₂CH₂SCF₃ | CH₂OH | H | O | 0 |
| A-2038 | H | H | H | H | H | CH₂SOCF₃ | CH₂OH | H | O | 0 |
| A-2039 | H | H | H | H | H | CH₂CH₂SOCF₃ | CH₂OH | H | O | 0 |
| A-2040 | H | H | H | H | H | CH₂CH₂CH₂SOCF₂ | CH₂OH | H | O | 0 |
| A-2041 | H | H | H | H | H | CH₂SO₂CF₃ | CH₂OH | H | O | 0 |
| A-2042 | H | H | H | H | H | CH₂CH₂SO₂CF₃ | CH₂OH | H | O | 0 |
| A-2043 | H | H | H | H | H | CH₂CH₂CH₂SO₂CF₃ | CH₂OH | H | O | 0 |
| A-2044 | H | H | H | H | H | CH₂C(═O)NHCH₂CHF₂ | CH₂OH | H | O | 0 |
| A-2045 | H | H | H | H | H | CH₂C(═O)NHCH₂CF₃ | CH₂OH | H | O | 0 |
| A-2046 | H | H | H | H | H | H | NH₂ | H | O | 0 |
| A-2047 | H | H | H | H | H | CH₃ | NH₂ | H | O | 0 |
| A-2048 | H | H | H | H | H | CH₂CH₃ | NH₂ | H | O | 0 |
| A-2049 | H | H | H | H | H | CH(CH₃)₂ | NH₂ | H | O | 0 |
| A-2050 | H | H | H | H | H | CH₂CH₂CH₃ | NH₂ | H | O | 0 |
| A-2051 | H | H | H | H | H | CH₂CH(CH₃)₂ | NH₂ | H | O | 0 |
| A-2052 | H | H | H | H | H | CH(CH₃)CH₂CH₃ | NH₂ | H | O | 0 |
| A-2053 | H | H | H | H | H | CH₂C(CH₃)₃ | NH₂ | H | O | 0 |
| A-2054 | H | H | H | H | H | CH₂(CH₂)₂CH₃ | NH₂ | H | O | 0 |
| A-2055 | H | H | H | H | H | CH₂(CH₂)₃CH₃ | NH₂ | H | O | 0 |
| A-2056 | H | H | H | H | H | CF₃ | NH₂ | H | O | 0 |
| A-2057 | H | H | H | H | H | CHF₂ | NH₂ | H | O | 0 |
| A-2058 | H | H | H | H | H | CH₂CF₃ | NH₂ | H | O | 0 |
| A-2059 | H | H | H | H | H | CH₂CHF₂ | NH₂ | H | O | 0 |
| A-2060 | H | H | H | H | H | CH₂CClF₂ | NH₂ | H | O | 0 |
| A-2061 | H | H | H | H | H | CH₂CBrF₂ | NH₂ | H | O | 0 |
| A-2062 | H | H | H | H | H | CF₂CF₃ | NH₂ | H | O | 0 |
| A-2063 | H | H | H | H | H | CF₂CHF₂ | NH₂ | H | O | 0 |
| A-2064 | H | H | H | H | H | CH₂CH₂CF₃ | NH₂ | H | O | 0 |
| A-2065 | H | H | H | H | H | CH₂CF₂CF₃ | NH₂ | H | O | 0 |
| A-2066 | H | H | H | H | H | CH₂CF₂CHF₂ | NH₂ | H | O | 0 |
| A-2067 | H | H | H | H | H | CF₂CHFCF | NH₂ | H | O | 0 |
| A-2068 | H | H | H | H | H | CF₂CHFCF₃ | NH₂ | H | O | 0 |
| A-2069 | H | H | H | H | H | CH₂CF₂CF₂CF₃ | NH₂ | H | O | 0 |

TABLE 35

| Compound | R¹ | R² | R³ | R⁴ | R⁵ | R⁶ | R⁷ | R⁸ | X | n |
|---|---|---|---|---|---|---|---|---|---|---|
| A-2070 | H | H | H | H | H | CH₂CF₂CHFCF₃ | NH₂ | H | O | 0 |
| A-2071 | H | H | H | H | H | CH₂CH₂CH₂CF₃ | NH₂ | H | O | 0 |
| A-2072 | H | H | H | H | H | CH₂CH₂CF₂CF₃ | NH₂ | H | O | 0 |
| A-2073 | H | H | H | H | H | CF₂CF₂CF₂CF₃ | NH₂ | H | O | 0 |
| A-2074 | H | H | H | H | H | CH₂CH₂CH(CF₃)₂ | NH₂ | H | O | 0 |
| A-2075 | H | H | H | H | H | CF₂CF₂CF₂CF₂CF₃ | NH₂ | H | O | 0 |
| A-2076 | H | H | H | H | H | CH₂CF₂CF₂CF₂CF₃ | NH₂ | H | O | 0 |
| A-2077 | H | H | H | H | H | CH₂CH₂CH₂CH₂CF₃ | NH₂ | H | O | 0 |
| A-2078 | H | H | H | H | H | CH₂CF₂CF₂CF₂CHF₂ | NH₂ | H | O | 0 |
| A-2079 | H | H | H | H | H | CH₂CH₂OCH₂CF₃ | NH₂ | H | O | 0 |
| A-2080 | H | H | H | H | H | CF₂CHFOCF₂ | NH₂ | H | O | 0 |
| A-2081 | H | H | H | H | H | CF₂CHFOCH₂CF₃ | NH₂ | H | O | 0 |
| A-2082 | H | H | H | H | H | CH₂CH₂CF═CF₂ | NH₂ | H | O | 0 |
| A-2083 | H | H | H | H | H | CH₂CH₂CH═CF₂ | NH₂ | H | O | 0 |
| A-2084 | H | H | H | H | H | CH₂C≡CCH₃ | NH₂ | H | O | 0 |
| A-2085 | H | H | H | H | H | CH₂C≡CCF₃ | NH₂ | H | O | 0 |
| A-2086 | H | H | H | H | H | CH₂C≡CI | NH₂ | H | O | 0 |
| A-2087 | H | H | H | H | H | CH₂(2,2-difluorocyclopropyl) | NH₂ | H | O | 0 |

TABLE 35-continued

| Compound | R¹ | R² | R³ | R⁴ | R⁵ | R⁶ | R⁷ | R⁸ | X | n |
|---|---|---|---|---|---|---|---|---|---|---|
| A-2088 | H | H | H | H | H | $CH_2$(2,2-dichlorocyclopropyl) | $NH_2$ | H | O | 0 |
| A-2089 | H | H | H | H | H | $CH_2CH_2$(2,2-difluorocyclopropyl) | $NH_2$ | H | O | 0 |
| A-2090 | H | H | H | H | H | $CH_2CH_2$(2,2-dichlorocyclopropyl) | $NH_2$ | H | O | 0 |
| A-2091 | H | H | H | H | H | $CH_2SCH_3$ | $NH_2$ | H | O | 0 |
| A-2092 | H | H | H | H | H | $CH_2SCH_2CH_3$ | $NH_2$ | H | O | 0 |
| A-2093 | H | H | H | H | H | $CH_2CH_2SCH_3$ | $NH_2$ | H | O | 0 |
| A-2094 | H | H | H | H | H | $CH_2SOCH_3$ | $NH_2$ | H | O | 0 |
| A-2095 | H | H | H | H | H | $CH_2CH_2SOCH_3$ | $NH_2$ | H | O | 0 |
| A-2096 | H | H | H | H | H | $CH_2SO_2CH_2$ | $NH_2$ | H | O | 0 |
| A-2097 | H | H | H | H | H | $CH_2CH_2SO_2CH_3$ | $NH_2$ | H | O | 0 |
| A-2098 | H | H | H | H | H | $CH_2SCF_3$ | $NH_2$ | H | O | 0 |
| A-2099 | H | H | H | H | H | $CH_2SCHF_2$ | $NH_2$ | H | O | 0 |
| A-2100 | H | H | H | H | H | $CH_2SCH_2CF_3$ | $NH_2$ | H | O | 0 |
| A-2101 | H | H | H | H | H | $CH_2SCH_2CHF_2$ | $NH_2$ | H | O | 0 |
| A-2102 | H | H | H | H | H | $CH_2SCF_2CF_3$ | $NH_2$ | H | O | 0 |
| A-2103 | H | H | H | H | H | $CH_2CH_2SCF_2$ | $NH_2$ | H | O | 0 |
| A-2104 | H | H | H | H | H | $CH_2SOCF_3$ | $NH_2$ | H | O | 0 |
| A-2105 | H | H | H | H | H | $CH_2CH_2SOCF_3$ | $NH_2$ | H | O | 0 |
| A-2106 | H | H | H | H | H | $CH_2CH_2CH_2SOCF_3$ | $NH_2$ | H | O | 0 |
| A-2107 | H | H | H | H | H | $CH_2SO_2CF_3$ | $NH_2$ | H | O | 0 |
| A-2108 | H | H | H | H | H | $CH_2CH_2SO_2CF_3$ | $NH_2$ | H | O | 0 |
| A-2109 | H | H | H | H | H | $CH_2CH_2CH_2SO_2CF_3$ | $NH_2$ | H | O | 0 |
| A-2110 | H | H | H | H | H | $CH_2C(=O)NHCH_2CHF_2$ | $NH_2$ | H | O | 0 |
| A-2111 | H | H | H | H | H | $CH_2C(=O)NHCH_2CF_3$ | $NH_2$ | H | O | 0 |
| A-2112 | H | H | H | H | H | H | $C(=O)CH_3$ | H | O | 0 |
| A-2113 | H | H | H | H | H | $CH_3$ | $C(=O)CH_3$ | H | O | 0 |
| A-2114 | H | H | H | H | H | $CH_2CH_3$ | $C(=O)CH_3$ | H | O | 0 |
| A-2115 | H | H | H | H | H | $CH(CH_3)_2$ | $C(=O)CH_3$ | H | O | 0 |
| A-2116 | H | H | H | H | H | $CH_2CH_2CH_3$ | $C(=O)CH_3$ | H | O | 0 |
| A-2117 | H | H | H | H | H | $CH_2CH(CH_3)_2$ | $C(=O)CH_3$ | H | O | 0 |
| A-2118 | H | H | H | H | H | $CH_2C(CH_3)_3$ | $C(=O)CH_3$ | H | O | 0 |
| A-2119 | H | H | H | H | H | $CH(CH_3)CH_2CH_3$ | $C(=O)CH_3$ | H | O | 0 |
| A-2120 | H | H | H | H | H | $CH_2(CH_2)_2CH_3$ | $C(=O)CH_3$ | H | O | 0 |
| A-2121 | H | H | H | H | H | $CH_2(CH_2)_3CH_3$ | $C(=O)CH_3$ | H | O | 0 |
| A-2122 | H | H | H | H | H | $CH_2(CH_2)_4CH_3$ | $C(=O)CH_3$ | H | O | 0 |
| A-2123 | H | H | H | H | H | $CH_2(CH_2)_6CH_3$ | $C(=O)CH_3$ | H | O | 0 |
| A-2124 | H | H | H | H | H | $CH_2OCH_3$ | $C(=O)CH_3$ | H | O | 0 |
| A-2125 | H | H | H | H | H | $CH_2OCH_2CH_3$ | $C(=O)CH_3$ | H | O | 0 |
| A-2126 | H | H | H | H | H | $CH_2CH_2OCH_3$ | $C(=O)CH_3$ | H | O | 0 |
| A-2127 | H | H | H | H | H | $CH_2CH_2OCH_2CH_3$ | $C(=O)CH_3$ | H | O | 0 |
| A-2128 | H | H | H | H | H | $CF_3$ | $C(=O)CH_3$ | H | O | 0 |
| A-2129 | H | H | H | H | H | $CHF_2$ | $C(=O)CH_3$ | H | O | 0 |
| A-2130 | H | H | H | H | H | $CH_2CF_3$ | $C(=O)CH_3$ | H | O | 0 |

TABLE 36

| Compound | R¹ | R² | R³ | R⁴ | R⁵ | R⁶ | R⁷ | R⁸ | X | n |
|---|---|---|---|---|---|---|---|---|---|---|
| A-2131 | H | H | H | H | H | $CH_2CHF_2$ | $C(=O)CH_3$ | H | O | 0 |
| A-2132 | H | H | H | H | H | $CH_2CClF_2$ | $C(=O)CH_3$ | H | O | 0 |
| A-2133 | H | H | H | H | H | $CH_2CBrF_2$ | $C(=O)CH_3$ | H | O | 0 |
| A-2134 | H | H | H | H | H | $CF_2CF_3$ | $C(=O)CH_3$ | H | O | 0 |
| A-2135 | H | H | H | H | H | $CF_2CHF_2$ | $C(=O)CH_3$ | H | O | 0 |
| A-2136 | H | H | H | H | H | $CH_2CH_2CF_3$ | $C(=O)CH_3$ | H | O | 0 |
| A-2137 | H | H | H | H | H | $CH_2CF_2CF_3$ | $C(=O)CH_3$ | H | O | 0 |
| A-2138 | H | H | H | H | H | $CH_2CF_2CHF_2$ | $C(=O)CH_3$ | H | O | 0 |
| A-2139 | H | H | H | H | H | $CF_2CHFCF_3$ | $C(=O)CH_3$ | H | O | 0 |
| A-2140 | H | H | H | H | H | $CF_2CF_2CF_3$ | $C(=O)CH_3$ | H | O | 0 |
| A-2141 | H | H | H | H | H | $CH_2CF_2CF_2CF_3$ | $C(=O)CH_3$ | H | O | 0 |
| A-2142 | H | H | H | H | H | $CH_2CF_2CHFCF_3$ | $C(=O)CH_3$ | H | O | 0 |
| A-2143 | H | H | H | H | H | $CH_2CH_2CH_2CF_3$ | $C(=O)CH_3$ | H | O | 0 |
| A-2144 | H | H | H | H | H | $CH_2CH_2CF_2CF_3$ | $C(=O)CH_3$ | H | O | 0 |
| A-2145 | H | H | H | H | H | $CF_2CF_2CF_2CF_3$ | $C(=O)CH_3$ | H | O | 0 |
| A-2146 | H | H | H | H | H | $CH_2CH_2CH(CF_3)_2$ | $C(=O)CH_3$ | H | O | 0 |
| A-2147 | H | H | H | H | H | $CF_2CF_2CF_2CF_2CF_3$ | $C(=O)CH_3$ | H | O | 0 |
| A-2148 | H | H | H | H | H | $CH_2CF_2CF_2CF_2CF_3$ | $C(=O)CH_3$ | H | O | 0 |
| A-2149 | H | H | H | H | H | $CH_2CH_2CH_2CH_2CF_3$ | $C(=O)CH_3$ | H | O | 0 |
| A-2150 | H | H | H | H | H | $CH_2CF_2CF_2CF_2CHF_2$ | $C(=O)CH_3$ | H | O | 0 |
| A-2151 | H | H | H | H | H | $CH_2CF_2CF(CF_3)CF_2C(CF_3)_3$ | $C(=O)CH_3$ | H | O | 0 |
| A-2152 | H | H | H | H | H | $CF_2CHFOCH_3$ | $C(=O)CH_3$ | H | O | 0 |
| A-2153 | H | H | H | H | H | $CF_2CHFOCH_2CH_3$ | $C(=O)CH_3$ | H | O | 0 |
| A-2154 | H | H | H | H | H | $CH_2CH_2OCH_2CH_3$ | $C(=O)CH_3$ | H | O | 0 |
| A-2155 | H | H | H | H | H | $CF_2CHFOCF_3$ | $C(=O)CH_3$ | H | O | 0 |
| A-2156 | H | H | H | H | H | $CF_2CHFOCF_2CF_3$ | $C(=O)CH_3$ | H | O | 0 |
| A-2157 | H | H | H | H | H | $CF_2CHFOCF_2CF_2CF_3$ | $C(=O)CH_3$ | H | O | 0 |

TABLE 36-continued

| Compound | R¹ | R² | R³ | R⁴ | R⁵ | R⁶ | R⁷ | R⁸ | X | n |
|---|---|---|---|---|---|---|---|---|---|---|
| A-2158 | H | H | H | H | H | CH₂CH=CH₂ | C(=O)CH₃ | H | O | 0 |
| A-2159 | H | H | H | H | H | CH₂CH=CHCl | C(=O)CH₃ | H | O | 0 |
| A-2160 | H | H | H | H | H | CH₂CH=CCl₂ | C(=O)CH₃ | H | O | 0 |
| A-2161 | H | H | H | H | H | CH₂CH₂CF=CF₂ | C(=O)CH₃ | H | O | 0 |
| A-2162 | H | H | H | H | H | CH₂CH₂CH=CF₂ | C(=O)CH₃ | H | O | 0 |
| A-2163 | H | H | H | H | H | CH₂C≡CH | C(=O)CH₃ | H | O | 0 |
| A-2164 | H | H | H | H | H | CH₂C≡CCH₃ | C(=O)CH₃ | H | O | 0 |
| A-2165 | H | H | H | H | H | CH₂C≡CI | C(=O)CH₃ | H | O | 0 |
| A-2166 | H | H | H | H | H | CH₂C≡CCF₃ | C(=O)CH₃ | H | O | 0 |
| A-2167 | H | H | H | H | H | cyclobutyl | C(=O)CH₃ | H | O | 0 |
| A-2168 | H | H | H | H | H | cyclopentyl | C(=O)CH₃ | H | O | 0 |
| A-2169 | H | H | H | H | H | cyclohexyl | C(=O)CH₃ | H | O | 0 |
| A-2170 | H | H | H | H | H | 4,4-difluorocyclohexyl | C(=O)CH₃ | H | O | 0 |
| A-2171 | H | H | H | H | H | CH₂(cyclopropyl) | C(=O)CH₃ | H | O | 0 |
| A-2172 | H | H | H | H | H | CH₂(cyclobutyl) | C(=O)CH₃ | H | O | 0 |
| A-2173 | H | H | H | H | H | CH₂(cyclopentyl) | C(=O)CH₃ | H | O | 0 |
| A-2174 | H | H | H | H | H | CH₂CH₂(cyclopropyl) | C(=O)CH₃ | H | O | 0 |
| A-2175 | H | H | H | H | H | CH₂(2,2-difluorocyclopropyl) | C(=O)CH₃ | H | O | 0 |
| A-2176 | H | H | H | H | H | CH₂(2,2-dichlorocyclopropyl) | C(=O)CH₃ | H | O | 0 |
| A-2177 | H | H | H | H | H | CH₂(4,4-difluorocyclohexyl) | C(=O)CH₃ | H | O | 0 |
| A-2178 | H | H | H | H | H | CH₂CH₂(2,2-difluorocyclopropyl) | C(=O)CH₃ | H | O | 0 |
| A-2179 | H | H | H | H | H | CH₂CH₂(2,2-dichlorocyclopropyl) | C(=O)CH₃ | H | O | 0 |
| A-2180 | H | H | H | H | H | CH₂SCH₃ | C(=O)CH₃ | H | O | 0 |
| A-2181 | H | H | H | H | H | CH₂SCH₂CH₃ | C(=O)CH₃ | H | O | 0 |
| A-2182 | H | H | H | H | H | CH₂CH₂SCH₃ | C(=O)CH₃ | H | O | 0 |
| A-2183 | H | H | H | H | H | CH₂CH₂SCH₂CH₃ | C(=O)CH₃ | H | O | 0 |
| A-2184 | H | H | H | H | H | CH₂CH₂CH₂SCH₃ | C(=O)CH₃ | H | O | 0 |
| A-2185 | H | H | H | H | H | CH₂CH₂CH₂SCH₂CH₃ | C(=O)CH₃ | H | O | 0 |
| A-2186 | H | H | H | H | H | CH(CH₃)SCH₃ | C(=O)CH₃ | H | O | 0 |
| A-2187 | H | H | H | H | H | CH(CH₃)SCH₂CH₃ | C(=O)CH₃ | H | O | 0 |
| A-2188 | H | H | H | H | H | CH₂CH(CH₃)SCH₃ | C(=O)CH₃ | H | O | 0 |
| A-2189 | H | H | H | H | H | CH₂CH(CH₃)SCH₂CH₃ | C(=O)CH₃ | H | O | 0 |
| A-2190 | H | H | H | H | H | CH(CH₃)CH₂CH₂SCH₃ | C(=O)CH₃ | H | O | 0 |
| A-2191 | H | H | H | H | H | CH(CH₃)CH₂CH₂SCH₂CH₃ | C(=O)CH₃ | H | O | 0 |

TABLE 37

| Compound | R¹ | R² | R³ | R⁴ | R⁵ | R⁶ | R⁷ | R⁸ | X | n |
|---|---|---|---|---|---|---|---|---|---|---|
| A-2192 | H | H | H | H | H | CH₂CH(CH₃)CH₂SCH₃ | C(=O)CH₃ | H | O | 0 |
| A-2193 | H | H | H | H | H | CH₂CH(CH₃)CH₂SCH₂CH₃ | C(=O)CH₃ | H | O | 0 |
| A-2194 | H | H | H | H | H | CH₂CH₂CH(CH₃)SCH₃ | C(=O)CH₃ | H | O | 0 |
| A-2195 | H | H | H | H | H | CH₂CH₂CH(CH₃)SCH₂CH₃ | C(=O)CH₃ | H | O | 0 |
| A-2196 | H | H | H | H | H | CH₂SOCH₃ | C(=O)CH₃ | H | O | 0 |
| A-2197 | H | H | H | H | H | CH₂CH₂SOCH₃ | C(=O)CH₃ | H | O | 0 |
| A-2198 | H | H | H | H | H | CH₂CH₂CH₂SOCH₃ | C(=O)CH₃ | H | O | 0 |
| A-2199 | H | H | H | H | Id | CH(CH₃)SOCH₃ | C(=O)CH₃ | H | O | 0 |
| A-2200 | H | H | H | H | H | CH₂CH(CH₃)SOCH₃ | C(=O)CH₃ | H | O | 0 |
| A-2201 | H | H | H | H | H | CH(CH₃)CH₂CH₂SOCH₃ | C(=O)CH₃ | H | O | 0 |
| A-2202 | H | H | H | H | H | CH₂CH(CH₃)CH₂SOCH₃ | C(=O)CH₃ | H | O | 0 |
| A-2203 | H | H | H | H | H | CH₂CH₂CH(CH₃)SOCH₃ | C(=O)CH₃ | H | O | 0 |
| A-2204 | H | H | H | H | H | CH₂SO₂CH₃ | C(=O)CH₃ | H | O | 0 |
| A-2205 | H | H | H | H | H | CH₂CH₂SO₂CH₃ | C(=O)CH₃ | H | O | 0 |
| A-2206 | H | H | H | H | H | CH₂CH₂CH₂SO₂CH₃ | C(=O)CH₃ | H | O | 0 |
| A-2207 | H | H | H | H | H | CH(CH₃)SO₂CH₃ | C(=O)CH₃ | H | O | 0 |
| A-2208 | H | H | H | H | H | CH₂CH(CH₃)SO₂CH₃ | C(=O)CH₃ | H | O | 0 |
| A-2209 | H | H | H | H | H | CH(CH₃)CH₂CH₂SO₂CH₃ | C(=O)CH₃ | H | O | 0 |
| A-2210 | H | H | H | H | H | CH₂CH(CH₃)CH₂SO₂CH₃ | C(=O)CH₃ | H | O | 0 |
| A-2211 | H | H | H | H | H | CH₂CH₂CH(CH₃)SO₂CH₃ | C(=O)CH₃ | H | O | 0 |
| A-2212 | H | H | H | H | H | CH₂SCF₃ | C(=O)CH₃ | H | O | 0 |
| A-2213 | H | H | H | H | H | CH₂SCHF₂ | C(=O)CH₃ | H | O | 0 |
| A-2214 | H | H | H | H | H | CH₂SCH₂CF₃ | C(=O)CH₃ | H | O | 0 |
| A-2215 | H | H | H | H | H | CH₂SCH₂CHF₂ | C(=O)CH₃ | H | O | 0 |
| A-2216 | H | H | H | H | H | CH₂SCF₂CF₃ | C(=O)CH₃ | H | O | 0 |
| A-2217 | H | H | H | H | H | CH₂CH₂SCF₃ | C(=O)CH₃ | H | O | 0 |
| A-2218 | H | H | H | H | H | CH₂CH₂SCH₂CF₃ | C(=O)CH₃ | H | O | 0 |
| A-2219 | H | H | H | H | H | CH₂CH₂CH₂SCF₃ | C(=O)CH₃ | H | O | 0 |
| A-2220 | H | H | H | H | H | CH₂CH₂CH₂SCH₂CF₃ | C(=O)CH₃ | H | O | 0 |
| A-2221 | H | H | H | H | H | CH(CH₃)SCF₃ | C(=O)CH₃ | H | O | 0 |
| A-2222 | H | H | H | H | H | CH(CH₃)SCH₂CF₃ | C(=O)CH₃ | H | O | 0 |
| A-2223 | H | H | H | H | H | CH₂CH(CH₃)SCF₃ | C(=O)CH₃ | H | O | 0 |
| A-2224 | H | H | H | H | H | CH₂CH(CH₃)SCH₂CF₃ | C(=O)CH₃ | H | O | 0 |
| A-2225 | H | H | H | H | H | CH(CH₃)CH₂CH₂SCF₃ | C(=O)CH₃ | H | O | 0 |
| A-2226 | H | H | H | H | H | CH(CH₃)CH₂CH₂SCH₂CF₃ | C(=O)CH₃ | H | O | 0 |
| A-2227 | H | H | H | H | H | CH₂CH(CH₃)CH₂SCF₃ | C(=O)CH₃ | H | O | 0 |

TABLE 37-continued

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-2228 | H | H | H | H | H | CH$_2$CH(CH$_3$)CH$_2$SCH$_2$CF$_3$ | C(=O)CH$_3$ | H | O | 0 |
| A-2229 | H | H | H | H | H | CH$_2$CH$_2$CH(CH$_3$)SCF$_3$ | C(=O)CH$_3$ | H | O | 0 |
| A-2230 | H | H | H | H | H | CH$_2$CH$_2$CH(CH$_3$)SCH$_2$CF$_3$ | C(=O)CH$_3$ | H | O | 0 |
| A-2231 | H | H | H | H | H | CH$_2$SOCF$_3$ | C(=O)CH$_3$ | H | O | 0 |
| A-2232 | H | H | H | H | H | CH$_2$CH$_2$SOCF$_3$ | C(=O)CH$_3$ | H | O | 0 |
| A-2233 | H | H | H | H | H | CH$_2$CH$_2$CH$_2$SOCF$_3$ | C(=O)CH$_3$ | H | O | 0 |
| A-2234 | H | H | H | H | H | CH(CH$_3$)SOCF$_3$ | C(=O)CH$_3$ | H | O | 0 |
| A-2235 | H | H | H | H | H | CH$_2$CH(CH$_3$)SOCF$_3$ | C(=O)CH$_3$ | H | O | 0 |
| A-2236 | H | H | H | H | H | CH(CH$_3$)CH$_2$CH$_2$SOCF$_3$ | C(=O)CH$_3$ | H | O | 0 |
| A-2237 | H | H | H | H | H | CH$_2$CH(CH$_3$)CH$_2$SOCF$_3$ | C(=O)CH$_3$ | H | O | 0 |
| A-2238 | H | H | H | H | H | CH$_2$CH$_2$CH(CH$_3$)SOCF$_3$ | C(=O)CH$_3$ | H | O | 0 |
| A-2239 | H | H | H | H | H | CH$_2$SO$_2$CF$_3$ | C(=O)CH$_3$ | H | O | 0 |
| A-2240 | H | H | H | H | H | CH$_2$CH$_2$SO$_2$CF$_3$ | C(=O)CH$_3$ | H | O | 0 |
| A-2241 | H | H | H | H | H | CH$_2$CH$_2$CH$_2$SO$_2$CF$_3$ | C(=O)CH$_3$ | H | O | 0 |
| A-2242 | H | H | H | H | H | CH(CH$_3$)SO$_2$CF$_3$ | C(=O)CH$_3$ | H | O | 0 |
| A-2243 | H | H | H | H | H | CH$_2$CH(CH$_3$)SO$_2$CF$_3$ | C(=O)CH$_3$ | H | O | 0 |
| A-2244 | H | H | H | H | H | CH(CH$_3$)CH$_2$CH$_2$SO$_2$CF$_3$ | C(=O)CH$_3$ | H | O | 0 |
| A-2245 | H | H | H | H | H | CH$_2$CH(CH$_3$)CH$_2$SO$_2$CF$_3$ | C(=O)CH$_3$ | H | O | 0 |
| A-2246 | H | H | H | H | H | CH$_2$CH$_2$CH(CH$_3$)SO$_2$CF$_3$ | C(=O)CH$_3$ | H | O | 0 |
| A-2247 | H | H | H | H | H | CH$_2$C(=O)CH$_3$ | C(=O)CH$_3$ | H | O | 0 |
| A-2248 | H | H | H | H | H | CH$_2$C(=O)CH$_2$CH$_3$ | C(=O)CH$_3$ | H | O | 0 |
| A-2249 | H | H | H | H | H | CH$_2$C(=O)C(CH$_3$)$_3$ | C(=O)CH$_3$ | H | O | 0 |
| A-2250 | H | H | H | H | H | CH$_2$CH$_2$C(=O)CH$_3$ | C(=O)CH$_3$ | H | O | 0 |
| A-2251 | H | H | H | H | H | CH$_2$CH$_2$C(=O)C(CH$_3$)$_3$ | C(=O)CH$_3$ | H | O | 0 |
| A-2252 | H | H | H | H | H | CH$_2$C(=O)CF$_3$ | C(=O)CH$_3$ | H | O | 0 |

TABLE 38

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-2253 | H | H | H | H | H | CH$_2$CH$_2$C(=O)CF$_3$ | C(=O)CH$_3$ | H | O | 0 |
| A-2254 | H | H | H | H | H | CH$_2$C(=O)OCH$_3$ | C(=O)CH$_3$ | H | O | 0 |
| A-2255 | H | H | H | H | H | CH$_2$C(=O)OCH$_2$CH$_3$ | C(=O)CH$_3$ | H | O | 0 |
| A-2256 | H | H | H | H | H | CH$_2$C(=O)OC(CH$_3$)$_3$ | C(=O)CH$_3$ | H | O | 0 |
| A-2257 | H | H | H | H | H | CH$_2$CH$_2$C(=O)OCH$_3$ | C(=O)CH$_3$ | H | O | 0 |
| A-2258 | H | H | H | H | H | CH$_2$CH$_2$C(=O)OCH$_2$CH$_3$ | C(=O)CH$_3$ | H | O | 0 |
| A-2259 | H | H | H | H | H | CH$_2$CH$_2$C(=O)OC(CH$_3$)$_3$ | C(=O)CH$_3$ | H | O | 0 |
| A-2260 | H | H | H | H | H | CH$_2$C(=O)NH$_2$ | C(=O)CH$_3$ | H | O | 0 |
| A-2261 | H | H | H | H | H | CH$_2$CH$_2$C(=O)NH$_2$ | C(=O)CH$_3$ | H | O | 0 |
| A-2262 | H | H | H | H | H | CH$_2$C(=O)NHCH$_3$ | C(=O)CH$_3$ | H | O | 0 |
| A-2263 | H | H | H | H | H | CH$_2$C(=O)NHCH(CH$_3$)$_2$ | C(=O)CH$_3$ | H | O | 0 |
| A-2264 | H | H | H | H | H | CH$_2$CH$_2$C(=O)NHCH$_3$ | C(=O)CH$_3$ | H | O | 0 |
| A-2265 | H | H | H | H | H | CH$_2$CH$_2$C(=O)NHCH(CH$_3$)$_2$ | C(=O)CH$_3$ | H | O | 0 |
| A-2266 | H | H | H | H | H | CH$_2$C(=O)NHCH$_2$CHF$_2$ | C(=O)CH$_3$ | H | O | 0 |
| A-2267 | H | H | H | H | H | CH$_2$C(=O)NHCH$_2$CF$_3$ | C(=O)CH$_3$ | H | O | 0 |
| A-2268 | H | H | H | H | H | CH$_2$CH$_2$C(=O)NHCH$_2$CHF$_2$ | C(=O)CH$_3$ | H | O | 0 |
| A-2269 | H | H | H | H | H | CH$_2$CH$_2$C(=O)NHCH$_2$CF$_3$ | C(=O)CH$_3$ | H | O | 0 |
| A-2270 | H | H | H | H | H | CH$_2$C(=O)N(CH$_3$)$_2$ | C(=O)CH$_3$ | H | O | 0 |
| A-2271 | H | H | H | H | H | CH$_2$C(=O)N(CH$_2$CH$_3$)$_2$ | C(=O)CH$_3$ | H | O | 0 |
| A-2272 | H | H | H | H | H | CH$_2$CH$_2$C(=O)N(CH$_3$)$_2$ | C(=O)CH$_3$ | H | O | 0 |
| A-2273 | H | H | H | H | H | CH$_2$CH$_2$C(=O)N(CH$_2$CH$_3$)$_2$ | C(=O)CH$_3$ | H | O | 0 |
| A-2274 | H | H | H | H | H | CH$_2$CH$_2$OH | C(=O)CH$_3$ | H | O | 0 |
| A-2275 | H | H | H | H | H | CH$_2$CH(OH)CH$_3$ | C(=O)CH$_3$ | H | O | 0 |
| A-2276 | H | H | H | H | H | CH$_2$CH$_2$CH$_2$OH | C(=O)CH$_3$ | H | O | 0 |
| A-2277 | H | H | H | H | H | CH$_2$CH(OH)CH$_2$CH$_3$ | C(=O)CH$_3$ | H | O | 0 |
| A-2278 | H | H | H | H | H | CH$_2$CH(OH)C(CH$_3$)$_3$ | C(=O)CH$_3$ | H | O | 0 |
| A-2279 | H | H | H | H | H | CH$_2$CH$_2$CH(OH)CH$_3$ | C(=O)CH$_3$ | H | O | 0 |
| A-2280 | H | H | H | H | H | CH$_2$CH$_2$CH(OH)C(CH$_3$)$_3$ | C(=O)CH$_3$ | H | O | 0 |
| A-2281 | H | H | H | H | H | CH$_2$C(=NOH)CH$_3$ | C(=O)CH$_3$ | H | O | 0 |
| A-2282 | H | H | H | H | H | CH$_2$C(=NOH)CH$_2$CH$_3$ | C(=O)CH$_3$ | H | O | 0 |
| A-2283 | H | H | H | H | H | CH$_2$C(=NOH)C(CH$_3$)$_3$ | C(=O)CH$_3$ | H | O | 0 |
| A-2284 | H | H | H | H | H | CH$_2$C(=NOCH$_3$)CH$_3$ | C(=O)CH$_3$ | H | O | 0 |
| A-2285 | H | H | H | H | H | CH$_2$C(=NOCH$_3$)CH$_2$CH$_3$ | C(=O)CH$_3$ | H | O | 0 |
| A-2286 | H | H | H | H | H | CH$_2$C(=NOCH$_2$CH$_3$)CH$_3$ | C(=O)CH$_3$ | H | O | 0 |
| A-2287 | H | H | H | H | H | CH$_2$C(=NOCH$_2$CH$_3$)CH$_2$CH$_3$ | C(=O)CH$_3$ | H | O | 0 |
| A-2288 | H | H | H | H | H | CH$_2$C(=NOCH$_2$CF$_3$)CH$_3$ | C(=O)CH$_3$ | H | O | 0 |
| A-2289 | H | H | H | H | H | CH$_2$C(=NOCH$_2$CF$_3$)CH$_2$CH$_3$ | C(=O)CH$_3$ | H | O | 0 |
| A-2290 | H | H | H | H | H | CH$_2$Ph | C(=O)CH$_3$ | H | O | 0 |
| A-2291 | H | H | H | H | H | CH$_2$(2-F)Ph | C(=O)CH$_3$ | H | O | 0 |
| A-2292 | H | H | H | H | H | CH$_2$(3-F)Ph | C(=O)CH$_3$ | H | O | 0 |
| A-2293 | H | H | H | H | H | CH$_2$(4-F)Ph | C(=O)CH$_3$ | H | O | 0 |
| A-2294 | H | H | H | H | H | CH$_2$(2-Cl)Ph | C(=O)CH$_3$ | H | O | 0 |
| A-2295 | H | H | H | H | H | CH$_2$(3-Cl)Ph | C(=O)CH$_3$ | H | O | 0 |
| A-2296 | H | H | H | H | H | CH$_2$(4-Cl)Ph | C(=O)CH$_3$ | H | O | 0 |
| A-2297 | H | H | H | H | H | CH$_2$(2-CF$_3$)Ph | C(=O)CH$_3$ | H | O | 0 |

TABLE 38-continued

| Compound | R¹ | R² | R³ | R⁴ | R⁵ | R⁶ | R⁷ | R⁸ | X | n |
|---|---|---|---|---|---|---|---|---|---|---|
| A-2298 | H | H | H | H | H | CH$_2$(3-CF$_3$)Ph | C(=O)CH$_3$ | H | O | 0 |
| A-2299 | H | H | H | H | H | CH$_2$(4-CF$_3$)Ph | C(=O)CH$_3$ | H | O | 0 |
| A-2300 | H | H | H | H | H | CH$_2$(naphthalen-1-yl) | C(=O)CH$_3$ | H | O | 0 |
| A-2301 | H | H | H | H | H | CH$_2$(naphtnalen-2-yl) | C(=O)CH$_3$ | H | O | 0 |
| A-2302 | H | H | H | H | H | CH$_2$CH$_2$Ph | C(=O)CH$_3$ | H | O | 0 |
| A-2303 | H | H | H | H | H | H | C(=O)CH$_2$CH$_3$ | H | O | 0 |
| A-2304 | H | H | H | H | H | CH$_3$ | C(=O)CH$_2$CH$_3$ | H | O | 0 |
| A-2305 | H | H | H | H | H | CH$_2$CH$_3$ | C(=O)CH$_2$CH$_3$ | H | O | 0 |
| A-2306 | H | H | H | H | H | CH(CH$_3$)$_2$ | C(=O)CH$_2$CH$_3$ | H | O | 0 |
| A-2307 | H | H | H | H | H | CH$_2$CH$_2$CH$_3$ | C(=O)CH$_2$CH$_3$ | H | O | 0 |
| A-2308 | H | H | H | H | H | CH$_2$CH(CH$_3$)$_2$ | C(=O)CH$_2$CH$_3$ | H | O | 0 |
| A-2309 | H | H | H | H | H | CH(CH$_3$)CH$_2$CH$_3$ | C(=O)CH$_2$CH$_3$ | H | O | 0 |
| A-2310 | H | H | H | H | H | CH$_2$C(CH$_3$)$_3$ | C(=O)CH$_2$CH$_3$ | H | O | 0 |
| A-2311 | H | H | H | H | H | CH$_2$(CH$_2$)$_2$CH$_3$ | C(=O)CH$_2$CH$_3$ | H | O | 0 |
| A-2312 | H | H | H | H | H | CH$_2$(CH$_2$)$_3$CH$_3$ | C(=O)CH$_2$CH$_3$ | H | O | 0 |
| A-2313 | H | H | H | H | H | CF$_3$ | C(=O)CH$_2$CH$_3$ | H | O | 0 |

TABLE 39

| Compound | R¹ | R² | R³ | R⁴ | R⁵ | R⁶ | R⁷ | R⁸ | X | n |
|---|---|---|---|---|---|---|---|---|---|---|
| A-2314 | H | H | H | H | H | CHF$_2$ | C(=O)CH$_2$CH$_3$ | H | O | 0 |
| A-2315 | H | H | H | H | H | CH$_2$CF$_3$ | C(=O)CH$_2$CH$_3$ | H | O | 0 |
| A-2316 | H | H | H | H | H | CH$_2$CHF$_2$ | C(=O)CH$_2$CH$_3$ | H | O | 0 |
| A-2317 | H | H | H | H | H | CH$_2$CClF$_2$ | C(=O)CH$_2$CH$_3$ | H | O | 0 |
| A-2318 | H | H | H | H | H | CH$_2$CBrF$_2$ | C(=O)CH$_2$CH$_3$ | H | O | 0 |
| A-2319 | H | H | H | H | H | CF$_2$CF$_3$ | C(=O)CH$_2$CH$_3$ | H | O | 0 |
| A-2320 | H | H | H | H | H | CF$_2$CHF$_2$ | C(=O)CH$_2$CH$_3$ | H | O | 0 |
| A-2321 | H | H | H | H | H | CH$_2$CH$_2$CF$_3$ | C(=O)CH$_2$CH$_3$ | H | O | 0 |
| A-2322 | H | H | H | H | H | CH$_2$CF$_2$CF$_3$ | C(=O)CH$_2$CH$_3$ | H | O | 0 |
| A-2323 | H | H | H | H | H | CH$_2$CF$_2$CHF$_2$ | C(=O)CH$_2$CH$_3$ | H | O | 0 |
| A-2324 | H | H | H | H | H | CF$_2$CHFCF$_3$ | C(=O)CH$_2$CH$_3$ | H | O | 0 |
| A-2325 | H | H | H | H | H | CF$_2$CF$_2$CF$_3$ | C(=O)CH$_2$CH$_3$ | H | O | 0 |
| A-2326 | H | H | H | H | H | CH$_2$CF$_2$CF$_2$CF$_3$ | C(=O)CH$_2$CH$_3$ | H | O | 0 |
| A-2327 | H | H | H | H | H | CH$_2$CF$_2$CHFCF$_3$ | C(=O)CH$_2$CH$_3$ | H | O | 0 |
| A-2328 | H | H | H | H | H | CH$_2$CH$_2$CH$_2$CF$_3$ | C(=O)CH$_2$CH$_3$ | H | O | 0 |
| A-2329 | H | H | H | H | H | CH$_2$CH$_2$CF$_2$CF$_3$ | C(=O)CH$_2$CH$_3$ | H | O | 0 |
| A-2330 | H | H | H | H | H | CF$_2$CF$_2$CF$_2$CF$_3$ | C(=O)CH$_2$CH$_3$ | H | O | 0 |
| A-2331 | H | H | H | H | H | CH$_2$CH$_2$CH(CF$_3$)$_2$ | C(=O)CH$_2$CH$_3$ | H | O | 0 |
| A-2332 | H | H | H | H | H | CF$_2$CF$_2$CF$_2$CF$_2$CF$_3$ | C(=O)CH$_2$CH$_3$ | H | O | 0 |
| A-2333 | H | H | H | H | H | CF$_2$CF$_2$CF$_2$CF$_2$CF$_3$ | C(=O)CH$_2$CH$_3$ | H | O | 0 |
| A-2334 | H | H | H | H | H | CH$_2$CH$_2$CH$_2$CH$_2$CF$_3$ | C(=O)CH$_2$CH$_3$ | H | O | 0 |
| A-2335 | H | H | H | H | H | CH$_2$CF$_2$CF$_2$CF$_2$CHF$_2$ | C(=O)CH$_2$CH$_3$ | H | O | 0 |
| A-2336 | H | H | H | H | H | CH$_2$CH$_2$OCH$_2$CF$_3$ | C(=O)CH$_2$CH$_3$ | H | O | 0 |
| A-2337 | H | H | H | H | H | CF$_2$CHFOCF$_3$ | C(=O)CH$_2$CH$_3$ | H | O | 0 |
| A-2338 | H | H | H | H | H | CF$_2$CHFOCF$_2$CF$_3$ | C(=O)CH$_2$CH$_3$ | H | O | 0 |
| A-2339 | H | H | H | H | H | CH$_2$CH$_2$CF=CF$_2$ | C(=O)CH$_2$CH$_3$ | H | O | 0 |
| A-2340 | H | H | H | H | H | CH$_2$CH$_2$CH=CF$_2$ | C(=O)CH$_2$CH$_3$ | H | O | 0 |
| A-2341 | H | H | H | H | H | CH$_2$C≡CCH$_3$ | C(=O)CH$_2$CH$_3$ | H | O | 0 |
| A-2342 | H | H | H | H | H | CH$_2$C≡CCF$_3$ | C(=O)CH$_2$CH$_3$ | H | O | 0 |
| A-2343 | H | H | H | H | H | CH$_2$C≡CI | C(=O)CH$_2$CH$_3$ | H | O | 0 |
| A-2344 | H | H | H | H | H | CH$_2$(2,2-difluorocyclopropyl) | C(=O)CH$_2$CH$_3$ | H | O | 0 |
| A-2345 | H | H | H | H | H | CH$_2$(2,2-dichlorocyclopropyl) | C(=O)CH$_2$CH$_3$ | H | O | 0 |
| A-2346 | H | H | H | H | H | CH$_2$CH$_2$(2,2-difluorocyclopropyl) | C(=O)CH$_2$CH$_3$ | H | O | 0 |
| A-2347 | H | H | H | H | H | CH$_2$CH$_2$(2,2-dichlorocyclopropyl) | C(=O)CH$_2$CH$_3$ | H | O | 0 |
| A-2348 | H | H | H | H | H | CH$_2$SCH$_3$ | C(=O)CH$_2$CH$_3$ | H | O | 0 |
| A-2349 | H | H | H | H | H | CH$_2$SCH$_2$CH$_3$ | C(=O)CH$_2$CH$_3$ | H | O | 0 |
| A-2350 | H | H | H | H | H | CH$_2$CH$_2$SCH$_3$ | C(=O)CH$_2$CH$_3$ | H | O | 0 |
| A-2351 | H | H | H | H | H | CH$_2$SOCH$_3$ | C(=O)CH$_2$CH$_3$ | H | O | 0 |
| A-2352 | H | H | H | H | H | CH$_2$CH$_2$SOCH$_3$ | C(=O)CH$_2$CH$_3$ | H | O | 0 |
| A-2353 | H | H | H | H | H | CH$_2$SO$_2$CH$_3$ | C(=O)CH$_2$CH$_3$ | H | O | 0 |
| A-2354 | H | H | H | H | H | CH$_2$CH$_2$SO$_2$CH$_3$ | C(=O)CH$_2$CH$_3$ | H | O | 0 |
| A-2355 | H | H | H | H | H | CH$_2$SCF$_3$ | C(=O)CH$_2$CH$_3$ | H | O | 0 |
| A-2356 | H | H | H | H | H | CH$_2$SCHF$_2$ | C(=O)CH$_2$CH$_3$ | H | O | 0 |
| A-2357 | H | H | H | H | H | CH$_2$SCH$_2$CF$_3$ | C(=O)CH$_2$CH$_3$ | H | O | 0 |
| A-2358 | H | H | H | H | H | CH$_2$SCH$_2$CHF$_2$ | C(=O)CH$_2$CH$_3$ | H | O | 0 |
| A-2359 | H | H | H | H | H | CH$_2$SCF$_2$CF$_3$ | C(=O)CH$_2$CH$_3$ | H | O | 0 |
| A-2360 | H | H | H | H | H | CH$_2$CH$_2$SCF$_3$ | C(=O)CH$_2$CH$_3$ | H | O | 0 |
| A-2361 | H | H | H | H | H | CH$_2$SOCF$_3$ | C(=O)CH$_2$CH$_3$ | H | O | 0 |
| A-2362 | H | H | H | H | H | CH$_2$CH$_2$SOCF$_3$ | C(=O)CH$_2$CH$_3$ | H | O | 0 |
| A-2363 | H | H | H | H | H | CH$_2$CH$_2$CH$_2$SOCF$_3$ | C(=O)CH$_2$CH$_3$ | H | O | 0 |
| A-2364 | H | H | H | H | H | CH$_2$SO$_2$CF$_3$ | C(=O)CH$_2$CH$_3$ | H | O | 0 |
| A-2365 | H | H | H | H | H | CH$_2$CH$_2$SO$_2$CF$_3$ | C(=O)CH$_2$CH$_3$ | H | O | 0 |
| A-2366 | H | H | H | H | H | CH$_2$CH$_2$CH$_2$SO$_2$CF$_3$ | C(=O)CH$_2$CH$_3$ | H | O | 0 |
| A-2367 | H | H | H | H | H | CH$_2$C(=O)NHCH$_2$CHF$_2$ | C(=O)CH$_2$CH$_3$ | H | O | 0 |

TABLE 39-continued

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-2368 | H | H | H | H | H | CH$_2$C(=O)NHCH$_2$CF$_3$ | C(=O)CH$_2$CH$_3$ | H | O | 0 |
| A-2369 | H | H | H | H | H | H | C(=O)CH(CH$_3$)$_2$ | H | O | 0 |
| A-2370 | H | H | H | H | H | CH$_3$ | C(=O)CH(CH$_3$)$_2$ | H | O | 0 |
| A-2371 | H | H | H | H | H | CH$_2$CH$_3$ | C(=O)CH(CH$_3$)$_2$ | H | O | 0 |
| A-2372 | H | H | H | H | H | CH(CH$_3$)$_2$ | C(=O)CH(CH$_3$)$_2$ | H | O | 0 |
| A-2373 | H | H | H | H | H | CH$_2$CH$_2$CH$_3$ | C(=O)CH(CH$_3$)$_2$ | H | O | 0 |
| A-2374 | H | H | H | H | H | CH$_2$CH(CH$_3$)$_2$ | C(=O)CH(CH3)$_2$ | H | O | 0 |

TABLE 40

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-2375 | H | H | H | H | H | CH(CH$_3$)CH$_2$CH$_3$ | C(=O)CH(CH$_3$)$_2$ | H | O | 0 |
| A-2376 | H | H | H | H | H | CH$_2$C(CH$_3$)$_3$ | C(=O)CH(CH$_3$)$_2$ | H | O | 0 |
| A-2377 | H | H | H | H | H | CH$_2$(CH$_2$)$_2$CH$_3$ | C(=O)CH(CH$_3$)$_2$ | H | O | 0 |
| A-2378 | H | H | H | H | H | CH$_2$(CH$_2$)$_3$CH$_3$ | C(=O)CH(CH$_3$)$_2$ | H | O | 0 |
| A-2379 | H | H | H | H | H | CF$_3$ | C(=O)CH(CH$_3$)$_2$ | H | O | 0 |
| A-2380 | H | H | H | H | H | CHF$_2$ | C(=O)CH(CH$_3$)$_2$ | H | O | 0 |
| A-2381 | H | H | H | H | H | CH$_2$CF$_3$ | C(=O)CH(CH$_3$)$_2$ | H | O | 0 |
| A-2382 | H | H | H | H | H | CH$_2$CHF$_2$ | C(=O)CH(CH$_3$)$_2$ | H | O | 0 |
| A-2383 | H | H | H | H | H | CH$_2$CClF$_2$ | C(=O)CH(CH$_3$)$_2$ | H | O | 0 |
| A-2384 | H | H | H | H | H | CH$_2$CBrF$_2$ | C(=O)CH(CH$_3$)$_2$ | H | O | 0 |
| A-2385 | H | H | H | H | H | CF$_2$CF$_3$ | C(=O)CH(CH$_3$)$_2$ | H | O | 0 |
| A-2386 | H | H | H | H | H | CF$_2$CHF$_2$ | C(=O)CH(CH$_3$)$_2$ | H | O | 0 |
| A-2387 | H | H | H | H | H | CH$_2$CH$_2$CF$_3$ | C(=O)CH(CH$_3$)$_2$ | H | O | 0 |
| A-2388 | H | H | H | H | H | CH$_2$CF$_2$CF$_3$ | C(=O)CH(CH$_3$)$_2$ | H | O | 0 |
| A-2389 | H | H | H | H | H | CH$_2$CF$_2$CHF$_2$ | C(=O)CH(CH$_3$)$_2$ | H | O | 0 |
| A-2390 | H | H | H | H | H | CF$_2$CHFCF$_3$ | C(=O)CH(CH$_3$)$_2$ | H | O | 0 |
| A-2391 | H | H | H | H | H | CF$_2$CF$_2$CF$_3$ | C(=O)CH(CH$_3$)$_2$ | H | O | 0 |
| A-2392 | H | H | H | H | H | CH$_2$CF$_2$CF$_2$CF$_3$ | C(=O)CH(CH$_3$)$_2$ | H | O | 0 |
| A-2393 | H | H | H | H | H | CH$_2$CF$_2$CHFCF$_3$ | C(=O)CH(CH$_3$)$_2$ | H | O | 0 |
| A-2394 | H | H | H | H | H | CH$_2$CH$_3$CH$_2$CF$_3$ | C(=O)CH(CH$_3$)$_2$ | H | O | 0 |
| A-2395 | H | H | H | H | H | CH$_2$CH$_2$CF$_2$CF$_3$ | C(=O)CH(CH$_3$)$_2$ | H | O | 0 |
| A-2396 | H | H | H | H | H | CF$_2$CF$_2$CF$_2$CF$_3$ | C(=O)CH(CH$_3$)$_2$ | H | O | 0 |
| A-2397 | H | H | H | H | H | CH$_2$CH$_2$CH(CF$_3$)$_2$ | C(=O)CH(CH$_3$)$_2$ | H | O | 0 |
| A-2398 | H | H | H | H | H | CF$_2$CF$_2$CF$_2$CF$_2$CF$_3$ | C(=O)CH(CH$_3$)$_2$ | H | O | 0 |
| A-2399 | H | H | H | H | H | CH$_2$CF$_2$CF$_2$CF$_2$CF$_3$ | C(=O)CH(CH$_3$)$_2$ | H | O | 0 |
| A-2400 | H | H | H | H | H | CH$_2$CH$_2$CH$_2$CH$_2$CF$_3$ | C(=O)CH(CH$_3$)$_2$ | H | O | 0 |
| A-2401 | H | H | H | H | H | CH$_2$CF$_2$CF$_2$CF$_2$CHF$_2$ | C(=O)CH(CH$_3$)$_2$ | H | O | 0 |
| A-2402 | H | H | H | H | H | CH$_2$CH$_2$OCH$_2$CF$_3$ | C(=O)CH(CH$_3$)$_2$ | H | O | 0 |
| A-2403 | H | H | H | H | H | CF$_2$CHFOCF$_3$ | C(=O)CH(CH$_3$)$_2$ | H | O | 0 |
| A-2404 | H | H | H | H | H | CF$_2$CHFOCF$_2$CF$_3$ | C(=O)CH(CH$_3$)$_2$ | H | O | 0 |
| A-2405 | H | H | H | H | H | CH$_2$CH$_2$CF=CF$_2$ | C(=O)CH(CH$_3$)$_2$ | H | O | 0 |
| A-2406 | H | H | H | H | H | CH$_2$CH$_2$CH=CF$_2$ | C(=O)CH(CH$_3$)$_2$ | H | O | 0 |
| A-2407 | H | H | H | H | H | CH$_2$C≡CCH$_3$ | C(=O)CH(CH$_3$)$_2$ | H | O | 0 |
| A-2408 | H | H | H | H | H | CH$_2$C≡CCF$_3$ | C(=O)CH(CH$_3$)$_2$ | H | O | 0 |
| A-2409 | H | H | H | H | H | CH$_2$C≡CI | C(=O)CH(CH$_3$)$_2$ | H | O | 0 |
| A-2410 | H | H | H | H | H | CH$_2$(2,2-difluorocyclopropyl) | C(=O)CH(CH$_3$)$_2$ | H | O | 0 |
| A-2411 | H | H | H | H | H | CH$_2$(2,2-dichlorocyclopropyl) | C(=O)CH(CH$_3$)$_2$ | H | O | 0 |
| A-2412 | H | H | H | H | H | CH$_2$CH$_2$(2,2-difluorocyclopropyl) | C(=O)CH(CH$_3$)$_2$ | H | O | 0 |
| A-2413 | H | H | H | H | H | CH$_2$CH$_2$(2,2-dichlorocyclopropyl) | C(=O)CH(CH$_3$)$_2$ | H | O | 0 |
| A-2414 | H | H | H | H | H | CH$_2$SCH$_3$ | C(=O)CH(CH$_3$)$_2$ | H | O | 0 |
| A-2415 | H | H | H | H | H | CH$_2$SCH$_2$CH$_3$ | C(=O)CH(CH$_3$)$_2$ | H | O | 0 |
| A-2416 | H | H | H | H | H | CH$_2$CH$_2$SCH$_3$ | C(=O)CH(CH$_3$)$_2$ | H | O | 0 |
| A-2417 | H | H | H | H | H | CH$_2$SOCH$_3$ | C(=O)CH(CH$_3$)$_2$ | H | O | 0 |
| A-2418 | H | H | H | H | H | CH$_2$CH$_2$SOCH$_3$ | C(=O)CH(CH$_3$)$_2$ | H | O | 0 |
| A-2419 | H | H | H | H | H | CH$_2$SO$_2$CH$_3$ | C(=O)CH(CH$_3$)$_2$ | H | O | 0 |
| A-2420 | H | H | H | H | H | CH$_2$CH$_2$SO$_3$CH$_3$ | C(=O)CH(CH$_3$)$_2$ | H | O | 0 |
| A-2421 | H | H | H | H | H | CH$_2$SCF$_3$ | C(=O)CH(CH$_3$)$_2$ | H | O | 0 |
| A-2422 | H | H | H | H | H | CH$_2$SCHF$_2$ | C(=O)CH(CH$_3$)$_2$ | H | O | 0 |
| A-2423 | H | H | H | H | H | CH$_2$SCH$_2$CF$_3$ | C(=O)CH(CH$_3$)$_2$ | H | O | 0 |
| A-2424 | H | H | H | H | H | CH$_2$SCH$_2$CHF$_2$ | C(=O)CH(CH$_3$)$_2$ | H | O | 0 |
| A-2425 | H | H | H | H | H | CH$_2$SCF$_2$CF$_3$ | C(=O)CH(CH$_3$)$_2$ | H | O | 0 |
| A-2426 | H | H | H | H | H | CH$_2$CH$_2$SCF$_3$ | C(=O)CH(CH$_3$)$_2$ | H | O | 0 |
| A-2427 | H | H | H | H | H | CH$_2$SOCF$_3$ | C(=O)CH(CH$_3$)$_2$ | H | O | 0 |
| A-2428 | H | H | H | H | H | CH$_2$CH$_2$SOCF$_3$ | C(=O)CH(CH$_3$)$_2$ | H | O | 0 |
| A-2429 | H | H | H | H | H | CH$_2$CH$_2$CH$_2$SOCF$_3$ | C(=O)CH(CH$_3$)$_2$ | H | O | 0 |
| A-2430 | H | H | H | H | H | CH$_2$SO$_2$CF$_3$ | C(=O)CH(CH$_3$)$_2$ | H | O | 0 |
| A-2431 | H | H | H | H | H | CH$_2$CH$_2$SO$_2$CF$_3$ | C(=O)CH(CH$_3$)$_2$ | H | O | 0 |
| A-2432 | H | H | H | H | H | CH$_2$CH$_2$CH$_2$SO$_2$CF$_3$ | C(=O)CH(CH$_3$)$_2$ | H | O | 0 |
| A-2433 | H | H | H | H | H | CH$_2$C(=O)NHCH$_2$CHF$_2$ | C(=O)CH(CH$_3$)$_2$ | H | O | 0 |
| A-2434 | H | H | H | H | H | CH$_2$C(=O)NHCH$_2$CF$_3$ | C(=O)CH(CH$_3$)$_2$ | H | O | 0 |
| A-2435 | H | H | H | H | H | H | C(=O)CH$_2$OCH$_3$ | H | O | 0 |

TABLE 41

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-2436 | H | H | H | H | H | $CH_3$ | $C(=O)CH_2OCH_3$ | H | O | 0 |
| A-2437 | H | H | H | H | H | $CH_2CH_3$ | $C(=O)CH_2OCH_3$ | H | O | 0 |
| A-2438 | H | H | H | H | H | $CH(CH_3)_2$ | $C(=O)CH_2OCH_3$ | H | O | 0 |
| A-2439 | H | H | H | H | H | $CH_2CH_2CH_3$ | $C(=O)CH_2OCH_3$ | H | O | 0 |
| A-2440 | H | H | H | H | H | $CH_2CH(CH_3)_2$ | $C(=O)CH_2OCH_3$ | H | O | 0 |
| A-2441 | H | H | H | H | H | $CH(CH_3)CH_2CH_3$ | $C(=O)CH_2OCH_3$ | H | O | 0 |
| A-2442 | H | H | H | H | H | $CH_2C(CH_3)_3$ | $C(=O)CH_2OCH_3$ | H | O | 0 |
| A-2443 | H | H | H | H | H | $CH_2(CH_2)_2CH_3$ | $C(=O)CH_2OCH_3$ | H | O | 0 |
| A-2444 | H | H | H | H | H | $CH_2(CH_2)_3CH_3$ | $C(=O)CH_2OCH_3$ | H | O | 0 |
| A-2445 | H | H | H | H | H | $CF_3$ | $C(=O)CH_2OCH_3$ | H | O | 0 |
| A-2446 | H | H | H | H | H | $CHF_2$ | $C(=O)CH_2OCH_3$ | H | O | 0 |
| A-2447 | H | H | H | H | H | $CH_2CF_3$ | $C(=O)CH_2OCH_3$ | H | O | 0 |
| A-2448 | H | H | H | H | H | $CH_2CHF_2$ | $C(=O)CH_2OCH_3$ | H | O | 0 |
| A-2449 | H | H | H | H | H | $CH_2CClF_2$ | $C(=O)CH_2OCH_3$ | H | O | 0 |
| A-2450 | H | H | H | H | H | $CH_2CBrF_2$ | $C(=O)CH_2OCH_3$ | H | O | 0 |
| A-2451 | H | H | H | H | H | $CF_2CF_3$ | $C(=O)CH_2OCH_3$ | H | O | 0 |
| A-2452 | H | H | H | H | H | $CF_2CHF_2$ | $C(=O)CH_2OCH_3$ | H | O | 0 |
| A-2453 | H | H | H | H | H | $CH_2CH_2CF_3$ | $C(=O)CH_2OCH_3$ | H | O | 0 |
| A-2454 | H | H | H | H | H | $CH_2CF_2CF_3$ | $C(=O)CH_2OCH_3$ | H | O | 0 |
| A-2455 | H | H | H | H | H | $CH_2CF_2CHF_2$ | $C(=O)CH_2OCH_3$ | H | O | 0 |
| A-2456 | H | H | H | H | H | $CF_2CHFCF_3$ | $C(=O)CH_2OCH_3$ | H | O | 0 |
| A-2457 | H | H | H | H | H | $CF_2CF_2CF_3$ | $C(=O)CH_2OCH_3$ | H | O | 0 |
| A-2458 | H | H | H | H | H | $CH_2CF_2CF_2CF_3$ | $C(=O)CH_2OCH_3$ | H | O | 0 |
| A-2459 | H | H | H | H | H | $CH_2CF_2CHFCF_3$ | $C(=O)CH_2OCH_3$ | H | O | 0 |
| A-2460 | H | H | H | H | H | $CH_2CH_2CH_2CF_3$ | $C(=O)CH_2OCH_3$ | H | O | 0 |
| A-2461 | H | H | H | H | H | $CH_2CH_2CF_2CF_3$ | $C(=O)CH_2OCH_3$ | H | O | 0 |
| A-2462 | H | H | H | H | H | $CF_2CF_2CE_2CF_3$ | $C(=O)CH_2OCH_3$ | H | O | 0 |
| A-2463 | H | H | H | H | H | $CH_2CH_2CH(CF_3)_2$ | $C(=O)CH_2OCH_3$ | H | O | 0 |
| A-2464 | H | H | H | H | H | $CF_2CF_2CF_2CF_2CF_3$ | $C(=O)CH_2OCH_3$ | H | O | 0 |
| A-2465 | H | H | H | H | H | $CH_2CF_2CF_2CF_2CF_3$ | $C(=O)CH_2OCH_3$ | H | O | 0 |
| A-2466 | H | H | H | H | H | $CH_2CH_2CH_2CH_2CF_3$ | $C(=O)CH_2OCH_3$ | H | O | 0 |
| A-2467 | H | H | H | H | H | $CH_2CF_2CF_2CF_2CHF_2$ | $C(=O)CH_2OCH_3$ | H | O | 0 |
| A-2468 | H | H | H | H | H | $CH_2CH_2OCH_2CF_3$ | $C(=O)CH_2OCH_3$ | H | O | 0 |
| A-2469 | H | H | H | H | H | $CF_2CHFOCF_3$ | $C(=O)CH_2OCH_3$ | H | O | 0 |
| A-2470 | H | H | H | H | H | $CF_2CHFOCF_2CF_3$ | $C(=O)CH_2OCH_3$ | H | O | 0 |
| A-2471 | H | H | H | H | H | $CH_2CH_2CF=CF_2$ | $C(=O)CH_2OCH_3$ | H | O | 0 |
| A-2472 | H | H | H | H | H | $CH_2CH_2CH=CF_2$ | $C(=O)CH_2OCH_3$ | H | O | 0 |
| A-2473 | H | H | H | H | H | $CH_2C\equiv CCH_3$ | $C(=O)CH_2OCH_3$ | H | O | 0 |
| A-2474 | H | H | H | H | H | $CH_2C\equiv CCF_3$ | $C(=O)CH_2OCH_3$ | H | O | 0 |
| A-2475 | H | H | H | H | H | $CH_2C\equiv CI$ | $C(=O)CH_2OCH_3$ | H | O | 0 |
| A-2476 | H | H | H | H | H | $CH_2$(2,2-difluorocyclopropyl) | $C(=O)CH_2OCH_3$ | H | O | 0 |
| A-2477 | H | H | H | H | H | $CH_2$(2,2-dichlorocyclopropyl) | $C(=O)CH_2OCH_3$ | H | O | 0 |
| A-2478 | H | H | H | H | H | $CH_2CH_2$(2,2-difluorocyclopropyl) | $C(=O)CH_2OCH_3$ | H | O | 0 |
| A-2479 | H | H | H | H | H | $CH_2CH_2$(2,2-dichlorocyclopropyl) | $C(=O)CH_2OCH_3$ | H | O | 0 |
| A-2480 | H | H | H | H | H | $CH_2SCH_3$ | $C(=O)CH_2OCH_3$ | H | O | 0 |
| A-2481 | H | H | H | H | H | $CH_2SCH_2CH_3$ | $C(=O)CH_2OCH_3$ | H | O | 0 |
| A-2482 | H | H | H | H | H | $CH_2CH_2SCH_3$ | $C(=O)CH_2OCH_3$ | H | O | 0 |
| A-2483 | H | H | H | H | H | $CH_2SOCH_3$ | $C(=O)CH_2OCH_3$ | H | O | 0 |
| A-2484 | H | H | H | H | H | $CF_2CH_2SOCH_3$ | $C(=O)CH_2OCH_3$ | H | O | 0 |
| A-2485 | H | H | H | H | H | $CH_2SO_2CH_3$ | $C(=O)CH_2OCH_3$ | H | O | 0 |
| A-2486 | H | H | H | H | H | $CH_2CH_2SO_2CH_3$ | $C(=O)CH_2OCH_3$ | H | O | 0 |
| A-2487 | H | H | H | H | H | $CH_2SCF_3$ | $C(=O)CH_2OCH_3$ | H | O | 0 |
| A-2488 | H | H | H | H | H | $CH_2SCHF_2$ | $C(=O)CH_2OCH_3$ | H | O | 0 |
| A-2489 | H | H | H | H | H | $CH_2SCH_2CF_3$ | $C(=O)CH_2OCH_3$ | H | O | 0 |
| A-2490 | H | H | H | H | H | $CH_2SCH_2CHF_2$ | $C(=O)CH_2OCH_3$ | H | O | 0 |
| A-2491 | H | H | H | H | H | $CH_2SCF_2CF_3$ | $C(=O)CH_2OCH_3$ | H | O | 0 |
| A-2492 | H | H | H | H | H | $CH_2CH_2SCF_3$ | $C(=O)CH_2OCH_3$ | H | O | 0 |
| A-2493 | H | H | H | H | H | $CH_2SOCF_3$ | $C(=O)CH_2OCH_3$ | H | O | 0 |
| A-2494 | H | H | H | H | H | $CH_2CH_2SOCF_3$ | $C(=O)CH_2OCH_3$ | H | O | 0 |
| A-2495 | H | H | H | H | H | $CH_2CH_2CH_2SOCF_3$ | $C(=O)CH_2OCH_3$ | H | O | 0 |
| A-2496 | H | H | H | H | H | $CH_2SO_2CF_3$ | $C(=O)CH_2OCH_3$ | H | O | 0 |

TABLE 42

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-2497 | H | H | H | H | H | $CH_2CH_2SO_2CF_3$ | $C(=O)CH_2OCH_3$ | H | O | 0 |
| A-2498 | H | H | H | H | H | $CH_2CH_2CH_2SO_2CF_3$ | $C(=O)CH_2OCH_3$ | H | O | 0 |
| A-2499 | H | H | H | H | H | $CH_2C(=O)NHCH_2CHF_2$ | $C(=O)CH_2OCH_3$ | H | O | 0 |
| A-2500 | H | H | H | H | H | $CH_2C(=O)NHCH_2CF_3$ | $C(=O)CH_2OCH_3$ | H | O | 0 |
| A-2501 | H | H | H | H | H | H | $C(=O)$cyclopropyl | H | O | 0 |
| A-2502 | H | H | H | H | H | $CH_3$ | $C(=O)$cyclopropyl | H | O | 0 |
| A-2503 | H | H | H | H | H | $CH_2CH_3$ | $C(=O)$cyclopropyl | H | O | 0 |
| A-2504 | H | H | H | H | H | $CH(CH_3)_2$ | $C(=O)$cyclopropyl | H | O | 0 |
| A-2505 | H | H | H | H | H | $CH_2CH_2CH_3$ | $C(=O)$cyclopropyl | H | O | 0 |

TABLE 42-continued

| Compound | R¹ | R² | R³ | R⁴ | R⁵ | R⁶ | R⁷ | R⁸ | X | n |
|---|---|---|---|---|---|---|---|---|---|---|
| A-2506 | H | H | H | H | H | CH$_2$CH(CH$_3$)$_2$ | C(=O)cyclopropyl | H | O | 0 |
| A-2507 | H | H | H | H | H | CH(CH$_3$)CH$_2$CH$_3$ | C(=O)cyclopropyl | H | O | 0 |
| A-2508 | H | H | H | H | H | CH$_2$C(CH$_3$)$_3$ | C(=O)cyclopropyl | H | O | 0 |
| A-2509 | H | H | H | H | H | CH$_2$(CH$_2$)$_2$CH$_3$ | C(=O)cyclopropyl | H | O | 0 |
| A-2510 | H | H | H | H | H | CH$_2$(CH$_2$)$_3$CH$_3$ | C(=O)cyclopropyl | H | O | 0 |
| A-2511 | H | H | H | H | H | CF$_3$ | C(=O)cyclopropyl | H | O | 0 |
| A-2512 | H | H | H | H | H | CHF$_2$ | C(=O)cyclopropyl | H | O | 0 |
| A-2513 | H | H | H | H | H | CH$_2$CF$_3$ | C(=O)cyclopropyl | H | O | 0 |
| A-2514 | H | H | H | H | H | CH$_2$CHF$_2$ | C(=O)cyclopropyl | H | O | 0 |
| A-2515 | H | H | H | H | H | CH$_2$CClF$_2$ | C(=O)cyclopropyl | H | O | 0 |
| A-2516 | H | H | H | H | H | CH$_2$CBrF$_2$ | C(=O)cyclopropyl | H | O | 0 |
| A-2517 | H | H | H | H | H | CF$_2$CF$_3$ | C(=O)cyclopropyl | H | O | 0 |
| A-2518 | H | H | H | H | H | CF$_2$CHF$_2$ | C(=O)cyclopropyl | H | O | 0 |
| A-2519 | H | H | H | H | H | CH$_2$CH$_2$CF$_3$ | C(=O)cyclopropyl | H | O | 0 |
| A-2520 | H | H | H | H | H | CH$_2$CF$_2$CF$_3$ | C(=O)cyclopropyl | H | O | 0 |
| A-2521 | H | H | H | H | H | CH$_2$CF$_2$CHF$_2$ | C(=O)cyclopropyl | H | O | 0 |
| A-2522 | H | H | H | H | H | CF$_2$CHFCF$_3$ | C(=O)cyclopropyl | H | O | 0 |
| A-2523 | H | H | H | H | H | CF$_2$CF$_2$CF$_3$ | C(=O)cyclopropyl | H | O | 0 |
| A-2524 | H | H | H | H | H | CH$_2$CF$_2$CF$_2$CF$_3$ | C(=O)cyclopropyl | H | O | 0 |
| A-2525 | H | H | H | H | H | CH$_2$CF$_2$CHFCF$_3$ | C(=O)cyclopropyl | H | O | 0 |
| A-2526 | H | H | H | H | H | CH$_2$CH$_2$CH$_2$CF$_3$ | C(=O)cyclopropyl | H | O | 0 |
| A-2527 | H | H | H | H | H | CH$_2$CH$_2$CF$_2$CF$_3$ | C(=O)cyclopropyl | H | O | 0 |
| A-2528 | H | H | H | H | H | CF$_2$CF$_2$CF$_2$CF$_3$ | C(=O)cyclopropyl | H | O | 0 |
| A-2529 | H | H | H | H | H | CH$_2$CH$_2$CH(CF$_3$)$_2$ | C(=O)cyclopropyl | H | O | 0 |
| A-2530 | H | H | H | H | H | CF$_2$CF$_2$CF$_2$CF$_2$CF$_3$ | C(=O)cyclopropyl | H | O | 0 |
| A-2531 | H | H | H | H | H | CH$_2$CF$_2$CF$_2$CF$_2$CF$_3$ | C(=O)cyclopropyl | H | O | 0 |
| A-2532 | H | H | H | H | H | CH$_2$CH$_2$CH$_2$CH$_2$CF$_3$ | C(=O)cyclopropyl | H | O | 0 |
| A-2533 | H | H | H | H | H | CH$_2$CF$_2$CF$_2$CF$_2$CHF$_2$ | C(=O)cyclopropyl | H | O | 0 |
| A-2534 | H | H | H | H | H | CH$_2$CH$_2$OCH$_2$CF$_3$ | C(=O)cyclopropyl | H | O | 0 |
| A-2535 | H | H | H | H | H | CF$_2$CHFOCF$_3$ | C(=O)cyclopropyl | H | O | 0 |
| A-2536 | H | H | H | H | H | CF$_2$CHFOCF$_2$CF$_3$ | C(=O)cyclopropyl | H | O | 0 |
| A-2537 | H | H | H | H | H | CH$_2$CH$_2$CF=CF$_2$ | C(=O)cyclopropyl | H | O | 0 |
| A-2538 | H | H | H | H | H | CH$_2$CH$_2$CH=CF$_2$ | C(=O)cyclopropyl | H | O | 0 |
| A-2539 | H | H | H | H | H | CH$_2$C≡CCH$_3$ | C(=O)cyclopropyl | H | O | 0 |
| A-2540 | H | H | H | H | H | CH$_2$C≡CCF$_3$ | C(=O)cyclopropyl | H | O | 0 |
| A-2541 | H | H | H | H | H | CH$_2$C≡CI | C(=O)cyclopropyl | H | O | 0 |
| A-2542 | H | H | H | H | H | CH$_2$(2,2-difluorocyclopropyl) | C(=O)cyclopropyl | H | O | 0 |
| A-2543 | H | H | H | H | H | CH$_2$(2,2-dichlorocyclopropyl) | C(=O)cyclopropyl | H | O | 0 |
| A-2544 | H | H | H | H | H | CH$_2$CH$_2$(2,2-difluorocyclopropyl) | C(=O)cyclopropyl | H | O | 0 |
| A-2545 | H | H | H | H | H | CH$_2$CH$_2$(2,2-dichlorocyclopropyl) | C(=O)cyclopropyl | H | O | 0 |
| A-2546 | H | H | H | H | H | CH$_2$SCH$_3$ | C(=O)cyclopropyl | H | O | 0 |
| A-2547 | H | H | H | H | H | CH$_2$SCH$_2$CH$_3$ | C(=O)cyclopropyl | H | O | 0 |
| A-2548 | H | H | H | H | H | CH$_2$CH$_2$SCH$_3$ | C(=O)cyclopropyl | H | O | 0 |
| A-2549 | H | H | H | H | H | CH$_2$SOCH$_3$ | C(=O)cyclopropyl | H | O | 0 |
| A-2550 | H | H | H | H | H | CH$_2$CH$_2$SOCH$_3$ | C(=O)cyclopropyl | H | O | 0 |
| A-2551 | H | H | H | H | H | CH$_2$SO$_2$CH$_3$ | C(=O)cyclopropyl | H | O | 0 |
| A-2552 | H | H | H | H | H | CH$_2$CH$_2$SO$_2$CH$_3$ | C(=O)cyclopropyl | H | O | 0 |
| A-2553 | H | H | H | H | H | CH$_2$SCF$_3$ | C(=O)cyclopropyl | H | O | 0 |
| A-2554 | H | H | H | H | H | CH$_2$SCHF$_2$ | C(=O)cyclopropyl | H | O | 0 |
| A-2555 | H | H | H | H | H | CH$_2$SCH$_2$CF$_3$ | C(=O)cyclopropyl | H | O | 0 |
| A-2556 | H | H | H | H | H | CH$_2$SCH$_2$CHF$_2$ | C(=O)cyclopropyl | H | O | 0 |
| A-2557 | H | H | H | H | H | CH$_2$SCF$_2$CF$_3$ | C(=O)cyclopropyl | H | O | 0 |

TABLE 43

| Compound | R¹ | R² | R³ | R⁴ | R⁵ | R⁶ | R⁷ | R⁸ | X | n |
|---|---|---|---|---|---|---|---|---|---|---|
| A-2558 | H | H | H | H | H | CH$_2$CH$_2$SCF$_3$ | C(=O)cyclopropyl | H | O | 0 |
| A-2559 | H | H | H | H | H | CH$_2$SOCF$_3$ | C(=O)cyclopropyl | H | O | 0 |
| A-2560 | H | H | H | H | H | CH$_2$CH$_2$SOCF$_3$ | C(=O)cyclopropyl | H | O | 0 |
| A-2561 | H | H | H | H | H | CH$_2$CH$_2$CH$_2$SOCF$_3$ | C(=O)cyclopropyl | H | O | 0 |
| A-2562 | H | H | H | H | H | CH$_2$SO$_2$CF$_3$ | C(=O)cyclopropyl | H | O | 0 |
| A-2563 | H | H | H | H | H | CH$_2$CH$_2$SO$_2$CF$_3$ | C(=O)cyclopropyl | H | O | 0 |
| A-2564 | H | H | H | H | H | CH$_2$CH$_2$CH$_2$SO$_2$CF$_3$ | C(=O)cyclopropyl | H | O | 0 |
| A-2565 | H | H | H | H | H | CH$_2$C(=O)NHCH$_2$CHF$_2$ | C(=O)cyclopropyl | H | O | 0 |
| A-2566 | H | H | H | H | H | CH$_2$C(=O)NHCH$_2$CF$_3$ | C(=O)cyclopropyl | H | O | 0 |
| A-2567 | H | H | H | H | H | H | C(=O)OCH$_3$ | H | O | 0 |
| A-2568 | H | H | H | H | H | CH$_3$ | C(=O)OCH$_3$ | H | O | 0 |
| A-2569 | H | H | H | H | H | CH$_2$CH$_3$ | C(=O)OCH$_3$ | H | O | 0 |
| A-2570 | H | H | H | H | H | CH(CH$_3$)$_2$ | C(=O)OCH$_3$ | H | O | 0 |
| A-2571 | H | H | H | H | H | CH$_2$CH$_2$CH$_3$ | C(=O)OCH$_3$ | H | O | 0 |
| A-2572 | H | H | H | H | H | CH$_2$CH(CH$_3$)$_2$ | C(=O)OCH$_3$ | H | O | 0 |
| A-2573 | H | H | H | H | H | CH$_2$C(CH$_3$)$_3$ | C(=O)OCH$_3$ | H | O | 0 |
| A-2574 | H | H | H | H | H | CH(CH$_3$)CH$_2$CH$_3$ | C(=O)OCH$_3$ | H | O | 0 |
| A-2575 | H | H | H | H | H | CH$_2$(CH$_2$)$_2$CH$_3$ | C(=O)OCH$_3$ | H | O | 0 |

TABLE 43-continued

| Compound | R¹ | R² | R³ | R⁴ | R⁵ | R⁶ | R⁷ | R⁸ | X | n |
|---|---|---|---|---|---|---|---|---|---|---|
| A-2576 | H | H | H | H | H | $CH_2(CH_2)_3CH_3$ | $C(=O)OCH_3$ | H | O | 0 |
| A-2577 | H | H | H | H | H | $CH_2(CH_2)_4CH_3$ | $C(=O)OCH_3$ | H | O | 0 |
| A-2578 | H | H | H | H | H | $CHACH_2)_6CH_3$ | $C(=O)OCH_3$ | H | O | 0 |
| A-2579 | H | H | H | H | H | $CH_2OCH_3$ | $C(=O)OCH_3$ | H | O | 0 |
| A-2580 | H | H | H | H | H | $CH_2OCH_2CH_3$ | $C(=O)OCH_3$ | H | O | 0 |
| A-2581 | H | H | H | H | H | $CH_2CH_2OCH_3$ | $C(=O)OCH_3$ | H | O | 0 |
| A-2582 | H | H | H | H | H | $CH_2CH_2OCH_2CH_3$ | $C(=O)OCH_3$ | H | O | 0 |
| A-2583 | H | H | H | H | H | $CF_3$ | $C(=O)OCH_3$ | H | O | 0 |
| A-2584 | H | H | H | H | H | $CHF_2$ | $C(=O)OCH_3$ | H | O | 0 |
| A-2585 | H | H | H | H | H | $CH_2CF_3$ | $C(=O)OCH_3$ | H | O | 0 |
| A-2586 | H | H | H | H | H | $CH_2CHF_2$ | $C(=O)OCH_3$ | H | O | 0 |
| A-2587 | H | H | H | H | H | $CH_2CClF_2$ | $C(=O)OCH_3$ | H | O | 0 |
| A-2588 | H | H | H | H | H | $CH_2CBrF_2$ | $C(=O)OCH_3$ | H | O | 0 |
| A-2589 | H | H | H | H | H | $CF_2CF_3$ | $C(=O)OCH_3$ | H | O | 0 |
| A-2590 | H | H | H | H | H | $CF_2CHF_2$ | $C(=O)OCH_3$ | H | O | 0 |
| A-2591 | H | H | H | H | H | $CH_2CH_2CF_3$ | $C(=O)OCH_3$ | H | O | 0 |
| A-2592 | H | H | H | H | H | $CH_2CF_2CF_3$ | $C(=O)OCH_3$ | H | O | 0 |
| A-2593 | H | H | H | H | H | $CH_2CF_2CHF_2$ | $C(=O)OCH_3$ | H | O | 0 |
| A-2594 | H | H | H | H | H | $CF_2CHFCF_3$ | $C(=O)OCH_3$ | H | O | 0 |
| A-2595 | H | H | H | H | H | $CF_2CF_2CF_3$ | $C(=O)OCH_3$ | H | O | 0 |
| A-2596 | H | H | H | H | H | $CH_2CF_2CF_2CF_3$ | $C(=O)OCH_3$ | H | O | 0 |
| A-2597 | H | H | H | H | H | $CH_2CF_2CHFCF_3$ | $C(=O)OCH_3$ | H | O | 0 |
| A-2598 | H | H | H | H | H | $CH_2CH_2CH_2CF_3$ | $C(=O)OCH_3$ | H | O | 0 |
| A-2599 | H | H | H | H | H | $CH_2CH_2CF_2CF_3$ | $C(=O)OCH_3$ | H | O | 0 |
| A-2600 | H | H | H | H | H | $CF_2CF_2CF_2CF_3$ | $C(=O)OCH_3$ | H | O | 0 |
| A-2601 | H | H | H | H | H | $CH_2CH_2CH(CF_3)_2$ | $C(=O)OCH_3$ | H | O | 0 |
| A-2602 | H | H | H | H | H | $CF_2CF_2CF_2CF_2CF_3$ | $C(=O)OCH_3$ | H | O | 0 |
| A-2603 | H | H | H | H | H | $CH_2CF_2CF_2CF_2CF_3$ | $C(=O)OCH_3$ | H | O | 0 |
| A-2604 | H | H | H | H | H | $CH_2CH_2CH_2CH_2CF_3$ | $C(=O)OCH_3$ | H | O | 0 |
| A-2605 | H | H | H | H | H | $CH_2CF_2CF_2CF_2CHF_2$ | $C(=O)OCH_3$ | H | O | 0 |
| A-2606 | H | H | H | H | H | $CH_2CF_2CF(CF_3)CF_2C(CF_3)_3$ | $C(=O)OCH_3$ | H | O | 0 |
| A-2607 | H | H | H | H | H | $CF_2CHFOCH_3$ | $C(=O)OCH_3$ | H | O | 0 |
| A-2608 | H | H | H | H | H | $CF_2CHFOCH_2CH_3$ | $C(=O)OCH_3$ | H | O | 0 |
| A-2609 | H | H | H | H | H | $CH_2CH_2OCH_2CF_3$ | $C(=O)OCH_3$ | H | O | 0 |
| A-2610 | H | H | H | H | H | $CF_2CHFOCF_3$ | $C(=O)OCH_3$ | H | O | 0 |
| A-2611 | H | H | H | H | H | $CF_2CHFOCF_2CF_3$ | $C(=O)OCH_3$ | H | O | 0 |
| A-2612 | H | H | H | H | H | $CF_2CHFOCF_2CF_2CF_3$ | $C(=O)OCH_3$ | H | O | 0 |
| A-2613 | H | H | H | H | H | $CH_2CH=CH_2$ | $C(=O)OCH_3$ | H | O | 0 |
| A-2614 | H | H | H | H | H | $CH_2CH=CHCl$ | $C(=O)OCH_3$ | H | O | 0 |
| A-2615 | H | H | H | H | H | $CH_2CH=CCl_2$ | $C(=O)OCH_3$ | H | O | 0 |
| A-2616 | H | H | H | H | H | $CH_2CH_2CF=CF_2$ | $C(=O)OCH_3$ | H | O | 0 |
| A-2617 | H | H | H | H | H | $CH_2CH_2CH=CF_2$ | $C(=O)OCH_3$ | H | O | 0 |
| A-2618 | H | H | H | H | H | $CH_2C\equiv CH$ | $C(=O)OCH_3$ | H | O | 0 |

TABLE 44

| Compound | R¹ | R² | R³ | R⁴ | R⁵ | R⁶ | R⁷ | R⁸ | X | n |
|---|---|---|---|---|---|---|---|---|---|---|
| A-2619 | H | H | H | H | H | $CH_2C\equiv CCH_3$ | $C(=O)OCH_3$ | H | O | 0 |
| A-2620 | H | H | H | H | H | $CH_2C\equiv CI$ | $C(=O)OCH_3$ | H | O | 0 |
| A-2621 | H | H | H | H | H | $CH_2C\equiv CCF_3$ | $C(=O)OCH_3$ | H | O | 0 |
| A-2622 | H | H | H | H | H | cyclobutyl | $C(=O)OCH_3$ | H | O | 0 |
| A-2623 | H | H | H | H | H | cyclopentyl | $C(=O)OCH_3$ | H | O | 0 |
| A-2624 | H | H | H | H | H | cyclohexyl | $C(=O)OCH_3$ | H | O | 0 |
| A-2625 | H | H | H | H | H | 4,4-difluorocyclohexyl | $C(=O)OCH_3$ | H | O | 0 |
| A-2626 | H | H | H | H | H | $CH_2$(cyclopropyl) | $C(=O)OCH_3$ | H | O | 0 |
| A-2627 | H | H | H | H | H | $CH_2$(cyclobutyl) | $C(=O)OCH_3$ | H | O | 0 |
| A-2628 | H | H | H | H | H | $CH_2$(cyclopentyl) | $C(=O)OCH_3$ | H | O | 0 |
| A-2629 | H | H | H | H | H | $CH_2CH_2$(cyclopropyl) | $C(=O)OCH_3$ | H | O | 0 |
| A-2630 | H | H | H | H | H | $CH_2$(2,2-difluorocyclopropyl) | $C(=O)OCH_3$ | H | O | 0 |
| A-2631 | H | H | H | H | H | $CH_2$(2,2-dichlorocyclopropyl) | $C(=O)OCH_3$ | H | O | 0 |
| A-2632 | H | H | H | H | H | $CH_2$(4,4-difluorocyclohexyl) | $C(=O)OCH_3$ | H | O | 0 |
| A-2633 | H | H | H | H | H | $CH_2$(2,2-difluorocyclopropyl) | $C(=O)OCH_3$ | H | O | 0 |
| A-2634 | H | H | H | H | H | $CH_2$(2,2-dichlorocyclopropyl) | $C(=O)OCH_3$ | H | O | 0 |
| A-2635 | H | H | H | H | H | $CH_2SCH_3$ | $C(=O)OCH_3$ | H | O | 0 |
| A-2636 | H | H | H | H | H | $CH_2SCH_2CH_3$ | $C(=O)OCH_3$ | H | O | 0 |
| A-2637 | H | H | H | H | H | $CH_2CH_2SCH_3$ | $C(=O)OCH_3$ | H | O | 0 |
| A-2638 | H | H | H | H | H | $CH_2CH_2SCH_2CH_3$ | $C(=O)OCH_3$ | H | O | 0 |
| A-2639 | H | H | H | H | H | $CH_2CH_2CH_2SCH_3$ | $C(=O)OCH_3$ | H | O | 0 |
| A-2640 | H | H | H | H | H | $CH_2CH_2CH_2SCH_2CH_3$ | $C(=O)OCH_3$ | H | O | 0 |
| A-2641 | H | H | H | H | H | $CH(CH_3)SCH_3$ | $C(=O)OCH_3$ | H | O | 0 |
| A-2642 | H | H | H | H | H | $CH(CH_3)SCH_2CH_3$ | $C(=O)OCH_3$ | H | O | 0 |
| A-2643 | H | H | H | H | H | $CH_2CH(CH_3)SCH_3$ | $C(=O)OCH_3$ | H | O | 0 |
| A-2644 | H | H | H | H | H | $CH_2CH(CH_3)SCH_2CH_3$ | $C(=O)OCH_3$ | H | O | 0 |
| A-2645 | H | H | H | H | H | $CH(CH_3)CH_2CH_2SCH_3$ | $C(=O)OCH_3$ | H | O | 0 |

TABLE 44-continued

| Compound | R¹ | R² | R³ | R⁴ | R⁵ | R⁶ | R⁷ | R⁸ | X | n |
|---|---|---|---|---|---|---|---|---|---|---|
| A-2646 | H | H | H | H | H | CH(CH₃)CH₂CH₂SCH₂CH₃ | C(=O)OCH₃ | H | O | 0 |
| A-2647 | H | H | H | H | H | CH₂CH(CH₃)CH₂SCH₃ | C(=O)OCH₃ | H | O | 0 |
| A-2648 | H | H | H | H | H | CH₂CH(CH₃)CH₂SCH₂CH₃ | C(=O)OCH₃ | H | O | 0 |
| A-2649 | H | H | H | H | H | CH₂CH₂CH(CH₃)SCH₃ | C(=O)OCH₃ | H | O | 0 |
| A-2650 | H | H | H | H | H | CH₂CH₂CH(CH₃)SCH₂CH₃ | C(=O)OCH₃ | H | O | 0 |
| A-2651 | H | H | H | H | H | CH₂SOCH₃ | C(=O)OCH₃ | H | O | 0 |
| A-2652 | H | H | H | H | H | CH₂CH₂SOCH₃ | C(=O)OCH₃ | H | O | 0 |
| A-2653 | H | H | H | H | H | CH₂CH₂CH₂SOCH₃ | C(=O)OCH₃ | H | O | 0 |
| A-2654 | H | H | H | H | H | CH(CH₃)SOCH₃ | C(=O)OCH₃ | H | O | 0 |
| A-2655 | H | H | H | H | H | CH₂CH(CH₃)SOCH₃ | C(=O)OCH₃ | H | O | 0 |
| A-2656 | H | H | H | H | H | CH(CH₃)CH₂CH₂SOCH₃ | C(=O)OCH₃ | H | O | 0 |
| A-2657 | H | H | H | H | H | CH₂CH(CH₃)CH₂SOCH₃ | C(=O)OCH₃ | H | O | 0 |
| A-2658 | H | H | H | H | H | CH₂CH₂CH(CH₃)SOCH₃ | C(=O)OCH₃ | H | O | 0 |
| A-2659 | H | H | H | H | H | CH₂SO₂CH₃ | C(=O)OCH₃ | H | O | 0 |
| A-2660 | H | H | H | H | H | CH₂CH₂SO₂CH₃ | C(=O)OCH₃ | H | O | 0 |
| A-2661 | H | H | H | H | H | CH₂CH₂CH₂SO₂CH₃ | C(=O)OCH₃ | H | O | 0 |
| A-2662 | H | H | H | H | H | CH(CH₃)SO₂CH₃ | C(=O)OCH₃ | H | O | 0 |
| A-2663 | H | H | H | H | H | CH₂CH(CH₃)SO₂CH₃ | C(=O)OCH₃ | H | O | 0 |
| A-2664 | H | H | H | H | H | CH(CH₃)CH₂CH₂SO₂CH₃ | C(=O)OCH₃ | H | O | 0 |
| A-2665 | H | H | H | H | H | CH₂CH(CH₃)CH₂SO₂CH₃ | C(=O)OCH₃ | H | O | 0 |
| A-2666 | H | H | H | H | H | CH₂CH₂CH(CH₃)SO₂CH₃ | C(=O)OCH₃ | H | O | 0 |
| A-2667 | H | H | H | H | H | CH₂SCF₃ | C(=O)OCH₃ | H | O | 0 |
| A-2668 | H | H | H | H | H | CH₂SCHF₂ | C(=O)OCH₃ | H | O | 0 |
| A-2669 | H | H | H | H | H | CH₂SCH₂CF₃ | C(=O)OCH₃ | H | O | 0 |
| A-2670 | H | H | H | H | H | CH₂SCH₂CHF₂ | C(=O)OCH₃ | H | O | 0 |
| A-2671 | H | H | H | H | H | CH₂SCF₂CF₃ | C(=O)OCH₃ | H | O | 0 |
| A-2672 | H | H | H | H | H | CH₂CH₂SCF₃ | C(=O)OCH₃ | H | O | 0 |
| A-2673 | H | H | H | H | H | CH₂CH₂SCH₂CF₃ | C(=O)OCH₃ | H | O | 0 |
| A-2674 | H | H | H | H | H | CH₂CH₂CH₂SCF₃ | C(=O)OCH₃ | H | O | 0 |
| A-2675 | H | H | H | H | H | CH₂CH₂CH₂SCH₂CF₃ | C(=O)OCH₃ | H | O | 0 |
| A-2676 | H | H | H | H | H | CH(CH₃)SCF₃ | C(=O)OCH₃ | H | O | 0 |
| A-2677 | H | H | H | H | H | CH(CH₃)SCH₂CF₃ | C(=O)OCH₃ | H | O | 0 |
| A-2678 | H | H | H | H | H | CH₂CH(CH₃)SCF₃ | C(=O)OCH₃ | H | O | 0 |
| A-2679 | H | H | H | H | H | CH₂CH(CH₃)SCH₂CF₃ | C(=O)OCH₃ | H | O | 0 |

TABLE 45

| Compound | R¹ | R² | R³ | R⁴ | R⁵ | R⁶ | R⁷ | R⁸ | X | n |
|---|---|---|---|---|---|---|---|---|---|---|
| A-2680 | H | H | H | H | H | CH(CH₃)CH₂CH₂SCF₃ | C(=O)OCH₃ | H | O | 0 |
| A-2681 | H | H | H | H | H | CH(CH₃)CH₂CH₂SCH₂CF₃ | C(=O)OCH₃ | H | O | 0 |
| A-2682 | H | H | H | H | H | CH₂CH(CH₃)CH₂SCF₃ | C(=O)OCH₃ | H | O | 0 |
| A-2683 | H | H | H | H | H | CH₂CH(CH₃)CH₂SCH₂CF₃ | C(=O)OCH₃ | H | O | 0 |
| A-2684 | H | H | H | H | H | CH₂CH₂CH(CH₃)SCF₃ | C(=O)OCH₃ | H | O | 0 |
| A-2685 | H | H | H | H | H | CH₂CH₂CH(CH₃)SCH₂CF₃ | C(=O)OCH₃ | H | O | 0 |
| A-2686 | H | H | H | H | H | CH₂SOCF₃ | C(=O)OCH₃ | H | O | 0 |
| A-2687 | H | H | H | H | H | CH₂CH₂SOCF₃ | C(=O)OCH₃ | H | O | 0 |
| A-2688 | H | H | H | H | H | CH₂CH₂CH₂SOCF₃ | C(=O)OCH₃ | H | O | 0 |
| A-2689 | H | H | H | H | H | CH(CH₃)SOCF₃ | C(=O)OCH₃ | H | O | 0 |
| A-2690 | H | H | H | H | H | CH₂CH(CH₃)SOCF₃ | C(=O)OCH₃ | H | O | 0 |
| A-2691 | H | H | H | H | H | CH(CH₃)CH₂CH₂SOCF₃ | C(=O)OCH₃ | H | O | 0 |
| A-2692 | H | H | H | H | H | CH₂CH(CH₃)CH₂SOCF₃ | C(=O)OCH₃ | H | O | 0 |
| A-2693 | H | H | H | H | H | CH₂CH₂CH(CH₃)SOCF₃ | C(=O)OCH₃ | H | O | 0 |
| A-2694 | H | H | H | H | H | CH₂SO₂CF₃ | C(=O)OCH₃ | H | O | 0 |
| A-2695 | H | H | H | H | H | CH₂CH₂SO₂CF₃ | C(=O)OCH₃ | H | O | 0 |
| A-2696 | H | H | H | H | H | CH₂CH₂CH₂SO₂CF₃ | C(=O)OCH₃ | H | O | 0 |
| A-2697 | H | H | H | H | H | CH(CH₃)SO₂CF₃ | C(=O)OCH₃ | H | O | 0 |
| A-2698 | H | H | H | H | H | CH₂CH(CH₃)SO₂CF₃ | C(=O)OCH₃ | H | O | 0 |
| A-2699 | H | H | H | H | H | CH(CH₃)CH₂CH₂SO₂CF₃ | C(=O)OCH₃ | H | O | 0 |
| A-2700 | H | H | H | H | H | CH₂CH(CH₃)CH₂SO₂CF₃ | C(=O)OCH₃ | H | O | 0 |
| A-2701 | H | H | H | H | H | CH₂CH₂CH(CH₃)SO₂CF₃ | C(=O)OCH₃ | H | O | 0 |
| A-2702 | H | H | H | H | H | CH₂C(=O)CH₃ | C(=O)OCH₃ | H | O | 0 |
| A-2703 | H | H | H | H | H | CH₂C(=O)CH₂CH₃ | C(=O)OCH₃ | H | O | 0 |
| A-2704 | H | H | H | H | H | CH₂C(=O)C(CH₃)₃ | C(=O)OCH₃ | H | O | 0 |
| A-2705 | H | H | H | H | H | CH₂CH₂C(=O)CH₃ | C(=O)OCH₃ | H | O | 0 |
| A-2706 | H | H | H | H | H | CH₂CH₂C(=O)C(CH₃)₃ | C(=O)OCH₃ | H | O | 0 |
| A-2707 | H | H | H | H | H | CH₂C(=O)CF₃ | C(=O)OCH₃ | H | O | 0 |
| A-2708 | H | H | H | H | H | CH₂CH₂C(=O)CF₃ | C(=O)OCH₃ | H | O | 0 |
| A-2709 | H | H | H | H | H | CH₂C(=O)OCH₃ | C(=O)OCH₃ | H | O | 0 |
| A-2710 | H | H | H | H | H | CH₂C(=O)OCH₂CH₃ | C(=O)OCH₃ | H | O | 0 |
| A-2711 | H | H | H | H | H | CH₂C(=O)OC(CH₃)₃ | C(=O)OCH₃ | H | O | 0 |
| A-2712 | H | H | H | H | H | CH₂CH₂C(=O)OCH₃ | C(=O)OCH₃ | H | O | 0 |
| A-2713 | H | H | H | H | H | CH₂CH₂C(=O)OCH₂CH₃ | C(=O)OCH₃ | H | O | 0 |
| A-2714 | H | H | H | H | H | CH₂CH₂C(=O)OC(CH₃)₃ | C(=O)OCH₃ | H | O | 0 |
| A-2715 | H | H | H | H | H | CH₂C(=O)NH₂ | C(=O)OCH₃ | H | O | 0 |

TABLE 45-continued

| Compound | R¹ | R² | R³ | R⁴ | R⁵ | R⁶ | R⁷ | R⁸ | X | n |
|---|---|---|---|---|---|---|---|---|---|---|
| A-2716 | H | H | H | H | H | CH$_2$CH$_2$C(=O)NH$_2$ | C(=O)OCH$_3$ | H | O | 0 |
| A-2717 | H | H | H | H | H | CH$_2$C(=O)NHCH$_3$ | C(=O)OCH$_3$ | H | O | 0 |
| A-2718 | H | H | H | H | H | CH$_2$C(=O)NHCH(CH$_3$)$_2$ | C(=O)OCH$_3$ | H | O | 0 |
| A-2719 | H | H | H | H | H | CH$_2$CH$_2$C(=O)NHCH$_3$ | C(=O)OCH$_3$ | H | O | 0 |
| A-2720 | H | H | H | H | H | CH$_2$CH$_2$C(=O)NHCH(CH$_3$)$_2$ | C(=O)OCH$_3$ | H | O | 0 |
| A-2721 | H | H | H | H | H | CH$_2$C(=O)NHCH$_2$CHF$_2$ | C(=O)OCH$_3$ | H | O | 0 |
| A-2722 | H | H | H | H | H | CH$_2$C(=O)NHCH$_2$CF$_3$ | C(=O)OCH$_3$ | H | O | 0 |
| A-2723 | H | H | H | H | H | CH$_2$CH$_2$C(=O)NHCH$_2$CHF$_2$ | C(=O)OCH$_3$ | H | O | 0 |
| A-2724 | H | H | H | H | H | CH$_2$CH$_2$C(=O)NHCH$_2$CF$_3$ | C(=O)OCH$_3$ | H | O | 0 |
| A-2725 | H | H | H | H | H | CH$_2$C(=O)N(CH$_3$)$_2$ | C(=O)OCH$_3$ | H | O | 0 |
| A-2726 | H | H | H | H | H | CH$_2$C(=O)N(CH$_2$CH$_3$)$_2$ | C(=O)OCH$_3$ | H | O | 0 |
| A-2727 | H | H | H | H | H | CH$_2$CH$_2$C(=O)N(CH$_3$)$_2$ | C(=O)OCH$_3$ | H | O | 0 |
| A-2728 | H | H | H | H | H | CH$_2$CH$_2$C(=O)N(CH$_2$CH$_3$)$_2$ | C(=O)OCH$_3$ | H | O | 0 |
| A-2729 | H | H | H | H | H | CH$_2$CH$_2$OH | C(=O)OCH$_3$ | H | O | 0 |
| A-2730 | H | H | H | H | H | CH$_2$CH(OH)CH$_3$ | C(=O)OCH$_3$ | H | O | 0 |
| A-2731 | H | H | H | H | H | CH$_2$CH$_2$CH$_2$OH | C(=O)OCH$_3$ | H | O | 0 |
| A-2732 | H | H | H | H | H | CH$_2$CH(OH)CH$_2$CH$_3$ | C(=O)OCH$_3$ | H | O | 0 |
| A-2733 | H | H | H | H | H | CH$_2$CH(OH)C(CH$_3$)$_3$ | C(=O)OCH$_3$ | H | O | 0 |
| A-2734 | H | H | H | H | H | CH$_2$CH$_2$CH(OH)CH$_3$ | C(=O)OCH$_3$ | H | O | 0 |
| A-2735 | H | H | H | H | H | CH$_2$CH$_2$CH(OH)C(CH$_3$)$_3$ | C(=O)OCH$_3$ | H | O | 0 |
| A-2736 | H | H | H | H | H | CH$_2$C(=NOH)CH$_3$ | C(=O)OCH$_3$ | H | O | 0 |
| A-2737 | H | H | H | H | H | CH$_2$C(=NOH)CH$_2$CH$_3$ | C(=O)OCH$_3$ | H | O | 0 |
| A-2738 | H | H | H | H | H | CH$_2$C(=NOH)C(CH$_3$)$_3$ | C(=O)OCH$_3$ | H | O | 0 |
| A-2739 | H | H | H | H | H | CH$_2$C(=NOCH$_3$)CH$_3$ | C(=O)OCH$_3$ | H | O | 0 |
| A-2740 | H | H | H | H | H | CH$_2$C(=NOCH$_3$)CH$_2$CH$_3$ | C(=O)OCH$_3$ | H | O | 0 |

TABLE 46

| Compound | R¹ | R² | R³ | R⁴ | R⁵ | R⁶ | R⁷ | R⁸ | X | n |
|---|---|---|---|---|---|---|---|---|---|---|
| A-2741 | H | H | H | H | H | CH$_2$C(=NOCH$_2$CH$_3$)CH$_3$ | C(=O)OCH$_3$ | H | O | 0 |
| A-2742 | H | H | H | H | H | CH$_2$C(=NOCH$_2$CH$_3$)CH$_2$CH$_3$ | C(=O)OCH$_3$ | H | O | 0 |
| A-2743 | H | H | H | H | H | CH$_2$C(=NOCH$_2$CF$_3$)CH$_3$ | C(=O)OCH$_3$ | H | O | 0 |
| A-2744 | H | H | H | H | H | CH$_2$C(=NOCH$_2$CF$_3$)CH$_2$CH$_3$ | C(=O)OCH$_3$ | H | O | 0 |
| A-2745 | H | H | H | H | H | CH$_2$Ph | C(=O)OCH$_3$ | H | O | 0 |
| A-2746 | H | H | H | H | H | CH$_2$(2-F)Ph | C(=O)OCH$_3$ | H | O | 0 |
| A-2747 | H | H | H | H | H | CH$_2$(3-F)Ph | C(=O)OCH$_3$ | H | O | 0 |
| A-2748 | H | H | H | H | H | CH$_2$(4-F)Ph | C(=O)OCH$_3$ | H | O | 0 |
| A-2749 | H | H | H | H | H | CH$_2$(2-Cl)Ph | C(=O)OCH$_3$ | H | O | 0 |
| A-2750 | H | H | H | H | H | CH$_2$(3-Cl)Ph | C(=O)OCH$_3$ | H | O | 0 |
| A-2751 | H | H | H | H | H | CH$_2$(4-Cl)Ph | C(=O)OCH$_3$ | H | O | 0 |
| A-2752 | H | H | H | H | H | CH$_2$(2-CF$_3$)Ph | C(=O)OCH$_3$ | H | O | 0 |
| A-2753 | H | H | H | H | H | CH$_2$(3-CF$_3$)Ph | C(=O)OCH$_3$ | H | O | 0 |
| A-2754 | H | H | H | H | H | CH$_2$(4-CF$_3$)Ph | C(=O)OCH$_3$ | H | O | 0 |
| A-2755 | H | H | H | H | H | CH$_2$(naphthalen-1-yl) | C(=O)OCH$_3$ | H | O | 0 |
| A-2756 | H | H | H | H | H | CH$_2$(naphthalen-2-yl) | C(=O)OCH$_3$ | H | O | 0 |
| A-2757 | H | H | H | H | H | CH$_2$CH$_2$Ph | C(=O)OCH$_3$ | H | O | 0 |
| A-2758 | H | H | H | H | H | H | C(=O)OCH$_2$CH$_3$ | H | O | 0 |
| A-2759 | H | H | H | H | H | CH$_3$ | C(=O)OCH$_2$CH$_3$ | H | O | 0 |
| A-2760 | H | H | H | H | H | CH$_2$CH$_3$ | C(=O)OCH$_2$CH$_3$ | H | O | 0 |
| A-2761 | H | H | H | H | H | CH(CH$_3$)$_2$ | C(=O)OCH$_2$CH$_3$ | H | O | 0 |
| A-2762 | H | H | H | H | H | CH$_2$CH$_2$CH$_3$ | C(=O)OCH$_2$CH$_3$ | H | O | 0 |
| A-2763 | H | H | H | H | H | CH$_2$CH(CH$_3$)$_2$ | C(=O)OCH$_2$CH$_3$ | H | O | 0 |
| A-2764 | H | H | H | H | H | CH(CH$_3$)CH$_2$CH$_3$ | C(=O)OCH$_2$CH$_3$ | H | O | 0 |
| A-2765 | H | H | H | H | H | CH$_2$C(CH$_3$)$_3$ | C(=O)OCH$_2$CH$_3$ | H | O | 0 |
| A-2766 | H | H | H | H | H | CH$_2$(CH$_2$)$_2$CH$_3$ | C(=O)OCH$_2$CH$_3$ | H | O | 0 |
| A-2767 | H | H | H | H | H | CH$_2$(CH$_2$)$_3$CH$_3$ | C(=O)OCH$_2$CH$_3$ | H | O | 0 |
| A-2768 | H | H | H | H | H | CF$_3$ | C(=O)OCH$_2$CH$_3$ | H | O | 0 |
| A-2769 | H | H | H | H | H | CHF$_2$ | C(=O)OCH$_2$CH$_3$ | H | O | 0 |
| A-2770 | H | H | H | H | H | CH$_2$CF$_3$ | C(=O)OCH$_2$CH$_3$ | H | O | 0 |
| A-2771 | H | H | H | H | H | CH$_2$CHF$_2$ | C(=O)OCH$_2$CH$_3$ | H | O | 0 |
| A-2772 | H | H | H | H | H | CH$_2$CClF$_2$ | C(=O)OCH$_2$CH$_3$ | H | O | 0 |
| A-2773 | H | H | H | H | H | CH$_2$CBrF$_2$ | C(=O)OCH$_2$CH$_3$ | H | O | 0 |
| A-2774 | H | H | H | H | H | CF$_2$CF$_3$ | C(=O)OCH$_2$CH$_3$ | H | O | 0 |
| A-2775 | H | H | H | H | H | CF$_2$CHF$_2$ | C(=O)OCH$_2$CH$_3$ | H | O | 0 |
| A-2776 | H | H | H | H | H | CH$_2$CH$_2$CF$_3$ | C(=O)OCH$_2$CH$_3$ | H | O | 0 |
| A-2777 | H | H | H | H | H | CH$_2$CF$_2$CF$_3$ | C(=O)OCH$_2$CH$_3$ | H | O | 0 |
| A-2778 | H | H | H | H | H | CH$_2$CF$_2$CHF$_2$ | C(=O)OCH$_2$CH$_3$ | H | O | 0 |
| A-2779 | H | H | H | H | H | CF$_2$CHFCF$_3$ | C(=O)OCH$_2$CH$_3$ | H | O | 0 |
| A-2780 | H | H | H | H | H | CF$_2$CF$_2$CF$_3$ | C(=O)OCH$_2$CH$_3$ | H | O | 0 |
| A-2781 | H | H | H | H | H | CH$_2$CF$_2$CF$_2$CF$_3$ | C(=O)OCH$_2$CH$_3$ | H | O | 0 |
| A-2782 | H | H | H | H | H | CH$_2$CF$_2$CHFCF$_3$ | C(=O)OCH$_2$CH$_3$ | H | O | 0 |
| A-2783 | H | H | H | H | H | CH$_2$CH$_2$CH$_2$CF$_3$ | C(=O)OCH$_2$CH$_3$ | H | O | 0 |
| A-2784 | H | H | H | H | H | CH$_2$CH$_2$CF$_2$CF$_3$ | C(=O)OCH$_2$CH$_3$ | H | O | 0 |
| A-2785 | H | H | H | H | H | CF$_2$CF$_2$CF$_2$CF$_3$ | C(=O)OCH$_2$CH$_3$ | H | O | 0 |

TABLE 46-continued

| Compound | R¹ | R² | R³ | R⁴ | R⁵ | R⁶ | R⁷ | R⁸ | X | n |
|---|---|---|---|---|---|---|---|---|---|---|
| A-2786 | H | H | H | H | H | $CH_2CH_2CH(CF_3)_2$ | $C(=O)OCH_2CH_3$ | H | O | 0 |
| A-2787 | H | H | H | H | H | $CF_2CF_2CF_2CF_2CF_3$ | $C(=O)OCH_2CH_3$ | H | O | 0 |
| A-2788 | H | H | H | H | H | $CH_2CF_2CF_2CF_2CF_3$ | $C(=O)OCH_2CH_3$ | H | O | 0 |
| A-2789 | H | H | H | H | H | $CH_2CH_2CH_2CH_2CF_3$ | $C(=O)OCH_2CH_3$ | H | O | 0 |
| A-2790 | H | H | H | H | H | $CH_2CF_2CF_2CF_2CHF_2$ | $C(=O)OCH_2CH_3$ | H | O | 0 |
| A-2791 | H | H | H | H | H | $CH_2CH_2OCH_2CF_3$ | $C(=O)OCH_2CH_3$ | H | O | 0 |
| A-2792 | H | H | H | H | H | $CF_2CHFOCF_3$ | $C(=O)OCH_2CH_3$ | H | O | 0 |
| A-2793 | H | H | H | H | H | $CF_2CHFOCF_2CF_3$ | $C(=O)OCH_2CH_3$ | H | O | 0 |
| A-2794 | H | H | H | H | H | $CH_2CH_2CF=CF_2$ | $C(=O)OCH_2CH_3$ | H | O | 0 |
| A-2795 | H | H | H | H | H | $CH_2CH_2CH=CF_2$ | $C(=O)OCH_2CH_3$ | H | O | 0 |
| A-2796 | H | H | H | H | H | $CH_2C≡CCH_3$ | $C(=O)OCH_2CH_3$ | H | O | 0 |
| A-2797 | H | H | H | H | H | $CH_2C≡CCF_3$ | $C(=O)OCH_2CH_3$ | H | O | 0 |
| A-2798 | H | H | H | H | H | $CH_2C≡CI$ | $C(=O)OCH_2CH_3$ | H | O | 0 |
| A-2799 | H | H | H | H | H | $CH_2$(2,2-difluorocyclopropyl) | $C(=O)OCH_2CH_3$ | H | O | 0 |
| A-2800 | H | H | H | H | H | $CH_2$(2,2-dichlorocyclopropyl) | $C(=O)OCH_2CH_3$ | H | O | 0 |
| A-2801 | H | H | H | H | H | $CH_2CH_2$(2,2-difluorocyclopropyl) | $C(=O)OCH_2CH_3$ | H | O | 0 |

TABLE 47

| Compound | R¹ | R² | R³ | R⁴ | R⁵ | R⁶ | R⁷ | R⁸ | X | n |
|---|---|---|---|---|---|---|---|---|---|---|
| A-2802 | H | H | H | H | H | $CH_2CH_2$(2,2-dichlorocyclopropyl) | $C(=O)OCH_2CH_3$ | H | O | 0 |
| A-2803 | H | H | H | H | H | $CH_2SCH_3$ | $C(=O)OCH_2CH_3$ | H | O | 0 |
| A-2804 | H | H | H | H | H | $CH_2SCH_2CH_3$ | $C(=O)OCH_2CH_3$ | H | O | 0 |
| A-2805 | H | H | H | H | H | $CH_2CH_2SCH_3$ | $C(=O)OCH_2CH_3$ | H | O | 0 |
| A-2806 | H | H | H | H | H | $CH_2SOCH_3$ | $C(=O)OCH_2CH_3$ | H | O | 0 |
| A-2807 | H | H | H | H | H | $CH_2CH_2SOCH_3$ | $C(=O)OCH_2CH_3$ | H | O | 0 |
| A-2808 | H | H | H | H | H | $CH_2SO_2CH_3$ | $C(=O)OCH_2CH_3$ | H | O | 0 |
| A-2809 | H | H | H | H | H | $CH_2CH_2SO_2CH_3$ | $C(=O)OCH_2CH_3$ | H | O | 0 |
| A-2810 | H | H | H | H | H | $CH_2SCF_3$ | $C(=O)OCH_2CH_3$ | H | O | 0 |
| A-2811 | H | H | H | H | H | $CH_2SCHF_2$ | $C(=O)OCH_2CH_3$ | H | O | 0 |
| A-2812 | H | H | H | H | H | $CH_2SCH_2CF_3$ | $C(=O)OCH_2CH_3$ | H | O | 0 |
| A-2813 | H | H | H | H | H | $CH_2SCH_2CHF_3$ | $C(=O)OCH_2CH_3$ | H | O | 0 |
| A-2814 | H | H | H | H | H | $CH_2SCF_2CF_3$ | $C(=O)OCH_2CH_3$ | H | O | 0 |
| A-2815 | H | H | H | H | H | $CH_2CH_2SCF_3$ | $C(=O)OCH_2CH_3$ | H | O | 0 |
| A-2816 | H | H | H | H | H | $CH_2SOCF_3$ | $C(=O)OCH_2CH_3$ | H | O | 0 |
| A-2817 | H | H | H | H | H | $CH_2CH_2SOCF_3$ | $C(=O)OCH_2CH_3$ | H | O | 0 |
| A-2818 | H | H | H | H | H | $CH_2CH_2CH_2SOCF_3$ | $C(=O)OCH_2CH_3$ | H | O | 0 |
| A-2819 | H | H | H | H | H | $CH_2SO_2CF_3$ | $C(=O)OCH_2CH_3$ | H | O | 0 |
| A-2820 | H | H | H | H | H | $CH_2CH_2SO_2CF_3$ | $C(=O)OCH_2CH_3$ | H | O | 0 |
| A-2821 | H | H | H | H | H | $CH_2CH_2CH_2SO_2CF_3$ | $C(=O)OCH_2CH_3$ | H | O | 0 |
| A-2822 | H | H | H | H | H | $CH_2C(=O)NHCH_2CHF_2$ | $C(=O)OCH_2CH_3$ | H | O | 0 |
| A-2823 | H | H | H | H | H | $CH_2C(=O)NHCH_2CF_3$ | $C(=O)OCH_2CH_3$ | H | O | 0 |
| A-2824 | H | H | H | H | H | H | $C(=O)OCH(CH_3)_2$ | H | O | 0 |
| A-2825 | H | H | H | H | H | $CH_3$ | $C(=O)OCH(CH_3)_2$ | H | O | 0 |
| A-2826 | H | H | H | H | H | $CH_2CH_3$ | $C(=O)OCH(CH_3)_2$ | H | O | 0 |
| A-2827 | H | H | H | H | H | $CH(CH_3)_2$ | $C(=O)OCH(CH_3)_2$ | H | O | 0 |
| A-2828 | H | H | H | H | H | $CH_2CH_2CH_3$ | $C(=O)OCH(CH_3)_2$ | H | O | 0 |
| A-2829 | H | H | H | H | H | $CH_2CH(CH_3)_2$ | $C(=O)OCH(CH_3)_2$ | H | O | 0 |
| A-2830 | H | H | H | H | H | $CH(CH_3)CH_2CH_3$ | $C(=O)OCH(CH_3)_2$ | H | O | 0 |
| A-2831 | H | H | H | H | H | $CH_2C(CH_3)_3$ | $C(=O)OCH(CH_3)_2$ | H | O | 0 |
| A-2832 | H | H | H | H | H | $CH_2(CH_2)_2CH_3$ | $C(=O)OCH(CH_3)_2$ | H | O | 0 |
| A-2833 | H | H | H | H | H | $CH_2(CH_2)_3CH_3$ | $C(=O)OCH(CH_3)_2$ | H | O | 0 |
| A-2834 | H | H | H | H | H | $CF_3$ | $C(=O)OCH(CH_3)_2$ | H | O | 0 |
| A-2835 | H | H | H | H | H | $CHF_2$ | $C(=O)OCH(CH_3)_2$ | H | O | 0 |
| A-2836 | H | H | H | H | H | $CH_2CF_3$ | $C(=O)OCH(CH_3)_2$ | H | O | 0 |
| A-2837 | H | H | H | H | H | $CH_2CHF_2$ | $C(=O)OCH(CH_3)_2$ | H | O | 0 |
| A-2838 | H | H | H | H | H | $CH_2CClF_2$ | $C(=O)OCH(CH_3)_2$ | H | O | 0 |
| A-2839 | H | H | H | H | H | $CH_2CBrF_2$ | $C(=O)OCH(CH_3)_2$ | H | O | 0 |
| A-2840 | H | H | H | H | H | $CF_2CF_3$ | $C(=O)OCH(CH_3)_2$ | H | O | 0 |
| A-2841 | H | H | H | H | H | $CF_2CHF_2$ | $C(=O)OCH(CH_3)_2$ | H | O | 0 |
| A-2842 | H | H | H | H | H | $CH_2CH_2CF_3$ | $C(=O)OCH(CH_3)_2$ | H | O | 0 |
| A-2843 | H | H | H | H | H | $CH_2CF_2CF_3$ | $C(=O)OCH(CH_3)_2$ | H | O | 0 |
| A-2044 | H | H | H | H | H | $CH_2CF_2CHF_2$ | $C(=O)OCH(CH_3)_2$ | H | O | 0 |
| A-2845 | H | H | H | H | H | $CF_2CHFCF_3$ | $C(=O)OCH(CH_3)_2$ | H | O | 0 |
| A-2846 | H | H | H | H | H | $CF_2CF_2CF_3$ | $C(=O)OCH(CH_3)_2$ | H | O | 0 |
| A-2847 | H | H | H | H | H | $CH_2CF_2CF_2CF_3$ | $C(=O)OCH(CH_3)_2$ | H | O | 0 |
| A-2848 | H | H | H | H | H | $CH_2CF_2CHFCF_3$ | $C(=O)OCH(CH_3)_2$ | H | O | 0 |
| A-2849 | H | H | H | H | H | $CH_2CH_2CH_2CF_3$ | $C(=O)OCH(CH_3)_2$ | H | O | 0 |
| A-2850 | H | H | H | H | H | $CH_2CH_2CH_2CF_3$ | $C(=O)OCH(CH_3)_2$ | H | O | 0 |
| A-2851 | H | H | H | H | H | $CF_2CF_2CF_2CF_3$ | $C(=O)OCH(CH_3)_2$ | H | O | 0 |
| A-2852 | H | H | H | H | H | $CH_2CH_2CH(CF_3)_2$ | $C(=O)OCH(CH_3)_2$ | H | O | 0 |
| A-2853 | H | H | H | H | H | $CF_2CF_2CF_2CF_2CF_3$ | $C(=O)OCH(CH_3)_2$ | H | O | 0 |
| A-2854 | H | H | H | H | H | $CH_2CF_2CF_2CF_2CF_3$ | $C(=O)OCH(CH_3)_2$ | H | O | 0 |

TABLE 47-continued

| Compound | R¹ | R² | R³ | R⁴ | R⁵ | R⁶ | R⁷ | R⁸ | X | n |
|---|---|---|---|---|---|---|---|---|---|---|
| A-2855 | H | H | H | H | H | CH₂CH₂CH₂CH₂CF₃ | C(=O)OCH(CH₃)₂ | H | O | 0 |
| A-2856 | H | H | H | H | H | CH₂CF₂CF₂CF₂CHF₂ | C(=O)OCH(CH₃)₂ | H | O | 0 |
| A-2857 | H | H | H | H | H | CH₂CH₂OCH₂CF₃ | C(=O)OCH(CH₃)₂ | H | O | 0 |
| A-2858 | H | H | H | H | H | CF₂CHFOCF₃ | C(=O)OCH(CH₃)₂ | H | O | 0 |
| A-2859 | H | H | H | H | H | CF₂CHFOCF₂CF₃ | C(=O)OCH(CH₃)₂ | H | O | 0 |
| A-2860 | H | H | H | H | H | CH₂CH₂CF=CF₂ | C(=O)OCH(CH₃)₂ | H | O | 0 |
| A-2861 | H | H | H | H | H | CH₂CH₂CH=CF₂ | C(=O)OCH(CH₃)₂ | H | O | 0 |
| A-2862 | H | H | H | H | H | CH₂C≡CCH₃ | C(=O)OCH(CH₃)₂ | H | O | 0 |

TABLE 48

| Compound | R¹ | R² | R³ | R⁴ | R⁵ | R⁶ | R⁷ | R⁸ | X | n |
|---|---|---|---|---|---|---|---|---|---|---|
| A-2863 | H | H | H | H | H | CH₂C≡CCF₃ | C(=O)OCH(CH₃)₂ | H | O | 0 |
| A-2864 | H | H | H | H | H | CH₂C≡CI | C(=O)OCH(CH₃)₂ | H | O | 0 |
| A-2865 | H | H | H | H | H | CH₂(2,2-difluorecyclopropyl) | C(=O)OCH(CH₃)₂ | H | O | 0 |
| A-2866 | H | H | H | H | H | CH₂(2,2-dichlorocyclopropyl) | C(=O)OCH(CH₃)₂ | H | O | 0 |
| A-2867 | H | H | H | H | H | CH₂CH₂(2,2-difluorocyclopropyl) | C(=O)OCH(CH₃)₂ | H | O | 0 |
| A-2868 | H | H | H | H | H | CH₂CH₂(2,2-dichlorocyclopropyl) | C(=O)OCH(CH₃)₂ | H | O | 0 |
| A-2869 | H | H | H | H | H | CH₂SCH₃ | C(=O)OCH(CH₃)₂ | H | O | 0 |
| A-2870 | H | H | H | H | H | CH₂SCH₂CH₃ | C(=O)OCH(CH₃)₂ | H | O | 0 |
| A-2871 | H | H | H | H | H | CH₂CH₂SCH₃ | C(=O)OCH(CH₃)₂ | H | O | 0 |
| A-2872 | H | H | H | H | H | CH₂SOCH₃ | C(=O)OCH(CH₃)₂ | H | O | 0 |
| A-2873 | H | H | H | H | H | CH₂CH₂SOCH₃ | C(=O)OCH(CH₃)₂ | H | O | 0 |
| A-2874 | H | H | H | H | H | CH₂SO₂CH₃ | C(=O)OCH(CH₃)₂ | H | O | 0 |
| A-2875 | H | H | H | H | H | CH₂CH₂SO₂CH₃ | C(=O)OCH(CH₃)₂ | H | O | 0 |
| A-2876 | H | H | H | H | H | CH₂SCF₃ | C(=O)OCH(CH₃)₂ | H | O | 0 |
| A-2877 | H | H | H | H | H | CH₂SCHF₂ | C(=O)OCH(CH₃)₂ | H | O | 0 |
| A-2878 | H | H | H | H | H | CH₂SCH₂CF₃ | C(=O)OCH(CH₃)₂ | H | O | 0 |
| A-2879 | H | H | H | H | H | CH₂SCH₂CHF₂ | C(=O)OCH(CH₃)₂ | H | O | 0 |
| A-2880 | H | H | H | H | H | CH₂SCF₂CF₃ | C(=O)OCH(CH₃)₂ | H | O | 0 |
| A-2881 | H | H | H | H | H | CH₂CH₂SCF₃ | C(=O)OCH(CH₃)₂ | H | O | 0 |
| A-2882 | H | H | H | H | H | CH₂SOCF₂ | C(=O)OCH(CH₃)₂ | H | O | 0 |
| A-2883 | H | H | H | H | H | CH₂CH₂SOCF₃ | C(=O)OCH(CH₃)₂ | H | O | 0 |
| A-2884 | H | H | H | H | H | CH₂CH₂CH₂SOCF₃ | C(=O)OCH(CH₃)₂ | H | O | 0 |
| A-2885 | H | H | H | H | H | CH₂SO₂CF₃ | C(=O)OCH(CH₃)₂ | H | O | 0 |
| A-2886 | H | H | H | H | H | CH₂CH₂SO₂CF₃ | C(=O)OCH(CH₃)₂ | H | O | 0 |
| A-2887 | H | H | H | H | H | CH₂CH₂CH₂SO₂CF₃ | C(=O)OCH(CH₃)₂ | H | O | 0 |
| A-2888 | H | H | H | H | H | CH₂C(=O)NHCH₂CHF₂ | C(=O)OCH(CH₃)₂ | H | O | 0 |
| A-2889 | H | H | H | H | H | CH₂C(=O)NHCH₂CF₃ | C(=O)OCH(CH₃)₂ | H | O | 0 |
| A-2890 | H | H | H | H | H | H | C(=O)N(CH₃)₂ | H | O | 0 |
| A-2891 | H | H | H | H | H | CH₃ | C(=O)N(CH₃)₂ | H | O | 0 |
| A-2892 | H | H | H | H | H | CH₂CH₃ | C(=O)N(CH₃)₂ | H | O | 0 |
| A-2893 | H | H | H | H | H | CH(CH₃)₂ | C(=O)N(CH₃)₂ | H | O | 0 |
| A-2894 | H | H | H | H | H | CH₂CH₂CH₃ | C(=O)N(CH₃)₂ | H | O | 0 |
| A-2895 | H | H | H | H | H | CH₂CH(CH₃)₂ | C(=O)N(CH₃)₂ | H | O | 0 |
| A-2896 | H | H | H | H | H | CH(CH₃)CH₂CH₃ | C(=O)N(CH₃)₂ | H | O | 0 |
| A-2897 | H | H | H | H | H | CH₂C(CH₃)₃ | C(=O)N(CH₃)₂ | H | O | 0 |
| A-2898 | H | H | H | H | H | CH₂(CH₂)₂CH₃ | C(=O)N(CH₃)₂ | H | O | 0 |
| A-2899 | H | H | H | H | H | CH₂(CH₂)₃CH₃ | C(=O)N(CH₃)₂ | H | O | 0 |
| A-2900 | H | H | H | H | H | CF₃ | C(=O)N(CH₃)₂ | H | O | 0 |
| A-2901 | H | H | H | H | H | CHF₂ | C(=O)N(CH₃)₂ | H | O | 0 |
| A-2902 | H | H | H | H | H | CH₂CF₃ | C(=O)N(CH₃)₂ | H | O | 0 |
| A-2903 | H | H | H | H | H | CH₂CHF₂ | C(=O)N(CH₃)₂ | H | O | 0 |
| A-2904 | H | H | H | H | H | CH₂CClF₂ | C(=O)N(CH₃)₂ | H | O | 0 |
| A-2905 | H | H | H | H | H | CH₂CBrF₂ | C(=O)N(CH₃)₂ | H | O | 0 |
| A-2906 | H | H | H | H | H | CF₂CF₃ | C(=O)N(CH₃)₂ | H | O | 0 |
| A-2907 | H | H | H | H | H | CF₂CHF₂ | C(=O)N(CH₃)₂ | H | O | 0 |
| A-2908 | H | H | H | H | H | CH₂CH₂CF₃ | C(=O)N(CH₃)₂ | H | O | 0 |
| A-2909 | H | H | H | H | H | CH₂CF₂CF₃ | C(=O)N(CH₃)₂ | H | O | 0 |
| A-2910 | H | H | H | H | H | CH₂CF₂CHF₂ | C(=O)N(CH₃)₂ | H | O | 0 |
| A-2911 | H | H | H | H | H | CF₂CHFCF₃ | C(=O)N(CH₃)₂ | H | O | 0 |
| A-2912 | H | H | H | H | H | CF₂CF₂CF₃ | C(=O)N(CH₃)₂ | H | O | 0 |
| A-2913 | H | H | H | H | H | CH₂CF₂CF₂CF₃ | C(=O)N(CH₃)₂ | H | O | 0 |
| A-2914 | H | H | H | H | H | CH₂CF₂CHFCF₃ | C(=O)N(CH₃)₂ | H | O | 0 |
| A-2915 | H | H | H | H | H | CH₂CH₂CH₂CF₃ | C(=O)N(CH₃)₂ | H | O | 0 |
| A-2916 | H | H | H | H | H | CH₂CF₂CH₂CF₃ | C(=O)N(CH₃)₂ | H | O | 0 |
| A-2917 | H | H | H | H | H | CF₂CF₂CF₂CF₃ | C(=O)N(CH₃)₂ | H | O | 0 |
| A-2918 | H | H | H | H | H | CH₂CH₂CH(CF₃)₂ | C(=O)N(CH₃)₂ | H | O | 0 |
| A-2919 | H | H | H | H | H | CF₂CF₂CF₂CF₂CF₃ | C(=O)N(CH₃)₂ | H | O | 0 |
| A-2920 | H | H | H | H | H | CH₂CF₂CF₂CF₂CF₃ | C(=O)N(CH₃)₂ | H | O | 0 |

TABLE 48-continued

| Compound | R¹ | R² | R³ | R⁴ | R⁵ | R⁶ | R⁷ | R⁸ | X | n |
|---|---|---|---|---|---|---|---|---|---|---|
| A-2921 | H | H | H | H | H | $CH_2CH_2CH_2CH_2CF_3$ | $C(=O)N(CH_3)_2$ | H | O | 0 |
| A-2922 | H | H | H | H | H | $CH_2CF_2CF_2CF_2CHF_2$ | $C(=O)N(CH_3)_2$ | H | O | 0 |
| A-2923 | H | H | H | H | H | $CH_2CH_2OCH_2CF_3$ | $C(=O)N(CH_3)_2$ | H | O | 0 |

TABLE 49

| Compound | R¹ | R² | R³ | R⁴ | R⁵ | R⁶ | R⁷ | R⁸ | X | n |
|---|---|---|---|---|---|---|---|---|---|---|
| A-2924 | H | H | H | H | H | $CF_2CHFOCF_3$ | $C(=O)N(CH_3)_2$ | H | O | 0 |
| A-2925 | H | H | H | H | H | $CF_2CHFOCF_2CF_3$ | $C(=O)N(CH_3)_2$ | H | O | 0 |
| A-2926 | H | H | H | H | H | $CH_2CH_2CF=CF_2$ | $C(=O)N(CH_3)_2$ | H | O | 0 |
| A-2927 | H | H | H | H | H | $CH_2CH_2CH=CF_2$ | $C(=O)N(CH_3)_2$ | H | O | 0 |
| A-2928 | H | H | H | H | H | $CH_2C\equiv CCH_3$ | $C(=O)N(CH_3)_2$ | H | O | 0 |
| A-2929 | H | H | H | H | H | $CH_2C\equiv CCF_3$ | $C(=O)N(CH_3)_2$ | H | O | 0 |
| A-2930 | H | H | H | H | H | $CH_2C\equiv CI$ | $C(=O)N(CH_3)_2$ | H | O | 0 |
| A-2931 | H | H | H | H | H | $CH_2$(2,2-difluorocyclopropyl) | $C(=O)N(CH_3)_2$ | H | O | 0 |
| A-2932 | H | H | H | H | H | $CH_2$(2,2-dichlorocyclopropyl) | $C(=O)N(CH_3)_2$ | H | O | 0 |
| A-2933 | H | H | H | H | H | $CH_2CH_2$(2,2-difluorocyclopropyl) | $C(=O)N(CH_3)_2$ | H | O | 0 |
| A-2934 | H | H | H | H | H | $CH_2CH_2$(2,2-dichlorocyclopropyl) | $C(=O)N(CH_3)_2$ | H | O | 0 |
| A-2935 | H | H | H | H | H | $CH_2SCH_3$ | $C(=O)N(CH_3)_2$ | H | O | 0 |
| A-2936 | H | H | H | H | H | $CH_2SCH_2CH_3$ | $C(=O)N(CH_3)_2$ | H | O | 0 |
| A-2937 | H | H | H | H | H | $CH_2CH_2SCH_3$ | $C(=O)N(CH_3)_2$ | H | O | 0 |
| A-2938 | H | H | H | H | H | $CH_2SOCH_3$ | $C(=O)N(CH_3)_2$ | H | O | 0 |
| A-2939 | H | H | H | H | H | $CH_2CH_2SOCH_3$ | $C(=O)N(CH_3)_2$ | H | O | 0 |
| A-2940 | H | H | H | H | H | $CH_2SO_2CH_3$ | $C(=O)N(CH_3)_2$ | H | O | 0 |
| A-2941 | H | H | H | H | H | $CH_2CH_2SO_2CH_3$ | $C(=O)N(CH_3)_2$ | H | O | 0 |
| A-2942 | H | H | H | H | H | $CH_2SCF_3$ | $C(=O)N(CH_3)_2$ | H | O | 0 |
| A-2943 | H | H | H | H | H | $CH_2SCHF_2$ | $C(=O)N(CH_3)_2$ | H | O | 0 |
| A-2944 | H | H | H | H | H | $CH_2SCH_2CF_3$ | $C(=O)N(CH_3)_2$ | H | O | 0 |
| A-2945 | H | H | H | H | H | $CH_2SCH_2CHF_2$ | $C(=O)N(CH_3)_2$ | H | O | 0 |
| A-2946 | H | H | H | H | H | $CH_2SCF_2CF_3$ | $C(=O)N(CH_3)_2$ | H | O | 0 |
| A-2947 | H | H | H | H | H | $CH_2CH_2SCF_3$ | $C(=O)N(CH_3)_2$ | H | O | 0 |
| A-2948 | H | H | H | H | H | $CH_2SOCF_3$ | $C(=O)N(CH_3)_2$ | H | O | 0 |
| A-2949 | H | H | H | H | H | $CH_2CH_2SOCF_3$ | $C(=O)N(CH_3)_2$ | H | O | 0 |
| A-2950 | H | H | H | H | H | $CH_2CH_2CH_2SOCF_3$ | $C(=O)N(CH_3)_2$ | H | O | 0 |
| A-2951 | H | H | H | H | H | $CH_2SO_2CF_3$ | $C(=O)N(CH_3)_2$ | H | O | 0 |
| A-2952 | H | H | H | H | H | $CH_2CH_2SO_2CF_3$ | $C(=O)N(CH_3)_2$ | H | O | 0 |
| A-2953 | H | H | H | H | H | $CH_2CH_2CH_2SO_2CF_3$ | $C(=O)N(CH_3)_2$ | H | O | 0 |
| A-2954 | H | H | H | H | H | $CH_2C(=O)NHCH_2CHF_2$ | $C(=O)N(CH_3)_2$ | H | O | 0 |
| A-2955 | H | H | H | H | H | $CH_2C(=O)NHCH_2CF_3$ | $C(=O)N(CH_3)_2$ | H | O | 0 |
| A-2956 | H | H | H | H | H | H | $C(=O)(4-Cl)Ph$ | H | O | 0 |
| A-2957 | H | H | H | H | H | $CH_3$ | $C(=O)(4-Cl)Ph$ | H | O | 0 |
| A-2958 | H | H | H | H | H | $CH_2CH_3$ | $C(=O)(4-Cl)Ph$ | H | O | 0 |
| A-2959 | H | H | H | H | H | $CH(CH_3)_2$ | $C(=O)(4-Cl)Ph$ | H | O | 0 |
| A-2960 | H | H | H | H | H | $CH_2CH_2CH_3$ | $C(=O)(4-Cl)Ph$ | H | O | 0 |
| A-2961 | H | H | H | H | H | $CH_2CH(CH_3)_2$ | $C(=O)(4-Cl)Ph$ | H | O | 0 |
| A-2962 | H | H | H | H | H | $CH(CH_2)CH_2CH_3$ | $C(=O)(4-Cl)Ph$ | H | O | 0 |
| A-2963 | H | H | H | H | H | $CH_2C(CH_3)_3$ | $C(=O)(4-Cl)Ph$ | H | O | 0 |
| A-2964 | H | H | H | H | H | $CH_2(CH_2)_2CH_3$ | $C(=O)(4-Cl)Ph$ | H | O | 0 |
| A-2965 | H | H | H | H | H | $CH_2(CH_2)_3CH_3$ | $C(=O)(4-Cl)Ph$ | H | O | 0 |
| A-2966 | H | H | H | H | H | $CF_3$ | $C(=O)(4-Cl)Ph$ | H | O | 0 |
| A-2967 | H | H | H | H | H | $CHF_2$ | $C(=O)(4-Cl)Ph$ | H | O | 0 |
| A-2968 | H | H | H | H | H | $CH_2CF_3$ | $C(=O)(4-Cl)Ph$ | H | O | 0 |
| A-2969 | H | H | H | H | H | $CH_2CHF_2$ | $C(=O)(4-Cl)Ph$ | H | O | 0 |
| A-2970 | H | H | H | H | H | $CH_2CClF_2$ | $C(=O)(4-Cl)Ph$ | H | O | 0 |
| A-2971 | H | H | H | H | H | $CH_2CBrF_2$ | $C(=O)(4-Cl)Ph$ | H | O | 0 |
| A-2972 | H | H | H | H | H | $CF_2CF_3$ | $C(=O)(4-Cl)Ph$ | H | O | 0 |
| A-2973 | H | H | H | H | H | $CF_2CHF_2$ | $C(=O)(4-Cl)Ph$ | H | O | 0 |
| A-2974 | H | H | H | H | H | $CH_2CH_2CF_3$ | $C(=O)(4-Cl)Ph$ | H | O | 0 |
| A-2975 | H | H | H | H | H | $CH_2CF_2CF_3$ | $C(=O)(4-Cl)Ph$ | H | O | 0 |
| A-2976 | H | H | H | H | H | $CH_2CF_2CHF_2$ | $C(=O)(4-Cl)Ph$ | H | O | 0 |
| A-2977 | H | H | H | H | H | $CF_2CHFCF_3$ | $C(=O)(4-Cl)Ph$ | H | O | 0 |
| A-2978 | H | H | H | H | H | $CF_2CF_2CF_3$ | $C(=O)(4-Cl)Ph$ | H | O | 0 |
| A-2979 | H | H | H | H | H | $CH_2CF_2CF_2CF_3$ | $C(=O)(4-Cl)Ph$ | H | O | 0 |
| A-2980 | H | H | H | H | H | $CH_2CF_2CHFCF_3$ | $C(=O)(4-Cl)Ph$ | H | O | 0 |
| A-2981 | H | H | H | H | H | $CH_2CH_2CH_2CF_3$ | $C(=O)(4-Cl)Ph$ | H | O | 0 |
| A-2982 | H | H | H | H | H | $CH_2CH_2CF_2CF_3$ | $C(=O)(4-Cl)Ph$ | H | O | 0 |
| A-2983 | H | H | H | H | H | $CF_2CF_2CF_2CF_3$ | $C(=O)(4-Cl)Ph$ | H | O | 0 |
| A-2984 | H | H | H | H | H | $CH_2CH_2CH(CF_3)_2$ | $C(=O)(4-Cl)Ph$ | H | O | 0 |

TABLE 50

| Compound | R¹ | R² | R³ | R⁴ | R⁵ | R⁶ | R⁷ | R⁸ | X | n |
|---|---|---|---|---|---|---|---|---|---|---|
| A-2985 | H | H | H | H | H | $CF_2CF_2CF_2CF_2CF_3$ | C(=O)(4-Cl)Ph | H | O | 0 |
| A-2986 | H | H | H | H | H | $CH_2CF_2CF_2CF_2CF_3$ | C(=O)(4-Cl)Ph | H | O | 0 |
| A-2987 | H | H | H | H | H | $CH_2CH_2CH_2CH_2CF_3$ | C(=O)(4-Cl)Ph | H | O | 0 |
| A-2988 | H | H | H | H | H | $CH_2CF_2CF_2CF_2CHF_2$ | C(=O)(4-Cl)Ph | H | O | 0 |
| A-2989 | H | H | H | H | H | $CH_2CH_2OCH_2CF_3$ | C(=O)(4-Cl)Ph | H | O | 0 |
| A-2990 | H | H | H | H | H | $CF_2CHFOCF_3$ | C(=O)(4-Cl)Ph | H | O | 0 |
| A-2991 | H | H | H | H | H | $CF_2CHFOCF_2CF_3$ | C(=O)(4-Cl)Ph | H | O | 0 |
| A-2992 | H | H | H | H | H | $CH_2CH_2CF=CF_2$ | C(=O)(4-Cl)Ph | H | O | 0 |
| A-2993 | H | H | H | H | H | $CH_2CH_2CH=CF_2$ | C(=O)(4-Cl)Ph | H | O | 0 |
| A-2994 | H | H | H | H | H | $CH_2C\equiv CCH_3$ | C(=O)(4-Cl)Ph | H | O | 0 |
| A-2995 | H | H | H | H | H | $CH_2C\equiv CCF_3$ | C(=O)(4-Cl)Ph | H | O | 0 |
| A-2996 | H | H | H | H | H | $CH_2C\equiv CI$ | C(=O)(4-Cl)Ph | H | O | 0 |
| A-2997 | H | H | H | H | H | $CH_2$(2,2-difluorocyclopropyl) | C(=O)(4-Cl)Ph | H | O | 0 |
| A-2998 | H | H | H | H | H | $CH_2$(2,2-dichlorocyclopropyl) | C(=O)(4-Cl)Ph | H | O | 0 |
| A-2999 | H | H | H | H | H | $CH_2CH_2$(2,2-difluorocyclopropyl) | C(=O)(4-Cl)Ph | H | O | 0 |
| A-3000 | H | H | H | H | H | $CH_2CH_2$(2,2-dichlorocyclopropyl) | C(=O)(4-Cl)Ph | H | O | 0 |
| A-3001 | H | H | H | H | H | $CH_2SCH_3$ | C(=O)(4-Cl)Ph | H | O | 0 |
| A-3002 | H | H | H | H | H | $CH_2SCH_2CH_3$ | C(=O)(4-Cl)Ph | H | O | 0 |
| A-3003 | H | H | H | H | H | $CH_2CH_2SCH_3$ | C(=O)(4-Cl)Ph | H | O | 0 |
| A-3004 | H | H | H | H | H | $CH_2SOCH_3$ | C(=O)(4-Cl)Ph | H | O | 0 |
| A-3005 | H | H | H | H | H | $CH_2CH_2SOCH_3$ | C(=O)(4-Cl)Ph | H | O | 0 |
| A-3006 | H | H | H | H | H | $CH_2SO_2CH_3$ | C(=O)(4-Cl)Ph | H | O | 0 |
| A-3007 | H | H | H | H | H | $CH_2CH_2SO_2CH_3$ | C(=O)(4-Cl)Ph | H | O | 0 |
| A-3008 | H | H | H | H | H | $CH_2SCF_3$ | C(=O)(4-Cl)Ph | H | O | 0 |
| A-3009 | H | H | H | H | H | $CH_2SCHF_2$ | C(=O)(4-Cl)Ph | H | O | 0 |
| A-3010 | H | H | H | H | H | $CH_2SCH_2CF_3$ | C(=O)(4-Cl)Ph | H | O | 0 |
| A-3011 | H | H | H | H | H | $CH_2SCH_2CHF_2$ | C(=O)(4-Cl)Ph | H | O | 0 |
| A-3012 | H | H | H | H | H | $CH_2SCF_2CF_3$ | C(=O)(4-Cl)Ph | H | O | 0 |
| A-3013 | H | H | H | H | H | $CH_2CH_2SCF_3$ | C(=O)(4-Cl)Ph | H | O | 0 |
| A-3014 | H | H | H | H | H | $CH_2SOCF_3$ | C(=O)(4-Cl)Ph | H | O | 0 |
| A-3015 | H | H | H | H | H | $CH_2CH_2SOCF_3$ | C(=O)(4-Cl)Ph | H | O | 0 |
| A-3016 | H | H | H | H | H | $CH_2CH_2CH_2SOCF_3$ | C(=O)(4-Cl)Ph | H | O | 0 |
| A-3017 | H | H | H | H | H | $CH_2SO_2CF_3$ | C(=O)(4-Cl)Ph | H | O | 0 |
| A-3018 | H | H | H | H | H | $CH_2CH_2SO_2CF_3$ | C(=O)(4-Cl)Ph | H | O | 0 |
| A-3019 | H | H | H | H | H | $CH_2CH_2CH_2SO_2CF_3$ | C(=O)(4-Cl)Ph | H | O | 0 |
| A-3020 | H | H | H | H | H | $CH_2C(=O)NHCH_2CHF_2$ | C(=O)(4-Cl)Ph | H | O | 0 |
| A-3021 | H | H | H | H | H | $CH_2C(=O)NHCH_2CF_3$ | C(=O)(4-Cl)Ph | H | O | 0 |
| A-3022 | H | H | H | H | H | H | C(=O)(2,6-$Cl_2$)pyridin-4-yl | H | O | 0 |
| A-3023 | H | H | H | H | H | $CH_3$ | C(=O)(2,6-$Cl_2$)pyridin-4-yl | H | O | 0 |
| A-3024 | H | H | H | H | H | $CH_2CH_3$ | C(=O)(2,6-$Cl_2$)pyridin-4-yl | H | O | 0 |
| A-3025 | H | H | H | H | H | $CH(CH_3)_2$ | C(=O)(2,6-$Cl_2$)pyridin-4-yl | H | O | 0 |
| A-3026 | H | H | H | H | H | $CH_2CH_2CH_3$ | C(=O)(2,6-$Cl_2$)pyridin-4-yl | H | O | 0 |
| A-3027 | H | H | H | H | H | $CH_2CH(CH_3)_2$ | C(=O)(2,6-$Cl_2$)pyridin-4-yl | H | O | 0 |
| A-3028 | H | H | H | H | H | $CH(CH_3)CH_2CH_3$ | C(=O)(2,6-$Cl_2$)pyridin-4-yl | H | O | 0 |
| A-3029 | H | H | H | H | H | $CH_2C(CH_3)_3$ | C(=O)(2,6-$Cl_2$)pyridin-4-yl | H | O | 0 |
| A-3030 | H | H | H | H | H | $CH_2(CH_2)_2CH_3$ | C(=O)(2,6-$Cl_2$)pyridin-4-yl | H | O | 0 |
| A-3031 | H | H | H | H | H | $CH_2(CH_2)_3CH_3$ | C(=O)(2,6-$Cl_2$)pyridin-4-yl | H | O | 0 |
| A-3032 | H | H | H | H | H | $CF_3$ | C(=O)(2,6-$Cl_2$)pyridin-4-yl | H | O | 0 |
| A-3033 | H | H | H | H | H | $CHF_2$ | C(=O)(2,6-$Cl_2$)pyridin-4-yl | H | O | 0 |
| A-3034 | H | H | H | H | H | $CH_2CF_3$ | C(=O)(2,6-$Cl_2$)pyridin-4-yl | H | O | 0 |
| A-3035 | H | H | H | H | H | $CH_2CHF_2$ | C(=O)(2,6-$Cl_2$)pyridin-4-yl | H | O | 0 |
| A-3036 | H | H | H | H | H | $CH_2CClF_2$ | C(=O)(2,6-$Cl_2$)pyridin-4-yl | H | O | 0 |
| A-3037 | H | H | H | H | H | $CH_2CBrF_2$ | C(=O)(2,6-$Cl_2$)pyridin-4-yl | H | O | 0 |
| A-3038 | H | H | H | H | H | $CF_2CF_3$ | C(=O)(2,6-$Cl_2$)pyridin-4-yl | H | O | 0 |
| A-3039 | H | H | H | H | H | $CF_2CHF_2$ | C(=O)(2,6-$Cl_2$)pyridin-4-yl | H | O | 0 |
| A-3040 | H | H | H | H | H | $CH_2CH_2CF_3$ | C(=O)(2,6-$Cl_2$)pyridin-4-yl | H | O | 0 |
| A-3041 | H | H | H | H | H | $CH_2CF_2CF_3$ | C(=O)(2,6-$Cl_2$)pyridin-4-yl | H | O | 0 |
| A-3042 | H | H | H | H | H | $CH_2CF_2CHF_2$ | C(=O)(2,6-$Cl_2$)pyridin-4-yl | H | O | 0 |
| A-3043 | H | H | H | H | H | $CF_2CHFCF_3$ | C(=O)(2,6-$Cl_2$)pyridin-4-yl | H | O | 0 |
| A-3044 | H | H | H | H | H | $CF_2CF_2CF_3$ | C(=O)(2,6-$Cl_2$)pyridin-4-yl | H | O | 0 |
| A-3045 | H | H | H | H | H | $CH_2CF_2CF_2CF_3$ | C(=O)(2,6-$Cl_2$)pyridin-4-yl | H | O | 0 |

TABLE 51

| Compound | R¹ | R² | R³ | R⁴ | R⁵ | R⁶ | R⁷ | R⁸ | X | n |
|---|---|---|---|---|---|---|---|---|---|---|
| A-3046 | H | H | H | H | H | $CH_2CF_2CHFCF_3$ | C(=O)(2,6-$Cl_2$)pyridin-4-yl | H | O | 0 |
| A-3047 | H | H | H | H | H | $CH_2CH_2CH_2CF_3$ | C(=O)(2,6-$Cl_2$)pyridin-4-yl | H | O | 0 |
| A-3048 | H | H | H | H | H | $CH_2CH_2CF_2CF_3$ | C(=O)(2,6-$Cl_2$)pyridin-4-yl | H | O | 0 |
| A-3049 | H | H | H | H | H | $CF_2CF_2CF_2CF_3$ | C(=O)(2,6-$Cl_2$)pyridin-4-yl | H | O | 0 |
| A-3050 | H | H | H | H | H | $CH_2CH_2CH(CF_3)_2$ | C(=O)(2,6-$Cl_2$)pyridin-4-yl | H | O | 0 |
| A-3051 | H | H | H | H | H | $CF_2CF_2CF_2CF_2CF_3$ | C(=O)(2,6-$Cl_2$)pyridin-4-yl | H | O | 0 |
| A-3052 | H | H | H | H | H | $CH_2CF_2CF_2CF_2CF_3$ | C(=O)(2,6-$Cl_2$)pyridin-4-yl | H | O | 0 |
| A-3053 | H | H | H | H | H | $CH_2CH_2CH_2CH_2CF_3$ | C(=O)(2,6-$Cl_2$)pyridin-4-yl | H | O | 0 |
| A-3054 | H | H | H | H | H | $CH_2CF_2CF_2CF_2CHF_2$ | C(=O)(2,6-$Cl_2$)pyridin-4-yl | H | O | 0 |

TABLE 51-continued

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-3055 | H | H | H | H | H | CH$_2$CH$_2$OCH$_2$CF$_3$ | C(=O)(2,6-Cl$_2$)pyridin-4-yl | H | O | 0 |
| A-3056 | H | H | H | H | H | CF$_2$CHFOCF$_3$ | C(=O)(2,6-Cl$_2$)pyridin-4-yl | H | O | 0 |
| A-3057 | H | H | H | H | H | CF$_2$CHFOCF$_2$CF$_3$ | C(=O)(2,6-Cl$_2$)pyridin-4-yl | H | O | 0 |
| A-3058 | H | H | H | H | H | CH$_2$CH$_2$CF=CF$_2$ | C(=O)(2,6-Cl$_2$)pyridin-4-yl | H | O | 0 |
| A-3059 | H | H | H | H | H | CH$_2$CH$_2$CH=CF$_2$ | C(=O)(2,6-Cl$_2$)pyridin-4-yl | H | O | 0 |
| A-3060 | H | H | H | H | H | CH$_2$C≡CCH$_3$ | C(=O)(2,6-Cl$_2$)pyridin-4-yl | H | O | 0 |
| A-3061 | H | H | H | H | H | CH$_2$C≡CCF$_3$ | C(=O)(2,6-Cl$_2$)pyridin-4-yl | H | O | 0 |
| A-3062 | H | H | H | H | H | CH$_2$C≡CI | C(=O)(2,6-Cl$_2$)pyridin-4-yl | H | O | 0 |
| A-3063 | H | H | H | H | H | CH$_2$(2,2-difluorocyclopropyl) | C(=O)(2,6-Cl$_2$)pyridin-4-yl | H | O | 0 |
| A-3064 | H | H | H | H | H | CH$_2$(2,2-dichlorocyclopropyl) | C(=O)(2,6-Cl$_2$)pyridin-4-yl | H | O | 0 |
| A-3065 | H | H | H | H | H | CH$_2$CH$_2$(2,2-difluorocyclopropyl) | C(=O)(2,6-Cl$_2$)pyridin-4-yl | H | O | 0 |
| A-3066 | H | H | H | H | H | CH$_2$CH$_2$(2,2-dichlorocyclopropyl) | C(=O)(2,6-Cl$_2$)pyridin-4-yl | H | O | 0 |
| A-3067 | H | H | H | H | H | CH$_2$SCH$_3$ | C(=O)(2,6-Cl$_2$)pyridin-4-yl | H | O | 0 |
| A-3068 | H | H | H | H | H | CH$_2$SCH$_2$CH$_3$ | C(=O)(2,6-Cl$_2$)pyridin-4-yl | H | O | 0 |
| A-3069 | H | H | H | H | H | CH$_2$CH$_2$SCH$_3$ | C(=O)(2,6-Cl$_2$)pyridin-4-yl | H | O | 0 |
| A-3070 | H | H | H | H | H | CH$_2$SOCH$_3$ | C(=O)(2,6-Cl$_2$)pyridin-4-yl | H | O | 0 |
| A-3071 | H | H | H | H | H | CH$_2$CH$_2$SOCH$_3$ | C(=O)(2,6-Cl$_2$)pyridin-4-yl | H | O | 0 |
| A-3072 | H | H | H | H | H | CH$_2$SO$_2$CH$_3$ | C(=O)(2,6-Cl$_2$)pyridin-4-yl | H | O | 0 |
| A-3073 | H | H | H | H | H | CH$_2$CH$_2$SO$_2$CH$_3$ | C(=O)(2,6-Cl$_2$)pyridin-4-yl | H | O | 0 |
| A-3074 | H | H | H | H | H | CH$_2$SCF$_3$ | C(=O)(2,6-Cl$_2$)pyridin-4-yl | H | O | 0 |
| A-3075 | H | H | H | H | H | CH$_2$SCHF$_2$ | C(=O)(2,6-Cl$_2$)pyridin-4-yl | H | O | 0 |
| A-3076 | H | H | H | H | H | CH$_2$SCH$_2$CF$_3$ | C(=O)(2,6-Cl$_2$)pyridin-4-yl | H | O | 0 |
| A-3077 | H | H | H | H | H | CH$_2$SCH$_2$CHF$_2$ | C(=O)(2,6-Cl$_2$)pyridin-4-yl | H | O | 0 |
| A-3078 | H | H | H | H | H | CH$_2$SCF$_2$CF$_3$ | C(=O)(2,6-Cl$_2$)pyridin-4-yl | H | O | 0 |
| A-3079 | H | H | H | H | H | CH$_2$CH$_2$SCF$_3$ | C(=O)(2,6-Cl$_2$)pyridin-4-yl | H | O | 0 |
| A-3080 | H | H | H | H | H | CH$_2$SOCF$_3$ | C(=O)(2,6-Cl$_2$)pyridin-4-yl | H | O | 0 |
| A-3081 | H | H | H | H | H | CH$_2$CH$_2$SOCF$_3$ | C(=O)(2,6-Cl$_2$)pyridin-4-yl | H | O | 0 |
| A-3082 | H | H | H | H | H | CH$_2$CH$_2$CH$_2$SOCF$_3$ | C(=O)(2,6-Cl$_2$)pyridin-4-yl | H | O | 0 |
| A-3083 | H | H | H | H | H | CH$_2$SO$_2$CF$_3$ | C(=O)(2,6-Cl$_2$)pyridin-4-yl | H | O | 0 |
| A-3084 | H | H | H | H | H | CH$_2$CH$_2$SO$_2$CF$_3$ | C(=O)(2,6-Cl$_2$)pyridin-4-yl | H | O | 0 |
| A-3085 | H | H | H | H | H | CH$_2$CH$_2$CH$_2$SO$_2$CF$_3$ | C(=O)(2,6-Cl$_2$)pyridin-4-yl | H | O | 0 |
| A-3086 | H | H | H | H | H | CH$_2$C(=O)NHCH$_2$CHF$_2$ | C(=O)(2,6-Cl$_2$)pyridin-4-yl | H | O | 0 |
| A-3087 | H | H | H | H | H | CH$_2$C(=O)NHCH$_2$CF$_3$ | C(=O)(2,6-Cl$_2$)pyridin-4-yl | H | O | 0 |
| A-3088 | H | H | H | H | H | H | C(=S)OCH$_3$ | H | O | 0 |
| A-3089 | H | H | H | H | H | CH$_3$ | C(=S)OCH$_3$ | H | O | 0 |
| A-3090 | H | H | H | H | H | CH$_2$CH$_3$ | C(=S)OCH$_3$ | H | O | 0 |
| A-3091 | H | H | H | H | H | CH(CH$_3$)$_2$ | C(=S)OCH$_3$ | H | O | 0 |
| A-3092 | H | H | H | H | H | CH$_2$CH$_2$CH$_3$ | C(=S)OCH$_3$ | H | O | 0 |
| A-3093 | H | H | H | H | H | CH$_2$CH(CH$_3$)$_2$ | C(=S)OCH$_3$ | H | O | 0 |
| A-3094 | H | H | H | H | H | CH(CH$_3$)CH$_2$CH$_3$ | C(=S)OCH$_3$ | H | O | 0 |
| A-3095 | H | H | H | H | H | CH$_2$C(CH$_3$)$_3$ | C(=S)OCH$_3$ | H | O | 0 |
| A-3096 | H | H | H | H | H | CH$_2$(CH$_2$)$_2$CH$_3$ | C(=S)OCH$_3$ | H | O | 0 |
| A-3097 | H | H | H | H | H | CH$_2$(CH$_2$)$_3$CH$_3$ | C(=S)OCH$_3$ | H | O | 0 |
| A-3098 | H | H | H | H | H | CF$_3$ | C(=S)OCH$_3$ | H | O | 0 |
| A-3099 | H | H | H | H | H | CHF$_2$ | C(=S)OCH$_3$ | H | O | 0 |
| A-3100 | H | H | H | H | H | CH$_2$CF$_3$ | C(=S)OCH$_3$ | H | O | 0 |
| A-3101 | H | H | H | H | H | CH$_2$CHF$_2$ | C(=S)OCH$_3$ | H | O | 0 |
| A-3102 | H | H | H | H | H | CH$_2$CClF$_2$ | C(=S)OCH$_3$ | H | O | 0 |
| A-3103 | H | H | H | H | H | CH$_2$CBrF$_2$ | C(=S)OCH$_3$ | H | O | 0 |
| A-3104 | H | H | H | H | H | CF$_2$CF$_3$ | C(=S)OCH$_3$ | H | O | 0 |
| A-3105 | H | H | H | H | H | CF$_2$CHF$_2$ | C(=S)OCH$_3$ | H | O | 0 |
| A-3106 | H | H | H | H | H | CH$_2$CH$_2$CF$_3$ | C(=S)OCH$_3$ | H | O | 0 |

TABLE 52

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-3107 | H | H | H | H | H | CH$_2$CF$_2$CF$_3$ | C(=S)OCH$_3$ | H | O | 0 |
| A-3108 | H | H | H | H | H | CH$_2$CF$_2$CHF$_2$ | C(=S)OCH$_3$ | H | O | 0 |
| A-3109 | H | H | H | H | H | CF$_2$CHFCF$_3$ | C(=S)OCH$_3$ | H | O | 0 |
| A-3110 | H | H | H | H | H | CF$_2$CF$_2$CF$_3$ | C(=S)OCH$_3$ | H | O | 0 |
| A-3111 | H | H | H | H | H | CH$_2$CF$_2$CF$_2$CF$_3$ | C(=S)OCH$_3$ | H | O | 0 |
| A-3112 | H | H | H | H | H | CH$_2$CF$_2$CHFCF$_3$ | C(=S)OCH$_3$ | H | O | 0 |
| A-3113 | H | H | H | H | H | CH$_2$CH$_2$CH$_2$CF$_3$ | C(=S)OCH$_3$ | H | O | 0 |
| A-3114 | H | H | H | H | H | CH$_2$CH$_2$CF$_2$CF$_3$ | C(=S)OCH$_3$ | H | O | 0 |
| A-3115 | H | H | H | H | H | CF$_2$CF$_2$CF$_2$CF$_3$ | C(=S)OCH$_3$ | H | O | 0 |
| A-3116 | H | H | H | H | H | CH$_2$CH$_2$CH(CF$_3$)$_2$ | C(=S)OCH$_3$ | H | O | 0 |
| A-3117 | H | H | H | H | H | CF$_2$CF$_2$CF$_2$CF$_2$CF$_3$ | C(=S)OCH$_3$ | H | O | 0 |
| A-3118 | H | H | H | H | H | CH$_2$CF$_2$CF$_2$CF$_2$CF$_3$ | C(=S)OCH$_3$ | H | O | 0 |
| A-3119 | H | H | H | H | H | CH$_2$CH$_2$CH$_2$CH$_2$CF$_3$ | C(=S)OCH$_3$ | H | O | 0 |
| A-3120 | H | H | H | H | H | CH$_2$CF$_2$CF$_2$CF$_2$CHF$_2$ | C(=S)OCH$_3$ | H | O | 0 |
| A-3121 | H | H | H | H | H | CH$_2$CH$_2$OCH$_2$CF$_3$ | C(=S)OCH$_3$ | H | O | 0 |
| A-3122 | H | H | H | H | H | CF$_2$CHFOCF$_3$ | C(=S)OCH$_3$ | H | O | 0 |
| A-3123 | H | H | H | H | H | CF$_2$CHFOCF$_2$CF$_3$ | C(=S)OCH$_3$ | H | O | 0 |
| A-3124 | H | H | H | H | H | CH$_2$CH$_2$CF=CF$_2$ | C(=S)OCH$_3$ | H | O | 0 |

TABLE 52-continued

| Compound | R¹ | R² | R³ | R⁴ | R⁵ | R⁶ | R⁷ | R⁸ | X | n |
|---|---|---|---|---|---|---|---|---|---|---|
| A-3125 | H | H | H | H | H | CH$_2$CH$_2$CH=CF$_2$ | C(=S)OCH$_3$ | H | O | 0 |
| A-3126 | H | H | H | H | H | CH$_2$C≡CCH$_3$ | C(=S)OCH$_3$ | H | O | 0 |
| A-3127 | H | H | H | H | H | CH$_2$C≡CCF$_3$ | C(=S)OCH$_3$ | H | O | 0 |
| A-3128 | H | H | H | H | H | CH$_2$C≡CI | C(=S)OCH$_3$ | H | O | 0 |
| A-3129 | H | H | H | H | H | CH$_2$(2,2-difluorocyclopropyl) | C(=S)OCH$_3$ | H | O | 0 |
| A-3130 | H | H | H | H | H | CH$_2$(2,2-dichlorocyclopropyl) | C(=S)OCH$_3$ | H | O | 0 |
| A-3131 | H | H | H | H | H | CH$_2$CH$_2$(2,2-difluorocyclopropyl) | C(=S)OCH$_3$ | H | O | 0 |
| A-3132 | H | H | H | H | H | CH$_2$CH$_2$(2,2-dichlorocyclopropyl) | C(=S)OCH$_3$ | H | O | 0 |
| A-3133 | H | H | H | H | H | CH$_2$SCH$_3$ | C(=S)OCH$_3$ | H | O | 0 |
| A-3134 | H | H | H | H | H | CH$_2$SCH$_2$CH$_3$ | C(=S)OCH$_3$ | H | O | 0 |
| A-3135 | H | H | H | H | H | CH$_2$CH$_2$SCH$_3$ | C(=S)OCH$_3$ | H | O | 0 |
| A-3136 | H | H | H | H | H | CH$_2$SOCH$_3$ | C(=S)OCH$_3$ | H | O | 0 |
| A-3137 | H | H | H | H | H | CH$_2$CH$_2$SOCH$_3$ | C(=S)OCH$_3$ | H | O | 0 |
| A-3138 | H | H | H | H | H | CH$_2$SO$_2$CH$_3$ | C(=S)OCH$_3$ | H | O | 0 |
| A-3139 | H | H | H | H | H | CH$_2$CH$_2$SO$_2$CH$_3$ | C(=S)OCH$_3$ | H | O | 0 |
| A-3140 | H | H | H | H | H | CH$_2$SCF$_3$ | C(=S)OCH$_3$ | H | O | 0 |
| A-3141 | H | H | H | H | H | CH$_2$SCHF$_2$ | C(=S)OCH$_3$ | H | O | 0 |
| A-3142 | H | H | H | H | H | CH$_2$SCH$_2$CF$_3$ | C(=S)OCH$_3$ | H | O | 0 |
| A-3143 | H | H | H | H | H | CH$_2$SCH$_2$CHF$_2$ | C(=S)OCH$_3$ | H | O | 0 |
| A-3144 | H | H | H | H | H | CH$_2$SCF$_2$CF$_3$ | C(=S)OCH$_3$ | H | O | 0 |
| A-3145 | H | H | H | H | H | CH$_2$CH$_2$SCF$_3$ | C(=S)OCH$_3$ | H | O | 0 |
| A-3146 | H | H | H | H | H | CH$_2$SOCF$_3$ | C(=S)OCH$_3$ | H | O | 0 |
| A-3147 | H | H | H | H | H | CH$_2$CH$_2$SOCF$_3$ | C(=S)OCH$_3$ | H | O | 0 |
| A-3148 | H | H | H | H | H | CH$_2$CH$_2$CH$_2$SOCF$_3$ | C(=S)OCH$_3$ | H | O | 0 |
| A-3149 | H | H | H | H | H | CH$_2$SO$_2$CF$_3$ | C(=S)OCH$_3$ | H | O | 0 |
| A-3150 | H | H | H | H | H | CH$_2$CH$_2$SO$_2$CF$_3$ | C(=S)OCH$_3$ | H | O | 0 |
| A-3151 | H | H | H | H | H | CH$_2$CH$_2$CH$_2$SO$_2$CF$_3$ | C(=S)OCH$_3$ | H | O | 0 |
| A-3152 | H | H | H | H | H | CH$_2$C(=O)NHCH$_2$CHF$_2$ | C(=S)OCH$_3$ | H | O | 0 |
| A-3153 | H | H | H | H | H | CH$_2$C(=O)NHCH$_2$CF$_3$ | C(=S)OCH$_3$ | H | O | 0 |
| A-3154 | H | H | H | H | H | H | C(=S)N(CH$_3$)$_2$ | H | O | 0 |
| A-3155 | H | H | H | H | H | CH$_3$ | C(=S)N(CH$_3$)$_2$ | H | O | 0 |
| A-3156 | H | H | H | H | H | CH$_2$CH$_3$ | C(=S)N(CH$_3$)$_2$ | H | O | 0 |
| A-3157 | H | H | H | H | H | CH(CH$_3$)$_2$ | C(=S)N(CH$_3$)$_2$ | H | O | 0 |
| A-3158 | H | H | H | H | H | CH$_2$CH$_2$CH$_3$ | C(=S)N(CH$_3$)$_2$ | H | O | 0 |
| A-3159 | H | H | H | H | H | CH$_2$CH(CH$_3$)$_2$ | C(=S)N(CH$_3$)$_2$ | H | O | 0 |
| A-3160 | H | H | H | H | H | CH(CH$_3$)CH$_2$CH$_3$ | C(=S)N(CH$_3$)$_2$ | H | O | 0 |
| A-3161 | H | H | H | H | H | CH$_2$C(CH$_3$)$_3$ | C(=S)N(CH$_3$)$_2$ | H | O | 0 |
| A-3162 | H | H | H | H | H | CH$_2$(CH$_2$)$_2$CH$_3$ | C(=S)N(CH$_3$)$_2$ | H | O | 0 |
| A-3163 | H | H | H | H | H | CH$_2$(CH$_2$)$_3$CH$_3$ | C(=S)N(CH$_3$)$_2$ | H | O | 0 |
| A-3164 | H | H | H | H | H | CF$_3$ | C(=S)N(CH$_3$)$_2$ | H | O | 0 |
| A-3165 | H | H | H | H | H | CHF$_2$ | C(=S)N(CH$_3$)$_2$ | H | O | 0 |
| A-3166 | H | H | H | H | H | CH$_2$CF$_3$ | C(=S)N(CH$_3$)$_2$ | H | O | 0 |
| A-3167 | H | H | H | H | H | CH$_2$CHF$_2$ | C(=S)N(CH$_3$)$_2$ | H | O | 0 |

TABLE 53

| Compound | R¹ | R² | R³ | R⁴ | R⁵ | R⁶ | R⁷ | R⁸ | X | n |
|---|---|---|---|---|---|---|---|---|---|---|
| A-3168 | H | H | H | H | H | CH$_2$CClF$_2$ | C(=S)N(CH$_3$)$_2$ | H | O | 0 |
| A-3169 | H | H | H | H | H | CH$_2$CBrF$_2$ | C(=S)N(CH$_3$)$_2$ | H | O | 0 |
| A-3170 | H | H | H | H | H | CF$_2$CF$_3$ | C(=S)N(CH$_3$)$_2$ | H | O | 0 |
| A-3171 | H | H | H | H | H | CF$_2$CHF$_2$ | C(=S)N(CH$_3$)$_2$ | H | O | 0 |
| A-3172 | H | H | H | H | H | CH$_2$CH$_2$CF$_3$ | C(=S)N(CH$_3$)$_2$ | H | O | 0 |
| A-3173 | H | H | H | H | H | CH$_2$CF$_2$CF$_3$ | C(=S)N(CH$_3$)$_2$ | H | O | 0 |
| A-3174 | H | H | H | H | H | CH$_2$CF$_2$CHF$_2$ | C(=S)N(CH$_3$)$_2$ | H | O | 0 |
| A-3175 | H | H | H | H | H | CF$_2$CHFCF$_3$ | C(=S)N(CH$_3$)$_2$ | H | O | 0 |
| A-3176 | H | H | H | H | H | CF$_2$CF$_2$CF$_3$ | C(=S)N(CH$_3$)$_2$ | H | O | 0 |
| A-3177 | H | H | H | H | H | CH$_2$CF$_2$CF$_2$CF$_3$ | C(=S)N(CH$_3$)$_2$ | H | O | 0 |
| A-3178 | H | H | H | H | H | CH$_2$CF$_2$CHFCF$_3$ | C(=S)N(CH$_3$)$_2$ | H | O | 0 |
| A-3179 | H | H | H | H | H | CH$_2$CH$_2$CH$_2$CF$_3$ | C(=S)N(CH$_3$)$_2$ | H | O | 0 |
| A-3180 | H | H | H | H | H | CH$_2$CH$_2$CF$_2$CF$_3$ | C(=S)N(CH$_3$)$_2$ | H | O | 0 |
| A-3181 | H | H | H | H | H | CF$_2$CF$_2$CF$_2$CF$_3$ | C(=S)N(CH$_3$)$_2$ | H | O | 0 |
| A-3182 | H | H | H | H | H | CH$_2$CH$_2$CH(CF$_3$)$_2$ | C(=S)N(CH$_3$)$_2$ | H | O | 0 |
| A-3183 | H | H | H | H | H | CF$_2$CF$_2$CF$_2$CF$_2$CF$_3$ | C(=S)N(CH$_3$)$_2$ | H | O | 0 |
| A-3184 | H | H | H | H | H | CH$_2$CF$_2$CF$_2$CF$_2$CF$_3$ | C(=S)N(CH$_3$)$_2$ | H | O | 0 |
| A-3185 | H | H | H | H | H | CH$_2$CH$_2$CH$_2$CH$_2$CF$_3$ | C(=S)N(CH$_3$)$_2$ | H | O | 0 |
| A-3186 | H | H | H | H | H | CH$_2$CF$_2$CF$_2$CF$_2$CHF$_2$ | C(=S)N(CH$_3$)$_2$ | H | O | 0 |
| A-3187 | H | H | H | H | H | CH$_2$CH$_2$OCH$_2$CF$_3$ | C(=S)N(CH$_3$)$_2$ | H | O | 0 |
| A-3188 | H | H | H | H | H | CF$_2$CHFOCF$_3$ | C(=S)N(CH$_3$)$_2$ | H | O | 0 |
| A-3189 | H | H | H | H | H | CF$_2$CHFOCF$_2$CF$_3$ | C(=S)N(CH$_3$)$_2$ | H | O | 0 |
| A-3190 | H | H | H | H | H | CH$_2$CH$_2$CF=CF$_2$ | C(=S)N(CH$_3$)$_2$ | H | O | 0 |
| A-3191 | H | H | H | H | H | CH$_2$CH$_2$CH=CF$_2$ | C(=S)N(CH$_3$)$_2$ | H | O | 0 |
| A-3192 | H | H | H | H | H | CH$_2$C≡CCH$_3$ | C(=S)N(CH$_3$)$_2$ | H | O | 0 |
| A-3193 | H | H | H | H | H | CH$_2$C≡CCF$_3$ | C(=S)N(CH$_3$)$_2$ | H | O | 0 |
| A-3194 | H | H | H | H | H | CH$_2$C≡CI | C(=S)N(CH$_3$)$_2$ | H | O | 0 |

TABLE 53-continued

| Compound | R¹ | R² | R³ | R⁴ | R⁵ | R⁶ | R⁷ | R⁸ | X | n |
|---|---|---|---|---|---|---|---|---|---|---|
| A-3195 | H | H | H | H | H | CH$_2$(2,2-difluorocyclopropyl) | C(=S)N(CH$_3$)$_2$ | H | O | 0 |
| A-3196 | H | H | H | H | H | CH$_2$(2,2-dichlorocyclopropyl) | C(=S)N(CH$_3$)$_2$ | H | O | 0 |
| A-3197 | H | H | H | H | H | CH$_2$CH$_2$(2,2-difluorocyclopropyl) | C(=S)N(CH$_3$)$_2$ | H | O | 0 |
| A-3198 | H | H | H | H | H | CH$_2$CH$_2$(2,2-dichlorocyclopropyl) | C(=S)N(CH$_3$)$_2$ | H | O | 0 |
| A-3199 | H | H | H | H | H | CH$_2$SCH$_3$ | C(=S)N(CH$_3$)$_2$ | H | O | 0 |
| A-3200 | H | H | H | H | H | CH$_2$SCH$_2$CH$_3$ | C(=S)N(CH$_3$)$_2$ | H | O | 0 |
| A-3201 | H | H | H | H | H | CH$_2$CH$_2$SCH$_3$ | C(=S)N(CH$_3$)$_2$ | H | O | 0 |
| A-3202 | H | H | H | H | H | CH$_2$SOCH$_3$ | C(=S)N(CH$_3$)$_2$ | H | O | 0 |
| A-3203 | H | H | H | H | H | CH$_2$CH$_2$SOCH$_3$ | C(=S)N(CH$_3$)$_2$ | H | O | 0 |
| A-3204 | H | H | H | H | H | CH$_2$SO$_2$CH$_3$ | C(=S)N(CH$_3$)$_2$ | H | O | 0 |
| A-3205 | H | H | H | H | H | CH$_2$CH$_2$SO$_2$CH$_3$ | C(=S)N(CH$_3$)$_2$ | H | O | 0 |
| A-3206 | H | H | H | H | H | CH$_2$SCF$_3$ | C(=S)N(CH$_3$)$_2$ | H | O | 0 |
| A-3207 | H | H | H | H | H | CH$_2$SCHF$_2$ | C(=S)N(CH$_3$)$_2$ | H | O | 0 |
| A-3208 | H | H | H | H | H | CH$_2$SCH$_2$CF$_3$ | C(=S)N(CH$_3$)$_2$ | H | O | 0 |
| A-3209 | H | H | H | H | H | CH$_2$SCH$_2$CHF$_2$ | C(=S)N(CH$_3$)$_2$ | H | O | 0 |
| A-3210 | H | H | H | H | H | CH$_2$SCF$_2$CF$_3$ | C(=S)N(CH$_3$)$_2$ | H | O | 0 |
| A-3211 | H | H | H | H | H | CH$_2$CH$_2$SCF$_3$ | C(=S)N(CH$_3$)$_2$ | H | O | 0 |
| A-3212 | H | H | H | H | H | CH$_2$SOCF$_3$ | C(=S)N(CH$_3$)$_2$ | H | O | 0 |
| A-3213 | H | H | H | H | H | CH$_2$CH$_2$SOCF$_3$ | C(=S)N(CH$_3$)$_2$ | H | O | 0 |
| A-3214 | H | H | H | H | H | CH$_2$CH$_2$CH$_2$SOCF$_3$ | C(=S)N(CH$_3$)$_2$ | H | O | 0 |
| A-3215 | H | H | H | H | H | CH$_2$SO$_2$CF$_3$ | C(=S)N(CH$_3$)$_2$ | H | O | 0 |
| A-3216 | H | H | H | H | H | CH$_2$CH$_2$SO$_2$CF$_3$ | C(=S)N(CH$_3$)$_2$ | H | O | 0 |
| A-3217 | H | H | H | H | H | CH$_2$CH$_2$CH$_2$SO$_2$CF$_3$ | C(=S)N(CH$_3$)$_2$ | H | O | 0 |
| A-3218 | H | H | H | H | H | CH$_2$C(=O)NHCH$_2$CHF$_2$ | C(=S)N(CH$_3$)$_2$ | H | O | 0 |
| A-3219 | H | H | H | H | H | CH$_2$C(=O)NHCH$_2$CF$_3$ | C(=S)N(CH$_3$)$_2$ | H | O | 0 |
| A-3220 | H | H | H | H | H | H | S(=O)$_2$CH$_3$ | H | O | 0 |
| A-3221 | H | H | H | H | H | CH$_3$ | S(=O)$_2$CH$_3$ | H | O | 0 |
| A-3222 | H | H | H | H | H | CH$_2$CH$_3$ | S(=O)$_2$CH$_3$ | H | O | 0 |
| A-3223 | H | H | H | H | H | CH(CH$_3$)$_2$ | S(=O)$_2$CH$_3$ | H | O | 0 |
| A-3224 | H | H | H | H | H | CH$_2$CH$_2$CH$_3$ | S(=O)$_2$CH$_3$ | H | O | 0 |
| A-3225 | H | H | H | H | H | CH$_2$CH(CH$_3$)$_2$ | S(=O)$_2$CH$_3$ | H | O | 0 |
| A-3226 | H | H | H | H | H | CH(CH$_3$)CH$_2$CH$_3$ | S(=O)$_2$CH$_3$ | H | O | 0 |
| A-3227 | H | H | H | H | H | CH$_2$C(CH$_3$)$_3$ | S(=O)$_2$CH$_3$ | H | O | 0 |
| A-3228 | H | H | H | H | H | CH$_2$(CH$_2$)$_2$CH$_3$ | S(=O)$_2$CH$_3$ | H | O | 0 |

TABLE 54

| Compound | R¹ | R² | R³ | R⁴ | R⁵ | R⁶ | R⁷ | R⁸ | X | n |
|---|---|---|---|---|---|---|---|---|---|---|
| A-3229 | H | H | H | H | H | CH$_2$(CH$_2$)$_3$CH$_3$ | S(=O)$_2$CH$_3$ | H | O | 0 |
| A-3230 | H | H | H | H | H | CF$_3$ | S(=O)$_2$CH$_3$ | H | O | 0 |
| A-3231 | H | H | H | H | H | CHF$_2$ | S(=O)$_2$CH$_3$ | H | O | 0 |
| A-3232 | H | H | H | H | H | CH$_2$CF$_3$ | S(=O)$_2$CH$_3$ | H | O | 0 |
| A-3233 | H | H | H | H | H | CH$_2$CHF$_2$ | S(=O)$_2$CH$_3$ | H | O | 0 |
| A-3234 | H | H | H | H | H | CH$_2$CClF$_2$ | S(=O)$_2$CH$_3$ | H | O | 0 |
| A-3235 | H | H | H | H | H | CH$_2$CBrF$_2$ | S(=O)$_2$CH$_3$ | H | O | 0 |
| A-3236 | H | H | H | H | H | CF$_2$CF$_3$ | S(=O)$_2$CH$_3$ | H | O | 0 |
| A-3237 | H | H | H | H | H | CF$_2$CHF$_2$ | S(=O)$_2$CH$_3$ | H | O | 0 |
| A-3238 | H | H | H | H | H | CH$_2$CH$_2$CF$_3$ | S(=O)$_2$CH$_3$ | H | O | 0 |
| A-3239 | H | H | H | H | H | CH$_2$CF$_2$CF$_3$ | S(=O)$_2$CH$_3$ | H | O | 0 |
| A-3240 | H | H | H | H | H | CH$_2$CF$_2$CHF$_2$ | S(=O)$_2$CH$_3$ | H | O | 0 |
| A-3241 | H | H | H | H | H | CF$_2$CHFCF$_3$ | S(=O)$_2$CH$_3$ | H | O | 0 |
| A-3242 | H | H | H | H | H | CF$_2$CF$_2$CF$_3$ | S(=O)$_2$CH$_3$ | H | O | 0 |
| A-3243 | H | H | H | H | H | CH$_2$CF$_2$CF$_2$CF$_3$ | S(=O)$_2$CH$_3$ | H | O | 0 |
| A-3244 | H | H | H | H | H | CH$_2$CF$_2$CHFCF$_3$ | S(=O)$_2$CH$_3$ | H | O | 0 |
| A-3245 | H | H | H | H | H | CH$_2$CH$_2$CH$_2$CF$_3$ | S(=O)$_2$CH$_3$ | H | O | 0 |
| A-3246 | H | H | H | H | H | CH$_2$CH$_2$CF$_2$CF$_3$ | S(=O)$_2$CH$_3$ | H | O | 0 |
| A-3247 | H | H | H | H | H | CF$_2$CF$_2$CF$_2$CF$_3$ | S(=O)$_2$CH$_3$ | H | O | 0 |
| A-3248 | H | H | H | H | H | CH$_2$CH$_2$CH(CF$_3$)$_2$ | S(=O)$_2$CH$_3$ | H | O | 0 |
| A-3249 | H | H | H | H | H | CF$_2$CF$_2$CF$_2$CF$_2$CF$_3$ | S(=O)$_2$CH$_3$ | H | O | 0 |
| A-3250 | H | H | H | H | H | CH$_2$CF$_2$CF$_2$CF$_2$CF$_3$ | S(=O)$_2$CH$_3$ | H | O | 0 |
| A-3251 | H | H | H | H | H | CH$_2$CH$_2$CH$_2$CH$_2$CF$_3$ | S(=O)$_2$CH$_3$ | H | O | 0 |
| A-3252 | H | H | H | H | H | CH$_2$CF$_2$CF$_2$CF$_2$CHF$_2$ | S(=O)$_2$CH$_3$ | H | O | 0 |
| A-3253 | H | H | H | H | H | CH$_2$CH$_2$OCH$_2$CF$_3$ | S(=O)$_2$CH$_3$ | H | O | 0 |
| A-3254 | H | H | H | H | H | CF$_2$CHFOCF$_3$ | S(=O)$_2$CH$_3$ | H | O | 0 |
| A-3255 | H | H | H | H | H | CF$_2$CHFOCF$_2$CF$_3$ | S(=O)$_2$CH$_3$ | H | O | 0 |
| A-3256 | H | H | H | H | H | CH$_2$CH$_2$CF=CF$_2$ | S(=O)$_2$CH$_3$ | H | O | 0 |
| A-3257 | H | H | H | H | H | CH$_2$CH$_2$CH=CF$_2$ | S(=O)$_2$CH$_3$ | H | O | 0 |
| A-3258 | H | H | H | H | H | CH$_2$C≡CCH$_3$ | S(=O)$_2$CH$_3$ | H | O | 0 |
| A-3259 | H | H | H | H | H | CH$_2$C≡CCF$_3$ | S(=O)$_2$CH$_3$ | H | O | 0 |
| A-3260 | H | H | H | H | H | CH$_2$C≡CI | S(=O)$_2$CH$_3$ | H | O | 0 |
| A-3261 | H | H | H | H | H | CH$_2$(2,2-difluorocyclopropyl) | S(=O)$_2$CH$_3$ | H | O | 0 |
| A-3262 | H | H | H | H | H | CH$_2$(2,2-dichlorocyclopropyl) | S(=O)$_2$CH$_3$ | H | O | 0 |
| A-3263 | H | H | H | H | H | CH$_2$CH$_2$(2,2-difluorocyclopropyl) | S(=O)$_2$CH$_3$ | H | O | 0 |
| A-3264 | H | H | H | H | H | CH$_2$CH$_2$(2,2-dichlorocyclopropyl) | S(=O)$_2$CH$_3$ | H | O | 0 |

TABLE 54-continued

| Compound | R¹ | R² | R³ | R⁴ | R⁵ | R⁶ | R⁷ | R⁸ | X | n |
|---|---|---|---|---|---|---|---|---|---|---|
| A-3265 | H | H | H | H | H | $CH_2SCH_3$ | $S(=O)_2CH_3$ | H | O | 0 |
| A-3266 | H | H | H | H | H | $CH_2SCH_2CH_3$ | $S(=O)_2CH_3$ | H | O | 0 |
| A-3267 | H | H | H | H | H | $CH_2CH_2SCH_3$ | $S(=O)_2CH_3$ | H | O | 0 |
| A-3268 | H | H | H | H | H | $CH_2SOCH_3$ | $S(=O)_2CH_3$ | H | O | 0 |
| A-3269 | H | H | H | H | H | $CH_2CH_2SOCH_3$ | $S(=O)_2CH_3$ | H | O | 0 |
| A-3270 | H | H | H | H | H | $CH_2SO_2CH_3$ | $S(=O)_2CH_3$ | H | O | 0 |
| A-3271 | H | H | H | H | H | $CH_2CH_2SO_2CH_3$ | $S(=O)_2CH_3$ | H | O | 0 |
| A-3272 | H | H | H | H | H | $CH_2SCF_3$ | $S(=O)_2CH_3$ | H | O | 0 |
| A-3273 | H | H | H | H | H | $CH_2SCHF_2$ | $S(=O)_2CH_3$ | H | O | 0 |
| A-3274 | H | H | H | H | H | $CH_2SCH_2CF_3$ | $S(=O)_2CH_3$ | H | O | 0 |
| A-3275 | H | H | H | H | H | $CH_2SCH_2CHF_2$ | $S(=O)_2CH_3$ | H | O | 0 |
| A-3276 | H | H | H | H | H | $CH_2SCF_2CF_3$ | $S(=O)_2CH_3$ | H | O | 0 |
| A-3277 | H | H | H | H | H | $CH_2CH_2SCF_3$ | $S(=O)_2CH_3$ | H | O | 0 |
| A-3278 | H | H | H | H | H | $CH_2SOCF_3$ | $S(=O)_2CH_3$ | H | O | 0 |
| A-3279 | H | H | H | H | H | $CH_2CH_2SOCF_3$ | $S(=O)_2CH_3$ | H | O | 0 |
| A-3280 | H | H | H | H | H | $CH_2CH_2CH_2SOCF_3$ | $S(=O)_2CH_3$ | H | O | 0 |
| A-3281 | H | H | H | H | H | $CH_2SO_2CF_3$ | $S(=O)_2CH_3$ | H | O | 0 |
| A-3282 | H | H | H | H | H | $CH_2CH_2SO_2CF_3$ | $S(=O)_2CH_3$ | H | O | 0 |
| A-3283 | H | H | H | H | H | $CH_2CH_2CH_2SO_2CF_3$ | $S(=O)_2CH_3$ | H | O | 0 |
| A-3284 | H | H | H | H | H | $CH_2C(=O)NHCH_2CHF_2$ | $S(=O)_2CH_3$ | H | O | 0 |
| A-3285 | H | H | H | H | H | $CH_2C(=O)NHCH_2CF_3$ | $S(=O)_2CH_3$ | H | O | 0 |
| A-3286 | H | H | H | H | H | H | $S(=O)_2N(CH_3)_2$ | H | O | 0 |
| A-3287 | H | H | H | H | H | $CH_3$ | $S(=O)_2N(CH_3)_2$ | H | O | 0 |
| A-3288 | H | H | H | H | H | $CH_2CH_3$ | $S(=O)_2N(CH_3)_2$ | H | O | 0 |
| A-3289 | H | H | H | H | H | $CH(CH_3)_2$ | $S(=O)_2N(CH_3)_2$ | H | O | 0 |

TABLE 55

| Compound | R¹ | R² | R³ | R⁴ | R⁵ | R⁶ | R⁷ | R⁸ | X | n |
|---|---|---|---|---|---|---|---|---|---|---|
| A-3290 | H | H | H | H | H | $CH_2CH_2CH_3$ | $S(=O)_2N(CH_3)_2$ | H | O | 0 |
| A-3291 | H | H | H | H | H | $CH_2CH(CH_3)_2$ | $S(=O)_2N(CH_3)_2$ | H | O | 0 |
| A-3292 | H | H | H | H | H | $CH(CH_3)CH_2CH_3$ | $S(=O)_2N(CH_3)_2$ | H | O | 0 |
| A-3293 | H | H | H | H | H | $CH_2C(CH_3)_3$ | $S(=O)_2N(CH_3)_2$ | H | O | 0 |
| A-3294 | H | H | H | H | H | $CH_2(CH_2)_2CH_3$ | $S(=O)_2N(CH_3)_2$ | H | O | 0 |
| A-3295 | H | H | H | H | H | $CH_2(CH_2)_3CH_3$ | $S(=O)_2N(CH_3)_2$ | H | O | 0 |
| A-3296 | H | H | H | H | H | $CF_3$ | $S(=O)_2N(CH_3)_2$ | H | O | 0 |
| A-3297 | H | H | H | H | H | $CHF_2$ | $S(=O)_2N(CH_3)_2$ | H | O | 0 |
| A-3298 | H | H | H | H | H | $CH_2CF_3$ | $S(=O)_2N(CH_3)_2$ | H | O | 0 |
| A-3299 | H | H | H | H | H | $CH_2CHF_2$ | $S(=O)_2N(CH_3)_2$ | H | O | 0 |
| A-3300 | H | H | H | H | H | $CH_2CClF_2$ | $S(=O)_2N(CH_3)_2$ | H | O | 0 |
| A-3301 | H | H | H | H | H | $CH_2CBrF_2$ | $S(=O)_2N(CH_3)_2$ | H | O | 0 |
| A-3302 | H | H | H | H | H | $CF_2CF_3$ | $S(=O)_2N(CH_3)_2$ | H | O | 0 |
| A-3303 | H | H | H | H | H | $CF_2CHF_2$ | $S(=O)_2N(CH_3)_2$ | H | O | 0 |
| A-3304 | H | H | H | H | H | $CH_2CH_2CF_3$ | $S(=O)_2N(CH_3)_2$ | H | O | 0 |
| A-3305 | H | H | H | H | H | $CH_2CF_2CF_3$ | $S(=O)_2N(CH_3)_2$ | H | O | 0 |
| A-3306 | H | H | H | H | H | $CH_2CF_2CHF_2$ | $S(=O)_2N(CH_3)_2$ | H | O | 0 |
| A-3307 | H | H | H | H | H | $CF_2CHFCF_3$ | $S(=O)_2N(CH_3)_2$ | H | O | 0 |
| A-3308 | H | H | H | H | H | $CF_2CF_2CF_3$ | $S(=O)_2N(CH_3)_2$ | H | O | 0 |
| A-3309 | H | H | H | H | H | $CH_2CF_2CF_2CF_3$ | $S(=O)_2N(CH_3)_2$ | H | O | 0 |
| A-3310 | H | H | H | H | H | $CH_2CF_2CHFCF_3$ | $S(=O)_2N(CH_3)_2$ | H | O | 0 |
| A-3311 | H | H | H | H | H | $CH_2CH_2CH_2CF_3$ | $S(=O)_2N(CH_3)_2$ | H | O | 0 |
| A-3312 | H | H | H | H | H | $CH_2CH_2CF_2CF_3$ | $S(=O)_2N(CH_3)_2$ | H | O | 0 |
| A-3313 | H | H | H | H | H | $CF_2CF_2CF_2CF_3$ | $S(=O)_2N(CH_3)_2$ | H | O | 0 |
| A-3314 | H | H | H | H | H | $CH_2CH_2CH(CF_3)_2$ | $S(=O)_2N(CH_3)_2$ | H | O | 0 |
| A-3315 | H | H | H | H | H | $CF_2CF_2CF_2CF_2CF_3$ | $S(=O)_2N(CH_3)_2$ | H | O | 0 |
| A-3316 | H | H | H | H | H | $CH_2CF_2CF_2CF_2CF_3$ | $S(=O)_2N(CH_3)_2$ | H | O | 0 |
| A-3317 | H | H | H | H | H | $CH_2CH_2CH_2CH_2CF_3$ | $S(=O)_2N(CH_3)_2$ | H | O | 0 |
| A-3318 | H | H | H | H | H | $CH_2CF_2CF_2CF_2CHF_2$ | $S(=O)_2N(CH_3)_2$ | H | O | 0 |
| A-3319 | H | H | H | H | H | $CH_2CH_2OCH_2CF_3$ | $S(=O)_2N(CH_3)_2$ | H | O | 0 |
| A-3320 | H | H | H | H | H | $CF_2CHFOCF_3$ | $S(=O)_2N(CH_3)_2$ | H | O | 0 |
| A-3321 | H | H | H | H | H | $CF_2CHFOCF_2CF_3$ | $S(=O)_2N(CH_3)_2$ | H | O | 0 |
| A-3322 | H | H | H | H | H | $CH_2CH_2CF=CF_2$ | $S(=O)_2N(CH_3)_2$ | H | O | 0 |
| A-3323 | H | H | H | H | H | $CH_2CH_2CH=CF_2$ | $S(=O)_2N(CH_3)_2$ | H | O | 0 |
| A-3324 | H | H | H | H | H | $CH_2C\equiv CCH_3$ | $S(=O)_2N(CH_3)_2$ | H | O | 0 |
| A-3325 | H | H | H | H | H | $CH_2C\equiv CCF_3$ | $S(=O)_2N(CH_3)_2$ | H | O | 0 |
| A-3326 | H | H | H | H | H | $CH_2C\equiv CI$ | $S(=O)_2N(CH_3)_2$ | H | O | 0 |
| A-3327 | H | H | H | H | H | $CH_2$(2,2-difluorocyclopropyl) | $S(=O)_2N(CH_3)_2$ | H | O | 0 |
| A-3328 | H | H | H | H | H | $CH_2$(2,2-dichlorocyclopropyl) | $S(=O)_2N(CH_3)_2$ | H | O | 0 |
| A-3329 | H | H | H | H | H | $CH_2CH_2$(2,2-difluorocyclopropyl) | $S(=O)_2N(CH_3)_2$ | H | O | 0 |
| A-3330 | H | H | H | H | H | $CH_2CH_2$(2,2-dichlorocyclopropyl) | $S(=O)_2N(CH_3)_2$ | H | O | 0 |

TABLE 55-continued

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-3331 | H | H | H | H | H | $CH_2SCH_3$ | $S(=O)_2N(CH_3)_2$ | H | O | 0 |
| A-3332 | H | H | H | H | H | $CH_2SCH_2CH_3$ | $S(=O)_2N(CH_3)_2$ | H | O | 0 |
| A-3333 | H | H | H | H | H | $CH_2CH_2SCH_3$ | $S(=O)_2N(CH_3)_2$ | H | O | 0 |
| A-3334 | H | H | H | H | H | $CH_2SOCH_3$ | $S(=O)_2N(CH_3)_2$ | H | O | 0 |
| A-3335 | H | H | H | H | H | $CH_2CH_2SOCH_3$ | $S(=O)_2N(CH_3)_2$ | H | O | 0 |
| A-3336 | H | H | H | H | H | $CH_2SO_2CH_3$ | $S(=O)_2N(CH_3)_2$ | H | O | 0 |
| A-3337 | H | H | H | H | H | $CH_2CH_2SO_2CH_3$ | $S(=O)_2N(CH_3)_2$ | H | O | 0 |
| A-3338 | H | H | H | H | H | $CH_2SCF_3$ | $S(=O)_2N(CH_3)_2$ | H | O | 0 |
| A-3339 | H | H | H | H | H | $CH_2SCHF_2$ | $S(=O)_2N(CH_3)_2$ | H | O | 0 |
| A-3340 | H | H | H | H | H | $CH_2SCH_2CF_3$ | $S(=O)_2N(CH_3)_2$ | H | O | 0 |
| A-3341 | H | H | H | H | H | $CH_2SCH_2CHF_2$ | $S(=O)_2N(CH_3)_2$ | H | O | 0 |
| A-3342 | H | H | H | H | H | $CH_2SCF_2CF_3$ | $S(=O)_2N(CH_3)_2$ | H | O | 0 |
| A-3343 | H | H | H | H | H | $CH_2CH_2SCF_3$ | $S(=O)_2N(CH_3)_2$ | H | O | 0 |
| A-3344 | H | H | H | H | H | $CH_2SOCF_3$ | $S(=O)_2N(CH_3)_2$ | H | O | 0 |
| A-3345 | H | H | H | H | H | $CH_2CH_2SOCF_3$ | $S(=O)_2N(CH_3)_2$ | H | O | 0 |
| A-3346 | H | H | H | H | H | $CH_2CH_2CH_2SOCF_3$ | $S(=O)_2N(CH_3)_2$ | H | O | 0 |
| A-3347 | H | H | H | H | H | $CH_2SO_2CF_3$ | $S(=O)_2N(CH_3)_2$ | H | O | 0 |
| A-3348 | H | H | H | H | H | $CH_2CH_2SO_2CF_3$ | $S(=O)_2N(CH_3)_2$ | H | O | 0 |
| A-3349 | H | H | H | H | H | $CH_2CH_2CH_2SO_2CF_3$ | $S(=O)_2N(CH_3)_2$ | H | O | 0 |
| A-3350 | H | H | H | H | H | $CH_2C(=O)NHCH_2CHF_2$ | $S(=O)_2N(CH_3)_2$ | H | O | 0 |

TABLE 56

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-3351 | H | H | H | H | H | $CH_2C(=O)NHCH_2CF_3$ | $S(=O)_2N(CH_3)_2$ | H | O | 0 |
| A-3352 | H | H | H | H | H | H | $CH_2N(CH_3)_2$ | H | O | 0 |
| A-3353 | H | H | H | H | H | $CH_3$ | $CH_2N(CH_3)_2$ | H | O | 0 |
| A-3354 | H | H | H | H | H | $CH_2CH_3$ | $CH_2N(CH_3)_2$ | H | O | 0 |
| A-3355 | H | H | H | H | H | $CH(CH_3)_2$ | $CH_2N(CH_3)_2$ | H | O | 0 |
| A-3356 | H | H | H | H | H | $CH_2CH_2CH_3$ | $CH_2N(CH_3)_2$ | H | O | 0 |
| A-3357 | H | H | H | H | H | $CH_2CH(CH_3)_2$ | $CH_2N(CH_3)_2$ | H | O | 0 |
| A-3358 | H | H | H | H | H | $CH(CH_3)CH_2CH_3$ | $CH_2N(CH_3)_2$ | H | O | 0 |
| A-3359 | H | H | H | H | H | $CH_2C(CH_3)_3$ | $CH_2N(CH_3)_2$ | H | O | 0 |
| A-3360 | H | H | H | H | H | $CH_2(CH_2)_3CH_3$ | $CH_2N(CH_3)_2$ | H | O | 0 |
| A-3361 | H | H | H | H | H | $CH_2(CH_2)_2CH_3$ | $CH_2N(CH_3)_2$ | H | O | 0 |
| A-3362 | H | H | H | H | H | $CF_3$ | $CH_2N(CH_3)_2$ | H | O | 0 |
| A-3363 | H | H | H | H | H | $CHF_2$ | $CH_2N(CH_3)_2$ | H | O | 0 |
| A-3364 | H | H | H | H | H | $CH_2CF_3$ | $CH_2N(CH_3)_2$ | H | O | 0 |
| A-3365 | H | H | H | H | H | $CH_2CHF_2$ | $CH_2N(CH_3)_2$ | H | O | 0 |
| A-3366 | H | H | H | H | H | $CH_2CClF_2$ | $CH_2N(CH_3)_2$ | H | O | 0 |
| A-3367 | H | H | H | H | H | $CH_2CBrF_2$ | $CH_2N(CH_3)_2$ | H | O | 0 |
| A-3368 | H | H | H | H | H | $CF_2CF_3$ | $CH_2N(CH_3)_2$ | H | O | 0 |
| A-3369 | H | H | H | H | H | $CF_2CHF_2$ | $CH_2N(CH_3)_2$ | H | O | 0 |
| A-3370 | H | H | H | H | H | $CH_2CH_2CF_3$ | $CH_2N(CH_3)_2$ | H | O | 0 |
| A-3371 | H | H | H | H | H | $CH_2CF_2CF_3$ | $CH_2N(CH_3)_2$ | H | O | 0 |
| A-3372 | H | H | H | H | H | $CH_2CF_2CHF_2$ | $CH_2N(CH_3)_2$ | H | O | 0 |
| A-3373 | H | H | H | H | H | $CF_2CHFCF_3$ | $CH_2N(CH_3)_2$ | H | O | 0 |
| A-3374 | H | H | H | H | H | $CF_2CF_2CF_3$ | $CH_2N(CH_3)_2$ | H | O | 0 |
| A-3375 | H | H | H | H | H | $CH_2CF_2CF_2CF_3$ | $CH_2N(CH_3)_2$ | H | O | 0 |
| A-3376 | H | H | H | H | H | $CH_2CF_2CHFCF_3$ | $CH_2N(CH_3)_2$ | H | O | 0 |
| A-3377 | H | H | H | H | H | $CH_2CH_2CH_2CF_3$ | $CH_2N(CH_3)_2$ | H | O | 0 |
| A-3378 | H | H | H | H | H | $CH_2CH_2CF_2CF_3$ | $CH_2N(CH_3)_2$ | H | O | 0 |
| A-3379 | H | H | H | H | H | $CF_2CF_2CF_2CF_3$ | $CH_2N(CH_3)_2$ | H | O | 0 |
| A-3380 | H | H | H | H | H | $CH_2CH_2CH(CF_3)_2$ | $CH_2N(CH_3)_2$ | H | O | 0 |
| A-3381 | H | H | H | H | H | $CF_2CF_2CF_2CF_2CF_3$ | $CH_2N(CH_3)_2$ | H | O | 0 |
| A-3382 | H | H | H | H | H | $CH_2CF_2CF_2CF_2CF_3$ | $CH_2N(CH_3)_2$ | H | O | 0 |
| A-3383 | H | H | H | H | H | $CH_2CH_2CH_2CH_2CF_3$ | $CH_2N(CH_3)_2$ | H | O | 0 |
| A-3384 | H | H | H | H | H | $CH_2CF_2CF_2CF_2CHF_2$ | $CH_2N(CH_3)_2$ | H | O | 0 |
| A-3385 | H | H | H | H | H | $CH_2CH_2OCH_2CF_3$ | $CH_2N(CH_3)_2$ | H | O | 0 |
| A-3386 | H | H | H | H | H | $CF_2CHFOCF_3$ | $CH_2N(CH_3)_2$ | H | O | 0 |
| A-3387 | H | H | H | H | H | $CF_2CHFOCF_2CF_3$ | $CH_2N(CH_3)_2$ | H | O | 0 |
| A-3388 | H | H | H | H | H | $CH_2CH_2CF=CF_2$ | $CH_2N(CH_3)_2$ | H | O | 0 |
| A-3389 | H | H | H | H | H | $CH_2CH_2CH=CF_2$ | $CH_2N(CH_3)_2$ | H | O | 0 |
| A-3390 | H | H | H | H | H | $CH_2C\equiv CCH_3$ | $CH_2N(CH_3)_2$ | H | O | 0 |
| A-3391 | H | H | H | H | H | $CH_2C\equiv CCF_3$ | $CH_2N(CH_3)_2$ | H | O | 0 |
| A-3392 | H | H | H | H | H | $CH_2C\equiv CI$ | $CH_2N(CH_3)_2$ | H | O | 0 |
| A-3393 | H | H | H | H | H | $CH_2(2,2\text{-difluorocyclopropyl})$ | $CH_2N(CH_3)_2$ | H | O | 0 |
| A-3394 | H | H | H | H | H | $CH_2(2,2\text{-dichlorocyclopropyl})$ | $CH_2N(CH_3)_2$ | H | O | 0 |
| A-3395 | H | H | H | H | H | $CH_2CH_2(2,2\text{-difluorocyclopropyl})$ | $CH_2N(CH_3)_2$ | H | O | 0 |
| A-3396 | H | H | H | H | H | $CH_2CH_2(2,2\text{-dichlorocyclopropyl})$ | $CH_2N(CH_3)_2$ | H | O | 0 |
| A-3397 | H | H | H | H | H | $CH_2SCH_3$ | $CH_2N(CH_3)_2$ | H | O | 0 |
| A-3398 | H | H | H | H | H | $CH_2SCH_2CH_3$ | $CH_2N(CH_3)_2$ | H | O | 0 |
| A-3399 | H | H | H | H | H | $CH_2CH_2SCH_3$ | $CH_2N(CH_3)_2$ | H | O | 0 |
| A-3400 | H | H | H | H | H | $CH_2SOCH_3$ | $CH_2N(CH_3)_2$ | H | O | 0 |

TABLE 56-continued

| Compound | R¹ | R² | R³ | R⁴ | R⁵ | R⁶ | R⁷ | R⁸ | X | n |
|---|---|---|---|---|---|---|---|---|---|---|
| A-3401 | H | H | H | H | H | CH₂CH₂SOCH₃ | CH₂N(CH₃)₂ | H | O | 0 |
| A-3402 | H | H | H | H | H | CH₂SO₂CH₃ | CH₂N(CH₃)₂ | H | O | 0 |
| A-3403 | H | H | H | H | H | CH₂CH₂SO₂CH₃ | CH₂N(CH₃)₂ | H | O | 0 |
| A-3404 | H | H | H | H | H | CH₂SCF₃ | CH₂N(CH₃)₂ | H | O | 0 |
| A-3405 | H | H | H | H | H | CH₂SCHF₂ | CH₂N(CH₃)₂ | H | O | 0 |
| A-3406 | H | H | H | H | H | CH₂SCH₂CF₃ | CH₂N(CH₃)₂ | H | O | 0 |
| A-3407 | H | H | H | H | H | CH₂SCH₂CHF₂ | CH₂N(CH₃)₂ | H | O | 0 |
| A-3408 | H | H | H | H | H | CH₂SCF₂CF₃ | CH₂N(CH₃)₂ | H | O | 0 |
| A-3409 | H | H | H | H | H | CH₂CH₂SCF₃ | CH₂N(CH₃)₂ | H | O | 0 |
| A-3410 | H | H | H | H | H | CH₂CH₂SOCF₃ | CH₂N(CH₃)₂ | H | O | 0 |
| A-3411 | H | H | H | H | H | CH₂CH₂SOCF₃ | CH₂N(CH₃)₂ | H | O | 0 |

TABLE 57

| Compound | R¹ | R² | R³ | R⁴ | R⁵ | R⁶ | R⁷ | R⁸ | X | n |
|---|---|---|---|---|---|---|---|---|---|---|
| A-3412 | H | H | H | H | H | CH₂CH₂CH₂SOCF₃ | CH₂N(CH₃)₂ | H | O | 0 |
| A-3413 | H | H | H | H | H | CH₂SO₂CF₃ | CH₂N(CH₃)₂ | H | O | 0 |
| A-3414 | H | H | H | H | H | CH₂CH₂SO₂CF₃ | CH₂N(CH₃)₂ | H | O | 0 |
| A-3415 | H | H | H | H | H | CH₂CH₂CH₂SO₂CF₃ | CH₂N(CH₃)₂ | H | O | 0 |
| A-3416 | H | H | H | H | H | CH₂O(=O)NHCH₂CHF₂ | CH₂N(CH₃)₂ | H | O | 0 |
| A-3417 | H | H | H | H | H | CH₂C(=O)NHCH₂CF₃ | CH₂N(CH₃)₂ | H | O | 0 |
| A-3418 | H | H | H | H | H | H | CH₂(pyrrolidin-1-yl) | H | O | 0 |
| A-3419 | H | H | H | H | H | CH₃ | CH₂(pyrrolidin-1-yl) | H | O | 0 |
| A-3420 | H | H | H | H | H | CH₂CH₃ | CH₂(pyrrolidin-1-yl) | H | O | 0 |
| A-3421 | H | H | H | H | H | CH(CH₃)₂ | CH₂(pyrrolidin-1-yl) | H | O | 0 |
| A-3422 | H | H | H | H | H | CH₂CH₂CH₃ | CH₂(pyrrolidin-1-yl) | H | O | 0 |
| A-3423 | H | H | H | H | H | CH₂CH(CH₃)₂ | CH₂(pyrrolidin-1-yl) | H | O | 0 |
| A-3424 | H | H | H | H | H | CH(CH₃)CH₂CH₃ | CH₂(pyrrolidin-1-yl) | H | O | 0 |
| A-3425 | H | H | H | H | H | CH₂C(CH₃)₃ | CH₂(pyrrolidin-1-yl) | H | O | 0 |
| A-3426 | H | H | H | H | H | CH₂(CH₂)₂CH₃ | CH₂(pyrrolidin-1-yl) | H | O | 0 |
| A-3427 | H | H | H | H | H | CH₂(CH₂)₃CH₃ | CH₂(pyrrolidin-1-yl) | H | O | 0 |
| A-3428 | H | H | H | H | H | CF₃ | CH₂(pyrrolidin-1-yl) | H | O | 0 |
| A-3429 | H | H | H | H | H | CHF₂ | CH₂(pyrrolidin-1-yl) | H | O | 0 |
| A-3430 | H | H | H | H | H | CH₂CF₃ | CH₂(pyrrolidin-1-yl) | H | O | 0 |
| A-3431 | H | H | H | H | H | CH₂CHF₂ | CH₂(pyrrolidin-1-yl) | H | O | 0 |
| A-3432 | H | H | H | H | H | CH₂CClF₂ | CH₂(pyrrolidin-1-yl) | H | O | 0 |
| A-3433 | H | H | H | H | H | CH₂CBrF₂ | CH₂(pyrrolidin-1-yl) | H | O | 0 |
| A-3434 | H | H | H | H | H | CF₂CF₃ | CH₂(pyrrolidin-1-yl) | H | O | 0 |
| A-3435 | H | H | H | H | H | CF₂CHF₂ | CH₂(pyrrolidin-1-yl) | H | O | 0 |
| A-3436 | H | H | H | H | H | CH₂CH₂CF₃ | CH₂(pyrrolidin-1-yl) | H | O | 0 |
| A-3437 | H | H | H | H | H | CH₂CF₂CF₃ | CH₂(pyrrolidin-1-yl) | H | O | 0 |
| A-3438 | H | H | H | H | H | CH₂CF₂CHF₂ | CH₂(pyrrolidin-1-yl) | H | O | 0 |
| A-3439 | H | H | H | H | H | CF₂CHFCF₃ | CH₂(pyrrolidin-1-yl) | H | O | 0 |
| A-3440 | H | H | H | H | H | CF₂CF₂CF₃ | CH₂(pyrrolidin-1-yl) | H | O | 0 |
| A-3441 | H | H | H | H | H | CH₂CF₂CF₂CF₃ | CH₂(pyrrolidin-1-yl) | H | O | 0 |
| A-3442 | H | H | H | H | H | CH₂CF₂CHFCF₃ | CH₂(pyrrolidin-1-yl) | H | O | 0 |
| A-3443 | H | H | H | H | H | CH₂CH₂CH₂CF₃ | CH₂(pyrrolidin-1-yl) | H | O | 0 |
| A-3444 | H | H | H | H | H | CH₂CF₂CF₂CF₃ | CH₂(pyrrolidin-1-yl) | H | O | 0 |
| A-3445 | H | H | H | H | H | CF₂CF₂CF₂CF₃ | CH₂(pyrrolidin-1-yl) | H | O | 0 |
| A-3446 | H | H | H | H | H | CH₂CH₂CH(CF₃)₂ | CH₂(pyrrolidin-1-yl) | H | O | 0 |
| A-3447 | H | H | H | H | H | CF₂CF₂CF₂CF₂CF₃ | CH₂(pyrrolidin-1-yl) | H | O | 0 |
| A-3448 | H | H | H | H | H | CH₂CF₂CF₂CF₂CF₃ | CH₂(pyrrolidin-1-yl) | H | O | 0 |
| A-3449 | H | H | H | H | H | CH₂CH₂CH₂CH₂CF₃ | CH₂(pyrrolidin-1-yl) | H | O | 0 |
| A-3450 | H | H | H | H | H | CH₂CF₂CF₂CF₂CHF₂ | CH₂(pyrrolidin-1-yl) | H | O | 0 |
| A-3451 | H | H | H | H | H | CH₂CH₂OCH₂CF₃ | CH₂(pyrrolidin-1-yl) | H | O | 0 |
| A-3452 | H | H | H | H | H | CF₂CHFOCF₃ | CH₂(pyrrolidin-1-yl) | H | O | 0 |
| A-3453 | H | H | H | H | H | CF₂CHFOCF₂CF₃ | CH₂(pyrrolidin-1-yl) | H | O | 0 |
| A-3454 | H | H | H | H | H | CH₂CH₂CF=CF₂ | CH₂(pyrrolidin-1-yl) | H | O | 0 |
| A-3455 | H | H | H | H | H | CH₂CH₂CH=CF₂ | CH₂(pyrrolidin-1-yl) | H | O | 0 |
| A-3456 | H | H | H | H | H | CH₂C≡CCH₃ | CH₂(pyrrolidin-1-yl) | H | O | 0 |
| A-3457 | H | H | H | H | H | CH₂C≡CCF₃ | CH₂(pyrrolidin-1-yl) | H | O | 0 |
| A-3458 | H | H | H | H | H | CH₂C≡CI | CH₂(pyrrolidin-1-yl) | H | O | 0 |
| A-3459 | H | H | H | H | H | CH₂(2,2-difluorocyclopropyl) | CH₂(pyrrolidin-1-yl) | H | O | 0 |
| A-3460 | H | H | H | H | H | CH₂(2,2-dichlorocyclopropyl) | CH₂(pyrrolidin-1-yl) | H | O | 0 |
| A-3461 | H | H | H | H | H | CH₂CH₂(2,2-difluorocyclopropyl) | CH₂(pyrrolidin-1-yl) | H | O | 0 |
| A-3462 | H | H | H | H | H | CH₂CH₂(2,2-dichlorocyclopropyl) | CH₂(pyrrolidin-1-yl) | H | O | 0 |
| A-3463 | H | H | H | H | H | CH₂SCH₃ | CH₂(pyrrolidin-1-yl) | H | O | 0 |
| A-3464 | H | H | H | H | H | CH₂SCH₂CH₃ | CH₂(pyrrolidin-1-yl) | H | O | 0 |
| A-3465 | H | H | H | H | H | CH₂CH₂SCH₃ | CH₂(pyrrolidin-1-yl) | H | O | 0 |
| A-3466 | H | H | H | H | H | CH₂SOCH₃ | CH₂(pyrrolidin-1-yl) | H | O | 0 |
| A-3467 | H | H | H | H | H | CH₂CH₂SOCH₃ | CH₂(pyrrolidin-1-yl) | H | O | 0 |
| A-3468 | H | H | H | H | H | CH₂SO₂CH₃ | CH₂(pyrrolidin-1-yl) | H | O | 0 |
| A-3469 | H | H | H | H | H | CH₂CH₂SO₂CH₃ | CH₂(pyrrolidin-1-yl) | H | O | 0 |

TABLE 57-continued

| Compound | R¹ | R² | R³ | R⁴ | R⁵ | R⁶ | R⁷ | R⁸ | X | n |
|---|---|---|---|---|---|---|---|---|---|---|
| A-3470 | H | H | H | H | H | CH$_2$SCF$_3$ | CH$_2$(pyrrolidin-1-yl) | H | O | 0 |
| A-3471 | H | H | H | H | H | CH$_2$SCHF$_2$ | CH$_2$(pyrrolidin-1-yl) | H | O | 0 |
| A-3472 | H | H | H | H | H | CH$_2$SCH$_2$CF$_3$ | CH$_2$(pyrrolidin-1-yl) | H | O | 0 |

TABLE 58

| Compound | R¹ | R² | R³ | R⁴ | R⁵ | R⁶ | R⁷ | R⁸ | X | n |
|---|---|---|---|---|---|---|---|---|---|---|
| A-3473 | H | H | H | H | H | CH$_2$SCH$_2$CHF$_2$ | CH$_2$(pyrrolidin-1-yl) | H | O | 0 |
| A-3474 | H | H | H | H | H | CH$_2$SCF$_2$CF$_3$ | CH$_2$(pyrrolidin-1-yl) | H | O | 0 |
| A-3475 | H | H | H | H | H | CH$_2$CH$_2$SCF$_3$ | CH$_2$(pyrrolidin-1-yl) | H | O | 0 |
| A-3476 | H | H | H | H | H | CH$_2$SOCF$_3$ | CH$_2$(pyrrolidin-1-yl) | H | O | 0 |
| A-3477 | H | H | H | H | H | CH$_2$CH$_2$SOCF$_3$ | CH$_2$(pyrrolidin-1-yl) | H | O | 0 |
| A-3478 | H | H | H | H | H | CH$_2$CH$_2$CH$_2$SOCF$_3$ | CH$_2$(pyrrolidin-1-yl) | H | O | 0 |
| A-3479 | H | H | H | H | H | CH$_2$SO$_2$CF$_3$ | CH$_2$(pyrrolidin-1-yl) | H | O | 0 |
| A-3480 | H | H | H | H | H | CH$_2$CH$_2$SO$_2$CF$_3$ | CH$_2$(pyrrolidin-1-yl) | H | O | 0 |
| A-3481 | H | H | H | H | H | CH$_2$CH$_2$CH$_2$SO$_2$CF$_3$ | CH$_2$(pyrrolidin-1-yl) | H | O | 0 |
| A-3482 | H | H | H | H | H | CH$_2$C(=O)NHCH$_2$CHF$_2$ | CH$_2$(pyrrolidin-1-yl) | H | O | 0 |
| A-3483 | H | H | H | H | H | CH$_2$C(=O)NHCH$_2$CF$_3$ | CH$_2$(pyrrolidin-1-yl) | H | O | 0 |
| A-3484 | H | H | H | H | H | H | CH$_2$C(=O)OCH$_3$ | H | O | 0 |
| A-3485 | H | H | H | H | H | CH$_3$ | CH$_2$C(=O)OCH$_3$ | H | O | 0 |
| A-3486 | H | H | H | H | H | CH$_2$CH$_3$ | CH$_2$C(=O)OCH$_3$ | H | O | 0 |
| A-3487 | H | H | H | H | H | CH(CH$_3$)$_2$ | CH$_2$C(=O)OCH$_3$ | H | O | 0 |
| A-3488 | H | H | H | H | H | CH$_2$CH$_2$CH$_3$ | CH$_2$C(=O)OCH$_3$ | H | O | 0 |
| A-3489 | H | H | H | H | H | CH$_2$CH(CH$_3$)$_2$ | CH$_2$C(=O)OCH$_3$ | H | O | 0 |
| A-3490 | H | H | H | H | H | CH(CH$_3$)CH$_2$CH$_3$ | CH$_2$C(=O)OCH$_3$ | H | O | 0 |
| A-3491 | H | H | H | H | H | CH$_2$C(CH$_3$)$_3$ | CH$_2$C(=O)OCH$_3$ | H | O | 0 |
| A-3492 | H | H | H | H | H | CH$_2$(CH$_2$)$_2$CH$_3$ | CH$_2$C(=O)OCH$_3$ | H | O | 0 |
| A-3493 | H | H | H | H | H | CH$_2$(CH$_2$)$_3$CH$_3$ | CH$_2$C(=O)OCH$_3$ | H | O | 0 |
| A-3494 | H | H | H | H | H | CF$_3$ | CH$_2$C(=O)OCH$_3$ | H | O | 0 |
| A-3495 | H | H | H | H | H | CHF$_2$ | CH$_2$C(=O)OCH$_3$ | H | O | 0 |
| A-3496 | H | H | H | H | H | CH$_2$CF$_3$ | CH$_2$C(=O)OCH$_3$ | H | O | 0 |
| A-3497 | H | H | H | H | H | CH$_2$CHF$_2$ | CH$_2$C(=O)OCH$_3$ | H | O | 0 |
| A-3498 | H | H | H | H | H | CH$_2$CClF$_2$ | CH$_2$C(=O)OCH$_3$ | H | O | 0 |
| A-3499 | H | H | H | H | H | CH$_2$CBrF$_2$ | CH$_2$C(=O)OCH$_3$ | H | O | 0 |
| A-3500 | H | H | H | H | H | CF$_2$CF$_3$ | CH$_2$C(=O)OCH$_3$ | H | O | 0 |
| A-3501 | H | H | H | H | H | CF$_2$CHF$_2$ | CH$_2$C(=O)OCH$_3$ | H | O | 0 |
| A-3502 | H | H | H | H | H | CH$_2$CH$_2$CF$_3$ | CH$_2$C(=O)OCH$_3$ | H | O | 0 |
| A-3503 | H | H | H | H | H | CH$_2$CF$_2$CF$_3$ | CH$_2$C(=O)OCH$_3$ | H | O | 0 |
| A-3504 | H | H | H | H | H | CH$_2$CF$_2$CHF$_2$ | CH$_2$C(=O)OCH$_3$ | H | O | 0 |
| A-3505 | H | H | H | H | H | CF$_2$CHFCF$_3$ | CH$_2$C(=O)OCH$_3$ | H | O | 0 |
| A-3506 | H | H | H | H | H | CF$_2$CF$_2$CF$_3$ | CH$_2$C(=O)OCH$_3$ | H | O | 0 |
| A-3507 | H | H | H | H | H | CH$_2$CF$_2$CF$_2$CF$_3$ | CH$_2$C(=O)OCH$_3$ | H | O | 0 |
| A-3508 | H | H | H | H | H | CH$_2$CF$_2$CHFCF$_3$ | CH$_2$C(=O)OCH$_3$ | H | O | 0 |
| A-3509 | H | H | H | H | H | CH$_2$CH$_2$CH$_2$CF$_3$ | CH$_2$C(=O)OCH$_3$ | H | O | 0 |
| A-3510 | H | H | H | H | H | CH$_2$CH$_2$CF$_2$CF$_3$ | CH$_2$C(=O)OCH$_3$ | H | O | 0 |
| A-3511 | H | H | H | H | H | CF$_2$CF$_2$CF$_2$CF$_3$ | CH$_2$C(=O)OCH$_3$ | H | O | 0 |
| A-3512 | H | H | H | H | H | CH$_2$CH$_2$CH(CF$_3$)$_2$ | CH$_2$C(=O)OCH$_3$ | H | O | 0 |
| A-3513 | H | H | H | H | H | CF$_2$CF$_2$CF$_2$CF$_2$CF$_3$ | CH$_2$C(=O)OCH$_3$ | H | O | 0 |
| A-3514 | H | H | H | H | H | CH$_2$CF$_2$CF$_2$CF$_2$CF$_3$ | CH$_2$C(=O)OCH$_3$ | H | O | 0 |
| A-3515 | H | H | H | H | H | CH$_2$CH$_2$CH$_2$CH$_2$CF$_3$ | CH$_2$C(=O)OCH$_3$ | H | O | 0 |
| A-3516 | H | H | H | H | H | CH$_2$CF$_2$CF$_2$CF$_2$CHF$_2$ | CH$_2$C(=O)OCH$_3$ | H | O | 0 |
| A-3517 | H | H | H | H | H | CH$_2$CH$_2$OCH$_2$CF$_3$ | CH$_2$C(=O)OCH$_3$ | H | O | 0 |
| A-3518 | H | H | H | H | H | CF$_2$CHFOCF$_3$ | CH$_2$C(=O)OCH$_3$ | H | O | 0 |
| A-3519 | H | H | H | H | H | CF$_2$CHFOCF$_2$CF$_3$ | CH$_2$C(=O)OCH$_3$ | H | O | 0 |
| A-3520 | H | H | H | H | H | CH$_2$CH$_2$CF=CF$_2$ | CH$_2$C(=O)OCH$_3$ | H | O | 0 |
| A-3521 | H | H | H | H | H | CH$_2$CH$_2$CH=CF$_2$ | CH$_2$C(=O)OCH$_3$ | H | O | 0 |
| A-3522 | H | H | H | H | H | CH$_2$C≡CCH$_3$ | CH$_2$C(=O)OCH$_3$ | H | O | 0 |
| A-3523 | H | H | H | H | H | CH$_2$C≡CCF$_3$ | CH$_2$C(=O)OCH$_3$ | H | O | 0 |
| A-3524 | H | H | H | H | H | CH$_2$C≡CI | CH$_2$C(=O)OCH$_3$ | H | O | 0 |
| A-3525 | H | H | H | H | H | CH$_2$(2,2-difluorocyclopropyl) | CH$_2$C(=O)OCH$_3$ | H | O | 0 |
| A-3526 | H | H | H | H | H | CH$_2$(2,2-dichlorocyclopropyl) | CH$_2$C(=O)OCH$_3$ | H | O | 0 |
| A-3527 | H | H | H | H | H | CH$_2$CH$_2$(2,2-dichlorocyclopropyl) | CH$_2$C(=O)OCH$_3$ | H | O | 0 |
| A-3528 | H | H | H | H | H | CH$_2$CH$_2$(2,2-dichlorocyclopropyl) | CH$_2$C(=O)OCH$_3$ | H | O | 0 |
| A-3529 | H | H | H | H | H | CH$_2$SCH$_3$ | CH$_2$C(=O)OCH$_3$ | H | O | 0 |
| A-3530 | H | H | H | H | H | CH$_2$SCH$_2$CH$_3$ | CH$_2$C(=O)OCH$_3$ | H | O | 0 |
| A-3531 | H | H | H | H | H | CH$_2$CH$_2$SCH$_3$ | CH$_2$C(=O)OCH$_3$ | H | O | 0 |
| A-3532 | H | H | H | H | H | CH$_2$SOCH$_3$ | CH$_2$C(=O)OCH$_3$ | H | O | 0 |
| A-3533 | H | H | H | H | H | CH$_2$CH$_2$SOCH$_3$ | CH$_2$C(=O)OCH$_3$ | H | O | 0 |

TABLE 59

| Compound | R¹ | R² | R³ | R³ | R⁵ | R⁶ | R⁷ | R⁸ | X | n |
|---|---|---|---|---|---|---|---|---|---|---|
| A-3534 | H | H | H | H | H | $CH_2SO_2CH_3$ | $CH_2C(=O)OCH_3$ | H | O | 0 |
| A-3535 | H | H | H | H | H | $CH_2CH_2SO_2CH_3$ | $CH_2C(=O)OCH_3$ | H | O | 0 |
| A-3536 | H | H | H | H | H | $CH_2SCF_3$ | $CH_2C(=O)OCH_3$ | H | O | 0 |
| A-3537 | H | H | H | H | H | $CH_2SCHF_2$ | $CH_2C(=O)OCH_3$ | H | O | 0 |
| A-3538 | H | H | H | H | H | $CH_2SCH_2CF_3$ | $CH_2C(=O)OCH_3$ | H | O | 0 |
| A-3539 | H | H | H | H | H | $CH_2SCH_2CHF_2$ | $CH_2C(=O)OCH_3$ | H | O | 0 |
| A-3540 | H | H | H | H | H | $CH_2SCF_2CF_3$ | $CH_2C(=O)OCH_3$ | H | O | 0 |
| A-3541 | H | H | H | H | H | $CH_2CH_2SCF_3$ | $CH_2C(=O)OCH_3$ | H | O | 0 |
| A-3542 | H | H | H | H | H | $CH_2SOCF_3$ | $CH_2C(=O)OCH_3$ | H | O | 0 |
| A-3543 | H | H | H | H | H | $CH_2CH_2SOCF_3$ | $CH_2C(=O)OCH_3$ | H | O | 0 |
| A-3544 | H | H | H | H | H | $CH_2CH_2CH_2SOCF_3$ | $CH_2C(=O)OCH_3$ | H | O | 0 |
| A-3545 | H | H | H | H | H | $CH_2SO_2CF_3$ | $CH_2C(=O)OCH_3$ | H | O | 0 |
| A-3546 | H | H | H | H | H | $CH_2CH_2SO_2CF_3$ | $CH_2C(=O)OCH_3$ | H | O | 0 |
| A-3547 | H | H | H | H | H | $CH_2CH_2CH_2SO_2CF_3$ | $CH_2C(=O)OCH_3$ | H | O | 0 |
| A-3548 | H | H | H | H | H | $CH_2C(=O)NHCH_2CHF_2$ | $CH_2C(=O)OCH_3$ | H | O | 0 |
| A-3549 | H | H | H | H | H | $CH_2C(=O)NHCH_2CF_3$ | $CH_2C(=O)OCH_3$ | H | O | 0 |
| A-3550 | H | H | H | H | H | H | $CH_2C(=O)NH_2$ | H | O | 0 |
| A-3551 | H | H | H | H | H | $CH_3$ | $CH_2C(=O)NH_2$ | H | O | 0 |
| A-3552 | H | H | H | H | H | $CH_2CH_3$ | $CH_2C(=O)NH_2$ | H | O | 0 |
| A-3553 | H | H | H | H | H | $CH(CH_3)_2$ | $CH_2C(=O)NH_2$ | H | O | 0 |
| A-3554 | H | H | H | H | H | $CH_2CH_2CH_3$ | $CH_2C(=O)NH_2$ | H | O | 0 |
| A-3555 | H | H | H | H | H | $CH_2CH(CH_3)_2$ | $CH_2C(=O)NH_2$ | H | O | 0 |
| A-3556 | H | H | H | H | H | $CH(CH_3)CH_2CH_3$ | $CH_2C(=O)NH_2$ | H | O | 0 |
| A-3557 | H | H | H | H | H | $CH_2C(CH_3)_3$ | $CH_2C(=O)NH_2$ | H | O | 0 |
| A-3558 | H | H | H | H | H | $CH_2(CH_2)_2CH_3$ | $CH_2C(=O)NH_2$ | H | O | 0 |
| A-3559 | H | H | H | H | H | $CH_2(CH_2)_3CH_3$ | $CH_2C(=O)NH_2$ | H | O | 0 |
| A-3560 | H | H | H | H | H | $CF_3$ | $CH_2C(=O)NH_2$ | H | O | 0 |
| A-3561 | H | H | H | H | H | $CHF_2$ | $CH_2C(=O)NH_2$ | H | O | 0 |
| A-3562 | H | H | H | H | H | $CH_2CF_3$ | $CH_2C(=O)NH_2$ | H | O | 0 |
| A-3563 | H | H | H | H | H | $CH_2CHF_2$ | $CH_2C(=O)NH_2$ | H | O | 0 |
| A-3564 | H | H | H | H | H | $CH_2CClF_2$ | $CH_2C(=O)NH_2$ | H | O | 0 |
| A-3565 | H | H | H | H | H | $CH_2CBrF_2$ | $CH_2C(=O)NH_2$ | H | O | 0 |
| A-3566 | H | H | H | H | H | $CF_2CF_3$ | $CH_2C(=O)NH_2$ | H | O | 0 |
| A-3567 | H | H | H | H | H | $CF_2CHF_2$ | $CH_2C(=O)NH_2$ | H | O | 0 |
| A-3568 | H | H | H | H | H | $CH_2CH_2CF_3$ | $CH_2C(=O)NH_2$ | H | O | 0 |
| A-3569 | H | H | H | H | H | $CH_2CF_2CF_3$ | $CH_2C(=O)NH_2$ | H | O | 0 |
| A-3570 | H | H | H | H | H | $CH_2CF_2CHF_2$ | $CH_2C(=O)NH_2$ | H | O | 0 |
| A-3571 | H | H | H | H | H | $CF_2CHFCF_3$ | $CH_2C(=O)NH_2$ | H | O | 0 |
| A-3572 | H | H | H | H | H | $CF_2CF_2CF_3$ | $CH_2C(=O)NH_2$ | H | O | 0 |
| A-3573 | H | H | H | H | H | $CH_2CF_2CF_2CF_3$ | $CH_2C(=O)NH_2$ | H | O | 0 |
| A-3574 | H | H | H | H | H | $CH_2CF_2CHFCF_3$ | $CH_2C(=O)NH_2$ | H | O | 0 |
| A-3575 | H | H | H | H | H | $CH_2CH_2CH_2CF_3$ | $CH_2C(=O)NH_2$ | H | O | 0 |
| A-3576 | H | H | H | H | H | $CH_2CH_2CF_2CF_3$ | $CH_2C(=O)NH_2$ | H | O | 0 |
| A-3577 | H | H | H | H | H | $CF_2CF_2CF_2CF_3$ | $CH_2C(=O)NH_2$ | H | O | 0 |
| A-3578 | H | H | H | H | H | $CH_2CH_2CH(CF_3)_2$ | $CH_2C(=O)NH_2$ | H | O | 0 |
| A-3579 | H | H | H | H | H | $CF_2CF_2CF_2CF_2CF_3$ | $CH_2C(=O)NH_2$ | H | O | 0 |
| A-3580 | H | H | H | H | H | $CH_2CF_2CF_2CF_2CF_3$ | $CH_2C(=O)NH_2$ | H | O | 0 |
| A-3581 | H | H | H | H | H | $CH_2CH_2CH_2CH_2CF_3$ | $CH_2C(=O)NH_2$ | H | O | 0 |
| A-3582 | H | H | H | H | H | $CH_2CF_2CF_2CF_2CHF_2$ | $CH_2C(=O)NH_2$ | H | O | 0 |
| A-3583 | H | H | H | H | H | $CH_2CH_2OCH_2CF_3$ | $CH_2C(=O)NH_2$ | H | O | 0 |
| A-3584 | H | H | H | H | H | $CF_2CHFOCF_3$ | $CH_2C(=O)NH_2$ | H | O | 0 |
| A-3585 | H | H | H | H | H | $CF_2CHFOCF_2CF_3$ | $CH_2C(=O)NH_2$ | H | O | 0 |
| A-3586 | H | H | H | H | H | $CH_2CH_2CF=CF_2$ | $CH_2C(=O)NH_2$ | H | O | 0 |
| A-3587 | H | H | H | H | H | $CH_2CH_2CH=CF_2$ | $CH_2C(=O)NH_2$ | H | O | 0 |
| A-3588 | H | H | H | H | H | $CH_2C\equiv CCH_3$ | $CH_2C(=O)NH_2$ | H | O | 0 |
| A-3589 | H | H | H | H | H | $CH_2C\equiv CCF_3$ | $CH_2C(=O)NH_2$ | H | O | 0 |
| A-3590 | H | H | H | H | H | $CH_2C\equiv Cl$ | $CH_2C(=O)NH_2$ | H | O | 0 |
| A-3591 | H | H | H | H | H | $CH_2$(2,2-difluorocyclopropyl) | $CH_2C(=O)NH_2$ | H | O | 0 |
| A-3592 | H | H | H | H | H | $CH_2$(2,2-dichlorocyclopropyl) | $CH_2C(=O)NH_2$ | H | O | 0 |
| A-3593 | H | H | H | H | H | $CH_2CH_2$(2,2-difluorocyclopropyl) | $CH_2C(=O)NH_2$ | H | O | 0 |
| A-3594 | H | H | H | H | H | $CH_2CH_2$(2,2-dichlorocyclopropyl) | $CH_2C(=O)NH_2$ | H | O | 0 |

TABLE 60

| Compound | R¹ | R² | R³ | R⁴ | R⁵ | R⁶ | R⁷ | R⁸ | X | n |
|---|---|---|---|---|---|---|---|---|---|---|
| A-3595 | H | H | H | H | H | $CH_2SCH_3$ | $CH_2C(=O)NH_2$ | H | O | 0 |
| A-3596 | H | H | H | H | H | $CH_2SCH_2CH_3$ | $CH_2C(=O)NH_2$ | H | O | 0 |
| A-3597 | H | H | H | H | H | $CH_2CH_2SCH_3$ | $CH_2C(=O)NH_2$ | H | O | 0 |
| A-3598 | H | H | H | H | H | $CH_2SOCH_3$ | $CH_2C(=O)NH_2$ | H | O | 0 |
| A-3599 | H | H | H | H | H | $CH_2CH_2SOCH_3$ | $CH_2C(=O)NH_2$ | H | O | 0 |
| A-3600 | H | H | H | H | H | $CH_2SO_2CH_3$ | $CH_2C(=O)NH_2$ | H | O | 0 |
| A-3601 | H | H | H | H | H | $CH_2CH_2SO_2CH_3$ | $CH_2C(=O)NH_2$ | H | O | 0 |
| A-3602 | H | H | H | H | H | $CH_2SCF_3$ | $CH_2C(=O)NH_2$ | H | O | 0 |
| A-3603 | H | H | H | H | H | $CH_2SCHF_2$ | $CH_2C(=O)NH_2$ | H | O | 0 |

TABLE 60-continued

| Compound | R¹ | R² | R³ | R⁴ | R⁵ | R⁶ | R⁷ | R⁸ | X | n |
|---|---|---|---|---|---|---|---|---|---|---|
| A-3604 | H | H | H | H | H | CH₂SCH₂CF₃ | CH₂C(=O)NH₂ | H | O | 0 |
| A-3605 | H | H | H | H | H | CH₂SCH₂CHF₂ | CH₂C(=O)NH₂ | H | O | 0 |
| A-3606 | H | H | H | H | H | CH₂SCF₂CF₃ | CH₂C(=O)NH₂ | H | O | 0 |
| A-3607 | H | H | H | H | H | CH₂CH₂SCF₃ | CH₂C(=O)NH₂ | H | O | 0 |
| A-3608 | H | H | H | H | H | CH₂SOCF₃ | CH₂C(=O)NH₂ | H | O | 0 |
| A-3609 | H | H | H | H | H | CH₂CH₂SOCF₃ | CH₂C(=O)NH₂ | H | O | 0 |
| A-3610 | H | H | H | H | H | CH₂CH₂CH₂SOCF₃ | CH₂C(=O)NH₂ | H | O | 0 |
| A-3611 | H | H | H | H | H | CH₂SO₂CF₃ | CH₂C(=O)NH₂ | H | O | 0 |
| A-3612 | H | H | H | H | H | CH₂CH₂SO₂CF₃ | CH₂C(=O)NH₂ | H | O | 0 |
| A-3613 | H | H | H | H | H | CH₂CH₂CH₂SO₂CF₃ | CH₂C(=O)NH₂ | H | O | 0 |
| A-3614 | H | H | H | H | H | CH₂C(=O)NHCH₂CHF₂ | CH₂C(=O)NH₂ | H | O | 0 |
| A-3615 | H | H | H | H | H | CH₂C(=O)NHCH₂CF₃ | CH₂C(=O)NH₂ | H | O | 0 |
| A-3616 | H | H | H | H | H | H | CH=NOCH₃ | H | O | 0 |
| A-3617 | H | H | H | H | H | CH₃ | CH=NOCH₃ | H | O | 0 |
| A-3618 | H | H | H | H | H | CH₂CH₃ | CH=NOCH₃ | H | O | 0 |
| A-3619 | H | H | H | H | H | CH(CH₃)₂ | CH=NOCH₃ | H | O | 0 |
| A-3620 | H | H | H | H | H | CH₂CH₂CH₃ | CH=NOCH₃ | H | O | 0 |
| A-3621 | H | H | H | H | H | CH₂CH(CH₃)₂ | CH=NOCH₃ | H | O | 0 |
| A-3622 | H | H | H | H | H | CH(CH₃)CH₂CH₃ | CH=NOCH₃ | H | O | 0 |
| A-3623 | H | H | H | H | H | CH₂C(CH₃)₃ | CH=NOCH₃ | H | O | 0 |
| A-3624 | H | H | H | H | H | CH₂(CH₂)₂CH₃ | CH=NOCH₃ | H | O | 0 |
| A-3625 | H | H | H | H | H | CH₂(CH₂)₃CH₃ | CH=NOCH₃ | H | O | 0 |
| A-3626 | H | H | H | H | H | CF₃ | CH=NOCH₃ | H | O | 0 |
| A-3627 | H | H | H | H | H | CHF₂ | CH=NOCH₃ | H | O | 0 |
| A-3628 | H | H | H | H | H | CH₂CF₃ | CH=NOCH₃ | H | O | 0 |
| A-3629 | H | H | H | H | H | CH₂CHF₂ | CH=NOCH₃ | H | O | 0 |
| A-3630 | H | H | H | H | H | CH₂CClF₂ | CH=NOCH₃ | H | O | 0 |
| A-3631 | H | H | H | H | H | CH₂CBrF₂ | CH=NOCH₃ | H | O | 0 |
| A-3632 | H | H | H | H | H | CF₂CF₃ | CH=NOCH₃ | H | O | 0 |
| A-3633 | H | H | H | H | H | CF₂CHF₂ | CH=NOCH₃ | H | O | 0 |
| A-3634 | H | H | H | H | H | CH₂CH₂CF₃ | CH=NOCH₃ | H | O | 0 |
| A-3635 | H | H | H | H | H | CH₂CF₂CF₃ | CH=NOCH₃ | H | O | 0 |
| A-3636 | H | H | H | H | H | CH₂CF₂CHF₂ | CH=NOCH₃ | H | O | 0 |
| A-3637 | H | H | H | H | H | CF₂CHFCF₃ | CH=NOCH₃ | H | O | 0 |
| A-3638 | H | H | H | H | H | CF₂CF₂CF₃ | CH=NOCH₃ | H | O | 0 |
| A-3639 | H | H | H | H | H | CH₂CF₂CF₂CF₃ | CH=NOCH₃ | H | O | 0 |
| A-3640 | H | H | H | H | H | CH₂CF₂CHFCF₃ | CH=NOCH₃ | H | O | 0 |
| A-3641 | H | H | H | H | H | CH₂CH₂CH₂CF₃ | CH=NOCH₃ | H | O | 0 |
| A-3642 | H | H | H | H | H | CH₂CH₂CF₂CF₃ | CH=NOCH₃ | H | O | 0 |
| A-3643 | H | H | H | H | H | CF₂CF₂CF₂CF₃ | CH=NOCH₃ | H | O | 0 |
| A-3644 | H | H | H | H | H | CH₂CH₂CH(CF₃)₂ | CH=NOCH₃ | H | O | 0 |
| A-3645 | H | H | H | H | H | CF₂CF₂CF₂CF₂CF₃ | CH=NOCH₃ | H | O | 0 |
| A-3646 | H | H | H | H | H | CH₂CF₂CF₂CF₂CF₃ | CH=NOCH₃ | H | O | 0 |
| A-3647 | H | H | H | H | H | CH₂CH₂CH₂CH₂CF₃ | CH=NOCH₃ | H | O | 0 |
| A-3648 | H | H | H | H | H | CF₂CF₂CF₂CHF₂ | CH=NOCH₃ | H | O | 0 |
| A-3649 | H | H | H | H | H | CH₂CH₂OCH₂CF₃ | CH=NOCH₃ | H | O | 0 |
| A-3650 | H | H | H | H | H | CF₂CHFOCF₃ | CH=NOCH₃ | H | O | 0 |
| A-3651 | H | H | H | H | H | CF₂CHFOCF₂CF₃ | CH=NOCH₃ | H | O | 0 |
| A-3652 | H | H | H | H | H | CH₂CH₂CF=CF₂ | CH=NOCH₃ | H | O | 0 |
| A-3653 | H | H | H | H | H | CH₂CH₂CH=CF₂ | CH=NOCH₃ | H | O | 0 |
| A-3654 | H | H | H | H | H | CH₂C≡CCH₃ | CH=NOCH₃ | H | O | 0 |
| A-3655 | H | H | H | H | H | CH₂C≡CCF₃ | CH=NOCH₃ | H | O | 0 |

TABLE 61

| Compound | R¹ | R² | R³ | R⁴ | R⁵ | R⁶ | R⁷ | R⁸ | X | n |
|---|---|---|---|---|---|---|---|---|---|---|
| A-3656 | H | H | H | H | H | CH₂C≡CI | CH=NOCH₃ | H | O | 0 |
| A-3657 | H | H | H | H | H | CH₂(2,2-difluorocyclopropyl) | CH=NOCH₃ | H | O | 0 |
| A-3658 | H | H | H | H | H | CH₂(2,2-dichlorocyclopropyl) | CH=NOCH₃ | H | O | 0 |
| A-3659 | H | H | H | H | H | CH₂CH₂(2,2-difluorocyclopropyl) | CH=NOCH₃ | H | O | 0 |
| A-3660 | H | H | H | H | H | CH₂CH₂(2,2-dichlorocyclopropyl) | CH=NOCH₃ | H | O | 0 |
| A-3661 | H | H | H | H | H | CH₂SCH₃ | CH=NOCH₃ | H | O | 0 |
| A-3662 | H | H | H | H | H | CH₂SCH₂CH₃ | CH=NOCH₃ | H | O | 0 |
| A-3663 | H | H | H | H | H | CH₂CH₂SCH₃ | CH=NOCH₃ | H | O | 0 |
| A-3664 | H | H | H | H | H | CH₂SOCH₃ | CH=NOCH₃ | H | O | 0 |
| A-3665 | H | H | H | H | H | CH₂CH₂SOCH₃ | CH=NOCH₃ | H | O | 0 |
| A-3666 | H | H | H | H | H | CH₂SO₂CH₃ | CH=NOCH₃ | H | O | 0 |
| A-3667 | H | H | H | H | H | CH₂CH₂SO₂CH₃ | CH=NOCH₃ | H | O | 0 |
| A-3668 | H | H | H | H | H | CH₂SCF₃ | CH=NOCH₃ | H | O | 0 |
| A-3669 | H | H | H | H | H | CH₂SCHF₂ | CH=NOCH₃ | H | O | 0 |
| A-3670 | H | H | H | H | H | CH₂SCH₂CF₃ | CH=NOCH₃ | H | O | 0 |
| A-3671 | H | H | H | H | H | CH₂SCH₂CHF₂ | CH=NOCH₃ | H | O | 0 |
| A-3672 | H | H | H | H | H | CH₂SCF₂CF₃ | CH=NOCH₃ | H | O | 0 |
| A-3673 | H | H | H | H | H | CH₂CH₂SCF₃ | CH=NOCH₃ | H | O | 0 |

TABLE 61-continued

| Compound | R¹ | R² | R³ | R⁴ | R⁵ | R⁶ | R⁷ | R⁸ | X | n |
|---|---|---|---|---|---|---|---|---|---|---|
| A-3674 | H | H | H | H | H | CH₂SOCF₃ | CH=NOCH₃ | H | O | 0 |
| A-3675 | H | H | H | H | H | CH₂CH₂SOCF₃ | CH=NOCH₃ | H | O | 0 |
| A-3676 | H | H | H | H | H | CH₂CH₂CH₂SOCF₃ | CH=NOCH₃ | H | O | 0 |
| A-3677 | H | H | H | H | H | CH₂SO₂CF₃ | CH=NOCH₃ | H | O | 0 |
| A-3678 | H | H | H | H | H | CH₂CH₂SO₂CF₃ | CH=NOCH₃ | H | O | 0 |
| A-3679 | H | H | H | H | H | CH₂CH₂CH₂SO₂CF₃ | CH=NOCH₃ | H | O | 0 |
| A-3680 | H | H | H | H | H | CH₂C(=O)NHCH₂CHF₂ | CH=NOCH₃ | H | O | 0 |
| A-3681 | H | H | H | H | H | CH₂C(=O)NHCH₂CF₃ | CH=NOCH₃ | H | O | 0 |
| A-3682 | H | H | H | H | H | H | =CHN(CH₃)₂ | | O | 0 |
| A-3683 | H | H | H | H | H | CH₃ | =CHN(CH₃)₂ | | O | 0 |
| A-3684 | H | H | H | H | H | CH₂CH₃ | =CHN(CH₃)₂ | | O | 0 |
| A-3685 | H | H | H | H | H | CH(CH₃)₂ | =CHN(CH₃)₂ | | O | 0 |
| A-3686 | H | H | H | H | H | CH₂CH₂CH₃ | =CHN(CH₃)₂ | | O | 0 |
| A-3687 | H | H | H | H | H | CH₂CH(CH₃)₂ | =CHN(CH₃)₂ | | O | 0 |
| A-3688 | H | H | H | H | H | CH(CH₃)CH₂CH₃ | =CHN(CH₃)₂ | | O | 0 |
| A-3689 | H | H | H | H | H | CH₂C(CH₃)₃ | =CHN(CH₃)₂ | | O | 0 |
| A-3690 | H | H | H | H | H | CH₂(CH₂)₂CH₃ | =CHN(CH₃)₂ | | O | 0 |
| A-3691 | H | H | H | H | H | CH₂(CH₂)₃CH₃ | =CHN(CH₃)₂ | | O | 0 |
| A-3692 | H | H | H | H | H | CF₃ | =CHN(CH₃)₂ | | O | 0 |
| A-3693 | H | H | H | H | H | CHF₂ | =CHN(CH₃)₂ | | O | 0 |
| A-3694 | H | H | H | H | H | CH₂CF₃ | =CHN(CH₃)₂ | | O | 0 |
| A-3695 | H | H | H | H | H | CH₂CHF₂ | =CHN(CH₃)₂ | | O | 0 |
| A-3696 | H | H | H | H | H | CH₂CClF₂ | =CHN(CH₃)₂ | | O | 0 |
| A-3697 | H | H | H | H | H | CH₂CBrF₂ | =CHN(CH₃)₂ | | O | 0 |
| A-3698 | H | H | H | H | H | CF₂CF₃ | =CHN(CH₃)₂ | | O | 0 |
| A-3699 | H | H | H | H | H | CF₂CHF₂ | =CHN(CH₃)₂ | | O | 0 |
| A-3700 | H | H | H | H | H | CH₂CH₂CF₃ | =CHN(CH₃)₂ | | O | 0 |
| A-3701 | H | H | H | H | H | CH₂CF₂CF₃ | =CHN(CH₃)₂ | | O | 0 |
| A-3702 | H | H | H | H | H | CH₂CF₂CHF₂ | =CHN(CH₃)₂ | | O | 0 |
| A-3703 | H | H | H | H | H | CF₂CHFCF₃ | =CHN(CH₃)₂ | | O | 0 |
| A-3704 | H | H | H | H | H | CF₂CF₂CF₃ | =CHN(CH₃)₂ | | O | 0 |
| A-3705 | H | H | H | H | H | CH₂CF₂CF₂CF₃ | =CHN(CH₃)₂ | | O | 0 |
| A-3706 | H | H | H | H | H | CH₂CF₂CHFCF₃ | =CHN(CH₃)₂ | | O | 0 |
| A-3707 | H | H | H | H | H | CH₂CH₂CH₂CF₃ | =CHN(CH₃)₂ | | O | 0 |
| A-3708 | H | H | H | H | H | CH₂CH₂CF₂CF₃ | =CHN(CH₃)₂ | | O | 0 |
| A-3709 | H | H | H | H | H | CF₂CF₂CF₂CF₃ | =CHN(CH₃)₂ | | O | 0 |
| A-3710 | H | H | H | H | H | CH₂CH₂CH(CF₃)₂ | =CHN(CH₃)₂ | | O | 0 |
| A-3711 | H | H | H | H | H | CF₂CF₂CF₂CF₂CF₃ | =CHN(CH₃)₂ | | O | 0 |
| A-3712 | H | H | H | H | H | CH₂CF₂CF₂CF₂CF₃ | =CHN(CH₃)₂ | | O | 0 |
| A-3713 | H | H | H | H | H | CH₂CH₂CH₂CH₂CF₃ | =CHN(CH₃)₂ | | O | 0 |
| A-3714 | H | H | H | H | H | CH₂CF₂CF₂CF₃CHF₂ | =CHN(CH₃)₂ | | O | 0 |
| A-3715 | H | H | H | H | H | CH₂CH₂OCH₂CF₃ | =CHN(CH₃)₂ | | O | 0 |
| A-3716 | H | H | H | H | H | CF₂CHFOCF₃ | =CHN(CH₃)₂ | | O | 0 |

TABLE 62

| Compound | R¹ | R² | R³ | R⁴ | R⁵ | R⁶ | R⁷ | R⁸ | X | n |
|---|---|---|---|---|---|---|---|---|---|---|
| A-3717 | H | H | H | H | H | CF₂CHFOCF₂CF₃ | =CHN(CH₃)₂ | | O | 0 |
| A-3718 | H | H | H | H | H | CH₂CH₂CF=CF₂ | =CHN(CH₃)₂ | | O | 0 |
| A-3719 | H | H | H | H | H | CH₂CH₂CH=CF₂ | =CHN(CH₃)₂ | | O | 0 |
| A-3720 | H | H | H | H | H | CH₂C≡CCH₃ | =CHN(CH₃)₂ | | O | 0 |
| A-3721 | H | H | H | H | H | CH₂C≡CCF₃ | =CHN(CH₃)₂ | | O | 0 |
| A-3722 | H | H | H | H | H | CH₂C≡CI | =CHN(CH₃)₂ | | O | 0 |
| A-3723 | H | H | H | H | H | CH₂(2,2-difluorocyclopropyl) | =CHN(CH₃)₂ | | O | 0 |
| A-3724 | H | H | H | H | H | CH₂(2,2-dichlorocyclopropyl) | =CHN(CH₃)₂ | | O | 0 |
| A-3725 | H | H | H | H | H | CH₂CH₂(2,2-difluorocyclopropyl) | =CHN(CH₃)₂ | | O | 0 |
| A-3726 | H | H | H | H | H | CH₂CH₂(2,2-dichlorocyclopropyl) | =CHN(CH₃)₂ | | O | 0 |
| A-3727 | H | H | H | H | H | CH₂SCH₃ | =CHN(CH₃)₂ | | O | 0 |
| A-3728 | H | H | H | H | H | CH₂SCH₂CH₃ | =CHN(CH₃)₂ | | O | 0 |
| A-3729 | H | H | H | H | H | CH₂CH₂SCH₃ | =CHN(CH₃)₂ | | O | 0 |
| A-3730 | H | H | H | H | H | CH₂SOCH₃ | =CHN(CH₃)₂ | | O | 0 |
| A-3731 | H | H | H | H | H | CH₂CH₂SOCH₃ | =CHN(CH₃)₂ | | O | 0 |
| A-3732 | H | H | H | H | H | CH₂SO₂CH₃ | =CHN(CH₃)₂ | | O | 0 |
| A-3733 | H | H | H | H | H | CH₂CH₂SO₂CH₃ | =CHN(CH₃)₂ | | O | 0 |
| A-3734 | H | H | H | H | H | CH₂SCF₃ | =CHN(CH₃)₂ | | O | 0 |
| A-3735 | H | H | H | H | H | CH₂SCHF₂ | =CHN(CH₃)₂ | | O | 0 |
| A-3736 | H | H | H | H | H | CH₂SCH₂CF₃ | =CHN(CH₃)₂ | | O | 0 |
| A-3737 | H | H | H | H | H | CH₂SCH₂CHF₂ | =CHN(CH₃)₂ | | O | 0 |
| A-3738 | H | H | H | H | H | CH₂SCF₂CF₃ | =CHN(CH₃)₂ | | O | 0 |
| A-3739 | H | H | H | H | H | CH₂CH₂SCF₃ | =CHN(CH₃)₂ | | O | 0 |
| A-3740 | H | H | H | H | H | CH₂SOCF₃ | =CHN(CH₃)₂ | | O | 0 |
| A-3741 | H | H | H | H | H | CH₂CH₂SOCF₃ | =CHN(CH₃)₂ | | O | 0 |
| A-3742 | H | H | H | H | H | CH₂CH₂CH₂SOCF₃ | =CHN(CH₃)₂ | | O | 0 |
| A-3743 | H | H | H | H | H | CH₂SO₂CF₃ | =CHN(CH₃)₂ | | O | 0 |

TABLE 62-continued

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-3744 | H | H | H | H | H | $CH_2CH_2SO_2CF_3$ | $=CHN(CH_3)_2$ | | O | 0 |
| A-3745 | H | H | H | H | H | $CH_2CH_2CH_2SO_2CF_3$ | $=CHN(CH_3)_2$ | | O | 0 |
| A-3746 | H | H | H | H | H | $CH_2C(=O)NHCH_2CHF_2$ | $=CHN(CH_3)_2$ | | O | 0 |
| A-3747 | H | H | H | H | H | $CH_2C(=O)NHCH_2CF_3$ | $=CHN(CH_3)_2$ | | O | 0 |
| A-3748 | H | H | H | H | H | H | $CH_3$ | $CH_3$ | O | 0 |
| A-3749 | H | H | H | H | H | $CH_3$ | $CH_3$ | $CH_3$ | O | 0 |
| A-3750 | H | H | H | H | H | $CH_2CH_3$ | $CH_3$ | $CH_3$ | O | 0 |
| A-3751 | H | H | H | H | H | $CH(CH_3)_2$ | $CH_3$ | $CH_3$ | O | 0 |
| A-3752 | H | H | H | H | H | $CH_2CH_2CH_3$ | $CH_3$ | $CH_3$ | O | 0 |
| A-3753 | H | H | H | H | H | $CH_2CH(CH_3)_2$ | $CH_3$ | $CH_3$ | O | 0 |
| A-3754 | H | H | H | H | H | $CH(CH_3)CH_2CH_3$ | $CH_3$ | $CH_3$ | O | 0 |
| A-3755 | H | H | H | H | H | $CH_2C(CH_3)_3$ | $CH_3$ | $CH_3$ | O | 0 |
| A-3756 | H | H | H | H | H | $CH_2(CH_2)_2CH_3$ | $CH_3$ | $CH_3$ | O | 0 |
| A-3757 | H | H | H | H | H | $CH_2(CH_2)_3CH_3$ | $CH_3$ | $CH_3$ | O | 0 |
| A-3758 | H | H | H | H | H | $CH_2(CH_2)_4CH_3$ | $CH_3$ | $CH_3$ | O | 0 |
| A-3759 | H | H | H | H | H | $CH_2(CH_2)_6CH_3$ | $CH_3$ | $CH_3$ | O | 0 |
| A-3760 | H | H | H | H | H | $CH_2OCH_3$ | $CH_3$ | $CH_3$ | O | 0 |
| A-3761 | H | H | H | H | H | $CH_2OCH_2CH_3$ | $CH_3$ | $CH_3$ | O | 0 |
| A-3762 | H | H | H | H | H | $CH_2CH_2OCH_3$ | $CH_3$ | $CH_3$ | O | 0 |
| A-3763 | H | H | H | H | H | $CH_2CH_2OCH_2CH_3$ | $CH_3$ | $CH_3$ | O | 0 |
| A-3764 | H | H | H | H | H | $CF_3$ | $CH_3$ | $CH_3$ | O | 0 |
| A-3765 | H | H | H | H | H | $CHF_2$ | $CH_3$ | $CH_3$ | O | 0 |
| A-3766 | H | H | H | H | H | $CH_2CF_3$ | $CH_3$ | $CH_3$ | O | 0 |
| A-3767 | H | H | H | H | H | $CH_2CHF_2$ | $CH_3$ | $CH_3$ | O | 0 |
| A-3768 | H | H | H | H | H | $CH_2CClF_2$ | $CH_3$ | $CH_3$ | O | 0 |
| A-3769 | H | H | H | H | H | $CH_2CBrF_2$ | $CH_3$ | $CH_3$ | O | 0 |
| A-3770 | H | H | H | H | H | $CF_2CF_3$ | $CH_3$ | $CH_3$ | O | 0 |
| A-3771 | H | H | H | H | H | $CF_2CHF_2$ | $CH_3$ | $CH_3$ | O | 0 |
| A-3772 | H | H | H | H | H | $CH_2CH_2CF_3$ | $CH_3$ | $CH_3$ | O | 0 |
| A-3773 | H | H | H | H | H | $CH_2CF_2CF_3$ | $CH_3$ | $CH_3$ | O | 0 |
| A-3774 | H | H | H | H | H | $CH_2CF_2CHF_2$ | $CH_3$ | $CH_3$ | O | 0 |
| A-3775 | H | H | H | H | H | $CF_2CHFCF_3$ | $CH_3$ | $CH_3$ | O | 0 |
| A-3776 | H | H | H | H | H | $CF_2CF_2CF_3$ | $CH_3$ | $CH_3$ | O | 0 |
| A-3777 | H | H | H | H | H | $CH_2CF_2CF_2CF_2$ | $CH_3$ | $CH_3$ | O | 0 |

TABLE 63

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-3778 | H | H | H | H | H | $CH_2CF_2CHFCF_3$ | $CH_3$ | $CH_3$ | O | 0 |
| A-3779 | H | H | H | H | H | $CH_2CF_2CH_2CF_3$ | $CH_3$ | $CH_3$ | O | 0 |
| A-3780 | H | H | H | H | H | $CH_2CH_2CF_2CF_3$ | $CH_3$ | $CH_3$ | O | 0 |
| A-3781 | H | H | H | H | H | $CF_2CF_2CF_2CF_3$ | $CH_3$ | $CH_3$ | O | 0 |
| A-3782 | H | H | H | H | H | $CH_2CH_2CH(CF_3)_2$ | $CH_3$ | $CH_3$ | O | 0 |
| A-3783 | H | H | H | H | H | $CF_2CF_2CF_2CF_2CF_3$ | $CH_3$ | $CH_3$ | O | 0 |
| A-3784 | H | H | H | H | H | $CH_2CF_2CF_2CF_2CF_3$ | $CH_3$ | $CH_3$ | O | 0 |
| A-3785 | H | H | H | H | H | $CH_2CH_2CH_2CH_2CF_3$ | $CH_3$ | $CH_3$ | O | 0 |
| A-3786 | H | H | H | H | H | $CH_2CF_2CF_2CF_2CHF_2$ | $CH_3$ | $CH_3$ | O | 0 |
| A-3787 | H | H | H | H | H | $CH_2CF_2CF(CF_3)CF_2C(CF_3)_3$ | $CH_3$ | $CH_3$ | O | 0 |
| A-3788 | H | H | H | H | H | $CF_2CHFOCH_3$ | $CH_3$ | $CH_3$ | O | 0 |
| A-3789 | H | H | H | H | H | $CF_2CHFOCH_2CH_3$ | $CH_3$ | $CH_3$ | O | 0 |
| A-3790 | H | H | H | H | H | $CH_2CH_2OCH_2CF_3$ | $CH_3$ | $CH_3$ | O | 0 |
| A-3791 | H | H | H | H | H | $CF_2CHFOCF_3$ | $CH_3$ | $CH_3$ | O | 0 |
| A-3792 | H | H | H | H | H | $CF_2CHFOCF_2CF_3$ | $CH_3$ | $CH_3$ | O | 0 |
| A-3793 | H | H | H | H | H | $CF_2CHFOCF_2CF_2CF_3$ | $CH_3$ | $CH_3$ | O | 0 |
| A-3794 | H | H | H | H | H | $CH_2CH=CH_2$ | $CH_3$ | $CH_3$ | O | 0 |
| A-3795 | H | H | H | H | H | $CH_2CH=CHCl$ | $CH_3$ | $CH_3$ | O | 0 |
| A-3796 | H | H | H | H | H | $CH_2CH=CCl_2$ | $CH_3$ | $CH_3$ | O | 0 |
| A-3797 | H | H | H | H | H | $CH_2CH_2CF=CF_2$ | $CH_3$ | $CH_3$ | O | 0 |
| A-3798 | H | H | H | H | H | $CH_2CH_2CH=CF_2$ | $CH_3$ | $CH_3$ | O | 0 |
| A-3799 | H | H | H | H | H | $CH_2C\equiv CH$ | $CH_3$ | $CH_3$ | O | 0 |
| A-3800 | H | H | H | H | H | $CH_2C\equiv CCH_3$ | $CH_3$ | $CH_3$ | O | 0 |
| A-3801 | H | H | H | H | H | $CH_2C\equiv CCF_3$ | $CH_3$ | $CH_3$ | O | 0 |
| A-3802 | H | H | H | H | H | $CH_2C\equiv CI$ | $CH_3$ | $CH_3$ | O | 0 |
| A-3803 | H | H | H | H | H | cyclobutyl | $CH_3$ | $CH_3$ | O | 0 |
| A-3804 | H | H | H | H | H | cyclopentyl | $CH_3$ | $CH_3$ | O | 0 |
| A-3805 | H | H | H | H | H | cyclohexyl | $CH_3$ | $CH_3$ | O | 0 |
| A-3806 | H | H | H | H | H | 4,4-difluorocyclohexyl | $CH_3$ | $CH_3$ | O | 0 |
| A-3807 | H | H | H | H | H | $CH_2$(cyclopropyl) | $CH_3$ | $CH_3$ | O | 0 |
| A-3808 | H | H | H | H | H | $CH_2$(cyclobutyl) | $CH_3$ | $CH_3$ | O | 0 |
| A-3809 | H | H | H | H | H | $CH_2$(cyclopentyl) | $CH_3$ | $CH_3$ | O | 0 |
| A-3810 | H | H | H | H | H | $CH_2CH_2$(cyclopropyl) | $CH_3$ | $CH_3$ | O | 0 |
| A-3811 | H | H | H | H | H | $CH_2$(2,2-difluorocyclopropyl) | $CH_3$ | $CH_3$ | O | 0 |
| A-3812 | H | H | H | H | H | $CH_2$(2,2-dichlorocyclopropyl) | $CH_3$ | $CH_3$ | O | 0 |
| A-3813 | H | H | H | H | H | $CH_2$(4,4-difluorocyclohexyl) | $CH_3$ | $CH_3$ | O | 0 |

TABLE 63-continued

| Compound | R¹ | R² | R³ | R⁴ | R⁵ | R⁶ | R⁷ | R⁸ | X | n |
|---|---|---|---|---|---|---|---|---|---|---|
| A-3814 | H | H | H | H | H | CH₂CH₂(2,2-difluorocyclopropyl) | CH₃ | CH₃ | O | 0 |
| A-3815 | H | H | H | H | H | CH₂CH₂(2,2-dichlorocyclopropyl) | CH₃ | CH₃ | O | 0 |
| A-3816 | H | H | H | H | H | CH₂SCH₃ | CH₃ | CH₃ | O | 0 |
| A-3817 | H | H | H | H | H | CH₂SCH₂CH₃ | CH₃ | CH₃ | O | 0 |
| A-3818 | H | H | H | H | H | CH₂CH₂SCH₃ | CH₃ | CH₃ | O | 0 |
| A-3819 | H | H | H | H | H | CH₂CH₂SCH₂CH₃ | CH₃ | CH₃ | O | 0 |
| A-3820 | H | H | H | H | H | CH₂CH₂CH₂SCH₃ | CH₃ | CH₃ | O | 0 |
| A-3821 | H | H | H | H | H | CH₂CH₂CH₂SCH₂CH₃ | CH₃ | CH₃ | O | 0 |
| A-3822 | H | H | H | H | H | CH(CH₃)SCH₃ | CH₃ | CH₃ | O | 0 |
| A-3823 | H | H | H | H | H | CH(CH₃)SCH₂CH₃ | CH₃ | CH₃ | O | 0 |
| A-3824 | H | H | H | H | H | CH₂CH(CH₃)SCH₃ | CH₃ | CH₃ | O | 0 |
| A-3825 | H | H | H | H | H | CH₂CH(CH₃)SCH₂CH₃ | CH₃ | CH₃ | O | 0 |
| A-3826 | H | H | H | H | H | CH(CH₃)CH₂CH₂SCH₃ | CH₃ | CH₃ | O | 0 |
| A-3827 | H | H | H | H | H | CH(CH₃)CH₂CH₂SCH₂CH₃ | CH₃ | CH₃ | O | 0 |
| A-3828 | H | H | H | H | H | CH₂CH(CH₃)CH₂SCH₃ | CH₃ | CH₃ | O | 0 |
| A-3829 | H | H | H | H | H | CH₂CH(CH₃)CH₂SCH₂CH₃ | CH₃ | CH₃ | O | 0 |
| A-3830 | H | H | H | H | H | CH₂CH₂CH(CH₃)SCH₃ | CH₃ | CH₃ | O | 0 |
| A-3831 | H | H | H | H | H | CH₂CH₂CH(CH₃)SCH₂CH₃ | CH₃ | CH₃ | O | 0 |
| A-3832 | H | H | H | H | H | CH₂SOCH₃ | CH₃ | CH₃ | O | 0 |
| A-3833 | H | H | H | H | H | CH₂CH₂SOCH₃ | CH₃ | CH₃ | O | 0 |
| A-3834 | H | H | H | H | H | CH₂CH₂CH₂SOCH₃ | CH₃ | CH₃ | O | 0 |
| A-3835 | H | H | H | H | H | CH(CH₃)SOCH₃ | CH₃ | CH₃ | O | 0 |
| A-3836 | H | H | H | H | H | CH₂CH(CH₃)SOCH₃ | CH₃ | CH₃ | O | 0 |
| A-3837 | H | H | H | H | H | CH(CH₃)CH₂CH₂SOCH₃ | CH₃ | CH₃ | O | 0 |
| A-3838 | H | H | H | H | H | CH₂CH(CH₃)CH₂SOCH₃ | CH₃ | CH₃ | O | 0 |

TABLE 64

| Compound | R¹ | R² | R³ | R⁴ | R⁵ | R⁶ | R⁷ | R⁸ | X | n |
|---|---|---|---|---|---|---|---|---|---|---|
| A-3839 | H | H | H | H | H | CH₂CH₂CH(CH₃)SOCH₃ | CH₃ | CH₃ | O | 0 |
| A-3840 | H | H | H | H | H | CH₂SO₂CH₃ | CH₃ | CH₃ | O | 0 |
| A-3841 | H | H | H | H | H | CH₂CH₂SO₂CH₃ | CH₃ | CH₃ | O | 0 |
| A-3842 | H | H | H | H | H | CH₂CH₂CH₂SO₂CH₃ | CH₃ | CH₃ | O | 0 |
| A-3843 | H | H | H | H | H | CH(CH₃)SO₂CH₃ | CH₃ | CH₃ | O | 0 |
| A-3844 | H | H | H | H | H | CH₂CH(CH₃)SO₂CH₃ | CH₃ | CH₃ | O | 0 |
| A-3845 | H | H | H | H | H | CH(CH₃)CH₂CH₂SO₂CH₃ | CH₃ | CH₃ | O | 0 |
| A-3846 | H | H | H | H | H | CH₂CH(CH₃)CH₂SO₂CH₃ | CH₃ | CH₃ | O | 0 |
| A-3847 | H | H | H | H | H | CH₂CH₂CH(CH₃)SO₂CH₃ | CH₃ | CH₃ | O | 0 |
| A-3848 | H | H | H | H | H | CH₂SCF₃ | CH₃ | CH₃ | O | 0 |
| A-3849 | H | H | H | H | H | CH₂SCHF₂ | CH₃ | CH₃ | O | 0 |
| A-3850 | H | H | H | H | H | CH₂SCH₂CF₃ | CH₃ | CH₃ | O | 0 |
| A-3851 | H | H | H | H | H | CH₂SCH₂CHF₂ | CH₃ | CH₃ | O | 0 |
| A-3852 | H | H | H | H | H | CH₂SCF₂CF₃ | CH₃ | CH₃ | O | 0 |
| A-3853 | H | H | H | H | H | CH₂CH₂SCF₃ | CH₃ | CH₃ | O | 0 |
| A-3854 | H | H | H | H | H | CH₂CH₂SCH₂CF₃ | CH₃ | CH₃ | O | 0 |
| A-3855 | H | H | H | H | H | CH₂CH₂CH₂SCF₃ | CH₃ | CH₃ | O | 0 |
| A-3856 | H | H | H | H | H | CH₂CH₂CH₂SCH₂CF₃ | CH₃ | CH₃ | O | 0 |
| A-3857 | H | H | H | H | H | CH(CH₃)SCF₃ | CH₃ | CH₃ | O | 0 |
| A-3858 | H | H | H | H | H | CH(CH₃)SCH₂CF₃ | CH₃ | CH₃ | O | 0 |
| A-3859 | H | H | H | H | H | CH₂CH(CH₃)SCF₃ | CH₃ | CH₃ | O | 0 |
| A-3860 | H | H | H | H | H | CH₂CH(CH₃)SCH₂CF₃ | CH₃ | CH₃ | O | 0 |
| A-3861 | H | H | H | H | H | CH(CH₃)CH₂CH₂SCF₃ | CH₃ | CH₃ | O | 0 |
| A-3862 | H | H | H | H | H | CH(CH₃)CH₂CH₂SCH₂CF₃ | CH₃ | CH₃ | O | 0 |
| A-3863 | H | H | H | H | H | CH₂CH(CH₃)CH₂SCF₃ | CH₃ | CH₃ | O | 0 |
| A-3864 | H | H | H | H | H | CH₂CH(CH₃)CH₂SCH₂CF₃ | CH₃ | CH₃ | O | 0 |
| A-3865 | H | H | H | H | H | CH₂CH₂CH(CH₃)SCF₃ | CH₃ | CH₃ | O | 0 |
| A-3866 | H | H | H | H | H | CH₂CH₂CH(CH₃)SCH₂CF₃ | CH₃ | CH₃ | O | 0 |
| A-3867 | H | H | H | H | H | CH₂SOCF₃ | CH₃ | CH₃ | O | 0 |
| A-3868 | H | H | H | H | H | CH₂CH₂SOCF₃ | CH₃ | CH₃ | O | 0 |
| A-3869 | H | H | H | H | H | CH₂CH₂CH₂SOCF₃ | CH₃ | CH₃ | O | 0 |
| A-3870 | H | H | H | H | H | CH(CH₃)SOCF₃ | CH₃ | CH₃ | O | 0 |
| A-3871 | H | H | H | H | H | CH₂CH(CH₃)SOCF₃ | CH₃ | CH₃ | O | 0 |
| A-3872 | H | H | H | H | H | CH(CH₃)CH₂CH₂SOCF₃ | CH₃ | CH₃ | O | 0 |
| A-3873 | H | H | H | H | H | CH₂CH(CH₃)CH₂SOCF₃ | CH₃ | CH₃ | O | 0 |
| A-3874 | H | H | H | H | H | CH₂CH₂CH(CH₃)SOCF₃ | CH₃ | CH₃ | O | 0 |
| A-3875 | H | H | H | H | H | CH₂SO₂CF₃ | CH₃ | CH₃ | O | 0 |
| A-3876 | H | H | H | H | H | CH₂CH₂SO₂CF₃ | CH₃ | CH₃ | O | 0 |
| A-3877 | H | H | H | H | H | CH₂CH₂CH₂SO₂CF₃ | CH₃ | CH₃ | O | 0 |
| A-3878 | H | H | H | H | H | CH(CH₃)SO₂CF₃ | CH₃ | CH₃ | O | 0 |
| A-3879 | H | H | H | H | H | CH₂CH(CH₃)SO₂CF₃ | CH₃ | CH₃ | O | 0 |
| A-3880 | H | H | H | H | H | CH(CH₃)CH₂CH₂SO₂CF₃ | CH₃ | CH₃ | O | 0 |
| A-3881 | H | H | H | H | H | CH₂CH(CH₃)CH₂SO₂CF₃ | CH₃ | CH₃ | O | 0 |
| A-3882 | H | H | H | H | H | CH₂CH₂CH(CH₃)SO₂CF₃ | CH₃ | CH₃ | O | 0 |
| A-3883 | H | H | H | H | H | CH₂C(=O)CH₃ | CH₃ | CH₃ | O | 0 |

TABLE 64-continued

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-3884 | H | H | H | H | H | $CH_2C(=O)CH_2CH_3$ | $CH_3$ | $CH_3$ | O | 0 |
| A-3885 | H | H | H | H | H | $CH_2C(=O)C(CH_3)_3$ | $CH_3$ | $CH_3$ | O | 0 |
| A-3886 | H | H | H | H | H | $CH_2CH_2C(=O)CH_3$ | $CH_3$ | $CH_3$ | O | 0 |
| A-3887 | H | H | H | H | H | $CH_2CH_2C(=O)C(CH_3)_3$ | $CH_3$ | $CH_3$ | O | 0 |
| A-3888 | H | H | H | H | H | $CH_2C(=O)CF_3$ | $CH_3$ | $CH_3$ | O | 0 |
| A-3889 | H | H | H | H | H | $CH_2CH_2C(=O)CF_3$ | $CH_3$ | $CH_3$ | O | 0 |
| A-3890 | H | H | H | H | H | $CH_2C(=O)OCH_3$ | $CH_3$ | $CH_3$ | O | 0 |
| A-3891 | H | H | H | H | H | $CH_2C(=O)OCH_2CH_3$ | $CH_3$ | $CH_3$ | O | 0 |
| A-3892 | H | H | H | H | H | $CH_2C(=O)OC(CH_3)_3$ | $CH_3$ | $CH_3$ | O | 0 |
| A-3893 | H | H | H | H | H | $CH_2CH_2C(=O)OCH_3$ | $CH_3$ | $CH_3$ | O | 0 |
| A-3894 | H | H | H | H | H | $CH_2CH_2C(=O)OCH_2CH_3$ | $CH_3$ | $CH_3$ | O | 0 |
| A-3895 | H | H | H | H | H | $CH_2CH_2C(=O)OC(CH_3)_3$ | $CH_3$ | $CH_3$ | O | 0 |
| A-3896 | H | H | H | H | H | $CH_2C(=O)NH_2$ | $CH_3$ | $CH_3$ | O | 0 |
| A-3897 | H | H | H | H | H | $CH_2CH_2C(=O)NH_2$ | $CH_3$ | $CH_3$ | O | 0 |
| A-3898 | H | H | H | H | H | $CH_2C(=O)NHCH_3$ | $CH_3$ | $CH_3$ | O | 0 |
| A-3899 | H | H | H | H | H | $CH_2C(=O)NHCH(CH_3)_2$ | $CH_3$ | $CH_3$ | O | 0 |

TABLE 65

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-3900 | H | H | H | H | H | $CH_2CH_2C(=O)NHCH_3$ | $CH_3$ | $CH_3$ | O | 0 |
| A-3901 | H | H | H | H | H | $CH_2CH_2C(=O)NHCH(CH_3)_2$ | $CH_3$ | $CH_3$ | O | 0 |
| A-3902 | H | H | H | H | H | $CH_2C(=O)NHCH_2CHF_2$ | $CH_3$ | $CH_3$ | O | 0 |
| A-3903 | H | H | H | H | H | $CH_2C(=O)NHCH_2CF_3$ | $CH_3$ | $CH_3$ | O | 0 |
| A-3904 | H | H | H | H | H | $CH_2CH_2C(=O)NHCH_2CHF_2$ | $CH_3$ | $CH_3$ | O | 0 |
| A-3905 | H | H | H | H | H | $CH_2CH_2C(=O)NHCH_2CF_3$ | $CH_3$ | $CH_3$ | O | 0 |
| A-3906 | H | H | H | H | H | $CH_2C(=O)N(CH_3)_2$ | $CH_3$ | $CH_3$ | O | 0 |
| A-3907 | H | H | H | H | H | $CH_2C(=O)N(CH_2CH_3)_2$ | $CH_3$ | $CH_3$ | O | 0 |
| A-3908 | H | H | H | H | H | $CH_2CH_2C(=O)N(CH_3)_2$ | $CH_3$ | $CH_3$ | O | 0 |
| A-3909 | H | H | H | H | H | $CH_2CH_2C(=O)N(CH_2CH_3)_2$ | $CH_3$ | $CH_3$ | O | 0 |
| A-3910 | H | H | H | H | H | $CH_2CH_2OH$ | $CH_3$ | $CH_3$ | O | 0 |
| A-3911 | H | H | H | H | H | $CH_2CH(OH)CH_3$ | $CH_3$ | $CH_3$ | O | 0 |
| A-3912 | H | H | H | H | H | $CH_2CH_2CH_2OH$ | $CH_3$ | $CH_3$ | O | 0 |
| A-3913 | H | H | H | H | H | $CH_2CH(OH)CH_2CH_3$ | $CH_3$ | $CH_3$ | O | 0 |
| A-3914 | H | H | H | H | H | $CH_2CH(OH)C(CH_3)_3$ | $CH_3$ | $CH_3$ | O | 0 |
| A-3915 | H | H | H | H | H | $CH_2CH_2CH(OH)CH_3$ | $CH_3$ | $CH_3$ | O | 0 |
| A-3916 | H | H | H | H | H | $CH_2CH_2CH(OH)C(CH_3)_3$ | $CH_3$ | $CH_3$ | O | 0 |
| A-3917 | H | H | H | H | H | $CH_2C(=NOH)CH_3$ | $CH_3$ | $CH_3$ | O | 0 |
| A-3918 | H | H | H | H | H | $CH_2C(=NOH)CH_2CH_3$ | $CH_3$ | $CH_3$ | O | 0 |
| A-3919 | H | H | H | H | H | $CH_2C(=NOH)C(CH_3)_3$ | $CH_3$ | $CH_3$ | O | 0 |
| A-3920 | H | H | H | H | H | $CH_2C(=NOCH_3)CH_3$ | $CH_3$ | $CH_3$ | O | 0 |
| A-3921 | H | H | H | H | H | $CH_2C(=NOCH_3)CH_2CH_3$ | $CH_3$ | $CH_3$ | O | 0 |
| A-3922 | H | H | H | H | H | $CH_2C(=NOCH_2CH_3)CH_3$ | CH | $CH_3$ | O | 0 |
| A-3923 | H | H | H | H | H | $CH_2C(=NOCH_2CH_3)CH_2CH_3$ | $CH_3$ | $CH_3$ | O | 0 |
| A-3924 | H | H | H | H | H | $CH_2C(=NOCH_2CF_3)CH_3$ | $CH_3$ | $CH_3$ | O | 0 |
| A-3925 | H | H | H | H | H | $CH_2C(=NOCH_2CF_3)CH_2CH_3$ | $CH_3$ | $CH_3$ | O | 0 |
| A-3926 | H | H | H | H | H | $CH_2Ph$ | $CH_3$ | $CH_3$ | O | 0 |
| A-3927 | H | H | H | H | H | $CH_2(2-F)Ph$ | $CH_3$ | $CH_3$ | O | 0 |
| A-3928 | H | H | H | H | H | $CH_2(3-F)Ph$ | $CH_3$ | $CH_3$ | O | 0 |
| A-3929 | H | H | H | H | H | $CH_2(4-F)Ph$ | $CH_3$ | $CH_3$ | O | 0 |
| A-3930 | H | H | H | H | H | $CH_2(2-Cl)Ph$ | $CH_3$ | $CH_3$ | O | 0 |
| A-3931 | H | H | H | H | H | $CH_2(3-Cl)Ph$ | $CH_3$ | $CH_3$ | O | 0 |
| A-3932 | H | H | H | H | H | $CH_2(4-Cl)Ph$ | $CH_3$ | $CH_3$ | O | 0 |
| A-3933 | H | H | H | H | H | $CH_2(2-CF_3)Ph$ | $CH_3$ | $CH_3$ | O | 0 |
| A-3934 | H | H | H | H | H | $CH_2(3-CF_3)Ph$ | $CH_3$ | $CH_3$ | O | 0 |
| A-3935 | H | H | H | H | H | $CH_2(4-CF_3)Ph$ | $CH_3$ | $CH_3$ | O | 0 |
| A-3936 | H | H | H | H | H | $CH_2(naphthalen-1-yl)$ | $CH_3$ | $CH_3$ | O | 0 |
| A-3937 | H | H | H | H | H | $CH_2(naphthalen-2-yl)$ | $CH_3$ | $CH_3$ | O | 0 |
| A-3938 | H | H | H | H | H | $CH_2CH_2Ph$ | $CH_3$ | $CH_3$ | O | 0 |
| A-3939 | H | H | H | H | H | H | $CH_2CN$ | $CH_2CN$ | O | 0 |
| A-3940 | H | H | H | H | H | $CH_3$ | $CH_2CN$ | $CH_2CN$ | O | 0 |
| A-3941 | H | H | H | H | H | $CH_2CH_3$ | $CH_2CN$ | $CH_2CN$ | O | 0 |
| A-3942 | H | H | H | H | H | $CH(CH_3)_2$ | $CH_2CN$ | $CH_2CN$ | O | 0 |
| A-3943 | H | H | H | H | H | $CH_2CH_2CH_3$ | $CH_2CN$ | $CH_2CN$ | O | 0 |
| A-3944 | H | H | H | H | H | $CH_2CH(CH_3)_2$ | $CH_2CN$ | $CH_2CN$ | O | 0 |
| A-3945 | H | H | H | H | H | $CH(CH_3)CH_2CH_3$ | $CH_2CN$ | $CH_2CN$ | O | 0 |
| A-3946 | H | H | H | H | H | $CH_2C(CH_3)_3$ | $CH_2CN$ | $CH_2CN$ | O | 0 |
| A-3947 | H | H | H | H | H | $CH_2(CH_2)_2CH_3$ | $CH_3CN$ | $CH_2CN$ | O | 0 |
| A-3948 | H | H | H | H | H | $CH_2(CH_2)_3CH_3$ | $CH_2CN$ | $CH_2CN$ | O | 0 |
| A-3949 | H | H | H | H | H | $CF_3$ | $CH_2CN$ | $CH_2CN$ | O | 0 |
| A-3950 | H | H | H | H | H | $CHF_2$ | $CH_2CN$ | $CH_2CN$ | O | 0 |
| A-3951 | H | H | H | H | H | $CH_2CF_3$ | $CH_2CN$ | $CH_2CN$ | O | 0 |
| A-3952 | H | H | H | H | H | $CH_2CHF_2$ | $CH_2CN$ | $CH_2CN$ | O | 0 |
| A-3953 | H | H | H | H | H | $CH_2CClF_2$ | $CH_2CN$ | $CH_2CN$ | O | 0 |

TABLE 65-continued

| Compound | R¹ | R² | R³ | R⁴ | R⁵ | R⁶ | R⁷ | R⁸ | X | n |
|---|---|---|---|---|---|---|---|---|---|---|
| A-3954 | H | H | H | H | H | CH₂CBrF₂ | CH₂CN | CH₂CN | O | 0 |
| A-3955 | H | H | H | H | H | CF₂CF₃ | CH₂CN | CH₂CN | O | 0 |
| A-3956 | H | H | H | H | H | CF₂CHF₂ | CH₂CN | CH₂CN | O | 0 |
| A-3957 | H | H | H | H | H | CH₂CH₂CF₃ | CH₂CN | CH₂CN | O | 0 |
| A-3958 | H | H | H | H | H | CH₂CF₂CF₃ | CH₂CN | CH₂CN | O | 0 |
| A-3959 | H | H | H | H | H | CH₂CF₂CHF₂ | CH₂CN | CH₂CN | O | 0 |
| A-3960 | H | H | H | H | H | CF₂CHFCF₃ | CH₂CN | CH₂CN | O | 0 |

TABLE 66

| Compound | R¹ | R² | R³ | R⁴ | R⁵ | R⁶ | R⁷ | R⁸ | X | n |
|---|---|---|---|---|---|---|---|---|---|---|
| A-3961 | H | H | H | H | H | CF₂CF₂CF₃ | CH₂CN | CH₂CN | O | 0 |
| A-3962 | H | H | H | H | H | CH₂CF₂CF₂CF₃ | CH₂CN | CH₂CN | O | 0 |
| A-3963 | H | H | H | H | H | CH₂CF₂CHFCF₃ | CH₂CN | CH₂CN | O | 0 |
| A-3964 | H | H | H | H | H | CH₂CH₂CH₂CF₃ | CH₂CN | CH₂CN | O | 0 |
| A-3965 | H | H | H | H | H | CH₂CH₂CF₂CF₃ | CH₂CN | CH₂CN | O | 0 |
| A-3966 | H | H | H | H | H | CF₂CF₂CF₂CF₃ | CH₂CN | CH₂CN | O | 0 |
| A-3967 | H | H | H | H | H | CH₂CH₂CH(CF₃)₂ | CH₂CN | CH₂CN | O | 0 |
| A-3968 | H | H | H | H | H | CF₂CF₂CF₂CF₂CF₃ | CH₂CN | CH₂CN | O | 0 |
| A-3969 | H | H | H | H | H | CH₂CF₂CF₂CF₂CF₃ | CH₂CN | CH₂CN | O | 0 |
| A-3970 | H | H | H | H | H | CH₂CH₂CH₂CH₂CF₃ | CH₂CN | CH₂CN | O | 0 |
| A-3971 | H | H | H | H | H | CH₂CF₂CF₂CF₂CHF₂ | CH₂CN | CH₂CN | O | 0 |
| A-3972 | H | H | H | H | H | CH₂CH₂OCH₂CF₃ | CH₂CN | CH₂CN | O | 0 |
| A-3973 | H | H | H | H | H | CF₂CHFOCF₃ | CH₂CN | CH₂CN | O | 0 |
| A-3974 | H | H | H | H | H | CF₂CHFOCF₂CF₃ | CH₂CN | CH₂CN | O | 0 |
| A-3975 | H | H | H | H | H | CH₂CH₂CF=CF₂ | CH₂CN | CH₂CN | O | 0 |
| A-3976 | H | H | H | H | H | CH₂CH₂CH=CF₂ | CH₂CN | CH₂CN | O | 0 |
| A-3977 | H | H | H | H | H | CH₂C≡CCH₃ | CH₂CN | CH₂CN | O | 0 |
| A-3978 | H | H | H | H | H | CH₂C≡CCF₃ | CH₂CN | CH₂CN | O | 0 |
| A-3979 | H | H | H | H | H | CH₂C≡CI | CH₂CN | CH₂CN | O | 0 |
| A-3980 | H | H | H | H | H | CH₂(2,2-difluorocyclopropyl) | CH₂CN | CH₂CN | O | 0 |
| A-3981 | H | H | H | H | H | CH₂(2,2-dichlorocyclopropyl) | CH₂CN | CH₂CN | O | 0 |
| A-3982 | H | H | H | H | H | CH₂CH₂(2,2-difluorocyclopropyl) | CH₂CN | CH₂CN | O | 0 |
| A-3983 | H | H | H | H | H | CH₂CH₂(2,2-dichlorocyclopropyl) | CH₂CN | CH₂CN | O | 0 |
| A-3984 | H | H | H | H | H | CH₂SCH₃ | CH₂CN | CH₂CN | O | 0 |
| A-3985 | H | H | H | H | H | CH₂SCH₂CH₃ | CH₂CN | CH₂CN | O | 0 |
| A-3986 | H | H | H | H | H | CH₂CH₂SCH₃ | CH₂CN | CH₂CN | O | 0 |
| A-3987 | H | H | H | H | H | CH₂SOCH₃ | CH₂CN | CH₂CN | O | 0 |
| A-3988 | H | H | H | H | H | CH₂CH₂SOCH₃ | CH₂CN | CH₂CN | O | 0 |
| A-3989 | H | H | H | H | H | CH₂SO₂CH₃ | CH₂CN | CH₂CN | O | 0 |
| A-3990 | H | H | H | H | H | CH₂CH₂SO₂CH₃ | CH₂CN | CH₂CN | O | 0 |
| A-3991 | H | H | H | H | H | CH₂SCF₃ | CH₂CN | CH₂CN | O | 0 |
| A-3992 | H | H | H | H | H | CH₂SCHF₂ | CH₂CN | CH₂CN | O | 0 |
| A-3993 | H | H | H | H | H | CH₂SCH₂CF₃ | CH₂CN | CH₂CN | O | 0 |
| A-3994 | H | H | H | H | H | CH₂SCH₂CHF₂ | CH₂CN | CH₂CN | O | 0 |
| A-3995 | H | H | H | H | H | CH₂SCF₂CF₃ | CH₂CN | CH₂CN | O | 0 |
| A-3996 | H | H | H | H | H | CH₂CH₂SCF₃ | CH₂CN | CH₂CN | O | 0 |
| A-3997 | H | H | H | H | H | CH₂SOCF₃ | CH₂CN | CH₂CN | O | 0 |
| A-3998 | H | H | H | H | H | CH₂CH₂SOCF₃ | CH₂CN | CH₂CN | O | 0 |
| A-3999 | H | H | H | H | H | CH₂CH₂CH₂SOCF₃ | CH₂CN | CH₂CN | O | 0 |
| A-4000 | H | H | H | H | H | CH₂SO₂CF₃ | CH₂CN | CH₂CN | O | 0 |
| A-4001 | H | H | H | H | H | CH₂CH₂SO₂CF₃ | CH₂CN | CH₂CN | O | 0 |
| A-4002 | H | H | H | H | H | CH₂CH₂CH₂SO₂CF₃ | CH₂CN | CH₂CN | O | 0 |
| A-4003 | H | H | H | H | H | CH₂C(=O)NHCH₂CHF₂ | CH₂CN | CH₂CN | O | 0 |
| A-4004 | H | H | H | H | H | CH₂C(=O)NHCH₂CF₃ | CH₂CN | CH₂CN | O | 0 |
| A-4005 | H | H | H | H | H | H | —CH₂CH₂—O—CH₂CH₂— | | O | 0 |
| A-4006 | H | H | H | H | H | CH₃ | —CH₂CH₂—O—CH₂CH₂— | | O | 0 |
| A-4007 | H | H | H | H | H | CH₂CH₃ | —CH₂CH₂—O—CH₂CH₂— | | O | 0 |
| A-4008 | H | H | H | H | H | CH(CH₃)₂ | —CH₂CH₂—O—CH₂CH₂— | | O | 0 |
| A-4009 | H | H | H | H | H | CH₂CH₂CH₃ | —CH₂CH₂—O—CH₂CH₂— | | O | 0 |
| A-4010 | H | H | H | H | H | CH₂CH(CH₃)₂ | —CH₂CH₂—O—CH₂CH₂— | | O | 0 |
| A-4011 | H | H | H | H | H | CH(CH₃)CH₂CH₃ | —CH₂CH₂—O—CH₂CH₂— | | O | 0 |
| A-4012 | H | H | H | H | H | CH₂C(CH₃)₃ | —CH₂CH₂—O—CH₂CH₂— | | O | 0 |
| A-4013 | H | H | H | H | H | CH₂(CH₂)₂CH₃ | —CH₂CH₂—O—CH₂CH₂— | | O | 0 |
| A-4014 | H | H | H | H | H | CH₂(CH₂)₃CH₃ | —CH₂CH₂—O—CH₂CH₂— | | O | 0 |
| A-4015 | H | H | H | H | H | CF₃ | —CH₂CH₂—O—CH₂CH₂— | | O | 0 |
| A-4016 | H | H | H | H | H | CHF₂ | —CH₂CH₂—O—CH₂CH₂— | | O | 0 |
| A-4017 | H | H | H | H | H | CH₂CF₃ | —CH₂CH₂—O—CH₂CH₂— | | O | 0 |
| A-4018 | H | H | H | H | H | CH₂CHF₂ | —CH₂CH₂—O—CH₂CH₂— | | O | 0 |
| A-4019 | H | H | H | H | H | CH₂CClF₂ | —CH₂CH₂—O—CH₂CH₂— | | O | 0 |
| A-4020 | H | H | H | H | H | CH₂CBrF₂ | —CH₂CH₂—O—CH₂CH₂— | | O | 0 |
| A-4021 | H | H | H | H | H | CF₂CF₃ | —CH₂CH₂—O—CH₂CH₂— | | O | 0 |

TABLE 67

| Compound | R¹ | R² | R³ | R⁴ | R⁵ | R⁶ | R⁷ | R⁸ | X | n |
|---|---|---|---|---|---|---|---|---|---|---|
| A-4022 | H | H | H | H | H | $CF_3CHF_2$ | $-CH_2CH_2-O-CH_2CH_2-$ | | O | 0 |
| A-4023 | H | H | H | H | H | $CH_2CH_2CF_3$ | $-CH_2CH_2-O-CH_2CH_2-$ | | O | 0 |
| A-4024 | H | H | H | H | H | $CH_2CF_2CF_3$ | $-CH_2CH_2-O-CH_2CH_2-$ | | O | 0 |
| A-4025 | H | H | H | H | H | $CH_2CF_2CHF_2$ | $-CH_2CH_2-O-CH_2CH_2-$ | | O | 0 |
| A-4026 | H | H | H | H | H | $CF_2CHFCF_3$ | $-CH_2CH_2-O-CH_2CH_2-$ | | O | 0 |
| A-4027 | H | H | H | H | H | $CF_2CF_2CF_3$ | $-CH_2CH_2-O-CH_2CH_2-$ | | O | 0 |
| A-4028 | H | H | H | H | H | $CH_2CF_2CF_2CF_3$ | $-CH_2CH_2-O-CH_2CH_2-$ | | O | 0 |
| A-4029 | H | H | H | H | H | $CH_2CH_2CH_2CF_3$ | $-CH_2CH_2-O-CH_2CH_2-$ | | O | 0 |
| A-4030 | H | H | H | H | H | $CH_2CH_2CF_2CF_3$ | $-CH_2CH_2-O-CH_2CH_2-$ | | O | 0 |
| A-4031 | H | H | H | H | H | $CF_2CF_2CF_2CF_3$ | $-CH_2CH_2-O-CH_2CH_2-$ | | O | 0 |
| A-4032 | H | H | H | H | H | $CH_2CH_2CH(CF_3)_2$ | $-CH_2CH_2-O-CH_2CH_2-$ | | O | 0 |
| A-4033 | H | H | H | H | H | $CF_2CF_2CF_2CF_2CF_3$ | $-CH_2CH_2-O-CH_2CH_2-$ | | O | 0 |
| A-4034 | H | H | H | H | H | $CH_2CF_2CF_2CF_2CF_3$ | $-CH_2CH_2-O-CH_2CH_2-$ | | O | 0 |
| A-4035 | H | H | H | H | H | $CH_2CH_2CH_2CH_3CF_3$ | $-CH_2CH_2-O-CH_2CH_2-$ | | O | 0 |
| A-4036 | H | H | H | H | H | $CH_2CF_2CF_2CF_2CHF_2$ | $-CH_2CH_2-O-CH_2CH_2-$ | | O | 0 |
| A-4037 | H | H | H | H | H | $CH_2CH_2OCH_2CF_3$ | $-CH_2CH_2-O-CH_2CH_2-$ | | O | 0 |
| A-4038 | H | H | H | H | H | $CF_2CHFOCF_3$ | $-CH_2CH_2-O-CH_2CH_2-$ | | O | 0 |
| A-4039 | H | H | H | H | H | $CF_2CHFOCF_2CF_3$ | $-CH_2CH_2-O-CH_2CH_2-$ | | O | 0 |
| A-4040 | H | H | H | H | H | $CH_2CH_2CF=CF_2$ | $-CH_2CH_2-O-CH_2CH_2-$ | | O | 0 |
| A-4041 | H | H | H | H | H | $CH_2CH_2CH=CF_2$ | $-CH_2CH_2-O-CH_2CH_2-$ | | O | 0 |
| A-4042 | H | H | H | H | H | $CH_2C\equiv CCH_3$ | $-CH_2CH_2-O-CH_2CH_2-$ | | O | 0 |
| A-4043 | H | H | H | H | H | $CH_2C\equiv CCF_3$ | $-CH_2CH_2-O-CH_2CH_2-$ | | O | 0 |
| A-4044 | H | H | H | H | H | $CH_2C\equiv Cl$ | $-CH_2CH_2-O-CH_2CH_2-$ | | O | 0 |
| A-4045 | H | H | H | H | H | $CH_2$(2,2-difluorocyclopropyl) | $-CH_2CH_2-O-CH_2CH_2-$ | | O | 0 |
| A-4046 | H | H | H | H | H | $CH_2$(2,2-dichlorocyclopropyl) | $-CH_2CH_2-O-CH_2CH_2-$ | | O | 0 |
| A-4047 | H | H | H | H | H | $CH_2CH_2$(2,2-difluorocyclopropyl) | $-CH_2CH_2-O-CH_2CH_2-$ | | O | 0 |
| A-4048 | H | H | H | H | H | $CH_2CH_2$(2,2-diCHlorOcyclopropyl) | $-CH_2CH_2-O-CH_2CH_2-$ | | O | 0 |
| A-4049 | H | H | H | H | H | $CH_2SCH_3$ | $-CH_2CH_2-O-CH_2CH_2-$ | | O | 0 |
| A-4050 | H | H | H | H | H | $CH_2SCH_2CH_3$ | $-CH_2CH_2-O-CH_2CH_2-$ | | O | 0 |
| A-4051 | H | H | H | H | H | $CH_2CH_2SCH_3$ | $-CH_2CH_2-O-CH_2CH_2-$ | | O | 0 |
| A-4052 | H | H | H | H | H | $CH_2SOCH_3$ | $-CH_2CH_2-O-CH_2CH_2-$ | | O | 0 |
| A-4053 | H | H | H | H | H | $CH_2CH_2SOCH_3$ | $-CH_2CH_2-O-CH_2CH_2-$ | | O | 0 |
| A-4054 | H | H | H | H | H | $CH_2SO_2CH_3$ | $-CH_2CH_2-O-CH_2CH_2-$ | | O | 0 |
| A-4055 | H | H | H | H | H | $CH_2CH_2SO_2CH_3$ | $-CH_2CH_2-O-CH_2CH_2-$ | | O | 0 |
| A-4056 | H | H | H | H | H | $CH_2SCF_3$ | $-CH_2CH_2-O-CH_2CH_2-$ | | O | 0 |
| A-4057 | H | H | H | H | H | $CH_2SCHF_2$ | $-CH_2CH_2-O-CH_2CH_2-$ | | O | 0 |
| A-4058 | H | H | H | H | H | $CH_2SCH_2CF_3$ | $-CH_2CH_2-O-CH_2CH_2-$ | | O | 0 |
| A-4059 | H | H | H | H | H | $CH_2SCH_2CHF_2$ | $-CH_2CH_2-O-CH_2CH_2-$ | | O | 0 |
| A-4060 | H | H | H | H | H | $CH_2SCF_2CF_3$ | $-CH_2CH_2-O-CH_2CH_2-$ | | O | 0 |
| A-4061 | H | H | H | H | H | $CH_2CH_2SCF_3$ | $-CH_2CH_2-O-CH_2CH_2-$ | | O | 0 |
| A-4062 | H | H | H | H | H | $CH_2SOCF_3$ | $-CH_2CH_2-O-CH_2CH_2-$ | | O | 0 |
| A-4063 | H | H | H | H | H | $CH_2CH_2SOCF_3$ | $-CH_2CH_2-O-CH_2CH_2-$ | | O | 0 |
| A-4064 | H | H | H | H | H | $CH_2CH_2CH_2SOCF_3$ | $-CH_2CH_2-O-CH_2CH_2-$ | | O | 0 |
| A-4065 | H | H | H | H | H | $CH_2SO_2CF_3$ | $-CH_2CH_2-O-CH_2CH_2-$ | | O | 0 |
| A-4066 | H | H | H | H | H | $CH_2CH_2SO_2CF_3$ | $-CH_2CH_2-O-CH_2CH_2-$ | | O | 0 |
| A-4067 | H | H | H | H | H | $CH_2CH_2CH_2SO_2CF_3$ | $-CH_2CH_2-O-CH_2CH_2-$ | | O | 0 |
| A-4068 | H | H | H | H | H | $CH_2C(=O)NHCH_2CHF_2$ | $-CH_2CH_2-O-CH_2CH_2-$ | | O | 0 |
| A-4069 | H | H | H | H | H | $CH_2C(=O)NHCH_2CF_3$ | $-CH_2CH_2-O-CH_2CH_2-$ | | O | 0 |
| A-4070 | H | $CF_3$ | H | H | H | H | H | H | O | 0 |
| A-4071 | H | $CF_3$ | H | H | H | $CH_3$ | H | H | O | 0 |
| A-4072 | H | $CF_3$ | H | H | H | $CH_2CH_3$ | H | H | O | 0 |
| A-4073 | H | $CF_3$ | H | H | H | $CH(CH_3)_2$ | H | H | O | 0 |
| A-4074 | H | $CF_3$ | H | H | H | $CH_2CH_2CH_3$ | H | H | O | 0 |
| A-4075 | H | $CF_3$ | H | H | H | $CH_2CH(CH_3)_2$ | H | H | O | 0 |
| A-4076 | H | $CF_3$ | H | H | H | $CH(CH_3)CH_2CH_3$ | H | H | O | 0 |
| A-4077 | H | $CF_3$ | H | H | H | $CH_2C(CH_3)_3$ | H | H | O | 0 |
| A-4078 | H | $CF_3$ | H | H | H | $CH_2(CH_2)_2CH_3$ | H | H | O | 0 |
| A-4079 | H | $CF_3$ | H | H | H | $CH_2(CH_2)_3CH_3$ | H | H | O | 0 |
| A-4080 | H | $CF_3$ | H | H | H | $CH_2(CH_2)_4CH_3$ | H | H | O | 0 |
| A-4081 | H | $CF_3$ | H | H | H | $CH_2(CH_2)_6CH_3$ | H | H | O | 0 |
| A-4082 | H | $CF_3$ | H | H | H | $CH_2OCH_3$ | H | H | O | 0 |

TABLE 68

| Compound | R¹ | R² | R³ | R⁴ | R⁵ | R⁶ | R⁷ | R⁸ | X | n |
|---|---|---|---|---|---|---|---|---|---|---|
| A-4083 | H | $CF_3$ | H | H | H | $CH_2OCH_2CH_3$ | H | H | O | 0 |
| A-4084 | H | $CF_3$ | H | H | H | $CH_2CH_2OCH_3$ | H | H | O | 0 |
| A-4085 | H | $CF_3$ | H | H | H | $CH_2CH_2OCH_2CH_3$ | H | H | O | 0 |
| A-4086 | H | $CF_3$ | H | H | H | $CF_3$ | H | H | O | 0 |
| A-4087 | H | $CF_3$ | H | H | H | $CHF_2$ | H | H | O | 0 |
| A-4088 | H | $CF_3$ | H | H | H | $CH_2CF_3$ | H | H | O | 0 |
| A-4089 | H | $CF_3$ | H | H | H | $CH_2CHF_2$ | H | H | O | 0 |
| A-4090 | H | $CF_3$ | H | H | H | $CH_2CClF_2$ | H | H | O | 0 |
| A-4091 | H | $CF_3$ | H | H | H | $CH_2CBrF_2$ | H | H | O | 0 |

TABLE 68-continued

| Compound | R¹ | R² | R³ | R⁴ | R⁵ | R⁶ | R⁷ | R⁸ | X | n |
|---|---|---|---|---|---|---|---|---|---|---|
| A-4092 | H | $CF_3$ | H | H | H | $CF_2CF_3$ | H | H | O | 0 |
| A-4093 | H | $CF_3$ | H | H | H | $CF_2CHF_2$ | H | H | O | 0 |
| A-4094 | H | $CF_3$ | H | H | H | $CH_2CH_2CF_3$ | H | H | O | 0 |
| A-4095 | H | $CF_3$ | H | H | H | $CH_2CF_2CF_3$ | H | H | O | 0 |
| A-4096 | H | $CF_3$ | H | H | H | $CH_2CF_2CHF_2$ | H | H | O | 0 |
| A-4097 | H | $CF_3$ | H | H | H | $CF_2CHFCF_3$ | H | H | O | 0 |
| A-4098 | H | $CF_3$ | H | H | H | $CF_2CF_2CF_3$ | H | H | O | 0 |
| A-4099 | H | $CF_3$ | H | H | H | $CH_2CF_2CF_2CF_3$ | H | H | O | 0 |
| A-4100 | H | $CF_3$ | H | H | H | $CH_2CF_2CHFCF_3$ | H | H | O | 0 |
| A-4101 | H | $CF_3$ | H | H | H | $CH_2CH_2CH_2CF_3$ | H | H | O | 0 |
| A-4102 | H | $CF_3$ | H | H | H | $CH_2CH_2CF_2CF_3$ | H | H | O | 0 |
| A-4103 | H | $CF_3$ | H | H | H | $CF_2CF_2CF_2CF_3$ | H | H | O | 0 |
| A-4104 | H | $CF_3$ | H | H | H | $CH_2CH_2CH(CF_3)_2$ | H | H | O | 0 |
| A-4105 | H | $CF_3$ | H | H | H | $CF_2CF_2CF_2CF_2CF_3$ | H | H | O | 0 |
| A-4106 | H | $CF_3$ | H | H | H | $CH_2CF_2CF_2CF_2CF_3$ | H | H | O | 0 |
| A-4107 | H | $CF_3$ | H | H | H | $CH_2CH_2CH_2CH_2CF_3$ | H | H | O | 0 |
| A-4108 | H | $CF_3$ | H | H | H | $CH_2CF_2CF_2CF_2CHF_2$ | H | H | O | 0 |
| A-4109 | H | $CF_3$ | H | H | H | $CH_2CF_2CF(CF_3)CF_2C(CF_3)_3$ | H | H | O | 0 |
| A-4110 | H | $CF_3$ | H | H | H | $CF_2CHFOCH_3$ | H | H | O | 0 |
| A-4111 | H | $CF_3$ | H | H | H | $CF_2CHFOCH_2CH_3$ | H | H | O | 0 |
| A-4112 | H | $CF_3$ | H | H | H | $CH_2CH_2OCH_2CF_3$ | H | H | O | 0 |
| A-4113 | H | $CF_3$ | H | H | H | $CF_2CHFOCF_3$ | H | H | O | 0 |
| A-4114 | H | $CF_3$ | H | H | H | $CF_2CHFOCF_2CF_3$ | H | H | O | 0 |
| A-4115 | H | $CF_3$ | H | H | H | $CF_2CHFOCF_2CF_2CF_3$ | H | H | O | 0 |
| A-4116 | H | $CF_3$ | H | H | H | $CH_2CH=CH_2$ | H | H | O | 0 |
| A-4117 | H | $CF_3$ | H | H | H | $CH_2CH=CHCl$ | H | H | O | 0 |
| A-4118 | H | $CF_3$ | H | H | H | $CH_2CH=CCl_2$ | H | H | O | 0 |
| A-4119 | H | $CF_3$ | H | H | H | $CH_2CH_2CF=CF_2$ | H | H | O | 0 |
| A-4120 | H | $CF_3$ | H | H | H | $CH_2CH_2CH=CF_2$ | H | H | O | 0 |
| A-4121 | H | $CF_3$ | H | H | H | $CH_2C\equiv CH$ | H | H | O | 0 |
| A-4122 | H | $CF_3$ | H | H | H | $CH_2C\equiv CCH_3$ | H | H | O | 0 |
| A-4123 | H | $CF_3$ | H | H | H | $CH_2C\equiv CCF_3$ | H | H | O | 0 |
| A-4124 | H | $CF_3$ | H | H | H | $CH_2C\equiv CI$ | H | H | O | 0 |
| A-4125 | H | $CF_3$ | H | H | H | cyclobutyl | H | H | O | 0 |
| A-4126 | H | $CF_3$ | H | H | H | cyclopentyl | H | H | O | 0 |
| A-4127 | H | $CF_3$ | H | H | H | cyclohexyl | H | H | O | 0 |
| A-4128 | H | $CF_3$ | H | H | H | 4,4-difluorocyclohexyl | H | H | O | 0 |
| A-4129 | H | $CF_3$ | H | H | H | $CH_2$(cyclopropyl) | H | H | O | 0 |
| A-4130 | H | $CF_3$ | H | H | H | $CH_2$(cyclobutyl) | H | H | O | 0 |
| A-4131 | H | $CF_3$ | H | H | H | $CH_2$(cyclopentyl) | H | H | O | 0 |
| A-4132 | H | $CF_3$ | H | H | H | $CH_2CH_2$(cyclopropyl) | H | H | O | 0 |
| A-4133 | H | $CF_3$ | H | H | H | $CH_2$(2,2-difluorocyclopropyl) | H | H | O | 0 |
| A-4134 | H | $CF_3$ | H | H | H | $CH_2$(2,2-dichlorocyclopropyl) | H | H | O | 0 |
| A-4135 | H | $CF_3$ | H | H | H | $CH_2$(4,4-difluorocyclohexyl) | H | H | O | 0 |
| A-4136 | H | $CF_3$ | H | H | H | $CH_2CH_2$(2,2-difluorocyclopropyl) | H | H | O | 0 |
| A-4137 | H | $CF_3$ | H | H | H | $CH_2CH_2$(2,2-dichlorocyclopropyl) | H | H | O | 0 |
| A-4138 | H | $CF_3$ | H | H | H | $CH_2SCH_3$ | H | H | O | 0 |
| A-4139 | H | $CF_3$ | H | H | H | $CH_2SCH_2CH_3$ | H | H | O | 0 |
| A-4140 | H | $CF_3$ | H | H | H | $CH_2CH_2SCH_3$ | H | H | O | 0 |
| A-4141 | H | $CF_3$ | H | H | H | $CH_2CH_2SCH_2CH_3$ | H | H | O | 0 |
| A-4142 | H | $CF_3$ | H | H | H | $CH_2CH_2CH_2SCH_3$ | H | H | O | 0 |
| A-4143 | H | $CF_3$ | H | H | H | $CH_2CH_2CH_2SCH_2CH_3$ | H | H | O | 0 |

TABLE 69

| Compound | R¹ | R² | R³ | R⁴ | R⁵ | R⁶ | R⁷ | R⁸ | X | n |
|---|---|---|---|---|---|---|---|---|---|---|
| A-4144 | H | $CF_3$ | H | H | H | $CH(CH_3)SCH_3$ | H | H | O | 0 |
| A-4145 | H | $CF_3$ | H | H | H | $CH(CH_3)SCH_2CH_3$ | H | H | O | 0 |
| A-4146 | H | $CF_3$ | H | H | H | $CH_2CH(CH_3)SCH_3$ | H | H | O | 0 |
| A-4147 | H | $CF_3$ | H | H | H | $CH_2CH(CH_3)SCH_2CH_3$ | H | H | O | 0 |
| A-4148 | H | $CF_3$ | H | H | H | $CH(CH_3)CH_2CH_2SCH_3$ | H | H | O | 0 |
| A-4149 | H | $CF_3$ | H | H | H | $CH(CH_3)CH_2CH_2SCH_2CH_3$ | H | H | O | 0 |
| A-4150 | H | $CF_3$ | H | H | H | $CH_2CH(CH_3)CH_2SCH_3$ | H | H | O | 0 |
| A-4151 | H | $CF_3$ | H | H | H | $CH_2CH(CH_3)CH_2SCH_2CH_3$ | H | H | O | 0 |
| A-4152 | H | $CF_3$ | H | H | H | $CH_2CH_2CH(CH_3)SCH_3$ | H | H | O | 0 |
| A-4153 | H | $CF_3$ | H | H | H | $CH_2CH_2CH(CH_3)SCH_2CH_3$ | H | H | O | 0 |
| A-4154 | H | $CF_3$ | H | H | H | $CH_2SOCH_3$ | H | H | O | 0 |
| A-4155 | H | $CF_3$ | H | H | H | $CH_2CH_2SOCH_3$ | H | H | O | 0 |
| A-4156 | H | $CF_3$ | H | H | H | $CH_2CH_2CH_2SOCH_3$ | H | H | O | 0 |
| A-4157 | H | $CF_3$ | H | H | H | $CH(CH_3)SOCH_3$ | H | H | O | 0 |
| A-4158 | H | $CF_3$ | H | H | H | $CH_2CH(CH_3)SOCH_3$ | H | H | O | 0 |
| A-4159 | H | $CF_3$ | H | H | H | $CH(CH_3)CH_2CH_2SOCH_3$ | H | H | O | 0 |
| A-4160 | H | $CF_3$ | H | H | H | $CH_2CH(CH_3)CH_2SOCH_3$ | H | H | O | 0 |
| A-4161 | H | $CF_3$ | H | H | H | $CH_2CH_2CH(CH_3)SOCH_3$ | H | H | O | 0 |

TABLE 69-continued

| Compound | R¹ | R² | R³ | R⁴ | R⁵ | R⁶ | R⁷ | R⁸ | X | n |
|---|---|---|---|---|---|---|---|---|---|---|
| A-4162 | H | CF₃ | H | H | H | CH₂SO₂CH₃ | H | H | O | 0 |
| A-4163 | H | CF₃ | H | H | H | CH₂CH₂SO₂CH₃ | H | H | O | 0 |
| A-4164 | H | CF₃ | H | H | H | CH₂CH₂CH₂SC₂CH₃ | H | H | O | 0 |
| A-4165 | H | CF₃ | H | H | H | CH(CH₃)SO₂CH₃ | H | H | O | 0 |
| A-4166 | H | CF₃ | H | H | H | CH₂CH(CH₃)SO₂CH₃ | H | H | O | 0 |
| A-4167 | H | CF₃ | H | H | H | CH(CH₃)CH₂CH₂SO₂CH₃ | H | H | O | 0 |
| A-4168 | H | CF₃ | H | H | H | CH₂CH(CH₃)CH₂SO₂CH₃ | H | H | O | 0 |
| A-4169 | H | CF₃ | H | H | H | CH₂CH₂CH(CH₃)SO₂CH₃ | H | H | O | 0 |
| A-4170 | H | CF₃ | H | H | H | CH₂SCF₃ | H | H | O | 0 |
| A-4171 | H | CF₃ | H | H | H | CH₂SCHF₂ | H | H | O | 0 |
| A-4172 | H | CF₃ | H | H | H | CH₂SCH₂CF₃ | H | H | O | 0 |
| A-4173 | H | CF₃ | H | H | H | CH₂SCH₂CHF₂ | H | H | O | 0 |
| A-4174 | H | CF₃ | H | H | H | CH₂SCF₂CF₃ | H | H | O | 0 |
| A-4175 | H | CF₃ | H | H | H | CH₂CH₂SCF₃ | H | H | O | 0 |
| A-4176 | H | CF₃ | H | H | H | CH₂CH₂SCH₂CF₃ | H | H | O | 0 |
| A-4177 | H | CF₃ | H | H | H | CH₂CH₂CH₂SCF₃ | H | H | O | 0 |
| A-4178 | H | CF₃ | H | H | H | CH₂CH₂CH₂SCH₂CF₃ | H | H | O | 0 |
| A-4179 | H | CF₃ | H | H | H | CH(CH₃)SCF₃ | H | H | O | 0 |
| A-4180 | H | CF₃ | H | H | H | CH(CH₃)SCH₂CF₃ | H | H | O | 0 |
| A-4181 | H | CF₃ | H | H | H | CH₂CH(CH₃)SCF₃ | H | H | O | 0 |
| A-4182 | H | CF₃ | H | H | H | CH₂CH(CH₃)SCH₂CF₃ | H | H | O | 0 |
| A-4183 | H | CF₃ | H | H | H | CH(CH₃)CH₂CH₂SCF₃ | H | H | O | 0 |
| A-4184 | H | CF₃ | H | H | H | CH(CH₃)CH₂CH₂SCH₂CF₃ | H | H | O | 0 |
| A-4185 | H | CF₃ | H | H | H | CH₂CH(CH₃)CH₂SCF₃ | H | H | O | 0 |
| A-4186 | H | CF₃ | H | H | H | CH₂CH(CH₃)CH₂SCH₂CF₃ | H | H | O | 0 |
| A-4187 | H | CF₃ | H | H | H | CH₂CH₂CH(CH₃)SCF₃ | H | H | O | 0 |
| A-4188 | H | CF₃ | H | H | H | CH₂CH₂CH(CH₃)SCH₂CF₃ | H | H | O | 0 |
| A-4189 | H | CF₃ | H | H | H | CH₂SOCF₃ | H | H | O | 0 |
| A-4190 | H | CF₃ | H | H | H | CH₂CH₂SOCF₃ | H | H | O | 0 |
| A-4191 | H | CF₃ | H | H | H | CH₂CH₂CH₂SOCF₃ | H | H | O | 0 |
| A-4192 | H | CF₃ | H | H | H | CH(CH₃)SOCF₃ | H | H | O | 0 |
| A-4193 | H | CF₃ | H | H | H | CH₂CH(CH₃)SOCF₃ | H | H | O | 0 |
| A-4194 | H | CF₃ | H | H | H | CH(CH₃)CH₂CH₂SOCF₃ | H | H | O | 0 |
| A-4195 | H | CF₃ | H | H | H | CH₂CH(CH₃)CH₂SOCF₃ | H | H | O | 0 |
| A-4196 | H | CF₃ | H | H | H | CH₂CH₂CH(CH₃)SOCF₃ | H | H | O | 0 |
| A-4197 | H | CF₃ | H | H | H | CH₂SO₂CF₃ | H | H | O | 0 |
| A-4198 | H | CF₃ | H | H | H | CH₂CH₂SO₂CF₃ | H | H | O | 0 |
| A-4199 | H | CF₃ | H | H | H | CH₂CH₂CH₂SO₂CF₃ | H | H | O | 0 |
| A-4200 | H | CF₃ | H | H | H | CH(CH₃)SO₂CF₃ | H | H | O | 0 |
| A-4201 | H | CF₃ | H | H | H | CH₂CH(CH₃)SO₂CF₃ | H | H | O | 0 |
| A-4202 | H | CF₃ | H | H | H | CH(CH₃)CH₂CH₂SO₂CF₃ | H | H | O | 0 |
| A-4203 | H | CF₃ | H | H | H | CH₂CH(CH₃)CH₂SO₂CF₃ | H | H | O | 0 |
| A-4204 | H | CF₃ | H | H | H | CH₂CH₂CH(CH₃)SO₂CF₃ | H | H | O | 0 |

TABLE 70

| Compound | R¹ | R² | R³ | R⁴ | R⁵ | R⁶ | R⁷ | R⁸ | X | n |
|---|---|---|---|---|---|---|---|---|---|---|
| A-4205 | H | CF₃ | H | H | H | CH₂C(=O)CH₃ | H | H | O | 0 |
| A-4206 | H | CF₃ | H | H | H | CH₂C(=O)CH₂CH₃ | H | H | O | 0 |
| A-4207 | H | CF₃ | H | H | H | CH₂C(=O)C(CH₃)₃ | H | H | O | 0 |
| A-4208 | H | CF₃ | H | H | H | CH₂CH₂C(=O)CH₃ | H | H | O | 0 |
| A-4209 | H | CF₃ | H | H | H | CH₂CH₂C(=O)C(CH₃)₃ | H | H | O | 0 |
| A-4210 | H | CF₃ | H | H | H | CH₂C(=O)CF₃ | H | H | O | 0 |
| A-4211 | H | CF₃ | H | H | H | CH₂CH₂C(=O)CF₃ | H | H | O | 0 |
| A-4212 | H | CF₃ | H | H | H | CH₂C(=O)OCH₃ | H | H | O | 0 |
| A-4213 | H | CF₃ | H | H | H | CH₂C(=O)OCH₂CH₃ | H | H | O | 0 |
| A-4214 | H | CF₃ | H | H | H | CH₂C(=O)OC(CH₃)₃ | H | H | O | 0 |
| A-4215 | H | CF₃ | H | H | H | CH₂CH₂C(=O)OCH₃ | H | H | O | 0 |
| A-4216 | H | CF₃ | H | H | H | CH₂CH₂C(=O)OCH₂CH₃ | H | H | O | 0 |
| A-4217 | H | CF₃ | H | H | H | CH₂CH₂C(=O)OC(CH₃)₃ | H | H | O | 0 |
| A-4218 | H | CF₃ | H | H | H | CH₂C(=O)NH₂ | H | H | O | 0 |
| A-4219 | H | CF₃ | H | H | H | CH₂CH₂C(=O)NH₂ | H | H | O | 0 |
| A-4220 | H | CF₃ | H | H | H | CH₂C(=O)NHCH₃ | H | H | O | 0 |
| A-4221 | H | CF₃ | H | H | H | CH₂C(=O)NHCH(CH₃)₂ | H | H | O | 0 |
| A-4222 | H | CF₃ | H | H | H | CH₂CH₂C(=O)NHCH₃ | H | H | O | 0 |
| A-4223 | H | CF₃ | H | H | H | CH₂CH₂C(=O)NHCH(CH₃)₂ | H | H | O | 0 |
| A-4224 | H | CF₃ | H | H | H | CH₂C(=O)NHCH₂CHF₂ | H | H | O | 0 |
| A-4225 | H | CF₃ | H | H | H | CH₂C(=O)NHCH₂CF₃ | H | H | O | 0 |
| A-4226 | H | CF₃ | H | H | H | CH₂CH₂C(=O)NHCH₂CHF₂ | H | H | O | 0 |
| A-4227 | H | CF₃ | H | H | H | CH₂CH₂C(=O)NHCH₂CF₃ | H | H | O | 0 |
| A-4228 | H | CF₃ | H | H | H | CH₂C(=O)N(CH₃)₂ | H | H | O | 0 |
| A-4229 | H | CF₃ | H | H | H | CH₂C(=O)N(CH₂CH₃)₂ | H | H | O | 0 |
| A-4230 | H | CF₃ | H | H | H | CH₂CH₂C(=O)N(CH₃)₂ | H | H | O | 0 |
| A-4231 | H | CF₃ | H | H | H | CH₂CH₂C(=O)N(CH₂CH₃)₂ | H | H | O | 0 |

TABLE 70-continued

| Compound | R¹ | R² | R³ | R⁴ | R⁵ | R⁶ | R⁷ | R⁸ | X | n |
|---|---|---|---|---|---|---|---|---|---|---|
| A-4232 | H | CF$_3$ | H | H | H | CH$_2$CH$_2$OH | H | H | O | 0 |
| A-4233 | H | CF$_3$ | H | H | H | CH$_2$CH(OH)CH$_3$ | H | H | O | 0 |
| A-4234 | H | CF$_3$ | H | H | H | CH$_2$CH$_2$CH$_2$OH | H | H | O | 0 |
| A-4235 | H | CF$_3$ | H | H | H | CH$_2$CH(OH)CH$_2$CH$_3$ | H | H | O | 0 |
| A-4236 | H | CF$_3$ | H | H | H | CH$_2$CH(OH)C(CH$_3$)$_3$ | H | H | O | 0 |
| A-4237 | H | CF$_3$ | H | H | H | CH$_2$CH$_2$CH(OH)CH$_3$ | H | H | O | 0 |
| A-4238 | H | CF$_3$ | H | H | H | CH$_2$CH$_2$CH(OH)C(CH$_3$)$_3$ | H | H | O | 0 |
| A-4239 | H | CF$_3$ | H | H | H | CH$_2$C(=NOH)CH$_3$ | H | H | O | 0 |
| A-4240 | H | CF$_3$ | H | H | H | CH$_2$C(=NOH)CH$_2$CH$_3$ | H | H | O | 0 |
| A-4241 | H | CF$_3$ | H | H | H | CH$_2$C(=NOH)C(CH$_3$)$_3$ | H | H | O | 0 |
| A-4242 | H | CF$_3$ | H | H | H | CH$_2$C(=NOCH$_3$)CH$_3$ | H | H | O | 0 |
| A-4243 | H | CF$_3$ | H | H | H | CH$_2$C(=NOCH$_3$)CH$_2$CH$_3$ | H | H | O | 0 |
| A-4244 | H | CF$_3$ | H | H | H | CH$_2$C(=NOCH$_2$CH$_3$)CH$_3$ | H | H | O | 0 |
| A-4245 | H | CF$_3$ | H | H | H | CH$_2$C(=NOCH$_2$CH$_3$)CH$_2$CH$_3$ | H | H | O | 0 |
| A-4246 | H | CF$_3$ | H | H | H | CH$_2$C(=NOCH$_2$CF$_3$)CH$_3$ | H | H | O | 0 |
| A-4247 | H | CF$_3$ | H | H | H | CH$_2$C(=NOCH$_2$CF$_3$)CH$_2$CH$_3$ | H | H | O | 0 |
| A-4248 | H | CF$_3$ | H | H | H | CH$_2$Ph | H | H | O | 0 |
| A-4249 | H | CF$_3$ | H | H | H | CH$_2$(2-F)Ph | H | H | O | 0 |
| A-4250 | H | CF$_3$ | H | H | H | CH$_2$(3-F)Ph | H | H | O | 0 |
| A-4251 | H | CF$_3$ | H | H | H | CH$_2$(4-F)Ph | H | H | O | 0 |
| A-4252 | H | CF$_3$ | H | H | H | CH$_2$(2-Cl)Ph | H | H | O | 0 |
| A-4253 | H | CF$_3$ | H | H | H | CH$_2$(3-Cl)Ph | H | H | O | 0 |
| A-4254 | H | CF$_3$ | H | H | H | CH$_2$(4-Cl)Ph | H | H | O | 0 |
| A-4255 | H | CF$_3$ | H | H | H | CH$_2$(2-CF$_3$)Ph | H | H | O | 0 |
| A-4256 | H | CF$_3$ | H | H | H | CH$_2$(3-CF$_3$)PH | H | H | O | 0 |
| A-4257 | H | CF$_3$ | H | H | H | CH$_2$(4-CF$_3$)Ph | H | H | O | 0 |
| A-4258 | H | CF$_3$ | H | H | H | CH$_2$(naphthalen-1-yl) | H | H | O | 0 |
| A-4259 | H | CF$_3$ | H | H | H | CH$_2$(naphthalen-2-yl) | H | H | O | 0 |
| A-4260 | H | CF$_3$ | H | H | H | CH$_2$CH$_2$Ph | H | H | O | 0 |
| A-4261 | H | H | F | H | H | H | H | H | O | 0 |
| A-4262 | H | H | F | H | H | CH$_3$ | H | H | O | 0 |
| A-4263 | H | H | F | H | H | CH$_2$CH$_3$ | H | H | O | 0 |
| A-4264 | H | H | F | H | H | CH(CH$_3$)$_2$ | H | H | O | 0 |
| A-4265 | H | H | F | H | H | CH$_2$CH$_2$CH$_3$ | H | H | O | 0 |

TABLE 71

| Compound | R¹ | R² | R³ | R⁴ | R⁵ | R⁶ | R⁷ | R⁸ | X | n |
|---|---|---|---|---|---|---|---|---|---|---|
| A-4266 | H | H | F | H | H | CH$_2$CH(CH$_3$)$_2$ | H | H | O | 0 |
| A-4267 | H | H | F | H | H | CH(CH$_3$)CH$_2$CH$_3$ | H | H | O | 0 |
| A-4268 | H | H | F | H | H | CH$_2$C(CH$_3$)$_3$ | H | H | O | 0 |
| A-4269 | H | H | F | H | H | CH$_2$(CH$_2$)$_2$CH$_3$ | H | H | O | 0 |
| A-4270 | H | H | F | H | H | CH$_2$(CH$_2$)$_3$CH$_3$ | H | H | O | 0 |
| A-4271 | H | H | F | H | H | CH$_2$(CH$_2$)$_4$CH$_3$ | H | H | O | 0 |
| A-4272 | H | H | F | H | H | CH$_2$(CH$_2$)$_6$CH$_3$ | H | H | O | 0 |
| A-4273 | H | H | F | H | H | CH$_2$OCH$_3$ | H | H | O | 0 |
| A-4274 | H | H | F | H | H | CH$_2$OCH$_2$CH$_3$ | H | H | O | 0 |
| A-4275 | H | H | F | H | H | CH$_2$CH$_2$OCH$_3$ | H | H | O | 0 |
| A-4276 | H | H | F | H | H | CH$_2$CH$_2$OCH$_2$CH$_3$ | H | H | O | 0 |
| A-4277 | H | H | F | H | H | CF$_3$ | H | H | O | 0 |
| A-4278 | H | H | F | H | H | CHF$_2$ | H | H | O | 0 |
| A-4279 | H | H | F | H | H | CH$_2$CF$_3$ | H | H | O | 0 |
| A-4280 | H | H | F | H | H | CH$_2$CHF$_2$ | H | H | O | 0 |
| A-4281 | H | H | F | H | H | CH$_2$CClF$_2$ | H | H | O | 0 |
| A-4282 | H | H | F | H | H | CH$_2$CBrF$_2$ | H | H | O | 0 |
| A-4283 | H | H | F | H | H | CF$_2$CF$_3$ | H | H | O | 0 |
| A-4284 | H | H | F | H | H | CF$_2$CHF$_2$ | H | H | O | 0 |
| A-4285 | H | H | F | H | H | CH$_2$CH$_2$CF$_3$ | H | H | O | 0 |
| A-4286 | H | H | F | H | H | CH$_2$CF$_2$CF$_3$ | H | H | O | 0 |
| A-4287 | H | H | F | H | H | CH$_2$CF$_2$CHF$_2$ | H | H | O | 0 |
| A-4288 | H | H | F | H | H | CF$_2$CHFCF$_3$ | H | H | O | 0 |
| A-4289 | H | H | F | H | H | CF$_2$CF$_2$CF$_3$ | H | H | O | 0 |
| A-4290 | H | H | F | H | H | CH$_2$CF$_2$CF$_2$CF$_3$ | H | H | O | 0 |
| A-4291 | H | H | F | H | H | CH2CF$_2$CHFCF$_3$ | H | H | O | 0 |
| A-4292 | H | H | F | H | H | CH$_2$CH$_2$CH$_2$CF$_3$ | H | H | O | 0 |
| A-4293 | H | H | F | H | H | CH$_2$CH$_2$CF$_2$CF$_3$ | H | H | O | 0 |
| A-4294 | H | H | F | H | H | CF$_2$CF$_2$CF$_2$CF$_3$ | H | H | O | 0 |
| A-4295 | H | H | F | H | H | CH$_2$CH$_2$CH(CF$_3$)$_2$ | H | H | O | 0 |
| A-4296 | H | H | F | H | H | CF$_2$CF$_2$CF$_2$CF$_2$CF$_3$ | H | H | O | 0 |
| A-4297 | H | H | F | H | H | CH$_2$CF$_2$CF$_2$CF$_2$CF$_3$ | H | H | O | 0 |
| A-4298 | H | H | F | H | H | CH$_2$CH$_2$CH$_2$CH$_2$CF$_3$ | H | H | O | 0 |
| A-4299 | H | H | F | H | H | CH$_2$CF$_2$CF$_2$CF$_2$CHF$_2$ | H | H | O | 0 |
| A-4300 | H | H | F | H | H | CH$_2$CF$_2$CF(CF$_3$)CF$_2$C(CF$_3$)$_3$ | H | H | O | 0 |
| A-4301 | H | H | F | H | H | CF$_2$CHFOCH$_3$ | H | H | O | 0 |

TABLE 71-continued

| Compound | R¹ | R² | R³ | R⁴ | R⁵ | R⁶ | R⁷ | R⁸ | X | n |
|---|---|---|---|---|---|---|---|---|---|---|
| A-4302 | H | H | F | H | H | CF$_2$CHFOCH$_2$CH$_3$ | H | H | O | 0 |
| A-4303 | H | H | F | H | H | CH$_2$CH$_2$OCH$_2$CF$_3$ | H | H | O | 0 |
| A-4304 | H | H | F | H | H | CF$_2$CHFOCF$_3$ | H | H | O | 0 |
| A-4305 | H | H | F | H | H | CF$_2$CHFOCF$_2$CF$_3$ | H | H | O | 0 |
| A-4306 | H | H | F | H | H | CF$_2$CHFOCF$_2$CF$_2$CF$_3$ | H | H | O | 0 |
| A-4307 | H | H | F | H | H | CH$_2$CH=CH$_2$ | H | H | O | 0 |
| A-4308 | H | H | F | H | H | CH$_2$CH=CHCl | H | H | O | 0 |
| A-4309 | H | H | F | H | H | CH$_2$CH=CCl$_2$ | H | H | O | 0 |
| A-4310 | H | H | F | H | H | CH$_2$CH$_2$CF=CF$_2$ | H | H | O | 0 |
| A-4311 | H | H | F | H | H | CH$_2$CH$_2$CH=CF$_2$ | H | H | O | 0 |
| A-4312 | H | H | F | H | H | CH$_2$C≡CH | H | H | O | 0 |
| A-4313 | H | H | F | H | H | CH$_2$C≡CCH$_3$ | H | H | O | 0 |
| A-4314 | H | H | F | H | H | CH$_2$C≡CF$_3$ | H | H | O | 0 |
| A-4315 | H | H | F | H | H | CH$_2$C≡CI | H | H | O | 0 |
| A-4316 | H | H | F | H | H | cyclobutyl | H | H | O | 0 |
| A-4317 | H | H | F | H | H | cyclopentyl | H | H | O | 0 |
| A-4318 | H | H | F | H | H | cyclohexyl | H | H | O | 0 |
| A-4319 | H | H | F | H | H | 4,4-difluorocyclohexyl | H | H | O | 0 |
| A-4320 | H | H | F | H | H | CH$_2$(cyclopropyl) | H | H | O | 0 |
| A-4321 | H | H | F | H | H | CH$_2$(cyclobutyl) | H | H | O | 0 |
| A-4322 | H | H | F | H | H | CH$_2$(cyclopentyl) | H | H | O | 0 |
| A-4323 | H | H | F | H | H | CH$_2$CH$_2$(cyclopropyl) | H | H | O | 0 |
| A-4324 | H | H | F | H | H | CH$_2$(2,2-difluorocyclopropyl) | H | H | O | 0 |
| A-4325 | H | H | F | H | H | CH$_2$(2,2-dichlorocyclopropyl) | H | H | O | 0 |
| A-4326 | H | H | F | H | H | CH$_2$(4,4-difluorocyclohexyl) | H | H | O | 0 |

TABLE 72

| Compound | R¹ | R² | R³ | R⁴ | R⁵ | R⁶ | R⁷ | R⁸ | X | n |
|---|---|---|---|---|---|---|---|---|---|---|
| A-4327 | H | H | F | H | H | CH$_2$CH$_2$(2,2-difluorocyclopropyl) | H | H | O | 0 |
| A-4328 | H | H | F | H | H | CH$_2$CH$_2$(2,2-dichlorocyclopropyl) | H | H | O | 0 |
| A-4329 | H | H | F | H | H | CH$_2$SCH$_3$ | H | H | O | 0 |
| A-4330 | H | H | F | H | H | CH$_2$SCH$_2$CH$_3$ | H | H | O | 0 |
| A-4331 | H | H | F | H | H | CH$_2$CH$_2$SCH$_3$ | H | H | O | 0 |
| A-4332 | H | H | F | H | H | CH$_2$CH$_2$SCH$_2$CH$_3$ | H | H | O | 0 |
| A-4333 | H | H | F | H | H | CH$_2$CH$_2$CH$_2$SCH$_3$ | H | H | O | 0 |
| A-4334 | H | H | F | H | H | CH$_2$CH$_2$CH$_2$SCH$_2$CH$_3$ | H | H | O | 0 |
| A-4335 | H | H | F | H | H | CH(CH$_3$)SCH$_3$ | H | H | O | 0 |
| A-4336 | H | H | F | H | H | CH(CH$_3$)SCH$_2$CH$_3$ | H | H | O | 0 |
| A-4337 | H | H | F | H | H | CH$_2$CH(CH$_3$)SCH$_3$ | H | H | O | 0 |
| A-4338 | H | H | F | H | H | CH$_2$CH(CH$_3$)SCH$_2$CH$_3$ | H | H | O | 0 |
| A-4339 | H | H | F | H | H | CH(CH$_3$)CH$_2$CH$_2$SCH$_3$ | H | H | O | 0 |
| A-4340 | H | H | F | H | H | CH(CH$_3$)CH$_2$CH$_2$SCH$_2$CH$_3$ | H | H | O | 0 |
| A-4341 | H | H | F | H | H | CH$_3$CH(CH$_3$)CH$_2$SCH$_3$ | H | H | O | 0 |
| A-4342 | H | H | F | H | H | CH$_2$CH(CH$_3$)CH$_2$SCH$_2$CH$_3$ | H | H | O | 0 |
| A-4343 | H | H | F | H | H | CH$_2$CH$_2$CH(CH$_3$)SCH$_3$ | H | H | O | 0 |
| A-4344 | H | H | F | H | H | CH$_2$CH$_2$CH(CH$_3$)SCH$_2$CH$_3$ | H | H | O | 0 |
| A-4345 | H | H | F | H | H | CH$_2$SOCH$_3$ | H | H | O | 0 |
| A-4346 | H | H | F | H | H | CH$_2$CH$_2$SOCH$_3$ | H | H | O | 0 |
| A-4347 | H | H | F | H | H | CH$_2$CH$_2$CH$_2$SOCH$_3$ | H | H | O | 0 |
| A-4348 | H | H | F | H | H | CH(CH$_3$)SOCH$_3$ | H | H | O | 0 |
| A-4349 | H | H | F | H | H | CH$_2$CH(CH$_3$)SOCH$_3$ | H | H | O | 0 |
| A-4350 | H | H | F | H | H | CH(CH$_3$)CH$_2$CH$_2$SOCH$_3$ | H | H | O | 0 |
| A-4351 | H | H | F | H | H | CH$_2$CH(CH$_3$)CH$_2$SOCH$_3$ | H | H | O | 0 |
| A-4352 | H | H | F | H | H | CH$_2$CH$_2$CH(CH$_3$)SOCH$_3$ | H | H | O | 0 |
| A-4353 | H | H | F | H | H | CH$_2$SO$_2$CH$_3$ | H | H | O | 0 |
| A-4354 | H | H | F | H | H | CH$_2$CH$_2$SO$_2$CH$_3$ | H | H | O | 0 |
| A-4355 | H | H | F | H | H | CH$_2$CH$_2$CH$_2$SO$_2$CH$_3$ | H | H | O | 0 |
| A-4356 | H | H | F | H | H | CH(CH$_3$)SO$_2$CH$_3$ | H | H | O | 0 |
| A-4357 | H | H | F | H | H | CH$_2$CH(CH$_3$)SO$_2$CH$_3$ | H | H | O | 0 |
| A-4358 | H | H | F | H | H | CH(CH$_3$)CH$_2$CH$_2$SO$_2$CH$_3$ | H | H | O | 0 |
| A-4359 | H | H | F | H | H | CH$_2$CH(CH$_3$)CH$_2$SO$_2$CH$_3$ | H | H | O | 0 |
| A-4360 | H | H | F | H | H | CH$_2$CH$_2$CH(CH$_3$)SO$_2$CH$_3$ | H | H | O | 0 |
| A-4361 | H | H | F | H | H | CH$_2$SCF$_3$ | H | H | O | 0 |
| A-4362 | H | H | F | H | H | CH$_2$SCHF$_2$ | H | H | O | 0 |
| A-4363 | H | H | F | H | H | CH$_2$SCH$_2$CF$_3$ | H | H | O | 0 |
| A-4364 | H | H | F | H | H | CH$_2$SCH$_2$CHF$_2$ | H | H | O | 0 |
| A-4365 | H | H | F | H | H | CH$_2$SCF$_2$CF$_3$ | H | H | O | 0 |
| A-4366 | H | H | F | H | H | CH$_2$CH$_2$SCF$_3$ | H | H | O | 0 |
| A-4367 | H | H | F | H | H | CH$_2$CH$_2$SCH$_2$CF$_3$ | H | H | O | 0 |
| A-4368 | H | H | F | H | H | CH$_2$CH$_2$CH$_2$SCF$_3$ | H | H | O | 0 |
| A-4369 | H | H | F | H | H | CH$_2$CH$_2$CH$_2$SCH$_2$CF$_3$ | H | H | O | 0 |
| A-4370 | H | H | F | H | H | CH(CH$_3$)SCF$_3$ | H | H | O | 0 |
| A-4371 | H | H | F | H | H | CH(CH$_3$)SCH$_2$CF$_3$ | H | H | O | 0 |

TABLE 72-continued

| Compound | R¹ | R² | R³ | R⁴ | R⁵ | R⁶ | R⁷ | R⁸ | X | n |
|---|---|---|---|---|---|---|---|---|---|---|
| A-4372 | H | H | F | H | H | CH$_2$CH(CH$_3$)SCF$_3$ | H | H | O | 0 |
| A-4373 | H | H | F | H | H | CH$_2$CH(CH$_3$)SCH$_2$CF$_3$ | H | H | O | 0 |
| A-4374 | H | H | F | H | H | CH(CH$_3$)CH$_2$CH$_2$SCF$_3$ | H | H | O | 0 |
| A-4375 | H | H | F | H | H | CH(CH$_3$)CH$_2$CH$_2$SCH$_2$CF$_3$ | H | H | O | 0 |
| A-4376 | H | H | F | H | H | CH$_2$CH(CH$_3$)CH$_2$SCF$_3$ | H | H | O | 0 |
| A-4377 | H | H | F | H | H | CH$_2$CH(CH$_3$)CH$_3$SCH$_2$CF$_3$ | H | H | O | 0 |
| A-4378 | H | H | F | H | H | CH$_2$CH$_2$CH(CH$_3$)SCF$_3$ | H | H | O | 0 |
| A-4379 | H | H | F | H | H | CH$_2$CH$_2$CH(CH$_3$)SCH$_2$CF$_3$ | H | H | O | 0 |
| A-4380 | H | H | F | H | H | CH$_2$SOCF$_3$ | H | H | O | 0 |
| A-4381 | H | H | F | H | H | CH$_2$CH$_2$SOCF$_3$ | H | H | O | 0 |
| A-4382 | H | H | F | H | H | CH$_2$CH$_2$CH$_2$SOCF$_3$ | H | H | O | 0 |
| A-4383 | H | H | F | H | H | CH(CH$_3$)SOCF$_3$ | H | H | O | 0 |
| A-4384 | H | H | F | H | H | CH$_2$CH(CH$_3$)SOCF$_2$ | H | H | O | 0 |
| A-4385 | H | H | F | H | H | CH(CH$_3$)CH$_2$CH$_2$SOCF$_3$ | H | H | O | 0 |
| A-4386 | H | H | F | H | H | CH$_2$CH(CH$_3$)CH$_2$SOCF$_3$ | H | H | O | 0 |
| A-4387 | H | H | F | H | H | CH$_2$CH$_2$CH(CH$_3$)SOCF$_3$ | H | H | O | 0 |

TABLE 73

| Compound | R¹ | R² | R³ | R⁴ | R⁵ | R⁶ | R⁷ | R⁸ | X | n |
|---|---|---|---|---|---|---|---|---|---|---|
| A-4388 | H | H | F | H | H | CH$_2$SO$_2$CF$_3$ | H | H | O | 0 |
| A-4389 | H | H | F | H | H | CH$_2$CH$_2$SO$_2$CF$_3$ | H | H | O | 0 |
| A-4390 | H | H | F | H | H | CH$_2$CH$_2$CH$_2$SO$_2$CF$_3$ | H | H | O | 0 |
| A-4391 | H | H | F | H | H | CH(CH$_3$)SO$_2$CF$_3$ | H | H | O | 0 |
| A-4392 | H | H | F | H | H | CH$_2$CH(CH$_3$)SO$_2$CF$_3$ | H | H | O | 0 |
| A-4393 | H | H | F | H | H | CH(CH$_3$)CH$_2$CH$_2$SO$_2$CF$_3$ | H | H | O | 0 |
| A-4394 | H | H | F | H | H | CH$_2$CH(CH$_3$)CH$_2$SO$_2$CF$_3$ | H | H | O | 0 |
| A-4395 | H | H | F | H | H | CH$_2$CH$_2$CH(CH$_3$)SO$_2$CF$_3$ | H | H | O | 0 |
| A-4396 | H | H | F | H | H | CH$_2$C(=O)CH$_3$ | H | H | O | 0 |
| A-4397 | H | H | F | H | H | CH$_2$C(=O)CH$_2$CH$_3$ | H | H | O | 0 |
| A-4398 | H | H | F | H | H | CH$_2$C(=O)C(CH$_3$)$_3$ | H | H | O | 0 |
| A-4399 | H | H | F | H | H | CH$_2$CH$_2$C(=O)CH$_3$ | H | H | O | 0 |
| A-4400 | H | H | F | H | H | CH$_2$CH$_2$C(=O)C(CH$_3$)$_3$ | H | H | O | 0 |
| A-4401 | H | H | F | H | H | CH$_2$C(=O)CF$_3$ | H | H | O | 0 |
| A-4402 | H | H | F | H | H | CH$_2$CH$_2$C(=O)CF$_3$ | H | H | O | 0 |
| A-4403 | H | H | F | H | H | CH$_2$C(=O)OCH$_3$ | H | H | O | 0 |
| A-4404 | H | H | F | H | H | CH$_2$C(=O)OCH$_2$CH$_3$ | H | H | O | 0 |
| A-4405 | H | H | F | H | H | CH$_2$C(=O)OC(CH$_3$)$_3$ | H | H | O | 0 |
| A-4406 | H | H | F | H | H | CH$_2$CH$_2$C(=O)OCH$_3$ | H | H | O | 0 |
| A-4407 | H | H | F | H | H | CH$_2$CH$_2$C(=O)OCH$_2$CH$_3$ | H | H | O | 0 |
| A-4408 | H | H | F | H | H | CH$_2$CH$_2$C(=O)OC(CH$_3$)$_3$ | H | H | O | 0 |
| A-4409 | H | H | F | H | H | CH$_2$C(=O)NH$_2$ | H | H | O | 0 |
| A-4410 | H | H | F | H | H | CH$_2$CH$_2$C(=O)NH$_2$ | H | H | O | 0 |
| A-4411 | H | H | F | H | H | CH$_2$C(=O)NHCH$_3$ | H | H | O | 0 |
| A-4412 | H | H | F | H | H | CH$_2$C(=O)NHCH(CH$_3$)$_2$ | H | H | O | 0 |
| A-4413 | H | H | F | H | H | CH$_2$CH$_2$C(=O)NHCH$_3$ | H | H | O | 0 |
| A-4414 | H | H | F | H | H | CH$_2$CH$_2$C(=O)NHCH(CH$_3$)$_2$ | H | H | O | 0 |
| A-4415 | H | H | F | H | H | CH$_2$C(=O)NHCH$_2$CHF$_2$ | H | H | O | 0 |
| A-4416 | H | H | F | H | H | CH$_2$C(=O)NHCH$_2$CF$_3$ | H | H | O | 0 |
| A-4417 | H | H | F | H | H | CH$_2$CH$_2$C(=O)NHCH$_2$CHF$_2$ | H | H | O | 0 |
| A-4418 | H | H | F | H | H | CH$_2$CH$_2$C(=O)NHCH$_2$CF$_3$ | H | H | O | 0 |
| A-4419 | H | H | F | H | H | CH$_2$C(=O)N(CH$_3$)$_2$ | H | H | O | 0 |
| A-4420 | H | H | F | H | H | CH$_2$C(=O)N(CH$_2$CH$_3$)$_2$ | H | H | O | 0 |
| A-4421 | H | H | F | H | H | CH$_2$CH$_2$C(=O)N(CH$_3$)$_2$ | H | H | O | 0 |
| A-4422 | H | H | F | H | H | CH$_2$CH$_2$C(=O)N(CH$_2$CH$_3$)$_2$ | H | H | O | 0 |
| A-4423 | H | H | F | H | H | CH$_2$CH$_2$OH | H | H | O | 0 |
| A-4424 | H | H | F | H | H | CH$_2$CH(OH)CH$_3$ | H | H | O | 0 |
| A-4425 | H | H | F | H | H | CH$_2$CH$_2$CH$_2$OH | H | H | O | 0 |
| A-4426 | H | H | F | H | H | CH$_2$CH(OH)CH$_2$CH$_3$ | H | H | O | 0 |
| A-4427 | H | H | F | H | H | CH$_2$CH(OH)C(CH$_3$)$_3$ | H | H | O | 0 |
| A-4428 | H | H | F | H | H | CH$_2$CH$_2$CH(OH)CH$_3$ | H | H | O | 0 |
| A-4429 | H | H | F | H | H | CH$_2$CH$_2$CH(OH)C(CH$_3$)$_3$ | H | H | O | 0 |
| A-4430 | H | H | F | H | H | CH$_2$C(=NOH)CH$_3$ | H | H | O | 0 |
| A-4431 | H | H | F | H | H | CH$_2$C(=NOH)CH$_2$CH$_3$ | H | H | O | 0 |
| A-4432 | H | H | F | H | H | CH$_2$C(=NOH)C(CH$_3$)$_3$ | H | H | O | 0 |
| A-4433 | H | H | F | H | H | CH$_2$C(=NOCH$_3$)CH$_3$ | H | H | O | 0 |
| A-4434 | H | H | F | H | H | CH$_2$C(=NOCH$_3$)CH$_2$CH$_3$ | H | H | O | 0 |
| A-4435 | H | H | F | H | H | CH$_2$C(=NOCH$_2$CH$_3$)CH$_3$ | H | H | O | 0 |
| A-4436 | H | H | F | H | H | CH$_2$C(=NOCH$_2$CH$_3$)CH$_2$CH$_3$ | H | H | O | 0 |
| A-4437 | H | H | F | H | H | CH$_2$C(=NOCH$_2$CF$_3$)CH$_3$ | H | H | O | 0 |
| A-4438 | H | H | F | H | H | CH$_2$C(=NOCH$_2$CF$_3$)CH$_2$CH$_3$ | H | H | O | 0 |
| A-4439 | H | H | F | H | H | CH$_2$Ph | H | H | O | 0 |
| A-4440 | H | H | F | H | H | CH$_2$(2-F)Ph | H | H | O | 0 |
| A-4441 | H | H | F | H | H | CH$_2$(3-F)Ph | H | H | O | 0 |

TABLE 73-continued

| Compound | R¹ | R² | R³ | R⁴ | R⁵ | R⁶ | R⁷ | R⁸ | X | n |
|---|---|---|---|---|---|---|---|---|---|---|
| A-4442 | H | H | F | H | H | CH$_2$(4-F)Ph | H | H | O | 0 |
| A-4443 | H | H | F | H | H | CH$_2$(2-Cl)Ph | H | H | O | 0 |
| A-4444 | H | H | F | H | H | CH$_2$(3-Cl)Ph | H | H | O | 0 |
| A-4445 | H | H | F | H | H | CH$_2$(4-Cl)Ph | H | H | O | 0 |
| A-4446 | H | H | F | H | H | CH$_2$(2-CF$_3$)Ph | H | H | O | 0 |
| A-4447 | H | H | F | H | H | CH$_2$(3-CF$_3$)Ph | H | H | O | 0 |
| A-4448 | H | H | F | H | H | CH$_2$(4-CF$_3$)Ph | H | H | O | 0 |

TABLE 74

| Compound | R¹ | R² | R³ | R⁴ | R⁵ | R⁶ | R⁷ | R⁸ | X | n |
|---|---|---|---|---|---|---|---|---|---|---|
| A-4449 | H | H | H | H | H | CH$_2$(naphthalen-1-yl) | H | H | O | 0 |
| A-4450 | H | H | H | H | H | CH$_2$(naphthalen-2-yl) | H | H | O | 0 |
| A-4451 | H | H | H | H | H | CH$_2$CH$_2$Ph | H | H | O | 0 |
| A-4452 | Cl | H | H | H | H | H | H | H | O | 0 |
| A-4453 | Cl | H | H | H | H | CH$_3$ | H | H | O | 0 |
| A-4454 | Cl | H | H | H | H | CH$_2$CH$_3$ | H | H | O | 0 |
| A-4455 | Cl | H | H | H | H | CH(CH$_3$)$_2$ | H | H | O | 0 |
| A-4455 | Cl | H | H | H | H | CH$_2$CH$_2$CH$_3$ | H | H | O | 0 |
| A-4457 | Cl | H | H | H | H | CH$_2$CH(CH$_3$)$_2$ | H | H | O | 0 |
| A-4458 | Cl | H | H | H | H | CH(CH$_3$)CH$_2$CH$_3$ | H | H | O | 0 |
| A-4459 | Cl | H | H | H | H | CH$_2$C(CH$_3$)$_3$ | H | H | O | 0 |
| A-4460 | Cl | H | H | H | H | CH$_2$(CH$_2$)$_2$CH$_3$ | H | H | O | 0 |
| A-4451 | Cl | H | H | H | H | CH$_2$(CH$_2$)$_3$CH$_3$ | H | H | O | 0 |
| A-4462 | Cl | H | H | H | H | CH$_2$(CH$_2$)$_4$CH$_3$ | H | H | O | 0 |
| A-4463 | Cl | H | H | H | H | CH$_2$(CH$_2$)$_6$CH$_3$ | H | H | O | 0 |
| A-4464 | Cl | H | H | H | H | CH$_2$OCH$_3$ | H | H | O | 0 |
| A-4465 | Cl | H | H | H | H | CH$_2$OCH$_2$CH$_3$ | H | H | O | 0 |
| A-4466 | Cl | H | H | H | H | CH$_2$CH$_2$OCH$_3$ | H | H | O | 0 |
| A-4467 | Cl | H | H | H | H | CH$_2$CH$_2$OCH$_2$CH$_3$ | H | H | O | 0 |
| A-4458 | Cl | H | H | H | H | CF$_3$ | H | H | O | 0 |
| A-4459 | Cl | H | H | H | H | CHF$_2$ | H | H | O | 0 |
| A-4470 | Cl | H | H | H | H | CH$_2$CF$_3$ | H | H | O | 0 |
| A-4471 | Cl | H | H | H | H | CH$_2$CHF$_2$ | H | H | O | 0 |
| A-4472 | Cl | H | H | H | H | CH$_2$CClF$_2$ | H | H | O | 0 |
| A-4473 | Cl | H | H | H | H | CH$_2$CBrF$_2$ | H | H | O | 0 |
| A-4474 | Cl | H | H | H | H | CF$_2$CF$_3$ | H | H | O | 0 |
| A-4475 | Cl | H | H | H | H | CF$_2$CHF$_2$ | H | H | O | 0 |
| A-4476 | Cl | H | H | H | H | CH$_2$CH$_2$CF$_3$ | H | H | O | 0 |
| A-4477 | Cl | H | H | H | H | CH$_2$CF$_2$CF$_3$ | H | H | O | 0 |
| A-4478 | Cl | H | H | H | H | CH$_2$CF$_2$CHF$_2$ | H | H | O | 0 |
| A-4479 | Cl | H | H | H | H | CF$_2$CHFCF$_3$ | H | H | O | 0 |
| A-4480 | Cl | H | H | H | H | CF$_2$CF$_2$CF$_3$ | H | H | O | 0 |
| A-4481 | Cl | H | H | H | H | CH$_2$CF$_2$CF$_2$CF$_3$ | H | H | O | 0 |
| A-4482 | Cl | H | H | H | H | CH$_2$CH$_2$CH$_2$CF$_3$ | H | H | O | 0 |
| A-4483 | Cl | H | H | H | H | CH$_2$CH$_2$CF$_2$CF$_3$ | H | H | O | 0 |
| A-4484 | Cl | H | H | H | H | CF$_2$CF$_2$CF$_2$CF$_3$ | H | H | O | 0 |
| A-4485 | Cl | H | H | H | H | CH$_2$CH$_2$CH(CF$_3$)$_2$ | H | H | O | 0 |
| A-4486 | Cl | H | H | H | H | CF$_2$CF$_2$CF$_2$CF$_2$CF$_3$ | H | H | O | 0 |
| A-4487 | Cl | H | H | H | H | CH$_2$CF$_2$CF$_2$CF$_2$CF$_3$ | H | H | O | 0 |
| A-4488 | Cl | H | H | H | H | CH$_2$CH$_2$CH$_2$CH$_2$CF$_3$ | H | H | O | 0 |
| A-4489 | Cl | H | H | H | H | CH$_2$CF$_2$CF$_2$CF$_2$CHF$_2$ | H | H | O | 0 |
| A-4490 | Cl | H | H | H | H | CH$_2$CF$_2$CF(CF$_3$)CF$_2$C(CF$_3$)$_3$ | H | H | O | 0 |
| A-4491 | Cl | H | H | H | H | CF$_2$CHFOCH$_3$ | H | H | O | 0 |
| A-4492 | Cl | H | H | H | H | CF$_2$CHFOCH$_2$CH$_3$ | H | H | O | 0 |
| A-4493 | Cl | H | H | H | H | CH$_2$CH$_2$OCH$_2$CF$_3$ | H | H | O | 0 |
| A-4494 | Cl | H | H | H | H | CF$_2$CHFOCF$_3$ | H | H | O | 0 |
| A-4495 | Cl | H | H | H | H | CF$_2$CHFOCF$_2$CF$_3$ | H | H | O | 0 |
| A-4495 | Cl | H | H | H | H | CF$_2$CHFOCF$_2$CF$_2$CF$_3$ | H | H | O | 0 |
| A-4497 | Cl | H | H | H | H | CH$_2$CH=CH$_2$ | H | H | O | 0 |
| A-4498 | Cl | H | H | H | H | CH$_2$CH=CHCl | H | H | O | 0 |
| A-4499 | Cl | H | H | H | H | CH$_2$CH=CCl$_2$ | H | H | O | 0 |
| A-4500 | Cl | H | H | H | H | CH$_2$CH$_2$CF=CF$_2$ | H | H | O | 0 |
| A-4501 | Cl | H | H | H | H | CH$_2$CH$_2$CH=CF$_2$ | H | H | O | 0 |
| A-4502 | Cl | H | H | H | H | CH$_2$C≡CH | H | H | O | 0 |
| A-4503 | Cl | H | H | H | H | CH$_2$C≡CCH$_3$ | H | H | O | 0 |
| A-4504 | Cl | H | H | H | H | CH$_2$C≡CF$_3$ | H | H | O | 0 |
| A-4505 | Cl | H | H | H | H | CH$_2$C≡Cl | H | H | O | 0 |
| A-4506 | Cl | H | H | H | H | cyclobutyl | H | H | O | 0 |
| A-4507 | Cl | H | H | H | H | cyclopentyl | H | H | O | 0 |
| A-4508 | Cl | H | H | H | H | cyclohexyl | H | H | O | 0 |
| A-4509 | Cl | H | H | H | H | 4,4-difluorocyclohexyl | H | H | O | 0 |

TABLE 75

| Compound | R¹ | R² | R³ | R³ | R⁵ | R⁶ | R⁷ | R⁸ | X | n |
|---|---|---|---|---|---|---|---|---|---|---|
| A-4510 | Cl | H | H | H | H | CH$_2$(cyclopropyl) | H | H | O | 0 |
| A-4511 | Cl | H | H | H | H | CH$_2$(cyclobutyl) | H | H | O | 0 |
| A-4512 | Cl | H | H | H | H | CH$_2$(cyclopertyl) | H | H | O | 0 |
| A-4513 | Cl | H | H | H | H | CH$_2$CH$_2$(cyclopropyl) | H | H | O | 0 |
| A-4514 | Cl | H | H | H | H | CH$_2$(2,2-difluorocyclopropyl) | H | H | O | 0 |
| A-4515 | Cl | H | H | H | H | CH$_2$(2,2-dichlorocyclopropyl) | H | H | O | 0 |
| A-4516 | Cl | H | H | H | H | CH$_2$(4,4-difluorocyclohexyl) | H | H | O | 0 |
| A-4517 | Cl | H | H | H | H | CH$_2$CH$_2$(2,2-difluorocyclopropyl) | H | H | O | 0 |
| A-4518 | Cl | H | H | H | H | CH$_2$CH$_2$(2,2-dichlorocyclopropyl) | H | H | O | 0 |
| A-4519 | Cl | H | H | H | H | CH$_2$SCH$_3$ | H | H | O | 0 |
| A-4520 | Cl | H | H | H | H | CH$_2$SCH$_2$CH$_3$ | H | H | O | 0 |
| A-4521 | Cl | H | H | H | H | CH$_2$CH$_2$SCH$_3$ | H | H | O | 0 |
| A-4522 | Cl | H | H | H | H | CH$_2$CH$_2$SCH$_2$CH$_3$ | H | H | O | 0 |
| A-4523 | Cl | H | H | H | H | CH$_2$CH$_2$CH$_2$SCH$_3$ | H | H | O | 0 |
| A-4524 | Cl | H | H | H | H | CH$_2$CH$_2$CH$_2$SCH$_2$CH$_3$ | H | H | O | 0 |
| A-4525 | Cl | H | H | H | H | CH(CH$_3$)SCH$_3$ | H | H | O | 0 |
| A-4526 | Cl | H | H | H | H | CH(CH$_3$)SCH$_2$CH$_3$ | H | H | O | 0 |
| A-4527 | Cl | H | H | H | H | CH$_2$CH(CH$_3$)SCH$_3$ | H | H | O | 0 |
| A-4528 | Cl | H | H | H | H | CH$_2$CH(CH$_3$)SCH$_2$CH$_3$ | H | H | O | 0 |
| A-4529 | Cl | H | H | H | H | CH(CH$_3$)CH$_2$CH$_2$SCH$_3$ | H | H | O | 0 |
| A-4530 | Cl | H | H | H | H | CH(CH$_3$)CH$_2$CH$_2$SCH$_2$CH$_3$ | H | H | O | 0 |
| A-4531 | Cl | H | H | H | H | CH$_2$CH(CH$_3$)CH$_2$SCH$_3$ | H | H | O | 0 |
| A-4532 | Cl | H | H | H | H | CH$_2$CH(CH$_3$)CH$_2$SCH$_2$CH$_3$ | H | H | O | 0 |
| A-4533 | Cl | H | H | H | H | CH$_2$CH$_2$CH(CH$_3$)SCH$_3$ | H | H | O | 0 |
| A-4534 | Cl | H | H | H | H | CH$_2$CH$_2$CH(CH$_3$)SCH$_2$CH$_3$ | H | H | O | 0 |
| A-4535 | Cl | H | H | H | H | CH$_2$SOCH$_3$ | H | H | O | 0 |
| A-4536 | Cl | H | H | H | H | CH$_2$CH$_2$SOCH$_3$ | H | H | O | 0 |
| A-4537 | Cl | H | H | H | H | CH$_2$CH$_2$CH$_2$SOCH$_3$ | H | H | O | 0 |
| A-4538 | Cl | H | H | H | H | CH(CH$_3$)SOCH$_3$ | H | H | O | 0 |
| A-4539 | Cl | H | H | H | H | CH$_2$CH(CH$_3$)SOCH$_3$ | H | H | O | 0 |
| A-4540 | Cl | H | H | H | H | CH(CH$_3$)CH$_2$CH$_2$SOCH$_3$ | H | H | O | 0 |
| A-4541 | Cl | H | H | H | H | CH$_2$CH(CH$_3$)CH$_2$SOCH$_3$ | H | H | O | 0 |
| A-4542 | Cl | H | H | H | H | CH$_2$CH$_2$CH(CH$_3$)SOCH$_3$ | H | H | O | 0 |
| A-4543 | Cl | H | H | H | H | CH$_2$SO$_2$CH$_3$ | H | H | O | 0 |
| A-4544 | Cl | H | H | H | H | CH$_2$CH$_2$SO$_2$CH$_3$ | H | H | O | 0 |
| A-4545 | Cl | H | H | H | H | CH$_2$CH$_2$CH$_2$SO$_2$CH$_3$ | H | H | O | 0 |
| A-4546 | Cl | H | H | H | H | CH(CH$_3$)SO$_2$CH$_3$ | H | H | O | 0 |
| A-4547 | Cl | H | H | H | H | CH$_2$CH(CH$_3$)SO$_2$CH$_3$ | H | H | O | 0 |
| A-4548 | Cl | H | H | H | H | CH(CH$_3$)CH$_2$CH$_2$SO$_2$CH$_3$ | H | H | O | 0 |
| A-4549 | Cl | H | H | H | H | CH$_2$CH(CH$_3$)CH$_2$SO$_2$CH$_3$ | H | H | O | 0 |
| A-4550 | Cl | H | H | H | H | CH$_2$CH$_2$CH(CH$_3$)SO$_2$CH$_3$ | H | H | O | 0 |
| A-4551 | Cl | H | H | H | H | CH$_2$SCF$_3$ | H | H | O | 0 |
| A-4552 | Cl | H | H | H | H | CH$_2$SCHF$_2$ | H | H | O | 0 |
| A-4553 | Cl | H | H | H | H | CH$_2$SCH$_2$CF$_3$ | H | H | O | 0 |
| A-4554 | Cl | H | H | H | H | CH$_2$SCH$_2$CHF$_2$ | H | H | O | 0 |
| A-4555 | Cl | H | H | H | H | CH$_2$SCF$_2$CF$_3$ | H | H | O | 0 |
| A-4556 | Cl | H | H | H | H | CH$_2$CH$_2$SCF$_3$ | H | H | O | 0 |
| A-4557 | Cl | H | H | H | H | CH$_2$CH$_2$SCH$_2$CF$_3$ | H | H | O | 0 |
| A-4558 | Cl | H | H | H | H | CH$_2$CH$_2$CH$_2$SCF$_3$ | H | H | O | 0 |
| A-4559 | Cl | H | H | H | H | CH$_2$CH$_2$CH$_2$SCH$_2$CF$_3$ | H | H | O | 0 |
| A-4560 | Cl | H | H | H | H | CH(CH$_3$)SCF$_3$ | H | H | O | 0 |
| A-4561 | Cl | H | H | H | H | CH(CH$_3$)SCH$_2$CF$_3$ | H | H | O | 0 |
| A-4562 | Cl | H | H | H | H | CH$_2$CH(CH$_3$)SCF$_3$ | H | H | O | 0 |
| A-4563 | Cl | H | H | H | H | CH$_2$CH(CH$_3$)SCH$_2$CF$_3$ | H | H | O | 0 |
| A-4564 | Cl | H | H | H | H | CH(CH$_3$)CH$_2$CH$_2$SCF$_3$ | H | H | O | 0 |
| A-4565 | Cl | H | H | H | H | CH(CH$_3$)CH$_2$CH$_2$SCH$_2$CF$_3$ | H | H | O | 0 |
| A-4566 | Cl | H | H | H | H | CH$_2$CH(CH$_3$)CH$_2$SCF$_3$ | H | H | O | 0 |
| A-4567 | Cl | H | H | H | H | CH$_2$CH(CH$_3$)CH$_2$SCH$_2$CF$_3$ | H | H | O | 0 |
| A-4568 | Cl | H | H | H | H | CH$_2$CH$_2$CH(CH$_3$)SCF$_3$ | H | H | O | 0 |
| A-4569 | Cl | H | H | H | H | CH$_2$CH$_2$CH(CH$_3$)SCH$_2$CF$_3$ | H | H | O | 0 |
| A-4570 | Cl | H | H | H | H | CH$_2$SOCF$_3$ | H | H | O | 0 |

TABLE 76

| Compound | R¹ | R² | R³ | R⁴ | R⁵ | R⁶ | R⁷ | R⁸ | X | n |
|---|---|---|---|---|---|---|---|---|---|---|
| A-4571 | Cl | H | H | H | H | CH$_2$CH$_2$SOCF$_3$ | H | H | O | 0 |
| A-4572 | Cl | H | H | H | H | CH$_2$CH$_2$CH$_2$SOCF$_3$ | H | H | O | 0 |
| A-4573 | Cl | H | H | H | H | CH(CH$_3$)SOCF$_3$ | H | H | O | 0 |
| A-4574 | Cl | H | H | H | H | CH$_2$CH(CH$_3$)SOCF$_3$ | H | H | O | 0 |
| A-4575 | Cl | H | H | H | H | CH(CH$_3$)CH$_2$CH$_2$SOCF$_3$ | H | H | O | 0 |
| A-4576 | Cl | H | H | H | H | CH$_2$CH(CH$_3$)CH$_2$SOCF$_3$ | H | H | O | 0 |
| A-4577 | Cl | H | H | H | H | CH$_2$CH$_2$CH(CH$_3$)SOCF$_3$ | H | H | O | 0 |
| A-4578 | Cl | H | H | H | H | CH$_2$SO$_2$CF$_3$ | H | H | O | 0 |
| A-4579 | Cl | H | H | H | H | CH$_2$CH$_2$SO$_2$CF$_3$ | H | H | O | 0 |

TABLE 76-continued

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-4580 | Cl | H | H | H | H | CH$_2$CH$_2$CH$_2$SO$_2$CF$_3$ | H | H | O | 0 |
| A-4581 | Cl | H | H | H | H | CH(CH$_3$)SO$_2$CF$_3$ | H | H | O | 0 |
| A-4582 | Cl | H | H | H | H | CH$_2$CH(CH$_3$)SO$_2$CF$_3$ | H | H | O | 0 |
| A-4583 | Cl | H | H | H | H | CH(CH$_3$)CH$_2$CH$_2$SO$_2$CF$_3$ | H | H | O | 0 |
| A-4584 | Cl | H | H | H | H | CH$_2$CH(CH$_3$)CH$_2$SO$_2$CF$_3$ | H | H | O | 0 |
| A-4585 | Cl | H | H | H | H | CH$_2$CH$_2$CH(CH$_3$)SO$_2$CF$_3$ | H | H | O | 0 |
| A-4586 | Cl | H | H | H | H | CH$_2$C(=O)CH$_3$ | H | H | O | 0 |
| A-4587 | Cl | H | H | H | H | CH$_2$C(=O)CH$_2$CH$_3$ | H | H | O | 0 |
| A-4588 | Cl | H | H | H | H | CH$_2$C(=O)C(CH$_3$)$_3$ | H | H | O | 0 |
| A-4589 | Cl | H | H | H | H | CH$_2$CH$_2$C(=O)CH$_3$ | H | H | O | 0 |
| A-4590 | Cl | H | H | H | H | CH$_2$CH$_2$C(=O)C(CH$_3$)$_3$ | H | H | O | 0 |
| A-4591 | Cl | H | H | H | H | CH$_2$C(=O)CF$_3$ | H | H | O | 0 |
| A-4592 | Cl | H | H | H | H | CH$_2$CH$_2$C(=O)CF$_3$ | H | H | O | 0 |
| A-4593 | Cl | H | H | H | H | CH$_2$C(=O)OCH$_3$ | H | H | O | 0 |
| A-4594 | Cl | H | H | H | H | CH$_2$C(=O)OCH$_2$CH$_3$ | H | H | O | 0 |
| A-4595 | Cl | H | H | H | H | CH$_2$C(=O)OC(CH$_3$)$_3$ | H | H | O | 0 |
| A-4596 | Cl | H | H | H | H | CH$_2$CH$_2$C(=O)OCH$_3$ | H | H | O | 0 |
| A-4597 | Cl | H | H | H | H | CH$_2$CH$_2$C(=O)OCH$_2$CH$_3$ | H | H | O | 0 |
| A-4598 | Cl | H | H | H | H | CH$_2$CH$_2$C(=O)OC(CH$_3$)$_3$ | H | H | O | 0 |
| A-4599 | Cl | H | H | H | H | CH$_2$C(=O)NH$_2$ | H | H | O | 0 |
| A-4600 | Cl | H | H | H | H | CH$_2$CH$_2$C(=O)NH$_2$ | H | H | O | 0 |
| A-4601 | Cl | H | H | H | H | CH$_2$C(=O)NHCH$_3$ | H | H | O | 0 |
| A-4602 | Cl | H | H | H | H | CH$_2$C(=O)NHCH(CH$_3$)$_2$ | H | H | O | 0 |
| A-4603 | Cl | H | H | H | H | CH$_2$CH$_2$C(=O)NHCH$_3$ | H | H | O | 0 |
| A-4604 | Cl | H | H | H | H | CH$_2$CH$_2$C(=O)NHCH(CH$_3$)$_2$ | H | H | O | 0 |
| A-4605 | Cl | H | H | H | H | CH$_2$C(=O)NHCH$_2$CHF$_2$ | H | H | O | 0 |
| A-4606 | Cl | H | H | H | H | CH$_2$C(=O)NHCH$_2$CF$_3$ | H | H | O | 0 |
| A-4607 | Cl | H | H | H | H | CH$_2$CH$_2$C(=O)NHCH$_2$CHF$_2$ | H | H | O | 0 |
| A-4608 | Cl | H | H | H | H | CH$_2$CH$_2$C(=O)NHCH$_2$CF$_3$ | H | H | O | 0 |
| A-4609 | Cl | H | H | H | H | CH$_2$C(=O)N(CH$_3$)$_2$ | H | H | O | 0 |
| A-4610 | Cl | H | H | H | H | CH$_2$C(=O)N(CH$_2$CH$_3$)$_2$ | H | H | O | 0 |
| A-4611 | Cl | H | H | H | H | CH$_2$CH$_2$C(=O)N(CH$_3$)$_2$ | H | H | O | 0 |
| A-4612 | Cl | H | H | H | H | CH$_2$CH$_2$C(=O)N(CH$_2$CH$_3$)$_2$ | H | H | O | 0 |
| A-4613 | Cl | H | H | H | H | CH$_2$CH$_2$OH | H | H | O | 0 |
| A-4614 | Cl | H | H | H | H | CH$_2$CH(OH)CH$_3$ | H | H | O | 0 |
| A-4615 | Cl | H | H | H | H | CH$_2$CH$_2$CH$_2$OH | H | H | O | 0 |
| A-4616 | Cl | H | H | H | H | CH$_2$CH(OH)CH$_2$CH$_3$ | H | H | O | 0 |
| A-4617 | Cl | H | H | H | H | CH$_2$CH(OH)C(CH$_3$)$_3$ | H | H | O | 0 |
| A-4618 | Cl | H | H | H | H | CH$_2$CH$_2$CH(OH)CH$_3$ | H | H | O | 0 |
| A-4619 | Cl | H | H | H | H | CH$_2$CH$_2$CH(OH)C(CH$_3$)$_3$ | H | H | O | 0 |
| A-4620 | Cl | H | H | H | H | CH$_2$C(=NOH)CH$_3$ | H | H | O | 0 |
| A-4621 | Cl | H | H | H | H | CH$_2$C(=NOH)CH$_2$CH$_3$ | H | H | O | 0 |
| A-4622 | Cl | H | H | H | H | CH$_2$C(=NOH)C(CH$_3$)$_3$ | H | H | O | 0 |
| A-4623 | Cl | H | H | H | H | CH$_2$C(=NOCH$_3$)CH$_3$ | H | H | O | 0 |
| A-4624 | Cl | H | H | H | H | CH$_2$C(=NOCH$_3$)CH$_2$CH$_3$ | H | H | O | 0 |
| A-4625 | Cl | H | H | H | H | CH$_2$C(=NOCH$_2$CH$_3$)CH$_3$ | H | H | O | 0 |
| A-4626 | Cl | H | H | H | H | CH$_2$C(=NOCH$_2$CH$_3$)CH$_2$CH$_3$ | H | H | O | 0 |
| A-4627 | Cl | H | H | H | H | CH$_2$C(=NOCH$_2$CF$_3$)CH$_3$ | H | H | O | 0 |
| A-4628 | Cl | H | H | H | H | CH$_2$C(=NOCH$_2$CF$_3$)CH$_2$CH$_3$ | H | H | O | 0 |
| A-4629 | Cl | H | H | H | H | CH$_2$Ph | H | H | O | 0 |
| A-4630 | Cl | H | H | H | H | CH$_2$(2-F)Ph | H | H | O | 0 |
| A-4631 | Cl | H | H | H | H | CH$_2$(3-F)Ph | H | H | O | 0 |

TABLE 77

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-4632 | Cl | H | H | H | H | CH$_2$(4-F)Ph | H | H | O | 0 |
| A-4633 | Cl | H | H | H | H | CH$_2$(2-Cl)Ph | H | H | O | 0 |
| A-4634 | Cl | H | H | H | H | CH$_2$(3-Cl)Ph | H | H | O | 0 |
| A-4635 | Cl | H | H | H | H | CH$_2$(4-Cl)Ph | H | H | O | 0 |
| A-4636 | Cl | H | H | H | H | CH$_2$(2-CF$_3$)Ph | H | H | O | 0 |
| A-4637 | Cl | H | H | H | H | CH$_2$(3-CF$_3$)Ph | H | H | O | 0 |
| A-4638 | Cl | H | H | H | H | CH$_2$(4-CF$_3$)Ph | H | H | O | 0 |
| A-4639 | Cl | H | H | H | H | CH$_2$(naphthalen-1-yl) | H | H | O | 0 |
| A-4640 | Cl | H | H | H | H | CH$_2$(naphthalen-2-yl) | H | H | O | 0 |
| A-4641 | Cl | H | H | H | H | CH$_2$CH$_2$Ph | H | H | O | 0 |
| A-4642 | H | H | H | Cl | H | H | H | H | O | 0 |
| A-4643 | H | H | H | Cl | H | CH$_3$ | H | H | O | 0 |
| A-4644 | H | H | H | Cl | H | CH$_2$CH$_3$ | H | H | O | 0 |
| A-4645 | H | H | H | Cl | H | CH(CH$_3$)$_2$ | H | H | O | 0 |
| A-4646 | H | H | H | Cl | H | CH$_2$CH$_2$CH$_3$ | H | H | O | 0 |
| A-4647 | H | H | H | Cl | H | CH$_2$CH(CH$_3$)$_2$ | H | H | O | 0 |
| A-4648 | H | H | H | Cl | H | CH(CH$_3$)CH$_2$CH$_3$ | H | H | O | 0 |
| A-4649 | H | H | H | Cl | H | CH$_2$C(CH$_3$)$_3$ | H | H | O | 0 |

TABLE 77-continued

| Compound | R¹ | R² | R³ | R⁴ | R⁵ | R⁶ | R⁷ | R⁸ | X | n |
|---|---|---|---|---|---|---|---|---|---|---|
| A-4650 | H | H | H | Cl | H | CH₂(CH₂)₂CH₃ | H | H | O | 0 |
| A-4651 | H | H | H | Cl | H | CH₂(CH₂)₃CH₃ | H | H | O | 0 |
| A-4652 | H | H | H | Cl | H | CH₂(CH₂)₄CH₃ | H | H | O | 0 |
| A-4653 | H | H | H | Cl | H | CH₂(CH₂)₆CH₃ | H | H | O | 0 |
| A-4654 | H | H | H | Cl | H | CH₂OCH₃ | H | H | O | 0 |
| A-4655 | H | H | H | Cl | H | CH₂OCH₂CH₃ | H | H | O | 0 |
| A-4656 | H | H | H | Cl | H | CH₂CH₂OCH₃ | H | H | O | 0 |
| A-4657 | H | H | H | Cl | H | CH₂CH₂OCH₂CH₃ | H | H | O | 0 |
| A-4658 | H | H | H | Cl | H | CF₃ | H | H | O | 0 |
| A-4659 | H | H | H | Cl | H | CHF₂ | H | H | O | 0 |
| A-4660 | H | H | H | Cl | H | CH₂CF₃ | H | H | O | 0 |
| A-4661 | H | H | H | Cl | H | CH₂CHF₂ | H | H | O | 0 |
| A-4662 | H | H | H | Cl | H | CH₂CClF₂ | H | H | O | 0 |
| A-4663 | H | H | H | Cl | H | CH₂CBrF₂ | H | H | O | 0 |
| A-4664 | H | H | H | Cl | H | CF₂CF₃ | H | H | O | 0 |
| A-4665 | H | H | H | Cl | H | CF₂CHF₂ | H | H | O | 0 |
| A-4666 | H | H | H | Cl | H | CH₂CH₂CF₃ | H | H | O | 0 |
| A-4667 | H | H | H | Cl | H | CH₂CF₂CF₃ | H | H | O | 0 |
| A-4668 | H | H | H | Cl | H | CH₂CF₂CHF₂ | H | H | O | 0 |
| A-4669 | H | H | H | Cl | H | CF₂CHFCF₃ | H | H | O | 0 |
| A-4670 | H | H | H | Cl | H | CF₂CF₂CF₃ | H | H | O | 0 |
| A-4671 | H | H | H | Cl | H | CH₂CF₂CF₂CF₃ | H | H | O | 0 |
| A-4672 | H | H | H | Cl | H | CH₂CH₂CH₂CF₃ | H | H | O | 0 |
| A-4673 | H | H | H | Cl | H | CH₂CH₂CF₂CF₃ | H | H | O | 0 |
| A-4674 | H | H | H | Cl | H | CF₂CF₂CF₂CF₃ | H | H | O | 0 |
| A-4675 | H | H | H | Cl | H | CH₂CH₂CH(CF₃)₂ | H | H | O | 0 |
| A-4676 | H | H | H | Cl | H | CF₂CF₂CF₂CF₂CF₃ | H | H | O | 0 |
| A-4677 | H | H | H | Cl | H | CH₂CF₂CF₂CF₂CF₃ | H | H | O | 0 |
| A-4678 | H | H | H | Cl | H | CH₂CH₂CH₂CH₂CF₃ | H | H | O | 0 |
| A-4679 | H | H | H | Cl | H | CH₂CF₂CF₂CF₂CHF₂ | H | H | O | 0 |
| A-4680 | H | H | H | Cl | H | CH₂CF₂CF(CF₃)CF₂C(CF₃)₃ | H | H | O | 0 |
| A-4681 | H | H | H | Cl | H | CF₂CHFOCH₃ | H | H | O | 0 |
| A-4682 | H | H | H | Cl | H | CF₂CHFOCH₂CH₃ | H | H | O | 0 |
| A-4683 | H | H | H | Cl | H | CH₂CH₂OCH₂CF₃ | H | H | O | 0 |
| A-4684 | H | H | H | Cl | H | CF₂CHFOCF₃ | H | H | O | 0 |
| A-4685 | H | H | H | Cl | H | CF₂CHFOCF₂CF₃ | H | H | O | 0 |
| A-4686 | H | H | H | Cl | H | CF₂CHFOCF₂CF₂CF₃ | H | H | O | 0 |
| A-4687 | H | H | H | Cl | H | CH₂CH=CH₂ | H | H | O | 0 |
| A-4688 | H | H | H | Cl | H | CH₂CH=CHCl | H | H | O | 0 |
| A-4689 | H | H | H | Cl | H | CH₂CH=CCl₂ | H | H | O | 0 |
| A-4690 | H | H | H | Cl | H | CH₂CH₂CF=CF₂ | H | H | O | 0 |
| A-4691 | H | H | H | Cl | H | CH₂CH₂CH=CF₂ | H | H | O | 0 |
| A-4692 | H | H | H | Cl | H | CH₂C≡CH | H | H | O | 0 |

TABLE 78

| Compound | R¹ | R² | R³ | R⁴ | R⁵ | R⁶ | R⁷ | R⁸ | X | n |
|---|---|---|---|---|---|---|---|---|---|---|
| A-4693 | H | H | H | Cl | H | CH₂C≡CCH₃ | H | H | O | 0 |
| A-4694 | H | H | H | Cl | H | CH₂C≡CCF₃ | H | H | O | 0 |
| A-4695 | H | H | H | Cl | H | CH₂C≡CI | H | H | O | 0 |
| A-4696 | H | H | H | Cl | H | cyclobutyl | H | H | O | 0 |
| A-4697 | H | H | H | Cl | H | cyclopentyl | H | H | O | 0 |
| A-4698 | H | H | H | Cl | H | cyclohexyl | H | H | O | 0 |
| A-4699 | H | H | H | Cl | H | 4,4-difluorocyclohexyl | H | H | O | 0 |
| A-4700 | H | H | H | Cl | H | CH₂(cyclopropyl) | H | H | O | 0 |
| A-4701 | H | H | H | Cl | H | CH₂(cyclobutyl) | H | H | O | 0 |
| A-4702 | H | H | H | Cl | H | CH₂(cyclopentyl) | H | H | O | 0 |
| A-4703 | H | H | H | Cl | H | CH₂CH₂(cyclopropyl) | H | H | O | 0 |
| A-4704 | H | H | H | Cl | H | CH₂(2,2-difluororcyclopropyl) | H | H | O | 0 |
| A-4705 | H | H | H | Cl | H | CH₂(2,2-dichlorocyclopropyl) | H | H | O | 0 |
| A-4706 | H | H | H | Cl | H | CH₂(4,4-difluorocyclohexyl) | H | H | O | 0 |
| A-4707 | H | H | H | Cl | H | CH₂CH₂(2,2-difluorocyclopropyl) | H | H | O | 0 |
| A-4708 | H | H | H | Cl | H | CH₂CH₂(2,2-dichlorocyclopropyl) | H | H | O | 0 |
| A-4709 | H | H | H | Cl | H | CH₂SCH₃ | H | H | O | 0 |
| A-4710 | H | H | H | Cl | H | CH₂SCH₂CH₃ | H | H | O | 0 |
| A-4711 | H | H | H | Cl | H | CH₂CH₂SCH₃ | H | H | O | 0 |
| A-4712 | H | H | H | Cl | H | CH₂CH₂SCH₂CH₃ | H | H | O | 0 |
| A-4713 | H | H | H | Cl | H | CH₂CH₂CH₂SCH₃ | H | H | O | 0 |
| A-4714 | H | H | H | Cl | H | CH₂CH₂CH₂SCH₂CH₃ | H | H | O | 0 |
| A-4715 | H | H | H | Cl | H | CH(CH₃)SCH₃ | H | H | O | 0 |
| A-4716 | H | H | H | Cl | H | CH(CH₃)SCH₂CH₃ | H | H | O | 0 |
| A-4717 | H | H | H | Cl | H | CH₂CH(CH₃)SCH₃ | H | H | O | 0 |
| A-4718 | H | H | H | Cl | H | CH₂CH(CH₃)SCH₂CH₃ | H | H | O | 0 |
| A-4719 | H | H | H | Cl | H | CH(CH₃)CH₂CH₂SCH₃ | H | H | O | 0 |

TABLE 78-continued

| Compound | R¹ | R² | R³ | R⁴ | R⁵ | R⁶ | R⁷ | R⁸ | X | n |
|---|---|---|---|---|---|---|---|---|---|---|
| A-4720 | H | H | H | Cl | H | CH(CH$_3$)CH$_2$CH$_2$SCH$_2$CH$_3$ | H | H | O | 0 |
| A-4721 | H | H | H | Cl | H | CH$_2$CH(CH$_3$)CH$_2$SCH$_3$ | H | H | O | 0 |
| A-4722 | H | H | H | Cl | H | CH$_2$CH(CH$_3$)CH$_2$SCH$_2$CH$_3$ | H | H | O | 0 |
| A-4723 | H | H | H | Cl | H | CH$_2$CH$_2$CH(CH$_3$)SCH$_3$ | H | H | O | 0 |
| A-4724 | H | H | H | Cl | H | CH$_2$CH$_2$CH(CH$_3$)SCH$_2$CH$_3$ | H | H | O | 0 |
| A-4725 | H | H | H | Cl | H | CH$_2$SOCH$_3$ | H | H | O | 0 |
| A-4726 | H | H | H | Cl | H | CH$_2$CH$_2$SOCH$_3$ | H | H | O | 0 |
| A-4727 | H | H | H | Cl | H | CH$_2$CH$_2$CH$_2$SOCH$_3$ | H | H | O | 0 |
| A-4728 | H | H | H | Cl | H | CH(CH$_3$)SOCH$_3$ | H | H | O | 0 |
| A-4729 | H | H | H | Cl | H | CH$_2$CH(CH$_3$)SOCH$_3$ | H | H | O | 0 |
| A-4730 | H | H | H | Cl | H | CH(CH$_3$)CH$_2$CH$_2$SOCH$_3$ | H | H | O | 0 |
| A-4731 | H | H | H | Cl | H | CH$_2$CH(CH$_3$)CH$_2$SOCH$_3$ | H | H | O | 0 |
| A-4732 | H | H | H | Cl | H | CH$_2$CH$_2$CH(CH$_3$)SOCH$_3$ | H | H | O | 0 |
| A-4733 | H | H | H | Cl | H | CH$_2$SO$_2$CH$_3$ | H | H | O | 0 |
| A-4734 | H | H | H | Cl | H | CH$_2$CH$_2$SO$_2$CH$_3$ | H | H | O | 0 |
| A-4735 | H | H | H | Cl | H | CH$_2$CH$_2$CH$_2$SO$_2$CH$_3$ | H | H | O | 0 |
| A-4736 | H | H | H | Cl | H | CH(CH$_3$)SO$_2$CH$_3$ | H | H | O | 0 |
| A-4737 | H | H | H | Cl | H | CH$_2$CH(CH$_3$)SO$_2$CH$_3$ | H | H | O | 0 |
| A-4738 | H | H | H | Cl | H | CH(CH$_3$)CH$_2$CH$_2$SO$_2$CH$_3$ | H | H | O | 0 |
| A-4739 | H | H | H | Cl | H | CH$_2$CH(CH$_3$)CH$_2$SO$_2$CH$_3$ | H | H | O | 0 |
| A-4740 | H | H | H | Cl | H | CH$_2$CH$_2$CH(CH$_3$)SO$_2$CH$_3$ | H | H | O | 0 |
| A-4741 | H | H | H | Cl | H | CH$_2$SCF$_3$ | H | H | O | 0 |
| A-4742 | H | H | H | Cl | H | CH$_2$SCHF$_2$ | H | H | O | 0 |
| A-4743 | H | H | H | Cl | H | CH$_2$SCH$_2$CF$_3$ | H | H | O | 0 |
| A-4744 | H | H | H | Cl | H | CH$_2$SCH$_2$CHF$_2$ | H | H | O | 0 |
| A-4745 | H | H | H | Cl | H | CH$_2$SCF$_2$CF$_3$ | H | H | O | 0 |
| A-4746 | H | H | H | Cl | H | CH$_2$CH$_2$SCF$_3$ | H | H | O | 0 |
| A-4747 | H | H | H | Cl | H | CH$_2$CH$_2$SCH$_2$CF$_3$ | H | H | O | 0 |
| A-4748 | H | H | H | Cl | H | CH$_2$CH$_2$CH$_2$SCF$_3$ | H | H | O | 0 |
| A-4749 | H | H | H | Cl | H | CH$_2$CH$_2$CH$_2$SCH$_2$CF$_3$ | H | H | O | 0 |
| A-4750 | H | H | H | Cl | H | CH(CH$_3$)SCF$_3$ | H | H | O | 0 |
| A-4751 | H | H | H | Cl | H | CH(CH$_3$)SCH$_2$CF$_3$ | H | H | O | 0 |
| A-4752 | H | H | H | Cl | H | CH$_2$CH(CH$_3$)SCF$_3$ | H | H | O | 0 |
| A-4753 | H | H | H | Cl | H | CH$_2$CH(CH$_3$)SCH$_2$CF$_3$ | H | H | O | 0 |

TABLE 79

| Compound | R¹ | R² | R³ | R⁴ | R⁵ | R⁶ | R⁷ | R⁸ | X | n |
|---|---|---|---|---|---|---|---|---|---|---|
| A-4754 | H | H | H | Cl | H | CH(CH$_3$)CH$_2$CH$_2$SCF$_3$ | H | H | O | 0 |
| A-4755 | H | H | H | Cl | H | CH(CH$_3$)CH$_2$CH$_2$SCH$_2$CF$_3$ | H | H | O | 0 |
| A-4756 | H | H | H | Cl | H | CH$_2$CH(CH$_3$)CH$_2$SCF$_3$ | H | H | O | 0 |
| A-4757 | H | H | H | Cl | H | CH$_2$CH(CH$_3$)CH$_2$SCH$_2$CF$_3$ | H | H | O | 0 |
| A-4758 | H | H | H | Cl | H | CH$_2$CH$_2$CH(CH$_3$)SCF$_3$ | H | H | O | 0 |
| A-4759 | H | H | H | Cl | H | CH$_2$CH$_2$CH(CH$_3$)SCH$_2$CF$_3$ | H | H | O | 0 |
| A-4760 | H | H | H | Cl | H | CH$_2$SOCF$_3$ | H | H | O | 0 |
| A-4761 | H | H | H | Cl | H | CH$_2$CH$_2$SOCF$_3$ | H | H | O | 0 |
| A-4762 | H | H | H | Cl | H | CH$_2$CH$_2$CH$_2$SOCF$_3$ | H | H | O | 0 |
| A-4763 | H | H | H | Cl | H | CH(CH$_3$)SOCF$_3$ | H | H | O | 0 |
| A-4764 | H | H | H | Cl | H | CH$_2$CH(CH$_3$)SOCF$_3$ | H | H | O | 0 |
| A-4765 | H | H | H | Cl | H | CH(CH$_3$)CH$_2$CH$_2$SOCF$_3$ | H | H | O | 0 |
| A-4766 | H | H | H | Cl | H | CH$_2$CH(CH$_3$)CH$_2$SOCF$_3$ | H | H | O | 0 |
| A-4767 | H | H | H | Cl | H | CH$_2$CH$_2$CH(CH$_3$)SOCF$_3$ | H | H | O | 0 |
| A-4768 | H | H | H | Cl | H | CH$_2$SO$_2$CF$_3$ | H | H | O | 0 |
| A-4769 | H | H | H | Cl | H | CH$_2$CH$_2$SO$_2$CF$_3$ | H | H | O | 0 |
| A-4770 | H | H | H | Cl | H | CH$_2$CH$_2$CH$_2$SO$_2$CF$_3$ | H | H | O | 0 |
| A-4771 | H | H | H | Cl | H | CH(CH$_3$)SO$_2$CF$_3$ | H | H | O | 0 |
| A-4772 | H | H | H | Cl | H | CH$_2$CH(CH$_3$)SO$_2$CF$_3$ | H | H | O | 0 |
| A-4773 | H | H | H | Cl | H | CH(CH$_3$)CH$_2$CH$_2$SO$_2$CF$_3$ | H | H | O | 0 |
| A-4774 | H | H | H | Cl | H | CH$_2$CH(CH$_3$)CH$_2$SO$_2$CF$_3$ | H | H | O | 0 |
| A-4775 | H | H | H | Cl | H | CH$_2$CH$_2$CH(CH$_3$)SO$_2$CF$_3$ | H | H | O | 0 |
| A-4776 | H | H | H | Cl | H | CH$_2$C(=O)CH$_3$ | H | H | O | 0 |
| A-4777 | H | H | H | Cl | H | CH$_2$C(=O)CH$_2$CH$_3$ | H | H | O | 0 |
| A-4778 | H | H | H | Cl | H | CH$_2$C(=O)C(CH$_3$)$_3$ | H | H | O | 0 |
| A-4779 | H | H | H | Cl | H | CH$_2$CH$_2$C(=O)CH$_3$ | H | H | O | 0 |
| A-4780 | H | H | H | Cl | H | CH$_2$CH$_2$C(=O)C(CH$_3$)$_3$ | H | H | O | 0 |
| A-4781 | H | H | H | Cl | H | CH$_2$C(=O)CF$_3$ | H | H | O | 0 |
| A-4782 | H | H | H | Cl | H | CH$_2$CH$_2$C(=O)CF$_3$ | H | H | O | 0 |
| A-4783 | H | H | H | Cl | H | CH$_2$C(=O)OCH$_3$ | H | H | O | 0 |
| A-4784 | H | H | H | Cl | H | CH$_2$C(=O)OCH$_2$CH$_3$ | H | H | O | 0 |
| A-4785 | H | H | H | Cl | H | CH$_2$C(=O)OC(CH$_3$)$_3$ | H | H | O | 0 |
| A-4786 | H | H | H | Cl | H | CH$_2$CH$_2$C(=O)OCH$_3$ | H | H | O | 0 |
| A-4787 | H | H | H | Cl | H | CH$_2$CH$_2$C(=O)OCH$_2$CH$_3$ | H | H | O | 0 |
| A-4788 | H | H | H | Cl | H | CH$_2$CH$_2$C(=O)OC(CH$_3$)$_3$ | H | H | O | 0 |
| A-4789 | H | H | H | Cl | H | CH$_2$C(=O)NH$_2$ | H | H | O | 0 |

TABLE 79-continued

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-4790 | H | H | H | Cl | H | $CH_2CH_2C(=O)NH_2$ | H | H | O | 0 |
| A-4791 | H | H | H | Cl | H | $CH_2C(=O)NHCH_3$ | H | H | O | 0 |
| A-4792 | H | H | H | Cl | H | $CH_2C(=O)NHCH(CH_3)_2$ | H | H | O | 0 |
| A-4793 | H | H | H | Cl | H | $CH_2CH_2C(=O)NHCH_3$ | H | H | O | 0 |
| A-4794 | H | H | H | Cl | H | $CH_2CH_2C(=O)NHCH(CH_3)_2$ | H | H | O | 0 |
| A-4795 | H | H | H | Cl | H | $CH_2C(=O)NHCH_2CHF_2$ | H | H | O | 0 |
| A-4796 | H | H | H | Cl | H | $CH_2C(=C)NHCH_2CF_3$ | H | H | O | 0 |
| A-4797 | H | H | H | Cl | H | $CH_2CH_2C(=O)NHCH_2CHF_2$ | H | H | O | 0 |
| A-4798 | H | H | H | Cl | H | $CH_2CH_2C(=O)NHCH_2CF_3$ | H | H | O | 0 |
| A-4799 | H | H | H | Cl | H | $CH_2C(=O)N(CH_3)_2$ | H | H | O | 0 |
| A-4800 | H | H | H | Cl | H | $CH_2C(=O)N(CH_2CH_3)_2$ | H | H | O | 0 |
| A-4801 | H | H | H | Cl | H | $CH_2CH_2C(=O)N(CH_3)_2$ | H | H | O | 0 |
| A-4802 | H | H | H | Cl | H | $CH_2CH_2C(=O)N(CH_2CH_3)_2$ | H | H | O | 0 |
| A-4803 | H | H | H | Cl | H | $CH_2CH_2OH$ | H | H | O | 0 |
| A-4804 | H | H | H | Cl | H | $CH_2CH(OH)CH_3$ | H | H | O | 0 |
| A-4805 | H | H | H | Cl | H | $CH_2CH_2CH_2OH$ | H | H | O | 0 |
| A-4806 | H | H | H | Cl | H | $CH_2CH(OH)CH_2CH_3$ | H | H | O | 0 |
| A-4807 | H | H | H | Cl | H | $CH_2CH(OH)C(CH_3)_3$ | H | H | O | 0 |
| A-4808 | H | H | H | Cl | H | $CH_2CH_2CH(OH)CH_3$ | H | H | O | 0 |
| A-4809 | H | H | H | Cl | H | $CH_2CH_2CH(OH)C(CH_3)_3$ | H | H | O | 0 |
| A-4810 | H | H | H | Cl | H | $CH_2C(=NOH)CH_3$ | H | H | O | 0 |
| A-4811 | H | H | H | Cl | H | $CH_2C(=NOH)CH_2CH_3$ | H | H | O | 0 |
| A-4812 | H | H | H | Cl | H | $CH_2C(=NOH)C(CH_3)_3$ | H | H | O | 0 |
| A-4813 | H | H | H | Cl | H | $CH_2C(=NOCH_3)CH_3$ | H | H | O | 0 |
| A-4814 | H | H | H | Cl | H | $CH_2C(=NOCH_3)CH_2CH_3$ | H | H | O | 0 |

TABLE 80

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-4815 | H | H | H | Cl | H | $CH_2C(=NOCH_2CH_3)CH_3$ | H | H | O | 0 |
| A-4816 | H | H | H | Cl | H | $CH_2C(=NOCH_2CH_3)CH_2CH_3$ | H | H | O | 0 |
| A-4817 | H | H | H | Cl | H | $CH_2C(=NOCH_2CF_3)CH_3$ | H | H | O | 0 |
| A-4818 | H | H | H | Cl | H | $CH_2C(=NOCH_2CF_3)CH_2CH_3$ | H | H | O | 0 |
| A-4819 | H | H | H | Cl | H | $CH_2Ph$ | H | H | O | 0 |
| A-4820 | H | H | H | Cl | H | $CH_2(2-F)Ph$ | H | H | O | 0 |
| A-4821 | H | H | H | Cl | H | $CH_2(3-F)Ph$ | H | H | O | 0 |
| A-4822 | H | H | H | Cl | H | $CH_2(4-F)Ph$ | H | H | O | 0 |
| A-4823 | H | H | H | Cl | H | $CH_2(2-Cl)Ph$ | H | H | O | 0 |
| A-4824 | H | H | H | Cl | H | $CH_2(3-Cl)Ph$ | H | H | O | 0 |
| A-4825 | H | H | H | Cl | H | $CH_2(4-Cl)Ph$ | H | H | O | 0 |
| A-4826 | H | H | H | Cl | H | $CH_2(2-CF_3)Ph$ | H | H | O | 0 |
| A-4827 | H | H | H | Cl | H | $CH_2(3-CF_3)Ph$ | H | H | O | 0 |
| A-4828 | H | H | H | Cl | H | $CH_2(4-CF_3)Ph$ | H | H | O | 0 |
| A-4829 | H | H | H | Cl | H | $CH_2(naphthalen-1-yl)$ | H | H | O | 0 |
| A-4830 | H | H | H | Cl | H | $CH_2(naphthalen-2-yl)$ | H | H | O | 0 |
| A-4831 | H | H | H | Cl | H | $CH_2CH_2Ph$ | H | H | O | 0 |
| A-4832 | H | H | H | H | Cl | H | H | H | O | 0 |
| A-4833 | H | H | H | H | Cl | $CH_3$ | H | H | O | 0 |
| A-4834 | H | H | H | H | Cl | $CH_2CH_3$ | H | H | O | 0 |
| A-4835 | H | H | H | H | Cl | $CH(CH_3)_2$ | H | H | O | 0 |
| A-4836 | H | H | H | H | Cl | $CH_2CH_2CH_3$ | H | H | O | 0 |
| A-4837 | H | H | H | H | Cl | $CH_2CH(CH_3)_2$ | H | H | O | 0 |
| A-4838 | H | H | H | H | Cl | $CH(CH_3)CH_2CH_3$ | H | H | O | 0 |
| A-4839 | H | H | H | H | Cl | $CH_2C(CH_3)_3$ | H | H | O | 0 |
| A-4840 | H | H | H | H | Cl | $CH_2(CH_2)_2CH_3$ | H | H | O | 0 |
| A-4841 | H | H | H | H | Cl | $CH_2(CH_2)_3CH_3$ | H | H | O | 0 |
| A-4842 | H | H | H | H | Cl | $CH_2(CH_2)_4CH_3$ | H | H | O | 0 |
| A-4843 | H | H | H | H | Cl | $CH_2(CH_2)_6CH_3$ | H | H | O | 0 |
| A-4844 | H | H | H | H | Cl | $CH_2OCH_3$ | H | H | O | 0 |
| A-4845 | H | H | H | H | Cl | $CH_2OCH_2CH_3$ | H | H | O | 0 |
| A-4846 | H | H | H | H | Cl | $CH_2CH_2OCH_3$ | H | H | O | 0 |
| A-4847 | H | H | H | H | Cl | $CH_2CH_2OCH_2CH_3$ | H | H | O | 0 |
| A-4848 | H | H | H | H | Cl | $CF_3$ | H | H | O | 0 |
| A-4849 | H | H | H | H | Cl | $CHF_2$ | H | H | O | 0 |
| A-4850 | H | H | H | H | Cl | $CH_2CF_3$ | H | H | O | 0 |
| A-4851 | H | H | H | H | Cl | $CH_2CHF_2$ | H | H | O | 0 |
| A-4852 | H | H | H | H | Cl | $CH_2CClF_2$ | H | H | O | 0 |
| A-4853 | H | H | H | H | Cl | $CH_2CBrF_2$ | H | H | O | 0 |
| A-4854 | H | H | H | H | Cl | $CF_2CF_3$ | H | H | O | 0 |
| A-4855 | H | H | H | H | Cl | $CF_2CHF_2$ | H | H | O | 0 |
| A-4856 | H | H | H | H | Cl | $CH_2CH_2CF_3$ | H | H | O | 0 |
| A-4857 | H | H | H | H | Cl | $CH_2CF_2CF_3$ | H | H | O | 0 |
| A-4858 | H | H | H | H | Cl | $CH_2CF_2CHF_2$ | H | H | O | 0 |
| A-4859 | H | H | H | H | Cl | $CF_2CHFCF_3$ | H | H | O | 0 |

TABLE 80-continued

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-4860 | H | H | H | H | Cl | $CF_2CF_2CF_3$ | H | H | O | 0 |
| A-4861 | H | H | H | H | Cl | $CH_2CF_2CF_2CF_3$ | H | H | O | 0 |
| A-4862 | H | H | H | H | Cl | $CH_2CH_2CH_2CF_3$ | H | H | O | 0 |
| A-4863 | H | H | H | H | Cl | $CH_2CH_2CF_2CF_3$ | H | H | O | 0 |
| A-4864 | H | H | H | H | Cl | $CF_2CF_2CF_2CF_3$ | H | H | O | 0 |
| A-4865 | H | H | H | H | Cl | $CH_2CH_2CH(CF_3)_2$ | H | H | O | 0 |
| A-4866 | H | H | H | H | Cl | $CF_2CF_2CF_2CF_2CF_3$ | H | H | O | 0 |
| A-4867 | H | H | H | H | Cl | $CH_2CF_2CF_2CF_2CF_3$ | H | H | O | 0 |
| A-4868 | H | H | H | H | Cl | $CH_2CH_2CH_2CH_2CF_3$ | H | H | O | 0 |
| A-4869 | H | H | H | H | Cl | $CH_2CF_2CF_2CF_2CHF_2$ | H | H | O | 0 |
| A-4870 | H | H | H | H | Cl | $CH_2CF_2CF(CF_3)CF_2C(CF_3)_3$ | H | H | O | 0 |
| A-4871 | H | H | H | H | Cl | $CF_2CHFOCH_3$ | H | H | O | 0 |
| A-4872 | H | H | H | H | Cl | $CF_2CHFOCH_2CH_3$ | H | H | O | 0 |
| A-4873 | H | H | H | H | Cl | $CH_2CH_2OCH_2CF_3$ | H | H | O | 0 |
| A-4874 | H | H | H | H | Cl | $CF_2CHFOCF_3$ | H | H | O | 0 |
| A-4875 | H | H | H | H | Cl | $CF_2CHFOCF_2CF_3$ | H | H | O | 0 |

TABLE 81

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-4876 | H | H | H | H | Cl | $CF_2CHFOCF_2CF_2CF_3$ | H | H | O | 0 |
| A-4877 | H | H | H | H | Cl | $CH_2CH=CH_2$ | H | H | O | 0 |
| A-4878 | H | H | H | H | Cl | $CH_2CH=CHCl$ | H | H | O | 0 |
| A-4879 | H | H | H | H | Cl | $CH_2CH=CCl_2$ | H | H | O | 0 |
| A-4880 | H | H | H | H | Cl | $CH_2CH_2CF=CF_2$ | H | H | O | 0 |
| A-4881 | H | H | H | H | Cl | $CH_2CH_2CH=CF_2$ | H | H | O | 0 |
| A-4882 | H | H | H | H | Cl | $CH_2C\equiv CH$ | H | H | O | 0 |
| A-4883 | H | H | H | H | Cl | $CH_2C\equiv CCH_3$ | H | H | O | 0 |
| A-4884 | H | H | H | H | Cl | $CH_2C\equiv CCF_3$ | H | H | O | 0 |
| A-4885 | H | H | H | H | Cl | $CH_2C\equiv CI$ | H | H | O | 0 |
| A-4886 | H | H | H | H | Cl | cyclobutyl | H | H | O | 0 |
| A-4887 | H | H | H | H | Cl | cyclopentyl | H | H | O | 0 |
| A-4888 | H | H | H | H | Cl | cyclohexyl | H | H | O | 0 |
| A-4889 | H | H | H | H | Cl | 4,4-difluorocyclohexyl | H | H | O | 0 |
| A-4890 | H | H | H | H | Cl | $CH_2$(cyclopropyl) | H | H | O | 0 |
| A-4891 | H | H | H | H | Cl | $CH_2$(cyclobutyl) | H | H | O | 0 |
| A-4892 | H | H | H | H | Cl | $CH_2$(cyclopentyl) | H | H | O | 0 |
| A-4893 | H | H | H | H | Cl | $CH_2CH_2$(cyclopropyl) | H | H | O | 0 |
| A-4894 | H | H | H | H | Cl | $CH_2$(2,2-difluorocyclopropyl) | H | H | O | 0 |
| A-4895 | H | H | H | H | Cl | $CH_2$(2,2-dichlorocyclopropyl) | H | H | O | 0 |
| A-4896 | H | H | H | H | Cl | $CH_2$(4,4-difluorocyclohexyl) | H | H | O | 0 |
| A-4897 | H | H | H | H | Cl | $CH_2CH_2$(2,2-difluorocyclopropyl) | H | H | O | 0 |
| A-4898 | H | H | H | H | Cl | $CH_2CH_2$(2,2-dichlorocyclopropyl) | H | H | O | 0 |
| A-4899 | H | H | H | H | Cl | $CH_2SCH_3$ | H | H | O | 0 |
| A-4900 | H | H | H | H | Cl | $CH_2SCH_2CH_3$ | H | H | O | 0 |
| A-4901 | H | H | H | H | Cl | $CH_2CH_2SCH_3$ | H | H | O | 0 |
| A-4902 | H | H | H | H | Cl | $CH_2CH_2SCH_2CH_3$ | H | H | O | 0 |
| A-4903 | H | H | H | H | Cl | $CH_2CH_2CH_2SCH_3$ | H | H | O | 0 |
| A-4904 | H | H | H | H | Cl | $CH_2CH_2CH_2SCH_2CH_3$ | H | H | O | 0 |
| A-4905 | H | H | H | H | Cl | $CH(CH_3)SCH_3$ | H | H | O | 0 |
| A-4906 | H | H | H | H | Cl | $CH(CH_3)SCH_2CH_3$ | H | H | O | 0 |
| A-4907 | H | H | H | H | Cl | $CH_2CH(CH_3)SCH_3$ | H | H | O | 0 |
| A-4908 | H | H | H | H | Cl | $CH_2CH(CH_3)SCH_2CH_3$ | H | H | O | 0 |
| A-4909 | H | H | H | H | Cl | $CH(CH_3)CH_2CH_2SCH_3$ | H | H | O | 0 |
| A-4910 | H | H | H | H | Cl | $CH(CH_3)CH_2CH_2SCH_2CH_3$ | H | H | O | 0 |
| A-4911 | H | H | H | H | Cl | $CH_2CH(CH_3)CH_2SCH_3$ | H | H | O | 0 |
| A-4912 | H | H | H | H | Cl | $CH_2CH(CH_3)CH_2SCH_2CH_3$ | H | H | O | 0 |
| A-4913 | H | H | H | H | Cl | $CH_2CH_2CH(CH_3)SCH_3$ | H | H | O | 0 |
| A-4914 | H | H | H | H | Cl | $CH_2CH_2CH(CH_3)SCH_2CH_3$ | H | H | O | 0 |
| A-4915 | H | H | H | H | Cl | $CH_2SOCH_3$ | H | H | O | 0 |
| A-4916 | H | H | H | H | Cl | $CH_2CH_2SOCH_3$ | H | H | O | 0 |
| A-4917 | H | H | H | H | Cl | $CH_2CH_2CH_2SOCH_3$ | H | H | O | 0 |
| A-4918 | H | H | H | H | Cl | $CH(CH_3)SOCH_3$ | H | H | O | 0 |
| A-4919 | H | H | H | H | Cl | $CH_2CH(CH_3)SOCH_3$ | H | H | O | 0 |
| A-4920 | H | H | H | H | Cl | $CH(CH_3)CH_2CH_2SOCH_3$ | H | H | O | 0 |
| A-4921 | H | H | H | H | Cl | $CH_2CH(CH_3)CH_2SOCH_3$ | H | H | O | 0 |
| A-4922 | H | H | H | H | Cl | $CH_2CH_2CH(CH_3)SOCH_3$ | H | H | O | 0 |
| A-4923 | H | H | H | H | Cl | $CH_2SO_2CH_3$ | H | H | O | 0 |
| A-4924 | H | H | H | H | Cl | $CH_2CH_2SO_2CH_3$ | H | H | O | 0 |
| A-4925 | H | H | H | H | Cl | $CH_2CH_2CH_2SO_2CH_3$ | H | H | O | 0 |
| A-4926 | H | H | H | H | Cl | $CH(CH_3)SO_2CH_3$ | H | H | O | 0 |
| A-4927 | H | H | H | H | Cl | $CH_2CH(CH_3)SO_2CH_3$ | H | H | O | 0 |
| A-4928 | H | H | H | H | Cl | $CH(CH_3)CH_2CH_2SO_2CH_3$ | H | H | O | 0 |
| A-4929 | H | H | H | H | Cl | $CH_2CH(CH_3)CH_2SO_2CH_3$ | H | H | O | 0 |

TABLE 81-continued

| Compound | R¹ | R² | R³ | R⁴ | R⁵ | R⁶ | R⁷ | R⁸ | X | n |
|---|---|---|---|---|---|---|---|---|---|---|
| A-4930 | H | H | H | H | Cl | CH₂CH₂CH(CH₃)SO₂CH₃ | H | H | O | 0 |
| A-4931 | H | H | H | H | Cl | CH₂SCF₃ | H | H | O | 0 |
| A-4932 | H | H | H | H | Cl | CH₂SCHF₂ | H | H | O | 0 |
| A-4933 | H | H | H | H | Cl | CH₂SCH₂CF₃ | H | H | O | 0 |
| A-4934 | H | H | H | H | Cl | CH₂SCH₂CHF₂ | H | H | O | 0 |
| A-4935 | H | H | H | H | Cl | CH₂SCF₂CF₃ | H | H | O | 0 |
| A-4936 | H | H | H | H | Cl | CH₂CH₂SCF₃ | H | H | O | 0 |

TABLE 82

| Compound | R¹ | R² | R³ | R⁴ | R⁵ | R⁶ | R⁷ | R⁸ | X | n |
|---|---|---|---|---|---|---|---|---|---|---|
| A-4937 | H | H | H | H | Cl | CH₂CH₂SCH₂CF₃ | H | H | O | 0 |
| A-4938 | H | H | H | H | Cl | CH₂CH₂CH₂SCF₃ | H | H | O | 0 |
| A-4939 | H | H | H | H | Cl | CH₂CH₂CH₂SCH₂CF₃ | H | H | O | 0 |
| A-4940 | H | H | H | H | Cl | CH(CH₃)SCF₃ | H | H | O | 0 |
| A-4941 | H | H | H | H | Cl | CH(CH₃)SCH₂CF₃ | H | H | O | 0 |
| A-4942 | H | H | H | H | Cl | CH₂CH(CH₃)SCF₃ | H | H | O | 0 |
| A-4943 | H | H | H | H | Cl | CH₂CH(CH₃)SCH₂CF₃ | H | H | O | 0 |
| A-4944 | H | H | H | H | Cl | CH(CH₃)CH₂CH₂SCF₃ | H | H | O | 0 |
| A-4945 | H | H | H | H | Cl | CH(CH₃)CH₂CH₂SCH₂CF₃ | H | H | O | 0 |
| A-4946 | H | H | H | H | Cl | CH₂CH(CH₃)CH₂SCF₃ | H | H | O | 0 |
| A-4947 | H | H | H | H | Cl | CH₂CH(CH₃)CH₂SCH₂CF₃ | H | H | O | 0 |
| A-4948 | H | H | H | H | Cl | CH₂CH₂CH(CH₃)SCF₃ | H | H | O | 0 |
| A-4949 | H | H | H | H | Cl | CH₂CH₂CH(CH₃)SCH₂CF₃ | H | H | O | 0 |
| A-4950 | H | H | H | H | Cl | CH₂SOCF₃ | H | H | O | 0 |
| A-4951 | H | H | H | H | Cl | CH₂CH₂SOCF₃ | H | H | O | 0 |
| A-4952 | H | H | H | H | Cl | CH₂CH₂CH₂SOCF₃ | H | H | O | 0 |
| A-4953 | H | H | H | H | Cl | CH(CH₃)SOCF₃ | H | H | O | 0 |
| A-4954 | H | H | H | H | Cl | CH₂CH(CH₃)SOCF₃ | H | H | O | 0 |
| A-4955 | H | H | H | H | Cl | CH(CH₃)CH₂CH₂SOCF₃ | H | H | O | 0 |
| A-4956 | H | H | H | H | Cl | CH₂CH(CH₃)CH₂SOCF₃ | H | H | O | 0 |
| A-4957 | H | H | H | H | Cl | CH₂CH₂CH(CH₃)SOCF₃ | H | H | O | 0 |
| A-4958 | H | H | H | H | Cl | CH₂SO₂CF₃ | H | H | O | 0 |
| A-4959 | H | H | H | H | Cl | CH₂CH₂SO₂CF₃ | H | H | O | 0 |
| A-4960 | H | H | H | H | Cl | CH₂CH₂CH₂SO₂CF₃ | H | H | O | 0 |
| A-4961 | H | H | H | H | Cl | CH(CH₃)SC₂CF₃ | H | H | O | 0 |
| A-4962 | H | H | H | H | Cl | CH₂CH(CH₃)SO₂CF₃ | H | H | O | 0 |
| A-4963 | H | H | H | H | Cl | CH(CH₃)CH₂CH₂SO₂CF₃ | H | H | O | 0 |
| A-4964 | H | H | H | H | Cl | CH₂CH(CH₃)CH₂SO₂CF₃ | H | H | O | 0 |
| A-4965 | H | H | H | H | Cl | CH₂CH₂CH(CH₃)SO₂CF₃ | H | H | O | 0 |
| A-4966 | H | H | H | H | Cl | CH₂C(=O)CH₃ | H | H | O | 0 |
| A-4967 | H | H | H | H | Cl | CH₂C(=O)CH₂CH₃ | H | H | O | 0 |
| A-4968 | H | H | H | H | Cl | CH₂C(=O)C(CH₃)₃ | H | H | O | 0 |
| A-4969 | H | H | H | H | Cl | CH₂CH₂C(=O)CH₃ | H | H | O | 0 |
| A-4970 | H | H | H | H | Cl | CH₂CH₂C(=O)C(CH₃)₃ | H | H | O | 0 |
| A-4971 | H | H | H | H | Cl | CH₂C(=O)CF₃ | H | H | O | 0 |
| A-4972 | H | H | H | H | Cl | CH₂CH₂C(=O)CF₃ | H | H | O | 0 |
| A-4973 | H | H | H | H | Cl | CH₂C(=O)OCH₃ | H | H | O | 0 |
| A-4974 | H | H | H | H | Cl | CH₂C(=O)OCH₂CH₃ | H | H | O | 0 |
| A-4975 | H | H | H | H | Cl | CH₂C(=O)OC(CH₃)₃ | H | H | O | 0 |
| A-4976 | H | H | H | H | Cl | CH₂CH₂C(=O)OCH₃ | H | H | O | 0 |
| A-4977 | H | H | H | H | Cl | CH₂CH₂C(=O)OCH₂CH₃ | H | H | O | 0 |
| A-4978 | H | H | H | H | Cl | CH₂CH₂C(=O)OC(CH₃)₃ | H | H | O | 0 |
| A-4979 | H | H | H | H | Cl | CH₂C(=O)NH₂ | H | H | O | 0 |
| A-4980 | H | H | H | H | Cl | CH₂CH₂C(=O)NH₂ | H | H | O | 0 |
| A-4981 | H | H | H | H | Cl | CH₂C(=O)NHCH₃ | H | H | O | 0 |
| A-4982 | H | H | H | H | Cl | CH₂C(=O)NHCH(CH₃)₂ | H | H | O | 0 |
| A-4983 | H | H | H | H | Cl | CH₂CH₂C(=O)NHCH₃ | H | H | O | 0 |
| A-4984 | H | H | H | H | Cl | CH₂CH₂C(=O)NHCH(CH₃)₂ | H | H | O | 0 |
| A-4985 | H | H | H | H | Cl | CH₂C(=O)NHCH₂CHF₂ | H | H | O | 0 |
| A-4986 | H | H | H | H | Cl | CH₂C(=O)NHCH₂CF₃ | H | H | O | 0 |
| A-4987 | H | H | H | H | Cl | CH₂CH₂C(=O)NHCH₂CHF₂ | H | H | O | 0 |
| A-4988 | H | H | H | H | Cl | CH₂CH₂C(=O)NHCH₂CF₃ | H | H | O | 0 |
| A-4989 | H | H | H | H | Cl | CH₂C(=O)N(CH₃)₂ | H | H | O | 0 |
| A-4990 | H | H | H | H | Cl | CH₂C(=O)N(CH₂CH₃)₂ | H | H | O | 0 |
| A-4991 | H | H | H | H | Cl | CH₂CH₂C(=O)N(CH₃)₂ | H | H | O | 0 |
| A-4992 | H | H | H | H | Cl | CH₂CH₂C(=O)N(CH₂CH₃)₂ | H | H | O | 0 |
| A-4993 | H | H | H | H | Cl | CH₂OH | H | H | O | 0 |
| A-4994 | H | H | H | H | Cl | CH₂CH(OH)CH₃ | H | H | O | 0 |
| A-4995 | H | H | H | H | Cl | CH₂CH₂OH | H | H | O | 0 |
| A-4996 | H | H | H | H | Cl | CH₂CH(OH)CH₂CH₃ | H | H | O | 0 |
| A-4997 | H | H | H | H | Cl | CH₂CH(OH)C(CH₃)₃ | H | H | O | 0 |

TABLE 83

| Compound | R¹ | R² | R³ | R⁴ | R⁵ | R⁶ | R⁷ | R⁸ | X | n |
|---|---|---|---|---|---|---|---|---|---|---|
| A-4998 | H | H | H | H | Cl | $CH_2CH_2CH(OH)CH_3$ | H | H | O | 0 |
| A-4999 | H | H | H | H | Cl | $CH_2CH_2CH(OH)C(CH_3)_3$ | H | H | O | 0 |
| A-5000 | H | H | H | H | Cl | $CH_2C(=NOH)CH_3$ | H | H | O | 0 |
| A-5001 | H | H | H | H | Cl | $CH_2C(=NOH)CH_2CH_3$ | H | H | O | 0 |
| A-5002 | H | H | H | H | Cl | $CH_2C(=NOH)C(CH_3)_3$ | H | H | O | 0 |
| A-5003 | H | H | H | H | Cl | $CH_2C(=NOCH_3)CH_3$ | H | H | O | 0 |
| A-5004 | H | H | H | H | Cl | $CH_2C(=NOCH_3)CH_2CH_3$ | H | H | O | 0 |
| A-5005 | H | H | H | H | Cl | $CH_2C(=NOCH_2CH_3)CH_3$ | H | H | O | 0 |
| A-5006 | H | H | H | H | Cl | $CH_2C(=NOCH_2CH_3)CH_2CH_3$ | H | H | O | 0 |
| A-5007 | H | H | H | H | Cl | $CH_2C(=NOCH_2CF_3)CH_3$ | H | H | O | 0 |
| A-5008 | H | H | H | H | Cl | $CH_2C(=NOCH_2CF_3)CH_2CH_3$ | H | H | O | 0 |
| A-5009 | H | H | H | H | Cl | $CH_2Ph$ | H | H | O | 0 |
| A-5010 | H | H | H | H | Cl | $CH_2(2-F)Ph$ | H | H | O | 0 |
| A-5011 | H | H | H | H | Cl | $CH_2(3-F)Ph$ | H | H | O | 0 |
| A-5012 | H | H | H | H | Cl | $CH_2(4-F)Ph$ | H | H | O | 0 |
| A-5013 | H | H | H | H | Cl | $CH_2(2-Cl)Ph$ | H | H | O | 0 |
| A-5014 | H | H | H | H | Cl | $CH_2(3-Cl)Ph$ | H | H | O | 0 |
| A-5015 | H | H | H | H | Cl | $CH_2(4-Cl)Ph$ | H | H | O | 0 |
| A-5016 | H | H | H | H | Cl | $CH_2(2-CF_3)Ph$ | H | H | O | 0 |
| A-5017 | H | H | H | H | Cl | $CH_2(3-CF_3)Ph$ | H | H | O | 0 |
| A-5018 | H | H | H | H | Cl | $CH_2(4-CF_3)Ph$ | H | H | O | 0 |
| A-5019 | H | H | H | H | Cl | $CH_2$(naphthalen-1-yl) | H | H | O | 0 |
| A-5020 | H | H | H | H | Cl | $CH_2$(naphthalen-2-yl) | H | H | O | 0 |
| A-5021 | H | H | H | H | Cl | $CH_2CH_2Ph$ | H | H | O | 0 |
| A-5022 | H | H | H | H | F | H | H | H | O | 0 |
| A-5023 | H | H | H | H | F | $CH_3$ | H | H | O | 0 |
| A-5024 | H | H | H | H | F | $CH_2CH_3$ | H | H | O | 0 |
| A-5025 | H | H | H | H | F | $CH(CH_3)_2$ | H | H | O | 0 |
| A-5026 | H | H | H | H | F | $CH_2CH_2CH_3$ | H | H | O | 0 |
| A-5027 | H | H | H | H | F | $CH_2CH(CH_3)_2$ | H | H | O | 0 |
| A-5028 | H | H | H | H | F | $CH(CH_3)CH_2CH_3$ | H | H | O | 0 |
| A-5029 | H | H | H | H | F | $CH_2C(CH_3)_3$ | H | H | O | 0 |
| A-5030 | H | H | H | H | F | $CH_2(CH_2)_2CH_3$ | H | H | O | 0 |
| A-5031 | H | H | H | H | F | $CH_2(CH_2)_3CH_3$ | H | H | O | 0 |
| A-5032 | H | H | H | H | F | $CH_2(CH_2)_4CH_3$ | H | H | O | 0 |
| A-5033 | H | H | H | H | F | $CH_2(CH_2)_6CH_3$ | H | H | O | 0 |
| A-5034 | H | H | H | H | F | $CH_2OCH_3$ | H | H | O | 0 |
| A-5035 | H | H | H | H | F | $CH_2OCH_2CH_3$ | H | H | O | 0 |
| A-5036 | H | H | H | H | F | $CH_2CH_2OCH_3$ | H | H | O | 0 |
| A-5037 | H | H | H | H | F | $CH_2CH_2OCH_2CH_3$ | H | H | O | 0 |
| A-5038 | H | H | H | H | F | $CF_3$ | H | H | O | 0 |
| A-5039 | H | H | H | H | F | $CHF_2$ | H | H | O | 0 |
| A-5040 | H | H | H | H | F | $CH_2CF_3$ | H | H | O | 0 |
| A-5041 | H | H | H | H | F | $CH_2CHF_2$ | H | H | O | 0 |
| A-5042 | H | H | H | H | F | $CH_2CClF_2$ | H | H | O | 0 |
| A-5043 | H | H | H | H | F | $CH_2CBrF_2$ | H | H | O | 0 |
| A-5044 | H | H | H | H | F | $CF_2CF_3$ | H | H | O | 0 |
| A-5045 | H | H | H | H | F | $CF_2CHF_2$ | H | H | O | 0 |
| A-5046 | H | H | H | H | F | $CH_2CH_2CF_3$ | H | H | O | 0 |
| A-5047 | H | H | H | H | F | $CH_2CF_2CF_3$ | H | H | O | 0 |
| A-5048 | H | H | H | H | F | $CH_2CF_2CHF_2$ | H | H | O | 0 |
| A-5049 | H | H | H | H | F | $CF_2CHFCF_3$ | H | H | O | 0 |
| A-5050 | H | H | H | H | F | $CF_2CF_2CF_3$ | H | H | O | 0 |
| A-5051 | H | H | H | H | F | $CH_2CF_2CF_2CF_3$ | H | H | O | 0 |
| A-5052 | H | H | H | H | F | $CH_2CH_2CH_2CF_3$ | H | H | O | 0 |
| A-5053 | H | H | H | H | F | $CH_2CH_2CF_2CF_3$ | H | H | O | 0 |
| A-5054 | H | H | H | H | F | $CF_2CF_2CF_2CF_3$ | H | H | O | 0 |
| A-5055 | H | H | H | H | F | $CH_2CH_2CH(CF_3)_2$ | H | H | O | 0 |
| A-5056 | H | H | H | H | F | $CF_2CF_2CF_2CF_2CF_3$ | H | H | O | 0 |
| A-5057 | H | H | H | H | F | $CH_2CF_2CF_2CF_2CF_3$ | H | H | O | 0 |
| A-5058 | H | H | H | H | F | $CH_2CH_2CH_2CH_2CF_3$ | H | H | O | 0 |

TABLE 84

| Compound | R¹ | R² | R³ | R⁴ | R⁵ | R⁶ | R⁷ | R⁸ | X | n |
|---|---|---|---|---|---|---|---|---|---|---|
| A-5059 | H | H | H | H | F | $CH_2CF_2CF_2CF_2CHF_2$ | H | H | O | 0 |
| A-5060 | H | H | H | H | F | $CH_2CF_2CF(CF_3)CF_2C(CF_2)_3$ | H | H | O | 0 |
| A-5061 | H | H | H | H | F | $CF_2CHFOCH_3$ | H | H | O | 0 |
| A-5062 | H | H | H | H | F | $CF_2CHFOCH_2CH_3$ | H | H | O | 0 |
| A-5063 | H | H | H | H | F | $CH_2CH_2OCH_2CF_3$ | H | H | O | 0 |
| A-5064 | H | H | H | H | F | $CF_2CHFOCF_3$ | H | H | O | 0 |
| A-5065 | H | H | H | H | F | $CF_2CHFOCF_2CF_3$ | H | H | O | 0 |
| A-5066 | H | H | H | H | F | $CF_2CHFOCF_2CF_2CF_3$ | H | H | O | 0 |
| A-5067 | H | H | H | H | F | $CH_2CH=CH_2$ | H | H | O | 0 |

TABLE 84-continued

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-5068 | H | H | H | H | F | CH$_2$CH=CHCl | H | H | O | 0 |
| A-5069 | H | H | H | H | F | CH$_2$CH=CCl$_2$ | H | H | O | 0 |
| A-5070 | H | H | H | H | F | CH$_2$CH$_2$CF=CF$_2$ | H | H | O | 0 |
| A-5071 | H | H | H | H | F | CH$_2$CH$_2$CH=CF$_2$ | H | H | O | 0 |
| A-5072 | H | H | H | H | F | CH$_2$C≡CH | H | H | O | 0 |
| A-5073 | H | H | H | H | F | CH$_2$C≡CCH$_3$ | H | H | O | 0 |
| A-5074 | H | H | H | H | F | CH$_2$C≡CCF$_3$ | H | H | O | 0 |
| A-5075 | H | H | H | H | F | CH$_2$C≡CI | H | H | O | 0 |
| A-5076 | H | H | H | H | F | cyclobutyl | H | H | O | 0 |
| A-5077 | H | H | H | H | F | cyclopentyl | H | H | O | 0 |
| A-5078 | H | H | H | H | F | cyclohexyl | H | H | O | 0 |
| A-5079 | H | H | H | H | F | 4,4-difluorocyclohexyl | H | H | O | 0 |
| A-5080 | H | H | H | H | F | CH$_2$(cyclopropyl) | H | H | O | 0 |
| A-5081 | H | H | H | H | F | CH$_2$(cyclobutyl) | H | H | O | 0 |
| A-5082 | H | H | H | H | F | CH$_2$(cyclopentyl) | H | H | O | 0 |
| A-5083 | H | H | H | H | F | CH$_2$CH$_2$(cyclopropyl) | H | H | O | 0 |
| A-5084 | H | H | H | H | F | CH$_2$(2,2-difluorocyclopropyl) | H | H | O | 0 |
| A-5085 | H | H | H | H | F | CH$_2$(2,2-dichlorocyclopropyl) | H | H | O | 0 |
| A-5086 | H | H | H | H | F | CH$_2$(4,4-difluorocyclohexyl) | H | H | O | 0 |
| A-5087 | H | H | H | H | F | CH$_2$CH$_2$(2,2-difluorocyclopropyl) | H | H | O | 0 |
| A-5088 | H | H | H | H | F | CH$_2$CH$_2$(2,2-dichlorocyclopropyl) | H | H | O | 0 |
| A-5089 | H | H | H | H | F | CH$_2$SCH$_3$ | H | H | O | 0 |
| A-5090 | H | H | H | H | F | CH$_2$SCH$_2$CH$_3$ | H | H | O | 0 |
| A-5091 | H | H | H | H | F | CH$_2$CH$_2$SCH$_3$ | H | H | O | 0 |
| A-5092 | H | H | H | H | F | CH$_2$CH$_2$SCH$_2$CH$_3$ | H | H | O | 0 |
| A-5093 | H | H | H | H | F | CH$_2$CH$_2$CH$_2$SCH$_3$ | H | H | O | 0 |
| A-5094 | H | H | H | H | F | CH$_2$CH$_2$CH$_2$SCH$_2$CH$_3$ | H | H | O | 0 |
| A-5095 | H | H | H | H | F | CH(CH$_3$)SCH$_3$ | H | H | O | 0 |
| A-5096 | H | H | H | H | F | CH(CH$_3$)SCH$_2$CH$_3$ | H | H | O | 0 |
| A-5097 | H | H | H | H | F | CH$_2$CH(CH$_3$)SCH$_3$ | H | H | O | 0 |
| A-5098 | H | H | H | H | F | CH$_2$CH(CH$_3$)SCH$_2$CH$_3$ | H | H | O | 0 |
| A-5099 | H | H | H | H | F | CH(CH$_3$)CH$_2$CH$_2$SCH$_3$ | H | H | O | 0 |
| A-5100 | H | H | H | H | F | CH(CH$_3$)CH$_2$CH$_2$SCH$_2$CH$_3$ | H | H | O | 0 |
| A-5101 | H | H | H | H | F | CH$_2$CH(CH$_3$)CH$_2$SCH$_3$ | H | H | O | 0 |
| A-5102 | H | H | H | H | F | CH$_2$CH(CH$_3$)CH$_2$SCH$_2$CH$_3$ | H | H | O | 0 |
| A-5103 | H | H | H | H | F | CH$_2$CH$_2$CH(CH$_3$)SCH$_3$ | H | H | O | 0 |
| A-5104 | H | H | H | H | F | CH$_2$CH$_2$CH(CH$_3$)SCH$_2$CH$_3$ | H | H | O | 0 |
| A-5105 | H | H | H | H | F | CH$_2$SOCH$_3$ | H | H | O | 0 |
| A-5106 | H | H | H | H | F | CH$_2$CH$_2$SOCH$_3$ | H | H | O | 0 |
| A-5107 | H | H | H | H | F | CH$_2$CH$_2$CH$_2$SOCH$_3$ | H | H | O | 0 |
| A-5108 | H | H | H | H | F | CH(CH$_3$)SOCH$_3$ | H | H | O | 0 |
| A-5109 | H | H | H | H | F | CH$_2$CH(CH$_3$)SOCH$_3$ | H | H | O | 0 |
| A-5110 | H | H | H | H | F | CH(CH$_3$)CH$_2$CH$_2$SOCH$_3$ | H | H | O | 0 |
| A-5111 | H | H | H | H | F | CH$_2$CH(CH$_3$)CH$_2$SOCH$_3$ | H | H | O | 0 |
| A-5112 | H | H | H | H | F | CH$_2$CH$_2$CH(CH$_3$)SOCH$_3$ | H | H | O | 0 |
| A-5113 | H | H | H | H | F | CH$_2$SO$_2$CH$_3$ | H | H | O | 0 |
| A-5114 | H | H | H | H | F | CH$_2$CH$_2$SO$_2$CH$_3$ | H | H | O | 0 |
| A-5115 | H | H | H | H | F | CH$_2$CH$_2$CH$_2$SO$_2$CH$_3$ | H | H | O | 0 |
| A-5116 | H | H | H | H | F | CH(CH$_3$)SO$_2$CH$_3$ | H | H | O | 0 |
| A-5117 | H | H | H | H | F | CH$_2$CH(CH$_3$)SO$_2$CH$_3$ | H | H | O | 0 |
| A-5118 | H | H | H | H | F | CH(CH$_3$)CH$_2$CH$_2$SO$_2$CH$_3$ | H | H | O | 0 |
| A-5119 | H | H | H | H | F | CH$_2$CH(CH$_3$)CH$_2$SO$_2$CH$_3$ | H | H | O | 0 |

TABLE 85

| Compound | $R^1$ | $R^2$ | $R^3$ | $R^4$ | $R^5$ | $R^6$ | $R^7$ | $R^8$ | X | n |
|---|---|---|---|---|---|---|---|---|---|---|
| A-5120 | H | H | H | H | F | CH$_2$CH$_2$CH(CH$_3$)SO$_2$CH$_3$ | H | H | O | 0 |
| A-5121 | H | H | H | H | F | CH$_2$SCF$_3$ | H | H | O | 0 |
| A-5122 | H | H | H | H | F | CH$_2$SCHF$_2$ | H | H | O | 0 |
| A-5123 | H | H | H | H | F | CH$_2$SCH$_2$CF$_3$ | H | H | O | 0 |
| A-5124 | H | H | H | H | F | CH$_2$SCH$_2$CHF$_2$ | H | H | O | 0 |
| A-5125 | H | H | H | H | F | CH$_2$SCF$_2$CF$_3$ | H | H | O | 0 |
| A-5126 | H | H | H | H | F | CH$_2$CH$_2$SCF$_3$ | H | H | O | 0 |
| A-5127 | H | H | H | H | F | CH$_2$CH$_2$SCH$_2$CF$_3$ | H | H | O | 0 |
| A-5128 | H | H | H | H | F | CH$_2$CH$_2$CH$_2$SCF$_3$ | H | H | O | 0 |
| A-5129 | H | H | H | H | F | CH$_2$CH$_2$CH$_2$SCH$_2$CF$_3$ | H | H | O | 0 |
| A-5130 | H | H | H | H | F | CH(CH$_3$)SCF$_3$ | H | H | O | 0 |
| A-5131 | H | H | H | H | F | CH(CH$_3$)SCH$_2$CF$_3$ | H | H | O | 0 |
| A-5132 | H | H | H | H | F | CH$_2$CH(CH$_3$)SCF$_3$ | H | H | O | 0 |
| A-5133 | H | H | H | H | F | CH$_2$CH(CH$_3$)SCH$_2$CF$_3$ | H | H | O | 0 |
| A-5134 | H | H | H | H | F | CH(CH$_3$)CH$_2$CH$_2$SCF$_3$ | H | H | O | 0 |
| A-5135 | H | H | H | H | F | CH(CH$_3$)CH$_2$CH$_2$SCH$_2$CF$_3$ | H | H | O | 0 |
| A-5136 | H | H | H | H | F | CH$_2$CH(CH$_3$)CH$_2$SCF$_3$ | H | H | O | 0 |
| A-5137 | H | H | H | H | F | CH$_2$CH(CH$_3$)CH$_2$SCH$_2$CF$_3$ | H | H | O | 0 |

TABLE 85-continued

| Compound | R¹ | R² | R³ | R⁴ | R⁵ | R⁶ | R⁷ | R⁸ | X | n |
|---|---|---|---|---|---|---|---|---|---|---|
| A-5138 | H | H | H | H | F | CH$_2$CH$_2$CH(CH$_3$)SCF$_3$ | H | H | O | 0 |
| A-5139 | H | H | H | H | F | CH$_2$CH$_2$CH(CH$_3$)SCH$_2$CF$_3$ | H | H | O | 0 |
| A-5140 | H | H | H | H | F | CH$_2$SOCF$_3$ | H | H | O | 0 |
| A-5141 | H | H | H | H | F | CH$_2$CH$_2$SOCF$_3$ | H | H | O | 0 |
| A-5142 | H | H | H | H | F | CH$_2$CH$_2$CH$_2$SOCF$_3$ | H | H | O | 0 |
| A-5143 | H | H | H | H | F | CH(CH$_3$)SOCF$_3$ | H | H | O | 0 |
| A-5144 | H | H | H | H | F | CH$_2$CH(CH$_3$)SOCF$_3$ | H | H | O | 0 |
| A-5145 | H | H | H | H | F | CH(CH$_3$)CH$_2$CH$_2$SOCF$_3$ | H | H | O | 0 |
| A-5146 | H | H | H | H | F | CH$_2$CH(CH$_3$)CH$_2$SOCF$_3$ | H | H | O | 0 |
| A-5147 | H | H | H | H | F | CH$_2$CH$_2$CH(CH$_3$)SOCF$_3$ | H | H | O | 0 |
| A-5148 | H | H | H | H | F | CH$_2$SO$_2$CF$_3$ | H | H | O | 0 |
| A-5149 | H | H | H | H | F | CH$_2$CH$_2$SO$_2$CF$_3$ | H | H | O | 0 |
| A-5150 | H | H | H | H | F | CH$_2$CH$_2$CH$_2$SO$_2$CF$_3$ | H | H | O | 0 |
| A-5151 | H | H | H | H | F | CH(CH$_3$)SO$_2$CF$_3$ | H | H | O | 0 |
| A-5152 | H | H | H | H | F | CH$_2$CH(CH$_3$)SO$_2$CF$_3$ | H | H | O | 0 |
| A-5153 | H | H | H | H | F | CH(CH$_3$)CH$_2$CH$_2$SO$_2$CF$_3$ | H | H | O | 0 |
| A-5154 | H | H | H | H | F | CH$_2$CH(CH$_3$)CH$_2$SO$_2$CF$_3$ | H | H | O | 0 |
| A-5155 | H | H | H | H | F | CH$_2$CH$_2$CH(CH$_3$)SO$_2$CF$_3$ | H | H | O | 0 |
| A-5156 | H | H | H | H | F | CH$_2$C(=O)CH$_3$ | H | H | O | 0 |
| A-5157 | H | H | H | H | F | CH$_2$C(=O)CH$_2$CH$_3$ | H | H | O | 0 |
| A-5158 | H | H | H | H | F | CH$_2$C(=O)C(CH$_3$)$_3$ | H | H | O | 0 |
| A-5159 | H | H | H | H | F | CH$_2$CH$_2$C(=O)CH$_3$ | H | H | O | 0 |
| A-5160 | H | H | H | H | F | CH$_2$CH$_2$C(=O)C(CH$_3$)$_3$ | H | H | O | 0 |
| A-5161 | H | H | H | H | F | CH$_2$C(=O)CF$_3$ | H | H | O | 0 |
| A-5162 | H | H | H | H | F | CH$_2$CH$_2$C(=O)CF$_3$ | H | H | O | 0 |
| A-5163 | H | H | H | H | F | CH$_2$C(=O)OCH$_3$ | H | H | O | 0 |
| A-5164 | H | H | H | H | F | CH$_2$C(=O)OCH$_2$CH$_3$ | H | H | O | 0 |
| A-5165 | H | H | H | H | F | CH$_2$C(=O)OC(CH$_3$)$_3$ | H | H | O | 0 |
| A-5166 | H | H | H | H | F | CH$_2$CH$_2$C(=O)OCH$_3$ | H | H | O | 0 |
| A-5167 | H | H | H | H | F | CH$_2$CH$_2$C(=O)OCH$_2$CH$_3$ | H | H | O | 0 |
| A-5168 | H | H | H | H | F | CH$_2$CH$_2$C(=O)OC(CH$_3$)$_3$ | H | H | O | 0 |
| A-5169 | H | H | H | H | F | CH$_2$C(=O)NH$_2$ | H | H | O | 0 |
| A-5170 | H | H | H | H | F | CH$_2$CH$_2$C(=O)NH$_2$ | H | H | O | 0 |
| A-5171 | H | H | H | H | F | CH$_2$C(=O)NHCH$_3$ | H | H | O | 0 |
| A-5172 | H | H | H | H | F | CH$_2$C(=O)NHCH(CH$_3$)$_2$ | H | H | O | 0 |
| A-5173 | H | H | H | H | F | CH$_2$CH$_2$C(=O)NHCH$_3$ | H | H | O | 0 |
| A-5174 | H | H | H | H | F | CH$_2$CH$_2$C(=O)NHCH(CH$_3$)$_2$ | H | H | O | 0 |
| A-5175 | H | H | H | H | F | CH$_2$C(=O)NHCH$_2$CHF$_2$ | H | H | O | 0 |
| A-5176 | H | H | H | H | F | CH$_2$C(=O)NHCH$_2$CF$_3$ | H | H | O | 0 |
| A-5177 | H | H | H | H | F | CH$_2$CH$_2$C(=O)NHCH$_2$CHF$_2$ | H | H | O | 0 |
| A-5178 | H | H | H | H | F | CH$_2$CH$_2$C(=O)NHCH$_2$CF$_3$ | H | H | O | 0 |
| A-5179 | H | H | H | H | F | CH$_2$C(=O)N(CH$_3$)$_2$ | H | H | O | 0 |
| A-5180 | H | H | H | H | F | CH$_2$C(=O)N(CH$_2$CH$_3$)$_2$ | H | H | O | 0 |

TABLE 86

| Compound | R¹ | R² | R³ | R⁴ | R⁵ | R⁶ | R⁷ | R⁸ | X | n |
|---|---|---|---|---|---|---|---|---|---|---|
| A-5181 | H | H | H | H | F | CH$_2$CH$_2$C(=O)N(CH$_3$)$_2$ | H | H | O | 0 |
| A-5182 | H | H | H | H | F | CH$_2$CH$_2$C(=O)N(CH$_2$CH$_3$)$_2$ | H | H | O | 0 |
| A-5183 | H | H | H | H | F | CH$_2$CH$_2$OH | H | H | O | 0 |
| A-S184 | H | H | H | H | F | CH$_2$CH(OH)CH$_3$ | H | H | O | 0 |
| A-5185 | H | H | H | H | F | CH$_2$CH$_2$CH$_2$OH | H | H | O | 0 |
| A-5186 | H | H | H | H | F | CH$_2$CH(OH)CH$_2$CH$_3$ | H | H | O | 0 |
| A-5187 | H | H | H | H | F | CH$_2$CH(OH)C(CH$_3$)$_3$ | H | H | O | 0 |
| A-5188 | H | H | H | H | F | CH$_2$CH$_2$CH(OH)CH$_3$ | H | H | O | 0 |
| A-5189 | H | H | H | H | F | CH$_2$CH$_2$CH(OH)C(CH$_3$)$_3$ | H | H | O | 0 |
| A-5190 | H | H | H | H | F | CH$_2$C(=NOH)CH$_3$ | H | H | O | 0 |
| A-5191 | H | H | H | H | F | CH$_2$C(=NOH)CH$_2$CH$_3$ | H | H | O | 0 |
| A-5192 | H | H | H | H | F | CH$_2$C(=NOH)C(CH$_3$)$_3$ | H | H | O | 0 |
| A-5193 | H | H | H | H | F | CH$_2$C(=NOCH$_3$)CH$_3$ | H | H | O | 0 |
| A-5194 | H | H | H | H | F | CH$_2$C(=NOCH$_3$)CH$_2$CH$_3$ | H | H | O | 0 |
| A-5195 | H | H | H | H | F | CH$_2$C(=NOCH$_2$CH$_3$)CH$_3$ | H | H | O | 0 |
| A-5196 | H | H | H | H | F | CH$_2$C(=NOCH$_2$CH$_3$)CH$_2$CH$_3$ | H | H | O | 0 |
| A-5197 | H | H | H | H | F | CH$_2$C(=NOCH$_2$CF$_3$)CH$_3$ | H | H | O | 0 |
| A-5198 | H | H | H | H | F | CH$_2$C(=NOCH$_2$CF$_3$)CH$_2$CH$_3$ | H | H | O | 0 |
| A-5199 | H | H | H | H | F | CH$_2$Ph | H | H | O | 0 |
| A-5200 | H | H | H | H | F | CH$_2$(2-F)Ph | H | H | O | 0 |
| A-5201 | H | H | H | H | F | CH$_2$(3-F)Ph | H | H | O | 0 |
| A-5202 | H | H | H | H | F | CH$_2$(4-F)Ph | H | H | O | 0 |
| A-5203 | H | H | H | H | F | CH$_2$(2-Cl)Ph | H | H | O | 0 |
| A-5204 | H | H | H | H | F | CH$_2$(3-Cl)Ph | H | H | O | 0 |
| A-5205 | H | H | H | H | F | CH$_2$(4-Cl)Ph | H | H | O | 0 |
| A-520S | H | H | H | H | F | CH$_2$(2-CF$_3$)Ph | H | H | O | 0 |
| A-5207 | H | H | H | H | F | CH$_2$(3-CF$_3$)Ph | H | H | O | 0 |

TABLE 86-continued

| Compound | R¹ | R² | R³ | R⁴ | R⁵ | R⁶ | R⁷ | R⁸ | X | n |
|---|---|---|---|---|---|---|---|---|---|---|
| A-5208 | H | H | H | H | F | CH$_2$(4-CF$_3$)Ph | H | H | O | 0 |
| A-5209 | H | H | H | H | F | CH$_2$(naphthalen-1-yl) | H | H | O | 0 |
| A-5210 | H | H | H | H | F | CH$_2$(naphthalen-2-yl) | H | H | O | 0 |
| A-5211 | H | H | H | H | F | CH$_2$CH$_2$Ph | H | H | O | 0 |
| A-5212 | H | H | H | H | CH$_3$ | H | H | H | O | 0 |
| A-5213 | H | H | H | H | CH$_3$ | CH$_3$ | H | H | O | 0 |
| A-5214 | H | H | H | H | CH$_3$ | CH$_2$CH$_3$ | H | H | O | 0 |
| A-5215 | H | H | H | H | CH$_3$ | CH(CH$_3$)$_2$ | H | H | O | 0 |
| A-5216 | H | H | H | H | CH$_3$ | CH$_2$CH$_2$CH$_3$ | H | H | O | 0 |
| A-5217 | H | H | H | H | CH$_3$ | CH$_2$CH(CH$_3$)$_2$ | H | H | O | 0 |
| A-5218 | H | H | H | H | CH$_3$ | CH(CH$_3$)CH$_2$CH$_2$ | H | H | O | 0 |
| A-5219 | H | H | H | H | CH$_3$ | CH$_2$C(CH$_3$)$_3$ | H | H | O | 0 |
| A-5220 | H | H | H | H | CH$_3$ | CH$_2$(CH$_2$)$_2$CH$_3$ | H | H | O | 0 |
| A-5221 | H | H | H | H | CH$_3$ | CH$_2$(CH$_2$)$_3$CH$_3$ | H | H | O | 0 |
| A-5222 | H | H | H | H | CH$_3$ | CH$_2$(CH$_2$)$_4$CH$_3$ | H | H | O | 0 |
| A-5223 | H | H | H | H | CH$_3$ | CH$_2$(CH$_2$)$_6$CH$_3$ | H | H | O | 0 |
| A-5224 | H | H | H | H | CH$_3$ | CH$_2$OCH$_3$ | H | H | O | 0 |
| A-5225 | H | H | H | H | CH$_3$ | CH$_2$OCH$_2$CH$_3$ | H | H | O | 0 |
| A-5226 | H | H | H | H | CH$_3$ | CH$_2$CH$_2$OCH$_3$ | H | H | O | 0 |
| A-5227 | H | H | H | H | CH$_3$ | CH$_2$CH$_2$OCH$_2$CH$_3$ | H | H | O | 0 |
| A-5228 | H | H | H | H | CH$_3$ | CF$_3$ | H | H | O | 0 |
| A-5229 | H | H | H | H | CH$_3$ | CHF$_2$ | H | H | O | 0 |
| A-5230 | H | H | H | H | CH$_3$ | CH$_2$CF$_3$ | H | H | O | 0 |
| A-5231 | H | H | H | H | CH$_3$ | CH$_2$CHF$_2$ | H | H | O | 0 |
| A-5232 | H | H | H | H | CH$_3$ | CH$_2$CClF$_2$ | H | H | O | 0 |
| A-5233 | H | H | H | H | CH$_3$ | CH$_2$CBrF$_2$ | H | H | O | 0 |
| A-5234 | H | H | H | H | CH$_3$ | CF$_2$CF$_3$ | H | H | O | 0 |
| A-5235 | H | H | H | H | CH$_3$ | CF$_2$CHF$_2$ | H | H | O | 0 |
| A-5236 | H | H | H | H | CH$_3$ | CH$_2$CH$_2$CF$_3$ | H | H | O | 0 |
| A-5237 | H | H | H | H | CH$_3$ | CH$_2$CF$_2$CF$_3$ | H | H | O | 0 |
| A-5238 | H | H | H | H | CH$_3$ | CH$_2$CF$_2$CHF$_2$ | H | H | O | 0 |
| A-5239 | H | H | H | H | CH$_3$ | CF$_2$CHFCF$_3$ | H | H | O | 0 |
| A-5240 | H | H | H | H | CH$_3$ | CF$_2$CF$_2$CF$_3$ | H | H | O | 0 |
| A-5241 | H | H | H | H | CH$_3$ | CH$_2$CF$_2$CF$_2$CF$_3$ | H | H | O | 0 |

TABLE 87

| Compound | R¹ | R² | R³ | R⁴ | R⁵ | R⁶ | R⁷ | R⁸ | X | n |
|---|---|---|---|---|---|---|---|---|---|---|
| A-5242 | H | H | H | H | CH$_3$ | CH$_2$CH$_2$CH$_2$CF$_3$ | H | H | O | 0 |
| A-5243 | H | H | H | H | CH$_3$ | CH$_2$CH$_2$CF$_2$CF$_3$ | H | H | O | 0 |
| A-5244 | H | H | H | H | CH$_3$ | CF$_2$CF$_2$CF$_2$CF$_3$ | H | H | O | 0 |
| A-5245 | H | H | H | H | CH$_3$ | CH$_2$CH$_2$CH(CF$_3$)$_2$ | H | H | O | 0 |
| A-5246 | H | H | H | H | CH$_3$ | CF$_2$CF$_2$CF$_2$CF$_2$CF$_3$ | H | H | O | 0 |
| A-5247 | H | H | H | H | CH$_3$ | CH$_2$CF$_2$CF$_2$CF$_2$CF$_3$ | H | H | O | 0 |
| A-5248 | H | H | H | H | CH$_3$ | CH$_2$CH$_2$CH$_2$CH$_2$CF$_3$ | H | H | O | 0 |
| A-5249 | H | H | H | H | CH$_3$ | CH$_2$CF$_2$CF$_2$CF$_2$CHF$_2$ | H | H | O | 0 |
| A-5250 | H | H | H | H | CH$_3$ | CH$_2$CF$_2$CF(CF$_3$)CF$_2$C(CF$_3$)$_3$ | H | H | O | 0 |
| A-5251 | H | H | H | H | CH$_3$ | CF$_2$CHFOCH$_3$ | H | H | O | 0 |
| A-5252 | H | H | H | H | CH$_3$ | CF$_2$CHFOCH$_2$CH$_3$ | H | H | O | 0 |
| A-5253 | H | H | H | H | CH$_3$ | CH$_2$CH$_2$OCH$_2$CF$_3$ | H | H | O | 0 |
| A-S254 | H | H | H | H | CH$_3$ | CF$_2$CHFOCF$_3$ | H | H | O | 0 |
| A-5255 | H | H | H | H | CH$_3$ | CF$_2$CHFOCF$_2$CF$_3$ | H | H | O | 0 |
| A-5256 | H | H | H | H | CH$_3$ | CF$_2$CHFOCF$_2$CF$_2$CF$_3$ | H | H | O | 0 |
| A-5257 | H | H | H | H | CH$_3$ | CH$_2$CH=CH$_2$ | H | H | O | 0 |
| A-5258 | H | H | H | H | CH$_3$ | CH$_2$CH=CHCl | H | H | O | 0 |
| A-5259 | H | H | H | H | CH$_3$ | CH$_2$CH=CCl$_2$ | H | H | O | 0 |
| A-5260 | H | H | H | H | CH$_3$ | CH$_2$CH$_2$CF=CF$_2$ | H | H | O | 0 |
| A-5261 | H | H | H | H | CH$_3$ | CH$_2$CH$_2$CH=CF$_2$ | H | H | O | 0 |
| A-5262 | H | H | H | H | CH$_3$ | CH$_2$C≡CH | H | H | O | 0 |
| A-5263 | H | H | H | H | CH$_3$ | CH$_2$C≡CCH$_3$ | H | H | O | 0 |
| A-5264 | H | H | H | H | CH$_3$ | CH$_2$C≡CCF$_3$ | H | H | O | 0 |
| A-5265 | H | H | H | H | CH$_3$ | CH$_2$C≡CI | H | H | O | 0 |
| A-5266 | H | H | H | H | CH$_3$ | cyclobutyl | H | H | O | 0 |
| A-5267 | H | H | H | H | CH$_3$ | cyclopentyl | H | H | O | 0 |
| A-5268 | H | H | H | H | CH$_3$ | cyclohexyl | H | H | O | 0 |
| A-5269 | H | H | H | H | CH$_3$ | 4,4-difluorocyclohexyl | H | H | O | 0 |
| A-5270 | H | H | H | H | CH$_3$ | CH$_2$(cyclopropyl) | H | H | O | 0 |
| A-5271 | H | H | H | H | CH$_3$ | CH$_2$(cyclobutyl) | H | H | O | 0 |
| A-5272 | H | H | H | H | CH$_3$ | CH$_2$(cyclopentyl) | H | H | O | 0 |
| A-5273 | H | H | H | H | CH$_3$ | CH$_2$CH$_2$(cyclopropyl) | H | H | O | 0 |
| A-5274 | H | H | H | H | CH$_3$ | CH$_2$(2,2-difluorocyclopropyl) | H | H | O | 0 |
| A-5275 | H | H | H | H | CH$_3$ | CH$_2$(2,2-dichlorocyclopropyl) | H | H | O | 0 |
| A-5276 | H | H | H | H | CH$_3$ | CH$_2$(4,4-difluorocyclohexyl) | H | H | O | 0 |
| A-5277 | H | H | H | H | CH$_3$ | CH$_2$CH$_2$(2,2-difluorocyclopropyl) | H | H | O | 0 |

TABLE 87-continued

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-5278 | H | H | H | H | CH$_3$ | CH$_2$CH$_2$(2,2-dichlorocyclopropyl) | H | H | O | 0 |
| A-5279 | H | H | H | H | CH$_3$ | CH$_2$SCH$_3$ | H | H | O | 0 |
| A-5280 | H | H | H | H | CH$_3$ | CH$_2$SCH$_2$CH$_3$ | H | H | O | 0 |
| A-5281 | H | H | H | H | CH$_3$ | CH$_2$CH$_2$SCH$_3$ | H | H | O | 0 |
| A-5282 | H | H | H | H | CH$_3$ | CH$_2$CH$_2$SCH$_2$CH$_3$ | H | H | O | 0 |
| A-5283 | H | H | H | H | CH$_3$ | CH$_2$CH$_2$CH$_2$SCH$_3$ | H | H | O | 0 |
| A-5284 | H | H | H | H | CH$_3$ | CH$_2$CH$_2$CH$_2$SCH$_2$CH$_3$ | H | H | O | 0 |
| A-5285 | H | H | H | H | CH$_3$ | CH(CH$_3$)SCH$_3$ | H | H | O | 0 |
| A-5286 | H | H | H | H | CH$_3$ | CH(CH$_3$)SCH$_2$CH$_3$ | H | H | O | 0 |
| A-5287 | H | H | H | H | CH$_3$ | CH$_2$CH(CH$_3$)SCH$_3$ | H | H | O | 0 |
| A-5288 | H | H | H | H | CH$_3$ | CH$_2$CH(CH$_3$)SCH$_2$CH$_3$ | H | H | O | 0 |
| A-5289 | H | H | H | H | CH$_3$ | CH(CH$_3$)CH$_2$CH$_2$SCH$_3$ | H | H | O | 0 |
| A-5290 | H | H | H | H | CH$_3$ | CH(CH$_3$)CH$_2$CH$_2$SCH$_2$CH$_3$ | H | H | O | 0 |
| A-5291 | H | H | H | H | CH$_3$ | CH$_2$CH(CH$_3$)CH$_2$SCH$_3$ | H | H | O | 0 |
| A-5292 | H | H | H | H | CH$_3$ | CH$_2$CH(CH$_3$)CH$_2$SCH$_2$CH$_3$ | H | H | O | 0 |
| A-5293 | H | H | H | H | CH$_3$ | CH$_2$CH$_2$CH(CH$_3$)SCH$_3$ | H | H | O | 0 |
| A-5294 | H | H | H | H | CH$_3$ | CH$_2$CH$_2$CH(CH$_3$)SCH$_2$CH$_3$ | H | H | O | 0 |
| A-5295 | H | H | H | H | CH$_3$ | CH$_2$SOCH$_3$ | H | H | O | 0 |
| A-5296 | H | H | H | H | CH$_3$ | CH$_2$CH$_2$SOCH$_3$ | H | H | O | 0 |
| A-5297 | H | H | H | H | CH$_3$ | CH$_2$CH$_2$CH$_2$SOCH$_3$ | H | H | O | 0 |
| A-5298 | H | H | H | H | CH$_3$ | CH(CH$_3$)SOCH$_3$ | H | H | O | 0 |
| A-5299 | H | H | H | H | CH$_3$ | CH$_2$CH(CH$_3$)SOCH$_3$ | H | H | O | 0 |
| A-5300 | H | H | H | H | CH$_3$ | CH(CH$_3$)CH$_2$CH$_2$SOCH$_3$ | H | H | O | 0 |
| A-5301 | H | H | H | H | CH$_3$ | CH$_2$CH(CH$_3$)CH$_2$SOCH$_3$ | H | H | O | 0 |
| A-5302 | H | H | H | H | CH$_3$ | CH$_2$CH$_2$CH(CH$_3$)SOCH$_3$ | H | H | O | 0 |

TABLE 88

| Compound | R$^1$ | R$^2$ | R$^3$ | R$^4$ | R$^5$ | R$^6$ | R$^7$ | R$^8$ | X | n |
|---|---|---|---|---|---|---|---|---|---|---|
| A-5303 | H | H | H | H | CH$_3$ | CH$_2$SO$_2$CH$_3$ | H | H | O | 0 |
| A-5304 | H | H | H | H | CH$_3$ | CH$_2$CH$_2$SO$_2$CH$_3$ | H | H | O | 0 |
| A-5305 | H | H | H | H | CH$_3$ | CH$_2$CH$_2$CH$_2$SO$_2$CH$_3$ | H | H | O | 0 |
| A-5306 | H | H | H | H | CH$_3$ | CH(CH$_3$)SO$_2$CH$_3$ | H | H | O | 0 |
| A-5307 | H | H | H | H | CH$_3$ | CH$_2$CH(CH$_3$)SO$_2$CH$_3$ | H | H | O | 0 |
| A-5308 | H | H | H | H | CH$_3$ | CH(CH$_3$)CH$_2$CH$_2$SO$_2$CH$_3$ | H | H | O | 0 |
| A-5309 | H | H | H | H | CH$_3$ | CH$_2$CH(CH$_3$)CH$_2$SO$_2$CH$_3$ | H | H | O | 0 |
| A-5310 | H | H | H | H | CH$_3$ | CH$_2$CH$_2$CH(CH$_3$)SO$_2$CH$_3$ | H | H | O | 0 |
| A-5311 | H | H | H | H | CH$_3$ | CH$_2$SCF$_3$ | H | H | O | 0 |
| A-5312 | H | H | H | H | CH$_3$ | CH$_2$SCHF$_2$ | H | H | O | 0 |
| A-5313 | H | H | H | H | CH$_3$ | CH$_2$SCH$_2$CF$_3$ | H | H | O | 0 |
| A-5314 | H | H | H | H | CH$_3$ | CH$_2$SCH$_2$CHF$_2$ | H | H | O | 0 |
| A-5315 | H | H | H | H | CH$_3$ | CH$_2$SCF$_2$CF$_3$ | H | H | O | 0 |
| A-5316 | H | H | H | H | CH$_3$ | CH$_2$CH$_2$SCF$_3$ | H | H | O | 0 |
| A-5317 | H | H | H | H | CH$_3$ | CH$_2$CH$_2$SCH$_2$CF$_3$ | H | H | O | 0 |
| A-5318 | H | H | H | H | CH$_3$ | CH$_2$CH$_2$CH$_2$SCF$_3$ | H | H | O | 0 |
| A-5319 | H | H | H | H | CH$_3$ | CH$_2$CH$_2$CH$_2$SCH$_2$CF$_3$ | H | H | O | 0 |
| A-5320 | H | H | H | H | CH$_3$ | CH(CH$_3$)SCF$_3$ | H | H | O | 0 |
| A-5321 | H | H | H | H | CH$_3$ | CH(CH$_3$)SCH$_2$CF$_3$ | H | H | O | 0 |
| A-5322 | H | H | H | H | CH$_3$ | CH$_2$CH(CH$_3$)SCF$_3$ | H | H | O | 0 |
| A-5323 | H | H | H | H | CH$_3$ | CH$_2$CH(CH$_3$)SCH$_2$CF$_3$ | H | H | O | 0 |
| A-5324 | H | H | H | H | CH$_3$ | CH(CH$_3$)CH$_2$CH$_2$SCF$_3$ | H | H | O | 0 |
| A-5325 | H | H | H | H | CH$_3$ | CH(CH$_3$)CH$_2$CH$_2$SCH$_2$CF$_3$ | H | H | O | 0 |
| A-5326 | H | H | H | H | CH$_3$ | CH$_2$CH(CH$_3$)CH$_2$SCF$_3$ | H | H | O | 0 |
| A-5327 | H | H | H | H | CH$_3$ | CH$_2$CH(CH$_3$)CH$_2$SCH$_2$CF$_3$ | H | H | O | 0 |
| A-5328 | H | H | H | H | CH$_3$ | CH$_2$CH$_2$CH(CH$_3$)SCF$_3$ | H | H | O | 0 |
| A-5329 | H | H | H | H | CH$_3$ | CH$_2$CH$_2$CH(CH$_3$)SCH$_2$CF$_3$ | H | H | O | 0 |
| A-5330 | H | H | H | H | CH$_3$ | CH$_2$SOCF$_3$ | H | H | O | 0 |
| A-5331 | H | H | H | H | CH$_3$ | CH$_2$CH$_2$SOCF$_3$ | H | H | O | 0 |
| A-5332 | H | H | H | H | CH$_3$ | CH$_2$CH$_2$CH$_2$SOCF$_3$ | H | H | O | 0 |
| A-5333 | H | H | H | H | CH$_3$ | CH(CH$_3$)SOCF$_3$ | H | H | O | 0 |
| A-5334 | H | H | H | H | CH$_3$ | CH$_2$CH(CH$_3$)SOCF$_3$ | H | H | O | 0 |
| A-5335 | H | H | H | H | CH$_3$ | CH(CH$_3$)CH$_2$CH$_2$SOCF$_3$ | H | H | O | 0 |
| A-5336 | H | H | H | H | CH$_3$ | CH$_2$CH(CH$_3$)CH$_2$SOCF$_3$ | H | H | O | 0 |
| A-5337 | H | H | H | H | CH$_3$ | CH$_2$CH$_2$CH(CH$_3$)SOCF$_3$ | H | H | O | 0 |
| A-5338 | H | H | H | H | CH$_3$ | CH$_2$SO$_2$CF$_3$ | H | H | O | 0 |
| A-5339 | H | H | H | H | CH$_3$ | CH$_2$CH$_2$SO$_2$CF$_3$ | H | H | O | 0 |
| A-5340 | H | H | H | H | CH$_3$ | CH$_2$CH$_2$CH$_2$SO$_2$CF$_3$ | H | H | O | 0 |
| A-5341 | H | H | H | H | CH$_3$ | CH(CH$_3$)SO$_2$CF$_3$ | H | H | O | 0 |
| A-5342 | H | H | H | H | CH$_3$ | CH$_2$CH(CH$_3$)SO$_2$CF$_3$ | H | H | O | 0 |
| A-5343 | H | H | H | H | CH$_3$ | CH(CH$_3$)CH$_2$CH$_2$SO$_2$CF$_3$ | H | H | O | 0 |
| A-5344 | H | H | H | H | CH$_3$ | CH$_2$CH(CH$_3$)CH$_2$SO$_2$CF$_3$ | H | H | O | 0 |
| A-5345 | H | H | H | H | CH$_3$ | CH$_2$CH$_2$CH(CH$_3$)SO$_2$CF$_3$ | H | H | O | 0 |
| A-5346 | H | H | H | H | CH$_3$ | CH$_2$C(=O)CH$_3$ | H | H | O | 0 |
| A-5347 | H | H | H | H | CH$_3$ | CH$_2$C(=O)CH$_2$CH$_3$ | H | H | O | 0 |

TABLE 88-continued

| Compound | R¹ | R² | R³ | R⁴ | R⁵ | R⁶ | R⁷ | R⁸ | X | n |
|---|---|---|---|---|---|---|---|---|---|---|
| A-5348 | H | H | H | H | CH₃ | CH₂C(=O)C(CH₃)₃ | H | H | O | 0 |
| A-5349 | H | H | H | H | CH₃ | CH₂CH₂C(=O)CH₃ | H | H | O | 0 |
| A-S350 | H | H | H | H | CH₃ | CH₂CH₂C(=O)C(CH₃)₃ | H | H | O | 0 |
| A-5351 | H | H | H | H | CH₃ | CH₂C(=O)CF₃ | H | H | O | 0 |
| A-5352 | H | H | H | H | CH₃ | CH₂CH₂C(=O)CF₃ | H | H | O | 0 |
| A-53S3 | H | H | H | H | CH₃ | CH₂C(=O)OCH₃ | H | H | O | 0 |
| A-53S4 | H | H | H | H | CH₃ | CH₂C(=O)OCH₂CH₃ | H | H | O | 0 |
| A-5355 | H | H | H | H | CH₃ | CH₂C(=O)OC(CH₃)₃ | H | H | O | 0 |
| A-5356 | H | H | H | H | CH₃ | CH₂CH₂C(=O)OCH₃ | H | H | O | 0 |
| A-5357 | H | H | H | H | CH₃ | CH₂CH₂C(=O)OCH₂CH₃ | H | H | O | 0 |
| A-5358 | H | H | H | H | CH₃ | CH₂CH₂C(=O)OC(CH₃)₃ | H | H | O | 0 |
| A-5359 | H | H | H | H | CH₃ | CH₂C(=O)NH₂ | H | H | O | 0 |
| A-5360 | H | H | H | H | CH₃ | CH₂CH₂C(=O)NH₂ | H | H | O | 0 |
| A-5361 | H | H | H | H | CH₃ | CH₂C(=O)NHCH₃ | H | H | O | 0 |
| A-5362 | H | H | H | H | CH₃ | CH₂C(=O)NHCH(CH₃)₂ | H | H | O | 0 |
| A-5363 | H | H | H | H | CH₃ | CH₂CH₂C(=O)NHCH₃ | H | H | O | 0 |

TABLE 89

| Compound | R¹ | R² | R³ | R⁴ | R⁵ | R⁶ | R⁷ | R⁸ | X | n |
|---|---|---|---|---|---|---|---|---|---|---|
| A-5364 | H | H | H | H | CH₃ | CH₂CH₂C(=O)NHCH(CH₃)₂ | H | H | O | 0 |
| A-5365 | H | H | H | H | CH₃ | CH₂C(=O)NHCH₂CHF₂ | H | H | O | 0 |
| A-5366 | H | H | H | H | CH₃ | CH₂C(=O)NHCH₂CF₃ | H | H | O | 0 |
| A-5367 | H | H | H | H | CH₃ | CH₂CH₂C(=O)NHCH₂CHF₂ | H | H | O | 0 |
| A-5368 | H | H | H | H | CH₃ | CH₂CH₂C(=O)NHCH₂CF₃ | H | H | O | 0 |
| A-5369 | H | H | H | H | CH₃ | CH₂C(=O)N(CH₃)₂ | H | H | O | 0 |
| A-5370 | H | H | H | H | CH₃ | CH₂C(=O)N(CH₂CH₃)₂ | H | H | O | 0 |
| A-5371 | H | H | H | H | CH₃ | CH₂CH₂C(=O)N(CH₃)₂ | H | H | O | 0 |
| A-5372 | H | H | H | H | CH₃ | CH₂CH₂C(=O)N(CH₂CH₃)₂ | H | H | O | 0 |
| A-5373 | H | H | H | H | CH₃ | CH₂CH₂OH | H | H | O | 0 |
| A-5374 | H | H | H | H | CH₃ | CH₂CH(OH)CH₃ | H | H | O | 0 |
| A-5375 | H | H | H | H | CH₃ | CH₂CH₂CH₂OH | H | H | O | 0 |
| A-5376 | H | H | H | H | CH₃ | CH₂CH(OH)CH₂CH₃ | H | H | O | 0 |
| A-5377 | H | H | H | H | CH₃ | CH₂CH(OH)C(CH₃)₃ | H | H | O | 0 |
| A-5378 | H | H | H | H | CH₃ | CH₂CH₂CH(OH)CH₃ | H | H | O | 0 |
| A-5379 | H | H | H | H | CH₃ | CH₂CH₂CH(OH)C(CH₃)₃ | H | H | O | 0 |
| A-5380 | H | H | H | H | CH₃ | CH₂C(=NOH)CH₃ | H | H | O | 0 |
| A-5381 | H | H | H | H | CH₃ | CH₂C(=NOH)CH₂CH₃ | H | H | O | 0 |
| A-5382 | H | H | H | H | CH₃ | CH₂C(=NOH)C(CH₃)₃ | H | H | O | 0 |
| A-5383 | H | H | H | H | CH₃ | CH₂C(=NOCH₃)CH₃ | H | H | O | 0 |
| A-5384 | H | H | H | H | CH₃ | CH₂C(=NOCH₃)CH₂CH₃ | H | H | O | 0 |
| A-5385 | H | H | H | H | CH₃ | CH₂C(=NOCH₂CH₃)CH₃ | H | H | O | 0 |
| A-5386 | H | H | H | H | CH₃ | CH₂C(=NOCH₂CH₃)CH₂CH₃ | H | H | O | 0 |
| A-5387 | H | H | H | H | CH₃ | CH₂C(=NOCH₂CF₃)CH₃ | H | H | O | 0 |
| A-5388 | H | H | H | H | CH₃ | CH₂C(=NOCH₂CF₃)CH₂CH₃ | H | H | O | 0 |
| A-5389 | H | H | H | H | CH₃ | CH₂Ph | H | H | O | 0 |
| A-5390 | H | H | H | H | CH₃ | CH₂(2-F)Ph | H | H | O | 0 |
| A-5391 | H | H | H | H | CH₃ | CH₂(3-F)PH | H | H | O | 0 |
| A-5392 | H | H | H | H | CH₃ | CH₂(4-F)Ph | H | H | O | 0 |
| A-5393 | H | H | H | H | CH₃ | CH₂(2-Cl)Ph | H | H | O | 0 |
| A-5394 | H | H | H | H | CH₃ | CH₂(3-Cl)Ph | H | H | O | 0 |
| A-5395 | H | H | H | H | CH₃ | CH₂(4-Cl)Ph | H | H | O | 0 |
| A-5396 | H | H | H | H | CH₃ | CH₂(2-CF₃)Ph | H | H | O | 0 |
| A-5397 | H | H | H | H | CH₃ | CH₂(3-CF₃)Ph | H | H | O | 0 |
| A-5398 | H | H | H | H | CH₃ | CH₂(4-CF₃)Ph | H | H | O | 0 |
| A-5399 | H | H | H | H | CH₃ | CH₂(naphthalen-1-yl) | H | H | O | 0 |
| A-5400 | H | H | H | H | CH₃ | CH₂(naphthalen-2-yl) | H | H | O | 0 |
| A-5401 | H | H | H | H | CH₃ | CH₂CH₂Ph | H | H | O | 0 |
| A-5402 | H | H | H | H | H | H | H | H | S | 0 |
| A-5403 | H | H | H | H | H | CH₃ | H | H | S | 0 |
| A-5404 | H | H | H | H | H | CH₂CH₃ | H | H | S | 0 |
| A-5405 | H | H | H | H | H | CH(CH₃)₂ | H | H | S | 0 |
| A-5406 | H | H | H | H | H | CH₂CH₂CH₃ | H | H | S | 0 |
| A-5407 | H | H | H | H | H | CH₂CH(CH₃)₂ | H | H | S | 0 |
| A-5408 | H | H | H | H | H | CH(CH₃)CH₂CH₃ | H | H | S | 0 |
| A-5409 | H | H | H | H | H | CH₂C(CH₃)₃ | H | H | S | 0 |
| A-5410 | H | H | H | H | H | CH₂(CH₂)₂CH₃ | H | H | S | 0 |
| A-5411 | H | H | H | H | H | CH₂(CH₂)₃CH₃ | H | H | S | 0 |
| A-5412 | H | H | H | H | H | CF₃ | H | H | S | 0 |
| A-5413 | H | H | H | H | H | CHF₂ | H | H | S | 0 |
| A-5414 | H | H | H | H | H | CH₂CF₃ | H | H | S | 0 |
| A-5415 | H | H | H | H | H | CH₂CHF₂ | H | H | S | 0 |
| A-5416 | H | H | H | H | H | CH₂CClF₂ | H | H | S | 0 |
| A-5417 | H | H | H | H | H | CH₂CBrF₂ | H | H | S | 0 |

TABLE 89-continued

| Compound | R¹ | R² | R³ | R⁴ | R⁵ | R⁶ | R⁷ | R⁸ | X | n |
|---|---|---|---|---|---|---|---|---|---|---|
| A-5418 | H | H | H | H | H | CF$_2$CF$_3$ | H | H | S | 0 |
| A-5419 | H | H | H | H | H | CF$_2$CHF$_2$ | H | H | S | 0 |
| A-5420 | H | H | H | H | H | CH$_2$CH$_2$CF$_3$ | H | H | S | 0 |
| A-5421 | H | H | H | H | H | CH$_2$CF$_2$CF$_3$ | H | H | S | 0 |
| A-5422 | H | H | H | H | H | CH$_2$CF$_2$CHF$_2$ | H | H | S | 0 |
| A-5423 | H | H | H | H | H | CF$_2$CHFCF$_3$ | H | H | S | 0 |
| A-5424 | H | H | H | H | H | CF$_2$CF$_2$CF$_3$ | H | H | S | 0 |

TABLE 90

| Compound | R¹ | R² | R³ | R⁴ | R⁵ | R⁶ | R⁷ | R⁸ | X | n |
|---|---|---|---|---|---|---|---|---|---|---|
| A-5425 | H | H | H | H | H | CH$_2$CF$_2$CF$_2$CF$_3$ | H | H | S | 0 |
| A-5426 | H | H | H | H | H | CH$_2$CF$_2$CHFCF$_3$ | H | H | S | 0 |
| A-5427 | H | H | H | H | H | CH$_2$CH$_2$CH$_2$CF$_3$ | H | H | S | 0 |
| A-5428 | H | H | H | H | H | CH$_2$CH$_2$CF$_2$CF$_3$ | H | H | S | 0 |
| A-5429 | H | H | H | H | H | CF$_2$CF$_2$CF$_2$CF$_3$ | H | H | S | 0 |
| A-5430 | H | H | H | H | H | CH$_2$CH$_2$CH(CF$_3$)$_2$ | H | H | S | 0 |
| A-5431 | H | H | H | H | H | CF$_2$CF$_2$CF$_2$CF$_2$CF$_3$ | H | H | S | 0 |
| A-5432 | H | H | H | H | H | CH$_2$CF$_2$CF$_2$CF$_2$CF$_3$ | H | H | S | 0 |
| A-5433 | H | H | H | H | H | CH$_2$CH$_2$CH$_2$CH$_2$CF$_3$ | H | H | S | 0 |
| A-5434 | H | H | H | H | H | CH$_2$CF$_2$CF$_2$CF$_2$CHF$_2$ | H | H | S | 0 |
| A-5435 | H | H | H | H | H | CH$_2$CH$_2$OCH$_2$CF$_3$ | H | H | S | 0 |
| A-5436 | H | H | H | H | H | CF$_2$CHFOCF$_3$ | H | H | S | 0 |
| A-5437 | H | H | H | H | H | CF$_2$CHFOCF$_2$CF$_3$ | H | H | S | 0 |
| A-5438 | H | H | H | H | H | CH$_2$CH$_2$CF=CF$_2$ | H | H | S | 0 |
| A-5439 | H | H | H | H | H | CH$_2$CH$_2$CH=CF$_2$ | H | H | S | 0 |
| A-5440 | H | H | H | H | H | CH$_2$C≡CCH$_3$ | H | H | S | 0 |
| A-5441 | H | H | H | H | H | CH$_2$C≡CCF$_3$ | H | H | S | 0 |
| A-5442 | H | H | H | H | H | CH$_2$C≡CI | H | H | S | 0 |
| A-5443 | H | H | H | H | H | CH$_2$(2,2-difluorocyclopropyl) | H | H | S | 0 |
| A-5444 | H | H | H | H | H | CH$_2$(2,2-dichlorocyclopropyl) | H | H | S | 0 |
| A-5445 | H | H | H | H | H | CH$_2$CH$_2$(2,2-difluorocyclopropyl) | H | H | S | 0 |
| A-5446 | H | H | H | H | H | CH$_2$CH$_2$(2,2-dichlorocyclopropyl) | H | H | S | 0 |
| A-5447 | H | H | H | H | H | CH$_2$SCH$_3$ | H | H | S | 0 |
| A-5448 | H | H | H | H | H | CH$_2$SCH$_2$CH$_3$ | H | H | S | 0 |
| A-5449 | H | H | H | H | H | CH$_2$CH$_2$SCH$_3$ | H | H | S | 0 |
| A-5450 | H | H | H | H | H | CH$_2$SOCH$_3$ | H | H | S | 0 |
| A-5451 | H | H | H | H | H | CH$_2$CH$_2$SOCH$_3$ | H | H | S | 0 |
| A-5452 | H | H | H | H | H | CH$_2$SO$_2$CH$_3$ | H | H | S | 0 |
| A-5453 | H | H | H | H | H | CH$_2$CH$_2$SO$_2$CH$_3$ | H | H | S | 0 |
| A-5454 | H | H | H | H | H | CH$_2$SCF$_3$ | H | H | S | 0 |
| A-5455 | H | H | H | H | H | CH$_2$SCHF$_2$ | H | H | S | 0 |
| A-5456 | H | H | H | H | H | CH$_2$SCH$_2$CF$_3$ | H | H | S | 0 |
| A-5457 | H | H | H | H | H | CH$_2$SCH$_2$CHF$_2$ | H | H | S | 0 |
| A-5458 | H | H | H | H | H | CH$_2$SCF$_2$CF$_3$ | H | H | S | 0 |
| A-5459 | H | H | H | H | H | CH$_2$CH$_2$SCF$_3$ | H | H | S | 0 |
| A-5460 | H | H | H | H | H | CH$_2$SOCF$_3$ | H | H | S | 0 |
| A-5461 | H | H | H | H | H | CH$_2$CH$_2$SOCF$_3$ | H | H | S | 0 |
| A-5462 | H | H | H | H | H | CH$_2$CH$_2$CH$_2$SOCF$_3$ | H | H | S | 0 |
| A-5463 | H | H | H | H | H | CH$_2$SO$_2$CF$_3$ | H | H | S | 0 |
| A-5464 | H | H | H | H | H | CH$_2$CH$_2$SO$_2$CF$_3$ | H | H | S | 0 |
| A-5465 | H | H | H | H | H | CH$_2$CH$_2$CH$_2$SO$_2$CF$_3$ | H | H | S | 0 |
| A-5466 | H | H | H | H | H | CH$_2$C(=O)NHCH$_2$CHF$_2$ | H | H | S | 0 |
| A-5467 | H | H | H | H | H | CH$_2$C(=O)NHCH$_2$CF$_3$ | H | H | S | 0 |
| A-5468 | H | H | H | H | H | H | H | H | O | 1 |
| A-5469 | H | H | H | H | H | CH$_3$ | H | H | O | 1 |
| A-5470 | H | H | H | H | H | CH$_2$CH$_3$ | H | H | O | 1 |
| A-5471 | H | H | H | H | H | CH(CH$_3$)$_2$ | H | H | O | 1 |
| A-5472 | H | H | H | H | H | CH$_2$CH$_2$CH$_3$ | H | H | O | 1 |
| A-5473 | H | H | H | H | H | CH$_2$CH(CH$_3$)$_2$ | H | H | O | 1 |
| A-5474 | H | H | H | H | H | CH(CH$_3$)CH$_2$CH$_3$ | H | H | O | 1 |
| A-5475 | H | H | H | H | H | CH$_2$C(CH$_3$)$_3$ | H | H | O | 1 |
| A-5476 | H | H | H | H | H | CH$_2$(CH$_2$)$_2$CH$_3$ | H | H | O | 1 |
| A-5477 | H | H | H | H | H | CH$_2$(CH$_2$)$_3$CH$_3$ | H | H | O | 1 |
| A-5478 | H | H | H | H | H | CH$_2$(CH$_2$)$_4$CH$_3$ | H | H | O | 1 |
| A-5479 | H | H | H | H | H | CH$_2$(CH$_2$)$_6$CH$_3$ | H | H | O | 1 |
| A-5480 | H | H | H | H | H | CH$_2$OCH$_3$ | H | H | O | 1 |
| A-5481 | H | H | H | H | H | CH$_2$OCH$_2$CH$_3$ | H | H | O | 1 |
| A-5482 | H | H | H | H | H | CH$_2$CH$_2$OCH$_3$ | H | H | O | 1 |
| A-5483 | H | H | H | H | H | CH$_2$CH$_2$OCH$_2$CH$_3$ | H | H | O | 1 |
| A-5484 | H | H | H | H | H | CF$_3$ | H | H | O | 1 |
| A-5485 | H | H | H | H | H | CHF$_2$ | H | H | O | 1 |

TABLE 91

| Compound | R¹ | R² | R³ | R⁴ | R⁵ | R⁶ | R⁷ | R⁸ | X | n |
|---|---|---|---|---|---|---|---|---|---|---|
| A-5486 | H | H | H | H | H | CH$_2$CF$_3$ | H | H | O | 1 |
| A-5487 | H | H | H | H | H | CH$_2$CHF$_2$ | H | H | O | 1 |
| A-5488 | H | H | H | H | H | CH$_2$CClF$_2$ | H | H | O | 1 |
| A-5489 | H | H | H | H | H | CH$_2$CBrF$_2$ | H | H | O | 1 |
| A-5490 | H | H | H | H | H | CF$_2$CF$_3$ | H | H | O | 1 |
| A-5491 | H | H | H | H | H | CF$_2$CHF$_2$ | H | H | O | 1 |
| A-5492 | H | H | H | H | H | CH$_2$CH$_2$CF$_3$ | H | H | O | 1 |
| A-5493 | H | H | H | H | H | CH$_2$CF$_2$CF$_3$ | H | H | O | 1 |
| A-5494 | H | H | H | H | H | CH$_2$CF$_2$CHF$_2$ | H | H | O | 1 |
| A-5495 | H | H | H | H | H | CF$_2$CHFCF$_3$ | H | H | O | 1 |
| A-5496 | H | H | H | H | H | CF$_2$CF$_2$CF$_3$ | H | H | O | 1 |
| A-5497 | H | H | H | H | H | CH$_2$CF$_2$CF$_2$CF$_3$ | H | H | O | 1 |
| A-5498 | H | H | H | H | H | CH$_2$CH$_2$CH$_2$CF$_3$ | H | H | O | 1 |
| A-5499 | H | H | H | H | H | CH$_2$CH$_2$CF$_2$CF$_3$ | H | H | O | 1 |
| A-5500 | H | H | H | H | H | CF$_2$CF$_2$CF$_2$CF$_3$ | H | H | O | 1 |
| A-5501 | H | H | H | H | H | CH$_2$CH$_2$CH(CF$_3$)$_2$ | H | H | O | 1 |
| A-5502 | H | H | H | H | H | CF$_2$CF$_2$CF$_2$CF$_2$CF$_3$ | H | H | O | 1 |
| A-5503 | H | H | H | H | H | CH$_2$CF$_2$CF$_2$CF$_2$CF$_3$ | H | H | O | 1 |
| A-5504 | H | H | H | H | H | CH$_2$CH$_2$CH$_2$CH$_2$CF$_3$ | H | H | O | 1 |
| A-5505 | H | H | H | H | H | CH$_2$CF$_2$CF$_2$CF$_2$CHF$_2$ | H | H | O | 1 |
| A-5506 | H | H | H | H | H | CH$_2$CF$_2$CF(CF$_3$)CF$_2$C(CF$_3$)$_3$ | H | H | O | 1 |
| A-5507 | H | H | H | H | H | CF$_2$CHFOCH$_3$ | H | H | O | 1 |
| A-5508 | H | H | H | H | H | CF$_2$CHFOCH$_2$CH$_3$ | H | H | O | 1 |
| A-5509 | H | H | H | H | H | CH$_2$CH$_2$OCH$_2$CF$_3$ | H | H | O | 1 |
| A-5510 | H | H | H | H | H | CF$_2$CHFOCF$_3$ | H | H | O | 1 |
| A-5511 | H | H | H | H | H | CF$_2$CHFOCF$_2$CF$_3$ | H | H | O | 1 |
| A-5512 | H | H | H | H | H | CF$_2$CHFOCF$_2$CF$_2$CF$_3$ | H | H | O | 1 |
| A-5513 | H | H | H | H | H | CH$_2$CH=CH$_2$ | H | H | O | 1 |
| A-5514 | H | H | H | H | H | CH$_2$CH=CHCl | H | H | O | 1 |
| A-5515 | H | H | H | H | H | CH$_2$CH=CCl$_2$ | H | H | O | 1 |
| A-5516 | H | H | H | H | H | CH$_2$CH$_2$CF=CF$_2$ | H | H | O | 1 |
| A-5517 | H | H | H | H | H | CH$_2$CH$_2$CH=CF$_2$ | H | H | O | 1 |
| A-5518 | H | H | H | H | H | CH$_2$C≡CH | H | H | O | 1 |
| A-5519 | H | H | H | H | H | CH$_2$C≡CCH$_3$ | H | H | O | 1 |
| A-5520 | H | H | H | H | H | CH$_2$C≡CCF$_3$ | H | H | O | 1 |
| A-5521 | H | H | H | H | H | CH$_2$C≡Cl | H | H | O | 1 |
| A-5522 | H | H | H | H | H | cyclobutyl | H | H | O | 1 |
| A-5523 | H | H | H | H | H | cyclopentyl | H | H | O | 1 |
| A-5524 | H | H | H | H | H | cyclohexyl | H | H | O | 1 |
| A-5525 | H | H | H | H | H | 4,4-difluorocyclohexyl | H | H | O | 1 |
| A-5526 | H | H | H | H | H | CH$_2$(cyclopropyl) | H | H | O | 1 |
| A-5527 | H | H | H | H | H | CH$_2$(cyclobutyl) | H | H | O | 1 |
| A-5528 | H | H | H | H | H | CH$_2$(cyclopentyl) | H | H | O | 1 |
| A-5529 | H | H | H | H | H | CH$_2$CH$_2$(cyclopropyl) | H | H | O | 1 |
| A-5530 | H | H | H | H | H | CH$_2$(2,2-difluorocyclopropyl) | H | H | O | 1 |
| A-5531 | H | H | H | H | H | CH$_2$(2,2-dichlorocyclopropyl) | H | H | O | 1 |
| A-5532 | H | H | H | H | H | CH$_2$(4,4-difluorocyclohexyl) | H | H | O | 1 |
| A-5533 | H | H | H | H | H | CH$_2$CH$_2$(2,2-difluorocyclopropyl) | H | H | O | 1 |
| A-5534 | H | H | H | H | H | CH$_2$CH$_2$(2,2-dichlorocyclopropyl) | H | H | O | 1 |
| A-5535 | H | H | H | H | H | CH$_2$SCH$_3$ | H | H | O | 1 |
| A-5536 | H | H | H | H | H | CH$_2$SCH$_2$CH$_3$ | H | H | O | 1 |
| A-5537 | H | H | H | H | H | CH$_2$CH$_2$SCH$_3$ | H | H | O | 1 |
| A-5538 | H | H | H | H | H | CH$_2$CH$_2$SCH$_2$CH$_3$ | H | H | O | 1 |
| A-5539 | H | H | H | H | H | CH$_2$CH$_2$CH$_2$SCH$_3$ | H | H | O | 1 |
| A-5540 | H | H | H | H | H | CH$_2$CH$_2$CH$_2$SCH$_2$CH$_3$ | H | H | O | 1 |
| A-5541 | H | H | H | H | H | CH(CH$_3$)SCH$_3$ | H | H | O | 1 |
| A-5542 | H | H | H | H | H | CH(CH$_3$)SCH$_2$CH$_3$ | H | H | O | 1 |
| A-5543 | H | H | H | H | H | CH$_2$CH(CH$_3$)SCH$_3$ | H | H | O | 1 |
| A-5544 | H | H | H | H | H | CH$_2$CH(CH$_3$)SCH$_2$CH$_3$ | H | H | O | 1 |
| A-5545 | H | H | H | H | H | CH(CH$_3$)CH$_2$CH$_2$SCH$_3$ | H | H | O | 1 |
| A-5546 | H | H | H | H | H | CH(CH$_3$)CH$_2$CH$_2$SCH$_2$CH$_3$ | H | H | O | 1 |

TABLE 92

| Compound | R¹ | R² | R³ | R⁴ | R⁵ | R⁶ | R⁷ | R⁸ | X | n |
|---|---|---|---|---|---|---|---|---|---|---|
| A-5547 | H | H | H | H | H | CH$_2$CH(CH$_3$)CH$_2$SCH$_3$ | H | H | O | 1 |
| A-5548 | H | H | H | H | H | CH$_2$CH(CH$_3$)CH$_2$SCH$_2$CH$_3$ | H | H | O | 1 |
| A-5549 | H | H | H | H | H | CH$_2$CH$_2$CH(CH$_3$)SCH$_3$ | H | H | O | 1 |
| A-5550 | H | H | H | H | H | CH$_2$CH$_2$CH(CH$_3$)SCH$_2$CH$_3$ | H | H | O | 1 |
| A-5551 | H | H | H | H | H | CH$_2$SOCH$_3$ | H | H | O | 1 |
| A-5552 | H | H | H | H | H | CH$_2$CH$_2$SOCH$_3$ | H | H | O | 1 |
| A-5553 | H | H | H | H | H | CH$_2$CH$_2$CH$_2$SOCH$_3$ | H | H | O | 1 |
| A-5554 | H | H | H | H | H | CH(CH$_3$)SOCH$_3$ | H | H | O | 1 |
| A-5555 | H | H | H | H | H | CH$_2$CH(CH$_3$)SOCH$_3$ | H | H | O | 1 |

TABLE 92-continued

| Compound | R¹ | R² | R³ | R⁴ | R⁵ | R⁶ | R⁷ | R⁸ | X | n |
|---|---|---|---|---|---|---|---|---|---|---|
| A-5556 | H | H | H | H | H | CH(CH$_3$)CH$_2$CH$_2$SOCH$_3$ | H | H | O | 1 |
| A-5557 | H | H | H | H | H | CH$_2$CH(CH$_3$)CH$_2$SOCH$_3$ | H | H | O | 1 |
| A-5558 | H | H | H | H | H | CH$_2$CH$_2$CH(CH$_3$)SOCH$_3$ | H | H | O | 1 |
| A-5559 | H | H | H | H | H | CH$_2$SO$_2$CH$_3$ | H | H | O | 1 |
| A-5560 | H | H | H | H | H | CH$_2$CH$_2$SO$_2$CH$_3$ | H | H | O | 1 |
| A-5561 | H | H | H | H | H | CH$_2$CH$_2$CH$_2$SO$_2$CH$_3$ | H | H | O | 1 |
| A-5562 | H | H | H | H | H | CH(CH$_3$)SO$_2$CH$_3$ | H | H | O | 1 |
| A-5563 | H | H | H | H | H | CH$_2$CH(CH$_3$)SO$_2$CH$_3$ | H | H | O | 1 |
| A-5564 | H | H | H | H | H | CH(CH$_3$)CH$_2$CH$_2$SO$_2$CH$_3$ | H | H | O | 1 |
| A-5565 | H | H | H | H | H | CH$_2$CH(CH$_3$)CH$_2$SO$_2$CH$_3$ | H | H | O | 1 |
| A-5566 | H | H | H | H | H | CH$_2$CH$_2$CH(CH$_3$)SO$_2$CH$_3$ | H | H | O | 1 |
| A-5567 | H | H | H | H | H | CH$_2$SCF$_3$ | H | H | O | 1 |
| A-5568 | H | H | H | H | H | CH$_2$SCHF$_2$ | H | H | O | 1 |
| A-5569 | H | H | H | H | H | CH$_2$SCH$_2$CF$_3$ | H | H | O | 1 |
| A-5570 | H | H | H | H | H | CH$_2$SCH$_2$CHF$_2$ | H | H | O | 1 |
| A-5571 | H | H | H | H | H | CH$_2$SCF$_2$CF$_3$ | H | H | O | 1 |
| A-5572 | H | H | H | H | H | CH$_2$CH$_2$SCF$_3$ | H | H | O | 1 |
| A-5573 | H | H | H | H | H | CH$_2$CH$_2$SCH$_2$CF$_3$ | H | H | O | 1 |
| A-5574 | H | H | H | H | H | CH$_2$CH$_2$CH$_2$SCF$_3$ | H | H | O | 1 |
| A-5575 | H | H | H | H | H | CH$_2$CH$_2$CH$_2$SCH$_2$CF$_3$ | H | H | O | 1 |
| A-5576 | H | H | H | H | H | CH(CH$_3$)SCF$_3$ | H | H | O | 1 |
| A-5577 | H | H | H | H | H | CH(CH$_3$)SCH$_2$CF$_3$ | H | H | O | 1 |
| A-5578 | H | H | H | H | H | CH$_2$CH(CH$_3$)SCF$_3$ | H | H | O | 1 |
| A-5579 | H | H | H | H | H | CH$_2$CH(CH$_3$)SCH$_2$CF$_3$ | H | H | O | 1 |
| A-5580 | H | H | H | H | H | CH(CH$_3$)CH$_2$CH$_2$SCF$_3$ | H | H | O | 1 |
| A-5581 | H | H | H | H | H | CH(CH$_3$)CH$_2$CH$_2$SCH$_2$CF$_3$ | H | H | O | 1 |
| A-5582 | H | H | H | H | H | CH$_2$CH(CH$_3$)CH$_2$SCF$_3$ | H | H | O | 1 |
| A-5583 | H | H | H | H | H | CH$_2$CH(CH$_3$)CH$_2$SCH$_2$CF$_3$ | H | H | O | 1 |
| A-5584 | H | H | H | H | H | CH$_2$CH$_2$CH(CH$_3$)SCF$_3$ | H | H | O | 1 |
| A-5585 | H | H | H | H | H | CH$_2$CH$_2$CH(CH$_3$)SCH$_2$CF$_3$ | H | H | O | 1 |
| A-5586 | H | H | H | H | H | CH$_2$SOCF$_3$ | H | H | O | 1 |
| A-5587 | H | H | H | H | H | CH$_2$CH$_2$SOCF$_3$ | H | H | O | 1 |
| A-5588 | H | H | H | H | H | CH$_2$CH$_2$CH$_2$SOCF$_3$ | H | H | O | 1 |
| A-5589 | H | H | H | H | H | CH(CH$_3$)SOCF$_3$ | H | H | O | 1 |
| A-5590 | H | H | H | H | H | CH$_2$CH(CH$_3$)SOCF$_3$ | H | H | O | 1 |
| A-S591 | H | H | H | H | H | CH(CH$_3$)CH$_2$CH$_2$SOCF$_3$ | H | H | O | 1 |
| A-5592 | H | H | H | H | H | CH$_2$CH(CH$_3$)CH$_2$SOCF$_3$ | H | H | O | 1 |
| A-5593 | H | H | H | H | H | CH$_2$CH$_2$CH(CH$_3$)SOCF$_3$ | H | H | O | 1 |
| A-5594 | H | H | H | H | H | CH$_2$SO$_2$CF$_3$ | H | H | O | 1 |
| A-5595 | H | H | H | H | H | CH$_2$CH$_2$SO$_2$CF$_3$ | H | H | O | 1 |
| A-5596 | H | H | H | H | H | CH$_2$CH$_2$CH$_2$SO$_2$CF$_3$ | H | H | O | 1 |
| A-5597 | H | H | H | H | H | CH(CH$_3$)SO$_2$CF$_3$ | H | H | O | 1 |
| A-5598 | H | H | H | H | H | CH$_2$CH(CH$_3$)SO$_2$CF$_3$ | H | H | O | 1 |
| A-5599 | H | H | H | H | H | CH(CH$_3$)CH$_2$CH$_2$SO$_2$CF$_3$ | H | H | O | 1 |
| A-5600 | H | H | H | H | H | CH$_2$CH(CH$_3$)CH$_2$SO$_2$CF$_3$ | H | H | O | 1 |
| A-5601 | H | H | H | H | H | CH$_2$CH$_2$CH(CH$_3$)SO$_2$CF$_3$ | H | H | O | 1 |
| A-5602 | H | H | H | H | H | CH$_2$C(=O)CH$_3$ | H | H | O | 1 |
| A-5603 | H | H | H | H | H | CH$_2$C(=O)CH$_2$CH$_3$ | H | H | O | 1 |
| A-5604 | H | H | H | H | H | CH$_2$C(=O)C(CH$_3$)$_3$ | H | H | O | 1 |
| A-5605 | H | H | H | H | H | CH$_2$CH$_2$C(=O)CH$_3$ | H | H | O | 1 |
| A-5606 | H | H | H | H | H | CH$_2$CH$_2$C(=O)C(CH$_3$)$_3$ | H | H | O | 1 |
| A-5607 | H | H | H | H | H | CH$_2$C(=O)CF$_3$ | H | H | O | 1 |

TABLE 93

| Compound | R¹ | R² | R³ | R⁴ | R⁵ | R⁶ | R⁷ | R⁸ | X | n |
|---|---|---|---|---|---|---|---|---|---|---|
| A-5608 | H | H | H | H | H | CH$_2$CH$_2$C(=O)CF$_3$ | H | H | O | 1 |
| A-5609 | H | H | H | H | H | CH$_2$C(=O)OCH$_3$ | H | H | O | 1 |
| A-5610 | H | H | H | H | H | CH$_2$C(=O)OCH$_2$CH$_3$ | H | H | O | 1 |
| A-5611 | H | H | H | H | H | CH$_2$C(=O)OC(CH$_3$)$_3$ | H | H | O | 1 |
| A-5612 | H | H | H | H | H | CH$_2$CH$_2$C(=O)OCH$_3$ | H | H | O | 1 |
| A-5613 | H | H | H | H | H | CH$_2$CH$_2$C(=O)OCH$_2$CH$_3$ | H | H | O | 1 |
| A-5614 | H | H | H | H | H | CH$_2$CH$_2$C(=O)OC(CH$_3$)$_3$ | H | H | O | 1 |
| A-5615 | H | H | H | H | H | CH$_2$C(=O)NH$_2$ | H | H | O | 1 |
| A-5616 | H | H | H | H | H | CH$_2$CH$_2$C(=O)NH$_2$ | H | H | O | 1 |
| A-5617 | H | H | H | H | H | CH$_2$C(=O)NHCH$_3$ | H | H | O | 1 |
| A-5618 | H | H | H | H | H | CH$_2$C(=O)NHCH(CH$_2$)$_2$ | H | H | O | 1 |
| A-5619 | H | H | H | H | H | CH$_2$CH$_2$C(=O)NHCH$_3$ | H | H | O | 1 |
| A-5620 | H | H | H | H | H | CH$_2$CH$_2$C(=O)NHCH(CH$_3$)$_2$ | H | H | O | 1 |
| A-5621 | H | H | H | H | H | CH$_2$C(=O)NHCH$_2$CHF$_2$ | H | H | O | 1 |
| A-5622 | H | H | H | H | H | CH$_2$C(=O)NHCH$_2$CF$_3$ | H | H | O | 1 |
| A-5623 | H | H | H | H | H | CH$_2$CH$_2$C(=O)NHCH$_2$CHF$_2$ | H | H | O | 1 |
| A-5624 | H | H | H | H | H | CH$_2$CH$_2$C(=O)NHCH$_2$CF$_3$ | H | H | O | 1 |
| A-5625 | H | H | H | H | H | CH$_2$C(=O)N(CH$_3$)$_2$ | H | H | O | 1 |

TABLE 93-continued

| Compound | R¹ | R² | R³ | R⁴ | R⁵ | R⁶ | R⁷ | R⁸ | X | n |
|---|---|---|---|---|---|---|---|---|---|---|
| A-5626 | H | H | H | H | H | CH$_2$C(=O)N(CH$_2$CH$_3$)$_2$ | H | H | O | 1 |
| A-5627 | H | H | H | H | H | CH$_2$CH$_2$C(=O)N(CH$_3$)$_2$ | H | H | O | 1 |
| A-5628 | H | H | H | H | H | CH$_2$CH$_2$C(=O)N(CH$_2$CH$_3$)$_2$ | H | H | O | 1 |
| A-5629 | H | H | H | H | H | CH$_2$CH$_2$OH | H | H | O | 1 |
| A-5630 | H | H | H | H | H | CH$_2$CH(OH)CH$_3$ | H | H | O | 1 |
| A-5631 | H | H | H | H | H | CH$_2$CH$_2$CH$_2$OH | H | H | O | 1 |
| A-5632 | H | H | H | H | H | CH$_2$CH(OH)CH$_2$CH$_3$ | H | H | O | 1 |
| A-5633 | H | H | H | H | H | CH$_2$CH(OH)C(CH$_3$)$_3$ | H | H | O | 1 |
| A-5634 | H | H | H | H | H | CH$_2$CH$_2$CH(OH)CH$_3$ | H | H | O | 1 |
| A-5635 | H | H | H | H | H | CH$_2$CH$_2$CH(OH)C(CH$_3$)$_3$ | H | H | O | 1 |
| A-5636 | H | H | H | H | H | CH$_2$C(=NOH)CH$_3$ | H | H | O | 1 |
| A-5637 | H | H | H | H | H | CH$_2$C(=NOH)CH$_2$CH$_3$ | H | H | O | 1 |
| A-5638 | H | H | H | H | H | CH$_2$C(=NOH)C(CH$_3$)$_3$ | H | H | O | 1 |
| A-5639 | H | H | H | H | H | CH$_2$C(=NOCH$_3$)CH$_3$ | H | H | O | 1 |
| A-5640 | H | H | H | H | H | CH$_2$C(=NOCH$_3$)CH$_2$CH$_3$ | H | H | O | 1 |
| A-5641 | H | H | H | H | H | CH$_2$C(=NOCH$_2$CH$_3$)CH$_3$ | H | H | O | 1 |
| A-5642 | H | H | H | H | H | CH$_2$C(=NOCH$_2$CH$_3$)CH$_2$CH$_3$ | H | H | O | 1 |
| A-5643 | H | H | H | H | H | CH$_2$C(=NOCH$_2$CF$_3$)CH$_3$ | H | H | O | 1 |
| A-5644 | H | H | H | H | H | CH$_2$C(=NOCH$_2$CF$_3$)CH$_2$CH$_3$ | H | H | O | 1 |
| A-5645 | H | H | H | H | H | CH$_2$Ph | H | H | O | 1 |
| A-5646 | H | H | H | H | H | CH$_2$(2-F)Ph | H | H | O | 1 |
| A-5647 | H | H | H | H | H | CH$_2$(3-F)Ph | H | H | O | 1 |
| A-5648 | H | H | H | H | H | CH$_2$(4-F)Ph | H | H | O | 1 |
| A-5649 | H | H | H | H | H | CH$_2$(2-Cl)Ph | H | H | O | 1 |
| A-5650 | H | H | H | H | H | CH$_2$(3-Cl)Ph | H | H | O | 1 |
| A-5651 | H | H | H | H | H | CH$_2$(4-Cl)Ph | H | H | O | 1 |
| A-5652 | H | H | H | H | H | CH$_2$(2-CF$_3$)Ph | H | H | O | 1 |
| A-5653 | H | H | H | H | H | CH$_2$(3-CF$_3$)Ph | H | H | O | 1 |
| A-5654 | H | H | H | H | H | CH$_2$(4-CF$_3$)Ph | H | H | O | 1 |
| A-5655 | H | H | H | H | H | CH$_2$(naphthalen-1-yl) | H | H | O | 1 |
| A-5656 | H | H | H | H | H | CH$_2$(naphthalen-2-yl) | H | H | O | 1 |
| A-5657 | H | H | H | H | H | CH$_2$CH$_2$Ph | H | H | O | 1 |
| A-5658 | H | H | H | H | H | CH$_2$CH$_2$CF$_2$CF$_2$CF$_2$CF$_3$ | H | H | O | 0 |

TABLE 94

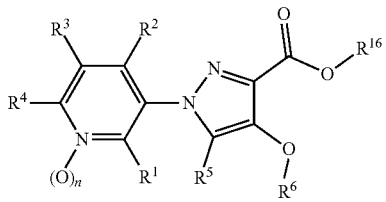

| Compound | R¹ | R² | R³ | R⁴ | R⁵ | R⁶ | R¹⁶ | n |
|---|---|---|---|---|---|---|---|---|
| B-0001 | H | H | H | H | H | H | H | 0 |
| B-0002 | H | H | H | H | H | CH$_3$ | H | 0 |
| B-0003 | H | H | H | H | H | CH$_2$CH$_3$ | H | 0 |
| B-0004 | H | H | H | H | H | CH(CH$_3$)$_2$ | H | 0 |
| B-0005 | H | H | H | H | H | C(CH$_3$)$_3$ | H | 0 |
| B-0006 | H | H | H | H | H | CH$_2$CH$_2$CH$_3$ | H | 0 |
| B-0007 | H | H | H | H | H | CH$_2$CH(CH$_3$)$_2$ | H | 0 |
| B-0008 | H | H | H | H | H | CH(CH$_3$)CH$_2$CH$_3$ | H | 0 |
| B-0009 | H | H | H | H | H | CH(CH$_2$CH$_3$)CH$_2$CH$_3$ | H | 0 |
| B-0010 | H | H | H | H | H | CH$_2$C(CH$_3$)$_3$ | H | 0 |
| B-0011 | H | H | H | H | H | CH$_2$(CH$_2$)$_2$CH$_3$ | H | 0 |
| B-0012 | H | H | H | H | H | CH$_2$CH$_2$CH(CH$_3$)$_2$ | H | 0 |
| B-0013 | H | H | H | H | H | CH$_2$CH(CH$_3$)CH$_2$CH$_3$ | H | 0 |
| B-0014 | H | H | H | H | H | CH(CH$_3$)CH$_2$CH$_2$CH$_3$ | H | 0 |
| B-0015 | H | H | H | H | H | CH$_2$CH(CH$_2$CH$_3$)CH$_2$CH$_3$ | H | 0 |
| B-0016 | H | H | H | H | H | CH(CH$_2$CH$_3$)CH$_2$CH$_2$CH$_3$ | H | 0 |
| B-0017 | H | H | H | H | H | CH$_2$CH$_2$C(CH$_3$)$_3$ | H | 0 |
| B-0018 | H | H | H | H | H | CH$_2$(CH$_2$)$_3$CH$_3$ | H | 0 |
| B-0019 | H | H | H | H | H | CH$_2$CH$_2$CH$_2$CH(CH$_3$)$_2$ | H | 0 |
| B-0020 | H | H | H | H | H | CH$_2$(CH$_2$)$_4$CH$_3$ | H | 0 |
| B-0021 | H | H | H | H | H | CH$_2$CH$_2$CH$_2$CH$_2$CH(CH$_3$)$_2$ | H | 0 |
| B-0022 | H | H | H | H | H | CH$_2$(CH$_2$)$_5$CH$_3$ | H | 0 |
| B-0023 | H | H | H | H | H | CH$_2$(CH$_2$)$_6$CH$_3$ | H | 0 |
| B-0024 | H | H | H | H | H | CH$_2$OCH$_3$ | H | 0 |
| B-0025 | H | H | H | H | H | CH$_2$OCH$_2$CH$_3$ | H | 0 |
| B-0026 | H | H | H | H | H | CH$_2$CH$_2$OCH$_3$ | H | 0 |
| B-0027 | H | H | H | H | H | CH$_2$CH$_2$OCH$_2$CH$_3$ | H | 0 |

TABLE 94-continued

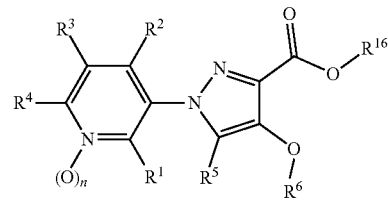

| Compound | R¹ | R² | R³ | R⁴ | R⁵ | R⁶ | R¹⁶ | n |
|---|---|---|---|---|---|---|---|---|
| B-0028 | H | H | H | H | H | CH$_2$CH$_2$CH$_2$OCH$_3$ | H | 0 |
| B-0029 | H | H | H | H | H | CH$_2$CH$_2$CH$_2$OCH$_2$CH$_3$ | H | 0 |
| B-0030 | H | H | H | H | H | CF$_3$ | H | 0 |
| B-0031 | H | H | H | H | H | CHF$_2$ | H | 0 |
| B-0032 | H | H | H | H | H | CH$_2$CF$_3$ | H | 0 |
| B-0033 | H | H | H | H | H | CH$_2$CHF$_2$ | H | 0 |
| B-0034 | H | H | H | H | H | CH$_2$CClF$_2$ | H | 0 |
| B-0035 | H | H | H | H | H | CF$_2$CHCl$_2$ | H | 0 |
| B-0036 | H | H | H | H | H | CF$_2$CCl$_3$ | H | 0 |
| B-0037 | H | H | H | H | H | CH$_2$CH$_2$Cl | H | 0 |
| B-0038 | H | H | H | H | H | CHClCHCl$_2$ | H | 0 |
| B-0039 | H | H | H | H | H | CH$_2$CCl$_3$ | H | 0 |
| B-0040 | H | H | H | H | H | CH$_2$CBrF$_2$ | H | 0 |
| B-0041 | H | H | H | H | H | CF$_2$CF$_3$ | H | 0 |
| B-0042 | H | H | H | H | H | CF$_2$CHF$_2$ | H | 0 |
| B-0043 | H | H | H | H | H | CH$_2$CH$_2$CF$_3$ | H | 0 |
| B-0044 | H | H | H | H | H | CH$_2$CF$_2$CF$_3$ | H | 0 |
| B-0045 | H | H | H | H | H | CH$_2$CF$_2$CHF$_2$ | H | 0 |
| B-0046 | H | H | H | H | H | CF$_2$CHFCF$_3$ | H | 0 |
| B-0047 | H | H | H | H | H | CF$_2$CF$_2$CF$_3$ | H | 0 |
| B-0048 | H | H | H | H | H | CH$_2$CH$_2$CH$_2$Cl | H | 0 |
| B-0049 | H | H | H | H | H | CH$_2$CHClCH$_2$Cl | H | 0 |
| B-0050 | H | H | H | H | H | CH$_2$CF$_2$CF$_2$CF$_3$ | H | 0 |
| B-0051 | H | H | H | H | H | CH$_2$CF$_2$CHFCF$_3$ | H | 0 |
| B-0052 | H | H | H | H | H | CH$_2$CH$_2$CH$_2$CF$_3$ | H | 0 |
| B-0053 | H | H | H | H | H | CH$_2$CH$_2$CF$_2$CF$_3$ | H | 0 |
| B-0054 | H | H | H | H | H | CF$_2$CF$_2$CF$_2$CF$_3$ | H | 0 |

TABLE 94-continued

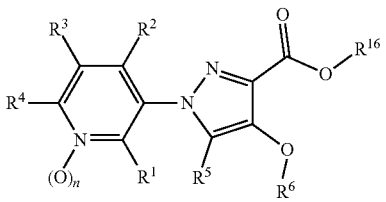

| Compound | $R^1$ | $R^2$ | $R^3$ | $R^4$ | $R^5$ | $R^6$ | $R^{16}$ | n |
|---|---|---|---|---|---|---|---|---|
| B-0055 | H | H | H | H | H | $CH_2CH_2CH(CF_3)_2$ | H | 0 |
| B-0056 | H | H | H | H | H | $CH_2CH_2CH(CH_3)CF_3$ | H | 0 |

TABLE 95

| Compound | $R^1$ | $R^2$ | $R^3$ | $R^4$ | $R^5$ | $R^6$ | $R^{16}$ | n |
|---|---|---|---|---|---|---|---|---|
| B-0057 | H | H | H | H | H | $CF_2CF_2CF_2CF_2CF_3$ | H | 0 |
| B-0058 | H | H | H | H | H | $CH_2CF_2CF_2CF_2CF_3$ | H | 0 |
| B-0059 | H | H | H | H | H | $CH_2CH_2CH_2CH_2CF_3$ | H | 0 |
| B-0060 | H | H | H | H | H | $CH_2CF_2CF_2CF_2CHF_2$ | H | 0 |
| B-0061 | H | H | H | H | H | $CH_2CF_2CF(CF_3)CF_2C(CF_3)_3$ | H | 0 |
| B-0062 | H | H | H | H | H | $CH_2CF_2CF_2CF_2CF_2CF_3$ | H | 0 |
| B-0063 | H | H | H | H | H | $CH_2CH_2CH_2CH_2CH_2CF_3$ | H | 0 |
| B-0064 | H | H | H | H | H | $CH_2CF_2CF_2CF_2CF_2CHF_2$ | H | 0 |
| B-0065 | H | H | H | H | H | $CH_2CF_2CF_2CF_2CF_2CF_2CF_3$ | H | 0 |
| B-0066 | H | H | H | H | H | $CH_2CH_2CH_2CH_2CH_2CH_2CF_3$ | H | 0 |
| B-0057 | H | H | H | H | H | $CH_2CF_2CF_2CF_2CF_2CF_2CHF_2$ | H | 0 |
| B-0068 | H | H | H | H | H | $CF_2CHFOCH_3$ | H | 0 |
| B-0069 | H | H | H | H | H | $CF_2CHFOCH_2CH_3$ | H | 0 |
| B-0070 | H | H | H | H | H | $CH_2CH_2OCH_2CF_3$ | H | 0 |
| B-0071 | H | H | H | H | H | $CF_2CHFOCF_3$ | H | 0 |
| B-0072 | H | H | H | H | H | $CF_2CHFOCF_2CF_3$ | H | 0 |
| B-0073 | H | H | H | H | H | $CF_2CHFOCF_2CF_2CF_3$ | H | 0 |
| B-0074 | H | H | H | H | H | $CH_2CH{=}CH_2$ | H | 0 |
| B-0075 | H | H | H | H | H | $CH_2CH{=}CHCl$ | H | 0 |
| B-0076 | H | H | H | H | H | $CH_2CH{=}CCl_2$ | H | 0 |
| B-0077 | H | H | H | H | H | $CH_2CH{=}C(CH_3)CF_3$ | H | 0 |
| B-0078 | H | H | H | H | H | $CH_2CH_3CF{=}CF_2$ | H | 0 |
| B-0079 | H | H | H | H | H | $CH_2CH_2CH{=}CF_2$ | H | 0 |
| B-0080 | H | H | H | H | H | $CH_2C{\equiv}CH$ | H | 0 |
| B-0081 | H | H | H | H | H | $CH_2C{\equiv}CCH_3$ | H | 0 |
| B-0082 | H | H | H | H | H | $CH_2C{\equiv}SCC(CH_3)_3$ | H | 0 |
| B-0083 | H | H | H | H | H | $CH_2C{\equiv}SC(cyclopropyl)$ | H | 0 |
| B-0084 | H | H | H | H | H | $CH_2C{\equiv}Cl$ | H | 0 |
| B-0085 | H | H | H | H | H | $CH_2C{\equiv}CCF_3$ | H | 0 |
| B-0086 | H | H | H | H | H | cyclopropyl | H | 0 |
| B-0087 | H | H | H | H | H | cyclobutyl | H | 0 |
| B-0088 | H | H | H | H | H | cyclopentyl | H | 0 |
| B-0089 | H | H | H | H | H | cyclohexyl | H | 0 |
| B-0090 | H | H | H | H | H | 4,4-difluorocyclohexyl | H | 0 |
| B-0091 | H | H | H | H | H | 4-trifluoromethylcyclohexyl | H | 0 |
| B-0092 | H | H | H | H | H | $CH_2$(cyclopropyl) | H | 0 |
| B-0093 | H | H | H | H | H | $CH_2$(cyclobutyl) | H | 0 |
| B-0094 | H | H | H | H | H | $CH_2$(cyclopentyl) | H | 0 |
| B-0095 | H | H | H | H | H | $CH_2$(cyclohexyl) | H | 0 |
| B-0096 | H | H | H | H | H | $CH_2CH_2$(cyclopropyl) | H | 0 |
| B-0097 | H | H | H | H | H | $CH_2$(2,2-difluorocyclopropyl) | H | 0 |
| B-0098 | H | H | H | H | H | $CH_2$(2,2-dichlorocyclopropyl) | H | 0 |
| B-0099 | H | H | H | H | H | $CH_2$(4,4-difluorocyclohexyl) | H | 0 |
| B-0100 | H | H | H | H | H | $CH_2CH_2$(2,2-difluorocyclopropyl) | H | 0 |
| B-0101 | H | H | H | H | H | $CH_2CH_2$(2,2-dichlorocyclopropyl) | H | 0 |
| B-0102 | H | H | H | H | H | $CH_2CH_2$(4,4-difluorocyclohexyl) | H | 0 |
| B-0103 | H | H | H | H | H | $CH_2SCH_3$ | H | 0 |
| B-0104 | H | H | H | H | H | $CH_2SCH_2CH_3$ | H | 0 |
| B-0105 | H | H | H | H | H | $CH_2CH_2SCH_3$ | H | 0 |
| B-0106 | H | H | H | H | H | $CH_2CH_2SCH_2CH_3$ | H | 0 |
| B-0107 | H | H | H | H | H | $CH_2CH_2CH_2SCH_3$ | H | 0 |
| B-0108 | H | H | H | H | H | $CH_2CH_2CH_2SCH_2CH_3$ | H | 0 |
| B-0109 | H | H | H | H | H | $CH(CH_3)SCH_3$ | H | 0 |
| B-0110 | H | H | H | H | H | $CH(CH_3)SCH_2CH_3$ | H | 0 |
| B-0111 | H | H | H | H | H | $CH_2CH(CH_3)SCH_3$ | H | 0 |
| B-0112 | H | H | H | H | H | $CH_2CH(CH_3)SCH_2CH_3$ | H | 0 |
| B-0113 | H | H | H | H | H | $CH_2CH_2SCH(CH_3)_2$ | H | 0 |
| B-0114 | H | H | H | H | H | $CH(CH_3)CH_2CH_2SCH_3$ | H | 0 |

TABLE 95-continued

| Compound | R¹ | R² | R³ | R⁴ | R⁵ | R⁶ | R¹⁶ | n |
|---|---|---|---|---|---|---|---|---|
| B-0115 | H | H | H | H | H | CH(CH$_3$)CH$_2$CH$_2$SCH$_2$CH$_3$ | H | 0 |
| B-0116 | H | H | H | H | H | CH$_2$CH(CH$_3$)CH$_2$SCH$_3$ | H | 0 |
| B-0117 | H | H | H | H | H | CH$_2$CH(CH$_3$)CH$_2$SCH$_2$CH$_3$ | H | 0 |

TABLE 96

| Compound | R¹ | R² | R³ | R⁴ | R⁵ | R⁶ | R¹⁶ | n |
|---|---|---|---|---|---|---|---|---|
| B-0118 | H | H | H | H | H | CH$_2$CH$_2$CH(CH$_3$)SCH$_3$ | H | 0 |
| B-0119 | H | H | H | H | H | CH$_2$CH$_2$CH(CH$_3$)SCH$_2$CH$_3$ | H | 0 |
| B-0120 | H | H | H | H | H | CH$_2$CH$_2$CH$_2$CH$_2$SCH$_3$ | H | 0 |
| B-0121 | H | H | H | H | H | CH$_2$CH$_2$CH$_2$CH$_2$SCH$_3$ | H | 0 |
| B-0122 | H | H | H | H | H | CH$_2$SOCH$_3$ | H | 0 |
| B-0123 | H | H | H | H | H | CH$_2$CH$_2$SOCH$_3$ | H | 0 |
| B-0124 | H | H | H | H | H | CH$_2$CH$_2$SOCH$_2$CH$_3$ | H | 0 |
| B-0125 | H | H | H | H | H | CH$_2$CH$_2$SOCH(CH$_3$)$_2$ | H | 0 |
| B-0126 | H | H | H | H | H | CH$_2$CH$_2$CH$_2$SOCH$_3$ | H | 0 |
| B-0127 | H | H | H | H | H | CH(CH$_3$)SOCH$_3$ | H | 0 |
| B-0128 | H | H | H | H | H | CH$_2$CH(CH$_3$)SOCH$_3$ | H | 0 |
| B-0129 | H | H | H | H | H | CH(CH$_3$)CH$_2$CH$_2$SOCH$_3$ | H | 0 |
| B-0130 | H | H | H | H | H | CH$_2$CH(CH$_3$)CH$_2$SOCH$_3$ | H | 0 |
| B-0131 | H | H | H | H | H | CH$_2$CH$_2$CH(CH$_3$)SOCH$_3$ | H | 0 |
| B-0132 | H | H | H | H | H | CH$_2$CH$_2$CH$_2$CH$_2$SOCH$_3$ | H | 0 |
| B-0133 | H | H | H | H | H | CH$_2$CH$_2$CH$_2$CH$_2$CH$_2$SOCH$_3$ | H | 0 |
| B-0134 | H | H | H | H | H | CH$_2$SO$_2$CH$_3$ | H | 0 |
| B-0135 | H | H | H | H | H | CH$_2$CH$_2$SO$_2$CH$_3$ | H | 0 |
| B-0136 | H | H | H | H | H | CH$_2$CH$_2$SO$_2$CH$_2$CH$_3$ | H | 0 |
| B-0137 | H | H | H | H | H | CH$_2$CH$_2$SO$_2$CH(CH$_3$)$_2$ | H | 0 |
| B-0138 | H | H | H | H | H | CH$_2$CH$_2$CH$_2$SO$_2$CH$_3$ | H | 0 |
| B-0139 | H | H | H | H | H | CH(CH$_3$)SO$_2$CH$_3$ | H | 0 |
| B-0140 | H | H | H | H | H | CH$_2$CH(CH$_3$)SO$_2$CH$_3$ | H | 0 |
| B-0141 | H | H | H | H | H | CH(CH$_3$)CH$_2$CH$_2$SO$_2$CH$_3$ | H | 0 |
| B-0142 | H | H | H | H | H | CH$_2$CH(CH$_3$)CH$_2$SO$_2$CH$_3$ | H | 0 |
| B-0143 | H | H | H | H | H | CH$_2$CH$_2$CH(CH$_3$)SO$_2$CH$_3$ | H | 0 |
| B-0144 | H | H | H | H | H | CH$_2$CH$_2$CH$_2$CH$_2$SO$_2$CH$_3$ | H | 0 |
| B-0145 | H | H | H | H | H | CH$_2$CH$_2$CH$_2$CH$_2$CH$_2$SO$_2$CH$_3$ | H | 0 |
| B-0146 | H | H | H | H | H | CH$_2$SCF$_3$ | H | 0 |
| B-0147 | H | H | H | H | H | CH$_2$SCHF$_2$ | H | 0 |
| B-0148 | H | H | H | H | H | CH$_2$SCH$_2$CF$_3$ | H | 0 |
| B-0149 | H | H | H | H | H | CH$_2$SCH$_2$CHF$_2$ | H | 0 |
| B-0150 | H | H | H | H | H | CH$_2$SCF$_2$CF$_3$ | H | 0 |
| B-0151 | H | H | H | H | H | CH$_2$CH$_2$SCF$_3$ | H | 0 |
| B-0152 | H | H | H | H | H | CH$_2$CH$_2$SCH$_2$CF$_3$ | H | 0 |
| B-0153 | H | H | H | H | H | CH$_2$CH$_2$CH$_2$SCF$_3$ | H | 0 |
| B-0154 | H | H | H | H | H | CH$_2$CH$_2$CH$_2$SCH$_2$CF$_3$ | H | 0 |
| B-0155 | H | H | H | H | H | CH(CH$_3$)SCF$_3$ | H | 0 |
| B-0156 | H | H | H | H | H | CH(CH$_3$)SCH$_2$CF$_3$ | H | 0 |
| B-0157 | H | H | H | H | H | CH$_2$CH(CH$_3$)SCF$_3$ | H | 0 |
| B-0158 | H | H | H | H | H | CH$_2$CH(CH$_3$)SCH$_2$CF$_3$ | H | 0 |
| B-0159 | H | H | H | H | H | CH(CH$_3$)CH$_2$CH$_2$SCF$_3$ | H | 0 |
| B-0160 | H | H | H | H | H | CH(CH$_3$)CH$_2$CH$_2$SCH$_2$CF$_3$ | H | 0 |
| B-0161 | H | H | H | H | H | CH$_2$CH(CH$_3$)CH$_2$SCF$_3$ | H | 0 |
| B-0162 | H | H | H | H | H | CH$_2$CH(CH$_3$)CH$_2$SCH$_2$CF$_3$ | H | 0 |
| B-0163 | H | H | H | H | H | CH$_2$CH$_2$CH(CH$_3$)SCF$_3$ | H | 0 |
| B-0164 | H | H | H | H | H | CH$_2$CH$_2$CH(CH$_3$)SCH$_2$CF$_3$ | H | 0 |
| B-0165 | H | H | H | H | H | CH$_2$CH$_2$CH$_2$CH$_3$SCF$_3$ | H | 0 |
| B-0166 | H | H | H | H | H | CH$_2$CH$_2$CH$_2$CH$_2$CH$_2$SCF$_3$ | H | 0 |
| B-0167 | H | H | H | H | H | CH$_2$SOCF$_3$ | H | 0 |
| B-0168 | H | H | H | H | H | CH$_2$CH$_2$SOCF$_3$ | H | 0 |
| B-0169 | H | H | H | H | H | CH$_2$CH$_2$CH$_2$SOCF$_3$ | H | 0 |
| B-0170 | H | H | H | H | H | CH(CH$_3$)SOCF$_3$ | H | 0 |
| B-0171 | H | H | H | H | H | CH$_2$CH(CH$_3$)SOCF$_3$ | H | 0 |
| B-0172 | H | H | H | H | H | CH(CH$_3$)CH$_2$CH$_2$SOCF$_3$ | H | 0 |
| B-0173 | H | H | H | H | H | CH$_2$CH(CH$_3$)CH$_2$SOCF$_3$ | H | 0 |
| B-0174 | H | H | H | H | H | CH$_2$CH$_2$CH(CH$_3$)SOCF$_S$ | H | 0 |
| B-0175 | H | H | H | H | H | CH$_2$SO$_2$CF$_3$ | H | 0 |
| B-0176 | H | H | H | H | H | CH$_2$CH$_2$SO$_3$CF$_3$ | H | 0 |
| B-0177 | H | H | H | H | H | CH$_2$CH$_2$SO$_2$CH$_2$CF$_3$ | H | 0 |
| B-0178 | H | H | H | H | H | CH$_2$CH$_2$CH$_2$SO$_2$CF$_3$ | H | 0 |

TABLE 97

| Compound | R¹ | R² | R³ | R⁴ | R⁵ | R⁶ | R¹⁶ | n |
|---|---|---|---|---|---|---|---|---|
| B-0179 | H | H | H | H | H | CH(CH$_3$)SO$_2$CF$_3$ | H | 0 |
| B-0180 | H | H | H | H | H | CH$_2$CH(CH$_3$)SO$_2$CF$_3$ | H | 0 |
| B-0181 | H | H | H | H | H | CH(CH$_3$)CH$_2$CH$_2$SO$_2$CF$_3$ | H | 0 |
| B-0182 | H | H | H | H | H | CH$_2$CH(CH$_3$)CH$_2$SO$_2$CF$_3$ | H | 0 |
| B-0183 | H | H | H | H | H | CH$_2$CH$_2$CH(CH$_3$)SO$_2$CF$_3$ | H | 0 |
| B-0184 | H | H | H | H | H | CH$_2$C(=O)CH$_3$ | H | 0 |
| B-0185 | H | H | H | H | H | CH$_2$C(=O)CH$_2$CH$_3$ | H | 0 |
| B-0186 | H | H | H | H | H | CH$_2$C(=O)C(CH$_3$)$_3$ | H | 0 |
| B-0187 | H | H | H | H | H | CH$_2$CF$_2$C(=O)CH$_3$ | H | 0 |
| B-0188 | H | H | H | H | H | CH$_2$CH$_2$C(=O)C(CH$_3$)$_3$ | H | 0 |
| B-0189 | H | H | H | H | H | CH$_2$C(=O)CF$_3$ | H | 0 |
| B-0190 | H | H | H | H | H | CH$_2$CH$_2$C(=O)CF$_3$ | H | 0 |
| B-0191 | H | H | H | H | H | CH$_2$C(=O)OCH$_3$ | H | 0 |
| B-0192 | H | H | H | H | H | CH$_2$C(=O)OCH$_2$CH$_2$ | H | 0 |
| B-0193 | H | H | H | H | H | CH$_2$C(=O)OC(CH$_3$)$_3$ | H | 0 |
| B-0194 | H | H | H | H | H | CH$_2$CH$_2$C(=O)OCH$_3$ | H | 0 |
| B-0195 | H | H | H | H | H | CH$_2$CH$_2$C(=O)OCH$_2$CH$_3$ | H | 0 |
| B-0196 | H | H | H | H | H | CH$_2$CH$_2$C(=O)OC(CH$_3$)$_3$ | H | 0 |
| B-0197 | H | H | H | H | H | CH$_2$C(=O)NH$_2$ | H | 0 |
| B-0198 | H | H | H | H | H | CH$_2$CH$_2$C(=O)NH$_2$ | H | 0 |
| B-0199 | H | H | H | H | H | CH$_2$C(=O)NHCH$_3$ | H | 0 |
| B-0200 | H | H | H | H | H | CH$_2$C(=O)NHCH(CH$_3$)$_2$ | H | 0 |
| B-0201 | H | H | H | H | H | CH$_2$CH$_2$C(=O)NHCH$_3$ | H | 0 |
| B-0202 | H | H | H | H | H | CH$_2$CH$_2$C(=O)NHCH(CH$_3$)$_2$ | H | 0 |
| B-0203 | H | H | H | H | H | CH$_2$C(=O)NH(cyclopropyl) | H | 0 |
| B-0204 | H | H | H | H | H | CH$_2$C(=O)NHCH$_2$CHF$_2$ | H | 0 |
| B-0205 | H | H | H | H | H | CH$_2$C(=O)NHCH$_2$CF$_3$ | H | 0 |
| B-0206 | H | H | H | H | H | CH$_2$CH$_2$C(=O)NHCH$_2$CHF$_2$ | H | 0 |
| B-0207 | H | H | H | H | H | CH$_2$CH$_2$C(=O)NHCH$_2$CF$_3$ | H | 0 |
| B-0208 | H | H | H | H | H | CH(CH$_3$)C(=O)NHCH$_2$CHF$_2$ | H | 0 |
| B-0209 | H | H | H | H | H | CH(CH$_3$)C(=O)NHCH$_2$CF$_3$ | H | 0 |
| B-0210 | H | H | H | H | H | C(CH$_3$)$_2$C(=O)NHCH$_2$CHF$_2$ | H | 0 |
| B-0211 | H | H | H | H | H | C(CH$_3$)$_2$C(=O)NHCH$_2$CF$_3$ | H | 0 |
| B-0212 | H | H | H | H | H | CH$_2$C(=O)N(CH$_3$)$_2$ | H | 0 |
| B-0213 | H | H | H | H | H | CH$_2$C(=O)N(CH$_2$CH$_3$)$_2$ | H | 0 |
| B-0214 | H | H | H | H | H | CH$_2$CH$_2$C(=O)N(CH$_3$)$_2$ | H | 0 |
| B-0215 | H | H | H | H | H | CH$_2$CH$_2$C(=O)N(CH$_2$CH$_3$)$_2$ | H | 0 |
| B-0216 | H | H | H | H | H | CH$_2$CH$_2$NHC(=O)OCH$_3$ | H | 0 |
| B-0217 | H | H | H | H | H | CH$_2$CH$_2$NHC(=O)OC(CH$_3$)$_3$ | H | 0 |
| B-0218 | H | H | H | H | H | CH$_2$CH$_2$CH$_2$NHC(=O)OCH$_3$ | H | 0 |
| B-0219 | H | H | H | H | H | CH$_2$CH$_2$CH$_2$NHC(=O)OC(CH$_3$)$_3$ | H | 0 |
| B-0220 | H | H | H | H | H | CH$_2$CH$_2$NHSO$_2$CHF$_2$ | H | 0 |
| B-0221 | H | H | H | H | H | CH$_2$CH$_2$NHSO$_2$CF$_3$ | H | 0 |
| B-0222 | H | H | H | H | H | CH$_2$CH$_2$CH$_2$NHSO$_2$CHF$_2$ | H | 0 |
| B-0223 | H | H | H | H | H | CH$_2$CH$_2$CH$_2$NHSO$_2$CF$_3$ | H | 0 |
| B-0224 | H | H | H | H | H | CH$_2$CH$_2$OH | H | 0 |
| B-0225 | H | H | H | H | H | CH$_2$CH(OH)CH$_3$ | H | 0 |
| B-0226 | H | H | H | H | H | CH$_2$CH$_2$CH$_2$OH | H | 0 |
| B-0227 | H | H | H | H | H | CH$_2$CH(OH)CH$_2$CH$_3$ | H | 0 |
| B-0228 | H | H | H | H | H | CH$_2$CH(OH)C(CH$_3$)$_3$ | H | 0 |
| B-0229 | H | H | H | H | H | CH$_2$CH$_2$CH(OH)CH$_3$ | H | 0 |
| B-0230 | H | H | H | H | H | CH$_2$CH$_2$CH(OH)C(CH$_3$)$_3$ | H | 0 |
| B-0231 | H | H | H | H | H | CH$_2$C(=NOH)CH$_3$ | H | 0 |
| B-0232 | H | H | H | H | H | CH$_2$C(=NOH)CH$_2$CH$_3$ | H | 0 |
| B-0233 | H | H | H | H | H | CH$_2$C(=NOH)C(CH$_3$)$_3$ | H | 0 |
| B-0234 | H | H | H | H | H | CH$_2$C(=NOCH$_3$)CH$_3$ | H | 0 |
| B-0235 | H | H | H | H | H | CH$_2$C(=NOCH$_3$)CH$_2$CH$_3$ | H | 0 |
| B-0236 | H | H | H | H | H | CH$_2$C(=NOCH$_2$CH$_3$)CH$_3$ | H | 0 |
| B-0237 | H | H | H | H | H | CH$_2$C(=NOCH$_2$CH$_3$)CH$_2$CH$_3$ | H | 0 |
| B-0238 | H | H | H | H | H | CH$_2$C(=NOCH$_2$CF$_3$)CH$_3$ | H | 0 |
| B-0239 | H | H | H | H | H | CH$_2$C(=NOCH$_2$CF$_3$)CH$_2$CH$_3$ | H | 0 |

TABLE 98

| Compound | R¹ | R² | R³ | R⁴ | R⁵ | R⁶ | R¹⁶ | n |
|---|---|---|---|---|---|---|---|---|
| B-0240 | H | H | H | H | H | CH$_2$Ph | H | 0 |
| B-0241 | H | H | H | H | H | CH$_2$(2-F)Ph | H | 0 |
| B-0242 | H | H | H | H | H | CH$_2$(3-F)Ph | H | 0 |
| B-0243 | H | H | H | H | H | CH$_2$(4-F)Ph | H | 0 |
| B-0244 | H | H | H | H | H | CH$_2$(2-Cl)Ph | H | 0 |
| B-0245 | H | H | H | H | H | CH$_2$(3-Cl)Ph | H | 0 |
| B-0246 | H | H | H | H | H | CH$_2$(4-Cl)Ph | H | 0 |
| B-0247 | H | H | H | H | H | CH$_2$(2-CF$_3$)Ph | H | 0 |
| B-0248 | H | H | H | H | H | CH$_2$(3-CF$_3$)Ph | H | 0 |

TABLE 98-continued

| Compound | R$^1$ | R$^2$ | R$^3$ | R$^4$ | R$^5$ | R$^6$ | R$^{16}$ | n |
|---|---|---|---|---|---|---|---|---|
| B-0249 | H | H | H | H | H | CH$_2$(4-CF$_3$)Ph | H | 0 |
| B-0250 | H | H | H | H | H | CH$_2$(2-F-4-CF$_3$)Ph | H | 0 |
| B-0251 | H | H | H | H | H | CH$_2$(napnthalen-1-yl) | H | 0 |
| B-0252 | H | H | H | H | H | CH$_2$(naphthalen-2-yl) | H | 0 |
| B-0253 | H | H | H | H | H | CH(CH$_3$)Ph | H | 0 |
| B-0254 | H | H | H | H | H | CH$_2$CH$_2$Ph | H | 0 |
| B-0255 | H | H | H | H | H | H | CH$_2$CH$_3$ | 0 |
| B-0256 | H | H | H | H | H | CH$_3$ | CH$_2$CH$_3$ | 0 |
| B-0257 | H | H | H | H | H | CH$_2$CH$_3$ | CH$_2$CH$_3$ | 0 |
| B-0258 | H | H | H | H | H | CH(CH$_3$)$_2$ | CH$_2$CH$_3$ | 0 |
| B-0259 | H | H | H | H | H | C(CH$_3$)$_3$ | CH$_2$CH$_3$ | 0 |
| B-0260 | H | H | H | H | H | CH$_2$CH$_2$CH$_3$ | CH$_2$CH$_3$ | 0 |
| B-0261 | H | H | H | H | H | CH$_2$CH(CH$_3$)$_2$ | CH$_2$CH$_3$ | 0 |
| B-0262 | H | H | H | H | H | CH(CH$_3$)CH$_2$CH$_3$ | CH$_2$CH$_3$ | 0 |
| B-0263 | H | H | H | H | H | CH(CH$_2$CH$_3$)CH$_2$CH$_3$ | CH$_2$CH$_3$ | 0 |
| B-0264 | H | H | H | H | H | CH$_2$C(CH$_3$)$_3$ | CH$_2$CH$_3$ | 0 |
| B-0265 | H | H | H | H | H | CH$_2$(CH$_2$)$_2$CH$_3$ | CH$_2$CH$_3$ | 0 |
| B-0266 | H | H | H | H | H | CH$_2$CH$_2$CH(CH$_3$)$_2$ | CH$_2$CH$_3$ | 0 |
| B-0267 | H | H | H | H | H | CH$_2$CH(CH$_3$)CH$_2$CH$_3$ | CH$_2$CH$_3$ | 0 |
| B-0268 | H | H | H | H | H | CH(CH$_3$)CH$_2$CH$_2$CH$_3$ | CH$_2$CH$_3$ | 0 |
| B-0269 | H | H | H | H | H | CH$_2$CH(CH$_2$CH$_3$)CH$_3$CH$_3$ | CH$_2$CH$_3$ | 0 |
| B-0270 | H | H | H | H | H | CH(CH$_2$CH$_3$)CH$_2$CH$_2$CH$_3$ | CH$_2$CH$_3$ | 0 |
| B-0271 | H | H | H | H | H | CH$_2$CH$_2$C(CH$_3$)$_3$ | CH$_2$CH$_3$ | 0 |
| B-0272 | H | H | H | H | H | CH$_2$(CH$_2$)$_3$CH$_3$ | CH$_2$CH$_3$ | 0 |
| B-0273 | H | H | H | H | H | CH$_2$CH$_2$CH$_2$CH(CH$_3$)$_3$ | CH$_2$CH$_3$ | 0 |
| B-0274 | H | H | H | H | H | CH$_2$(CH$_2$)$_4$CH$_3$ | CH$_2$CH$_3$ | 0 |
| B-0275 | H | H | H | H | H | CH$_2$CH$_2$CH$_2$CH$_2$CH(CH$_3$)$_2$ | CH$_2$CH$_3$ | 0 |
| B-0276 | H | H | H | H | H | CH$_2$(CH$_2$)$_5$CH$_3$ | CH$_2$CH$_3$ | 0 |
| B-0277 | H | H | H | H | H | CH$_2$(CH$_2$)$_6$CH$_3$ | CH$_2$CH$_3$ | 0 |
| B-0278 | H | H | H | H | H | CH$_2$OCH$_3$ | CH$_2$CH$_3$ | 0 |
| B-0279 | H | H | H | H | H | CH$_2$OCH$_2$CH$_3$ | CH$_2$CH$_3$ | 0 |
| B-0280 | H | H | H | H | H | CH$_2$CH$_2$OCH$_3$ | CH$_2$CH$_3$ | 0 |
| B-0281 | H | H | H | H | H | CH$_2$CH$_2$OCH$_2$CH$_3$ | CH$_2$CH$_3$ | 0 |
| B-0282 | H | H | H | H | H | CH$_2$CH$_2$CH$_2$OCH$_3$ | CH$_2$CH$_3$ | 0 |
| B-0283 | H | H | H | H | H | CH$_2$CH$_2$CH$_2$OCH$_2$CH$_3$ | CH$_2$CH$_3$ | 0 |
| B-0284 | H | H | H | H | H | CF$_3$ | CH$_2$CH$_3$ | 0 |
| B-0285 | H | H | H | H | H | CHF$_2$ | CH$_2$CH$_3$ | 0 |
| B-0286 | H | H | H | H | H | CH$_2$CF$_3$ | CH$_3$CH$_3$ | 0 |
| B-0287 | H | H | H | H | H | CH$_2$CHF$_2$ | CH$_2$CH$_3$ | 0 |
| B-0288 | H | H | H | H | H | CH$_2$CClF$_2$ | CH$_2$CH$_3$ | 0 |
| B-0289 | H | H | H | H | H | CF$_2$CHCl$_2$ | CH$_2$CH$_3$ | 0 |
| B-0290 | H | H | H | H | H | CF$_2$CCl$_3$ | CH$_2$CH$_3$ | 0 |
| B-0291 | H | H | H | H | H | CH$_2$CH$_2$Cl | CH$_2$CH$_3$ | 0 |
| B-0292 | H | H | H | H | H | CHClCHCl$_2$ | CH$_2$CH$_3$ | 0 |
| B-0293 | H | H | H | H | H | CH$_2$CCl$_3$ | CH$_2$CH$_3$ | 0 |
| B-0294 | H | H | H | H | H | CH$_2$CBrF$_2$ | CH$_2$CH$_3$ | 0 |
| B-0295 | H | H | H | H | H | CF$_2$CF$_3$ | CH$_2$CH$_3$ | 0 |
| B-0296 | H | H | H | H | H | CF$_2$CHF$_2$ | CH$_2$CH$_3$ | 0 |
| B-0297 | H | H | H | H | H | CH$_2$CH$_2$CF$_3$ | CH$_2$CH$_3$ | 0 |
| B-0298 | H | H | H | H | H | CH$_2$CF$_2$CF$_3$ | CH$_2$CH$_3$ | 0 |
| B-0299 | H | H | H | H | H | CH$_2$CF$_2$CHF$_2$ | CH$_2$CH$_3$ | 0 |
| B-0300 | H | H | H | H | H | CF$_2$CHFCF$_3$ | CH$_2$CH$_3$ | 0 |

TABLE 99

| Compound | R$^1$ | R$^2$ | R$^3$ | R$^4$ | R$^5$ | R$^6$ | R$^{16}$ | n |
|---|---|---|---|---|---|---|---|---|
| B-0301 | H | H | H | H | H | CF$_2$CF$_2$CF$_3$ | CH$_2$CH$_3$ | 0 |
| B-0302 | H | H | H | H | H | CH$_2$CH$_2$CH$_2$Cl | CH$_2$CH$_3$ | 0 |
| B-0303 | H | H | H | H | H | CH$_2$CHClCH$_2$Cl | CH$_2$CH$_3$ | 0 |
| B-0304 | H | H | H | H | H | CH$_2$CF$_2$CF$_2$CF$_3$ | CH$_2$CH$_3$ | 0 |
| B-0305 | H | H | H | H | H | CH$_2$CF$_2$CHFCF$_3$ | CH$_2$CH$_3$ | 0 |
| B-0306 | H | H | H | H | H | CH$_2$CH$_2$CH$_2$CF$_3$ | CH$_2$CH$_3$ | 0 |
| B-0307 | H | H | H | H | H | CH$_2$CH$_2$CF$_2$CF$_3$ | CH$_2$CH$_3$ | 0 |
| B-0308 | H | H | H | H | H | CF$_2$CF$_2$CF$_2$CF$_3$ | CH$_2$CH$_3$ | 0 |
| B-0309 | H | H | H | H | H | CH$_2$CH$_2$CH(CF$_3$)$_2$ | CH$_2$CH$_3$ | 0 |
| B-0310 | H | H | H | H | H | CH$_2$CH$_2$CH(CH$_3$)CF$_3$ | CH$_2$CH$_3$ | 0 |
| B-0311 | H | H | H | H | H | CF$_2$CF$_2$CF$_2$CF$_2$CF$_3$ | CH$_2$CH$_3$ | 0 |
| B-0312 | H | H | H | H | H | CH$_2$CF$_2$CF$_2$CF$_2$CF$_3$ | CH$_2$CH$_3$ | 0 |
| B-0313 | H | H | H | H | H | CH$_2$CH$_2$CH$_2$CH$_2$CF$_3$ | CH$_2$CH$_3$ | 0 |
| B-0314 | H | H | H | H | H | CH$_2$CF$_2$CF$_2$CF$_2$CHF$_3$ | CH$_2$CH$_3$ | 0 |
| B-0315 | H | H | H | H | H | CH$_2$CF$_2$CF(CF$_3$)CF$_2$C(CF$_3$)$_3$ | CH$_2$CH$_3$ | 0 |
| B-0316 | H | H | H | H | H | CH$_2$CF$_2$CF$_2$CF$_2$CF$_2$CF$_3$ | CH$_2$CH$_3$ | 0 |
| B-0317 | H | H | H | H | H | CH$_2$CH$_2$CH$_2$CH$_2$CH$_2$CF$_3$ | CH$_2$CH$_3$ | 0 |
| B-0318 | H | H | H | H | H | CH$_2$CF$_2$CF$_2$CF$_2$CF$_2$CHF$_2$ | CH$_2$CH$_3$ | 0 |

TABLE 99-continued

| Compound | R¹ | R² | R³ | R⁴ | R⁵ | R⁶ | R¹⁶ | n |
|---|---|---|---|---|---|---|---|---|
| B-0319 | H | H | H | H | H | CH$_2$CF$_2$CF$_2$CF$_2$CF$_2$CF$_2$CF$_2$ | CH$_2$CH$_3$ | 0 |
| B-0320 | H | H | H | H | H | CH$_2$CH$_2$CH$_2$CH$_2$CH$_2$CH$_2$CF$_3$ | CH$_2$CH$_3$ | 0 |
| B-0321 | H | H | H | H | H | CH$_2$CF$_2$CF$_2$CF$_2$CF$_2$CF$_2$CHF$_2$ | CH$_2$CH$_3$ | 0 |
| B-0322 | H | H | H | H | H | CF$_2$CHFOCH$_3$ | CH$_2$CH$_3$ | 0 |
| B-0323 | H | H | H | H | H | CF$_2$CHFOCH$_2$CH$_3$ | CH$_2$CH$_3$ | 0 |
| B-0324 | H | H | H | H | H | CH$_2$CH$_2$OCH$_2$CF$_3$ | CH$_2$CH$_3$ | 0 |
| B-0325 | H | H | H | H | H | CF$_2$CHFOCF$_3$ | CH$_2$CH$_3$ | 0 |
| B-0326 | H | H | H | H | H | CF$_2$CHFOCF$_2$CF$_3$ | CH$_2$CH$_3$ | 0 |
| B-0327 | H | H | H | H | H | CF$_2$CHFOCF$_2$CF$_2$CF$_3$ | CH$_2$CH$_3$ | 0 |
| B-0328 | H | H | H | H | H | CH$_2$CH=CH$_2$ | CH$_2$CH$_3$ | 0 |
| B-0329 | H | H | H | H | H | CH$_2$CH=CHCl | CH$_2$CH$_3$ | 0 |
| B-0330 | H | H | H | H | H | CH$_2$CH=CCl$_2$ | CH$_2$CH$_3$ | 0 |
| B-0331 | H | H | H | H | H | CH$_2$CH=C(CH$_3$)CF$_3$ | CH$_2$CH$_3$ | 0 |
| B-0332 | H | H | H | H | H | CH$_2$CH$_2$CF=CF$_2$ | CH$_2$CH$_3$ | 0 |
| B-0333 | H | H | H | H | H | CH$_2$CH$_2$CH$_2$CF$_2$ | CH$_2$CH$_3$ | 0 |
| B-0334 | H | H | H | H | H | CH$_2$C≡CH | CH$_2$CH$_3$ | 0 |
| B-0335 | H | H | H | H | H | CH$_2$C≡CCH$_3$ | CH$_2$CH$_3$ | 0 |
| B-0336 | H | H | H | H | H | CH$_2$C≡CC(CH$_3$)$_3$ | CH$_2$CH$_3$ | 0 |
| B-0337 | H | H | H | H | H | CH$_2$C≡C(cyclopropyl) | CH$_2$CH$_3$ | 0 |
| B-0338 | H | H | H | H | H | CH$_2$C≡CI | CH$_2$CH$_3$ | 0 |
| B-0339 | H | H | H | H | H | CH$_2$C≡CCF$_3$ | CH$_2$CH$_3$ | 0 |
| B-0340 | H | H | H | H | H | cyclopropyl | CH$_2$CH$_3$ | 0 |
| B-0341 | H | H | H | H | H | cyclobutyl | CH$_2$CH$_3$ | 0 |
| B-0342 | H | H | H | H | H | cyclopentyl | CH$_2$CH$_3$ | 0 |
| B-0343 | H | H | H | H | H | cyclohexyl | CH$_2$CH$_3$ | 0 |
| B-0344 | H | H | H | H | H | 4,4-difluorocyclohexyl | CH$_2$CH$_3$ | 0 |
| B-0345 | H | H | H | H | H | 4-trifluoromethylcyclohexyl | CH$_2$CH$_3$ | 0 |
| B-0346 | H | H | H | H | H | CH$_2$(cyclopropyl) | CH$_2$CH$_3$ | 0 |
| B-0347 | H | H | H | H | H | CH$_2$(cyclobutyl) | CH$_2$CH$_3$ | 0 |
| B-0348 | H | H | H | H | H | CH$_2$(cyclopentyl) | CH$_2$CH$_3$ | 0 |
| B-0349 | H | H | H | H | H | CH$_2$(cyclohexyl) | CH$_2$CH$_3$ | 0 |
| B-0350 | H | H | H | H | H | CH$_2$CH$_2$(cyclopropyl) | CH$_2$CH$_3$ | 0 |
| B-0351 | H | H | H | H | H | CH$_2$(2,2-difluorocyclopropyl) | CH$_2$CH$_3$ | 0 |
| B-0352 | H | H | H | H | H | CH$_2$(2,2-dichlorocyclopropyl) | CH$_2$CH$_3$ | 0 |
| B-0353 | H | H | H | H | H | CH$_2$(4,4-difluorocyclohexyl) | CH$_2$CH$_3$ | 0 |
| B-0354 | H | H | H | H | H | CH$_2$CH$_2$(2,2-difluorocyclopropyl) | CH$_2$CH$_3$ | 0 |
| B-0355 | H | H | H | H | H | CH$_2$CH$_2$(2,2-dichlorocyclopropyl) | CH$_2$CH$_3$ | 0 |
| B-0356 | H | H | H | H | H | CH$_2$CH$_2$(4,4-difluorocyclohexyl) | CH$_2$CH$_3$ | 0 |
| B-0357 | H | H | H | H | H | CH$_2$SCH$_3$ | CH$_2$CH$_3$ | 0 |
| B-0358 | H | H | H | H | H | CH$_2$SCH$_2$CH$_3$ | CH$_2$CH$_3$ | 0 |
| B-0359 | H | H | H | H | H | CH$_2$CH$_2$SCH$_3$ | CH$_2$CH$_3$ | 0 |
| B-0360 | H | H | H | H | H | CH$_2$CH$_2$SCH$_2$CH$_3$ | CH$_2$CH$_3$ | 0 |
| B-0361 | H | H | H | H | H | CH$_2$CH$_2$CH$_2$SCH$_3$ | CH$_2$CH$_3$ | 0 |

TABLE 100

| Compound | R¹ | R² | R³ | R⁴ | R⁵ | R⁶ | R¹⁶ | n |
|---|---|---|---|---|---|---|---|---|
| B-0362 | H | H | H | H | H | CH$_2$CH$_2$CH$_2$SCH$_2$CH$_3$ | CH$_2$CH$_3$ | 0 |
| B-0363 | H | H | H | H | H | CH(CH$_3$)SCH$_3$ | CH$_2$CH$_3$ | 0 |
| B-0364 | H | H | H | H | H | CH(CH$_3$)SCH$_2$CH$_3$ | CH$_2$CH$_3$ | 0 |
| B-0365 | H | H | H | H | H | CH$_2$CH(CH$_3$)SCH$_3$ | CH$_2$CH$_3$ | 0 |
| B-0366 | H | H | H | H | H | CH$_2$CH(CH$_3$)SCH$_2$CH$_3$ | CH$_2$CH$_3$ | 0 |
| B-0367 | H | H | H | H | H | CH$_2$CH$_2$SCH(CH$_3$)$_2$ | CH$_2$CH$_3$ | 0 |
| B-0368 | H | H | H | H | H | CH(CH$_3$)CH$_2$CH$_2$SCH$_3$ | CH$_2$CH$_3$ | 0 |
| B-0369 | H | H | H | H | H | CH(CH$_3$)CH$_2$CH$_2$SCH$_2$CH$_3$ | CH$_2$CH$_3$ | 0 |
| B-0370 | H | H | H | H | H | CH$_2$CH(CH$_3$)CH$_2$SCH$_3$ | CH$_2$CH$_3$ | 0 |
| B-0371 | H | H | H | H | H | CH$_2$CH(CH$_3$)CH$_2$SCH$_2$CH$_3$ | CH$_2$CH$_3$ | 0 |
| B-0372 | H | H | H | H | H | CH$_2$CH$_2$CH(CH$_3$)SCH$_3$ | CH$_2$CH$_3$ | 0 |
| B-0373 | H | H | H | H | H | CH$_2$CH$_2$CH(CH$_3$)SCH$_2$CH$_3$ | CH$_2$CH$_3$ | 0 |
| B-0374 | H | H | H | H | H | CH$_2$CH$_2$CH$_2$CH$_2$SCH$_3$ | CH$_2$CH$_3$ | 0 |
| B-0375 | H | H | H | H | H | CH$_2$CH$_2$CH$_2$CH$_2$CH$_2$SCH$_3$ | CH$_2$CH$_3$ | 0 |
| B-0376 | H | H | H | H | H | CH$_2$SOCH$_3$ | CH$_2$CH$_3$ | 0 |
| B-0377 | H | H | H | H | H | CH$_2$CH$_2$SOCH$_3$ | CH$_2$CH$_3$ | 0 |
| B-0378 | H | H | H | H | H | CH$_2$CH$_2$SOCH$_2$CH$_3$ | CH$_2$CH$_3$ | 0 |
| B-0379 | H | H | H | H | H | CH$_2$CH$_2$SOCH(CH$_3$)$_2$ | CH$_2$CH$_3$ | 0 |
| B-0380 | H | H | H | H | H | CH$_2$CH$_2$CH$_2$SOCH$_3$ | CH$_2$CH$_3$ | 0 |
| B-0381 | H | H | H | H | H | CH(CH$_3$)SOCH$_3$ | CH$_2$CH$_3$ | 0 |
| B-0382 | H | H | H | H | H | CH$_2$CH(CH$_3$)SOCH$_3$ | CH$_2$CH$_3$ | 0 |
| B-0383 | H | H | H | H | H | CH(CH$_3$)CH$_2$CH$_2$SOCH$_3$ | CH$_2$CH$_3$ | 0 |
| B-0384 | H | H | H | H | H | CH$_2$CH(CH$_3$)CH$_2$SOCH$_3$ | CH$_2$CH$_3$ | 0 |
| B-0385 | H | H | H | H | H | CH$_2$CH$_2$CH(CH$_3$)SOCH$_3$ | CH$_2$CH$_3$ | 0 |
| B-0386 | H | H | H | H | H | CH$_2$CH$_2$CH$_2$CH$_2$SOCH$_3$ | CH$_2$CH$_3$ | 0 |
| B-0387 | H | H | H | H | H | CH$_2$CH$_2$CH$_2$CH$_2$CH$_2$SOCH$_3$ | CH$_2$CH$_3$ | 0 |
| B-0388 | H | H | H | H | H | CH$_2$SO$_2$CH$_3$ | CH$_2$CH$_3$ | 0 |

TABLE 100-continued

| Compound | R¹ | R² | R³ | R⁴ | R⁵ | R⁶ | R¹⁶ | n |
|---|---|---|---|---|---|---|---|---|
| B-0389 | H | H | H | H | H | CH₂CH₂SO₂CH₃ | CH₂CH₃ | 0 |
| B-0390 | H | H | H | H | H | CH₂CH₂SO₂CH₂CH₃ | CH₂CH₃ | 0 |
| B-0391 | H | H | H | H | H | CH₂CH₂SO₂CH(CH₃)₂ | CH₂CH₃ | 0 |
| B-0392 | H | H | H | H | H | CH₂CH₂CH₂SO₂CH₃ | CH₂CH₃ | 0 |
| B-0393 | H | H | H | H | H | CH(CH₃)SO₂CH₃ | CH₂CH₃ | 0 |
| B-0394 | H | H | H | H | H | CH₂CH(CH₃)SO₂CH₃ | CH₂CH₃ | 0 |
| B-0395 | H | H | H | H | H | CH(CH₃)CH₂CH₂SO₂CH₃ | CH₂CH₃ | 0 |
| B-0396 | H | H | H | H | H | CH₂CH(CH₃)CH₂SO₂CH₃ | CH₂CH₃ | 0 |
| B-0397 | H | H | H | H | H | CH₂CH₂CH(CH₃)SO₂CH₃ | CH₂CH₃ | 0 |
| B-0398 | H | H | H | H | H | CH₂CH₂CH₂CH₂SO₂CH₃ | CH₂CH₃ | 0 |
| B-0399 | H | H | H | H | H | CH₂CH₂CH₂CH₂CH₂SO₂CH₃ | CH₂CH₃ | 0 |
| B-0400 | H | H | H | H | H | CH₂SCF₃ | CH₂CH₃ | 0 |
| B-0401 | H | H | H | H | H | CH₂SCHF₂ | CH₂CH₃ | 0 |
| B-0402 | H | H | H | H | H | CH₂SCH₂CF₃ | CH₂CH₃ | 0 |
| B-0403 | H | H | H | H | H | CH₂SCH₂CHF₂ | CH₂CH₃ | 0 |
| B-0404 | H | H | H | H | H | CH₂SCF₂CF₃ | CH₂CH₃ | 0 |
| B-0405 | H | H | H | H | H | CH₂CH₂SCF₃ | CH₂CH₃ | 0 |
| B-0406 | H | H | H | H | H | CH₂CH₂SCH₂CF₃ | CH₂CH₃ | 0 |
| B-0407 | H | H | H | H | H | CH₂CH₂CH₂SCF₃ | CH₂CH₃ | 0 |
| B-0408 | H | H | H | H | H | CH₂CH₂CH₂SCH₂CF₃ | CH₂CH₃ | 0 |
| B-0409 | H | H | H | H | H | CH(CH₃)SCF₃ | CH₂CH₃ | 0 |
| B-0410 | H | H | H | H | H | CH(CH₃)SCH₂CF₃ | CH₂CH₃ | 0 |
| B-0411 | H | H | H | H | H | CH₂CH(CH₃)SCF₃ | CH₂CH₃ | 0 |
| B-0412 | H | H | H | H | H | CH₂CH(CH₃)SCH₂CF₃ | CH₂CH₃ | 0 |
| B-0413 | H | H | H | H | H | CH(CH₃)CH₂CH₂SCF₃ | CH₂CH₃ | 0 |
| B-0414 | H | H | H | H | H | CH(CH₃)CH₂CH₂SCH₂CF₃ | CH₂CH₃ | 0 |
| B-0415 | H | H | H | H | H | CH₂CH(CH₃)CH₂SCF₃ | CH₂CH₃ | 0 |
| B-0416 | H | H | H | H | H | CH₂CH(CH₃)CH₂SCH₂CF₃ | CH₂CH₃ | 0 |
| B-0417 | H | H | H | H | H | CH₂CH₂CH(CH₃)SCF₃ | CH₂CH₃ | 0 |
| B-0418 | H | H | H | H | H | CH₂CH₂CH(CH₃)SCH₂CF₃ | CH₂CH₃ | 0 |
| B-0419 | H | H | H | H | H | CH₂CH₂CH₂CH₂SCF₃ | CH₂CH₃ | 0 |
| B-0420 | H | H | H | H | H | CH₂CH₂CH₂CH₂CH₂SCF₃ | CH₂CH₃ | 0 |
| B-0421 | H | H | H | H | H | CH₂SOCF₃ | CH₂CH₃ | 0 |
| B-0422 | H | H | H | H | H | CH₂CH₂SOCF₃ | CH₂CH₃ | 0 |

TABLE 101

| Compound | R¹ | R² | R³ | R⁴ | R⁵ | R⁶ | R¹⁶ | n |
|---|---|---|---|---|---|---|---|---|
| B-0423 | H | H | H | H | H | CH₂CH₂CH₂SOCF₃ | CH₂CH₃ | 0 |
| B-0424 | H | H | H | H | H | CH(CH₃)SOCF₃ | CH₂CH₃ | 0 |
| B-0425 | H | H | H | H | H | CH₂CH(CH₃)SOCF₃ | CH₂CH₃ | 0 |
| B-0426 | H | H | H | H | H | CH(CH₃)CH₂CH₂SOCF₃ | CH₂CH₃ | 0 |
| B-0427 | H | H | H | H | H | CH₂CH(CH₃)CH₂SOCF₃ | CH₂CH₃ | 0 |
| B-0428 | H | H | H | H | H | CH₂CH₂CH(CH₃)SOCF₃ | CH₂CH₃ | 0 |
| B-0429 | H | H | H | H | H | CH₂SO₂CF₃ | CH₂CH₃ | 0 |
| B-0430 | H | H | H | H | H | CH₂CH₂SO₂CF₃ | CH₂CH₃ | 0 |
| B-0431 | H | H | H | H | H | CH₂CH₂SO₃CH₂CF₃ | CH₂CH₃ | 0 |
| B-0432 | H | H | H | H | H | CH₂CH₂CH₂SO₂CF₃ | CH₂CH₃ | 0 |
| B-0433 | H | H | H | H | H | CH(CH₃)SO₂CF₃ | CH₂CH₃ | 0 |
| B-0434 | H | H | H | H | H | CH₂CH(CH₃)SO₂CF₃ | CH₂CH₃ | 0 |
| B-0435 | H | H | H | H | H | CH(CH₃)CH₂CH₂SO₂CF₃ | CH₂CH₃ | 0 |
| B-0436 | H | H | H | H | H | CH₂CH(CH₃)CH₂SO₃CF₃ | CH₂CH₃ | 0 |
| B-0437 | H | H | H | H | H | CH₂CH₂CH(CH₃)SO₂CF₃ | CH₂CH₃ | 0 |
| B-0438 | H | H | H | H | H | CH₂C(=O)CH₃ | CH₂CH₃ | 0 |
| B-0439 | H | H | H | H | H | CH₂C(=O)CH₂CH₃ | CH₂CH₃ | 0 |
| B-0440 | H | H | H | H | H | CH₂C(=O)C(CH₃)₃ | CH₂CH₃ | 0 |
| B-0441 | H | H | H | H | H | CH₂CH₂C(=O)CH₃ | CH₂CH₃ | 0 |
| B-0442 | H | H | H | H | H | CH₂CH₂C(=O)C(CH₃)₃ | CH₂CH₃ | 0 |
| B-0443 | H | H | H | H | H | CH₂C(=O)CF₃ | CH₂CH₃ | 0 |
| B-0444 | H | H | H | H | H | CH₂CH₂C(=O)CF₃ | CH₂CH₃ | 0 |
| B-0445 | H | H | H | H | H | CH₂C(=O)OCH₃ | CH₂CH₃ | 0 |
| B-0446 | H | H | H | H | H | CH₂C(=O)OCH₂CH₃ | CH₂CH₃ | 0 |
| B-0447 | H | H | H | H | H | CH₂C(=O)OC(CH₃)₃ | CH₂CH₃ | 0 |
| B-0448 | H | H | H | H | H | CH₂CH₂C(=O)OCH₃ | CH₂CH₃ | 0 |
| B-0449 | H | H | H | H | H | CH₂CH₂C(=O)OCH₂CH₃ | CH₂CH₃ | 0 |
| B-0450 | H | H | H | H | H | CH₂CH₂C(=O)OC(CH₃)₃ | CH₂CH₃ | 0 |
| B-0451 | H | H | H | H | H | CH₂C(=O)NH₂ | CH₂CH₃ | 0 |
| B-0452 | H | H | H | H | H | CH₂CH₂C(=O)NH₂ | CH₂CH₃ | 0 |
| B-0453 | H | H | H | H | H | CH₂C(=O)NHCH₃ | CH₂CH₃ | 0 |
| B-0454 | H | H | H | H | H | CH₂C(=O)NHCH(CH₃)₂ | CH₂CH₃ | 0 |
| B-0455 | H | H | H | H | H | CH₂CH₂C(=O)NHCH₃ | CH₂CH₃ | 0 |
| B-0456 | H | H | H | H | H | CH₂CH₂C(=O)NHCH(CH₃)₂ | CH₂CH₃ | 0 |
| B-0457 | H | H | H | H | H | CH₂C(=O)NH(cyclopropyl) | CH₂CH₃ | 0 |
| B-0458 | H | H | H | H | H | CH₂C(=O)NHCH₂CHF₂ | CH₂CH₃ | 0 |

TABLE 101-continued

| Compound | R$^1$ | R$^2$ | R$^3$ | R$^4$ | R$^5$ | R$^6$ | R$^{16}$ | n |
|---|---|---|---|---|---|---|---|---|
| B-0459 | H | H | H | H | H | CH$_2$C(=O)NHCH$_2$CF$_3$ | CH$_2$CH$_3$ | 0 |
| B-0460 | H | H | H | H | H | CH$_2$CH$_2$C(=O)NHCH$_2$CHF$_2$ | CH$_2$CH$_3$ | 0 |
| B-0461 | H | H | H | H | H | CH$_2$CH$_2$C(=O)NHCH$_2$CF$_3$ | CH$_2$CH$_3$ | 0 |
| B-0462 | H | H | H | H | H | CH(CH$_3$)C(=O)NHCH$_2$CHF$_2$ | CH$_2$CH$_3$ | 0 |
| B-0463 | H | H | H | H | H | CH(CH$_3$)C(=O)NHCH$_2$CF$_3$ | CH$_2$CH$_3$ | 0 |
| B-0464 | H | H | H | H | H | C(CH$_3$)$_2$C(=O)NHCH$_2$CHF$_2$ | CH$_2$CH$_3$ | 0 |
| B-0465 | H | H | H | H | H | C(CH$_3$)$_2$C(=O)NHCH$_2$CF$_3$ | CH$_2$CH$_3$ | 0 |
| B-0466 | H | H | H | H | H | CH$_2$C(=O)N(CH$_3$)$_2$ | CH$_2$CH$_3$ | 0 |
| B-0467 | H | H | H | H | H | CH$_2$C(=O)N(CH$_2$CH$_3$)$_2$ | CH$_2$CH$_3$ | 0 |
| B-0468 | H | H | H | H | H | CH$_2$CH$_2$C(=O)N(CH$_3$)$_2$ | CH$_2$CH$_3$ | 0 |
| B-0469 | H | H | H | H | H | CH$_2$CH$_2$C(=O)N(CH$_2$CH$_3$)$_2$ | CH$_2$CH$_3$ | 0 |
| B-0470 | H | H | H | H | H | CH$_2$CH$_2$NHC(=O)OCH$_3$ | CH$_2$CH$_3$ | 0 |
| B-0471 | H | H | H | H | H | CH$_2$CH$_2$NHC(=O)OC(CH$_3$)$_3$ | CH$_2$CH$_3$ | 0 |
| B-0472 | H | H | H | H | H | CH$_2$CH$_2$CH$_2$NHC(=O)OCH$_3$ | CH$_2$CH$_3$ | 0 |
| B-0473 | H | H | H | H | H | CH$_2$CH$_2$CH$_2$NHC(=O)OC(CH$_3$)$_3$ | CH$_2$CH$_3$ | 0 |
| B-0474 | H | H | H | H | H | CH$_2$CH$_2$NHSO$_2$CHF$_2$ | CH$_2$CH$_3$ | 0 |
| B-0475 | H | H | H | H | H | CH$_2$CH$_2$NHSO$_2$CF$_3$ | CH$_2$CH$_3$ | 0 |
| B-0476 | H | H | H | H | H | CH$_2$CH$_2$CH$_2$NHSO$_2$CHF$_3$ | CH$_2$CH$_3$ | 0 |
| B-0477 | H | H | H | H | H | CH$_2$CH$_2$CH$_2$NHSO$_2$CF$_3$ | CH$_2$CH$_3$ | 0 |
| B-0478 | H | H | H | H | H | CH$_2$CH$_2$OH | CH$_2$CH$_3$ | 0 |
| B-0479 | H | H | H | H | H | CH$_2$CH(OH)CH$_3$ | CH$_2$CH$_3$ | 0 |
| B-0480 | H | H | H | H | H | CH$_2$CH$_2$CH$_2$OH | CH$_2$CH$_3$ | 0 |
| B-0481 | H | H | H | H | H | CH$_2$CH(OH)CH$_2$CH$_3$ | CH$_2$CH$_3$ | 0 |
| B-0482 | H | H | H | H | H | CH$_2$CH(OH)C(CH$_3$)$_3$ | CH$_2$CH$_3$ | 0 |
| B-0483 | H | H | H | H | H | CH$_2$CH$_2$CH(OH)CH$_3$ | CH$_2$CH$_3$ | 0 |

TABLE 102

| Compound | R$^1$ | R$^2$ | R$^3$ | R$^4$ | R$^5$ | R$^6$ | R$^{16}$ | n |
|---|---|---|---|---|---|---|---|---|
| B-0484 | H | H | H | H | H | CH$_2$CH$_2$CH(OH)C(CH$_3$)$_3$ | CH$_2$CH$_3$ | 0 |
| B-0485 | H | H | H | H | H | CH$_2$C(=NOH)CH$_3$ | CH$_2$CH$_3$ | 0 |
| B-0486 | H | H | H | H | H | CH$_2$C(=NOH)CH$_2$CH$_3$ | CH$_2$CH$_3$ | 0 |
| B-0487 | H | H | H | H | H | CH$_2$C(=NOH)C(CH$_3$)$_3$ | CH$_2$CH$_3$ | 0 |
| B-0488 | H | H | H | H | H | CH$_2$C(=NOCH$_3$)CH$_3$ | CH$_2$CH$_3$ | 0 |
| B-0489 | H | H | H | H | H | CH$_2$C(=NOCH$_3$)CH$_2$CH$_3$ | CH$_2$CH$_3$ | 0 |
| B-0490 | H | H | H | H | H | CH$_2$C(=NOCH$_2$CH$_3$)CH$_3$ | CH$_2$CH$_3$ | 0 |
| B-0491 | H | H | H | H | H | CH$_2$C(=NOCH$_2$CH$_3$)CH$_2$CH$_3$ | CH$_2$CH$_3$ | 0 |
| B-0492 | H | H | H | H | H | CH$_2$C(=NOCH$_2$CF$_3$)CH$_3$ | CH$_2$CH$_3$ | 0 |
| B-0493 | H | H | H | H | H | CH$_2$C(=NOCH$_2$CF$_3$)CH$_2$CH$_3$ | CH$_2$CH$_3$ | 0 |
| B-0494 | H | H | H | H | H | CH$_2$Ph | CH$_2$CH$_3$ | 0 |
| B-0495 | H | H | H | H | H | CH$_2$(2-F)Ph | CH$_2$CH$_3$ | 0 |
| B-0496 | H | H | H | H | H | CH$_2$(3-F)Ph | CH$_2$CH$_3$ | 0 |
| B-0497 | H | H | H | H | H | CH$_2$(4-F)Ph | CH$_2$CH$_3$ | 0 |
| B-0498 | H | H | H | H | H | CH$_2$(2-Cl)Ph | CH$_2$CH$_3$ | 0 |
| B-0499 | H | H | H | H | H | CH$_2$(3-Cl)Ph | CH$_2$CH$_3$ | 0 |
| B-0500 | H | H | H | H | H | CH$_2$(4-Cl)Ph | CH$_2$CH$_3$ | 0 |
| B-0501 | H | H | H | H | H | CH$_2$(2-CF$_3$)Ph | CH$_2$CH$_3$ | 0 |
| B-0502 | H | H | H | H | H | CH$_2$(3-CF$_3$)Ph | CH$_2$CH$_3$ | 0 |
| B-0503 | H | H | H | H | H | CH$_2$(4-CF$_3$)Ph | CH$_2$CH$_3$ | 0 |
| B-0504 | H | H | H | H | H | CH$_2$(2-F-4-CF$_3$)Ph | CH$_2$CH$_3$ | 0 |
| B-0505 | H | H | H | H | H | CH$_2$(naphthalen)-1-yl) | CH$_2$CH$_3$ | 0 |
| B-0506 | H | H | H | H | H | CH$_2$(naphthalen-2-yl) | CH$_2$CH$_3$ | 0 |
| B-0507 | H | H | H | H | H | CH(CH$_3$)Ph | CH$_2$CH$_3$ | 0 |
| B-0508 | H | H | H | H | H | CH$_2$CH$_2$Ph | CH$_2$CH$_3$ | 0 |
| B-0509 | H | CF$_3$ | H | H | H | H | H | 0 |
| B-0510 | H | CF$_3$ | H | H | H | CH$_3$ | H | 0 |
| B-0511 | H | CF$_3$ | H | H | H | CH$_2$CH$_3$ | H | 0 |
| B-0512 | H | CF$_3$ | H | H | H | CH(CH$_3$)$_2$ | H | 0 |
| B-0513 | H | CF$_3$ | H | H | H | CH$_2$CH$_2$CH$_3$ | H | 0 |
| B-0514 | H | CF$_3$ | H | H | H | CH$_2$CH(CH$_3$)$_2$ | H | 0 |
| B-0515 | H | CF$_3$ | H | H | H | CH(CH$_3$)CH$_2$CH$_3$ | H | 0 |
| B-0516 | H | CF$_3$ | H | H | H | CH$_2$C(CH$_3$)$_3$ | H | 0 |
| B-0517 | H | CF$_3$ | H | H | H | CH$_2$(CH$_2$)$_2$CH$_3$ | H | 0 |
| B-0518 | H | CF$_3$ | H | H | H | CH$_2$(CH$_2$)$_3$CH$_3$ | H | 0 |
| B-0519 | H | CF$_3$ | H | H | H | CH$_2$(CH$_2$)$_4$CH$_3$ | H | 0 |
| B-0520 | H | CF$_3$ | H | H | H | CH$_2$(CH$_2$)$_6$CH$_3$ | H | 0 |
| B-0521 | H | CF$_3$ | H | H | H | CH$_2$OCH$_3$ | H | 0 |
| B-0522 | H | CF$_3$ | H | H | H | CH$_2$OCH$_2$CH$_3$ | H | 0 |
| B-0523 | H | CF$_3$ | H | H | H | CH$_2$CH$_2$OCH$_3$ | H | 0 |
| B-0524 | H | CF$_3$ | H | H | H | CH$_2$CH$_2$OCH$_2$CH$_3$ | H | 0 |
| B-0525 | H | CF$_3$ | H | H | H | CF$_3$ | H | 0 |
| B-0526 | H | CF$_3$ | H | H | H | CHF$_2$ | H | 0 |
| B-0527 | H | CF$_3$ | H | H | H | CH$_2$CF$_3$ | H | 0 |
| B-0528 | H | CF$_3$ | H | H | H | CH$_2$CHF$_2$ | H | 0 |

TABLE 102-continued

| Compound | R$^1$ | R$^2$ | R$^3$ | R$^4$ | R$^5$ | R$^6$ | R$^{16}$ | n |
|---|---|---|---|---|---|---|---|---|
| B-0529 | H | CF$_3$ | H | H | H | CH$_2$CClF$_2$ | H | 0 |
| B-0530 | H | CF$_3$ | H | H | H | CH$_2$CBrF$_2$ | H | 0 |
| B-0531 | H | CF$_3$ | H | H | H | CF$_2$CF$_3$ | H | 0 |
| B-0532 | H | CF$_3$ | H | H | H | CF$_2$CHF$_2$ | H | 0 |
| B-0533 | H | CF$_3$ | H | H | H | CH$_2$CH$_2$CF$_3$ | H | 0 |
| B-0534 | H | CF$_3$ | H | H | H | CH$_2$CF$_2$CF$_3$ | H | 0 |
| B-0535 | H | CF$_3$ | H | H | H | CH$_2$CF$_2$CHF$_2$ | H | 0 |
| B-0536 | H | CF$_3$ | H | H | H | CF$_2$CHFCF$_3$ | H | 0 |
| B-0537 | H | CF$_3$ | H | H | H | CF$_2$CF$_2$CF$_3$ | H | 0 |
| B-0538 | H | CF$_3$ | H | H | H | CH$_2$CF$_2$CF$_2$CF$_3$ | H | 0 |
| B-0539 | H | CF$_3$ | H | H | H | CH$_2$CH$_2$CH$_2$CF$_3$ | H | 0 |
| B-0540 | H | CF$_3$ | H | H | H | CH$_2$CF$_2$CHFCF$_3$ | H | 0 |
| B-0541 | H | CF$_3$ | H | H | H | CH$_2$CH$_2$CF$_2$CF$_3$ | H | 0 |
| B-0542 | H | CF$_3$ | H | H | H | CF$_2$CF$_2$CF$_2$CF$_3$ | H | 0 |
| B-0543 | H | CF$_3$ | H | H | H | CH$_2$CH$_2$CH(CF$_3$)$_2$ | H | 0 |
| B-0544 | H | CF$_3$ | H | H | H | CF$_2$CF$_2$CF$_2$CF$_2$CF$_3$ | H | 0 |

TABLE 103

| Compound | R$^1$ | R$^2$ | R$^3$ | R$^4$ | R$^5$ | R$^6$ | R$^{16}$ | n |
|---|---|---|---|---|---|---|---|---|
| B-0545 | H | CF$_3$ | H | H | H | CH$_2$CF$_2$CF$_2$CF$_2$CF$_3$ | H | 0 |
| B-0546 | H | CF$_3$ | H | H | H | CH$_2$CH$_2$CH$_2$CH$_2$CF$_3$ | H | 0 |
| B-0547 | H | CF$_3$ | H | H | H | CH$_2$CF$_2$CF$_2$CF$_2$CHF$_2$ | H | 0 |
| B-0548 | H | CF$_3$ | H | H | H | CH$_2$CF$_2$CF(CF$_3$)CF$_2$C(CR$_3$)$_3$ | H | 0 |
| B-0549 | H | CF$_3$ | H | H | H | CH$_2$CH$_2$CH$_2$CH$_2$CH$_2$CF$_3$ | H | 0 |
| B-0550 | H | CF$_3$ | H | H | H | CH$_2$CH$_2$CH$_2$CH$_2$CH$_2$CH$_2$CF$_3$ | H | 0 |
| B-0551 | H | CF$_3$ | H | H | H | CF$_2$CHFOCH$_3$ | H | 0 |
| B-0552 | H | CF$_3$ | H | H | H | CF$_2$CHFOCH$_2$CH$_3$ | H | 0 |
| B-0553 | H | CF$_3$ | H | H | H | CH$_2$CH$_2$OCH$_2$CF$_3$ | H | 0 |
| B-0554 | H | CF$_3$ | H | H | H | CF$_2$CHFOCF$_3$ | H | 0 |
| B-0555 | H | CF$_3$ | H | H | H | CF$_2$CHFOCF$_2$CF$_3$ | H | 0 |
| B-0556 | H | CF$_3$ | H | H | H | CH$_2$CHFOCF$_2$CF$_2$CF$_3$ | H | 0 |
| B-0557 | H | CF$_3$ | H | H | H | CH$_2$CH=CH$_2$ | H | 0 |
| B-0558 | H | CF$_3$ | H | H | H | CH$_2$CH=CHCl | H | 0 |
| B-0559 | H | CF$_3$ | H | H | H | CH$_2$CH=CCl$_2$ | H | 0 |
| B-0560 | H | CF$_3$ | H | H | H | CH$_2$CH$_2$CF=CF$_2$ | H | 0 |
| B-0561 | H | CF$_3$ | H | H | H | CH$_2$CH$_2$CH=CF$_2$ | H | 0 |
| B-0562 | H | CF$_3$ | H | H | H | CH$_2$C≡CH | H | 0 |
| B-0563 | H | CF$_3$ | H | H | H | CH$_2$C≡CCH$_3$ | H | 0 |
| B-0564 | H | CF$_3$ | H | H | H | CH$_2$C≡Cl | H | 0 |
| B-0565 | H | CF$_3$ | H | H | H | CH$_2$C≡CCF$_3$ | H | 0 |
| B-0566 | H | CF$_3$ | H | H | H | cyclobutyl | H | 0 |
| B-0567 | H | CF$_3$ | H | H | H | cyclopentyl | H | 0 |
| B-0568 | H | CF$_3$ | H | H | H | cyclohexyl | H | 0 |
| B-0569 | H | CF$_3$ | H | H | H | 4,4-difluorocyclohexyl | H | 0 |
| B-0570 | H | CF$_3$ | H | H | H | CH$_2$(cyclopropyl) | H | 0 |
| B-0571 | H | CF$_3$ | H | H | H | CH$_2$(cyclobutyl) | H | 0 |
| B-0572 | H | CF$_3$ | H | H | H | CH$_2$(cyclopentyl) | H | 0 |
| B-0573 | H | CF$_3$ | H | H | H | CH$_2$CH$_2$(cyclopropyl) | H | 0 |
| B-0574 | H | CF$_3$ | H | H | H | CH$_2$(2,2-difluorocyclopropyl) | H | 0 |
| B-0575 | H | CF$_3$ | H | H | H | CH$_2$(2,2-dichlorocydopropyl) | H | 0 |
| B-0576 | H | CF$_3$ | H | H | H | CH$_2$(4,4-difluorccyclohexyl) | H | 0 |
| B-0577 | H | CF$_3$ | H | H | H | CH$_2$CH$_3$(2,2-difluorocyclopropyl) | H | 0 |
| B-0578 | H | CF$_3$ | H | H | H | CH$_2$CH$_3$(2,2-dichlorocyclopropyl) | H | 0 |
| B-0579 | H | CF$_3$ | H | H | H | CH$_2$SCH$_3$ | H | 0 |
| B-0580 | H | CF$_3$ | H | H | H | CH$_2$SCH$_2$CH$_3$ | H | 0 |
| B-0581 | H | CF$_3$ | H | H | H | CH$_2$CH$_2$SCH$_3$ | H | 0 |
| B-0582 | H | CF$_3$ | H | H | H | CH$_2$CH$_3$SCH$_2$CH$_3$ | H | 0 |
| B-0583 | H | CF$_3$ | H | H | H | CH$_2$CH$_2$CH$_2$SCH$_3$ | H | 0 |
| B-0584 | H | CF$_3$ | H | H | H | CH$_2$CH$_2$CH$_2$SCH$_2$CH$_3$ | H | 0 |
| B-0585 | H | CF$_3$ | H | H | H | CH(CH$_3$)SCH$_3$ | H | 0 |
| B-0586 | H | CF$_3$ | H | H | H | CH(CH$_3$)SCH$_2$CH$_3$ | H | 0 |
| B-0587 | H | CF$_3$ | H | H | H | CH$_2$CH(CH$_3$)SCH$_3$ | H | 0 |
| B-0588 | H | CF$_3$ | H | H | H | CH$_2$CH(CH$_3$)SCH$_2$CH$_3$ | H | 0 |
| B-0589 | H | CF$_3$ | H | H | H | CH(CH$_3$)CH$_2$CH$_2$SCH$_3$ | H | 0 |
| B-0590 | H | CF$_3$ | H | H | H | CH(CH$_3$)CH$_2$CH$_2$SCH$_2$CH$_3$ | H | 0 |
| B-0591 | H | CF$_3$ | H | H | H | CH$_2$CH(CH$_3$)CH$_2$SCH$_3$ | H | 0 |
| B-0592 | H | CF$_3$ | H | H | H | CH$_2$CH(CH$_3$)CH$_2$SCH$_2$CH$_3$ | H | 0 |
| B-0593 | H | CF$_3$ | H | H | H | CH$_2$CH$_2$CH(CH$_3$)SCH$_3$ | H | 0 |
| B-0594 | H | CF$_3$ | H | H | H | CH$_2$CH$_2$CH(CH$_3$)SCH$_2$CH$_3$ | H | 0 |
| B-0595 | H | CF$_3$ | H | H | H | CH$_2$SOCH$_3$ | H | 0 |
| B-0596 | H | CF$_3$ | H | H | H | CH$_2$CH$_2$SOCH$_3$ | H | 0 |
| B-0597 | H | CF$_3$ | H | H | H | CH$_2$CH$_2$CH$_3$SOCH$_3$ | H | 0 |
| B-0598 | H | CF$_3$ | H | H | H | CH(CH$_3$)SOCH$_3$ | H | 0 |

TABLE 103-continued

| Compound | R¹ | R² | R³ | R⁴ | R⁵ | R⁶ | R¹⁶ | n |
|---|---|---|---|---|---|---|---|---|
| B-0599 | H | CF₃ | H | H | H | CH₂CH(CH₃)SOCH₃ | H | 0 |
| B-0600 | H | CF₃ | H | H | H | CH(CH₃)CH₂CH₂SOCH₃ | H | 0 |
| B-0601 | H | CF₃ | H | H | H | CH₂CH(CH₃)CH₂SOCH₃ | H | 0 |
| B-0602 | H | CF₃ | H | H | H | CH₂CH₂CH(CH₃)SOCH₃ | H | 0 |
| B-0603 | H | CF₃ | H | H | H | CH₂SO₂CH₃ | H | 0 |
| B-0604 | H | CF₃ | H | H | H | CH₂CH₂SO₂CH₃ | H | 0 |
| B-0605 | H | CF₃ | H | H | H | CH₂CH₂CH₂SO₂CH₃ | H | 0 |

TABLE 104

| Compound | R¹ | R² | R³ | R⁴ | R⁵ | R⁶ | R¹⁶ | n |
|---|---|---|---|---|---|---|---|---|
| B-0606 | H | CF₃ | H | H | H | CH(CH₃)SO₂CH₃ | H | 0 |
| B-0607 | H | CF₃ | H | H | H | CH₂CH(CH₃)SO₂CH₃ | H | 0 |
| B-0608 | H | CF₃ | H | H | H | CH(CH₃)CH₂CH₂SO₂CH₃ | H | 0 |
| B-0609 | H | CF₃ | H | H | H | CH₂CH(CH₃)CH₂SO₂CH₃ | H | 0 |
| B-0610 | H | CF₃ | H | H | H | CH₂CH₂CH(CH₃)SO₂CH₃ | H | 0 |
| B-0611 | H | CF₃ | H | H | H | CH₂SCF₃ | H | 0 |
| B-0612 | H | CF₃ | H | H | H | CH₂SCHF₂ | H | 0 |
| B-0613 | H | CF₃ | H | H | H | CH₂SCH₂CF₃ | H | 0 |
| B-0614 | H | CF₃ | H | H | H | CH₂SCH₂CHF₂ | H | 0 |
| B-0615 | H | CF₃ | H | H | H | CH₂SCF₂CF₃ | H | 0 |
| B-0616 | H | CF₃ | H | H | H | CH₂CH₂SCF₃ | H | 0 |
| B-0617 | H | CF₃ | H | H | H | CH₂CH₂SCH₂CF₃ | H | 0 |
| B-0618 | H | CF₃ | H | H | H | CH₂CH₂CH₂SCF₃ | H | 0 |
| B-0619 | H | CF₃ | H | H | H | CH₂CH₂CH₂SCH₂CF₃ | H | 0 |
| B-0620 | H | CF₃ | H | H | H | CH(CH₃)SCF₃ | H | 0 |
| B-0621 | H | CF₃ | H | H | H | CH(CH₃)SCH₂CF₃ | H | 0 |
| B-0622 | H | CF₃ | H | H | H | CH₃CH(CH₃)SCF₃ | H | 0 |
| B-0623 | H | CF₃ | H | H | H | CH₂CH(CH₃)SCH₂CF₃ | H | 0 |
| B-0624 | H | CF₃ | H | H | H | CH(CH₃)CH₂CH₂SCF₃ | H | 0 |
| B-0625 | H | CF₃ | H | H | H | CH(CH₃)CH₂CH₂SCH₂CF₃ | H | 0 |
| B-0626 | H | CF₃ | H | H | H | CH₂CH(CH₃)CH₂SCF₃ | H | 0 |
| B-0627 | H | CF₃ | H | H | H | CH₂CH(CH₃)CH₂SCH₂CF₃ | H | 0 |
| B-0628 | H | CF₃ | H | H | H | CH₂CH₂CH(CH₃)SCF₃ | H | 0 |
| B-0629 | H | CF₃ | H | H | H | CH₂CH₂CH(CH₃)SCH₂CF₃ | H | 0 |
| B-0630 | H | CF₃ | H | H | H | CH₂SOCF3 | H | 0 |
| B-0631 | H | CF₃ | H | H | H | CH₂CH₂SOCF₃ | H | 0 |
| B-0632 | H | CF₃ | H | H | H | CH₂CH₂CH₂SOCF₃ | H | 0 |
| B-0633 | H | CF₃ | H | H | H | CH(CH₃)SOCF₃ | H | 0 |
| B-0634 | H | CF₃ | H | H | H | CH₂CH(CH₃)SOCF₃ | H | 0 |
| B-0635 | H | CF₃ | H | H | H | CH(CH₃)CH₂CH₂SOCF₃ | H | 0 |
| B-0636 | H | CF₃ | H | H | H | CH₂CH(CH₃)CH₂SOCF₃ | H | 0 |
| B-0637 | H | CF₃ | H | H | H | CH₂CH₂CH(CH₃)SOCF₃ | H | 0 |
| B-0638 | H | CF₃ | H | H | H | CH₂SO₂CF₃ | H | 0 |
| B-0639 | H | CF₃ | H | H | H | CH₂CH₂SO₂CF₃ | H | 0 |
| B-0640 | H | CF₃ | H | H | H | CH₂CH₂CH₂SO₂CF₃ | H | 0 |
| B-0641 | H | CF₃ | H | H | H | CH(CH₃)SO₂CF₃ | H | 0 |
| B-0642 | H | CF₃ | H | H | H | CH₂CH(CH₃)SO₂CF₃ | H | 0 |
| B-0643 | H | CF₃ | H | H | H | CH(CH₃)CH₂CH₂SO₂CF₃ | H | 0 |
| B-0644 | H | CF₃ | H | H | H | CH₂CH(CH₃)CH₂SO₂CF₃ | H | 0 |
| B-0645 | H | CF₃ | H | H | H | CH₂CH₂CH(CH₃)SO₂CF₃ | H | 0 |
| B-0646 | H | CF₃ | H | H | H | CH₂C(=O)CH₃ | H | 0 |
| B-0647 | H | CF₃ | H | H | H | CH₂C(=O)CH₂CH₃ | H | 0 |
| B-0648 | H | CF₃ | H | H | H | CH₂C(=O)C(CH₃)₃ | H | 0 |
| B-0649 | H | CF₃ | H | H | H | CH₂CH₂C(=O)CH₃ | H | 0 |
| B-0650 | H | CF₃ | H | H | H | CH₂CH₂C(=O)C(CH₃)₃ | H | 0 |
| B-0651 | H | CF₃ | H | H | H | CH₂C(=O)CF₃ | H | 0 |
| B-0652 | H | CF₃ | H | H | H | CH₂CH₂C(=O)CF₃ | H | 0 |
| B-0653 | H | CF₃ | H | H | H | CH₂C(=O)OCH₃ | H | 0 |
| B-0654 | H | CF₃ | H | H | H | CH₂C(=O)OCH₂CH₃ | H | 0 |
| B-0655 | H | CF₃ | H | H | H | CH₂C(=O)OC(CH₃)₃ | H | 0 |
| B-0656 | H | CF₃ | H | H | H | CH₂CH₂C(=O)OCH₃ | H | 0 |
| B-0657 | H | CF₃ | H | H | H | CH₂CH₂C(=O)OCH₂CH₃ | H | 0 |
| B-0658 | H | CF₃ | H | H | H | CH₂CH₂C(=O)OC(CH₃)₃ | H | 0 |
| B-0659 | H | CF₃ | H | H | H | CH₂C(=O)NH₂ | H | 0 |
| B-0660 | H | CF₃ | H | H | H | CH₂CH₂C(=O)NH₂ | H | 0 |
| B-0661 | H | CF₃ | H | H | H | CH₂C(=O)NHCH₃ | H | 0 |
| B-0662 | H | CF₃ | H | H | H | CH₂C(=O)NHCH(CH₃)₂ | H | 0 |
| B-0663 | H | CF₃ | H | H | H | CH₂CH₂C(=O)NHCH₃ | H | 0 |
| B-0664 | H | CF₃ | H | H | H | CH₂CH₂C(O)NHCH(CH₃)₂ | H | 0 |
| B-0665 | H | CF₃ | H | H | H | CH₂C(=O)NHCH₂CHF₂ | H | 0 |
| B-0666 | H | CF₃ | H | H | H | CH₂C(=O)NHCH₂CF₃ | H | 0 |

TABLE 105

| Compound | R¹ | R² | R³ | R⁴ | R⁵ | R⁶ | R¹⁶ | n |
|---|---|---|---|---|---|---|---|---|
| B-0667 | H | $CF_3$ | H | H | H | $CH_2CH_2C(=O)NHCH_2CHF_2$ | H | 0 |
| B-0668 | H | $CF_3$ | H | H | H | $CH_2CH_2C(=O)NHCH_2CF_3$ | H | 0 |
| B-0669 | H | $CF_3$ | H | H | H | $CH_2C(=O)N(CH_3)_2$ | H | 0 |
| B-0670 | H | $CF_3$ | H | H | H | $CH_2C(=O)N(CH_2CH_3)_2$ | H | 0 |
| B-0671 | H | $CF_3$ | H | H | H | $CH_2CH_2C(=O)N(CH_3)_2$ | H | 0 |
| B-0672 | H | $CF_3$ | H | H | H | $CH_2CH_2C(=O)N(CH_2CH_3)_2$ | H | 0 |
| B-0673 | H | $CF_3$ | H | H | H | $CH_2CH_2OH$ | H | 0 |
| B-0674 | H | $CF_3$ | H | H | H | $CH_2CH(OH)CH_3$ | H | 0 |
| B-0675 | H | $CF_3$ | H | H | H | $CH_2CH_2CH_2OH$ | H | 0 |
| B-0676 | H | $CF_3$ | H | H | H | $CH_2CH(OH)CH_2CH_3$ | H | 0 |
| B-0677 | H | $CF_3$ | H | H | H | $CH_2CH(OH)C(CH_3)_3$ | H | 0 |
| B-0678 | H | $CF_3$ | H | H | H | $CH_2CH_2CH(OH)CH_3$ | H | 0 |
| B-0679 | H | $CF_3$ | H | H | H | $CH_2CH_2CH(OH)C(CH_3)_3$ | H | 0 |
| B-0680 | H | $CF_3$ | H | H | H | $CH_2C(=NOH)CH_3$ | H | 0 |
| B-0681 | H | $CF_3$ | H | H | H | $CH_2C(=NOH)CH_2CH_3$ | H | 0 |
| B-0682 | H | $CF_3$ | H | H | H | $CH_2C(=NOH)C(CH_3)_3$ | H | 0 |
| B-0683 | H | $CF_3$ | H | H | H | $CH_2C(=NOCH_3)CH_2$ | H | 0 |
| B-0684 | H | $CF_3$ | H | H | H | $CH_2C(=NOCH_2)CH_2CH_3$ | H | 0 |
| B-0685 | H | $CF_3$ | H | H | H | $CH_2C(=NOCH_2CH_3)CH_3$ | H | 0 |
| B-0686 | H | $CF_3$ | H | H | H | $CH_2C(=NOCH_2CH_3)CH_2CH_3$ | H | 0 |
| B-0687 | H | $CF_3$ | H | H | H | $CH_2C(=NOCH_2CF_3)CH_3$ | H | 0 |
| B-0688 | H | $CF_3$ | H | H | H | $CH_2C(=NOCH_2CF_3)CH_2CH_3$ | H | 0 |
| B-0689 | H | $CF_3$ | H | H | H | $CH_2Ph$ | H | 0 |
| B-0690 | H | $CF_3$ | H | H | H | $CH_2(2-F)Ph$ | H | 0 |
| B-0691 | H | $CF_3$ | H | H | H | $CH_2(3-F)Ph$ | H | 0 |
| B-0692 | H | $CF_3$ | H | H | H | $CH_2(4-F)Ph$ | H | 0 |
| B-0693 | H | $CF_3$ | H | H | H | $CH_2(2-Cl)Ph$ | H | 0 |
| B-0694 | H | $CF_3$ | H | H | H | $CH_2(3-Cl)Ph$ | H | 0 |
| B-0695 | H | $CF_3$ | H | H | H | $CH_2(4-Cl)Ph$ | H | 0 |
| B-0696 | H | $CF_3$ | H | H | H | $CH_2(2-CF_3)Ph$ | H | 0 |
| B-0697 | H | $CF_3$ | H | H | H | $CH_2(3-CF_3)Ph$ | H | 0 |
| B-0698 | H | $CF_3$ | H | H | H | $CH_2(4-CF_3)Ph$ | H | 0 |
| B-0699 | H | $CF_3$ | H | H | H | $CH_2(naphthalene-1-yl)$ | H | 0 |
| B-0700 | H | $CF_3$ | H | H | H | $CH_2(naphthalen-2-yl)$ | H | 0 |
| B-0701 | H | $CF_3$ | H | H | H | $CH_2CH_2Ph$ | H | 0 |
| B-0702 | H | $CF_3$ | H | H | H | H | $CH_2CH_3$ | 0 |
| B-0703 | H | $CF_3$ | H | H | H | $CH_3$ | $CH_2CH_3$ | 0 |
| B-0704 | H | $CF_3$ | H | H | H | $CH_2CH_3$ | $CH_2CH_3$ | 0 |
| B-0705 | H | $CF_3$ | H | H | H | $CH(CH_3)_2$ | $CH_2CH_3$ | 0 |
| B-0706 | H | $CF_3$ | H | H | H | $CH_2CH_2CH_3$ | $CH_2CH_3$ | 0 |
| B-0707 | H | $CF_3$ | H | H | H | $CH_2CH(CH_3)_2$ | $CH_2CH_3$ | 0 |
| B-0708 | H | $CF_3$ | H | H | H | $CH_2C(CH_3)_3$ | $CH_2CH_3$ | 0 |
| B-0709 | H | $CF_3$ | H | H | H | $CH(CH_3)CH_2CH_3$ | $CH_2CH_3$ | 0 |
| B-0710 | H | $CF_3$ | H | H | H | $CH_2(CH_2)_2CH_3$ | $CH_2CH_3$ | 0 |
| B-0711 | H | $CF_3$ | H | H | H | $CH_2(CH_2)_3CH_3$ | $CH_2CH_3$ | 0 |
| B-0712 | H | $CF_3$ | H | H | H | $CH_2(CH_2)_4CH_3$ | $CH_2CH_3$ | 0 |
| B-0713 | H | $CF_3$ | H | H | H | $CH_2(CH_2)_6CH_3$ | $CH_2CH_3$ | 0 |
| B-0714 | H | $CF_3$ | H | H | H | $CH_2OCH_3$ | $CH_2CH_3$ | 0 |
| B-0715 | H | $CF_3$ | H | H | H | $CH_2OCH_2CH_3$ | $CH_2CH_3$ | 0 |
| B-0716 | H | $CF_3$ | H | H | H | $CH_2CH_2OCH_3$ | $CH_2CH_3$ | 0 |
| B-0717 | H | $CF_3$ | H | H | H | $CH_2CH_2OCH_2CH_3$ | $CH_2CH_3$ | 0 |
| B-0718 | H | $CF_3$ | H | H | H | $CF_3$ | $CH_2CH_3$ | 0 |
| B-0719 | H | $CF_3$ | H | H | H | $CHF_2$ | $CH_2CH_3$ | 0 |
| B-0720 | H | $CF_3$ | H | H | H | $CH_2CF_3$ | $CH_2CH_3$ | 0 |
| B-0721 | H | $CF_3$ | H | H | H | $CH_2CHF_2$ | $CH_2CH_3$ | 0 |
| B-0722 | H | $CF_3$ | H | H | H | $CH_2CClF_2$ | $CH_2CH_3$ | 0 |
| B-0723 | H | $CF_3$ | H | H | H | $CH_2CBrF_2$ | $CH_2CH_3$ | 0 |
| B-0724 | H | $CF_3$ | H | H | H | $CF_2CF_3$ | $CH_2CH_3$ | 0 |
| B-0725 | H | $CF_3$ | H | H | H | $CF_2CHF_2$ | $CH_2CH_3$ | 0 |
| B-0726 | H | $CF_3$ | H | H | H | $CH_2CH_2CF_3$ | $CH_2CH_3$ | 0 |
| B-0727 | H | $CF_3$ | H | H | H | $CH_2CF_2CF_3$ | $CH_2CH_3$ | 0 |

TABLE 106

| Compound | R¹ | R² | R³ | R⁴ | R⁵ | R⁶ | R¹⁶ | n |
|---|---|---|---|---|---|---|---|---|
| B-0728 | H | $CF_3$ | H | H | H | $CH_2CF_2CHF_2$ | $CH_2CH_3$ | 0 |
| B-0729 | H | $CF_3$ | H | H | H | $CF_2CHFCF_3$ | $CH_2CH_3$ | 0 |
| B-0730 | H | $CF_3$ | H | H | H | $CF_2CF_2CF_3$ | $CH_2CH_3$ | 0 |
| B-0731 | H | $CF_3$ | H | H | H | $CH_2CF_2CF_2CF_3$ | $CH_2CH_3$ | 0 |
| B-0732 | H | $CF_3$ | H | H | H | $CH_2CF_2CHFCF_3$ | $CH_2CH_3$ | 0 |
| B-0733 | H | $CF_3$ | H | H | H | $CH_2CH_2CH_2CF_3$ | $CH_2CH_3$ | 0 |
| B-0734 | H | $CF_3$ | H | H | H | $CH_2CH_2CF_2CF_3$ | $CH_2CH_3$ | 0 |
| B-0735 | H | $CF_3$ | H | H | H | $CF_2CF_2CF_2CF_3$ | $CH_2CH_3$ | 0 |
| B-0736 | H | $CF_3$ | H | H | H | $CH_2CH_2CH(CF_3)_2$ | $CH_2CH_3$ | 0 |

TABLE 106-continued

| Compound | $R^1$ | $R^2$ | $R^3$ | $R^4$ | $R^5$ | $R^6$ | $R^{16}$ | n |
|---|---|---|---|---|---|---|---|---|
| B-0737 | H | $CF_3$ | H | H | H | $CF_2CF_2CF_2CF_2CF_3$ | $CH_2CH_3$ | 0 |
| B-0738 | H | $CF_3$ | H | H | H | $CH_2CF_2CF_2CF_2CF_3$ | $CH_2CH_3$ | 0 |
| B-0739 | H | $CF_3$ | H | H | H | $CH_2CH_2CH_2CH_2CF_3$ | $CH_2CH_3$ | 0 |
| B-0740 | H | $CF_3$ | H | H | H | $CH_2CF_2CF_2CF_2CHF_2$ | $CH_2CH_3$ | 0 |
| B-0741 | H | $CF_3$ | H | H | H | $CH_2CF_2CF(CF_3)CF_2C(CF_3)_3$ | $CH_2CH_3$ | 0 |
| B-0742 | H | $CF_3$ | H | H | H | $CH_2CH_2CH_2CH_2CF_3$ | $CH_2CH_3$ | 0 |
| B-0743 | H | $CF_3$ | H | H | H | $CH_2CH_2CH_2CH_2CH_2CF_3$ | $CH_2CH_3$ | 0 |
| B-0744 | H | $CF_3$ | H | H | H | $CF_2CHFOCH_3$ | $CH_2CH_3$ | 0 |
| B-0745 | H | $CF_3$ | H | H | H | $CF_2CHFOCH_2CH_3$ | $CH_2CH_3$ | 0 |
| B-0746 | H | $CF_3$ | H | H | H | $CH_2CH_2OCH_2CF_3$ | $CH_2CH_3$ | 0 |
| B-0747 | H | $CF_3$ | H | H | H | $CF_2CHFCF_3$ | $CH_2CH_3$ | 0 |
| B-0748 | H | $CF_3$ | H | H | H | $CF_2CHFOCF_2CF_3$ | $CH_2CH_3$ | 0 |
| B-0749 | H | $CF_3$ | H | H | H | $CF_2CHFOCF_2CF_2CF_3$ | $CH_2CH_3$ | 0 |
| B-0750 | H | $CF_3$ | H | H | H | $CH_2CH=CH_2$ | $CH_2CH_3$ | 0 |
| B-0751 | H | $CF_3$ | H | H | H | $CH_2CH=CHCl$ | $CH_2CH_3$ | 0 |
| B-0752 | H | $CF_3$ | H | H | H | $CH_2CH=CCl_2$ | $CH_2CH_3$ | 0 |
| B-0753 | H | $CF_3$ | H | H | H | $CH_2CH_2CF=CF_2$ | $CH_2CH_3$ | 0 |
| B-0754 | H | $CF_3$ | H | H | H | $CH_2CH_2CH=CF_2$ | $CH_2CH_3$ | 0 |
| B-0755 | H | $CF_3$ | H | H | H | $CH_2C\equiv CH$ | $CH_2CH_3$ | 0 |
| B-0756 | H | $CF_3$ | H | H | H | $CH_2C\equiv CCH_3$ | $CH_2CH_3$ | 0 |
| B-0757 | H | $CF_3$ | H | H | H | $CH_2C\equiv CI$ | $CH_2CH_3$ | 0 |
| B-0758 | H | $CF_3$ | H | H | H | $CH_2C\equiv CCF_3$ | $CH_2CH_3$ | 0 |
| B-0759 | H | $CF_3$ | H | H | H | cyclobutyl | $CH_2CH_3$ | 0 |
| B-0760 | H | $CF_3$ | H | H | H | cyclopentyl | $CH_2CH_3$ | 0 |
| B-0761 | H | $CF_3$ | H | H | H | cyclohexyl | $CH_2CH_3$ | 0 |
| B-0762 | H | $CF_3$ | H | H | H | 4,4-difluorocyclohexyl | $CH_2CH_3$ | 0 |
| B-0763 | H | $CF_3$ | H | H | H | $CH_2$(cyclopropyl) | $CH_2CH_3$ | 0 |
| B-0764 | H | $CF_3$ | H | H | H | $CH_2$(cyclobutyl) | $CH_2CH_3$ | 0 |
| B-0765 | H | $CF_3$ | H | H | H | $CH_2$(cyclopentyl) | $CH_2CH_3$ | 0 |
| B-0766 | H | $CF_3$ | H | H | H | $CH_2CH_2$(cyclopropyl) | $CH_2CH_3$ | 0 |
| B-0767 | H | $CF_3$ | H | H | H | $CH_2$(2,2-difluorocyclopropyl) | $CH_2CH_3$ | 0 |
| B-0768 | H | $CF_3$ | H | H | H | $CH_2$(2,2-dichlorocyclopropyl) | $CH_2CH_3$ | 0 |
| B-0769 | H | $CF_3$ | H | H | H | $CH_2$(4,4-difluorocyclohexyl) | $CH_2CH_3$ | 0 |
| B-0770 | H | $CF_3$ | H | H | H | $CH_2CH_2$(2,2-difluorocyclopropyl) | $CH_2CH_3$ | 0 |
| B-0771 | H | $CF_3$ | H | H | H | $CH_2CH_2$(2,2-dichlorocyclopropyl) | $CH_2CH_3$ | 0 |
| B-0772 | H | $CF_3$ | H | H | H | $CH_2SCH_3$ | $CH_2CH_3$ | 0 |
| B-0773 | H | $CF_3$ | H | H | H | $CH_2SCH_2CH_3$ | $CH_2CH_3$ | 0 |
| B-0774 | H | $CF_3$ | H | H | H | $CH_2CH_2SCH_3$ | $CH_2CH_3$ | 0 |
| B-0775 | H | $CF_3$ | H | H | H | $CH_2CH_2SCH_2CH_3$ | $CH_2CH_3$ | 0 |
| B-0776 | H | $CF_3$ | H | H | H | $CH_2CH_2CH_2SCH_3$ | $CH_2CH_3$ | 0 |
| B-0777 | H | $CF_3$ | H | H | H | $CH_2CH_2CH_2SCH_2CH_3$ | $CH_2CH_3$ | 0 |
| B-0778 | H | $CF_3$ | H | H | H | $CH(CH_3)SCH_3$ | $CH_2CH_3$ | 0 |
| B-0779 | H | $CF_3$ | H | H | H | $CH(CH_3)SCH_2CH_3$ | $CH_2CH_3$ | 0 |
| B-0780 | H | $CF_3$ | H | H | H | $CH_2CH(CH_3)SCH_3$ | $CH_2CH_3$ | 0 |
| B-0781 | H | $CF_3$ | H | H | H | $CH_2CH(CH_3)SCH_2CH_3$ | $CH_2CH_3$ | 0 |
| B-0782 | H | $CF_3$ | H | H | H | $CH(CH_3)CH_2CH_2SCH_3$ | $CH_2CH_3$ | 0 |
| B-0783 | H | $CF_3$ | H | H | H | $CH(CH_3)CH_2CH_2SCH_2CH_3$ | $CH_2CH_3$ | 0 |
| B-0784 | H | $CF_3$ | H | H | H | $CH_2CH(CH_3)CH_2SCH_3$ | $CH_2CH_3$ | 0 |
| B-0785 | H | $CF_3$ | H | H | H | $CH_2CH(CH_3)CH_2SCH_2CH_3$ | $CH_2CH_3$ | 0 |
| B-0786 | H | $CF_3$ | H | H | H | $CH_2CH_2CH(CH_3)SCH_3$ | $CH_2CH_3$ | 0 |
| B-0787 | H | $CF_3$ | H | H | H | $CH_2CH_2CH(CH_3)SCH_2CH_3$ | $CH_2CH_3$ | 0 |
| B-0788 | H | $CF_3$ | H | H | H | $CH_2SOCH_3$ | $CH_2CH_3$ | 0 |

TABLE 107

| Compound | $R^1$ | $R^2$ | $R^3$ | $R^4$ | $R^5$ | $R^6$ | $R^{16}$ | n |
|---|---|---|---|---|---|---|---|---|
| B-0789 | H | $CF_3$ | H | H | H | $CH_2CH_2SOCH_3$ | $CH_2CH_3$ | 0 |
| B-0790 | H | $CF_3$ | H | H | H | $CH_2CH_2CH_2SOCH_3$ | $CH_2CH_3$ | 0 |
| B-0791 | H | $CF_3$ | H | H | H | $CH(CH_3)SOCH_3$ | $CH_2CH_3$ | 0 |
| B-0792 | H | $CF_3$ | H | H | H | $CH_2CH(CH_3)SOCH_3$ | $CH_2CH_3$ | 0 |
| B-0793 | H | $CF_3$ | H | H | H | $CH(CH_3)CH_2CH_2SOCH_3$ | $CH_2CH_3$ | 0 |
| B-0794 | H | $CF_3$ | H | H | H | $CH_2CH(CH_3)CH_2SOCH_3$ | $CH_2CH_3$ | 0 |
| B-0795 | H | $CF_3$ | H | H | H | $CH_2CH_2CH(CH_3)SOCH_3$ | $CH_2CH_3$ | 0 |
| B-0796 | H | $CF_3$ | H | H | H | $CH_2SO_2CH_3$ | $CH_2CH_3$ | 0 |
| B-0797 | H | $CF_3$ | H | H | H | $CH_2CH_2SO_2CH_3$ | $CH_2CH_3$ | 0 |
| B-0798 | H | $CF_3$ | H | H | H | $CH_2CH_2CH_2SO_2CH_3$ | $CH_2CH_3$ | 0 |
| B-0799 | H | $CF_3$ | H | H | H | $CH(CH_3)SO_2CH_3$ | $CH_2CH_3$ | 0 |
| B-0800 | H | $CF_3$ | H | H | H | $CH_2CH(CH_3)SO_2CH_3$ | $CH_2CH_3$ | 0 |
| B-0801 | H | $CF_3$ | H | H | H | $CH(CH_3)CH_2CH_2SO_2CH_3$ | $CH_2CH_3$ | 0 |
| B-0802 | H | $CF_3$ | H | H | H | $CH_2CH(CH_3)CH_2SO_2CH_3$ | $CH_2CH_3$ | 0 |
| B-0803 | H | $CF_3$ | H | H | H | $CH_2CH_2CH(CH_3)SO_2CH_3$ | $CH_2CH_3$ | 0 |
| B-0804 | H | $CF_3$ | H | H | H | $CH_2SCF_3$ | $CH_2CH_3$ | 0 |
| B-0805 | H | $CF_3$ | H | H | H | $CH_2SCHF_2$ | $CH_2CH_3$ | 0 |
| B-0806 | H | $CF_3$ | H | H | H | $CH_2SCH_2CF_3$ | $CH_2CH_3$ | 0 |

TABLE 107-continued

| Compound | R¹ | R² | R³ | R⁴ | R⁵ | R⁶ | R¹⁶ | n |
|---|---|---|---|---|---|---|---|---|
| B-0807 | H | CF₃ | H | H | H | CH₂SCH₂CHF₂ | CH₂CH₃ | 0 |
| B-0808 | H | CF₃ | H | H | H | CH₂SCF₂CF₃ | CH₂CH₃ | 0 |
| B-0809 | H | CF₃ | H | H | H | CH₂CH₂SCF₃ | CH₂CH₃ | 0 |
| B-0810 | H | CF₃ | H | H | H | CH₂CH₂SCH₂CF₃ | CH₂CH₃ | 0 |
| B-0811 | H | CF₃ | H | H | H | CH₂CH₂CH₂SCF₃ | CH₂CH₃ | 0 |
| B-0812 | H | CF₃ | H | H | H | CH₂CH₂CH₂SCH₂CF₃ | CH₂CH₃ | 0 |
| B-0813 | H | CF₃ | H | H | H | CH(CH₃)SCF₃ | CH₂CH₃ | 0 |
| B-0814 | H | CF₃ | H | H | H | CH(CH₃)SCH₂CF₃ | CH₂CH₃ | 0 |
| B-0815 | H | CF₃ | H | H | H | CH₂CH(CH₃)SCF₃ | CH₂CH₃ | 0 |
| B-0816 | H | CF₃ | H | H | H | CH₂CH(CH₃)SCH₂CF₃ | CH₂CH₃ | 0 |
| B-0817 | H | CF₃ | H | H | H | CH(CH₃)CH₂CH₂SCF₃ | CH₂CH₃ | 0 |
| B-0818 | H | CF₃ | H | H | H | CH(CH₃)CH₂CH₂SCH₂CF₃ | CH₂CH₃ | 0 |
| B-0819 | H | CF₃ | H | H | H | CH₂CH(CH₃)CH₂SCF₃ | CH₂CH₃ | 0 |
| B-0820 | H | CF₃ | H | H | H | CH₂CH(CH₃)CH₂SCH₂CF₃ | CH₂CH₃ | 0 |
| B-0821 | H | CF₃ | H | H | H | CH₂CH₂CH(CH₃)SCF₃ | CH₂CH₃ | 0 |
| B-0822 | H | CF₃ | H | H | H | CH₂CH₂CH(CH₃)SCH₂CF₃ | CH₂CH₃ | 0 |
| B-0823 | H | CF₃ | H | H | H | CH₂SOCF₃ | CH₂CH₃ | 0 |
| B-0824 | H | CF₃ | H | H | H | CH₂CH₂SOCF₃ | CH₂CH₃ | 0 |
| B-0825 | H | CF₃ | H | H | H | CH₂CH₂CH₂SOCF₃ | CH₂CH₃ | 0 |
| B-0826 | H | CF₃ | H | H | H | CH(CH₃)SOCF₃ | CH₂CH₃ | 0 |
| B-0827 | H | CF₃ | H | H | H | CH₂CH(CH₃)SOCF₃ | CH₂CH₃ | 0 |
| B-0828 | H | CF₃ | H | H | H | CH(CH₃)CH₂CH₂SOCF₃ | CH₂CH₃ | 0 |
| B-0829 | H | CF₃ | H | H | H | CH₂CH(CH₃)CH₂SOCF₃ | CH₂CH₃ | 0 |
| B-0830 | H | CF₃ | H | H | H | CH₂CH₂CH(CH₃)SOCF₃ | CH₂CH₃ | 0 |
| B-0831 | H | CF₃ | H | H | H | CH₂SO₂CF₃ | CH₂CH₃ | 0 |
| B-0832 | H | CF₃ | H | H | H | CH₂CH₂SO₂CF₃ | CH₂CH₃ | 0 |
| B-0833 | H | CF₃ | H | H | H | CH₂CH₂CH₂SO₂CF₃ | CH₂CH₃ | 0 |
| B-0834 | H | CF₃ | H | H | H | CH(CH₃)SO₂CF₃ | CH₂CH₃ | 0 |
| B-0835 | H | CF₃ | H | H | H | CH₂CH(CH₃)SO₂CF₃ | CH₂CH₃ | 0 |
| B-0836 | H | CF₃ | H | H | H | CH(CH₃)CH₂CH₂SO₂CF₃ | CH₂CH₃ | 0 |
| B-0837 | H | CF₃ | H | H | H | CH₂CH(CH₃)CH₂SO₂CF₃ | CH₂CH₃ | 0 |
| B-0838 | H | CF₃ | H | H | H | CH₂CH₂CH(CH₃)SO₂CF₃ | CH₂CH₃ | 0 |
| B-0839 | H | CF₃ | H | H | H | CH₂C(=O)CH₃ | CH₂CH₃ | 0 |
| B-0840 | H | CF₃ | H | H | H | CH₂C(=O)CH₂CH₃ | CH₂CH₃ | 0 |
| B-0841 | H | CF₃ | H | H | H | CH₂C(=O)C(CH₃)₃ | CH₂CH₃ | 0 |
| B-0842 | H | CF₃ | H | H | H | CH₂CH₂C(=O)CH₃ | CH₂CH₃ | 0 |
| B-0843 | H | CF₃ | H | H | H | CH₂CH₂C(=O)C(CH₃)₃ | CH₂CH₃ | 0 |
| B-0844 | H | CF₃ | H | H | H | CH₂C(=O)CF₃ | CH₂CH₃ | 0 |
| B-0845 | H | CF₃ | H | H | H | CH₂CH₂C(=O)CF₃ | CH₂CH₃ | 0 |
| B-0846 | H | CF₃ | H | H | H | CH₂C(=O)OCH₃ | CH₂CH₃ | 0 |
| B-0847 | H | CF₃ | H | H | H | CH₂C(=O)OCH₂CH₃ | CH₂CH₃ | 0 |
| B-0848 | H | CF₃ | H | H | H | CH₂C(=O)OC(CH₃)₃ | CH₂CH₃ | 0 |
| B-0849 | H | CF₃ | H | H | H | CH₂CH₂C(=O)OCH₃ | CH₂CH₃ | 0 |

TABLE 108

| Compound | R¹ | R² | R³ | R⁴ | R⁵ | R⁶ | R¹⁶ | n |
|---|---|---|---|---|---|---|---|---|
| B-0850 | H | CF₃ | H | H | H | CH₂CH₂C(=O)OCH₂CH₃ | CH₂CH₃ | 0 |
| B-0851 | H | CF₃ | H | H | H | CH₂CH₂C(=O)OC(CH₃)₃ | CH₂CH₃ | 0 |
| B-0852 | H | CF₃ | H | H | H | CH₂C(=O)NH₂ | CH₂CH₃ | 0 |
| B-0853 | H | CF₃ | H | H | H | CH₂CH₂C(=O)NH₂ | CH₂CH₃ | 0 |
| B-0854 | H | CF₃ | H | H | H | CH₂C(=O)NHCH₃ | CH₂CH₃ | 0 |
| B-0855 | H | CF₃ | H | H | H | CH₂C(=O)NHCH(CH₃)₂ | CH₂CH₃ | 0 |
| B-0856 | H | CF₃ | H | H | H | CH₂CH₂C(=O)NHCH₃ | CH₂CH₃ | 0 |
| B-0857 | H | CF₃ | H | H | H | CH₂CH₂C(=O)NHCH(CH₃)₂ | CH₂CH₃ | 0 |
| B-0858 | H | CF₃ | H | H | H | CH₂C(=O)NHCH₂CHF₂ | CH₂CH₃ | 0 |
| B-0859 | H | CF₃ | H | H | H | CH₂C(=O)NHCH₂CF₃ | CH₂CH₃ | 0 |
| B-0860 | H | CF₃ | H | H | H | CH₂CH₂C(=O)NHCH₂CHF₂ | CH₂CH₃ | 0 |
| B-0861 | H | CF₃ | H | H | H | CH₂CH₂C(=O)NHCH₂CF₃ | CH₂CH₃ | 0 |
| B-0862 | H | CF₃ | H | H | H | CH₂C(=O)N(CH₃)₂ | CH₂CH₃ | 0 |
| B-0863 | H | CF₃ | H | H | H | CH₂C(=O)N(CH₂CH₃)₂ | CH₂CH₃ | 0 |
| B-0864 | H | CF₃ | H | H | H | CH₂CH₂C(=O)N(CH₃)₂ | CH₂CH₃ | 0 |
| B-0865 | H | CF₃ | H | H | H | CH₂CH₂C(=O)N(CH₂CH₃)₂ | CH₂CH₃ | 0 |
| B-0866 | H | CF₃ | H | H | H | CH₂CH₂OH | CH₂CH₃ | 0 |
| B-0867 | H | CF₃ | H | H | H | CH₂CH(OH)CH₃ | CH₂CH₃ | 0 |
| B-0868 | H | CF₃ | H | H | H | CH₂CH₂CH₂OH | CH₂CH₃ | 0 |
| B-0869 | H | CF₃ | H | H | H | CH₂CH(OH)CH₂CH₃ | CH₂CH₃ | 0 |
| B-0870 | H | CF₃ | H | H | H | CH₂CH(OH)C(CH₃)₃ | CH₂CH₃ | 0 |
| B-0871 | H | CF₃ | H | H | H | CH₂CH₂CH(OH)CH₃ | CH₂CH₃ | 0 |
| B-0872 | H | CF₃ | H | H | H | CH₂CH₂CH(OH)C(CH₃)₃ | CH₂CH₃ | 0 |
| B-0873 | H | CF₃ | H | H | H | CH₂C(=NOH)CH₃ | CH₂CH₃ | 0 |
| B-0874 | H | CF₃ | H | H | H | CH₂C(=NOH)CH₂CH₃ | CH₂CH₃ | 0 |
| B-0875 | H | CF₃ | H | H | H | CH₂C(=NOH)C(CH₃)₃ | CH₂CH₃ | 0 |
| B-0876 | H | CF₃ | H | H | H | CH₂C(=NOCH₃)CH₃ | CH₂CH₃ | 0 |

TABLE 108-continued

| Compound | $R^1$ | $R^2$ | $R^3$ | $R^4$ | $R^5$ | $R^6$ | $R^{16}$ | n |
|---|---|---|---|---|---|---|---|---|
| B-0877 | H | $CF_3$ | H | H | H | $CH_2C(=NOCH_3)CH_2CH_3$ | $CH_2CH_3$ | 0 |
| B-0878 | H | $CF_3$ | H | H | H | $CH_2C(=NOCH_2CH_3)CH_3$ | $CH_2CH_3$ | 0 |
| B-0879 | H | $CF_3$ | H | H | H | $CH_2C(=NOCH_2CH_3)CH_2CH_3$ | $CH_2CH_3$ | 0 |
| B-0880 | H | $CF_3$ | H | H | H | $CH_2C(=NOCH_2CF_3)CH_3$ | $CH_2CH_3$ | 0 |
| B-0881 | H | $CF_3$ | H | H | H | $CH_2C(=NOCH_2CF_3)CH_2CH_3$ | $CH_2CH_3$ | 0 |
| B-0882 | H | $CF_3$ | H | H | H | $CH_2Ph$ | $CH_2CH_3$ | 0 |
| B-0883 | H | $CF_3$ | H | H | H | $CH_2(2\text{-}F)Ph$ | $CH_2CH_3$ | 0 |
| B-0884 | H | $CF_3$ | H | H | H | $CH_2(3\text{-}F)Ph$ | $CH_2CH_3$ | 0 |
| B-0885 | H | $CF_3$ | H | H | H | $CH_2(4\text{-}F)Ph$ | $CH_2CH_3$ | 0 |
| B-0886 | H | $CF_3$ | H | H | H | $CH_2(2\text{-}Cl)Ph$ | $CH_2CH_3$ | 0 |
| B-0887 | H | $CF_3$ | H | H | H | $CH_2(3\text{-}Cl)Ph$ | $CH_2CH_3$ | 0 |
| B-0888 | H | $CF_3$ | H | H | H | $CH_2(4\text{-}Cl)Ph$ | $CH_2CH_3$ | 0 |
| B-0889 | H | $CF_3$ | H | H | H | $CH_2(2\text{-}CF_3)Ph$ | $CH_2CH_3$ | 0 |
| B-0890 | H | $CF_3$ | H | H | H | $CH_2(3\text{-}CF_3)Ph$ | $CH_2CH_3$ | 0 |
| B-0891 | H | $CF_3$ | H | H | H | $CH_2(4\text{-}CF_3)Ph$ | $CH_2CH_3$ | 0 |
| B-0892 | H | $CF_3$ | H | H | H | $CH_2(\text{naphthalen-1-yl})$ | $CH_2CH_3$ | 0 |
| B-0893 | H | $CF_3$ | H | H | H | $CH_2(\text{naphthalen-2-yl})$ | $CH_2CH_3$ | 0 |
| B-0894 | H | $CF_3$ | H | H | H | $CH_2CH_2Ph$ | $CH_2CH_3$ | 0 |
| B-0895 | H | H | F | H | H | H | H | 0 |
| B-0896 | H | H | F | H | H | $CH_3$ | H | 0 |
| B-0897 | H | H | F | H | H | $CH_2CH_3$ | H | 0 |
| B-0898 | H | H | F | H | H | $CH(CH_3)_2$ | H | 0 |
| B-0899 | H | H | F | H | H | $CH_2CH_2CH_3$ | H | 0 |
| B-0900 | H | H | F | H | H | $CH_2CH(CH_3)_2$ | H | 0 |
| B-0901 | H | H | F | H | H | $CH_2C(CH_3)_3$ | H | 0 |
| B-0902 | H | H | F | H | H | $CH(CH_3)CH_2CH_3$ | H | 0 |
| B-0903 | H | H | F | H | H | $CH_2(CH_2)_2CH_3$ | H | 0 |
| B-0904 | H | H | F | H | H | $CH_2(CH_2)_3CH_3$ | H | 0 |
| B-0905 | H | H | F | H | H | $CH_2(CH_2)_4CH_3$ | H | 0 |
| B-0906 | H | H | F | H | H | $CH_2(CH_2)_6CH_3$ | H | 0 |
| B-0907 | H | H | F | H | H | $CH_2OCH_3$ | H | 0 |
| B-0908 | H | H | F | H | H | $CH_2OCH_2CH_3$ | H | 0 |
| B-0909 | H | H | F | H | H | $CH_2CH_2OCH_3$ | H | 0 |
| B-0910 | H | H | F | H | H | $CH_2CH_2OCH_2CH_3$ | H | 0 |

TABLE 109

| Compound | $R^1$ | $R^2$ | $R^3$ | $R^4$ | $R^5$ | $R^6$ | $R^{16}$ | n |
|---|---|---|---|---|---|---|---|---|
| B-0911 | H | H | F | H | H | $CF_3$ | H | 0 |
| B-0912 | H | H | F | H | H | $CHF_2$ | H | 0 |
| B-0913 | H | H | F | H | H | $CH_2CF_3$ | H | 0 |
| B-0914 | H | H | F | H | H | $CH_2CHF_2$ | H | 0 |
| B-0915 | H | H | F | H | H | $CH_2CClF_2$ | H | 0 |
| B-0916 | H | H | F | H | H | $CH_2CBrF_2$ | H | 0 |
| B-0917 | H | H | F | H | H | $CF_2CF_3$ | H | 0 |
| B-0918 | H | H | F | H | H | $CF_2CHF_2$ | H | 0 |
| B-0919 | H | H | F | H | H | $CH_2CH_3CF_3$ | H | 0 |
| B-0920 | H | H | F | H | H | $CH_2CF_2CF_3$ | H | 0 |
| B-0921 | H | H | F | H | H | $CH_2CF_2CHF_2$ | H | 0 |
| B-0922 | H | H | F | H | H | $CF_2CHFCF_3$ | H | 0 |
| B-0923 | H | H | F | H | H | $CF_2CF_2CF_3$ | H | 0 |
| B-0924 | H | H | F | H | H | $CH_2CF_2CF_2CF_3$ | H | 0 |
| B-0925 | H | H | F | H | H | $CH_2CF_2CHFCF_3$ | H | 0 |
| B-0926 | H | H | F | H | H | $CH_2CH_3CH_2CF_3$ | H | 0 |
| B-0927 | H | H | F | H | H | $CH_2CH_2CF_2CF_3$ | H | 0 |
| B-0928 | H | H | F | H | H | $CF_2CF_2CF_2CF_3$ | H | 0 |
| B-0929 | H | H | F | H | H | $CH_2CH_2CH(CF_3)_2$ | H | 0 |
| B-0930 | H | H | F | H | H | $CF_2CF_2CF_2CF_2CF_3$ | H | 0 |
| B-0931 | H | H | F | H | H | $CH_2CF_2CF_2CF_2CF_3$ | H | 0 |
| B-0932 | H | H | F | H | H | $CH_2CH_2CH_2CH_2CF_3$ | H | 0 |
| B-0933 | H | H | F | H | H | $CH_2CF_2CF_2CF_2CHF_2$ | H | 0 |
| B-0934 | H | H | F | H | H | $CH_2CF_2CF(CF_3)CF_2C(CF_3)_3$ | H | 0 |
| B-0935 | H | H | F | H | H | $CH_2CH_2CH_2CH_2CH_2CF_3$ | H | 0 |
| B-0936 | H | H | F | H | H | $CH_2CH_2CH_2CH_2CH_2CH_2CF_3$ | H | 0 |
| B-0937 | H | H | F | H | H | $CF_2CHFOCH_3$ | H | 0 |
| B-0938 | H | H | F | H | H | $CF_2CHFOCH_2CH_3$ | H | 0 |
| B-0939 | H | H | F | H | H | $CH_2CH_2OCH_2CF_3$ | H | 0 |
| B-0940 | H | H | F | H | H | $CF_2CHFOCF_3$ | H | 0 |
| B-0941 | H | H | F | H | H | $CF_2CHFOCF_2CF_3$ | H | 0 |
| B-0942 | H | H | F | H | H | $CF_2CHFOCF_2CF_2CF_3$ | H | 0 |
| B-0943 | H | H | F | H | H | $CH_2CH=CH_2$ | H | 0 |
| B-0944 | H | H | F | H | H | $CH_2CH=CHCl$ | H | 0 |
| B-0945 | H | H | F | H | H | $CH_2CH=CCl_2$ | H | 0 |
| B-0946 | H | H | F | H | H | $CH_2CH_2CF=CF_2$ | H | 0 |

TABLE 109-continued

| Compound | R¹ | R² | R³ | R⁴ | R⁵ | R⁶ | R¹⁶ | n |
|---|---|---|---|---|---|---|---|---|
| B-0947 | H | H | F | H | H | CH$_2$CH$_2$CH=CF$_2$ | H | 0 |
| B-0948 | H | H | F | H | H | CH$_2$C≡CH | H | 0 |
| B-0949 | H | H | F | H | H | CH$_2$C≡CCH$_3$ | H | 0 |
| B-0950 | H | H | F | H | H | CH$_2$C≡CCl | H | 0 |
| B-0951 | H | H | F | H | H | CH$_2$C≡CCF$_3$ | H | 0 |
| B-0952 | H | H | F | H | H | cyclobutyl | H | 0 |
| B-0953 | H | H | F | H | H | cyclopentyl | H | 0 |
| B-0954 | H | H | F | H | H | cyclohexyl | H | 0 |
| B-0955 | H | H | F | H | H | 4,4-difluorocyclohexyl | H | 0 |
| B-0956 | H | H | F | H | H | CH$_2$(cyclopropyl) | H | 0 |
| B-0957 | H | H | F | H | H | CH$_2$(cyclobutyl) | H | 0 |
| B-0958 | H | H | F | H | H | CH$_2$(cyclopentyl) | H | 0 |
| B-0959 | H | H | F | H | H | CH$_2$CH$_2$(cyclopropyl) | H | 0 |
| B-0960 | H | H | F | H | H | CH$_2$(2,2-difluorocyclopropyl) | H | 0 |
| B-0961 | H | H | F | H | H | CH$_2$(2,2-dichlorocyclopropyl) | H | 0 |
| B-0962 | H | H | F | H | H | CH$_2$(4,4-difluorocyclohexyl) | H | 0 |
| B-0963 | H | H | F | H | H | CH$_2$CH$_2$(2,2-difluorocyclopropyl) | H | 0 |
| B-0964 | H | H | F | H | H | CH$_2$CH$_2$(2,2-dichlorocyclopropyl) | H | 0 |
| B-0965 | H | H | F | H | H | CH$_2$SCH$_3$ | H | 0 |
| B-0966 | H | H | F | H | H | CH$_2$SCH$_2$CH$_3$ | H | 0 |
| B-0967 | H | H | F | H | H | CH$_2$CH$_2$SCH$_3$ | H | 0 |
| B-0968 | H | H | F | H | H | CH$_2$CH$_2$SCH$_2$CH$_3$ | H | 0 |
| B-0969 | H | H | F | H | H | CH$_2$CH$_2$CH$_2$SCH$_3$ | H | 0 |
| B-0970 | H | H | F | H | H | CH$_2$CH$_2$CH$_2$SCH$_2$CH$_3$ | H | 0 |
| B-0971 | H | H | F | H | H | CH(CH$_3$)SCH$_3$ | H | 0 |

TABLE 110

| Compound | R¹ | R² | R³ | R⁴ | R⁵ | R⁶ | R¹⁶ | n |
|---|---|---|---|---|---|---|---|---|
| B-0972 | H | H | F | H | H | CH(CH$_3$)SCH$_2$CH$_3$ | H | 0 |
| B-0973 | H | H | F | H | H | CH$_2$CH(CH$_3$)SCH$_3$ | H | 0 |
| B-0974 | H | H | F | H | H | CH$_2$CH(CH$_3$)SCH$_2$CH$_3$ | H | 0 |
| B-0975 | H | H | F | H | H | CH(CH$_3$)CH$_2$CH$_2$SCH$_3$ | H | 0 |
| B-0976 | H | H | F | H | H | CH(CH$_3$)CH$_2$CH$_2$SCH$_2$CH$_3$ | H | 0 |
| B-0977 | H | H | F | H | H | CH$_2$CH(CH$_3$)CH$_2$SCH$_3$ | H | 0 |
| B-0978 | H | H | F | H | H | CH$_2$CH(CH$_3$)CH$_2$SCH$_2$CH$_3$ | H | 0 |
| B-0979 | H | H | F | H | H | CH$_2$CH$_2$CH(CH$_3$)SCH$_3$ | H | 0 |
| B-0980 | H | H | F | H | H | CH$_2$CH$_2$CH(CH$_3$)SCH$_2$CH$_3$ | H | 0 |
| B-0981 | H | H | F | H | H | CH$_2$SOCH$_3$ | H | 0 |
| B-0982 | H | H | F | H | H | CH$_2$CH$_2$SOCH$_3$ | H | 0 |
| B-0983 | H | H | F | H | H | CH$_2$CH$_2$CH$_2$SOCH$_3$ | H | 0 |
| B-0984 | H | H | F | H | H | CH(CH$_3$)SOCH$_3$ | H | 0 |
| B-0985 | H | H | F | H | H | CH$_2$CH(CH$_3$)SOCH$_3$ | H | 0 |
| B-0986 | H | H | F | H | H | CH(CH$_3$)CH$_2$CH$_2$SOCH$_3$ | H | 0 |
| B-0987 | H | H | F | H | H | CH$_2$CH(CH$_3$)CH$_2$SOCH$_3$ | H | 0 |
| B-0988 | H | H | F | H | H | CH$_2$CH$_2$CH(CH$_3$)SOCH$_3$ | H | 0 |
| B-0989 | H | H | F | H | H | CH$_2$SO$_2$CH$_3$ | H | 0 |
| B-0990 | H | H | F | H | H | CH$_2$CH$_2$SO$_2$CH$_3$ | H | 0 |
| B-0991 | H | H | F | H | H | CH$_2$CH$_2$CH$_2$SO$_2$CH$_3$ | H | 0 |
| B-0992 | H | H | F | H | H | CH(CH$_3$)SO$_2$CH$_3$ | H | 0 |
| B-0993 | H | H | F | H | H | CH$_2$CH(CH$_3$)SO$_2$CH$_3$ | H | 0 |
| B-0994 | H | H | F | H | H | CH(CH$_3$)CH$_2$CH$_2$SO$_2$CH$_3$ | H | 0 |
| B-0995 | H | H | F | H | H | CH$_2$CH(CH$_3$)CH$_2$SO$_2$CH$_3$ | H | 0 |
| B-0996 | H | H | F | H | H | CH$_2$CH$_2$CH(CH$_3$)SO$_2$CH$_3$ | H | 0 |
| B-0997 | H | H | F | H | H | CH$_2$SCF$_3$ | H | 0 |
| B-0998 | H | H | F | H | H | CH$_2$SCHF$_2$ | H | 0 |
| B-0999 | H | H | F | H | H | CH$_2$SCH$_2$CF$_3$ | H | 0 |
| B-1000 | H | H | F | H | H | CH$_2$SCH$_2$CHF$_2$ | H | 0 |
| B-1001 | H | H | F | H | H | CH$_2$SCF$_2$CF$_3$ | H | 0 |
| B-1002 | H | H | F | H | H | CH$_2$CH$_2$SCF$_3$ | H | 0 |
| B-1003 | H | H | F | H | H | CH$_2$CH$_2$SCH$_2$CF$_3$ | H | 0 |
| B-1004 | H | H | F | H | H | CH$_2$CH$_2$CH$_2$SCF$_3$ | H | 0 |
| B-1005 | H | H | F | H | H | CH$_2$CH$_2$CH$_2$SCH$_2$CF$_3$ | H | 0 |
| B-1006 | H | H | F | H | H | CH(CH$_3$)SCF$_3$ | H | 0 |
| B-1007 | H | H | F | H | H | CH(CH$_3$)SCH$_2$CF$_3$ | H | 0 |
| B-1008 | H | H | F | H | H | CH$_2$CH(CH$_3$)SCF$_3$ | H | 0 |
| B-1009 | H | H | F | H | H | CH$_2$CH(CH$_3$)SCH$_2$CF$_3$ | H | 0 |
| B-1010 | H | H | F | H | H | CH(CH$_3$)CH$_2$CH$_2$SCF$_3$ | H | 0 |
| B-1011 | H | H | F | H | H | CH(CH$_3$)CH$_2$CH$_2$SCH$_2$CF$_3$ | H | 0 |
| B-1012 | H | H | F | H | H | CH$_2$CH(CH$_3$)CH$_2$SCF$_3$ | H | 0 |
| B-1013 | H | H | F | H | H | CH$_2$CH(CH$_3$)CH$_2$SCH$_2$CF$_3$ | H | 0 |
| B-1014 | H | H | F | H | H | CH$_2$CH$_2$CH(CH$_3$)SCF$_3$ | H | 0 |
| B-1015 | H | H | F | H | H | CH$_2$CH$_2$CH(CH$_3$)SCH$_2$CF$_3$ | H | 0 |
| B-1016 | H | H | F | H | H | CH$_2$SOCF$_3$ | H | 0 |

TABLE 110-continued

| Compound | R$^1$ | R$^2$ | R$^3$ | R$^4$ | R$^5$ | R$^6$ | R$^{16}$ | n |
|---|---|---|---|---|---|---|---|---|
| B-1017 | H | H | F | H | H | CH$_2$CH$_2$SOCF$_3$ | H | 0 |
| B-1018 | H | H | F | H | H | CH$_2$CH$_2$CH$_2$SOCF$_3$ | H | 0 |
| B-1019 | H | H | F | H | H | CH(CH$_3$)SOCF$_3$ | H | 0 |
| B-1020 | H | H | F | H | H | CH$_2$CH(CH$_3$)SOCF$_3$ | H | 0 |
| B-1021 | H | H | F | H | H | CH(CH$_3$)CH$_2$CH$_2$SOCF$_3$ | H | 0 |
| B-1022 | H | H | F | H | H | CH$_2$CH(CH$_3$)CH$_2$SOCF$_3$ | H | 0 |
| B-1023 | H | H | F | H | H | CH$_2$CH$_2$CH(CH$_3$)SOCF$_3$ | H | 0 |
| B-1024 | H | H | F | H | H | CH$_2$SO$_2$CF$_3$ | H | 0 |
| B-1025 | H | H | F | H | H | CH$_2$CH$_2$SO$_2$CF$_3$ | H | 0 |
| B-1026 | H | H | F | H | H | CH$_2$CH$_2$CH$_2$SO$_2$CF$_3$ | H | 0 |
| B-1027 | H | H | F | H | H | CH(CH$_3$)SO$_2$CF$_3$ | H | 0 |
| B-1028 | H | H | F | H | H | CH$_2$CH(CH$_3$)SO$_2$CF$_3$ | H | 0 |
| B-1029 | H | H | F | H | H | CH(CH$_3$)CH$_2$CH$_2$SO$_2$CF$_3$ | H | 0 |
| B-1030 | H | H | F | H | H | CH$_2$CH(CH$_3$)CH$_2$SO$_2$CF$_3$ | H | 0 |
| B-1031 | H | H | F | H | H | CH$_2$CH$_2$CH(CH$_3$)SO$_2$CF$_3$ | H | 0 |
| B-1032 | H | H | F | H | H | CH$_2$C(=O)CH$_3$ | H | 0 |

TABLE 111

| Compound | R$^1$ | R$^2$ | R$^3$ | R$^4$ | R$^5$ | R$^6$ | R$^{16}$ | n |
|---|---|---|---|---|---|---|---|---|
| B-1033 | H | H | F | H | H | CH$_2$C(=O)CH$_2$CH$_3$ | H | 0 |
| B-1034 | H | H | F | H | H | CH$_2$C(=O)C(CH$_3$)$_3$ | H | 0 |
| B-1035 | H | H | F | H | H | CH$_2$CH$_2$C(=O)CH$_3$ | H | 0 |
| B-1036 | H | H | F | H | H | CH$_2$CH$_2$C(=O)C(CH$_3$)$_3$ | H | 0 |
| B-1037 | H | H | F | H | H | CH$_2$C(=O)CF$_3$ | H | 0 |
| B-1038 | H | H | F | H | H | CH$_2$CH$_2$C(=O)CF$_3$ | H | 0 |
| B-1039 | H | H | F | H | H | CH$_2$C(=O)OCH$_3$ | H | 0 |
| B-1040 | H | H | F | H | H | CH$_2$C(=O)OCH$_2$CH$_3$ | H | 0 |
| B-1041 | H | H | F | H | H | CH$_2$C(=O)OC(CH$_3$)$_3$ | H | 0 |
| B-1042 | H | H | F | H | H | CH$_2$CH$_2$C(=O)OCH$_3$ | H | 0 |
| B-1043 | H | H | F | H | H | CH$_2$CH$_2$C(=O)OCH$_2$CH$_3$ | H | 0 |
| B-1044 | H | H | F | H | H | CH$_2$CH$_2$C(=O)OC(CH$_3$)$_3$ | H | 0 |
| B-1045 | H | H | F | H | H | CH$_2$C(=O)NH$_2$ | H | 0 |
| B-1046 | H | H | F | H | H | CH$_2$CH$_2$C(=O)NH$_2$ | H | 0 |
| B-1047 | H | H | F | H | H | CH$_2$C(=O)NHCH$_3$ | H | 0 |
| B-1048 | H | H | F | H | H | CH$_2$C(=O)NHCH(CH$_3$)$_2$ | H | 0 |
| B-1049 | H | H | F | H | H | CH$_2$CH$_2$C(=O)NHCH$_3$ | H | 0 |
| B-1050 | H | H | F | H | H | CH$_2$CH$_2$C(=O)NHCH(CH$_3$)$_2$ | H | 0 |
| B-1051 | H | H | F | H | H | CH$_2$C(=O)NHCH$_2$CHF$_2$ | H | 0 |
| B-1052 | H | H | F | H | H | CH$_2$C(=O)NHCH$_2$CF$_3$ | H | 0 |
| B-1053 | H | H | F | H | H | CH$_2$CH$_2$C(=O)NHCH$_2$CHF$_2$ | H | 0 |
| B-1054 | H | H | F | H | H | CH$_2$CH$_2$C(=O)NHCH$_2$CF$_3$ | H | 0 |
| B-1055 | H | H | F | H | H | CH$_2$C(=O)N(CH$_3$)$_2$ | H | 0 |
| B-1056 | H | H | F | H | H | CH$_2$C(=O)N(CH$_2$CH$_3$)$_2$ | H | 0 |
| B-1057 | H | H | F | H | H | CH$_2$CH$_2$C(=O)N(CH$_3$)$_2$ | H | 0 |
| B-1058 | H | H | F | H | H | CH$_2$CH$_2$C(=O)N(CH$_2$CH$_3$)$_2$ | H | 0 |
| B-1059 | H | H | F | H | H | CH$_2$CH$_2$OH | H | 0 |
| B-1060 | H | H | F | H | H | CH$_2$CH(OH)CH$_3$ | H | 0 |
| B-1061 | H | H | F | H | H | CH$_2$CH$_2$CH$_2$OH | H | 0 |
| B-1062 | H | H | F | H | H | CH$_3$CH(OH)CH$_2$CH$_3$ | H | 0 |
| B-1063 | H | H | F | H | H | CH$_3$CH(OH)C(CH$_3$)$_3$ | H | 0 |
| B-1064 | H | H | F | H | H | CH$_2$CH$_2$CH(OH)CH$_3$ | H | 0 |
| B-1065 | H | H | F | H | H | CH$_2$CH$_2$CH(OH)C(CH$_3$)$_3$ | H | 0 |
| B-1066 | H | H | F | H | H | CH$_2$C(=NOH)CH$_3$ | H | 0 |
| B-1067 | H | H | F | H | H | CH$_2$C(=NOH)CH$_2$CH$_3$ | H | 0 |
| B-1068 | H | H | F | H | H | CH$_2$C(=NOH)C(CH$_3$)$_3$ | H | 0 |
| B-1069 | H | H | F | H | H | CH$_2$C(=NOCH$_3$)CH$_3$ | H | 0 |
| B-1070 | H | H | F | H | H | CH$_2$C(=NOCH$_3$)CH$_2$CH$_3$ | H | 0 |
| B-1071 | H | H | F | H | H | CH$_2$C(=NOCH$_2$CH$_3$)CH$_3$ | H | 0 |
| B-1072 | H | H | F | H | H | CH$_2$C(=NOCH$_2$CH$_3$)CH$_2$CH$_3$ | H | 0 |
| B-1073 | H | H | F | H | H | CH$_2$C(=NOCH$_2$CF$_3$)CH$_3$ | H | 0 |
| B-1074 | H | H | F | H | H | CH$_2$C(=NOCH$_2$CF$_3$)CH$_2$CH$_3$ | H | 0 |
| B-1075 | H | H | F | H | H | CH$_2$Ph | H | 0 |
| B-1076 | H | H | F | H | H | CH$_2$(2-F)Ph | H | 0 |
| B-1077 | H | H | F | H | H | CH$_2$(3-F)Ph | H | 0 |
| B-1078 | H | H | F | H | H | CH$_2$(4-F)Ph | H | 0 |
| B-1079 | H | H | F | H | H | CH$_2$(2-Cl)Ph | H | 0 |
| B-1080 | H | H | F | H | H | CH$_2$(3-Cl)Ph | H | 0 |
| B-1081 | H | H | F | H | H | CH$_2$(4-Cl)Ph | H | 0 |
| B-1082 | H | H | F | H | H | CH$_2$(2-CF$_3$)Ph | H | 0 |
| B-1083 | H | H | F | H | H | CH$_2$(3-CF$_3$)Ph | H | 0 |
| B-1084 | H | H | F | H | H | CH$_2$(4-CF$_3$)Ph | H | 0 |
| B-1085 | H | H | F | H | H | CH$_2$(naphthalen-1-yl) | H | 0 |
| B-1086 | H | H | F | H | H | CH$_2$(naphthaLen-2-yl) | H | 0 |

TABLE 111-continued

| Compound | R¹ | R² | R³ | R⁴ | R⁵ | R⁶ | R¹⁶ | n |
|---|---|---|---|---|---|---|---|---|
| B-1087 | H | H | F | H | H | CH₂CH₂Ph | H | 0 |
| B-1088 | H | H | F | H | H | H | CH₂CH₃ | 0 |
| B-1089 | H | H | F | H | H | CH₃ | CH₂CH₃ | 0 |
| B-1090 | H | H | F | H | H | CH₂CH₃ | CH₂CH₃ | 0 |
| B-1091 | H | H | F | H | H | CH(CH₃)₂ | CH₂CH₃ | 0 |
| B-1092 | H | H | F | H | H | CH₂CH₂CH₃ | CH₂CH₃ | 0 |
| B-1093 | H | H | F | H | H | CH₂CH(CH₃)₂ | CH₂CH₃ | 0 |

TABLE 112

| Compound | R¹ | R² | R³ | R⁴ | R⁵ | R⁶ | R¹⁶ | n |
|---|---|---|---|---|---|---|---|---|
| B-1094 | H | H | F | H | H | CH(CH₃)CH₂CH₃ | CH₂CH₃ | 0 |
| B-1095 | H | H | F | H | H | CH₂C(CH₃)₃ | CH₂CH₃ | 0 |
| B-1096 | H | H | F | H | H | CH₂(CH₂)₂CH₃ | CH₂CH₃ | 0 |
| B-1097 | H | H | F | H | H | CH₂(CH₂)₃CH₃ | CH₂CH₃ | 0 |
| B-1098 | H | H | F | H | H | CH₂(CH₂)₄CH₃ | CH₂CH₃ | 0 |
| B-1099 | H | H | F | H | H | CH₂(CH₂)₆CH₃ | CH₂CH₃ | 0 |
| B-1100 | H | H | F | H | H | CH₂OCH₃ | CH₂CH₃ | 0 |
| B-1101 | H | H | F | H | H | CH₂OCH₂CH₃ | CH₂CH₃ | 0 |
| B-1102 | H | H | F | H | H | CH₂CH₂OCH₃ | CH₂CH₃ | 0 |
| B-1103 | H | H | F | H | H | CH₂CH₂OCH₂CH₃ | CH₂CH₃ | 0 |
| B-1104 | H | H | F | H | H | CF₃ | CH₂CH₃ | 0 |
| B-1105 | H | H | F | H | H | CHF₂ | CH₂CH₃ | 0 |
| B-1106 | H | H | F | H | H | CH₂CF₃ | CH₂CH₃ | 0 |
| B-1107 | H | H | F | H | H | CH₂CHF₂ | CH₂CH₃ | 0 |
| B-1108 | H | H | F | H | H | CH₂CClF₂ | CH₂CH₃ | 0 |
| B-1109 | H | H | F | H | H | CH₂CBrF₂ | CH₂CH₃ | 0 |
| B-1110 | H | H | F | H | H | CF₂CF₃ | CH₂CH₃ | 0 |
| B-1111 | H | H | F | H | H | CF₂CHF₂ | CH₂CH₃ | 0 |
| B-1112 | H | H | F | H | H | CH₂CH₂CF₃ | CH₂CH₃ | 0 |
| B-1113 | H | H | F | H | H | CH₂CF₂CF₃ | CH₂CH₃ | 0 |
| B-1114 | H | H | F | H | H | CH₂CF₂CHF₂ | CH₂CH₃ | 0 |
| B-1115 | H | H | F | H | H | CF₂CHFCF₃ | CH₂CH₃ | 0 |
| B-1116 | H | H | F | H | H | CF₂CF₂CF₃ | CH₂CH₃ | 0 |
| B-1117 | H | H | F | H | H | CH₂CF₂CF₂CF₃ | CH₂CH₃ | 0 |
| B-1118 | H | H | F | H | H | CH₂CF₂CFCF₃ | CH₂CH₃ | 0 |
| B-1119 | H | H | F | H | H | CH₂CH₂CH₂CF₃ | CH₂CH₃ | 0 |
| B-1120 | H | H | F | H | H | CH₂CH₂CF₂CF₃ | CH₂CH₃ | 0 |
| B-1121 | H | H | F | H | H | CF₂CF₂CF₂CF₃ | CH₂CH₃ | 0 |
| B-1122 | H | H | F | H | H | CH₂CH₂CH(CF₃)₂ | CH₂CH₃ | 0 |
| B-1123 | H | H | F | H | H | CF₂CF₂CF₂CF₂CF₃ | CH₂CH₃ | 0 |
| B-1124 | H | H | F | H | H | CH₂CF₂CF₂CF₂CF₃ | CH₂CH₃ | 0 |
| B-1125 | H | H | F | H | H | CH₂CH₂CH₂CH₂CF₃ | CH₂CH₃ | 0 |
| B-1126 | H | H | F | H | H | CH₂CF₂CF₂CF₂CHF₂ | CH₂CH₃ | 0 |
| B-1127 | H | H | F | H | H | CH₂CF₂CF(CF₃)CF₂C(CF₃)₃ | CH₂CH₃ | 0 |
| B-1128 | H | H | F | H | H | CH₂CH₂CH₂CH₂CH₂CF₃ | CH₂CH₃ | 0 |
| B-1129 | H | H | F | H | H | CH₂CH₂CH₂CH₂CH₂CH₂CF₃ | CH₂CH₃ | 0 |
| B-1130 | H | H | F | H | H | CF₂CHFOCH₃ | CH₂CH₃ | 0 |
| B-1131 | H | H | F | H | H | CF₂CHFOCH₂CH₃ | CH₂CH₃ | 0 |
| B-1132 | H | H | F | H | H | CH₂CH₂OCH₂CF₃ | CH₂CH₃ | 0 |
| B-1133 | H | H | F | H | H | CF₂CHFOCF₃ | CH₂CH₃ | 0 |
| B-1134 | H | H | F | H | H | CF₂CHFOCF₂CF₃ | CH₂CH₃ | 0 |
| B-1135 | H | H | F | H | H | CF₂CHFOCF₂CF₃ | CH₂CH₃ | 0 |
| B-1136 | H | H | F | H | H | CH₂CH=CH₂ | CH₂CH₃ | 0 |
| B-1137 | H | H | F | H | H | CH₂CH=CHCl | CH₂CH₃ | 0 |
| B-1138 | H | H | F | H | H | CH₂CH=CCl₂ | CH₂CH₃ | 0 |
| B-1139 | H | H | F | H | H | CH₂CH₂CF=CF₂ | CH₂CH₃ | 0 |
| B-1140 | H | H | F | H | H | CH₂CH₂CH=CF₂ | CH₂CH₃ | 0 |
| B-1141 | H | H | F | H | H | CH₂C≡CH | CH₂CH₃ | 0 |
| B-1142 | H | H | F | H | H | CH₂C≡CCH₃ | CH₂CH₃ | 0 |
| B-1143 | H | H | F | H | H | CH₂C≡CI | CH₂CH₃ | 0 |
| B-1144 | H | H | F | H | H | CH₂C≡CCF₃ | CH₂CH₃ | 0 |
| B-1145 | H | H | F | H | H | cyclobutyl | CH₂CH₃ | 0 |
| B-1146 | H | H | F | H | H | cyclopentyl | CH₂CH₃ | 0 |
| B-1147 | H | H | F | H | H | cyclohexyl | CH₂CH₃ | 0 |
| B-1148 | H | H | F | H | H | 4,4-difluorocyclohexyl | CH₂CH₃ | 0 |
| B-1149 | H | H | F | H | H | CH₂(cyclopropyl) | CH₂CH₃ | 0 |
| B-1150 | H | H | F | H | H | CH₂(cyclobutyl) | CH₂CH₃ | 0 |
| B-1151 | H | H | F | H | H | CH₂(cyclopentyl) | CH₂CH₃ | 0 |
| B-1152 | H | H | F | H | H | CH₂CH₂(cyclopropyl) | CH₂CH₃ | 0 |
| B-1153 | H | H | F | H | H | CH₂(2,2-difluorocyclopropyl) | CH₂CH₃ | 0 |
| B-1154 | H | H | F | H | H | CH₂(2,2-dichlorocyclopropyl) | CH₂CH₃ | 0 |

TABLE 113

| Compound | R¹ | R² | R³ | R⁴ | R⁵ | R⁶ | R¹⁶ | n |
|---|---|---|---|---|---|---|---|---|
| B-1155 | H | H | F | H | H | CH$_2$(4,4-difluorocyclohexyl) | CH$_2$CH$_3$ | 0 |
| B-1156 | H | H | F | H | H | CH$_2$CH$_2$(2,2-difluorocyclopropyl) | CH$_2$CH$_3$ | 0 |
| B-1157 | H | H | F | H | H | CH$_2$CH$_2$(2,2-dichlorocyclopropyl) | CH$_2$CH$_3$ | 0 |
| B-1158 | H | H | F | H | H | CH$_2$SCH$_3$ | CH$_2$CH$_3$ | 0 |
| B-1159 | H | H | F | H | H | CH$_2$SCH$_2$CH$_3$ | CH$_2$CH$_3$ | 0 |
| B-1160 | H | H | F | H | H | CH$_2$CH$_2$SCH$_3$ | CH$_2$CH$_3$ | 0 |
| B-1161 | H | H | F | H | H | CH$_2$CH$_2$SCH$_2$CH$_3$ | CH$_2$CH$_3$ | 0 |
| B-1162 | H | H | F | H | H | CH$_2$CH$_2$CH$_2$SCH$_3$ | CH$_2$CH$_3$ | 0 |
| B-1163 | H | H | F | H | H | CH$_2$CH$_2$CH$_2$SCH$_2$CH$_3$ | CH$_2$CH$_3$ | 0 |
| B-1164 | H | H | F | H | H | CH(CH$_3$)SCH$_3$ | CH$_2$CH$_3$ | 0 |
| B-1165 | H | H | F | H | H | CH(CH$_3$)SCH$_2$CH$_3$ | CH$_2$CH$_3$ | 0 |
| B-1166 | H | H | F | H | H | CH$_2$CH(CH$_3$)SCH$_3$ | CH$_2$CH$_3$ | 0 |
| B-1167 | H | H | F | H | H | CH$_2$CH(CH$_3$)SCH$_2$CH$_3$ | CH$_2$CH$_3$ | 0 |
| B-1168 | H | H | F | H | H | CH(CH$_3$)CH$_2$CH$_2$SCH$_3$ | CH$_2$CH$_3$ | 0 |
| B-1169 | H | H | F | H | H | CH(CH$_3$)CH$_2$CH$_2$SCH$_2$CH$_3$ | CH$_2$CH$_3$ | 0 |
| B-1170 | H | H | F | H | H | CH$_2$CH(CH$_3$)CH$_2$SCH$_3$ | CH$_2$CH$_3$ | 0 |
| B-1171 | H | H | F | H | H | CH$_2$CH(CH$_3$)CH$_2$SCH$_2$CH$_3$ | CH$_2$CH$_3$ | 0 |
| B-1172 | H | H | F | H | H | CH$_2$CH$_2$CH(CH$_3$)SCH$_3$ | CH$_2$CH$_3$ | 0 |
| B-1173 | H | H | F | H | H | CH$_2$CH$_2$CH(CH$_3$)SCH$_2$CH$_3$ | CH$_2$CH$_3$ | 0 |
| B-1174 | H | H | F | H | H | CH$_2$SOCH$_3$ | CH$_2$CH$_3$ | 0 |
| B-1175 | H | H | F | H | H | CH$_2$CH$_2$SOCH$_3$ | CH$_2$CH$_3$ | 0 |
| B-1176 | H | H | F | H | H | CH$_2$CH$_2$CH$_2$SOCH$_3$ | CH$_2$CH$_3$ | 0 |
| B-1177 | H | H | F | H | H | CH(CH$_3$)SOCH$_3$ | CH$_2$CH$_3$ | 0 |
| B-1178 | H | H | F | H | H | CH$_2$CH(CH$_3$)SOCH$_3$ | CH$_2$CH$_3$ | 0 |
| B-1179 | H | H | F | H | H | CH(CH$_3$)CH$_2$CH$_2$SOCH$_3$ | CH$_2$CH$_3$ | 0 |
| B-1180 | H | H | F | H | H | CH$_2$CH(CH$_3$)CH$_2$SOCH$_3$ | CH$_2$CH$_3$ | 0 |
| B-1181 | H | H | F | H | H | CH$_2$CH$_2$CH(CH$_3$)SOCH$_3$ | CH$_2$CH$_3$ | 0 |
| B-1182 | H | H | F | H | H | CH$_2$SO$_2$CH$_3$ | CH$_2$CH$_3$ | 0 |
| B-1183 | H | H | F | H | H | CH$_2$CH$_2$SO$_2$CH$_3$ | CH$_2$CH$_3$ | 0 |
| B-1184 | H | H | F | H | H | CH$_2$CH$_2$CH$_2$SO$_2$CH$_3$ | CH$_2$CH$_3$ | 0 |
| B-1185 | H | H | F | H | H | CH(CH$_3$)SO$_2$CH$_3$ | CH$_2$CH$_3$ | 0 |
| B-1186 | H | H | F | H | H | CH$_2$CH(CH$_3$)SO$_2$CH$_3$ | CH$_2$CH$_3$ | 0 |
| B-1187 | H | H | F | H | H | CH(CH$_3$)CH$_2$CH$_2$SO$_2$CH$_3$ | CH$_2$CH$_3$ | 0 |
| B-1188 | H | H | F | H | H | CH$_2$CH(CH$_3$)CH$_2$SO$_2$CH$_3$ | CH$_2$CH$_3$ | 0 |
| B-1189 | H | H | F | H | H | CH$_2$CH$_2$CH(CH$_3$)SO$_2$CH$_3$ | CH$_2$CH$_3$ | 0 |
| B-1190 | H | H | F | H | H | CH$_2$SCF$_3$ | CH$_2$CH$_3$ | 0 |
| B-1191 | H | H | F | H | H | CH$_2$SCHF$_2$ | CH$_2$CH$_3$ | 0 |
| B-1192 | H | H | F | H | H | CH$_2$SCH$_2$CF$_3$ | CH$_2$CH$_3$ | 0 |
| B-1193 | H | H | F | H | H | CH$_2$SCH$_2$CHF$_2$ | CH$_2$CH$_3$ | 0 |
| B-1194 | H | H | F | H | H | CH$_2$SCF$_2$CF$_3$ | CH$_2$CH$_3$ | 0 |
| B-1195 | H | H | F | H | H | CH$_2$CH$_2$SCF$_3$ | CH$_2$CH$_3$ | 0 |
| B-1196 | H | H | F | H | H | CH$_2$CH$_2$SCH$_2$CF$_3$ | CH$_2$CH$_3$ | 0 |
| B-1197 | H | H | F | H | H | CH$_2$CH$_2$CH$_2$SCF$_3$ | CH$_2$CH$_3$ | 0 |
| B-1198 | H | H | F | H | H | CH$_2$CH$_2$CH$_2$SCH$_2$CF$_3$ | CH$_2$CH$_3$ | 0 |
| B-1199 | H | H | F | H | H | CH(CH$_3$)SCF$_3$ | CH$_2$CH$_3$ | 0 |
| B-1200 | H | H | F | H | H | CH(CH$_3$)SCH$_2$CF$_3$ | CH$_2$CH$_3$ | 0 |
| B-1201 | H | H | F | H | H | CH$_2$CH(CH$_3$)SCF$_3$ | CH$_2$CH$_3$ | 0 |
| B-1202 | H | H | F | H | H | CH$_2$CH(CH$_3$)SCH$_2$CF$_3$ | CH$_2$CH$_3$ | 0 |
| B-1203 | H | H | F | H | H | CH(CH$_3$)CH$_2$CH$_2$SCF$_3$ | CH$_2$CH$_3$ | 0 |
| B-1204 | H | H | F | H | H | CH(CH$_3$)CH$_2$CH$_2$SCH$_2$CF$_3$ | CH$_2$CH$_3$ | 0 |
| B-1205 | H | H | F | H | H | CH$_2$CH(CH$_3$)CH$_2$SCF$_3$ | CH$_2$CH$_3$ | 0 |
| B-1206 | H | H | F | H | H | CH$_2$CH(CH$_3$)CH$_2$SCH$_2$CF$_3$ | CH$_2$CH$_3$ | 0 |
| B-1207 | H | H | F | H | H | CH$_2$CH$_2$CH(CH$_3$)SCF$_3$ | CH$_2$CH$_3$ | 0 |
| B-1208 | H | H | F | H | H | CH$_2$CH$_2$CH(CH$_3$)SCH$_2$CF$_3$ | CH$_2$CH$_3$ | 0 |
| B-1209 | H | H | F | H | H | CH$_2$SOCF$_3$ | CH$_2$CH$_3$ | 0 |
| B-1210 | H | H | F | H | H | CH$_2$CH$_2$SOCF$_3$ | CH$_2$CH$_3$ | 0 |
| B-1211 | H | H | F | H | H | CH$_2$CH$_2$CH$_2$SOCF$_3$ | CH$_2$CH$_3$ | 0 |
| B-1212 | H | H | F | H | H | CH(CH$_3$)SOCF$_3$ | CH$_2$CH$_3$ | 0 |
| B-1213 | H | H | F | H | H | CH$_2$CH(CH$_3$)SOCF$_3$ | CH$_2$CH$_3$ | 0 |
| B-1214 | H | H | F | H | H | CH(CH$_3$)CH$_2$CH$_2$SOCF$_3$ | CH$_2$CH$_3$ | 0 |
| B-1215 | H | H | F | H | H | CH$_2$CH(CH$_3$)CH$_2$SOCF$_3$ | CH$_2$CH$_3$ | 0 |

TABLE 114

| Compound | R¹ | R² | R³ | R⁴ | R⁵ | R⁶ | R¹⁶ | n |
|---|---|---|---|---|---|---|---|---|
| B-1216 | H | H | F | H | H | CH$_2$CH$_2$CH(CH$_3$)SOCF$_3$ | CH$_2$CH$_3$ | 0 |
| B-1217 | H | H | F | H | H | CH$_2$SO$_2$CF$_3$ | CH$_2$CH$_3$ | 0 |
| B-1218 | H | H | F | H | H | CH$_2$CH$_2$SO$_2$CF$_3$ | CH$_2$CH$_3$ | 0 |
| B-1219 | H | H | F | H | H | CH$_2$CH$_2$CH$_2$SO$_2$CF$_3$ | CH$_2$CH$_3$ | 0 |
| B-1220 | H | H | F | H | H | CH(CH$_3$)SO$_2$CF$_3$ | CH$_2$CH$_3$ | 0 |
| B-1221 | H | H | F | H | H | CH$_2$CH(CH$_3$)SO$_2$CF$_3$ | CH$_2$CH$_3$ | 0 |
| B-1222 | H | H | F | H | H | CH(CH$_3$)CH$_2$CH$_2$SO$_2$CF$_3$ | CH$_2$CH$_3$ | 0 |
| B-1223 | H | H | F | H | H | CH$_2$CH(CH$_3$)CH$_2$SO$_2$CF$_3$ | CH$_2$CH$_3$ | 0 |
| B-1224 | H | H | F | H | H | CH$_2$CH$_2$CH(CH$_3$)SO$_2$CF$_3$ | CH$_2$CH$_3$ | 0 |

TABLE 114-continued

| Compound | $R^1$ | $R^2$ | $R^3$ | $R^4$ | $R^5$ | $R^6$ | $R^{16}$ | n |
|---|---|---|---|---|---|---|---|---|
| B-1225 | H | H | F | H | H | $CH_2C(=O)CH_3$ | $CH_2CH_3$ | 0 |
| B-1226 | H | H | F | H | H | $CH_2C(=O)CH_2CH_3$ | $CH_2CH_3$ | 0 |
| B-1227 | H | H | F | H | H | $CH_2C(=O)C(CH_3)_3$ | $CH_2CH_3$ | 0 |
| B-1228 | H | H | F | H | H | $CH_2CH_2C(=O)CH_3$ | $CH_2CH_3$ | 0 |
| B-1229 | H | H | F | H | H | $CH_2CH_2C(=O)C(CH_3)_3$ | $CH_2CH_3$ | 0 |
| B-1230 | H | H | F | H | H | $CH_2C(=O)CF_3$ | $CH_2CH_3$ | 0 |
| B-1231 | H | H | F | H | H | $CH_2CH_2C(=O)CF_3$ | $CH_2CH_3$ | 0 |
| B-1232 | H | H | F | H | H | $CH_2C(=O)OCH_3$ | $CH_2CH_3$ | 0 |
| B-1233 | H | H | F | H | H | $CH_2C(=O)OCH_2CH_3$ | $CH_2CH_3$ | 0 |
| B-1234 | H | H | F | H | H | $CH_2C(=O)OC(CH_3)_3$ | $CH_2CH_3$ | 0 |
| B-1235 | H | H | F | H | H | $CH_2CH_2C(=O)OCH_3$ | $CH_2CH_3$ | 0 |
| B-1236 | H | H | F | H | H | $CH_2CH_2C(=O)OCH_2CH_3$ | $CH_2CH_3$ | 0 |
| B-1237 | H | H | F | H | H | $CH_2CH_2C(=O)OC(CH_3)_3$ | $CH_2CH_3$ | 0 |
| B-1238 | H | H | F | H | H | $CH_2C(=O)NH_2$ | $CH_2CH_3$ | 0 |
| B-1239 | H | H | F | H | H | $CH_2CH_2C(=O)NH_2$ | $CH_2CH_3$ | 0 |
| B-1240 | H | H | F | H | H | $CH_2C(=O)NHCH_3$ | $CH_2CH_3$ | 0 |
| B-1241 | H | H | F | H | H | $CH_2C(=O)NHCH(CH_3)_2$ | $CH_2CH_3$ | 0 |
| B-1242 | H | H | F | H | H | $CH_2CH_2C(=O)NHCH_3$ | $CH_2CH_3$ | 0 |
| B-1243 | H | H | F | H | H | $CH_2CH_2C(=O)NHCH(CH_3)_2$ | $CH_2CH_3$ | 0 |
| B-1244 | H | H | F | H | H | $CH_2C(=O)NHCH_2CHF_2$ | $CH_2CH_3$ | 0 |
| B-1245 | H | H | F | H | H | $CH_2C(=O)NHCH_2CF_3$ | $CH_2CH_3$ | 0 |
| B-1246 | H | H | F | H | H | $CH_2CH_2C(=O)NHCH_2CHF_2$ | $CH_2CH_3$ | 0 |
| B-1247 | H | H | F | H | H | $CH_2CH_2C(=O)NHCH_2CF_3$ | $CH_2CH_3$ | 0 |
| B-1248 | H | H | F | H | H | $CH_2C(=O)N(CH_3)_2$ | $CH_2CH_3$ | 0 |
| B-1249 | H | H | F | H | H | $CH_2C(=O)N(CH_2CH_3)_2$ | $CH_2CH_3$ | 0 |
| B-1250 | H | H | F | H | H | $CH_2CH_2C(=O)N(CH_3)_2$ | $CH_2CH_3$ | 0 |
| B-1251 | H | H | F | H | H | $CH_2CH_2C(=O)N(CH_2CH_3)_2$ | $CH_2CH_3$ | 0 |
| B-1252 | H | H | F | H | H | $CH_2CH_2CH$ | $CH_2CH_3$ | 0 |
| B-1253 | H | H | F | H | H | $CH_2CH(OH)CH_3$ | $CH_2CH_3$ | 0 |
| B-1254 | H | H | F | H | H | $CH_2CH_2CH_2OH$ | $CH_2CH_3$ | 0 |
| B-1255 | H | H | F | H | H | $CH_2CH(OH)CH_2CH_3$ | $CH_2CH_3$ | 0 |
| B-1256 | H | H | F | H | H | $CH_2CH(OH)C(CH_3)_3$ | $CH_2CH_3$ | 0 |
| B-1257 | H | H | F | H | H | $CH_2CH_2CH(OH)CH_3$ | $CH_2CH_3$ | 0 |
| B-1258 | H | H | F | H | H | $CH_2CH_2CH(OH)C(CH_3)_3$ | $CH_2CH_3$ | 0 |
| B-1259 | H | H | F | H | H | $CH_2C(=NOH)CH_3$ | $CH_2CH_3$ | 0 |
| B-1260 | H | H | F | H | H | $CH_2C(=NOH)CH_2CH_3$ | $CH_2CH_3$ | 0 |
| B-1261 | H | H | F | H | H | $CH_2C(=NOH)C(CH_3)_3$ | $CH_2CH_3$ | 0 |
| B-1262 | H | H | F | H | H | $CH_2C(=NOCH_3)CH_3$ | $CH_2CH_3$ | 0 |
| B-1263 | H | H | F | H | H | $CH_2C(=NOCH_3)CH_2CH_3$ | $CH_2CH_3$ | 0 |
| B-1264 | H | H | F | H | H | $CH_2C(=NOCH_2CH_3)CH_3$ | $CH_2CH_3$ | 0 |
| B-1265 | H | H | F | H | H | $CH_2C(=NOCH_2CH_3)CH_2CH_3$ | $CH_2CH_3$ | 0 |
| B-1266 | H | H | F | H | H | $CH_2C(=NOCH_2CF_3)CH_3$ | $CH_2CH_3$ | 0 |
| B-1267 | H | H | F | H | H | $CH_2C(=NOCH_2CF_3)CH_2CH_3$ | $CH_2CH_3$ | 0 |
| B-1268 | H | H | F | H | H | $CH_2Ph$ | $CH_2CH_3$ | 0 |
| B-1269 | H | H | F | H | H | $CH_2(2-F)Ph$ | $CH_2CH_3$ | 0 |
| B-1270 | H | H | F | H | H | $CH_2(3-F)Ph$ | $CH_2CH_3$ | 0 |
| B-1271 | H | H | F | H | H | $CH_2(4-F)Ph$ | $CH_2CH_3$ | 0 |
| B-1272 | H | H | F | H | H | $CH_2(2-Cl)Ph$ | $CH_2CH_3$ | 0 |
| B-1273 | H | H | F | H | H | $CH_2(3-Cl)Ph$ | $CH_2CH_3$ | 0 |
| B-1274 | H | H | F | H | H | $CH_2(4-Cl)Ph$ | $CH_2CH_3$ | 0 |
| B-1275 | H | H | F | H | H | $CH_2(2-CF_3)Ph$ | $CH_2CH_3$ | 0 |
| B-1276 | H | H | F | H | H | $CH_2(3-CF_3)Ph$ | $CH_2CH_3$ | 0 |

TABLE 115

| Compound | $R^1$ | $R^2$ | $R^3$ | $R^4$ | $R^5$ | $R^6$ | $R^{16}$ | n |
|---|---|---|---|---|---|---|---|---|
| B-1277 | H | H | F | H | H | $CH_2(4-CF_3)Ph$ | $CH_2CH_3$ | 0 |
| B-1278 | H | H | F | H | H | $CH_2(naphthalen-2-yl)$ | $CH_2CH_3$ | 0 |
| B-1279 | H | H | F | H | H | $CH_2(naphthalen-2-yl)$ | $CH_2CH_3$ | 0 |
| B-1280 | H | H | F | H | H | $CH_2CH_2Ph$ | $CH_2CH_3$ | 0 |
| B-1281 | Cl | H | H | H | H | H | H | 0 |
| B-1282 | Cl | H | H | H | H | $CH_3$ | H | 0 |
| B-1283 | Cl | H | H | H | H | $CH_2CH_3$ | H | 0 |
| B-1284 | Cl | H | H | H | H | $CH(CH_3)_2$ | H | 0 |
| B-1285 | Cl | H | H | H | H | $CH_2CH_2CH_3$ | H | 0 |
| B-1286 | Cl | H | H | H | H | $CH_2CH(CH_3)_2$ | H | 0 |
| B-1287 | Cl | H | H | H | H | $CH_2C(CH_3)_3$ | H | 0 |
| B-1288 | Cl | H | H | H | H | $CH(CH_3)CH_2CH_3$ | H | 0 |
| B-1289 | Cl | H | H | H | H | $CH_2(CH_2)_2CH_3$ | H | 0 |
| B-1290 | Cl | H | H | H | H | $CH_2(CH_2)_3CH_3$ | H | 0 |
| B-1291 | Cl | H | H | H | H | $CH_2(CH_2)_4CH_3$ | H | 0 |
| B-1292 | Cl | H | H | H | H | $CH_2(CH_2)_6CH_3$ | H | 0 |
| B-1293 | Cl | H | H | H | H | $CH_2OCH_3$ | H | 0 |
| B-1294 | Cl | H | H | H | H | $CH_2OCH_2CH_3$ | H | 0 |

TABLE 115-continued

| Compound | $R^1$ | $R^2$ | $R^3$ | $R^4$ | $R^5$ | $R^6$ | $R^{16}$ | n |
|---|---|---|---|---|---|---|---|---|
| B-1295 | Cl | H | H | H | H | $CH_2CH_2OCH_3$ | H | 0 |
| B-1296 | Cl | H | H | H | H | $CH_2CH_2OCH_2CH_3$ | H | 0 |
| B-1297 | Cl | H | H | H | H | $CF_3$ | H | 0 |
| B-1298 | Cl | H | H | H | H | $CHF_2$ | H | 0 |
| B-1299 | Cl | H | H | H | H | $CH_2CF_3$ | H | 0 |
| B-1300 | Cl | H | H | H | H | $CH_2CHF_2$ | H | 0 |
| B-1301 | Cl | H | H | H | H | $CH_2CClF_2$ | H | 0 |
| B-1302 | Cl | H | H | H | H | $CH_2CBrF_2$ | H | 0 |
| B-1303 | Cl | H | H | H | H | $CF_2CF_3$ | H | 0 |
| B-1304 | Cl | H | H | H | H | $CF_2CHF_2$ | H | 0 |
| B-1305 | Cl | H | H | H | H | $CH_2CH_2CF_3$ | H | 0 |
| B-1306 | Cl | H | H | H | H | $CH_2CF_2CF_3$ | H | 0 |
| B-1307 | Cl | H | H | H | H | $CH_2CF_2CHF_2$ | H | 0 |
| B-1308 | Cl | H | H | H | H | $CF_2CHFCF_3$ | H | 0 |
| B-1309 | Cl | H | H | H | H | $CF_2CF_2CF_3$ | H | 0 |
| B-1310 | Cl | H | H | H | H | $CH_2CF_2CF_2CF_3$ | H | 0 |
| B-1311 | Cl | H | H | H | H | $CH_2CF_2CHFCF_3$ | H | 0 |
| B-1312 | Cl | H | H | H | H | $CH_2CH_2CH_2CF_3$ | H | 0 |
| B-1313 | Cl | H | H | H | H | $CH_2CH_2CF_2CF_3$ | H | 0 |
| B-1314 | Cl | H | H | H | H | $CF_2CF_2CF_2CF_3$ | H | 0 |
| B-1315 | Cl | H | H | H | H | $CH_2CH_2CH(CF_3)_2$ | H | 0 |
| B-1316 | Cl | H | H | H | H | $CF_2CF_2CF_2CF_2CF_3$ | H | 0 |
| B-1317 | Cl | H | H | H | H | $CH_2CF_2CF_2CF_2CF_3$ | H | 0 |
| B-1318 | Cl | H | H | H | H | $CH_2CH_2CH_2CH_2CF_3$ | H | 0 |
| B-1319 | Cl | H | H | H | H | $CH_2CF_2CF_2CF_2CHF_2$ | H | 0 |
| B-1320 | Cl | H | H | H | H | $CH_2CF_2CF(CF_3)CF_2C(CF_3)_3$ | H | 0 |
| B-1321 | Cl | H | H | H | H | $CH_2CH_2CH_2CH_2CH_2CF_3$ | H | 0 |
| B-1322 | Cl | H | H | H | H | $CH_2CH_2CH_2CH_2CH_2CH_2CF_3$ | H | 0 |
| B-1323 | Cl | H | H | H | H | $CF_2CHFOCH_3$ | H | 0 |
| B-1324 | Cl | H | H | H | H | $CF_2CHFOCH_2CH_3$ | H | 0 |
| B-1325 | Cl | H | H | H | H | $CH_2CH_2OCH_2CF_3$ | H | 0 |
| B-1326 | Cl | H | H | H | H | $CF_2CHFCF_3$ | H | 0 |
| B-1327 | Cl | H | H | H | H | $CF_2CHFOCF_2CF_3$ | H | 0 |
| B-1328 | Cl | H | H | H | H | $CF_2CHFOCF_2CF_2CF_3$ | H | 0 |
| B-1329 | Cl | H | H | H | H | $CH_2CH=CH_2$ | H | 0 |
| B-1330 | Cl | H | H | H | H | $CH_2CH=CHCl$ | H | 0 |
| B-1331 | Cl | H | H | H | H | $CH_2CH=CCl_2$ | H | 0 |
| B-1332 | Cl | H | H | H | H | $CH_2CH_2CF=CF_2$ | H | 0 |
| B-1333 | Cl | H | H | H | H | $CH_2CH_2CH=CF_2$ | H | 0 |
| B-1334 | Cl | H | H | H | H | $CH_2C\equiv CH$ | H | 0 |
| B-1335 | Cl | H | H | H | H | $CH_2C\equiv CCH_3$ | H | 0 |
| B-1336 | Cl | H | H | H | H | $CH_2C\equiv Cl$ | H | 0 |
| B-1337 | Cl | H | H | H | H | $CH_2C\equiv CCF_3$ | H | 0 |

TABLE 116

| Compound | $R^1$ | $R^2$ | $R^3$ | $R^4$ | $R^5$ | $R^6$ | $R^{16}$ | n |
|---|---|---|---|---|---|---|---|---|
| B-1338 | Cl | H | H | H | H | cyclobutyl | H | 0 |
| B-1339 | Cl | H | H | H | H | cyclopentyl | H | 0 |
| B-1340 | Cl | H | H | H | H | cyclohexyl | H | 0 |
| B-1341 | Cl | H | H | H | H | 4,4-difluorocyclohexyl | H | 0 |
| B-1342 | Cl | H | H | H | H | $CH_2$(cyclopropyl) | H | 0 |
| B-1343 | Cl | H | H | H | H | $CH_2$(cyclobutyl) | H | 0 |
| B-1344 | Cl | H | H | H | H | $CH_2$(cyclopentyl) | H | 0 |
| B-1345 | Cl | H | H | H | H | $CH_2CH_2$(cyclopropyl) | H | 0 |
| B-1346 | Cl | H | H | H | H | $CH_2$(2,2-difluorocyclopropyl) | H | 0 |
| B-1347 | Cl | H | H | H | H | $CH_2$(2,2-dichlorocyclopropyl) | H | 0 |
| B-1348 | Cl | H | H | H | H | $CH_2$(4,4-difluorocyclohexyl) | H | 0 |
| B-1349 | Cl | H | H | H | H | $CH_2CH_2$(2,2-difluorocyclopropyl) | H | 0 |
| B-1350 | Cl | H | H | H | H | $CH_2CH_2$(2,2-dichlorocyclopropyl) | H | 0 |
| B-1351 | Cl | H | H | H | H | $CH_2SCH_3$ | H | 0 |
| B-1352 | Cl | H | H | H | H | $CH_2SCH_2CH_3$ | H | 0 |
| B-1353 | Cl | H | H | H | H | $CH_2CH_2SCH_3$ | H | 0 |
| B-1354 | Cl | H | H | H | H | $CH_2CH_2SCH_2CH_3$ | H | 0 |
| B-1355 | Cl | H | H | H | H | $CH_2CH_2CH_2SCH_3$ | H | 0 |
| B-1356 | Cl | H | H | H | H | $CH_2CH_2CH_2SCH_2CH_3$ | H | 0 |
| B-1357 | Cl | H | H | H | H | $CH(CH_3)SCH_3$ | H | 0 |
| B-1358 | Cl | H | H | H | H | $CH(CH_3)SCH_2CH_3$ | H | 0 |
| B-1359 | Cl | H | H | H | H | $CH_2CH(CH_3)SCH_3$ | H | 0 |
| B-1360 | Cl | H | H | H | H | $CH_2CH(CH_3)SCH_2CH_3$ | H | 0 |
| B-1361 | Cl | H | H | H | H | $CH(CH_3)CH_2CH_2SCH_3$ | H | 0 |
| B-1362 | Cl | H | H | H | H | $CH(CH_3)CH_2CH_2SCH_2CH_3$ | H | 0 |
| B-1363 | Cl | H | H | H | H | $CH_2CH(CH_3)CH_2SCH_3$ | H | 0 |
| B-1364 | Cl | H | H | H | H | $CH_2CH(CH_3)CH_2SCH_2CH_3$ | H | 0 |

TABLE 116-continued

| Compound | $R^1$ | $R^2$ | $R^3$ | $R^4$ | $R^5$ | $R^6$ | $R^{16}$ | n |
|---|---|---|---|---|---|---|---|---|
| B-1365 | Cl | H | H | H | H | $CH_2CH_2CH(CH_3)SCH_3$ | H | 0 |
| B-1366 | Cl | H | H | H | H | $CH_2CH_2CH(CH_3)SCH_2CH_3$ | H | 0 |
| B-1367 | Cl | H | H | H | H | $CH_2SOCH_3$ | H | 0 |
| B-1368 | Cl | H | H | H | H | $CH_2CH_2SOCH_3$ | H | 0 |
| B-1369 | Cl | H | H | H | H | $CH_2CH_2CH_2SOCH_3$ | H | 0 |
| B-1370 | Cl | H | H | H | H | $CH(CH_3)SOCH_3$ | H | 0 |
| B-1371 | Cl | H | H | H | H | $CH_2CH(CH_3)SOCH_3$ | H | 0 |
| B-1372 | Cl | H | H | H | H | $CH(CH_3)CH_2CH_2SOCH_3$ | H | 0 |
| B-1373 | Cl | H | H | H | H | $CH_2CH(CH_3)CH_2SOCH_3$ | H | 0 |
| B-1374 | Cl | H | H | H | H | $CH_2CH_2CH(CH_3)SOCH_3$ | H | 0 |
| B-1375 | Cl | H | H | H | H | $CH_2SO_2CH_3$ | H | 0 |
| B-1376 | Cl | H | H | H | H | $CH_2CH_2SO_2CH_3$ | H | 0 |
| B-1377 | Cl | H | H | H | H | $CH_2CH_2CH_2SO_2CH_3$ | H | 0 |
| B-1378 | Cl | H | H | H | H | $CH(CH_3)SO_2CH_3$ | H | 0 |
| B-1379 | Cl | H | H | H | H | $CH_2CH(CH_3)SO_2CH_3$ | H | 0 |
| B-1380 | Cl | H | H | H | H | $CH(CH_3)CH_2CH_2SO_2CH_3$ | H | 0 |
| B-1381 | Cl | H | H | H | H | $CH_2CH(CH_3)CH_2SO_2CH_3$ | H | 0 |
| B-1382 | Cl | H | H | H | H | $CH_2CH_2CH(CH_3)SO_2CH_3$ | H | 0 |
| B-1383 | Cl | H | H | H | H | $CH_2SCF_3$ | H | 0 |
| B-1384 | Cl | H | H | H | H | $CH_2SCHF_2$ | H | 0 |
| B-1385 | Cl | H | H | H | H | $CH_2SCH_2CF_3$ | H | 0 |
| B-1386 | Cl | H | H | H | H | $CH_2SCH_2CHF_2$ | H | 0 |
| B-1387 | Cl | H | H | H | H | $CH_2SCF_2CF_3$ | H | 0 |
| B-1388 | Cl | H | H | H | H | $CH_2CH_2SCF_3$ | H | 0 |
| B-1389 | Cl | H | H | H | H | $CH_2CH_2SCH_2CF_3$ | H | 0 |
| B-1390 | Cl | H | H | H | H | $CH_2CH_2CH_2SCF_3$ | H | 0 |
| B-1391 | Cl | H | H | H | H | $CH_2CH_2CH_2SCH_2CF_3$ | H | 0 |
| B-1392 | Cl | H | H | H | H | $CH(CH_3)SCF_3$ | H | 0 |
| B-1393 | Cl | H | H | H | H | $CH(CH_3)SCH_2CF_3$ | H | 0 |
| B-1394 | Cl | H | H | H | H | $CH_2CH(CH_3)SCF_3$ | H | 0 |
| B-1395 | Cl | H | H | H | H | $CH_2CH(CH_3)SCH_2CF_3$ | H | 0 |
| B-1396 | Cl | H | H | H | H | $CH(CH_3)CH_2CH_2SCF_3$ | H | 0 |
| B-1397 | Cl | H | H | H | H | $CH(CH_3)CH_2CH_2SCH_2CF_3$ | H | 0 |
| B-1398 | Cl | H | H | H | H | $CH_2CH(CH_3)CH_2SCF_3$ | H | 0 |

TABLE 117

| Compound | $R^1$ | $R^2$ | $R^3$ | $R^4$ | $R^5$ | $R^6$ | $R^{16}$ | n |
|---|---|---|---|---|---|---|---|---|
| B-1399 | Cl | H | H | H | H | $CH_2CH(CH_3)CH_2SCH_2CF_3$ | H | 0 |
| B-1400 | Cl | H | H | H | H | $CH_2CH_2CH(CH_3)SCF_3$ | H | 0 |
| B-1401 | Cl | H | H | H | H | $CH_2CH_2CH(CH_3)SCH_2CF_3$ | H | 0 |
| B-1402 | Cl | H | H | H | H | $CH_2SOCF_3$ | H | 0 |
| B-1403 | Cl | H | H | H | H | $CH_2CH_2SOCF_3$ | H | 0 |
| B-1404 | Cl | H | H | H | H | $CH_2CH_2CH_2SOCF_3$ | H | 0 |
| B-1405 | Cl | H | H | H | H | $CH(CH_3)SOCF_3$ | H | 0 |
| B-1406 | Cl | H | H | H | H | $CH_2CH(CH_3)SOCF_3$ | H | 0 |
| B-1407 | Cl | H | H | H | H | $CH(CH_3)CH_2CH_2SOCF_3$ | H | 0 |
| B-1408 | Cl | H | H | H | H | $CH_2CH(CH_3)CH_2SOCF_3$ | H | 0 |
| B-1409 | Cl | H | H | H | H | $CH_2CH_2CH(CH_3)SOCF_3$ | H | 0 |
| B-1410 | Cl | H | H | H | H | $CH_2SO_2CF_3$ | H | 0 |
| B-1411 | Cl | H | H | H | H | $CH_2CH_2SO_2CF_3$ | H | 0 |
| B-1412 | Cl | H | H | H | H | $CH_2CH_2CH_2SO_2CF_3$ | H | 0 |
| B-1413 | Cl | H | H | H | H | $CH(CH_3)SO_2CF_3$ | H | 0 |
| B-1414 | Cl | H | H | H | H | $CH_2CH(CH_3)SO_2CF_3$ | H | 0 |
| B-1415 | Cl | H | H | H | H | $CH(CH_3)CH_2CH_2SO_2CF_3$ | H | 0 |
| B-1416 | Cl | H | H | H | H | $CH_2CH(CH_3)CH_2SO_2CF_3$ | H | 0 |
| B-1417 | Cl | H | H | H | H | $CH_2CH_2CH(CH_3)SO_2CF_3$ | H | 0 |
| B-1418 | Cl | H | H | H | H | $CH_2C(=O)CH_3$ | H | 0 |
| B-1419 | Cl | H | H | H | H | $CH_2C(=O)CH_2CH_3$ | H | 0 |
| B-1420 | Cl | H | H | H | H | $CH_2C(=O)C(CH_3)_3$ | H | 0 |
| B-1421 | Cl | H | H | H | H | $CH_2CH_2C(=O)CH_3$ | H | 0 |
| B-1422 | Cl | H | H | H | H | $CH_2CH_2C(=O)C(CH_3)_3$ | H | 0 |
| B-1423 | Cl | H | H | H | H | $CH_2C(=O)CF_3$ | H | 0 |
| B-1424 | Cl | H | H | H | H | $CH_2CH_2C(=O)CF_3$ | H | 0 |
| B-1425 | Cl | H | H | H | H | $CH_2C(=O)OCH_3$ | H | 0 |
| B-1426 | Cl | H | H | H | H | $CH_2C(=O)OCH_2CH_3$ | H | 0 |
| B-1427 | Cl | H | H | H | H | $CH_2C(=O)OC(CH_3)_3$ | H | 0 |
| B-1428 | Cl | H | H | H | H | $CH_2CH_2C(=O)OCH_3$ | H | 0 |
| B-1429 | Cl | H | H | H | H | $CH_2CH_2C(=O)OCH_2CH_3$ | H | 0 |
| B-1430 | Cl | H | H | H | H | $CH_2CH_2C(=O)OC(CH_3)_3$ | H | 0 |
| B-1431 | Cl | H | H | H | H | $CH_2C(=O)NH_2$ | H | 0 |
| B-1432 | Cl | H | H | H | H | $CH_2CH_2C(=O)NH_2$ | H | 0 |
| B-1433 | Cl | H | H | H | H | $CH_2C(=O)NHCH_3$ | H | 0 |
| B-1434 | Cl | H | H | H | H | $CH_2C(=O)NHCH(CH_3)_2$ | H | 0 |

TABLE 117-continued

| Compound | R¹ | R² | R³ | R⁴ | R⁵ | R⁶ | R¹⁶ | n |
|---|---|---|---|---|---|---|---|---|
| B-1435 | Cl | H | H | H | H | CH$_2$CH$_2$C(=O)NHCH$_3$ | H | 0 |
| B-1436 | Cl | H | H | H | H | CH$_2$CH$_2$C(=O)NHCH(CH$_3$)$_2$ | H | 0 |
| B-1437 | Cl | H | H | H | H | CH$_2$C(=O)NHCH$_2$CHF$_2$ | H | 0 |
| B-1438 | Cl | H | H | H | H | CH$_2$C(=O)NHCH$_2$CF$_3$ | H | 0 |
| B-1439 | Cl | H | H | H | H | CH$_2$CH$_2$C(=O)NHCH$_2$CHF$_2$ | H | 0 |
| B-1440 | Cl | H | H | H | H | CH$_2$CH$_2$C(=O)NHCH$_2$CF$_3$ | H | 0 |
| B-1441 | Cl | H | H | H | H | CH$_2$C(=O)N(CH$_3$)$_2$ | H | 0 |
| B-1442 | Cl | H | H | H | H | CH$_2$C(=O)N(CH$_2$CH$_3$)$_2$ | H | 0 |
| B-1443 | Cl | H | H | H | H | CH$_2$CH$_2$C(=O)N(CH$_3$)$_2$ | H | 0 |
| B-1444 | Cl | H | H | H | H | CH$_2$CH$_2$C(=O)N(CH$_2$CH$_3$)$_2$ | H | 0 |
| B-1445 | Cl | H | H | H | H | CH$_2$CH$_2$OH | H | 0 |
| B-1446 | Cl | H | H | H | H | CH$_2$CH(OH)CH$_3$ | H | 0 |
| B-1447 | Cl | H | H | H | H | CH$_2$CH$_2$CH$_2$OH | H | 0 |
| B-1448 | Cl | H | H | H | H | CH$_2$CH(OH)CH$_2$CH$_3$ | H | 0 |
| B-1449 | Cl | H | H | H | H | CH$_2$CH(OH)C(CH$_3$)$_3$ | H | 0 |
| B-1450 | Cl | H | H | H | H | CH$_2$CH$_2$CH(OH)CH$_3$ | H | 0 |
| B-1451 | Cl | H | H | H | H | CH$_2$CH$_2$CH(OH)C(CH$_3$)$_3$ | H | 0 |
| B-1452 | Cl | H | H | H | H | CH$_2$C(=NOH)CH$_3$ | H | 0 |
| B-1453 | Cl | H | H | H | H | CH$_2$C(=NOH)CH$_2$CH$_3$ | H | 0 |
| B-1454 | Cl | H | H | H | H | CH$_2$C(=NOH)C(CH$_3$)$_3$ | H | 0 |
| B-1455 | Cl | H | H | H | H | CH$_2$C(=NOCH$_3$)CH$_3$ | H | 0 |
| B-1456 | Cl | H | H | H | H | CH$_2$C(=NOCH$_3$)CH$_2$CH$_3$ | H | 0 |
| B-1457 | Cl | H | H | H | H | CH$_2$C(=NOCH$_2$CH$_3$)CH$_3$ | H | 0 |
| B-1458 | Cl | H | H | H | H | CH$_2$C(=NOCH$_2$CH$_3$)CH$_2$CH$_3$ | H | 0 |
| B-1459 | Cl | H | H | H | H | CH$_2$C(=NOCH$_2$CF$_3$)CH$_3$ | H | 0 |

TABLE 118

| Compound | R¹ | R² | R³ | R⁴ | R⁵ | R⁶ | R¹⁶ | n |
|---|---|---|---|---|---|---|---|---|
| B-1460 | Cl | H | H | H | H | CH$_2$C(=NOCH$_2$CF$_3$)CH$_2$CH$_3$ | H | 0 |
| B-1461 | Cl | H | H | H | H | CH$_2$Ph | H | 0 |
| B-1462 | Cl | H | H | H | H | CH$_2$(2-F)Ph | H | 0 |
| B-1463 | Cl | H | H | H | H | CH$_2$(3-F)Ph | H | 0 |
| B-1464 | Cl | H | H | H | H | CH$_2$(4-F)Ph | H | 0 |
| B-1465 | Cl | H | H | H | H | CH$_2$(2-Cl)Ph | H | 0 |
| B-1466 | Cl | H | H | H | H | CH$_2$(3-Cl)Ph | H | 0 |
| B-1467 | Cl | H | H | H | H | CH$_2$(4-Cl)Ph | H | 0 |
| B-1468 | Cl | H | H | H | H | CH$_2$(2-CF$_3$)Ph | H | 0 |
| B-1469 | Cl | H | H | H | H | CH$_2$(3-CF$_3$)Ph | H | 0 |
| B-1470 | Cl | H | H | H | H | CH$_2$(4-CF$_3$)Ph | H | 0 |
| B-1471 | Cl | H | H | H | H | CH$_2$(naphthalen-1-yl) | H | 0 |
| B-1472 | Cl | H | H | H | H | CH$_2$(naphthalen-2-yl) | H | 0 |
| B-1473 | Cl | H | H | H | H | CH$_2$CH$_2$Ph | H | 0 |
| B-1474 | Cl | H | H | H | H | H | CH$_2$CH$_3$ | 0 |
| B-1475 | Cl | H | H | H | H | CH$_3$ | CH$_2$CH$_3$ | 0 |
| B-1476 | Cl | H | H | H | H | CH$_2$CH$_3$ | CH$_2$CH$_3$ | 0 |
| B-1477 | Cl | H | H | H | H | CH(CH$_3$)$_2$ | CH$_2$CH$_3$ | 0 |
| B-1478 | Cl | H | H | H | H | CH$_2$CH$_2$CH$_3$ | CH$_2$CH$_3$ | 0 |
| B-1479 | Cl | H | H | H | H | CH$_2$CH(CH$_3$)$_2$ | CH$_2$CH$_3$ | 0 |
| B-1480 | Cl | H | H | H | H | CH$_2$C(CH$_3$)$_3$ | CH$_2$CH$_3$ | 0 |
| B-1481 | Cl | H | H | H | H | CH(CH$_3$)CH$_2$CH$_3$ | CH$_2$CH$_3$ | 0 |
| B-1482 | Cl | H | H | H | H | CH$_2$(CH$_2$)$_2$CH$_3$ | CH$_2$CH$_3$ | 0 |
| B-1483 | Cl | H | H | H | H | CH$_2$(CH$_2$)$_3$CH$_3$ | CH$_2$CH$_3$ | 0 |
| B-1484 | Cl | H | H | H | H | CH$_2$(CH$_2$)$_4$CH$_3$ | CH$_2$CH$_3$ | 0 |
| B-1485 | Cl | H | H | H | H | CH$_2$(CH$_2$)$_6$CH$_3$ | CH$_2$CH$_3$ | 0 |
| B-1486 | Cl | H | H | H | H | CH$_2$OCH$_3$ | CH$_2$CH$_3$ | 0 |
| B-1487 | Cl | H | H | H | H | CH$_2$OCH$_2$CH$_3$ | CH$_2$CH$_3$ | 0 |
| B-1488 | Cl | H | H | H | H | CH$_2$CH$_2$OCH$_3$ | CH$_2$CH$_3$ | 0 |
| B-1489 | Cl | H | H | H | H | CH$_2$CH$_2$OCH$_2$CH$_3$ | CH$_2$CH$_3$ | 0 |
| B-1490 | Cl | H | H | H | H | CF$_3$ | CH$_2$CH$_3$ | 0 |
| B-1491 | Cl | H | H | H | H | CHF$_2$ | CH$_2$CH$_3$ | 0 |
| B-1492 | Cl | H | H | H | H | CH$_2$CF$_3$ | CH$_2$CH$_3$ | 0 |
| B-1493 | Cl | H | H | H | H | CH$_2$CHF$_2$ | CH$_2$CH$_3$ | 0 |
| B-1494 | Cl | H | H | H | H | CH$_2$CClF$_2$ | CH$_2$CH$_3$ | 0 |
| B-1495 | Cl | H | H | H | H | CH$_2$CBrF$_2$ | CH$_2$CH$_3$ | 0 |
| B-1496 | Cl | H | H | H | H | CF$_2$CF$_3$ | CH$_2$CH$_3$ | 0 |
| B-1497 | Cl | H | H | H | H | CF$_2$CHF$_2$ | CH$_2$CH$_3$ | 0 |
| B-1498 | Cl | H | H | H | H | CH$_2$CH$_2$CF$_3$ | CH$_2$CH$_3$ | 0 |
| B-1499 | Cl | H | H | H | H | CH$_2$CF$_2$CF$_3$ | CH$_2$CH$_3$ | 0 |
| B-1500 | Cl | H | H | H | H | CH$_2$CF$_2$CHF$_2$ | CH$_2$CH$_3$ | 0 |
| B-1501 | Cl | H | H | H | H | CF$_2$CHFCF$_3$ | CH$_2$CH$_3$ | 0 |
| B-1502 | Cl | H | H | H | H | CF$_2$CF$_2$CF$_3$ | CH$_2$CH$_3$ | 0 |
| B-1503 | Cl | H | H | H | H | CH$_2$CF$_2$CF$_2$CF$_3$ | CH$_2$CH$_3$ | 0 |
| B-1504 | Cl | H | H | H | H | CH$_2$CF$_2$CHFCF3 | CH$_2$CH$_3$ | 0 |

TABLE 118-continued

| Compound | R¹ | R² | R³ | R⁴ | R⁵ | R⁶ | R¹⁶ | n |
|---|---|---|---|---|---|---|---|---|
| B-1505 | Cl | H | H | H | H | $CH_2CH_2CH_2CF_3$ | $CH_2CH_3$ | 0 |
| B-1506 | Cl | H | H | H | H | $CH_2CH_2CF_2CF_3$ | $CH_2CH_3$ | 0 |
| B-1507 | Cl | H | H | H | H | $CF_2CF_2CF_2CF_3$ | $CH_2CH_3$ | 0 |
| B-1508 | Cl | H | H | H | H | $CH_2CH_2CH(CF_3)_2$ | $CH_2CH_3$ | 0 |
| B-1509 | Cl | H | H | H | H | $CF_2CF_2CF_2CF_2CF_3$ | $CH_2CH_3$ | 0 |
| B-1510 | Cl | H | H | H | H | $CH_2CF_2CF_2CF_2CF_3$ | $CH_2CH_3$ | 0 |
| B-1511 | Cl | H | H | H | H | $CH_2CH_2CH_2CH_2CF_3$ | $CH_2CH_3$ | 0 |
| B-1512 | Cl | H | H | H | H | $CH_2CF_2CF_2CF_2CHF_2$ | $CH_2CH_3$ | 0 |
| B-1513 | Cl | H | H | H | H | $CH_2CF_2CF(CF_3)CF_2C(CF_3)_3$ | $CH_2CH_3$ | 0 |
| B-1514 | Cl | H | H | H | H | $CH_2CH_2CH_2CH_2CH_2CF_3$ | $CH_2CH_3$ | 0 |
| B-1515 | Cl | H | H | H | H | $CH_2CH_2CH_2CH_2CH_2CH_2CF_3$ | $CH_2CH_3$ | 0 |
| B-1516 | Cl | H | H | H | H | $CF_2CHFOCH_3$ | $CH_2CH_3$ | 0 |
| B-1517 | Cl | H | H | H | H | $CF_2CHFOCH_2CH_3$ | $CH_2CH_3$ | 0 |
| B-1518 | Cl | H | H | H | H | $CH_2CH_2OCH_2CF_3$ | $CH_2CH_3$ | 0 |
| B-1519 | Cl | H | H | H | H | $CF_2CHFOCF_3$ | $CH_2CH_3$ | 0 |
| B-1520 | Cl | H | H | H | H | $CF_2CHFOCF_2CF_3$ | $CH_2CH_3$ | 0 |

TABLE 119

| Compound | R¹ | R² | R³ | R⁴ | R⁵ | R⁶ | R¹⁶ | n |
|---|---|---|---|---|---|---|---|---|
| B-1521 | Cl | H | H | H | H | $CF_2CHFOCF_2CF_2CF_3$ | $CH_2CH_3$ | 0 |
| B-1522 | Cl | H | H | H | H | $CH_2CH=CH_2$ | $CH_2CH_3$ | 0 |
| B-1523 | Cl | H | H | H | H | $CH_2CH=CHCl$ | $CH_2CH_3$ | 0 |
| B-1524 | Cl | H | H | H | H | $CH_2CH=CCl_2$ | $CH_2CH_3$ | 0 |
| B-1525 | Cl | H | H | H | H | $CH_2CH_2CF=CF_2$ | $CH_2CH_3$ | 0 |
| B-1526 | Cl | H | H | H | H | $CH_2CH_2CH=CF_2$ | $CH_2CH_3$ | 0 |
| B-1527 | Cl | H | H | H | H | $CH_2C\equiv CH$ | $CH_2CH_3$ | 0 |
| B-1528 | Cl | H | H | H | H | $CH_2C\equiv CCH_3$ | $CH_2CH_3$ | 0 |
| B-1529 | Cl | H | H | H | H | $CH_2C\equiv CI$ | $CH_2CH_3$ | 0 |
| B-1530 | Cl | H | H | H | H | $CH_2C\equiv CCF_3$ | $CH_2CH_3$ | 0 |
| B-1531 | Cl | H | H | H | H | cyclobutyl | $CH_2CH_3$ | 0 |
| B-1532 | Cl | H | H | H | H | cyclopentyl | $CH_2CH_3$ | 0 |
| B-1533 | Cl | H | H | H | H | cyclohexyl | $CH_2CH_3$ | 0 |
| B-1534 | Cl | H | H | H | H | 4,4-difluorocyclohexyl | $CH_2CH_3$ | 0 |
| B-1535 | Cl | H | H | H | H | $CH_2$(cyclopropyl) | $CH_2CH_3$ | 0 |
| B-1536 | Cl | H | H | H | H | $CH_2$(cyclobutyl) | $CH_2CH_3$ | 0 |
| B-1537 | Cl | H | H | H | H | $CH_2$(cyclopentyl) | $CH_2CH_3$ | 0 |
| B-1538 | Cl | H | H | H | H | $CH_2CH_2$(cyclopropyl) | $CH_2CH_3$ | 0 |
| B-1539 | Cl | H | H | H | H | $CH_2$(2,2-difluorocyclopropyl) | $CH_2CH_3$ | 0 |
| B-1540 | Cl | H | H | H | H | $CH_2$(2,2-dichlorocyclopropyl) | $CH_2CH_3$ | 0 |
| B-1541 | Cl | H | H | H | H | $CH_2$(4,4-difluorocyclohexyl) | $CH_2CH_3$ | 0 |
| B-1542 | Cl | H | H | H | H | $CH_2CH_2$(2,2-difluorocyclopropyl) | $CH_2CH_3$ | 0 |
| B-1543 | Cl | H | H | H | H | $CH_2CH_2$(2,2-dichlorocyclopropyl) | $CH_2CH_3$ | 0 |
| B-1544 | Cl | H | H | H | H | $CH_2SCH_3$ | $CH_2CH_3$ | 0 |
| B-1545 | Cl | H | H | H | H | $CH_2SCH_2CH_3$ | $CH_2CH_3$ | 0 |
| B-1546 | Cl | H | H | H | H | $CH_2CH_2SCH_3$ | $CH_2CH_3$ | 0 |
| B-1547 | Cl | H | H | H | H | $CH_2CH_2SCH_2CH_3$ | $CH_2CH_3$ | 0 |
| B-1548 | Cl | H | H | H | H | $CH_2CH_2CH_2SCH_3$ | $CH_2CH_3$ | 0 |
| B-1549 | Cl | H | H | H | H | $CH_2CH_2CH_2SCH_2CH_3$ | $CH_2CH_3$ | 0 |
| B-1550 | Cl | H | H | H | H | $CH(CH_3)SCH_3$ | $CH_2CH_3$ | 0 |
| B-1551 | Cl | H | H | H | H | $CH(CH_3)SCH_2CH_3$ | $CH_2CH_3$ | 0 |
| B-1552 | Cl | H | H | H | H | $CH_2CH(CH_3)SCH_3$ | $CH_2CH_3$ | 0 |
| B-1553 | Cl | H | H | H | H | $CH(CH_3)SCH_2CH_3$ | $CH_2CH_3$ | 0 |
| B-1554 | Cl | H | H | H | H | $CH(CH_3)CH_2CH_2SCH_3$ | $CH_2CH_3$ | 0 |
| B-1555 | Cl | H | H | H | H | $CH(CH_3)CH_2CH_2SCH_2CH_3$ | $CH_2CH_3$ | 0 |
| B-1556 | Cl | H | H | H | H | $CH_2CH(CH_3)CH_2SCH_3$ | $CH_2CH_3$ | 0 |
| B-1557 | Cl | H | H | H | H | $CH(CH_3)CH_2SCH_2CH_3$ | $CH_2CH_3$ | 0 |
| B-1558 | Cl | H | H | H | H | $CH_2CH_2CH(CH_3)SCH_3$ | $CH_2CH_3$ | 0 |
| B-1559 | Cl | H | H | H | H | $CH_2CH_2CH(CH_3)SCH_2CH_3$ | $CH_2CH_3$ | 0 |
| B-1560 | Cl | H | H | H | H | $CH_2SOCH_3$ | $CH_2CH_3$ | 0 |
| B-1561 | Cl | H | H | H | H | $CH_2CH_2SOCH_3$ | $CH_2CH_3$ | 0 |
| B-1562 | Cl | H | H | H | H | $CH_2CH_2CH_2SOCH_3$ | $CH_2CH_3$ | 0 |
| B-1563 | Cl | H | H | H | H | $CH(CH_3)SOCH_3$ | $CH_2CH_3$ | 0 |
| B-1564 | Cl | H | H | H | H | $CH_2CH(CH_3)SOCH_3$ | $CH_2CH_3$ | 0 |
| B-1565 | Cl | H | H | H | H | $CH(CH_3)CH_2CH_2SCCH_3$ | $CH_2CH_3$ | 0 |
| B-1566 | Cl | H | H | H | H | $CH_2CH(CH_3)CH_2SCCH_3$ | $CH_2CH_3$ | 0 |
| B-1567 | Cl | H | H | H | H | $CH_2CH_2CH(CH_3)SOCH_3$ | $CH_2CH_3$ | 0 |
| B-1568 | Cl | H | H | H | H | $CH_2SO_2CH_3$ | $CH_2CH_3$ | 0 |
| B-1569 | Cl | H | H | H | H | $CH_2CH_2SO_2CH_3$ | $CH_2CH_3$ | 0 |
| B-1570 | Cl | H | H | H | H | $CH_2CH_2CH_2SO_2CH_3$ | $CH_2CH_3$ | 0 |
| B-1571 | Cl | H | H | H | H | $CH(CH_3)SO_2CH_3$ | $CH_2CH_3$ | 0 |
| B-1572 | Cl | H | H | H | H | $CH_2CH(CH_3)SO_2CH_3$ | $CH_2CH_3$ | 0 |
| B-1573 | Cl | H | H | H | H | $CH(CH_3)CH_2CH_2SO_2CH_3$ | $CH_2CH_3$ | 0 |
| B-1574 | Cl | H | H | H | H | $CH_2CH(CH_3)CH_2SO_2CH_3$ | $CH_2CH_3$ | 0 |

TABLE 119-continued

| Compound | $R^1$ | $R^2$ | $R^3$ | $R^4$ | $R^5$ | $R^6$ | $R^{16}$ | n |
|---|---|---|---|---|---|---|---|---|
| B-1575 | Cl | H | H | H | H | $CH_2CH_2CH(CH_3)SO_2CH_3$ | $CH_2CH_3$ | 0 |
| B-1576 | Cl | H | H | H | H | $CH_2SCF_3$ | $CH_2CH_3$ | 0 |
| B-1577 | Cl | H | H | H | H | $CH_2SCHF_2$ | $CH_2CH_3$ | 0 |
| B-1578 | Cl | H | H | H | H | $CH_2SCH_2CF_3$ | $CH_2CH_3$ | 0 |
| B-1579 | Cl | H | H | H | H | $CH_2SCH_2CHF_2$ | $CH_2CH_3$ | 0 |
| B-1580 | Cl | H | H | H | H | $CH_2SCF_2CF_3$ | $CH_2CH_3$ | 0 |
| B-1581 | Cl | H | H | H | H | $CH_2CH_2SCF_3$ | $CH_2CH_3$ | 0 |

TABLE 120

| Compound | $R^1$ | $R^2$ | $R^3$ | $R^4$ | $R^5$ | $R^6$ | $R^{16}$ | n |
|---|---|---|---|---|---|---|---|---|
| B-1582 | Cl | H | H | H | H | $CH_2CH_2SCH_2CF_3$ | $CH_2CH_3$ | 0 |
| B-1583 | Cl | H | H | H | H | $CH_2CH_2CH_2SCF_3$ | $CH_2CH_3$ | 0 |
| B-1584 | Cl | H | H | H | H | $CH_2CH_2CH_2SCH_2CF_3$ | $CH_2CH_3$ | 0 |
| B-1585 | Cl | H | H | H | H | $CH(CH_3)SCF_3$ | $CH_2CH_3$ | 0 |
| B-1586 | Cl | H | H | H | H | $CH(CH_3)SCH_2CF_3$ | $CH_2CH_3$ | 0 |
| B-1587 | Cl | H | H | H | H | $CH_2CH(CH_3)SCF_3$ | $CH_2CH_2$ | 0 |
| B-1588 | Cl | H | H | H | H | $CH_2CH(CH_3)SCH_2CF_3$ | $CH_2CH_3$ | 0 |
| B-1589 | Cl | H | H | H | H | $CH(CH_3)CH_2CH_2SCF_3$ | $CH_2CH_3$ | 0 |
| B-1590 | Cl | H | H | H | H | $CH(CH_3)CH_2CH_2SCH_2CF_3$ | $CH_2CH_3$ | 0 |
| B-1591 | Cl | H | H | H | H | $CH_2CH(CH_3)CH_2SCF_3$ | $CH_2CH_3$ | 0 |
| B-1592 | Cl | H | H | H | H | $CH_2CH(CH_3)CH_2SCH_2CF_3$ | $CH_2CH_3$ | 0 |
| B-1593 | Cl | H | H | H | H | $CH_2CH_2CH(CH_3)SCF_3$ | $CH_2CH_3$ | 0 |
| B-1594 | Cl | H | H | H | H | $CH_2CH_2CH(CH_3)SCH_2CF_3$ | $CH_2CH_3$ | 0 |
| B-1595 | Cl | H | H | H | H | $CH_2SOCF_3$ | $CH_2CH_3$ | 0 |
| B-1596 | Cl | H | H | H | H | $CH_2CH_2SOCF_3$ | $CH_2CH_3$ | 0 |
| B-1597 | Cl | H | H | H | H | $CH_2CH_2CH_2SOCF_3$ | $CH_2CH_3$ | 0 |
| B-1598 | Cl | H | H | H | H | $CH(CH_3)SOCF_3$ | $CH_2CH_3$ | 0 |
| B-1599 | Cl | H | H | H | H | $CH_2CH(CH_3)SOCF_3$ | $CH_2CH_3$ | 0 |
| B-1600 | Cl | H | H | H | H | $CH(CH_3)CH_2CH_2SOCF_3$ | $CH_2CH_3$ | 0 |
| B-1601 | Cl | H | H | H | H | $CH_2CH(CH_3)CH_2SOCF_3$ | $CH_2CH_3$ | 0 |
| B-1602 | Cl | H | H | H | H | $CH_2CH_2CH(CH_3)SOCF_3$ | $CH_2CH_3$ | 0 |
| B-1603 | Cl | H | H | H | H | $CH_2SO_2CF_3$ | $CH_2CH_3$ | 0 |
| B-1604 | Cl | H | H | H | H | $CH_2CH_2SO_2CF_3$ | $CH_2CH_3$ | 0 |
| B-1605 | Cl | H | H | H | H | $CH_2CH_2CH_2SO_2CF_3$ | $CH_2CH_3$ | 0 |
| B-1606 | Cl | H | H | H | H | $CH(CH_3)SO_2CF_3$ | $CH_2CH_3$ | 0 |
| B-1607 | Cl | H | H | H | H | $CH_2CH(CH_3)SO_2CF_3$ | $CH_2CH_3$ | 0 |
| B-1608 | Cl | H | H | H | H | $CH(CH_3)CH_2CH_2SO_2CF_3$ | $CH_2CH_3$ | 0 |
| B-1609 | Cl | H | H | H | H | $CH_2CH(CH_3)CH_2SO_2CF_3$ | $CH_2CH_3$ | 0 |
| B-1610 | Cl | H | H | H | H | $CH_2CH_2CH(CH_3)SO_2CF_3$ | $CH_2CH_3$ | 0 |
| B-1611 | Cl | H | H | H | H | $CH_2C(=O)CH_3$ | $CH_2CH_3$ | 0 |
| B-1612 | Cl | H | H | H | H | $CH_2C(=O)CH_2CH_3$ | $CH_2CH_3$ | 0 |
| B-1613 | Cl | H | H | H | H | $CH_2C(=O)C(CH_3)_3$ | $CH_2CH_3$ | 0 |
| B-1614 | Cl | H | H | H | H | $CH_2CH_2C(=O)CH_3$ | $CH_2CH_3$ | 0 |
| B-1615 | Cl | H | H | H | H | $CH_2CH_2C(=O)C(CH_3)_3$ | $CH_2CH_3$ | 0 |
| B-1616 | Cl | H | H | H | H | $CH_2C(=O)CF_3$ | $CH_2CH_3$ | 0 |
| B-1617 | Cl | H | H | H | H | $CH_2CH_2C(=O)CF_3$ | $CH_2CH_3$ | 0 |
| B-1618 | Cl | H | H | H | H | $CH_2C(=O)OCH_3$ | $CH_2CH_3$ | 0 |
| B-1619 | Cl | H | H | H | H | $CH_2C(=O)OCH_2CH_3$ | $CH_2CH_3$ | 0 |
| B-1620 | Cl | H | H | H | H | $CH_2C(=O)OC(CH_3)_3$ | $CH_2CH_3$ | 0 |
| B-1621 | Cl | H | H | H | H | $CH_2CH_2C(=O)OCH_3$ | $CH_2CH_3$ | 0 |
| B-1622 | Cl | H | H | H | H | $CH_2CH_2C(=O)OCH_2CH_3$ | $CH_2CH_3$ | 0 |
| B-1623 | Cl | H | H | H | H | $CH_2CH_2C(=O)OC(CH_3)_3$ | $CH_2CH_3$ | 0 |
| B-1624 | Cl | H | H | H | H | $CH_2C(=O)NH_2$ | $CH_2CH_3$ | 0 |
| B-1625 | Cl | H | H | H | H | $CH_2CH_2C(=O)NH_2$ | $CH_2CH_3$ | 0 |
| B-1626 | Cl | H | H | H | H | $CH_2C(=O)NHCH_3$ | $CH_2CH_3$ | 0 |
| B-1627 | Cl | H | H | H | H | $CH_2C(=O)NHCH(CH_3)_2$ | $CH_2CH_3$ | 0 |
| B-1628 | Cl | H | H | H | H | $CH_2CH_2C(=O)NHCH_3$ | $CH_2CH_3$ | 0 |
| B-1629 | Cl | H | H | H | H | $CH_2CH_2C(=O)NHCH(CH_3)_2$ | $CH_2CH_3$ | 0 |
| B-1630 | Cl | H | H | H | H | $CH_2C(=O)NHCH_2CHF_2$ | $CH_2CH_3$ | 0 |
| B-1631 | Cl | H | H | H | H | $CH_2C(=O)NHCH_2CF_3$ | $CH_2CH_3$ | 0 |
| B-1632 | Cl | H | H | H | H | $CH_2CH_2C(=O)NHCH_2CHF_2$ | $CH_2CH_3$ | 0 |
| B-1633 | Cl | H | H | H | H | $CH_2CH_2C(=O)NHCH_2CF_3$ | $CH_2CH_3$ | 0 |
| B-1634 | Cl | H | H | H | H | $CH_2C(=O)N(CH_3)_2$ | $CH_2CH_3$ | 0 |
| B-1635 | Cl | H | H | H | H | $CH_2C(=O)N(CH_2CH_3)_2$ | $CH_2CH_3$ | 0 |
| B-1636 | Cl | H | H | H | H | $CH_2CH_2C(=O)N(CH_3)_2$ | $CH_2CH_3$ | 0 |
| B-1637 | Cl | H | H | H | H | $CH_2CH_2C(=O)N(CH_2CH_3)_2$ | $CH_2CH_3$ | 0 |
| B-1638 | Cl | H | H | H | H | $CH_2CH_2OH$ | $CH_2CH_3$ | 0 |
| B-1639 | Cl | H | H | H | H | $CH_2CH(OH)CH_3$ | $CH_2CH_3$ | 0 |
| B-1640 | Cl | H | H | H | H | $CH_2CH_2CH_2OH$ | $CH_2CH_3$ | 0 |
| B-1641 | Cl | H | H | H | H | $CH_2CH(OH)CH_2CH_3$ | $CH_2CH_3$ | 0 |
| B-1642 | Cl | H | H | H | H | $CH_2CH(OH)C(CH_3)_3$ | $CH_2CH_3$ | 0 |

TABLE 121

| Compound | $R^1$ | $R^2$ | $R^3$ | $R^4$ | $R^5$ | $R^6$ | $R^{16}$ | n |
|---|---|---|---|---|---|---|---|---|
| B-1643 | Cl | H | H | H | H | $CH_2CH_2CH(OH)CH_3$ | $CH_2CH_3$ | 0 |
| B-1644 | Cl | H | H | H | H | $CH_2CH_2CH(OH)C(CH_3)_3$ | $CH_2CH_3$ | 0 |
| B-1645 | Cl | H | H | H | H | $CH_2C(=NOH)CH_3$ | $CH_2CH_3$ | 0 |
| B-1646 | Cl | H | H | H | H | $CH_2C(=NOH)CH_2CH_3$ | $CH_2CH_3$ | 0 |
| B-1647 | Cl | H | H | H | H | $CH_2C(=NOH)C(CH_3)_3$ | $CH_2CH_3$ | 0 |
| B-1648 | Cl | H | H | H | H | $CH_2C(=NOCH_3)CH_3$ | $CH_2CH_3$ | 0 |
| B-1649 | Cl | H | H | H | H | $CH_2C(=NOCH_3)CH_2CH_3$ | $CH_2CH_3$ | 0 |
| B-1650 | Cl | H | H | H | H | $CH_2C(=NOCH_2CH_3)CH_3$ | $CH_2CH_3$ | 0 |
| B-1651 | Cl | H | H | H | H | $CH_2C(=NOCH_2CH_3)CH_2CH_3$ | $CH_2CH_3$ | 0 |
| B-1652 | Cl | H | H | H | H | $CH_2C(=NOCH_2CF_3)CH_3$ | $CH_2CH_3$ | 0 |
| B-1653 | Cl | H | H | H | H | $CH_2C(=NOCH_2CF_3)CH_2CH_3$ | $CH_2CH_3$ | 0 |
| B-1654 | Cl | H | H | H | H | $CH_2Ph$ | $CH_2CH_3$ | 0 |
| B-1555 | Cl | H | H | H | H | $CH_2(2-F)Ph$ | $CH_2CH_3$ | 0 |
| B-1656 | Cl | H | H | H | H | $CH_2(3-F)Ph$ | $CH_2CH_3$ | 0 |
| B-1657 | Cl | H | H | H | H | $CH_2(4-F)Ph$ | $CH_2CH_3$ | 0 |
| B-1658 | Cl | H | H | H | H | $CH_2(2-Cl)Ph$ | $CH_2CH_3$ | 0 |
| B-1659 | Cl | H | H | H | H | $CH_2(3-Cl)Ph$ | $CH_2CH_3$ | 0 |
| B-1560 | Cl | H | H | H | H | $CH_2(4-Cl)Ph$ | $CH_2CH_3$ | 0 |
| B-1661 | Cl | H | H | H | H | $CH_2(2-CF_3)Ph$ | $CH_2CH_3$ | 0 |
| B-1662 | Cl | H | H | H | H | $CH_2(3-CF_3)Ph$ | $CH_2CH_3$ | 0 |
| B-1663 | Cl | H | H | H | H | $CH_2(4-CF_3)Ph$ | $CH_2CH_3$ | 0 |
| B-1664 | Cl | H | H | H | H | $CH_2(naphthalen-1-yl)$ | $CH_2CH_3$ | 0 |
| B-1665 | Cl | H | H | H | H | $CH_2(naphthalen-2-yl)$ | $CH_2CH_3$ | 0 |
| B-1666 | Cl | H | H | H | H | $CH_2CH_2Ph$ | $CH_2CH_3$ | 0 |
| B-1667 | H | H | H | Cl | H | H | H | 0 |
| B-1668 | H | H | H | Cl | H | $CH_3$ | H | 0 |
| B-1669 | H | H | H | Cl | H | $CH_2CH_3$ | H | 0 |
| B-1670 | H | H | H | Cl | H | $CH(CH_3)_2$ | H | 0 |
| B-1671 | H | H | H | Cl | H | $CH_2CH_2CH_3$ | H | 0 |
| B-1672 | H | H | H | Cl | H | $CH_2CH(CH_3)_2$ | H | 0 |
| B-1673 | H | H | H | Cl | H | $CH_2C(CH_3)_3$ | H | 0 |
| B-1674 | H | H | H | Cl | H | $CH(CH_3)CH_2CH_3$ | H | 0 |
| B-1675 | H | H | H | Cl | H | $CH_2(CH_2)_2CH_3$ | H | 0 |
| B-1676 | H | H | H | Cl | H | $CH_2(CH_2)_3CH_3$ | H | 0 |
| B-1677 | H | H | H | Cl | H | $CH_2(CH_2)_4CH_3$ | H | 0 |
| B-1678 | H | H | H | Cl | H | $CH_2(CH_2)_6CH_3$ | H | 0 |
| B-1679 | H | H | H | Cl | H | $CH_2OCH_3$ | H | 0 |
| B-1680 | H | H | H | Cl | H | $CH_2OCH_2CH_3$ | H | 0 |
| B-1681 | H | H | H | Cl | H | $CH_2CH_2OCH_3$ | H | 0 |
| B-1682 | H | H | H | Cl | H | $CH_2CH_2OCH_2CH_3$ | H | 0 |
| B-1683 | H | H | H | Cl | H | $CF_3$ | H | 0 |
| B-1684 | H | H | H | Cl | H | $CHF_2$ | H | 0 |
| B-1685 | H | H | H | Cl | H | $CH_2CF_3$ | H | 0 |
| B-1686 | H | H | H | Cl | H | $CH_2CHF_2$ | H | 0 |
| B-1687 | H | H | H | Cl | H | $CH_2CClF_2$ | H | 0 |
| B-1688 | H | H | H | Cl | H | $CH_2CBrF_2$ | H | 0 |
| B-1689 | H | H | H | Cl | H | $CF_2CF_3$ | H | 0 |
| B-1690 | H | H | H | Cl | H | $CF_2CHF_2$ | H | 0 |
| B-1691 | H | H | H | Cl | H | $CH_2CH_2CF_3$ | H | 0 |
| B-1692 | H | H | H | Cl | H | $CH_2CF_2CF_3$ | H | 0 |
| B-1693 | H | H | H | Cl | H | $CH_2CF_2CHF_2$ | H | 0 |
| B-1694 | H | H | H | Cl | H | $CF_2CHFCF_3$ | H | 0 |
| B-1695 | H | H | H | Cl | H | $CF_2CF_2CF_3$ | H | 0 |
| B-1696 | H | H | H | Cl | H | $CH_2CF_2CF_2CF_3$ | H | 0 |
| B-1697 | H | H | H | Cl | H | $CH_2CF_2CHFCF_3$ | H | 0 |
| B-1698 | H | H | H | Cl | H | $CH_2CH_2CH_2CF_3$ | H | 0 |
| B-1699 | H | H | H | Cl | H | $CH_2CH_2CF_2CF_3$ | H | 0 |
| B-1700 | H | H | H | Cl | H | $CF_2CF_2CF_2CF_3$ | H | 0 |
| B-1701 | H | H | H | Cl | H | $CH_2CH_2CH(CF_3)_2$ | H | 0 |
| B-1702 | H | H | H | Cl | H | $CF_2CF_2CF_2CF_2CF_3$ | H | 0 |
| B-1703 | H | H | H | Cl | H | $CH_2CF_2CF_2CF_2CF_3$ | H | 0 |

TABLE 122

| Compound | $R^1$ | $R^2$ | $R^3$ | $R^4$ | $R^5$ | $R^6$ | $R^{16}$ | n |
|---|---|---|---|---|---|---|---|---|
| B-1704 | H | H | H | Cl | H | $CH_2CH_2CH_2CH_2CF_3$ | H | 0 |
| B-1705 | H | H | H | Cl | H | $CH_2CF_2CF_2CF_2CHF_2$ | H | 0 |
| B-1706 | H | H | H | Cl | H | $CH_2CF_2CF(CF_3)CF_2C(CF_3)_3$ | H | 0 |
| B-1707 | H | H | H | Cl | H | $CH_2CH_2CH_2CH_2CH_2CF_3$ | H | 0 |
| B-1708 | H | H | H | Cl | H | $CH_2CH_2CH_2CH_2CH_2CH_2CF_3$ | H | 0 |
| B-1709 | H | H | H | Cl | H | $CF_2CHFOCH_3$ | H | 0 |
| B-1710 | H | H | H | Cl | H | $CF_2CHOCH_2CH_3$ | H | 0 |
| B-1711 | H | H | H | Cl | H | $CH_2CH_2OCH_2CF_3$ | H | 0 |
| B-1712 | H | H | H | Cl | H | $CF_2CHFOCF_3$ | H | 0 |

TABLE 122-continued

| Compound | $R^1$ | $R^2$ | $R^3$ | $R^4$ | $R^5$ | $R^6$ | $R^{16}$ | n |
|---|---|---|---|---|---|---|---|---|
| B-1713 | H | H | H | Cl | H | $CF_2CHFCCF_2CF_3$ | H | 0 |
| B-1714 | H | H | H | Cl | H | $CF_2CHFOCF_2CF_3$ | H | 0 |
| B-1715 | H | H | H | Cl | H | $CH_2CH=CH_2$ | H | 0 |
| B-1716 | H | H | H | Cl | H | $CH_2CH=CHCl$ | H | 0 |
| B-1717 | H | H | H | Cl | H | $CH_2CH=CCl_2$ | H | 0 |
| B-1718 | H | H | H | Cl | H | $CH_2CH_2CF=CF_2$ | H | 0 |
| B-1719 | H | H | H | Cl | H | $CH_2CH_3CH=CF_2$ | H | 0 |
| B-1720 | H | H | H | Cl | H | $CH_2C\equiv CH$ | H | 0 |
| B-1721 | H | H | H | Cl | H | $CH_2C\equiv CCH_3$ | H | 0 |
| B-1722 | H | H | H | Cl | H | $CH_2C\equiv Cl$ | H | 0 |
| B-1723 | H | H | H | Cl | H | $CH_2C\equiv CCF_3$ | H | 0 |
| B-1724 | H | H | H | Cl | H | cyclobutyl | H | 0 |
| B-1725 | H | H | H | Cl | H | cyclopentyl | H | 0 |
| B-1726 | H | H | H | Cl | H | cyclohexyl | H | 0 |
| B-1727 | H | H | H | Cl | H | 4,4-difluorocyclohexyl | H | 0 |
| B-1728 | H | H | H | Cl | H | $CH_2$(cyclopropyl) | H | 0 |
| B-1729 | H | H | H | Cl | H | $CH_2$(cyclobutyl) | H | 0 |
| B-1730 | H | H | H | Cl | H | $CH_2$(cyclopentyl) | H | 0 |
| B-1731 | H | H | H | Cl | H | $CH_2CH_2$(cyclopropyl) | H | 0 |
| B-1732 | H | H | H | Cl | H | $CH_2$(2,2-difluorocyclopropyl) | H | 0 |
| B-1733 | H | H | H | Cl | H | $CH_2$(2,2-dichlorocyclopropyl) | H | 0 |
| B-1734 | H | H | H | Cl | H | $CH_2$(4,4-difluorocyclohexyl) | H | 0 |
| B-1735 | H | H | H | Cl | H | $CH_2CH_2$(2,2-difluorocyclopropyl) | H | 0 |
| B-1736 | H | H | H | Cl | H | $CH_2CH_2$(2,2-dichlorocyclopropyl) | H | 0 |
| B-1737 | H | H | H | Cl | H | $CH_2SCH_3$ | H | 0 |
| B-1738 | H | H | H | Cl | H | $CH_2SCH_2CH_3$ | H | 0 |
| B-1739 | H | H | H | Cl | H | $CH_2CH_2SCH_3$ | H | 0 |
| B-1740 | H | H | H | Cl | H | $CH_2CH_2SCH_2CH_3$ | H | 0 |
| B-1741 | H | H | H | Cl | H | $CH_2CH_2CH_2SCH_3$ | H | 0 |
| B-1742 | H | H | H | Cl | H | $CH_2CH_2CH_2SCH_2CH_3$ | H | 0 |
| B-1743 | H | H | H | Cl | H | $CH(CH_3)SCH_3$ | H | 0 |
| B-1744 | H | H | H | Cl | H | $CH(CH_3)SCH_2CH_3$ | H | 0 |
| B-1745 | H | H | H | Cl | H | $CH_2CH(CH_3)SCH_3$ | H | 0 |
| B-1746 | H | H | H | Cl | H | $CH_2CH(CH_3)SCH_2CH_3$ | H | 0 |
| B-1747 | H | H | H | Cl | H | $CH(CH_3)CH_2SCH_3$ | H | 0 |
| B-1748 | H | H | H | Cl | H | $CH(CH_3)CH_2CH_2SCH_2CH_3$ | H | 0 |
| B-1749 | H | H | H | Cl | H | $CH_2CH(CH_3)CH_2SCH_3$ | H | 0 |
| B-1750 | H | H | H | Cl | H | $CH_2CH(CH_3)CH_2SCH_2CH_3$ | H | 0 |
| B-1751 | H | H | H | Cl | H | $CH_2CH_2CH(CH_3)SCH_3$ | H | 0 |
| B-1752 | H | H | H | Cl | H | $CH_2CH_2CH(CH_3)SCH_2CH_3$ | H | 0 |
| B-1753 | H | H | H | Cl | H | $CH_2SOCH_3$ | H | 0 |
| B-1754 | H | H | H | Cl | H | $CH_2CH_2SOCH_3$ | H | 0 |
| B-1755 | H | H | H | Cl | H | $CH_2CH_2CH_2SOCH_3$ | H | 0 |
| B-1756 | H | H | H | Cl | H | $CH(CH_3)SOCH_3$ | H | 0 |
| B-1757 | H | H | H | Cl | H | $CH_2CH(CH_3)SOCH_3$ | H | 0 |
| B-1758 | H | H | H | Cl | H | $CH(CH_3)CH_2CH_2SOCH_3$ | H | 0 |
| B-1759 | H | H | H | Cl | H | $CH_2CH(CH_3)CH_2SOCH_3$ | H | 0 |
| B-1760 | H | H | H | Cl | H | $CH_2CH_2CH(CH_3)SOCH_3$ | H | 0 |
| B-1761 | H | H | H | Cl | H | $CH_2SO_2CH_3$ | H | 0 |
| B-1762 | H | H | H | Cl | H | $CH_2CH_2SO_2CH_3$ | H | 0 |
| B-1763 | H | H | H | Cl | H | $CH_2CH_2CH_2SO_2CH_3$ | H | 0 |
| B-1764 | H | H | H | Cl | H | $CH(CH_3)SO_2CH_3$ | H | 0 |

TABLE 123

| Compound | $R^1$ | $R^2$ | $R^3$ | $R^4$ | $R^5$ | $R^6$ | $R^{16}$ | n |
|---|---|---|---|---|---|---|---|---|
| B-1765 | H | H | H | Cl | H | $CH_2CH(CH_3)SO_2CH_3$ | H | 0 |
| B-1766 | H | H | H | Cl | H | $CH(CH_3)CH_2CH_2SO_2CH_3$ | H | 0 |
| B-1767 | H | H | H | Cl | H | $CH_2CH(CH_3)CH_2SO_2CH_3$ | H | 0 |
| B-1768 | H | H | H | Cl | H | $CH_2CH_2CH(CH_3)SO_2CH_3$ | H | 0 |
| B-1769 | H | H | H | Cl | H | $CH_2SCF_3$ | H | 0 |
| B-1770 | H | H | H | Cl | H | $CH_2SCHF_2$ | H | 0 |
| B-1771 | H | H | H | Cl | H | $CH_2SCH_2CF_3$ | H | 0 |
| B-1772 | H | H | H | Cl | H | $CH_2SCH_2CHF_2$ | H | 0 |
| B-1773 | H | H | H | Cl | H | $CH_2SCF_2CF_3$ | H | 0 |
| B-1774 | H | H | H | Cl | H | $CH_2CH_2SCF_3$ | H | 0 |
| B-1775 | H | H | H | Cl | H | $CH_2CH_2SCH_2CF_3$ | H | 0 |
| B-1776 | H | H | H | Cl | H | $CH_2CH_2CH_2SCF_3$ | H | 0 |
| B-1777 | H | H | H | Cl | H | $CH_2CH_2CH_2SCH_2CF_3$ | H | 0 |
| B-1778 | H | H | H | Cl | H | $CH(CH_3)SCF_3$ | H | 0 |
| B-1779 | H | H | H | Cl | H | $CH(CH_3)SCH_2CF_3$ | H | 0 |
| B-1780 | H | H | H | Cl | H | $CH_2CH(CH_3)SCF_3$ | H | 0 |
| B-1781 | H | H | H | Cl | H | $CH_2CH(CH_3)SCH_2CF_3$ | H | 0 |
| B-1782 | H | H | H | Cl | H | $CH(CH_3)CH_2CH_2SCF_3$ | H | 0 |

TABLE 123-continued

| Compound | R¹ | R² | R³ | R⁴ | R⁵ | R⁶ | R¹⁶ | n |
|---|---|---|---|---|---|---|---|---|
| B-1783 | H | H | H | Cl | H | CH(CH$_3$)CH$_2$CH$_2$SCH$_2$CF$_3$ | H | 0 |
| B-1784 | H | H | H | Cl | H | CH$_2$CH(CH$_3$)CH$_2$SCF$_3$ | H | 0 |
| B-1785 | H | H | H | Cl | H | CH$_2$CH(CH$_3$)CH$_2$SCH$_2$CF$_3$ | H | 0 |
| B-1786 | H | H | H | Cl | H | CH$_2$CH$_2$CH(CH$_3$)SCF$_3$ | H | 0 |
| B-1787 | H | H | H | Cl | H | CH$_2$CH$_2$CH(CH$_3$)SCH$_2$CF$_3$ | H | 0 |
| B-1788 | H | H | H | Cl | H | CH$_2$SOCF$_3$ | H | 0 |
| B-1789 | H | H | H | Cl | H | CH$_2$CH$_2$SOCF$_3$ | H | 0 |
| B-1790 | H | H | H | Cl | H | CH$_2$CH$_2$CH$_2$SOCF$_3$ | H | 0 |
| B-1791 | H | H | H | Cl | H | CH(CH$_3$)SOCF$_3$ | H | 0 |
| B-1792 | H | H | H | Cl | H | CH$_2$CH(CH$_3$)SOCF$_3$ | H | 0 |
| B-1793 | H | H | H | Cl | H | CH(CH$_3$)CH$_2$CH$_2$SOCF$_3$ | H | 0 |
| B-1794 | H | H | H | Cl | H | CH$_2$CH(CH$_3$)CH$_2$SOCF$_3$ | H | 0 |
| B-1795 | H | H | H | Cl | H | CH$_2$CH$_2$CH(CH$_3$)SOCF$_3$ | H | 0 |
| B-1796 | H | H | H | Cl | H | CH$_2$SO$_2$CF$_3$ | H | 0 |
| B-1797 | H | H | H | Cl | H | CH$_2$CH$_2$SO$_2$CF$_3$ | H | 0 |
| B-1798 | H | H | H | Cl | H | CH$_2$CH$_2$CH$_2$SO$_2$CF$_3$ | H | 0 |
| B-1799 | H | H | H | Cl | H | CH(CH$_3$)SO$_2$CF$_3$ | H | 0 |
| B-1800 | H | H | H | Cl | H | CH$_2$CH(CH$_3$)SO$_2$CF$_3$ | H | 0 |
| B-1801 | H | H | H | Cl | H | CH(CH$_3$)CH$_2$CH$_2$SO$_2$CF$_3$ | H | 0 |
| B-1802 | H | H | H | Cl | H | CH$_2$CH(CH$_3$)CH$_2$SO$_2$CF$_3$ | H | 0 |
| B-1803 | H | H | H | Cl | H | CH$_2$CH$_2$CH(CH$_3$)SO$_2$CF$_3$ | H | 0 |
| B-1804 | H | H | H | Cl | H | CH$_2$C(=O)CH$_3$ | H | 0 |
| B-1805 | H | H | H | Cl | H | CH$_2$C(=O)CH$_2$CH$_3$ | H | 0 |
| B-1806 | H | H | H | Cl | H | CH$_2$C(=O)C(CH$_3$)$_3$ | H | 0 |
| B-1807 | H | H | H | Cl | H | CH$_2$CH$_2$C(=O)CH$_3$ | H | 0 |
| B-1808 | H | H | H | Cl | H | CH$_2$CH$_2$C(=O)C(CH$_3$)$_3$ | H | 0 |
| B-1809 | H | H | H | Cl | H | CH$_2$C(=O)CF$_3$ | H | 0 |
| B-1810 | H | H | H | Cl | H | CH$_2$CH$_2$C(=O)CF$_3$ | H | 0 |
| B-1811 | H | H | H | Cl | H | CH$_2$C(=O)OCH$_3$ | H | 0 |
| B-1812 | H | H | H | Cl | H | CH$_2$C(=O)OCH$_2$CH$_3$ | H | 0 |
| B-1813 | H | H | H | Cl | H | CH$_2$C(=O)OC(CH$_3$)$_3$ | H | 0 |
| B-1814 | H | H | H | Cl | H | CH$_2$CH$_2$C(=O)OCH$_3$ | H | 0 |
| B-1815 | H | H | H | Cl | H | CH$_2$CH$_2$C(=O)OCH$_2$CH$_3$ | H | 0 |
| B-1816 | H | H | H | Cl | H | CH$_2$CH$_2$C(=O)OC(CH$_3$)$_3$ | H | 0 |
| B-1817 | H | H | H | Cl | H | CH$_2$C(=O)NH$_2$ | H | 0 |
| B-1818 | H | H | H | Cl | H | CH$_2$CH$_2$C(=O)NH$_2$ | H | 0 |
| B-1819 | H | H | H | Cl | H | CH$_2$C(=O)NHCH$_3$ | H | 0 |
| B-1820 | H | H | H | Cl | H | CH$_2$C(=O)NHCH(CH$_3$)$_2$ | H | 0 |
| B-1821 | H | H | H | Cl | H | CH$_2$CH$_2$C(=O)NHCH$_3$ | H | 0 |
| B-1822 | H | H | H | Cl | H | CH$_2$CH$_2$C(=O)NHCH(CH$_3$)$_2$ | H | 0 |
| B-1823 | H | H | H | Cl | H | CH$_2$C(=O)NHCH$_2$CHF$_2$ | H | 0 |
| B-1824 | H | H | H | Cl | H | CH$_2$C(=O)NHCH$_2$CF$_3$ | H | 0 |
| B-1825 | H | H | H | Cl | H | CH$_2$CH$_2$C(=O)NHCH$_2$CHF$_2$ | H | 0 |

TABLE 124

| Compound | R¹ | R² | R³ | R⁴ | R⁵ | R⁶ | R¹⁶ | n |
|---|---|---|---|---|---|---|---|---|
| B-1826 | H | H | H | Cl | H | CH$_2$CH$_2$C(=O)NHCH$_2$CF$_3$ | H | 0 |
| B-1827 | H | H | H | Cl | H | CH$_2$C(=O)N(CH$_3$)$_2$ | H | 0 |
| B-1828 | H | H | H | Cl | H | CH$_2$C(=O)N(CH$_2$CH$_3$)$_2$ | H | 0 |
| B-1829 | H | H | H | Cl | H | CH$_2$CH$_2$C(=O)N(CH$_3$)$_2$ | H | 0 |
| B-1830 | H | H | H | Cl | H | CH$_2$CH$_2$C(=O)N(CH$_2$CH$_3$)$_2$ | H | 0 |
| B-1831 | H | H | H | Cl | H | CH$_2$CH$_2$OH | H | 0 |
| B-1832 | H | H | H | Cl | H | CH$_2$CH(OH)CH$_3$ | H | 0 |
| B-1833 | H | H | H | Cl | H | CH$_2$CH$_2$CH$_2$OH | H | 0 |
| B-1834 | H | H | H | Cl | H | CH$_2$CH(OH)CH$_2$CH$_3$ | H | 0 |
| B-1835 | H | H | H | Cl | H | CH$_2$CH(OH)C(CH$_3$)$_3$ | H | 0 |
| B-1836 | H | H | H | Cl | H | CH$_2$CH$_2$CH(OH)CH$_3$ | H | 0 |
| B-1837 | H | H | H | Cl | H | CH$_2$CH$_2$CH(OH)C(CH$_3$)$_3$ | H | 0 |
| B-1838 | H | H | H | Cl | H | CH$_2$C(=NOH)CH$_3$ | H | 0 |
| B-1839 | H | H | H | Cl | H | CH$_2$C(=NOH)CH$_2$CH$_3$ | H | 0 |
| B-1840 | H | H | H | Cl | H | CH$_2$C(=NOH)C(CH$_3$)$_3$ | H | 0 |
| B-1841 | H | H | H | Cl | H | CH$_2$C(=NOCH$_3$)CH$_3$ | H | 0 |
| B-1842 | H | H | H | Cl | H | CH$_2$C(=NOCH$_3$)CH$_2$CH$_3$ | H | 0 |
| B-1843 | H | H | H | Cl | H | CH$_2$C(=NOCH$_2$CH$_3$)CH$_3$ | H | 0 |
| B-1844 | H | H | H | Cl | H | CH$_2$C(=NOCH$_2$CH$_3$)CH$_2$CH$_3$ | H | 0 |
| B-1845 | H | H | H | Cl | H | CH$_2$C(=NOCH$_2$CF$_3$)CH$_3$ | H | 0 |
| B-1846 | H | H | H | Cl | H | CH$_2$C(=NOCH$_2$CF$_3$)CH$_2$CH$_3$ | H | 0 |
| B-1847 | H | H | H | Cl | H | CH$_2$Ph | H | 0 |
| B-1848 | H | H | H | Cl | H | CH$_2$(2-F)Ph | H | 0 |
| B-1849 | H | H | H | Cl | H | CH$_2$(3-F)Ph | H | 0 |
| B-1850 | H | H | H | Cl | H | CH$_2$(4-F)Ph | H | 0 |
| B-1851 | H | H | H | Cl | H | CH$_2$(2-Cl)Ph | H | 0 |
| B-1852 | H | H | H | Cl | H | CH$_2$(3-Cl)Ph | H | 0 |

TABLE 124-continued

| Compound | $R^1$ | $R^2$ | $R^3$ | $R^4$ | $R^5$ | $R^6$ | $R^{16}$ | n |
|---|---|---|---|---|---|---|---|---|
| B-1853 | H | H | H | Cl | H | CH$_2$(4-Cl)Ph | H | 0 |
| B-1854 | H | H | H | Cl | H | CH$_2$(2-CF$_3$)Ph | H | 0 |
| B-1855 | H | H | H | Cl | H | CH$_2$(3-CF$_3$)Ph | H | 0 |
| B-1856 | H | H | H | Cl | H | CH$_2$(4-CF$_3$)Ph | H | 0 |
| B-1857 | H | H | H | Cl | H | CH$_2$(naphthalen-1-yl) | H | 0 |
| B-1858 | H | H | H | Cl | H | CH$_2$(naphthalen-2-yl) | H | 0 |
| B-1859 | H | H | H | Cl | H | CH$_2$CH$_2$Ph | H | 0 |
| B-1860 | H | H | H | Cl | H | H | CH$_2$CH$_3$ | 0 |
| B-1861 | H | H | H | Cl | H | CH$_3$ | CH$_2$CH$_3$ | 0 |
| B-1862 | H | H | H | Cl | H | CH$_2$CH$_3$ | CH$_2$CH$_3$ | 0 |
| B-1863 | H | H | H | Cl | H | CH(CH$_3$)$_2$ | CH$_2$CH$_3$ | 0 |
| B-1864 | H | H | H | Cl | H | CH$_2$CH$_2$CH$_3$ | CH$_2$CH$_3$ | 0 |
| B-1865 | H | H | H | Cl | H | CH$_2$CH(CH$_3$)$_2$ | CH$_2$CH$_3$ | 0 |
| B-1866 | H | H | H | Cl | H | CH$_2$C(CH$_3$)$_3$ | CH$_2$CH$_3$ | 0 |
| B-1867 | H | H | H | Cl | H | CH(CH$_3$)CH$_2$CH$_3$ | CH$_2$CH$_3$ | 0 |
| B-1868 | H | H | H | Cl | H | CH$_2$(CH$_2$)$_2$CH$_3$ | CH$_2$CH$_3$ | 0 |
| B-1869 | H | H | H | Cl | H | CH$_2$(CH$_2$)$_3$CH$_3$ | CH$_2$CH$_3$ | 0 |
| B-1870 | H | H | H | Cl | H | CH$_2$(CH$_2$)$_4$CH$_3$ | CH$_2$CH$_3$ | 0 |
| B-1871 | H | H | H | Cl | H | CH$_2$(CH$_2$)$_6$CH$_3$ | CH$_2$CH$_3$ | c |
| B-1872 | H | H | H | Cl | H | CH$_2$OCH$_3$ | CH$_2$CH$_3$ | 0 |
| B-1873 | H | H | H | Cl | H | CH$_2$OCH$_2$CH$_3$ | CH$_2$CH$_3$ | 0 |
| B-1874 | H | H | H | Cl | H | CH$_2$CH$_2$OCH$_3$ | CH$_2$CH$_3$ | 0 |
| B-1875 | H | H | H | Cl | H | CH$_2$CH$_2$OCH$_2$CH$_3$ | CH$_2$CH$_3$ | 0 |
| B-1876 | H | H | H | Cl | H | CF$_3$ | CH$_2$CH$_3$ | 0 |
| B-1877 | H | H | H | Cl | H | CHF$_2$ | CH$_2$CH$_3$ | 0 |
| B-1878 | H | H | H | Cl | H | CH$_2$CF$_3$ | CH$_2$CH$_3$ | 0 |
| B-1879 | H | H | H | Cl | H | CH$_2$CHF$_2$ | CH$_2$CH$_3$ | 0 |
| B-1880 | H | H | H | Cl | H | CH$_2$CClF$_2$ | CH$_2$CH$_3$ | 0 |
| B-1881 | H | H | H | Cl | H | CH$_2$CBrF$_2$ | CH$_2$CH$_3$ | 0 |
| B-1882 | H | H | H | Cl | H | CF$_2$CF$_3$ | CH$_2$CH$_3$ | 0 |
| B-1883 | H | H | H | Cl | H | CF$_2$CHF$_2$ | CH$_2$CH$_3$ | 0 |
| B-1884 | H | H | H | Cl | H | CH$_2$CH$_2$CF$_3$ | CH$_2$CH$_3$ | 0 |
| B-1885 | H | H | H | Cl | H | CH$_2$CF$_2$CF$_3$ | CH$_2$CH$_3$ | 0 |
| B-1886 | H | H | H | Cl | H | CH$_2$CF$_2$CHF$_2$ | CH$_2$CH$_3$ | 0 |

TABLE 125

| Compound | $R^1$ | $R^2$ | $R^3$ | $R^4$ | $R^5$ | $R^6$ | $R^{16}$ | n |
|---|---|---|---|---|---|---|---|---|
| B-1887 | H | H | H | Cl | H | CF$_2$CHFCF$_3$ | CH$_2$CH$_3$ | 0 |
| B-1888 | H | H | H | Cl | H | CF$_2$CF$_2$CF$_3$ | CH$_2$CH$_3$ | 0 |
| B-1889 | H | H | H | Cl | H | CH$_2$CF$_2$CF$_2$CF$_3$ | CH$_2$CH$_3$ | 0 |
| B-1890 | H | H | H | Cl | H | CH$_2$CF$_2$CHFCF$_3$ | CH$_2$CH$_3$ | 0 |
| B-1891 | H | H | H | Cl | H | CH$_2$CH$_2$CH$_2$CF$_3$ | CH$_2$CH$_3$ | 0 |
| B-1892 | H | H | H | Cl | H | CH$_2$CH$_2$CF$_2$CF$_3$ | CH$_2$CH$_3$ | 0 |
| B-1893 | H | H | H | Cl | H | CF$_2$CF$_2$CF$_2$CF$_3$ | CH$_2$CH$_3$ | 0 |
| B-1894 | H | H | H | Cl | H | CH$_2$CH$_2$CH(CF$_3$)$_2$ | CH$_2$CH$_3$ | 0 |
| B-1895 | H | H | H | Cl | H | CF$_2$CF$_2$CF$_2$CF$_2$CF$_3$ | CH$_2$CH$_3$ | 0 |
| B-1896 | H | H | H | Cl | H | CH$_2$CF$_2$CF$_2$CF$_2$CF$_3$ | CH$_2$CH$_3$ | 0 |
| B-1897 | H | H | H | Cl | H | CH$_2$CH$_2$CH$_2$CH$_2$CF$_3$ | CH$_2$CH$_3$ | 0 |
| B-1898 | H | H | H | Cl | H | CH$_2$CF$_2$CF$_2$CF$_2$CHF$_2$ | CH$_2$CH$_3$ | 0 |
| B-1899 | H | H | H | Cl | H | CH$_2$CF$_2$CF(CF$_3$)CF$_2$C(CF$_3$)$_3$ | CH$_2$CH$_3$ | 0 |
| B-1900 | H | H | H | Cl | H | CH$_2$CH$_2$CH$_2$CH$_2$CH$_2$CF$_3$ | CH$_2$CH$_3$ | 0 |
| B-1901 | H | H | H | Cl | H | CH$_2$CH$_2$CH$_2$CH$_2$CH$_2$CH$_2$CF$_3$ | CH$_2$CH$_3$ | 0 |
| B-1902 | H | H | H | Cl | H | CF$_2$CHFOCH$_3$ | CH$_2$CH$_3$ | 0 |
| B-1903 | H | H | H | Cl | H | CF$_2$CHFOCH$_2$CH$_3$ | CH$_2$CH$_3$ | 0 |
| B-1904 | H | H | H | Cl | H | CH$_2$CH$_2$OCH$_2$CF$_3$ | CH$_2$CH$_3$ | 0 |
| B-1905 | H | H | H | Cl | H | CF$_2$CHFOCF$_3$ | CH$_2$CH$_3$ | 0 |
| B-1906 | H | H | H | Cl | H | CF$_2$CHFOCF$_2$CF$_3$ | CH$_2$CH$_3$ | 0 |
| B-1907 | H | H | H | Cl | H | CF$_2$CHFOCF$_2$CF$_2$CF$_3$ | CH$_2$CH$_3$ | 0 |
| B-1908 | H | H | H | Cl | H | CH$_2$CH=CH$_2$ | CH$_2$CH$_3$ | 0 |
| B-1909 | H | H | H | Cl | H | CH$_2$CH=CHCl | CH$_2$CH$_3$ | 0 |
| B-1910 | H | H | H | Cl | H | CH$_2$CH=CCl$_2$ | CH$_2$CH$_3$ | 0 |
| B-1911 | H | H | H | Cl | H | CH$_2$CH$_2$CF=CF$_2$ | CH$_2$CH$_3$ | 0 |
| B-1912 | H | H | H | Cl | H | CH$_2$CH$_2$CH=CF$_2$ | CH$_2$CH$_3$ | 0 |
| B-1913 | H | H | H | Cl | H | CH$_2$C≡CH | CH$_2$CH$_3$ | 0 |
| B-1914 | H | H | H | Cl | H | CH$_2$C≡CCH$_3$ | CH$_2$CH$_3$ | 0 |
| B-1915 | H | H | H | Cl | H | CH$_2$C≡Cl | CH$_2$CH$_3$ | 0 |
| B-1916 | H | H | H | Cl | H | CH$_2$C≡CCF$_3$ | CH$_2$CH$_3$ | 0 |
| B-1917 | H | H | H | Cl | H | cyclobutyl | CH$_2$CH$_3$ | 0 |
| B-1918 | H | H | H | Cl | H | cyclopentyl | CH$_2$CH$_3$ | 0 |
| B-1919 | H | H | H | Cl | H | cyclohexyl | CH$_2$CH$_3$ | 0 |
| B-1920 | H | H | H | Cl | H | 4,4-difluorocyclohexyl | CH$_2$CH$_3$ | 0 |
| B-1921 | H | H | H | Cl | H | CH$_2$(cyclopropyl) | CH$_2$CH$_3$ | 0 |
| B-1922 | H | H | H | Cl | H | CH$_2$(cyclobutyl) | CH$_2$CH$_3$ | 0 |

TABLE 125-continued

| Compound | $R^1$ | $R^2$ | $R^3$ | $R^4$ | $R^5$ | $R^6$ | $R^{16}$ | n |
|---|---|---|---|---|---|---|---|---|
| B-1923 | H | H | H | Cl | H | CH$_2$(cyclopentyl) | CH$_2$CH$_3$ | 0 |
| B-1924 | H | H | H | Cl | H | CH$_2$CH$_2$(cyclopropyl) | CH$_2$CH$_3$ | 0 |
| B-1925 | H | H | H | Cl | H | CH$_2$(2,2-difluorocyclopropyl) | CH$_2$CH$_3$ | 0 |
| B-1926 | H | H | H | Cl | H | CH$_2$(2,2-dichlorocyclopropyl) | CH$_2$CH$_3$ | 0 |
| B-1927 | H | H | H | Cl | H | CH$_2$(4,4-difluorocyclohexyl) | CH$_2$CH$_3$ | 0 |
| B-1928 | H | H | H | Cl | H | CH$_2$CH$_2$(2,2-difluorocyclopropyl) | CH$_2$CH$_3$ | 0 |
| B-1929 | H | H | H | Cl | H | CH$_2$CH$_2$(2,2-dichlorocyclopropyl) | CH$_2$CH$_3$ | 0 |
| B-1930 | H | H | H | Cl | H | CH$_2$SCH$_3$ | CH$_2$CH$_3$ | 0 |
| B-1931 | H | H | H | Cl | H | CH$_2$SCH$_2$CH$_3$ | CH$_2$CH$_3$ | 0 |
| B-1932 | H | H | H | Cl | H | CH$_2$CH$_2$SCH$_3$ | CH$_2$CH$_3$ | 0 |
| B-1933 | H | H | H | Cl | H | CH$_2$CH$_2$SCH$_2$CH$_3$ | CH$_2$CH$_3$ | 0 |
| B-1934 | H | H | H | Cl | H | CH$_2$CH$_2$CH$_2$SCH$_3$ | CH$_2$CH$_3$ | 0 |
| B-1935 | H | H | H | Cl | H | CH$_2$CH$_2$CH$_2$SCH$_2$CH$_3$ | CH$_2$CH$_3$ | 0 |
| B-1936 | H | H | H | Cl | H | CH(CH$_3$)SCH$_3$ | CH$_2$CH$_3$ | 0 |
| B-1937 | H | H | H | Cl | H | CH(CH$_3$)SCH$_2$CH$_3$ | CH$_2$CH$_3$ | 0 |
| B-1938 | H | H | H | Cl | H | CH$_2$CH(CH$_3$)SCH$_3$ | CH$_2$CH$_3$ | 0 |
| B-1939 | H | H | H | Cl | H | CH$_2$CH(CH$_3$)SCH$_2$CH$_3$ | CH$_2$CH$_3$ | 0 |
| B-1940 | H | H | H | Cl | H | CH(CH$_3$)CH$_2$CH$_2$SCH$_3$ | CH$_2$CH$_3$ | 0 |
| B-1941 | H | H | H | Cl | H | CH(CH$_3$)CH$_2$CH$_2$SCH$_2$CH$_3$ | CH$_2$CH$_3$ | 0 |
| B-1942 | H | H | H | Cl | H | CH$_2$CH(CH$_3$)CH$_2$SCH$_3$ | CH$_2$CH$_3$ | 0 |
| B-1943 | H | H | H | Cl | H | CH$_2$CH(CH$_3$)CH$_2$SCH$_2$CH$_3$ | CH$_2$CH$_3$ | 0 |
| B-1944 | H | H | H | Cl | H | CH$_2$CH$_2$CH(CH$_3$)SCH$_3$ | CH$_2$CH$_3$ | 0 |
| B-1945 | H | H | H | Cl | H | CH$_2$CH$_2$CH(CH$_3$)SCH$_2$CH$_3$ | CH$_2$CH$_3$ | 0 |
| B-1946 | H | H | H | Cl | H | CH$_2$SOCH$_3$ | CH$_2$CH$_3$ | 0 |
| B-1947 | H | H | H | Cl | H | CH$_2$CH$_2$SOCH$_3$ | CH$_2$CH$_3$ | 0 |

TABLE 126

| Compound | $R^1$ | $R^2$ | $R^3$ | $R^4$ | $R^5$ | $R^6$ | $R^{16}$ | n |
|---|---|---|---|---|---|---|---|---|
| B-1948 | H | H | H | Cl | H | CH$_2$CH$_2$CH$_2$SOCH$_3$ | CH$_2$CH$_3$ | 0 |
| B-1949 | H | H | H | Cl | H | CH(CH$_3$)SOCH$_3$ | CH$_2$CH$_3$ | 0 |
| B-1950 | H | H | H | Cl | H | CH$_2$CH(CH$_3$)SOCH$_3$ | CH$_2$CH$_3$ | 0 |
| B-1951 | H | H | H | Cl | H | CH(CH$_3$)CH$_2$CH$_2$SOCH$_3$ | CH$_2$CH$_3$ | 0 |
| B-1952 | H | H | H | Cl | H | CH$_2$CH(CH$_3$)CH$_2$SOCH$_3$ | CH$_2$CH$_3$ | 0 |
| B-1953 | H | H | H | Cl | H | CH$_2$CH$_2$CH(CH$_3$)SOCH$_3$ | CH$_2$CH$_3$ | 0 |
| B-1954 | H | H | H | Cl | H | CH$_2$SO$_2$CH$_3$ | CH$_2$CH$_3$ | 0 |
| B-1955 | H | H | H | Cl | H | CH$_2$CH$_2$SO$_2$CH$_3$ | CH$_2$CH$_3$ | 0 |
| B-1956 | H | H | H | Cl | H | CH$_2$CH$_2$CH$_2$SO$_2$CH$_3$ | CH$_3$CH$_3$ | 0 |
| B-1957 | H | H | H | Cl | H | CH(CH$_3$)SO$_2$CH$_3$ | CH$_2$CH$_3$ | 0 |
| B-1958 | H | H | H | Cl | H | CH$_2$CH(CH$_3$)SO$_2$CH$_3$ | CH$_2$CH$_3$ | 0 |
| B-1959 | H | H | H | Cl | H | CH(CH$_3$)CH$_2$CH$_2$SO$_2$CH$_3$ | CH$_2$CH$_3$ | 0 |
| B-1960 | H | H | H | Cl | H | CH$_2$CH(CH$_3$)CH$_2$SO$_2$CH$_3$ | CH$_2$CH$_3$ | 0 |
| B-1961 | H | H | H | Cl | H | CH$_2$CH$_2$CH(CH$_3$)SO$_2$CH$_3$ | CH$_2$CH$_3$ | 0 |
| B-1962 | H | H | H | Cl | H | CH$_2$SCF$_3$ | CH$_2$CH$_3$ | 0 |
| B-1963 | H | H | H | Cl | H | CH$_2$SCHF$_2$ | CH$_2$CH$_3$ | 0 |
| B-1964 | H | H | H | Cl | H | CH$_2$SCH$_2$CF$_3$ | CH$_2$CH$_3$ | 0 |
| B-1965 | H | H | H | Cl | H | CH$_2$SCH$_2$CHF$_2$ | CH$_2$CH$_3$ | 0 |
| B-1966 | H | H | H | Cl | H | CH$_2$SCF$_2$CF$_3$ | CH$_2$CH$_3$ | 0 |
| B-1967 | H | H | H | Cl | H | CH$_2$CH$_2$SCF$_3$ | CH$_2$CH$_3$ | 0 |
| B-1968 | H | H | H | Cl | H | CH$_2$CH$_2$SCH$_2$CF$_3$ | CH$_2$CH$_3$ | 0 |
| B-1969 | H | H | H | Cl | H | CH$_2$CH$_2$CH$_2$SCF$_3$ | CH$_2$CH$_3$ | 0 |
| B-1970 | H | H | H | Cl | H | CH$_2$CH$_2$CH$_2$SCH$_2$CF$_3$ | CH$_2$CH$_3$ | 0 |
| B-1971 | H | H | H | Cl | H | CH(CH$_3$)SCF$_3$ | CH$_2$CH$_3$ | 0 |
| B-1972 | H | H | H | Cl | H | CH(CH$_3$)SCH$_2$CF$_3$ | CH$_2$CH$_3$ | 0 |
| B-1973 | H | H | H | Cl | H | CH$_2$CH(CH$_3$)SCF$_3$ | CH$_2$CH$_3$ | 0 |
| B-1974 | H | H | H | Cl | H | CH$_2$CH(CH$_3$)SCH$_2$CF$_3$ | CH$_2$CH$_3$ | 0 |
| B-1975 | H | H | H | Cl | H | CH(CH$_3$)CH$_2$CH$_2$SCF$_3$ | CH$_2$CH$_3$ | 0 |
| B-1976 | H | H | H | Cl | H | CH(CH$_3$)CH$_2$CH$_2$SCH$_2$CF$_3$ | CB$_2$CH$_3$ | 0 |
| B-1977 | H | H | H | Cl | H | CH$_2$CH(CH$_3$)CH$_2$SCF$_3$ | CH$_2$CH$_3$ | 0 |
| B-1978 | H | H | H | Cl | H | CH$_2$CH(CH$_3$)CH$_2$SCH$_2$CF$_3$ | CH$_2$CH$_3$ | 0 |
| B-1979 | H | H | H | Cl | H | CH$_2$CH$_2$CH(CH$_3$)SCF$_3$ | CH$_2$CH$_3$ | 0 |
| B-1980 | H | H | H | Cl | H | CH$_2$CH$_2$CH(CH$_3$)SCH$_2$CF$_3$ | CH$_2$CH$_3$ | 0 |
| B-1981 | H | H | H | Cl | H | CH$_2$SOCF$_3$ | CH$_2$CH$_3$ | 0 |
| B-1982 | H | H | H | Cl | H | CH$_2$CH$_2$SOCF$_3$ | CH$_2$CH$_3$ | 0 |
| B-1983 | H | H | H | Cl | H | CH$_2$CH$_2$CH$_2$SOCF$_3$ | CH$_2$CH$_3$ | 0 |
| B-1984 | H | H | H | Cl | H | CH(CH$_3$)SOCF$_3$ | CH$_2$CH$_3$ | 0 |
| B-1985 | H | H | H | Cl | H | CH$_2$CH(CH$_3$)SOCF$_3$ | CH$_2$CH$_3$ | 0 |
| B-1986 | H | H | H | Cl | H | CH(CH$_3$)CH$_2$CH$_2$SOCF$_3$ | CH$_2$CH$_3$ | 0 |
| B-1987 | H | H | H | Cl | H | CH$_2$CH(CH$_3$)CH$_2$SOCF$_3$ | CH$_2$CH$_3$ | 0 |
| B-1988 | H | H | H | Cl | H | CH$_2$CH$_2$CH(CH$_3$)SOCF$_3$ | CH$_2$CH$_3$ | 0 |
| B-1989 | H | H | H | Cl | H | CH$_2$SO$_2$CF$_3$ | CH$_2$CH$_3$ | 0 |
| B-1990 | H | H | H | Cl | H | CH$_2$CH$_2$SO$_2$CF$_3$ | CH$_2$CH$_3$ | 0 |
| B-1991 | H | H | H | Cl | H | CH$_2$CH$_2$CH$_2$SO$_2$CF$_3$ | CH$_2$CH$_3$ | 0 |
| B 1992 | H | H | H | Cl | H | CH(CH$_3$)SO$_2$CF$_3$ | CH$_2$CH$_3$ | 0 |

TABLE 126-continued

| Compound | R$^1$ | R$^2$ | R$^3$ | R$^4$ | R$^5$ | R$^6$ | R$^{16}$ | n |
|---|---|---|---|---|---|---|---|---|
| B-1993 | H | H | H | Cl | H | CH$_2$CH(CH$_3$)SO$_2$CF$_3$ | CH$_2$CH$_3$ | 0 |
| B-1994 | H | H | H | Cl | H | CH(CH$_3$)CH$_2$CH$_2$SO$_2$CF$_3$ | CH$_2$CH$_3$ | 0 |
| B-1995 | H | H | H | Cl | H | CH$_2$CH(CH$_3$)CH$_2$SO$_2$CF$_3$ | CH$_2$CH$_3$ | 0 |
| B-1996 | H | H | H | Cl | H | CH$_2$CH$_2$CH(CH$_3$)SO$_2$CF$_3$ | CH$_2$CH$_3$ | 0 |
| B-1997 | H | H | H | Cl | H | CH$_2$C(=O)CH$_3$ | CH$_2$CH$_3$ | 0 |
| B-1998 | H | H | H | Cl | H | CH$_2$C(=O)CH$_2$CH$_3$ | CH$_2$CH$_3$ | 0 |
| B-1999 | H | H | H | Cl | H | CH$_2$C(=O)C(CH$_3$)$_3$ | CH$_2$CH$_3$ | 0 |
| B-2000 | H | H | H | Cl | H | CH$_2$CH$_2$C(=O)CH$_3$ | CH$_2$CH$_3$ | 0 |
| B-2001 | H | H | H | Cl | H | CH$_2$CH$_2$C(=O)C(CH$_3$)$_3$ | CH$_2$CH$_3$ | 0 |
| B-2002 | H | H | H | Cl | H | CH$_2$C(=O)CF$_3$ | CH$_2$CH$_3$ | 0 |
| B-2003 | H | H | H | Cl | H | CH$_2$CH$_2$C(=O)CF$_3$ | CH$_2$CH$_3$ | 0 |
| B-2004 | H | H | H | Cl | H | CH$_2$C(=O)OCH$_3$ | CH$_2$CH$_3$ | 0 |
| B-2005 | H | H | H | Cl | H | CH$_2$C(=O)OCH$_2$CH$_3$ | CH$_2$CH$_3$ | 0 |
| B-2006 | H | H | H | Cl | H | CH$_2$C(=O)OC(CH$_3$)$_3$ | CH$_2$CH$_3$ | 0 |
| B-2007 | H | H | H | Cl | H | CH$_2$CH$_2$C(=O)OCH$_3$ | CH$_2$CH$_3$ | 0 |
| B-2008 | H | H | H | Cl | H | CH$_2$CH$_2$C(=O)OCH$_2$CH$_3$ | CH$_2$CH$_3$ | 0 |

TABLE 127

| Compound | R$^1$ | R$^2$ | R$^3$ | R$^4$ | R$^5$ | R$^6$ | R$^{16}$ | n |
|---|---|---|---|---|---|---|---|---|
| B-2009 | H | H | H | Cl | H | CH$_2$CH$_2$C(=O)OC(CH$_3$)$_3$ | CH$_2$CH$_3$ | 0 |
| B-2010 | H | H | H | Cl | H | CH$_2$C(=O)NH$_2$ | CH$_2$CH$_3$ | 0 |
| B-2011 | H | H | H | Cl | H | CH$_2$CH$_2$C(=O)NH$_2$ | CH$_2$CH$_3$ | 0 |
| B-2012 | H | H | H | Cl | H | CH$_2$C(=O)NHCH$_3$ | CH$_2$CH$_3$ | 0 |
| B-2013 | H | H | H | Cl | H | CH$_2$C(=O)NHCH(CH$_3$)$_2$ | CH$_2$CH$_3$ | 0 |
| B-2014 | H | H | H | Cl | H | CH$_2$CH$_2$C(=O)NHCH$_3$ | CH$_2$CH$_3$ | 0 |
| B-2015 | H | H | H | Cl | H | CH$_2$CH$_2$C(=O)NHCH(CH$_3$)$_2$ | CH$_2$CH$_3$ | 0 |
| B-2016 | H | H | H | Cl | H | CH$_2$C(=O)NHCH$_2$CHF$_2$ | CH$_2$CH$_3$ | 0 |
| B-2012 | H | H | H | Cl | H | CH$_2$C(=O)NHCH$_2$CF$_3$ | CH$_2$CH$_3$ | 0 |
| B-2018 | H | H | H | Cl | H | CH$_2$CH$_2$C(=O)NHCH$_2$CHF$_2$ | CH$_2$CH$_3$ | 0 |
| B-2019 | H | H | H | Cl | H | CH$_2$CH$_2$C(=O)NHCH$_2$CF$_3$ | CH$_2$CH$_3$ | 0 |
| B-2020 | H | H | H | Cl | H | CH$_2$C(=O)N(CH$_3$)$_2$ | CH$_2$CH$_3$ | 0 |
| B-2021 | H | H | H | Cl | H | CH$_2$C(=O)N(CH$_2$CH$_3$)$_2$ | CH$_2$CH$_3$ | 0 |
| B-2022 | H | H | H | Cl | H | CH$_2$CH$_2$C(=O)N(CH$_3$)$_2$ | CH$_2$CH$_3$ | 0 |
| B-2023 | H | H | H | Cl | H | CH$_2$CH$_2$C(=O)N(CH$_2$CH$_3$)$_2$ | CH$_2$CH$_3$ | 0 |
| B-2024 | H | H | H | Cl | H | CH$_2$CH$_2$OH | CH$_2$CH$_3$ | 0 |
| B-2025 | H | H | H | Cl | H | CH$_2$CH(OH)CH$_3$ | CH$_2$CH$_3$ | 0 |
| B-2026 | H | H | H | Cl | H | CH$_2$CH$_2$CH$_2$OH | CH$_2$CH$_3$ | 0 |
| B-2027 | H | H | H | Cl | H | CH$_2$CH(OH)CH$_2$CH$_3$ | CH$_2$CH$_3$ | 0 |
| B-2028 | H | H | H | Cl | H | CH$_2$CH(OH)C(CH$_3$)$_3$ | CH$_2$CH$_3$ | 0 |
| B-2029 | H | H | H | Cl | H | CH$_2$CH$_2$CH(OH)CH$_3$ | CH$_2$CH$_3$ | 0 |
| B-2030 | H | H | H | Cl | H | CH$_2$CH$_2$CH(OH)C(CH$_3$)$_3$ | CH$_2$CH$_3$ | 0 |
| B-2031 | H | H | H | Cl | H | CH$_2$C(=NOH)CH$_3$ | CH$_2$CH$_3$ | 0 |
| B-2032 | H | H | H | Cl | H | CH$_2$C(=NOH)CH$_2$CH$_3$ | CH$_2$CH$_3$ | 0 |
| B-2033 | H | H | H | Cl | H | CH$_2$C(=NOH)C(CH$_3$)$_3$ | CH$_2$CH$_3$ | 0 |
| B-2034 | H | H | H | Cl | H | CH$_2$C(=NOCH$_3$)CH$_3$ | CH$_2$CH$_3$ | 0 |
| B-2035 | H | H | H | Cl | H | CH$_2$C(=NOCH$_3$)CH$_2$CH$_3$ | CH$_2$CH$_3$ | 0 |
| B-2036 | H | H | H | Cl | H | CH$_2$C(=NOCH$_2$CH$_3$)CH$_3$ | CH$_2$CH$_3$ | 0 |
| B-2037 | H | H | H | Cl | H | CH$_2$C(=NOCH$_2$CH$_3$)CH$_2$CH$_3$ | CH$_2$CH$_3$ | 0 |
| B-2038 | H | H | H | Cl | H | CH$_2$C(=NOCH$_2$CF$_3$)CH$_3$ | CH$_2$CH$_3$ | 0 |
| B-2039 | H | H | H | Cl | H | CH$_2$C(=NOCH$_2$CF$_3$)CH$_2$CH$_3$ | CH$_2$CH$_3$ | 0 |
| B-2040 | H | H | H | Cl | H | CH$_2$Ph | CH$_2$CH$_3$ | 0 |
| B-2041 | H | H | H | Cl | H | CH$_2$(2-F)Ph | CH$_2$CH$_3$ | 0 |
| B-2042 | H | H | H | Cl | H | CH$_2$(3-F)Ph | CH$_2$CH$_3$ | 0 |
| B-2043 | H | H | H | Cl | H | CH$_2$(4-F)Ph | CH$_2$CH$_3$ | 0 |
| B-2044 | H | H | H | Cl | H | CH$_2$(2-Cl)Ph | CH$_2$CH$_3$ | 0 |
| B-2045 | H | H | H | Cl | H | CH$_2$(3-Cl)Ph | CH$_2$CH$_3$ | 0 |
| B-2046 | H | H | H | Cl | H | CH$_2$(4-Cl)Ph | CH$_2$CH$_3$ | 0 |
| B-2047 | H | H | H | Cl | H | CH$_2$(2-CF$_3$)Ph | CH$_2$CH$_3$ | 0 |
| B-2048 | H | H | H | Cl | H | CH$_2$(3-CF$_3$)Ph | CH$_2$CH$_3$ | 0 |
| B-2049 | H | H | H | Cl | H | CH$_2$(4-CF$_3$)Ph | CH$_2$CH$_3$ | 0 |
| B-2050 | H | H | H | Cl | H | CH$_2$(naphthalen-1-yl) | CH$_2$CH$_3$ | 0 |
| B-2051 | H | H | H | Cl | H | CH$_2$(naphthalen-2-yl) | CH$_2$CH$_3$ | 0 |
| B-2052 | H | H | H | Cl | H | CH$_2$CH$_2$Ph | CH$_2$CH$_3$ | 0 |
| B-2053 | H | H | H | H | Cl | H | H | 0 |
| B-2054 | H | H | H | H | Cl | CH$_3$ | H | 0 |
| B-2055 | H | H | H | H | Cl | CH$_2$CH$_3$ | H | 0 |
| B-2056 | H | H | H | H | Cl | CH(CH$_3$)$_2$ | H | 0 |
| B-2057 | H | H | H | H | Cl | CH$_2$CH$_2$CH$_3$ | H | 0 |
| B-2058 | H | H | H | H | Cl | CH$_2$CH(CH$_3$)$_2$ | H | 0 |
| B-2059 | H | H | H | H | Cl | CH$_2$C(CH$_3$)$_3$ | H | 0 |
| B-2060 | H | H | H | H | Cl | CH(CH$_3$)CH$_2$CH$_3$ | H | 0 |
| B-2061 | H | H | H | H | Cl | CH$_2$(CH$_2$)$_2$CH$_3$ | H | 0 |
| B-2062 | H | H | H | H | Cl | CH$_2$(CH$_2$)$_3$CH$_3$ | H | 0 |

TABLE 127-continued

| Compound | R$^1$ | R$^2$ | R$^3$ | R$^4$ | R$^5$ | R$^6$ | R$^{16}$ | n |
|---|---|---|---|---|---|---|---|---|
| B-2063 | H | H | H | H | Cl | CH$_2$(CH$_2$)$_4$CH$_3$ | H | 0 |
| B-2064 | H | H | H | H | Cl | CH$_2$(CH$_2$)$_6$CH$_3$ | H | 0 |
| B-2065 | H | H | H | H | Cl | CH$_2$OCH$_3$ | H | 0 |
| B-2066 | H | H | H | H | Cl | CH$_2$OCH$_2$CH$_3$ | H | 0 |
| B-2067 | H | H | H | H | Cl | CH$_2$CH$_2$OCH$_3$ | H | 0 |
| B-2068 | H | H | H | H | Cl | CH$_2$CH$_2$OCH$_2$CH$_3$ | H | 0 |
| B-2069 | H | H | H | H | Cl | CF$_3$ | H | 0 |

TABLE 128

| Compound | R$^1$ | R$^2$ | R$^3$ | R$^4$ | R$^5$ | R$^6$ | R$^{16}$ | n |
|---|---|---|---|---|---|---|---|---|
| B-2070 | H | H | H | H | Cl | CHF$_2$ | H | 0 |
| B-2071 | H | H | H | H | Cl | CH$_2$CF$_3$ | H | 0 |
| B-2072 | H | H | H | H | Cl | CH$_2$CHF$_2$ | H | 0 |
| B-2073 | H | H | H | H | Cl | CH$_3$CClF$_2$ | H | 0 |
| B-2074 | H | H | H | H | Cl | CH$_2$CBrF$_2$ | H | 0 |
| B-2075 | H | H | H | H | Cl | CF$_2$CF$_3$ | H | 0 |
| B-2076 | H | H | H | H | Cl | CF$_2$CHF$_2$ | H | 0 |
| B-2077 | H | H | H | H | Cl | CH$_2$CH$_2$CF$_3$ | H | 0 |
| B-2078 | H | H | H | H | Cl | CH$_2$CF$_2$CF$_3$ | H | 0 |
| B-2079 | H | H | H | H | Cl | CH$_2$CF$_2$CHF$_2$ | H | 0 |
| B-2080 | H | H | H | H | Cl | CF$_2$CHFCF$_3$ | H | 0 |
| B-2081 | H | H | H | H | Cl | CF$_2$CF$_2$CF$_3$ | H | 0 |
| B-2082 | H | H | H | H | Cl | CH$_2$CF$_2$CF$_2$CF$_3$ | H | 0 |
| B-2083 | H | H | H | H | Cl | CH$_2$CF$_2$CHFCF$_3$ | H | 0 |
| B-2084 | H | H | H | H | Cl | CH$_2$CH$_2$CH$_2$CF$_3$ | H | 0 |
| B-2085 | H | H | H | H | Cl | CH$_2$CH$_2$CF$_2$CF$_3$ | H | 0 |
| B-2086 | H | H | H | H | Cl | CF$_2$CF$_2$CF$_2$CF$_3$ | H | 0 |
| B-2087 | H | H | H | H | Cl | CH$_2$CH$_2$CH(CF$_3$)$_2$ | H | 0 |
| B-2088 | H | H | H | H | Cl | CF$_2$CF$_2$CF$_2$CF$_2$CF$_3$ | H | 0 |
| B-2089 | H | H | H | H | Cl | CF$_2$CF$_2$CF$_2$CF$_2$CF$_3$ | H | 0 |
| B-2090 | H | H | H | H | Cl | CH$_2$CH$_2$CH$_2$CH$_2$CF$_3$ | H | 0 |
| B-2091 | H | H | H | H | Cl | CH$_2$CF$_3$CF$_2$CF$_2$CHF$_2$ | H | 0 |
| B-2092 | H | H | H | H | Cl | CH$_2$CF$_2$CF(CF$_3$)CF$_2$C(CF$_3$)$_3$ | H | 0 |
| B-2093 | H | H | H | H | Cl | CH$_2$CH$_2$CH$_2$CH$_2$CF$_3$ | H | 0 |
| B-2094 | H | H | H | H | Cl | CH$_2$CH$_2$CH$_2$CH$_2$CH$_2$CF$_3$ | H | 0 |
| B-2095 | H | H | H | H | Cl | CF$_2$CHFOCH$_3$ | H | 0 |
| B-2096 | H | H | H | H | Cl | CF$_2$CHFOCH$_2$CH$_3$ | H | 0 |
| B-2097 | H | H | H | H | Cl | CH$_2$CH$_2$OCH$_2$CF$_3$ | H | 0 |
| B-2098 | H | H | H | H | Cl | CF$_2$CHFOCF$_3$ | H | 0 |
| B-2099 | H | H | H | H | Cl | CF$_2$CHFOCF$_2$CF$_3$ | H | 0 |
| B-2100 | H | H | H | H | Cl | CF$_2$CHFOCF$_2$CF$_2$CF$_3$ | H | 0 |
| B-2101 | H | H | H | H | Cl | CH$_2$CH=CH$_2$ | H | 0 |
| B-2102 | H | H | H | H | Cl | CH$_2$CH=CHCl | H | 0 |
| B-2103 | H | H | H | H | Cl | CH$_2$CH=CCl$_2$ | H | 0 |
| B-2104 | H | H | H | H | Cl | CH$_2$CH$_2$CF=CF$_2$ | H | 0 |
| B-2105 | H | H | H | H | Cl | CH$_2$CH$_2$CH=CF$_2$ | H | 0 |
| B-2106 | H | H | H | H | Cl | CH$_2$C≡CH | H | 0 |
| B-2107 | H | H | H | H | Cl | CH$_2$C≡CCH$_3$ | H | 0 |
| B-2108 | H | H | H | H | Cl | CH$_2$C≡Cl | H | 0 |
| B-2109 | H | H | H | H | Cl | CH$_2$C≡CCF$_3$ | H | 0 |
| B-2110 | H | H | H | H | Cl | cyclobutyl | H | 0 |
| B-2111 | H | H | H | H | Cl | cyclopentyl | H | 0 |
| B-2112 | H | H | H | H | Cl | cyclohexyl | H | 0 |
| B-2113 | H | H | H | H | Cl | 4,4-difluorocyclohexyl | H | 0 |
| B-2114 | H | H | H | H | Cl | CH$_2$(cyclopropyl) | H | 0 |
| B-2115 | H | H | H | H | Cl | CH$_2$(cyclobutyl) | H | 0 |
| B-2116 | H | H | H | H | Cl | CH$_2$(cyclopentyl) | H | 0 |
| B-2117 | H | H | H | H | Cl | CH$_2$CH$_2$(cyclopropyl) | H | 0 |
| B-2118 | H | H | H | H | Cl | CH$_2$(2,2-difluorocyclopropyl) | H | 0 |
| B-2119 | H | H | H | H | Cl | CH$_2$(2,2-dichlorocyclopropyl) | H | 0 |
| B-2120 | H | H | H | H | Cl | CH$_2$(4,4-fluorocyclohexyl) | H | 0 |
| B-2121 | H | H | H | H | Cl | CH$_2$CH$_2$(2,2-difluorocyclopropyl) | H | 0 |
| B-2122 | H | H | H | H | Cl | CH$_2$CH$_2$(2,2-dichlorocyclopropyl) | H | 0 |
| B-2123 | H | H | H | H | Cl | CH$_2$SCH$_3$ | H | 0 |
| B-2124 | H | H | H | H | Cl | CH$_2$SCH$_2$CH$_3$ | H | 0 |
| B-2125 | H | H | H | H | Cl | CH$_2$CH$_2$SCH$_3$ | H | 0 |
| B-2126 | H | H | H | H | Cl | CH$_3$CH$_2$SCH$_2$CH$_3$ | H | 0 |
| B-2127 | H | H | H | H | Cl | CH$_2$CH$_2$CH$_2$SCH$_3$ | H | 0 |
| B-2128 | H | H | H | H | Cl | CH$_2$CH$_2$CH$_2$SCH$_2$CH$_3$ | H | 0 |
| B-2129 | H | H | H | H | Cl | CH(CH$_3$)SCH$_3$ | H | 0 |
| B-2130 | H | H | H | H | Cl | CH(CH$_3$)SCH$_2$CH$_3$ | H | 0 |

TABLE 129

| Compound | R¹ | R² | R³ | R⁴ | R⁵ | R⁶ | R¹⁶ | n |
|---|---|---|---|---|---|---|---|---|
| B-2131 | H | H | H | H | Cl | CH$_2$CH(CH$_3$)SCH$_3$ | H | 0 |
| B-2132 | H | H | H | H | Cl | CH$_2$CH(CH$_3$)SCH$_2$CH$_3$ | H | 0 |
| B-2133 | H | H | H | H | Cl | CH(CH$_3$)CH$_2$CH$_2$SCH$_3$ | H | 0 |
| B-2134 | H | H | H | H | Cl | CH(CH$_3$)CH$_2$CH$_2$SCH$_2$CH$_3$ | H | 0 |
| B-2135 | H | H | H | H | Cl | CH$_2$CH(CH$_3$)CH$_2$SCH$_3$ | H | 0 |
| B-2136 | H | H | H | H | Cl | CH$_2$CH(CH$_3$)CH$_2$SCH$_2$CH$_3$ | H | 0 |
| B-2137 | H | H | H | H | Cl | CH$_2$CH$_2$CH(CH$_3$)SCH$_3$ | H | 0 |
| B-2138 | H | H | H | H | Cl | CH$_2$CH$_2$CH(CH$_3$)SCH$_2$CH$_3$ | H | 0 |
| B-2139 | H | H | H | H | Cl | CH$_2$SOCH$_3$ | H | 0 |
| B-2140 | H | H | H | H | Cl | CH$_2$CH$_2$SOCH$_3$ | H | 0 |
| B-2141 | H | H | H | H | Cl | CH$_2$CH$_2$CH$_2$SOCH$_3$ | H | 0 |
| B-2142 | H | H | H | H | Cl | CH(CH$_3$)SOCH$_3$ | H | 0 |
| B-2143 | H | H | H | H | Cl | CH$_2$CH(CH$_3$)SOCH$_3$ | H | 0 |
| B-2144 | H | H | H | H | Cl | CH(CH$_3$)CH$_2$CH$_2$SOCH$_3$ | H | 0 |
| B-2145 | H | H | H | H | Cl | CH$_2$CH(CH$_3$)CH$_2$SOCH$_3$ | H | 0 |
| B-2146 | H | H | H | H | Cl | CH$_2$CH$_2$CH(CH$_3$)SOCH$_3$ | H | 0 |
| B-2147 | H | H | H | H | Cl | CH$_2$SO$_2$CH$_3$ | H | 0 |
| B-2148 | H | H | H | H | Cl | CH$_2$CH$_2$SO$_2$CH$_3$ | H | 0 |
| B-2149 | H | H | H | H | Cl | CH$_2$CH$_2$CH$_2$SO$_2$CH$_3$ | H | 0 |
| B-2150 | H | H | H | H | Cl | CH(CH$_3$)SO$_2$CH$_3$ | H | 0 |
| B-2151 | H | H | H | H | Cl | CH$_2$CH(CH$_3$)SO$_2$CH$_3$ | H | 0 |
| B-2152 | H | H | H | H | Cl | CH(CH$_3$)CH$_2$CH$_2$SO$_2$CH$_3$ | H | 0 |
| B-2153 | H | H | H | H | Cl | CH$_2$CH(CH$_3$)CH$_2$SO$_2$CH$_3$ | H | 0 |
| B-2154 | H | H | H | H | Cl | CH$_2$CH$_2$CH(CH$_3$)SO$_2$CH$_3$ | H | 0 |
| B-2155 | H | H | H | H | Cl | CH$_2$SCF$_3$ | H | 0 |
| B-2156 | H | H | H | H | Cl | CH$_2$SCHF$_2$ | H | 0 |
| B-2157 | H | H | H | H | Cl | CH$_2$SCH$_2$CF$_3$ | H | 0 |
| B-2158 | H | H | H | H | Cl | CH$_2$SCH$_2$CHF$_2$ | H | 0 |
| B-2159 | H | H | H | H | Cl | CH$_2$SCF$_2$CF$_3$ | H | 0 |
| B-2160 | H | H | H | H | Cl | CH$_2$CH$_2$SCF$_3$ | H | 0 |
| B-2161 | H | H | H | H | Cl | CH$_2$CH$_2$SCH$_2$CF$_3$ | H | 0 |
| B-2162 | H | H | H | H | Cl | CH$_2$CH$_2$CH$_2$SCF$_3$ | H | 0 |
| B-2163 | H | H | H | H | Cl | CH$_2$CH$_2$CH$_2$SCH$_2$CF$_3$ | H | 0 |
| B-2164 | H | H | H | H | Cl | CH(CH$_3$)SCF$_3$ | H | 0 |
| B-2165 | H | H | H | H | Cl | CH(CH$_3$)SCH$_2$CF$_3$ | H | 0 |
| B-2166 | H | H | H | H | Cl | CH$_2$CH(CH$_3$)SCF$_3$ | H | 0 |
| B-2167 | H | H | H | H | Cl | CH$_2$CH(CH$_3$)SCH$_2$CF$_3$ | H | 0 |
| B-2168 | H | H | H | H | Cl | CH(CH$_3$)CH$_2$CH$_2$SCF$_3$ | H | 0 |
| B-2169 | H | H | H | H | Cl | CH(CH$_3$)CH$_2$CH$_2$SCH$_2$CF$_3$ | H | 0 |
| B-2170 | H | H | H | H | Cl | CH$_2$CH(CH$_3$)CH$_2$SCF$_3$ | H | 0 |
| B-2171 | H | H | H | H | Cl | CH$_2$CH(CH$_3$)CH$_2$SCH$_2$CF$_3$ | H | 0 |
| B-2172 | H | H | H | H | Cl | CH$_2$CH$_2$CH(CH$_3$)SCF$_3$ | H | 0 |
| B-2173 | H | H | H | H | Cl | CH$_2$CH$_2$CH(CH$_3$)SCH$_2$CF$_3$ | H | 0 |
| B-2174 | H | H | H | H | Cl | CH$_2$SOCF$_3$ | H | 0 |
| B-2175 | H | H | H | H | Cl | CH$_2$CH$_2$SOCF$_3$ | H | 0 |
| B-2176 | H | H | H | H | Cl | CH$_2$CH$_2$CH$_2$SOCF$_3$ | H | 0 |
| B-2177 | H | H | H | H | Cl | CH(CH$_3$)SOCF$_3$ | H | 0 |
| B-2178 | H | H | H | H | Cl | CH$_2$CH(CH$_3$)SOCF$_3$ | H | 0 |
| B-2179 | H | H | H | H | Cl | CH(CH$_3$)CH$_2$CH$_2$SOCF$_3$ | H | 0 |
| B-2180 | H | H | H | H | Cl | CH$_2$CH(CH$_3$)CH$_2$SOCF$_3$ | H | 0 |
| B-2181 | H | H | H | H | Cl | CH$_2$CH$_2$CH(CH$_3$)SOCF$_3$ | H | 0 |
| B-2182 | H | H | H | H | Cl | CH$_2$SO$_2$CF$_3$ | H | 0 |
| B-2183 | H | H | H | H | Cl | CH$_2$CH$_2$SO$_2$CF$_3$ | H | 0 |
| B-2184 | H | H | H | H | Cl | CH$_2$CH$_2$CH$_2$SO$_2$CF$_3$ | H | 0 |
| B-2185 | H | H | H | H | Cl | CH(CH$_3$)SO$_2$CF$_3$ | H | 0 |
| B-2186 | H | H | H | H | Cl | CH$_2$CH(CH$_3$)SO$_2$CF$_3$ | H | 0 |
| B-2187 | H | H | H | H | Cl | CH(CH$_3$)CH$_2$CH$_2$SO$_2$CF$_3$ | H | 0 |
| B-2188 | H | H | H | H | Cl | CH$_2$CH(CH$_3$)CH$_2$SO$_2$CF$_3$ | H | 0 |
| B-2189 | H | H | H | H | Cl | CH$_2$CH$_2$CH(CH$_3$)SO$_2$CF$_3$ | H | 0 |
| B-2190 | H | H | H | H | Cl | CH$_2$C(=O)CH$_3$ | H | 0 |
| B-2191 | H | H | H | H | Cl | CH$_2$C(=O)CH$_2$CH$_3$ | H | 0 |

TABLE 130

| Compound | R¹ | R² | R³ | R⁴ | R⁵ | R⁶ | R¹⁶ | n |
|---|---|---|---|---|---|---|---|---|
| B-2192 | H | H | H | H | Cl | CH$_2$C(=O)C(CH$_3$)$_3$ | H | 0 |
| B-2193 | H | H | H | H | Cl | CH$_2$CH$_2$C(=O)CH$_3$ | H | 0 |
| B-2194 | H | H | H | H | Cl | CH$_2$CH$_2$C(=O)C(CH$_3$)$_3$ | H | 0 |
| B-2195 | H | H | H | H | Cl | CH$_2$C(=O)CF$_3$ | H | 0 |
| B-2196 | H | H | H | H | Cl | CH$_2$CH$_2$C(=O)CF$_3$ | H | 0 |
| B-2197 | H | H | H | H | Cl | CH$_2$C(=O)OCH$_3$ | H | 0 |
| B-2198 | H | H | H | H | Cl | CH$_2$C(=O)OCH$_2$CH$_3$ | H | 0 |
| B-2199 | H | H | H | H | Cl | CH$_2$C(=O)OC(CH$_3$)$_3$ | H | 0 |
| B-2200 | H | H | H | H | Cl | CH$_2$CH$_2$C(=O)OCH$_3$ | H | 0 |

TABLE 130-continued

| Compound | $R^1$ | $R^2$ | $R^3$ | $R^4$ | $R^5$ | $R^6$ | $R^{16}$ | n |
|---|---|---|---|---|---|---|---|---|
| B-2201 | H | H | H | H | Cl | $CH_2CH_2C(=O)OCH_2CH_3$ | H | 0 |
| B-2202 | H | H | H | H | Cl | $CH_2CH_2C(=O)OC(CH_3)_3$ | H | 0 |
| B-2203 | H | H | H | H | Cl | $CH_2C(=O)NH_2$ | H | 0 |
| B-2204 | H | H | H | H | Cl | $CH_2CH_2C(=O)NH_2$ | H | 0 |
| B-2205 | H | H | H | H | Cl | $CH_2C(=O)NHCH_3$ | H | 0 |
| B-2206 | H | H | H | H | Cl | $CH_2C(=O)NHCH(CH_3)_2$ | H | 0 |
| B-2207 | H | H | H | H | Cl | $CH_2CH_2C(=O)NHCH_3$ | H | 0 |
| B-2208 | H | H | H | H | Cl | $CH_2CH_2C(=O)NHCH(CH_3)_2$ | H | 0 |
| B-2209 | H | H | H | H | Cl | $CH_2C(=O)NHCH_2CHF_2$ | H | 0 |
| B-2210 | H | H | H | H | Cl | $CH_2C(=O)NHCH_2CF_3$ | H | 0 |
| B-2211 | H | H | H | H | Cl | $CH_2CH_2C(=O)NHCH_2CHF_3$ | H | 0 |
| B-2212 | H | H | H | H | Cl | $CH_2CH_2C(=O)NHCH_2CF_3$ | H | 0 |
| B-2213 | H | H | H | H | Cl | $CH_2C(=O)N(CH_3)_2$ | H | 0 |
| B-2214 | H | H | H | H | Cl | $CH_2C(=O)N(CH_2CH_3)_2$ | H | 0 |
| B-2215 | H | H | H | H | Cl | $CH_2CH_2C(=O)N(CH_3)_2$ | H | 0 |
| B-2216 | H | H | H | H | Cl | $CH_2CH_2C(=O)N(CH_2CH_3)_2$ | H | 0 |
| B-2217 | H | H | H | H | Cl | $CH_2CH_2OH$ | H | 0 |
| B-2218 | H | H | H | H | Cl | $CH_2CH(OH)CH_3$ | H | 0 |
| B-2219 | H | H | H | H | Cl | $CH_2CH_2CH_2OH$ | H | 0 |
| B-2220 | H | H | H | H | Cl | $CH_2CH(OH)CH_2CH_3$ | H | 0 |
| B-2221 | H | H | H | H | Cl | $CH_2CH(OH)C(CH_3)_3$ | H | 0 |
| B-2222 | H | H | H | H | Cl | $CH_2CH_2CH(OH)CH_3$ | H | 0 |
| B-2223 | H | H | H | H | Cl | $CH_2CH_2CH(OH)C(CH_3)H$ | H | 0 |
| B-2224 | H | H | H | H | Cl | $CH_2C(=NOH)CH_3$ | H | 0 |
| B-2225 | H | H | H | H | Cl | $CH_2C(=NOH)CH_2CH_3$ | H | 0 |
| B-2226 | H | H | H | H | Cl | $CH_2C(=NOH)C(CH_3)_3$ | H | 0 |
| B-2227 | H | H | H | H | Cl | $CH_2C(=NOCH_3)CH_3$ | H | 0 |
| B-2228 | H | H | H | H | Cl | $CH_2C(=NOCH_3)CH_2CH_3$ | H | 0 |
| B-2229 | H | H | H | H | Cl | $CH_2C(=NOCH_2CH_3)CH_3$ | H | 0 |
| B-2230 | H | H | H | H | Cl | $CH_2C(=NOCH_2CH_3)CH_2CH_3$ | H | 0 |
| B-2231 | H | H | H | H | Cl | $CH_2C(=NOCH_2CF_3)CH_3$ | H | 0 |
| B-2232 | H | H | H | H | Cl | $CH_2C(=NOCH_2CF_3)CH_2CH_3$ | H | 0 |
| B-2233 | H | H | H | H | Cl | $CH_2Ph$ | H | 0 |
| B-2234 | H | H | H | H | Cl | $CH_2(2-F)Ph$ | H | 0 |
| B-2235 | H | H | H | H | Cl | $CH_2(3-F)Ph$ | H | 0 |
| B-2236 | H | H | H | H | Cl | $CH_2(4-F)Ph$ | H | 0 |
| B-2237 | H | H | H | H | Cl | $CH_2(2-Cl)Ph$ | H | 0 |
| B-2238 | H | H | H | H | Cl | $CH_2(3-Cl)Ph$ | H | 0 |
| B-2239 | H | H | H | H | Cl | $CH_2(4-Cl)Ph$ | H | 0 |
| B-2240 | H | H | H | H | Cl | $CH_2(2-CF_3)Ph$ | H | 0 |
| B-2241 | H | H | H | H | Cl | $CH_2(3-CF_3)Ph$ | H | 0 |
| B-2242 | H | H | H | H | Cl | $CH_2(4-CF_3)Ph$ | H | 0 |
| B-2243 | H | H | H | H | Cl | $CH_2(naphthalen-1-yl)$ | H | 0 |
| B-2244 | H | H | H | H | Cl | $CH_2(naphthalen-2-yl)$ | H | 0 |
| B-2245 | H | H | H | H | Cl | $CH_2CH_2Ph$ | H | 0 |
| B-2246 | H | H | H | H | Cl | H | $CH_2CH_3$ | 0 |
| B-2247 | H | H | H | H | Cl | $CH_3$ | $CH_2CH_3$ | 0 |
| B-2248 | H | H | H | H | Cl | $CH_2CH_3$ | $CH_2CH_3$ | 0 |
| B-2249 | H | H | H | H | Cl | $CH(CH_3)_2$ | $CH_2CH_3$ | 0 |
| B-2250 | H | H | H | H | Cl | $CH_2CH_2CH_3$ | $CH_2CH_3$ | 0 |
| B-2251 | H | H | H | H | Cl | $CH_2CH(CH_3)_2$ | $CH_2CH_3$ | 0 |
| B-2252 | H | H | H | H | Cl | $CH_2C(CH_3)_3$ | $CH_2CH_3$ | 0 |

TABLE 131

| Compound | $R^1$ | $R^2$ | $R^3$ | $R^4$ | $R^5$ | $R^6$ | $R^{16}$ | n |
|---|---|---|---|---|---|---|---|---|
| B-2253 | H | H | H | H | Cl | $CH(CH_3)CH_2CH_3$ | $CH_2CH_3$ | 0 |
| B-2254 | H | H | H | H | Cl | $CH_2(CH_2)_2CH_3$ | $CH_2CH_3$ | 0 |
| B-2255 | H | H | H | H | Cl | $CH_2(CH_2)_3CH_3$ | $CH_2CH_3$ | 0 |
| B-2256 | H | H | H | H | Cl | $CH_2(CH_2)_4CH_3$ | $CH_2CH_3$ | 0 |
| B-2257 | H | H | H | H | Cl | $CH_2(CH_2)_6CH_3$ | $CH_2CH_3$ | 0 |
| B-2258 | H | H | H | H | Cl | $CH_2OCH_3$ | $CH_2CH_3$ | 0 |
| B-2259 | H | H | H | H | Cl | $CH_2OCH_2CH_3$ | $CH_2CH_3$ | 0 |
| B-2260 | H | H | H | H | Cl | $CH_2CH_2OCH_3$ | $CH_2CH_3$ | 0 |
| B-2261 | H | H | H | H | Cl | $CH_2CH_2OCH_2CH_3$ | $CH_2CH_3$ | 0 |
| B-2262 | H | H | H | H | Cl | $CF_3$ | $CH_2CH_3$ | 0 |
| B-2263 | H | H | H | H | Cl | $CHF_2$ | $CH_2CH_3$ | 0 |
| B-2264 | H | H | H | H | Cl | $CH_2CF_3$ | $CH_2CH_3$ | 0 |
| B-2265 | H | H | H | H | Cl | $CH_2CHF_2$ | $CH_2CH_3$ | 0 |
| B-2266 | H | H | H | H | Cl | $CH_2CClF_2$ | $CH_2CH_3$ | 0 |
| B-22S7 | H | H | H | H | Cl | $CH_2CBrF_2$ | $CH_2CH_3$ | 0 |
| B-2268 | H | H | H | H | Cl | $CF_2CF_3$ | $CH_2CH_3$ | 0 |
| B-2269 | H | H | H | H | Cl | $CF_2CHF_2$ | $CH_2CH_3$ | 0 |
| B-2270 | H | H | H | H | Cl | $CH_2CH_2CF_3$ | $CH_2CH_3$ | 0 |

TABLE 131-continued

| Compound | R¹ | R² | R³ | R⁴ | R⁵ | R⁶ | R¹⁶ | n |
|---|---|---|---|---|---|---|---|---|
| B-2271 | H | H | H | H | Cl | CH₂CF₂CF₃ | CH₂CH₃ | 0 |
| B-2272 | H | H | H | H | Cl | CH₂CF₂CHF₂ | CH₂CH₃ | 0 |
| B-2273 | H | H | H | H | Cl | CF₂CHFCF₃ | CH₂CH₃ | 0 |
| B-2274 | H | H | H | H | Cl | CF₂CF₂CF₃ | CH₂CH₃ | 0 |
| B-2275 | H | H | H | H | Cl | CH₂CF₂CF₂CF₃ | CH₂CH₃ | 0 |
| B-2276 | H | H | H | H | Cl | CH₂CF₂CHFCF₃ | CH₂CH₃ | 0 |
| B-2277 | H | H | H | H | Cl | CH₂CH₂CH₂CF₃ | CH₂CH₃ | 0 |
| B-2278 | H | H | H | H | Cl | CH₂CH₂CF₂CF₃ | CH₂CH₃ | 0 |
| B-2279 | H | H | H | H | Cl | CF₂CF₂CF₂CF₃ | CH₂CH₃ | 0 |
| B-2280 | H | H | H | H | Cl | CH₂CH₂CH(CF₃)₂ | CH₂CH₃ | 0 |
| B-2281 | H | H | H | H | Cl | CF₂CF₂CF₂CF₃ | CH₂CH₃ | 0 |
| B-2282 | H | H | H | H | Cl | CH₂CF₂CF₂CF₂CF₃ | CH₂CH₃ | 0 |
| B-2283 | H | H | H | H | Cl | CH₂CH₂CH₂CH₂CF₃ | CH₂CH₃ | 0 |
| B-2284 | H | H | H | H | Cl | CH₂CF₂CF₂CF₂CHF₂ | CH₂CH₃ | 0 |
| B-2285 | H | H | H | H | Cl | CH₂CF₂CF(CF₃)CF₂C(CF₃)₃ | CH₂CH₃ | 0 |
| B-2286 | H | H | H | H | Cl | CH₂CH₂CH₂CH₂CH₂CF₃ | CH₂CH₃ | 0 |
| B-2287 | H | H | H | H | Cl | CH₂CH₂CH₂CH₂CH₂CH₂CF₃ | CH₂CH₃ | 0 |
| B-2288 | H | H | H | H | Cl | CF₂CHFOCH₃ | CH₂CH₃ | 0 |
| B-2289 | H | H | H | H | Cl | CF₂CHFOCH₂CH₃ | CH₂CH₃ | 0 |
| B-2290 | H | H | H | H | Cl | CH₂CH₂OCH₂CF₃ | CH₂CH₃ | 0 |
| B-2291 | H | H | H | H | Cl | CF₂CHFOCF₃ | CH₂CH₃ | 0 |
| B-2292 | H | H | H | H | Cl | CF₂CHFOCF₂CF₃ | CH₂CH₃ | 0 |
| B-2293 | H | H | H | H | Cl | CF₂CHFOCF₂CF₂CF₃ | CH₂CH₃ | 0 |
| B-2294 | H | H | H | H | Cl | CH₂CH=CH₂ | CH₂CH₃ | 0 |
| B-2295 | H | H | H | H | Cl | CH₂CH=CHCl | CH₂CH₃ | 0 |
| B-2296 | H | H | H | H | Cl | CH₂CH=CCl₂ | CH₂CH₃ | 0 |
| B-2297 | H | H | H | H | Cl | CH₂CH₂CF=CF₂ | CH₂CH₃ | 0 |
| B-2298 | H | H | H | H | Cl | CH₂CH₂CH=CF₂ | CH₂CH₃ | 0 |
| B-2299 | H | H | H | H | Cl | CH₂C≡CH | CH₂CH₃ | 0 |
| B-2300 | H | H | H | H | Cl | CH₂C≡CCH₃ | CH₂CH₃ | 0 |
| B-2301 | H | H | H | H | Cl | CH₂C≡Cl | CH₂CH₃ | 0 |
| B-2302 | H | H | H | H | Cl | CH₂C≡CCF₃ | CH₂CH₃ | 0 |
| 8-2303 | H | H | H | H | Cl | cyclobutyl | CH₂CH₃ | 0 |
| B-2304 | H | H | H | H | Cl | cyclopentyl | CH₂CH₃ | 0 |
| B-2305 | H | H | H | H | Cl | cyclohexyl | CH₂CH₃ | 0 |
| B-2306 | H | H | H | H | Cl | 4,4-difluorocyclohexyl | CH₂CH₃ | 0 |
| B-2307 | H | H | H | H | Cl | CH₂(cyclopropyl) | CH₂CH₃ | 0 |
| B-2308 | H | H | H | H | Cl | CH₂(cyclobutyl) | CH₂CH₃ | 0 |
| B-2309 | H | H | H | H | Cl | CH₂(cyclopentyl) | CH₂CH₃ | 0 |
| B-2310 | H | H | H | H | Cl | CH₂CH₂(cyclopropyl) | CH₂CH₃ | 0 |
| B-2311 | H | H | H | H | Cl | CH₂(2,2-difluorocydopropyl) | CH₂CH₃ | 0 |
| B-2312 | H | H | H | H | Cl | CH₂(2,2-dichlorocydopropyl) | CH₂CH₃ | 0 |
| B-2313 | H | H | H | H | Cl | CH₂(4,4-difluorocyclohexyl) | CH₂CH₃ | 0 |

TABLE 132

| Compound | R¹ | R² | R³ | R⁴ | R⁵ | R⁶ | R¹⁶ | n |
|---|---|---|---|---|---|---|---|---|
| B-2314 | H | H | H | H | Cl | CH₂CH₂(2,2-difluorocyclopropyl) | CH₂CH₃ | 0 |
| B-2315 | H | H | H | H | Cl | CH₂CH₂(2,2-dichlorocyclopropyl) | CH₃CH₃ | 0 |
| B-2316 | H | H | H | H | Cl | CH₂SCH₃ | CH₂CH₃ | 0 |
| B-2317 | H | H | H | H | Cl | CH₂SCH₂CH₃ | CH₂CH₃ | 0 |
| B-2318 | H | H | H | H | Cl | CH₂CH₂SCH₃ | CH₂CH₃ | 0 |
| B-2319 | H | H | H | H | Cl | CH₂CH₂SCH₂CH₃ | CH₂CH₃ | 0 |
| B-2320 | H | H | H | H | Cl | CH₂CH₂CH₂SCH₃ | CH₂CH₃ | 0 |
| B-2321 | H | H | H | H | Cl | CH₂CH₂CH₂SCH₂CH₃ | CH₂CH₃ | 0 |
| B-2322 | H | H | H | H | Cl | CH(CH₃)SCH₃ | CH₂CH₃ | 0 |
| B-2323 | H | H | H | H | Cl | CH(CH₃)SCH₂CH₃ | CH₂CH₃ | 0 |
| B-2324 | H | H | H | H | Cl | CH₂CH(CH₃)SCH₃ | CH₂CH₃ | 0 |
| B-2325 | H | H | H | H | Cl | CH₂CH(CH₃)SCH₂CH₃ | CH₂CH₃ | 0 |
| B-2326 | H | H | H | H | Cl | CH(CH₃)CH₂CH₂SCH₃ | CH₂CH₃ | 0 |
| B-2327 | H | H | H | H | Cl | CH(CH₃)CH₂CH₂SCH₂CH₃ | CH₂CH₃ | 0 |
| B-2328 | H | H | H | H | Cl | CH₂CH(CH₃)CH₂SCH₃ | CH₂CH₃ | 0 |
| B-2329 | H | H | H | H | Cl | CH₂CH(CH₃)CH₂SCH₂CH₃ | CH₂CH₃ | 0 |
| B-2330 | H | H | H | H | Cl | CH₂CH₂CH(CH₃)SCH₃ | CH₂CH₃ | 0 |
| B-2331 | H | H | H | H | Cl | CH₂CH₂CH(CH₃)SCH₂CH₃ | CH₂CH₃ | 0 |
| B-2332 | H | H | H | H | Cl | CH₂SOCH₃ | CH₂CH₃ | 0 |
| B-2333 | H | H | H | H | Cl | CH₂CH₂SOCH₃ | CH₂CH₃ | 0 |
| B-2334 | H | H | H | H | Cl | CH₂CH₂CH₂SOCH₃ | CH₂CH₃ | 0 |
| B-2335 | H | H | H | H | Cl | CH(CH₃)SOCH₃ | CH₂CH₃ | 0 |
| B-2336 | H | H | H | H | Cl | CH₂CH(CH₃)SOCH₃ | CH₂CH₃ | 0 |
| B-2337 | H | H | H | H | Cl | CH(CH₃)CH₂CH₂SOCH₃ | CH₂CH₃ | 0 |
| B-2338 | H | H | H | H | Cl | CH₂CH(CH₃)CH₂SOCH₃ | CH₂CH₃ | 0 |
| B-2339 | H | H | H | H | Cl | CH₂CH₂CH(CH₃)SOCH₃ | CH₂CH₃ | 0 |
| B-2340 | H | H | H | H | Cl | CH₂SO₂CH₃ | CH₂CH₃ | 0 |

TABLE 132-continued

| Compound | $R^1$ | $R^2$ | $R^3$ | $R^4$ | $R^5$ | $R^6$ | $R^{16}$ | n |
|---|---|---|---|---|---|---|---|---|
| B-2341 | H | H | H | H | Cl | CH$_2$H$_2$SO$_2$CH$_3$ | CH$_2$CH$_3$ | 0 |
| B-2342 | H | H | H | H | Cl | CH$_2$CH$_2$CH$_2$SO$_2$CH$_3$ | CH$_2$CH$_3$ | 0 |
| B-2343 | H | H | H | H | Cl | CH(CH$_3$)SO$_2$CH$_3$ | CH$_2$CH$_3$ | 0 |
| B-2344 | H | H | H | H | Cl | CH$_2$CH(CH$_3$)SO$_2$CH$_3$ | CH$_2$CH$_3$ | 0 |
| B-2345 | H | H | H | H | Cl | CH(CH$_3$)CH$_2$CH$_2$SO$_2$CH$_3$ | CH$_2$CH$_3$ | 0 |
| B-2346 | H | H | H | H | Cl | CH$_2$CH(CH$_3$)CH$_2$SO$_2$CH$_3$ | CH$_2$CH$_3$ | 0 |
| B-2347 | H | H | H | H | Cl | CH$_2$CH$_2$CH(CH$_3$)SO$_2$CH$_3$ | CH$_2$CH$_3$ | 0 |
| B-2348 | H | H | H | H | Cl | CH$_2$SCF$_3$ | CH$_2$CH$_3$ | 0 |
| B-2349 | H | H | H | H | Cl | CH$_2$SCHF$_2$ | CH$_2$CH$_3$ | 0 |
| B-2350 | H | H | H | H | Cl | CH$_2$SCH$_2$CF$_3$ | CH$_2$CH$_3$ | 0 |
| B-2351 | H | H | H | H | Cl | CH$_2$SCH$_2$CHF$_2$ | CH$_2$CH$_3$ | 0 |
| B-2352 | H | H | H | H | Cl | CH$_2$SCF$_2$CF$_3$ | CH$_2$CH$_3$ | 0 |
| B-2353 | H | H | H | H | Cl | CH$_2$CH$_2$SCF$_3$ | CH$_2$CH$_3$ | 0 |
| B-2354 | H | H | H | H | Cl | CH$_2$CH$_2$SCH$_2$CF$_3$ | CH$_2$CH$_3$ | 0 |
| B-2355 | H | H | H | H | Cl | CH$_2$CH$_2$CH$_2$SCF$_3$ | CH$_2$CH$_3$ | 0 |
| B-2356 | H | H | H | H | Cl | CH$_2$CH$_2$CH$_2$SCH$_2$CF$_3$ | CH$_2$CH$_3$ | 0 |
| B-2357 | H | H | H | H | Cl | CH(CH$_3$)SCF$_3$ | CH$_2$CH$_3$ | 0 |
| B-2358 | H | H | H | H | Cl | CH(CH$_3$)SCH$_2$CF$_3$ | CH$_2$CH$_3$ | 0 |
| B-2359 | H | H | H | H | Cl | CH$_2$CH(CH$_3$)SCF$_3$ | CH$_2$CH$_3$ | 0 |
| B-2360 | H | H | H | H | Cl | CH$_2$CH(CH$_3$)SCH$_2$CF$_3$ | CH$_2$CH$_3$ | 0 |
| B-2361 | H | H | H | H | Cl | CH(CH$_3$)CH$_2$CH$_2$SCF$_3$ | CH$_2$CH$_3$ | 0 |
| B-2362 | H | H | H | H | Cl | CH(CH$_3$)CH$_2$CH$_2$SCH$_2$CF$_3$ | CH$_2$CH$_3$ | 0 |
| B-2363 | H | H | H | H | Cl | CH$_2$CH(CH$_3$)CH$_2$SCF$_3$ | CH$_2$CH$_3$ | 0 |
| B-2364 | H | H | H | H | Cl | CH$_2$CH(CH$_3$)CH$_2$SCH$_2$CF$_3$ | CH$_2$CH$_3$ | 0 |
| B-2365 | H | H | H | H | Cl | CH$_2$CH$_2$CH(CH$_3$)SCF$_3$ | CH$_2$CH$_3$ | 0 |
| B-2366 | H | H | H | H | Cl | CH$_2$CH$_2$CH(CH$_3$)SCH$_2$CF$_3$ | CH$_2$CH$_3$ | 0 |
| B-2367 | H | H | H | H | Cl | CH$_2$SOCF$_3$ | CH$_2$CH$_3$ | 0 |
| B-2368 | H | H | H | H | Cl | CH$_2$CH$_2$SOCF$_3$ | CH$_2$CH$_3$ | 0 |
| B-2369 | H | H | H | H | Cl | CH$_2$CH$_2$CH$_2$SOCF$_3$ | CH$_2$CH$_3$ | 0 |
| B-2370 | H | H | H | H | Cl | CH(CH$_3$)SOCF$_3$ | CH$_2$CH$_3$ | 0 |
| B-2371 | H | H | H | H | Cl | CH$_2$CH(CH$_3$)SOCF$_3$ | CH$_2$CH$_3$ | 0 |
| B-2372 | H | H | H | H | Cl | CH(CH$_3$)CH$_2$CH$_2$SOCF$_3$ | CH$_2$CH$_3$ | 0 |
| B-2373 | H | H | H | H | Cl | CH$_2$CH(CH$_3$)CH$_2$SOCF$_3$ | CH$_2$CH$_3$ | 0 |
| B-2374 | H | H | H | H | Cl | CH$_2$CH$_2$CH(CH$_3$)SOCF$_3$ | CH$_2$CH$_3$ | 0 |

TABLE 133

| Compound | $R^1$ | $R^3$ | $R^3$ | $R^4$ | $R^5$ | $R^6$ | $R^{16}$ | n |
|---|---|---|---|---|---|---|---|---|
| B-2375 | H | H | H | H | Cl | CH$_2$SO$_2$CF$_3$ | CH$_2$CH$_3$ | 0 |
| B-2376 | H | H | H | H | Cl | CH$_2$CH$_2$SO$_2$CF$_3$ | CH$_2$CH$_3$ | 0 |
| B-2377 | H | H | H | H | Cl | CH$_2$CH$_2$CH$_2$SO$_2$CF$_3$ | CH$_2$CH$_3$ | 0 |
| B-2378 | H | H | H | H | Cl | CH(CH$_3$)SO$_2$CF$_3$ | CH$_2$CH$_3$ | 0 |
| B-2379 | H | H | H | H | Cl | CH$_2$CH(CH$_3$)SO$_2$CF$_3$ | CH$_2$CH$_3$ | 0 |
| B-2380 | H | H | H | H | Cl | CH(CH$_3$)CH$_2$CH$_2$SO$_2$CF$_3$ | CH$_2$CH$_3$ | 0 |
| B-2381 | H | H | H | H | Cl | CH$_2$CH(CH$_3$)CH$_2$SO$_2$CF$_3$ | CH$_2$CH$_3$ | 0 |
| B-2382 | H | H | H | H | Cl | CH$_2$CH$_2$CH(CH$_3$)SO$_2$CF$_3$ | CH$_2$CH$_3$ | 0 |
| B-2383 | H | H | H | H | Cl | CH$_2$C(=O)CH$_3$ | CH$_2$CH$_3$ | 0 |
| B-2384 | H | H | H | H | Cl | CH$_2$C(=O)CH$_2$CH$_3$ | CH$_2$CH$_3$ | 0 |
| B-2385 | H | H | H | H | Cl | CH$_2$C(=O)C(CH$_3$)$_3$ | CH$_2$CH$_3$ | 0 |
| B-2386 | H | H | H | H | Cl | CH$_2$CH$_2$C(=O)CH$_3$ | CH$_2$CH$_3$ | 0 |
| B-2387 | H | H | H | H | Cl | CH$_2$CH$_2$C(=O)C(CH$_3$)$_3$ | CH$_2$CH$_3$ | 0 |
| B-2388 | H | H | H | H | Cl | CH$_2$C(=O)CF$_3$ | CH$_2$CH$_3$ | 0 |
| B-2389 | H | H | H | H | Cl | CH$_2$CH$_2$C(=O)CF$_3$ | CH$_2$CH$_3$ | 0 |
| B-2390 | H | H | H | H | Cl | CH$_2$C(=O)OCH$_3$ | CH$_2$CH$_3$ | 0 |
| B-2391 | H | H | H | H | Cl | CH$_2$C(=O)OCH$_2$CH$_3$ | CH$_2$CH$_3$ | 0 |
| B-2392 | H | H | H | H | Cl | CH$_2$C(=O)OC(CH$_3$)$_3$ | CH$_2$CH$_3$ | 0 |
| B-2393 | H | H | H | H | Cl | CH$_2$CH$_2$C(=O)OCH$_3$ | CH$_2$CH$_3$ | 0 |
| B-2394 | H | H | H | H | Cl | CH$_2$CH$_2$C(=O)OCH$_2$CH$_3$ | CH$_2$CH$_3$ | 0 |
| B-2395 | H | H | H | H | Cl | CH$_2$CH$_2$C(=O)OC(CH$_3$)$_3$ | CH$_2$CH$_3$ | 0 |
| B-2396 | H | H | H | H | Cl | CH$_2$C(=O)NH$_2$ | CH$_2$CH$_3$ | 0 |
| B-2397 | H | H | H | H | Cl | CH$_2$CH$_2$C(=O)NH$_2$ | CH$_2$CH$_3$ | 0 |
| B-2398 | H | H | H | H | Cl | CH$_2$C(=O)NHCH$_3$ | CH$_2$CH$_3$ | 0 |
| B-2399 | H | H | H | H | Cl | CH$_2$C(=O)NHCH(CH$_3$)$_2$ | CH$_2$CH$_3$ | 0 |
| B-2400 | H | H | H | H | Cl | CH$_2$CH$_2$C(=O)NHCH$_3$ | CH$_2$CH$_3$ | 0 |
| B-2401 | H | H | H | H | Cl | CH$_2$CH$_2$C(=O)NHCH(CH$_3$)$_2$ | CH$_2$CH$_3$ | 0 |
| B-2402 | H | H | H | H | Cl | CH$_2$C(=O)NHCH$_2$CHF$_2$ | CH$_2$CH$_3$ | 0 |
| B-2403 | H | H | H | H | Cl | CH$_2$C(=O)NHCH$_2$CF$_3$ | CH$_2$CH$_3$ | 0 |
| B-2404 | H | H | H | H | Cl | CH$_2$CH$_2$C(=O)NHCH$_2$CHF$_2$ | CH$_2$CH$_3$ | 0 |
| B-2405 | H | H | H | H | Cl | CH$_2$CH$_2$C(=O)NHCH$_2$CF$_3$ | CH$_2$CH$_3$ | 0 |
| B-2406 | H | H | H | H | Cl | CH$_2$C(=O)N(CH$_3$)$_2$ | CH$_2$CH$_3$ | 0 |
| B-2407 | H | H | H | H | Cl | CH$_2$C(=O)N(CH$_2$CH$_3$)$_2$ | CH$_2$CH$_3$ | 0 |
| B-2408 | H | H | H | H | Cl | CH$_2$CH$_2$C(=O)N(CH$_3$)$_2$ | CH$_2$CH$_3$ | 0 |
| B-2409 | H | H | H | H | Cl | CH$_2$CH$_2$C(=O)N(CH$_2$CH$_3$)$_2$ | CH$_2$CH$_3$ | 0 |
| B-2410 | H | H | H | H | Cl | CH$_2$CH$_2$OH | CH$_2$CH$_3$ | 0 |

TABLE 133-continued

| Compound | $R^1$ | $R^3$ | $R^3$ | $R^4$ | $R^5$ | $R^6$ | $R^{16}$ | n |
|---|---|---|---|---|---|---|---|---|
| B-2411 | H | H | H | H | Cl | $CH_2CH(OH)CH_3$ | $CH_2CH_3$ | 0 |
| B-2412 | H | H | H | H | Cl | $CH_2CH_2CH_2OH$ | $CH_2CH_3$ | 0 |
| B-2413 | H | H | H | H | Cl | $CH_2CH(OH)CH_2CH_3$ | $CH_2CH_3$ | 0 |
| B-2414 | H | H | H | H | Cl | $CH_2CH(OH)C(CH_3)_3$ | $CH_2CH_3$ | 0 |
| B-2415 | H | H | H | H | Cl | $CH_2CH_2CH(OH)CH_3$ | $CH_2CH_3$ | 0 |
| B-2416 | H | H | H | H | Cl | $CH_2CH_2CH(OH)C(CH_3)_3$ | $CH_2CH_3$ | 0 |
| B-2417 | H | H | H | H | Cl | $CH_2C(=NOH)CH_3$ | $CH_2CH_3$ | 0 |
| B-2418 | H | H | H | H | Cl | $CH_2C(=NOH)CH_2CH_3$ | $CH_2CH_3$ | 0 |
| B-2419 | H | H | H | H | Cl | $CH_2C(=NOH)C(CH_3)_3$ | $CH_2CH_3$ | 0 |
| B-2420 | H | H | H | H | Cl | $CH_2C(=NOCH_3)CH_3$ | $CH_2CH_3$ | 0 |
| B-2421 | H | H | H | H | Cl | $CH_2C(=NOCH_3)CH_2CH_3$ | $CH_2CH_3$ | 0 |
| B-2422 | H | H | H | H | Cl | $CH_2C(=NOCH_2CH_3)CH_3$ | $CH_2CH_3$ | 0 |
| B-2423 | H | H | H | H | Cl | $CH_2C(=NOCH_2CH_3)CH_2CH_3$ | $CH_2CH_3$ | 0 |
| B-2424 | H | H | H | H | Cl | $CH_2C(=NOCH_2CF_3)CH_3$ | $CH_2CH_3$ | 0 |
| B-2425 | H | H | H | H | Cl | $CH_2C(=NOCH_2CF_3)CH_2CH_3$ | $CH_2CH_3$ | 0 |
| B-2426 | H | H | H | H | Cl | $CH_2Ph$ | $CH_2CH_3$ | 0 |
| B-2427 | H | H | H | H | Cl | $CH_2(2-F)Ph$ | $CH_2CH_3$ | 0 |
| B-2428 | H | H | H | H | Cl | $CH_2(3-F)Ph$ | $CH_2CH_3$ | 0 |
| B-2429 | H | H | H | H | Cl | $CH_2(4-F)Ph$ | $CH_2CH_3$ | 0 |
| B-2430 | H | H | H | H | Cl | $CH_2(2-Cl)Ph$ | $CH_2CH_3$ | 0 |
| B-2431 | H | H | H | H | Cl | $CH_2(3-Cl)Ph$ | $CH_2CH_3$ | 0 |
| B-2432 | H | H | H | H | Cl | $CH_2(4-Cl)Ph$ | $CH_2CH_3$ | 0 |
| B-2433 | H | H | H | H | Cl | $CH_2(2-CF_3)Ph$ | $CH_2CH_3$ | 0 |
| B-2434 | H | H | H | H | Cl | $CH_2(3-CF_3)Ph$ | $CH_2CH_3$ | 0 |
| B-2435 | H | H | H | H | Cl | $CH_2(4-CF_3)Ph$ | $CH_2CH_3$ | 0 |

TABLE 134

| Compound | $R^1$ | $R^2$ | $R^3$ | $R^4$ | $R^5$ | $R^6$ | $R^{16}$ | n |
|---|---|---|---|---|---|---|---|---|
| B-2436 | H | H | H | H | Cl | $CH_2$(naphthalen-1-yl) | $CH_2CH_3$ | 0 |
| B-2437 | H | H | H | H | Cl | $CH_2$(naphthalen-2-yl) | $CH_2CH_3$ | 0 |
| B-2438 | H | H | H | H | Cl | $CH_2CH_2Ph$ | $CH_2CH_3$ | 0 |
| B-2439 | H | H | H | H | F | H | H | 0 |
| B-2440 | H | H | H | H | F | $CH_3$ | H | 0 |
| B-2441 | H | H | H | H | F | $CH_2CH_3$ | H | 0 |
| B-2442 | H | H | H | H | F | $CH(CH_3)_2$ | H | 0 |
| B-2443 | H | H | H | H | F | $CH_2CH_2CH_3$ | H | 0 |
| B-2444 | H | H | H | H | F | $CH_2CH(CH_3)_2$ | H | 0 |
| B-2445 | H | H | H | H | F | $CH_2C(CH_3)_3$ | H | 0 |
| B-2446 | H | H | H | H | F | $CH(CH_3)CH_2CH_3$ | H | 0 |
| B-2447 | H | H | H | H | F | $CH_2(CH_2)_2CH_3$ | H | 0 |
| B-2448 | H | H | H | H | F | $CH_2(CH_2)_3CH_3$ | H | 0 |
| B-2449 | H | H | H | H | F | $CH_2(CH_2)_4CH_3$ | H | 0 |
| B-2450 | H | H | H | H | F | $CH_2(CH_2)_6CH_3$ | H | 0 |
| B-2451 | H | H | H | H | F | $CH_2OCH_3$ | H | 0 |
| B-2452 | H | H | H | H | F | $CH_2OCH_2CH_3$ | H | 0 |
| B-2453 | H | H | H | H | F | $CH_2CH_2OCH_3$ | H | 0 |
| B-2454 | H | H | H | H | F | $CH_2CH_2OCH_2CH_3$ | H | 0 |
| B-2455 | H | H | H | H | F | $CF_3$ | H | 0 |
| B-2456 | H | H | H | H | F | $CHF_2$ | H | 0 |
| B-2457 | H | H | H | H | F | $CH_2CF_3$ | H | 0 |
| B-2458 | H | H | H | H | F | $CH_2CHF_2$ | H | 0 |
| B-2459 | H | H | H | H | F | $CH_3CClF_2$ | H | 0 |
| B-2460 | H | H | H | H | F | $CH_2CBrF_2$ | H | 0 |
| B-2461 | H | H | H | H | F | $CF_2CF_3$ | H | 0 |
| B-2462 | H | H | H | H | F | $CF_2CHF_2$ | H | 0 |
| B-2463 | H | H | H | H | F | $CH_2CH_3CF_3$ | H | 0 |
| B-2464 | H | H | H | H | F | $CH_2CF_2CF_3$ | H | 0 |
| B-2465 | H | H | H | H | F | $CH_2CF_2CHF_2$ | H | 0 |
| B-2466 | H | H | H | H | F | $CF_2CHFCF_3$ | H | 0 |
| B-2467 | H | H | H | H | F | $CF_2CF_2CF_3$ | H | 0 |
| B-2468 | H | H | H | H | F | $CH_2CF_2CF_2CF_3$ | H | 0 |
| B-2469 | H | H | H | H | F | $CH_2CF_2CHFCF_3$ | H | 0 |
| B-2470 | H | H | H | H | F | $CH_2CH_2CH_2CF_3$ | H | 0 |
| B-2471 | H | H | H | H | F | $CH_2CH_2CF_2CF_3$ | H | 0 |
| B-2472 | H | H | H | H | F | $CF_2CF_2CF_2CF_3$ | H | 0 |
| B-2473 | H | H | H | H | F | $CH_2CH_2CH(CF_3)_2$ | H | 0 |
| B-2474 | H | H | H | H | F | $CF_2CF_2CF_2CF_2CF_3$ | H | 0 |
| B-2475 | H | H | H | H | F | $CF_2CF_2CF_2CF_2CF_3$ | H | 0 |
| B-2476 | H | H | H | H | F | $CH_2CH_2CH_2CH_2CF_3$ | H | 0 |
| B-2477 | H | H | H | H | F | $CH_2CF_2CF_2CF_2CHF_2$ | H | 0 |
| B-2478 | H | H | H | H | F | $CH_2CF_2CF(CF_3)CF_2C(CF_3)_3$ | H | 0 |
| B-2479 | H | H | H | H | F | $CH_2CH_2CH_2CH_2CH_2CF_3$ | H | 0 |
| B-2480 | H | H | H | H | F | $CH_2CH_2CH_2CH_2CH_2CH_2CF_3$ | H | 0 |

TABLE 134-continued

| Compound | $R^1$ | $R^2$ | $R^3$ | $R^4$ | $R^5$ | $R^6$ | $R^{16}$ | n |
|---|---|---|---|---|---|---|---|---|
| B-2481 | H | H | H | H | F | $CF_2CHFOCH_3$ | H | 0 |
| B-2482 | H | H | H | H | F | $CF_2CHFOCH_2CH_3$ | H | 0 |
| B-2483 | H | H | H | H | F | $CH_2CH_2OCH_2CF_3$ | H | 0 |
| B-2484 | H | H | H | H | F | $CF_2CHFOCF_3$ | H | 0 |
| B-2485 | H | H | H | H | F | $CF_2CHFOCF_2CF_3$ | H | 0 |
| B-2486 | H | H | H | H | F | $CF_2CHFOCF_2CF_2CF_3$ | H | 0 |
| B-2487 | H | H | H | H | F | $CH_2CH=CH_2$ | H | 0 |
| B-2488 | H | H | H | H | F | $CH_2CH=CHCl$ | H | 0 |
| B-2489 | H | H | H | H | F | $CH_2CH=CCl_2$ | H | 0 |
| B-2490 | H | H | H | H | F | $CH_2CH_2CF=CF_2$ | H | 0 |
| B-2491 | H | H | H | H | F | $CH_2CH_2CH=CF_2$ | H | 0 |
| B-2492 | H | H | H | H | F | $CH_2C\equiv CH$ | H | 0 |
| B-2493 | H | H | H | H | F | $CH_2C\equiv CCH_3$ | H | 0 |
| B-2494 | H | H | H | H | F | $CH_2C\equiv Cl$ | H | 0 |
| B-2495 | H | H | H | H | F | $CH_2C\equiv CCF_3$ | H | 0 |
| B-2496 | H | H | H | H | F | cyclobutyl | H | 0 |

TABLE 135

| Compound | $R^1$ | $R^2$ | $R^3$ | $R^4$ | $R^5$ | $R^6$ | $R^{16}$ | n |
|---|---|---|---|---|---|---|---|---|
| B-2497 | H | H | H | H | F | cyclopentyl | H | 0 |
| B-2498 | H | H | H | H | F | cyclohexyl | H | 0 |
| B-2499 | H | H | H | H | F | 4,4-difluorocyclohexyl | H | 0 |
| B-2500 | H | H | H | H | F | $CH_2$(cyclopropyl) | H | 0 |
| B-2501 | H | H | H | H | F | $CH_2$(cyclobutyl) | H | 0 |
| B-2502 | H | H | H | H | F | $CH_2$(cyclopentyl) | H | 0 |
| B-2503 | H | H | H | H | F | $CH_2CH_2$(cyclopropyl) | H | 0 |
| B-2504 | H | H | H | H | F | $CH_2$(2,2-difluorocyclopropyl) | H | 0 |
| B-2505 | H | H | H | H | F | $CH_2$(2,2-dichlorocyclopropyl) | H | 0 |
| B-2506 | H | H | H | H | F | $CH_2$(4,4-difluorocyclohexyl) | H | 0 |
| B-2507 | H | H | H | H | F | $CH_2CH_2$(2,2-difluorocyclopropyl) | H | 0 |
| B-2508 | H | H | H | H | F | $CH_2CH_2$(2,2-dichlorocyclopropyl) | H | 0 |
| B-2509 | H | H | H | H | F | $CH_2SCH_3$ | H | 0 |
| B-2510 | H | H | H | H | F | $CH_2SCH_2CH_3$ | H | 0 |
| B-2511 | H | H | H | H | F | $CH_2CH_2SCH_3$ | H | 0 |
| B-2512 | H | H | H | H | F | $CH_2CH_2SCH_2CH_3$ | H | 0 |
| B-2513 | H | H | H | H | F | $CH_2CH_2CH_2SCH_3$ | H | 0 |
| B-2514 | H | H | H | H | F | $CH_2CH_2CH_2SCH_2CH_3$ | H | 0 |
| B-2515 | H | H | H | H | F | $CH(CH_3)SCH_3$ | H | 0 |
| B-2516 | H | H | H | H | F | $CH(CH_3)SCH_2CH_3$ | H | 0 |
| B-2517 | H | H | H | H | F | $CH_2CH(CH_3)SCH_3$ | H | 0 |
| B-2518 | H | H | H | H | F | $CH_2CH(CH_3)SCH_2CH_3$ | H | 0 |
| B-2519 | H | H | H | H | F | $CH(CH_3)CH_2CH_2SCH_3$ | H | 0 |
| B-2520 | H | H | H | H | F | $CH(CH_3)CH_2CH_2SCH_2CH_3$ | H | 0 |
| B-2521 | H | H | H | H | F | $CH(CH_3)CH_2SCH_3$ | H | 0 |
| B-2522 | H | H | H | H | F | $CH_2CH(CH_3)CH_2SCH_2CH_3$ | H | 0 |
| B-2523 | H | H | H | H | F | $CH_2CH_2CH(CH_3)SCH_3$ | H | 0 |
| B-2524 | H | H | H | H | F | $CH_2CH_2CH(CH_3)SCH_2CH_3$ | H | 0 |
| B-2525 | H | H | H | H | F | $CH_2SOCH_3$ | H | 0 |
| B-2526 | H | H | H | H | F | $CH_2CH_2SOCH_3$ | H | 0 |
| B-2527 | H | H | H | H | F | $CH_2CH_2CH_2SOCH_3$ | H | 0 |
| B-2528 | H | H | H | H | F | $CH(CH_3)SOCH_3$ | H | 0 |
| B-2529 | H | H | H | H | F | $CH_2CH(CH_3)SOCH_3$ | H | 0 |
| B-2530 | H | H | H | H | F | $CH(CH_3)CH_2CH_2SOCH_3$ | H | 0 |
| B-2531 | H | H | H | H | F | $CH_2CH(CH_3)CH_2SOCH_3$ | H | 0 |
| B-2532 | H | H | H | H | F | $CH_2CH_2CH(CH_3)SOCH_3$ | H | 0 |
| B-2533 | H | H | H | H | F | $CH_2SO_2CH_3$ | H | 0 |
| B-2534 | H | H | H | H | F | $CH_2CH_2SO_2CH_3$ | H | 0 |
| B-2535 | H | H | H | H | F | $CH_2CH_2CH_2SO_2CH_3$ | H | 0 |
| B-2536 | H | H | H | H | F | $CH(CH_3)SO_2CH_3$ | H | 0 |
| B-2537 | H | H | H | H | F | $CH_2CH(CH_3)SO_2CH_3$ | H | 0 |
| B-2538 | H | H | H | H | F | $CH(CH_3)CH_2CH_2SO_2CH_3$ | H | 0 |
| B-2539 | H | H | H | H | F | $CH_2CH(CH_3)CH_2SO_2CH_3$ | H | 0 |
| B-2540 | H | H | H | H | F | $CH_2CH_2CH(CH_3)SO_2CH_3$ | H | 0 |
| B-2541 | H | H | H | H | F | $CH_2SCF_3$ | H | 0 |
| B-2542 | H | H | H | H | F | $CH_2SCHF_2$ | H | 0 |
| B-2543 | H | H | H | H | F | $CH_2SCH_2CF_3$ | H | 0 |
| B-2544 | H | H | H | H | F | $CH_2SCH_2CHF_2$ | H | 0 |
| B-2545 | H | H | H | H | F | $CH_2SCF_2CF_3$ | H | 0 |
| B-2546 | H | H | H | H | F | $CH_2CH_2SCF_3$ | H | 0 |
| B-2547 | H | H | H | H | F | $CH_2CH_2SCH_2CF_3$ | H | 0 |
| B-2548 | H | H | H | H | F | $CH_2CH_2CH_2SCF_3$ | H | 0 |
| B-2549 | H | H | H | H | F | $CH_2CH_2CH_2SCH_2CF_3$ | H | 0 |
| B-2550 | H | H | H | H | F | $CH(CH_3)SCF_3$ | H | 0 |

TABLE 135-continued

| Compound | R$^1$ | R$^2$ | R$^3$ | R$^4$ | R$^5$ | R$^6$ | R$^{16}$ | n |
|---|---|---|---|---|---|---|---|---|
| B-2551 | H | H | H | H | F | CH(CH$_3$)SCH$_2$CF$_3$ | H | 0 |
| B-2552 | H | H | H | H | F | CH$_2$CH(CH$_3$)SCF$_3$ | H | 0 |
| B-2553 | H | H | H | H | F | CH$_2$CH(CH$_3$)SCH$_2$CF$_3$ | H | 0 |
| B-2554 | H | H | H | H | F | CH(CH$_3$)CH$_2$CH$_2$SCF$_3$ | H | 0 |
| B-2555 | H | H | H | H | F | CH(CH$_3$)CH$_2$CH$_2$SCH$_2$CF$_3$ | H | 0 |
| B-2556 | H | H | H | H | F | CH$_2$CH(CH$_3$)CH$_2$SCF$_3$ | H | 0 |
| B-2557 | H | H | H | H | F | CH$_2$CH(CH$_3$)CH$_2$SCH$_2$CF$_3$ | H | 0 |

TABLE 136

| Compound | R$^1$ | R$^2$ | R$^3$ | R$^4$ | R$^5$ | R$^6$ | R$^{16}$ | n |
|---|---|---|---|---|---|---|---|---|
| B-2558 | H | H | H | H | F | CH$_2$CH$_2$CH(CH$_3$)SCF$_3$ | H | 0 |
| B-2559 | H | H | H | H | F | CH$_2$CH$_2$CH(CH$_3$)SCH$_2$CF$_3$ | H | 0 |
| B-2560 | H | H | H | H | F | CH$_2$SOCF$_3$ | H | 0 |
| B-2561 | H | H | H | H | F | CH$_2$CH$_2$SOCF$_3$ | H | 0 |
| B-2562 | H | H | H | H | F | CH$_2$CH$_2$CH$_2$SOCF$_3$ | H | 0 |
| B-2563 | H | H | H | H | F | CH(CH$_3$)SOCF$_3$ | H | 0 |
| B-2564 | H | H | H | H | F | CH$_2$CH(CH$_3$)SOCF$_3$ | H | 0 |
| B-2565 | H | H | H | H | F | CH(CH$_3$)CH$_2$CH$_2$SOCF$_3$ | H | 0 |
| B-2566 | H | H | H | H | F | CH$_2$CH(CH$_3$)CH$_2$SOCF$_3$ | H | 0 |
| B-2567 | H | H | H | H | F | CH$_2$CH$_2$CH(CH$_3$)SOCF$_3$ | H | 0 |
| B-2568 | H | H | H | H | F | CH$_2$SO$_2$CF$_3$ | H | 0 |
| B-2569 | H | H | H | H | F | CH$_2$CH$_2$SO$_2$CF$_3$ | H | 0 |
| B-2570 | H | H | H | H | F | CH$_2$CH$_2$CH$_2$SO$_2$CF$_3$ | H | 0 |
| B-2571 | H | H | H | H | F | CH(CH$_3$)SO$_2$CF$_3$ | H | 0 |
| B-2572 | H | H | H | H | F | CH$_2$CH(CH$_3$)SO$_2$CF$_3$ | H | 0 |
| B-2573 | H | H | H | H | F | CH(CH$_3$)CH$_2$CH$_2$SO$_2$CF$_3$ | H | 0 |
| B-2574 | H | H | H | H | F | CH$_2$CH(CH$_3$)CH$_2$SO$_2$CF$_3$ | H | 0 |
| B-2575 | H | H | H | H | F | CH$_2$CH$_2$CH(CH$_3$)SO$_2$CF$_3$ | H | 0 |
| B-2576 | H | H | H | H | F | CH$_2$C(=O)CH$_3$ | H | 0 |
| B-2577 | H | H | H | H | F | CH$_2$C(=O)CH$_2$CH$_3$ | H | 0 |
| B-2578 | H | H | H | H | F | CH$_2$C(=O)C(CH$_3$)$_3$ | H | 0 |
| B-2579 | H | H | H | H | F | CH$_2$CH$_2$C(=O)CH$_3$ | H | 0 |
| B-2580 | H | H | H | H | F | CH$_2$CH$_2$C(=O)C(CH$_3$)$_3$ | H | 0 |
| B-2581 | H | H | H | H | F | CH$_2$C(=O)CF$_3$ | H | 0 |
| B-2582 | H | H | H | H | F | CH$_2$CH$_2$C(=O)CF$_3$ | H | 0 |
| B-2583 | H | H | H | H | F | CH$_2$C(=O)OCH$_3$ | H | 0 |
| B-2584 | H | H | H | H | F | CH$_2$C(=O)OCH$_2$CH$_3$ | H | 0 |
| B-2585 | H | H | H | H | F | CH$_2$C(=O)OC(CH$_3$)$_3$ | H | 0 |
| B-2586 | H | H | H | H | F | CH$_2$CH$_2$C(=O)OCH$_3$ | H | 0 |
| B-2587 | H | H | H | H | F | CH$_2$CH$_2$C(=O)OCH$_2$CH$_3$ | H | 0 |
| B-2588 | H | H | H | H | F | CH$_2$CH$_2$C(=O)OC(CH$_3$)$_3$ | H | 0 |
| B-2589 | H | H | H | H | F | CH$_2$C(=O)NH$_2$ | H | 0 |
| B-2590 | H | H | H | H | F | CH$_2$CH$_2$C(=O)NH$_2$ | H | 0 |
| B-2591 | H | H | H | H | F | CH$_2$C(=O)NHCH$_3$ | H | 0 |
| B-2592 | H | H | H | H | F | CH$_2$C(=O)NHCH(CH$_3$)$_2$ | H | 0 |
| B-2593 | H | H | H | H | F | CH$_2$CH$_2$C(=O)NHCH$_3$ | H | 0 |
| B-2594 | H | H | H | H | F | CH$_2$CH$_2$C(=O)NHCH(CH$_3$)$_2$ | H | 0 |
| B-2595 | H | H | H | H | F | CH$_2$C(=O)NHCH$_2$CHF$_2$ | H | 0 |
| B-2596 | H | H | H | H | F | CH$_2$C(=O)NHCH$_2$CF$_3$ | H | 0 |
| B-2597 | H | H | H | H | F | CH$_2$CH$_2$C(=O)NHCH$_2$CHF$_2$ | H | 0 |
| B-2598 | H | H | H | H | F | CH$_2$CH$_2$C(=O)NHCH$_2$CF$_3$ | H | 0 |
| B-2599 | H | H | H | H | F | CH$_2$C(=O)N(CH$_3$)$_2$ | H | 0 |
| B-2600 | H | H | H | H | F | CH$_2$C(=O)N(CH$_2$CH$_3$)$_2$ | H | 0 |
| B-2601 | H | H | H | H | F | CH$_2$CH$_2$C(=O)N(CH$_3$)$_2$ | H | 0 |
| B-2602 | H | H | H | H | F | CH$_2$CH$_2$C(=O)N(CH$_2$CH$_3$)$_2$ | H | 0 |
| B-2603 | H | H | H | H | F | CH$_2$CH$_2$OH | H | 0 |
| B-2604 | H | H | H | H | F | CH$_2$CH(OH)CH$_3$ | H | 0 |
| B-2605 | H | H | H | H | F | CH$_2$CH$_2$CH$_2$OH | H | 0 |
| B-2606 | H | H | H | H | F | CH$_2$CH(OH)CH$_2$CH$_3$ | H | 0 |
| B-2607 | H | H | H | H | F | CH$_2$CH(OH)C(CH$_3$)$_3$ | H | 0 |
| B-2608 | H | H | H | H | F | CH$_2$CH$_2$CH(OH)CH$_3$ | H | 0 |
| B-2609 | H | H | H | H | F | CH$_2$CH$_2$CH(OH)C(CH$_3$)$_3$ | H | 0 |
| B-2610 | H | H | H | H | F | CH$_2$C(=NOH)CH$_3$ | H | 0 |
| B-2611 | H | H | H | H | F | CH$_2$C(=NOH)CH$_2$CH$_3$ | H | 0 |
| B-2612 | H | H | H | H | F | CH$_2$C(=NOH)C(CH$_3$)$_3$ | H | 0 |
| B-2613 | H | H | H | H | F | CH$_2$C(=NOCH$_3$)CH$_3$ | H | 0 |
| B-2614 | H | H | H | H | F | CH$_2$C(=NOCH$_3$)CH$_2$CH$_3$ | H | 0 |
| B-2615 | H | H | H | H | F | CH$_2$C(=NOCH$_2$CH$_3$)CH$_3$ | H | 0 |
| B-2616 | H | H | H | H | F | CH$_2$C(=NOCH$_2$CH$_3$)CH$_2$CH$_3$ | H | 0 |
| B-2617 | H | H | H | H | F | CH$_2$C(=NOCH$_2$CF$_3$)CH$_3$ | H | 0 |
| B-2618 | H | H | H | H | F | CH$_2$C(=NOCH$_2$CF$_3$)CH$_2$CH$_3$ | H | 0 |

TABLE 137

| Compound | R$^1$ | R$^2$ | R$^3$ | R$^4$ | R$^5$ | R$^6$ | R$^{16}$ | n |
|---|---|---|---|---|---|---|---|---|
| B-2619 | H | H | H | H | F | CH$_2$Ph | H | 0 |
| B-2620 | H | H | H | H | F | CH$_2$(2-F)Ph | H | 0 |
| B-2621 | H | H | H | H | F | CH$_2$(3-F)Ph | H | 0 |
| B-2622 | H | H | H | H | F | CH$_2$(4-F)Ph | H | 0 |
| B-2623 | H | H | H | H | F | CH$_2$(2-Cl)Ph | H | 0 |
| B-2624 | H | H | H | H | F | CH$_2$(3-Cl)Ph | H | 0 |
| B-2625 | H | H | H | H | F | CH$_2$(4-Cl)Ph | H | 0 |
| B-2626 | H | H | H | H | F | CH$_2$(2-CF$_3$)Ph | H | 0 |
| B-2627 | H | H | H | H | F | CH$_2$(3-CF$_3$)Ph | H | 0 |
| B-2628 | H | H | H | H | F | CH$_2$(4-CF$_3$)Ph | H | 0 |
| B-2629 | H | H | H | H | F | CH$_2$(naphthalen-1-yl) | H | 0 |
| B-2630 | H | H | H | H | F | CH$_2$(naphthalen-2-yl) | H | 0 |
| B-2631 | H | H | H | H | F | CH$_2$CH$_2$Ph | H | 0 |
| B-2632 | H | H | H | H | F | H | CH$_2$CH$_3$ | 0 |
| B-2633 | H | H | H | H | F | CH$_3$ | CH$_2$CH$_3$ | 0 |
| B-2634 | H | H | H | H | F | CH$_2$CH$_3$ | CH$_2$CH$_3$ | 0 |
| B-2635 | H | H | H | H | F | CH(CH$_3$)$_2$ | CH$_2$CH$_3$ | 0 |
| B-2636 | H | H | H | H | F | CH$_2$CH$_2$CH$_3$ | CH$_2$CH$_3$ | 0 |
| B-2637 | H | H | H | H | F | CH$_2$CH(CH$_3$)$_2$ | CH$_2$CH$_3$ | 0 |
| B-2638 | H | H | H | H | F | CH$_2$C(CH$_3$)$_3$ | CH$_2$CH$_3$ | 0 |
| B-2639 | H | H | H | H | F | CH(CH$_3$)CH$_2$CH$_3$ | CH$_2$CH$_3$ | 0 |
| B-2640 | H | H | H | H | F | CH$_2$(CH$_2$)$_2$CH$_3$ | CH$_2$CH$_3$ | 0 |
| B-2641 | H | H | H | H | F | CH$_2$(CH$_2$)$_3$CH$_3$ | CH$_2$CH$_3$ | 0 |
| B-2642 | H | H | H | H | F | CH$_2$(CH$_2$)$_4$CH$_3$ | CH$_2$CH$_3$ | 0 |
| B-2643 | H | H | H | H | F | CH$_2$(CH$_2$)$_6$CH$_3$ | CH$_2$CH$_3$ | 0 |
| B-2644 | H | H | H | H | F | CH$_2$OCH$_3$ | CH$_2$CH$_3$ | 0 |
| B-2645 | H | H | H | H | F | CH$_2$OCH$_2$CH$_3$ | CH$_2$CH$_3$ | 0 |
| B-2646 | H | H | H | H | F | CH$_2$CH$_2$OCH$_3$ | CH$_2$CH$_3$ | 0 |
| B-2647 | H | H | H | H | F | CH$_2$CH$_2$OCH$_2$CH$_3$ | CH$_2$CH$_3$ | 0 |
| B-2648 | H | H | H | H | F | CF$_3$ | CH$_2$CH$_3$ | 0 |
| B-2649 | H | H | H | H | F | CHF$_2$ | CH$_2$CH$_3$ | 0 |
| B-2650 | H | H | H | H | F | CH$_2$CF$_3$ | CH$_2$CH$_3$ | 0 |
| B-2651 | H | H | H | H | F | CH$_2$CHF$_2$ | CH$_2$CH$_3$ | 0 |
| B-2652 | H | H | H | H | F | CH$_2$CClF$_2$ | CH$_2$CH$_3$ | 0 |
| B-2653 | H | H | H | H | F | CH$_2$CBrF$_2$ | CH$_2$CH$_3$ | 0 |
| B-2654 | H | H | H | H | F | CF$_2$CF$_3$ | CH$_2$CH$_3$ | 0 |
| B-2655 | H | H | H | H | F | CF$_2$CHF$_2$ | CH$_2$CH$_3$ | 0 |
| B-2656 | H | H | H | H | F | CH$_2$CH$_2$CF$_3$ | CH$_2$CH$_3$ | 0 |
| B-2657 | H | H | H | H | F | CH$_2$CF$_2$CF$_3$ | CH$_2$CH$_3$ | 0 |
| B-2658 | H | H | H | H | F | CH$_2$CF$_2$CHF$_2$ | CH$_2$CH$_3$ | 0 |
| B-2659 | H | H | H | H | F | CF$_2$CHFCF$_3$ | CH$_2$CH$_3$ | 0 |
| B-2660 | H | H | H | H | F | CF$_2$CF$_2$CF$_3$ | CH$_2$CH$_3$ | 0 |
| B-2661 | H | H | H | H | F | CH$_2$CF$_2$CF$_2$CF$_3$ | CH$_2$CH$_3$ | 0 |
| B-2662 | H | H | H | H | F | CH$_2$CF$_2$CHFCF$_3$ | CH$_2$CH$_3$ | 0 |
| B-2663 | H | H | H | H | F | CH$_2$CH$_2$CH$_2$CF$_3$ | CH$_2$CH$_3$ | 0 |
| B-2664 | H | H | H | H | F | CH$_2$CH$_2$CF$_2$CF$_3$ | CH$_2$CH$_3$ | 0 |
| B-2665 | H | H | H | H | F | CF$_2$CF$_2$CF$_2$CF$_3$ | CH$_2$CH$_3$ | 0 |
| B-2666 | H | H | H | H | F | CH$_2$CH$_2$CH(CF$_3$)$_2$ | CH$_2$CH$_3$ | 0 |
| B-2667 | H | H | H | H | F | CF$_2$CF$_2$CF$_2$CF$_2$CF$_3$ | CH$_2$CH$_3$ | 0 |
| B-2668 | H | H | H | H | F | CH$_2$CF$_2$CF$_2$CF$_2$CF$_3$ | CH$_2$CH$_3$ | 0 |
| B-2669 | H | H | H | H | F | CH$_2$CH$_2$CH$_2$CH$_2$CF$_3$ | CH$_2$CH$_3$ | 0 |
| B-2670 | H | H | H | H | F | CH$_2$CF$_2$CF$_2$CF$_2$CHF$_2$ | CH$_2$CH$_3$ | 0 |
| B-2671 | H | H | H | H | F | CH$_2$CF$_2$CF(CF$_3$)CF$_2$C(CF$_3$)$_3$ | CH$_2$CH$_3$ | 0 |
| B-2672 | H | H | H | H | F | CH$_2$CH$_2$CH$_2$CH$_2$CF$_2$CF$_3$ | CH$_2$CH$_3$ | 0 |
| B-2673 | H | H | H | H | F | CH$_2$CH$_2$CH$_2$CH$_2$CH$_2$CH$_2$CF$_3$ | CH$_2$CH$_3$ | 0 |
| B-2674 | H | H | H | H | F | CF$_2$CHFOCH$_3$ | CH$_2$CH$_3$ | 0 |
| B-2675 | H | H | H | H | F | CF$_2$CHFOCH$_2$CH$_3$ | CH$_2$CH$_3$ | 0 |
| B-2676 | H | H | H | H | F | CH$_2$CH$_2$OCH$_2$CF$_3$ | CH$_2$CH$_3$ | 0 |
| B-2677 | H | H | H | H | F | CF$_2$CHFOCF$_3$ | CH$_2$CH$_3$ | 0 |
| B-2678 | H | H | H | H | F | CF$_2$CHFOCF$_2$CF$_3$ | CH$_2$CH$_3$ | 0 |
| B-2679 | H | H | H | H | F | CF$_2$CHFOCF$_2$CF$_2$CF$_3$ | CH$_2$CH$_3$ | 0 |

TABLE 138

| Compound | R$^1$ | R$^2$ | R$^3$ | R$^4$ | R$^5$ | R$^6$ | R$^{16}$ | n |
|---|---|---|---|---|---|---|---|---|
| B-2680 | H | H | H | H | F | CH$_2$CH=CH$_2$ | CH$_2$CH$_3$ | 0 |
| B-2681 | H | H | H | H | F | CH$_2$CH=CHCl | CH$_2$CH$_3$ | 0 |
| B-2682 | H | H | H | H | F | CH$_2$CH=CCl$_2$ | CH$_2$CH$_3$ | 0 |
| B-2683 | H | H | H | H | F | CH$_2$CH$_2$CF=CF$_2$ | CH$_2$CH$_3$ | 0 |
| B-2684 | H | H | H | H | F | CH$_2$CH$_2$CH=CF$_2$ | CH$_2$CH$_3$ | 0 |
| B-2685 | H | H | H | H | F | CH$_2$C≡CH | CH$_2$CH$_3$ | 0 |
| B-2686 | H | H | H | H | F | CH$_2$C≡CCH$_3$ | CH$_2$CH$_3$ | 0 |
| B-2687 | H | H | H | H | F | CH$_2$C≡Cl | CH$_2$CH$_3$ | 0 |
| B-2688 | H | H | H | H | F | CH$_2$C≡CCF$_3$ | CH$_2$CH$_3$ | 0 |

TABLE 138-continued

| Compound | $R^1$ | $R^2$ | $R^3$ | $R^4$ | $R^5$ | $R^6$ | $R^{16}$ | n |
|---|---|---|---|---|---|---|---|---|
| B-2689 | H | H | H | H | F | cyclobutyl | $CH_2CH_3$ | 0 |
| B-2690 | H | H | H | H | F | cyclopentyl | $CH_2CH_3$ | 0 |
| B-2691 | H | H | H | H | F | cyclohexyl | $CH_2CH_3$ | 0 |
| B-2692 | H | H | H | H | F | 4,4-difluorocyclohexyl | $CH_2CH_3$ | 0 |
| B-2693 | H | H | H | H | F | $CH_2$(cyclopropyl) | $CH_2CH_3$ | 0 |
| B-2694 | H | H | H | H | F | $CH_2$(cyclobutyl) | $CH_2CH_3$ | 0 |
| B-2695 | H | H | H | H | F | $CH_2$(cyclopentyl) | $CH_2CH_3$ | 0 |
| B-2696 | H | H | H | H | F | $CH_2CH_2$(cyclopropyl) | $CH_2CH_3$ | 0 |
| B-2697 | H | H | H | H | F | $CH_2$(2,2-difluorocyclopropyl) | $CH_2CH_3$ | 0 |
| B-2698 | H | H | H | H | F | $CH_2$(2,2-dichlorocyclopropyl) | $CH_2CH_3$ | 0 |
| B-2699 | H | H | H | H | F | $CH_2$(4,4-difluorocyclohexyl) | $CH_2CH_3$ | 0 |
| B-2700 | H | H | H | H | F | $CH_2CH_2$(2,2-difluorocyclopropyl) | $CH_2CH_3$ | 0 |
| B-2701 | H | H | H | H | F | $CH_2CH_2$(2,2-dichlorocyclopropyl) | $CH_2CH_3$ | 0 |
| B-2702 | H | H | H | H | F | $CH_2SCH_3$ | $CH_2CH_3$ | 0 |
| B-2703 | H | H | H | H | F | $CH_2SCH_2CH_3$ | $CH_2CH_3$ | 0 |
| B-2704 | H | H | H | H | F | $CH_2CH_2SCH_3$ | $CH_2CH_3$ | 0 |
| B-2705 | H | H | H | H | F | $CH_2CH_2SCH_2CH_3$ | $CH_2CH_3$ | 0 |
| B-2706 | H | H | H | H | F | $CH_2CH_2CH_2SCH_3$ | $CH_2CH_3$ | 0 |
| B-2707 | H | H | H | H | F | $CH_2CH_2CH_2SCH_2CH_3$ | $CH_2CH_3$ | 0 |
| B-2708 | H | H | H | H | F | $CH(CH_3)SCH_3$ | $CH_2CH_3$ | 0 |
| B-2709 | H | H | H | H | F | $CH(CH_3)SCH_2CH_3$ | $CH_2CH_3$ | 0 |
| B-2710 | H | H | H | H | F | $CH_2CH(CH_3)SCH_3$ | $CH_2CH_3$ | 0 |
| B-2711 | H | H | H | H | F | $CH_2CH(CH_3)SCH_2CH_3$ | $CH_2CH_3$ | 0 |
| B-2712 | H | H | H | H | F | $CH(CH_3)CH_2CH_2SCH_3$ | $CH_2CH_3$ | 0 |
| B-2713 | H | H | H | H | F | $CH(CH_3)CH_2CH_2SCH_2CH_3$ | $CH_2CH_3$ | 0 |
| B-2714 | H | H | H | H | F | $CH_2CH(CH_3)CH_2SCH_3$ | $CH_2CH_3$ | 0 |
| B-2715 | H | H | H | H | F | $CH_2CH(CH_3)CH_2SCH_2CH_3$ | $CH_2CH_3$ | 0 |
| B-2716 | H | H | H | H | F | $CH_2CH_2CH(CH_3)SCH_3$ | $CH_2CH_3$ | 0 |
| B-2717 | H | H | H | H | F | $CH_2CH_2CH(CH_3)SCH_2CH_3$ | $CH_2CH_3$ | 0 |
| B-2718 | H | H | H | H | F | $CH_2SOCH_3$ | $CH_2CH_3$ | 0 |
| B-2719 | H | H | H | H | F | $CH_2CH_2SOCH_3$ | $CH_2CH_3$ | 0 |
| B-2720 | H | H | H | H | F | $CH_2CH_2CH_2SOCH_3$ | $CH_2CH_3$ | 0 |
| B-2721 | H | H | H | H | F | $CH(CH_3)SOCH_3$ | $CH_2CH_3$ | 0 |
| B-2722 | H | H | H | H | F | $CH_2CH(CH_3)SOCH_3$ | $CH_2CH_3$ | 0 |
| B-2723 | H | H | H | H | F | $CH(CH_3)CH_2CH_2SOCH_3$ | $CH_2CH_3$ | 0 |
| B-2724 | H | H | H | H | F | $CH_2CH(CH_3)CH_2SOCH_3$ | $CH_2CH_3$ | 0 |
| B-2725 | H | H | H | H | F | $CH_2CH_2CH(CH_3)SOCH_3$ | $CH_2CH_3$ | 0 |
| B-2726 | H | H | H | H | F | $CH_2SO_2CH_3$ | $CH_2CH_3$ | 0 |
| B-2727 | H | H | H | H | F | $CH_2CH_2SO_2CH_3$ | $CH_2CH_3$ | 0 |
| B-2728 | H | H | H | H | F | $CH_2CH_2CH_2SO_2CH_3$ | $CH_2CH_3$ | 0 |
| B-2729 | H | H | H | H | F | $CH(CH_3)SO_2CH_3$ | $CH_2CH_3$ | 0 |
| B-2730 | H | H | H | H | F | $CH_2CH(CH_3)SO_2CH_3$ | $CH_2CH_3$ | 0 |
| B-2731 | H | H | H | H | F | $CH(CH_3)CH_2CH_2SO_2CH_3$ | $CH_2CH_3$ | 0 |
| B-2732 | H | H | H | H | F | $CH_2CH(CH_3)CH_2SO_2CH_3$ | $CH_2CH_3$ | 0 |
| B-2733 | H | H | H | H | F | $CH_2CH_2CH(CH_3)SO_2CH_3$ | $CH_2CH_3$ | 0 |
| B-2734 | H | H | H | H | F | $CH_2SCF_3$ | $CH_2CH_3$ | 0 |
| B-2735 | H | H | H | H | F | $CH_2SCHF_2$ | $CH_2CH_3$ | 0 |
| B-2736 | H | H | H | H | F | $CH_2SCH_2CF_3$ | $CH_2CH_3$ | 0 |
| B-2737 | H | H | H | H | F | $CH_2SCH_2CHF_2$ | $CH_2CH_3$ | 0 |
| B-2738 | H | H | H | H | F | $CH_2SCF_2CF_3$ | $CH_2CH_3$ | 0 |
| B-2739 | H | H | H | H | F | $CH_2CH_2SCF_3$ | $CH_2CH_3$ | 0 |
| B-2740 | H | H | H | H | F | $CH_2CH_2SCH_2CF_3$ | $CH_2CH_3$ | 0 |

TABLE 139

| Compound | $R^1$ | $R^2$ | $R^3$ | $R^4$ | $R^5$ | $R^6$ | $R^{16}$ | n |
|---|---|---|---|---|---|---|---|---|
| B-2741 | H | H | H | H | F | $CH_2CH_2CH_2SCF_3$ | $CH_2CH_3$ | 0 |
| B-2742 | H | H | H | H | F | $CH_2CH_2CH_2SCH_2CF_3$ | $CH_2CH_3$ | 0 |
| B-2743 | H | H | H | H | F | $CH(CH_3)SCF_3$ | $CH_2CH_3$ | 0 |
| B-2744 | H | H | H | H | F | $CH(CH_3)SCH_2CF_3$ | $CH_2CH_3$ | 0 |
| B-2745 | H | H | H | H | F | $CH_2CH(CH_3)SCF_3$ | $CH_2CH_3$ | 0 |
| B-2746 | H | H | H | H | F | $CH_2CH(CH_3)SCH_2CF_3$ | $CH_2CH_3$ | 0 |
| B-2747 | H | H | H | H | F | $CH(CH_3)CH_2CH_2SCF_3$ | $CH_2CH_3$ | 0 |
| B-2748 | H | H | H | H | F | $CH(CH_3)CH_2CH_2SCH_2CF_3$ | $CH_2CH_3$ | 0 |
| B-2749 | H | H | H | H | F | $CH_2CH(CH_3)CH_2SCF_3$ | $CH_2CH_3$ | 0 |
| B-2750 | H | H | H | H | F | $CH_2CH(CH_3)CH_2SCH_2CF_3$ | $CH_2CH_3$ | 0 |
| B-2751 | H | H | H | H | F | $CH_2CH_2CH(CH_3)SCF_3$ | $CH_2CH_3$ | 0 |
| B-2752 | H | H | H | H | F | $CH_2CH_2CH(CH_3)SCH_2CF_3$ | $CH_2CH_3$ | 0 |
| B-2753 | H | H | H | H | F | $CH_2SOCF_3$ | $CH_2CH_3$ | 0 |
| B-2754 | H | H | H | H | F | $CH_2CH_2SOCF_3$ | $CH_2CH_3$ | 0 |
| B-2755 | H | H | H | H | F | $CH_2CH_2CH_2SOCF_3$ | $CH_2CH_3$ | 0 |
| B-2756 | H | H | H | H | F | $CH(CH_3)SOCF_3$ | $CH_2CH_3$ | 0 |
| B-2757 | H | H | H | H | F | $CH_2CH(CH_3)SOCF_3$ | $CH_2CH_3$ | 0 |
| B-2758 | H | H | H | H | F | $CH(CH_3)CH_2CH_2SOCF_3$ | $CH_2CH_3$ | 0 |

TABLE 139-continued

| Compound | R$^1$ | R$^2$ | R$^3$ | R$^4$ | R$^5$ | R$^6$ | R$^{16}$ | n |
|---|---|---|---|---|---|---|---|---|
| B-2759 | H | H | H | H | F | CH$_2$CH(CH$_3$)CH$_2$SOCF$_3$ | CH$_2$CH$_3$ | 0 |
| B-2760 | H | H | H | H | F | CH$_2$CH$_2$CH(CH$_3$)SOCF$_3$ | CH$_2$CH$_3$ | 0 |
| B-2761 | H | H | H | H | F | CH$_2$SO$_2$CF$_3$ | CH$_2$CH$_3$ | 0 |
| B-2762 | H | H | H | H | F | CH$_2$CH$_2$SO$_2$CF$_3$ | CH$_2$CH$_3$ | 0 |
| B-2763 | H | H | H | H | F | CH$_2$CH$_2$CH$_2$SO$_2$CF$_3$ | CH$_2$CH$_3$ | 0 |
| B-2764 | H | H | H | H | F | CH(CH$_3$)SO$_2$CF$_3$ | CH$_2$CH$_3$ | 0 |
| B-2765 | H | H | H | H | F | CH$_2$CH(CH$_3$)SO$_2$CF$_3$ | CH$_2$CH$_3$ | 0 |
| B-2765 | H | H | H | H | F | CH(CH$_3$)CH$_2$CH$_2$SO$_2$CF$_3$ | CH$_2$CH$_3$ | 0 |
| B-2767 | H | H | H | H | F | CH$_2$CH(CH$_3$)CH$_2$SO$_2$CF$_3$ | CH$_2$CH$_3$ | 0 |
| B-2768 | H | H | H | H | F | CH$_2$CH$_2$CH(CH$_3$)SO$_2$CF$_3$ | CH$_2$CH$_3$ | 0 |
| B-2769 | H | H | H | H | F | CH$_2$C(=O)CH$_3$ | CH$_2$CH$_3$ | 0 |
| B-2770 | H | H | H | H | F | CH$_2$C(=O)CH$_2$CH$_3$ | CH$_2$CH$_3$ | 0 |
| B-2771 | H | H | H | H | F | CH$_2$C(=O)C(CH$_3$)$_3$ | CH$_2$CH$_3$ | 0 |
| B-2772 | H | H | H | H | F | CH$_2$CH$_2$C(=O)CH$_3$ | CH$_2$CH$_3$ | 0 |
| B-2773 | H | H | H | H | F | CH$_2$CH$_2$C(=O)C(CH$_3$)$_3$ | CH$_2$CH$_3$ | 0 |
| B-2774 | H | H | H | H | F | CH$_2$C(=O)CF$_3$ | CH$_2$CH$_3$ | 0 |
| B-2775 | H | H | H | H | F | CH$_2$CH$_2$C(=O)CF$_3$ | CH$_2$CH$_3$ | 0 |
| B-2776 | H | H | H | H | F | CH$_2$C(=O)OCH$_3$ | CH$_2$CH$_3$ | 0 |
| B-2777 | H | H | H | H | F | CH$_2$C(=O)OCH$_2$CH$_3$ | CH$_2$CH$_3$ | 0 |
| B-2778 | H | H | H | H | F | CH$_2$C(=O)OC(CH$_3$)$_3$ | CH$_2$CH$_3$ | 0 |
| B-2779 | H | H | H | H | F | CH$_2$CH$_2$C(=O)OCH$_3$ | CH$_2$CH$_3$ | 0 |
| B-2780 | H | H | H | H | F | CH$_2$CH$_2$C(=O)OCH$_2$CH$_3$ | CH$_2$CH$_3$ | 0 |
| B-2781 | H | H | H | H | F | CH$_2$CH$_2$C(=O)OC(CH$_3$)$_3$ | CH$_2$CH$_3$ | 0 |
| B-2782 | H | H | H | H | F | CH$_2$C(=O)NH$_2$ | CH$_2$CH$_3$ | 0 |
| B-2783 | H | H | H | H | F | CH$_2$CH$_2$C(=O)NH$_2$ | CH$_2$CH$_3$ | 0 |
| B-2784 | H | H | H | H | F | CH$_2$C(=O)NHCH$_3$ | CH$_2$CH$_3$ | 0 |
| B-2785 | H | H | H | H | F | CH$_2$C(=O)NHCH(CH$_3$)$_2$ | CH$_2$CH$_3$ | 0 |
| B-2786 | H | H | H | H | F | CH$_2$CH$_2$C(=O)NHCH$_3$ | CH$_2$CH$_3$ | 0 |
| B-2787 | H | H | H | H | F | CH$_2$CH$_2$C(=O)NHCH(CH$_3$)$_2$ | CH$_2$CH$_3$ | 0 |
| B-2788 | H | H | H | H | F | CH$_2$C(=O)NHCH$_2$CHF$_2$ | CH$_2$CH$_3$ | 0 |
| B-2789 | H | H | H | H | F | CH$_2$C(=O)NHCH$_2$CF$_3$ | CH$_2$CH$_3$ | 0 |
| B-2790 | H | H | H | H | F | CH$_2$CH$_2$C(=O)NHCH$_2$CHF$_2$ | CH$_2$CH$_3$ | 0 |
| B-2791 | H | H | H | H | F | CH$_2$CH$_2$C(=O)NHCH$_2$CF$_3$ | CH$_2$CH$_3$ | 0 |
| B-2792 | H | H | H | H | F | CH$_2$C(=O)N(CH$_3$)$_2$ | CH$_2$CH$_3$ | 0 |
| B-2793 | H | H | H | H | F | CH$_2$C(=O)N(CH$_2$CH$_3$)$_2$ | CH$_2$CH$_3$ | 0 |
| B-2794 | H | H | H | H | F | CH$_2$CH$_2$C(=O)N(CH$_3$)$_2$ | CH$_2$CH$_3$ | 0 |
| B-2795 | H | H | H | H | F | CH$_2$CH$_2$C(=O)N(CH$_2$CH$_3$)$_2$ | CH$_2$CH$_3$ | 0 |
| B-2796 | H | H | H | H | F | CH$_2$CH$_2$OH | CH$_2$CH$_3$ | 0 |
| B-2797 | H | H | H | H | F | CH$_2$CH(OH)CH$_3$ | CH$_2$CH$_3$ | 0 |
| B-2798 | H | H | H | H | F | CH$_2$CH$_2$CH$_2$OH | CH$_2$CH$_3$ | 0 |
| B-2799 | H | H | H | H | F | CH$_2$CH(OH)CH$_2$CH$_3$ | CH$_2$CH$_3$ | 0 |
| B-2800 | H | H | H | H | F | CH$_2$CH(OH)C(CH$_3$)$_3$ | CH$_2$CH$_3$ | 0 |
| B-2801 | H | H | H | H | F | CH$_2$CH$_2$CH(OH)CH$_3$ | CH$_2$CH$_3$ | 0 |

TABLE 140

| Compound | R$^1$ | R$^2$ | R$^3$ | R$^4$ | R$^5$ | R$^6$ | R$^{16}$ | n |
|---|---|---|---|---|---|---|---|---|
| B-2802 | H | H | H | H | F | CH$_2$CH$_3$CH(OH)C(CH$_3$)$_3$ | CH$_2$CH$_3$ | 0 |
| B-2803 | H | H | H | H | F | CH$_2$C(=NOH)CH$_3$ | CH$_2$CH$_3$ | 0 |
| B-2804 | H | H | H | H | F | CH$_2$C(=NOH)CH$_2$CH$_3$ | CH$_2$CH$_3$ | 0 |
| B-2805 | H | H | H | H | F | CH$_2$C(=NOH)C(CH$_3$)$_3$ | CH$_2$CH$_3$ | 0 |
| B-2806 | H | H | H | H | F | CH$_2$C(=NOCH$_3$)CH$_3$ | CH$_2$CH$_3$ | 0 |
| B-2807 | H | H | H | H | F | CH$_2$C(=NOCH$_3$)CH$_2$CH$_3$ | CH$_2$CH$_3$ | 0 |
| B-2808 | H | H | H | H | F | CH$_2$C(=NOCH$_2$CH$_3$)CH$_3$ | CH$_2$CH$_3$ | 0 |
| B-2809 | H | H | H | H | F | CH$_2$C(=NOCH$_2$CH$_3$)CH$_2$CH$_3$ | CH$_2$CH$_3$ | 0 |
| B-2810 | H | H | H | H | F | CH$_2$C(=NOCH$_2$CF$_3$)CH$_3$ | CH$_2$CH$_3$ | 0 |
| B-2811 | H | H | H | H | F | CH$_2$C(=NOCH$_2$CF$_3$)CH$_2$CH$_3$ | CH$_2$CH$_3$ | 0 |
| B-2812 | H | H | H | H | F | CH$_2$Ph | CH$_2$CH$_3$ | 0 |
| B-2813 | H | H | H | H | F | CH$_2$(2-F)Ph | CH$_2$CH$_3$ | 0 |
| B-2814 | H | H | H | H | F | CH$_2$(3-F)Ph | CH$_2$CH$_3$ | 0 |
| B-2815 | H | H | H | H | F | CH$_2$(4-F)Ph | CH$_2$CH$_3$ | 0 |
| B-2816 | H | H | H | H | F | CH$_2$(2-Cl)Ph | CH$_2$CH$_3$ | 0 |
| B-2817 | H | H | H | H | F | CH$_2$(3-Cl)Ph | CH$_2$CH$_3$ | 0 |
| B-2818 | H | H | H | H | F | CH$_2$(4-Cl)Ph | CH$_2$CH$_3$ | 0 |
| B-2819 | H | H | H | H | F | CH$_2$(2-CF$_3$)Ph | CH$_2$CH$_3$ | 0 |
| B-2820 | H | H | H | H | F | CH$_2$(3-CF$_3$)Ph | CH$_2$CH$_3$ | 0 |
| B-2821 | H | H | H | H | F | CH$_2$(4-CF$_3$)Ph | CK$_2$CH$_3$ | 0 |
| B-2822 | H | H | H | H | F | CH$_2$(naphthalen-1-yl) | CH$_2$CH$_3$ | 0 |
| B-2823 | H | H | H | H | F | CH$_2$(naphthalen-2-yl) | CH$_2$CH$_3$ | 0 |
| B-2824 | H | H | H | H | F | CH$_2$CH$_2$Ph | CH$_2$CH$_3$ | 0 |
| B-2825 | H | H | H | H | CH$_3$ | H | H | 0 |
| B-2826 | H | H | H | H | CH$_3$ | CH$_3$ | H | 0 |
| B-2827 | H | H | H | H | CH$_3$ | CH$_2$CH$_3$ | H | 0 |
| B-2828 | H | H | H | H | CH$_3$ | CH(CH$_3$)$_2$ | H | 0 |

TABLE 140-continued

| Compound | R$^1$ | R$^2$ | R$^3$ | R$^4$ | R$^5$ | R$^6$ | R$^{16}$ | n |
|---|---|---|---|---|---|---|---|---|
| B-2829 | H | H | H | H | CH$_3$ | CH$_2$CH$_2$CH$_3$ | H | 0 |
| B-2830 | H | H | H | H | CH$_3$ | CH$_2$CH(CH$_3$)$_2$ | H | 0 |
| B-2831 | H | H | H | H | CH$_3$ | CH$_2$C(CH$_3$)$_3$ | H | 0 |
| B-2832 | H | H | H | H | CH$_3$ | CH(CH$_3$)CH$_2$CH$_3$ | H | 0 |
| B-2833 | H | H | H | H | CH$_3$ | CH$_2$(CH$_2$)$_2$CH$_3$ | H | 0 |
| B-2834 | H | H | H | H | CH$_3$ | CH$_2$(CH$_2$)$_3$CH$_3$ | H | 0 |
| B-2835 | H | H | H | H | CH$_3$ | CH$_2$(CH$_2$)$_4$CH$_3$ | H | 0 |
| B-2836 | H | H | H | H | CH$_3$ | CH(CH$_2$)$_6$CH$_3$ | H | 0 |
| B-2837 | H | H | H | H | CH$_3$ | CH$_2$OCH$_3$ | H | 0 |
| B-2838 | H | H | H | H | CH$_3$ | CH$_2$OCH$_2$CH$_3$ | H | 0 |
| B-2839 | H | H | H | H | CH$_3$ | CH$_2$CH$_2$OCH$_3$ | H | 0 |
| B-2840 | H | H | H | H | CH$_3$ | CH$_2$CH$_2$OCH$_2$CH$_3$ | H | 0 |
| B-2841 | H | H | H | H | CH$_3$ | CF$_3$ | H | 0 |
| B-2842 | H | H | H | H | CH$_3$ | CHF$_2$ | H | 0 |
| B-2843 | H | H | H | H | CH$_3$ | CH$_2$CF$_3$ | H | 0 |
| B-2844 | H | H | H | H | CH$_3$ | CH$_2$CHF$_2$ | H | 0 |
| B-2845 | H | H | H | H | CH$_3$ | CH$_2$CClF$_2$ | H | 0 |
| B-2846 | H | H | H | H | CH$_3$ | CH$_2$CBrF$_2$ | H | 0 |
| B-2847 | H | H | H | H | CH$_3$ | CF$_2$CF$_3$ | H | 0 |
| B-2848 | H | H | H | H | CH$_3$ | CF$_2$CHF$_2$ | H | 0 |
| B-2849 | H | H | H | H | CH$_3$ | CH$_2$CH$_2$CF$_3$ | H | 0 |
| B-2850 | H | H | H | H | CH$_3$ | CH$_2$CF$_2$CF$_3$ | H | 0 |
| B-2851 | H | H | H | H | CH$_3$ | CH$_2$CF$_2$CHF$_2$ | H | 0 |
| B-2852 | H | H | H | H | CH$_3$ | CF$_2$CHFCF$_3$ | H | 0 |
| B-2853 | H | H | H | H | CH$_3$ | CF$_2$CF$_2$CF$_3$ | H | 0 |
| B-2854 | H | H | H | H | CH$_3$ | CH$_2$CF$_2$CF$_2$CF$_3$ | H | 0 |
| B-2855 | H | H | H | H | CH$_3$ | CH$_2$CF$_2$CHFCF$_3$ | H | 0 |
| B-2856 | H | H | H | H | CH$_3$ | CH$_2$CH$_2$CH$_2$CF$_3$ | H | 0 |
| B-2857 | H | H | H | H | CH$_3$ | CH$_2$CH$_2$CF$_2$CF$_3$ | H | 0 |
| B-2858 | H | H | H | H | CH$_3$ | CF$_2$CF$_2$CF$_2$CF$_3$ | H | 0 |
| B-2859 | H | H | H | H | CH$_3$ | CH$_2$CH$_2$CH(CF$_3$)$_2$ | H | 0 |
| B-2860 | H | H | H | H | CH$_3$ | CF$_2$CF$_2$CF$_2$CF$_2$CF$_3$ | H | 0 |
| B-2861 | H | H | H | H | CH$_3$ | CH$_2$CF$_2$CF$_2$CF$_2$CF$_3$ | H | 0 |
| B-2862 | H | H | H | H | CH$_3$ | CH$_2$CH$_2$CH$_2$CH$_2$CF$_3$ | H | 0 |

TABLE 141

| Compound | R$^1$ | R$^2$ | R$^3$ | R$^4$ | R$^5$ | R$^6$ | R$^{16}$ | n |
|---|---|---|---|---|---|---|---|---|
| B-2863 | H | H | H | H | CH$_3$ | CH$_2$CF$_2$CF$_2$CF$_2$CHF$_2$ | H | 0 |
| B-2864 | H | H | H | H | CH$_3$ | CH$_3$CF$_2$CF(CF$_3$)CF$_2$C(CF$_3$)$_3$ | H | 0 |
| B-2865 | H | H | H | H | CH$_3$ | CH$_2$CH$_2$CH$_2$CH$_2$CH$_2$CF$_3$ | H | 0 |
| B-2866 | H | H | H | H | CH$_3$ | CH$_2$CH$_2$CH$_2$CH$_2$CH$_2$CH$_2$CF$_3$ | H | 0 |
| B-2867 | H | H | H | H | CH$_3$ | CF$_2$CHFOCH$_3$ | H | 0 |
| B-2868 | H | H | H | H | CH$_3$ | CF$_2$CHFOCH$_2$CH$_3$ | H | 0 |
| B-2869 | H | H | H | H | CH$_3$ | CH$_2$CH$_2$OCH$_2$CF$_3$ | H | 0 |
| B-2870 | H | H | H | H | CH$_3$ | CF$_2$CHFOCF$_3$ | H | 0 |
| B-2871 | H | H | H | H | CH$_3$ | CF$_2$CHFOCF$_2$CF$_3$ | H | 0 |
| B-2872 | H | H | H | H | CH$_3$ | CF$_2$CHFOCF$_2$CF$_2$CF$_3$ | H | 0 |
| B-2873 | H | H | H | H | CH$_3$ | CH$_2$CH=CH$_2$ | H | 0 |
| B-2874 | H | H | H | H | CH$_3$ | CH$_2$CH=CHCl | H | 0 |
| B-2875 | H | H | H | H | CH$_3$ | CH$_2$CH=CCl$_2$ | H | 0 |
| B-2876 | H | H | H | H | CH$_3$ | CH$_2$CH$_2$CF=CF$_2$ | H | 0 |
| B-2877 | H | H | H | H | CH$_3$ | CH$_2$CH$_2$CH=CF$_2$ | H | 0 |
| B-2878 | H | H | H | H | CH$_3$ | CH$_2$C≡CH | H | 0 |
| B-2879 | H | H | H | H | CH$_3$ | CH$_2$C≡CCH$_3$ | H | 0 |
| B-2880 | H | H | H | H | CH$_3$ | CH$_2$C≡Cl | H | 0 |
| B-2881 | H | H | H | H | CH$_3$ | CH$_2$C≡CCF$_3$ | H | 0 |
| B-2882 | H | H | H | H | CH$_3$ | cyclobutyl | H | 0 |
| B-2883 | H | H | H | H | CH$_3$ | cyclopentyl | H | 0 |
| B-2884 | H | H | H | H | CH$_3$ | cyclohexyl | H | 0 |
| B-2885 | H | H | H | H | CH$_3$ | 4,4-difluorocyclohexyl | H | 0 |
| B-2886 | H | H | H | H | CH$_3$ | CH$_2$(cyclopropyl) | H | 0 |
| B-2887 | H | H | H | H | CH$_3$ | CH$_2$(cyclobutyl) | H | 0 |
| B-2888 | H | H | H | H | CH$_3$ | CH$_2$(cydopentyl) | H | 0 |
| B-2889 | H | H | H | H | CH$_3$ | CH$_2$CH$_2$(cyclopropyl) | H | 0 |
| B-2890 | H | H | H | H | CH$_3$ | CH$_2$(2,2-difluorocyclopropyl) | H | 0 |
| B-2891 | H | H | H | H | CH$_3$ | CH$_2$(2,2-dichlorocyclopropyl) | H | 0 |
| B-2892 | H | H | H | H | CH$_3$ | CH$_2$(4,4-fluorocyclohexyl) | H | 0 |
| B-2893 | H | H | H | H | CH$_3$ | CH$_2$CH$_2$(2,2-difluorocyclopropyl) | H | 0 |
| B-2894 | H | H | H | H | CH$_3$ | CH$_2$CH$_2$(2,2-dichlorocyclopropyl) | H | 0 |
| B-2895 | H | H | H | H | CH$_3$ | CH$_2$SCH$_3$ | H | 0 |
| B-2896 | H | H | H | H | CH$_3$ | CH$_2$SCH$_2$CH$_3$ | H | 0 |
| B-2897 | H | HI | H | H | CH$_3$ | CH$_2$CH$_2$SCH$_3$ | H | 0 |
| B-2898 | H | H | H | H | CH$_3$ | CH$_2$CH$_2$SCH$_2$CH$_3$ | H | 0 |

TABLE 141-continued

| Compound | R¹ | R² | R³ | R⁴ | R⁵ | R⁶ | R¹⁶ | n |
|---|---|---|---|---|---|---|---|---|
| B-2899 | H | H | H | H | CH₃ | CH₂CH₂CH₂SCH₃ | H | 0 |
| B-2900 | H | H | H | H | CH₃ | CH₂CH₂CH₂SCH₂CH₃ | H | 0 |
| B-2901 | H | H | H | H | CH₃ | CH(CH₃)SCH₃ | H | 0 |
| B-2902 | H | H | H | H | CH₃ | CH(CH₃)SCH₂CH₃ | H | 0 |
| B-2903 | H | H | H | H | CH₃ | CH₂CH(CH₃)SCH₃ | H | 0 |
| B-2904 | H | H | H | H | CH₃ | CH₂CH(CH₃)SCH₂CH₃ | H | 0 |
| B-2905 | H | H | H | H | CH₃ | CH(CH₃)CH₂CH₂SCH₃ | H | 0 |
| B-2906 | H | H | H | H | CH₃ | CH(CH₃)CH₂CH₂SCH₂CH₃ | H | 0 |
| B-2907 | H | H | H | H | CH₃ | CH₂CH(CH₃)CH₂SCH₃ | H | 0 |
| B-2908 | H | H | H | H | CH₃ | CH₂CH(CH₃)CH₂SCH₂CH₃ | H | 0 |
| B-2909 | H | H | H | H | CH₃ | CH₂CH₂CH(CH₃)SCH₃ | H | 0 |
| B-2910 | H | H | H | H | CH₃ | CH₂CH₂CH(CH₃)SCH₂CH₃ | H | 0 |
| B-2911 | H | H | H | H | CH₃ | CH₂SOCH₃ | H | 0 |
| B-2912 | H | H | H | H | CH₃ | CH₂CH₂SOCH₃ | H | 0 |
| B-2913 | H | H | H | H | CH₃ | CH₂CH₂CH₂SOCH₃ | H | 0 |
| B-2914 | H | H | H | H | CH₃ | CH(CH₃)SOCH₃ | H | 0 |
| B-2915 | H | H | H | H | CH₃ | CH₂CH(CH₃)SOCH₃ | H | 0 |
| B-2916 | H | H | H | H | CH₃ | CH(CH₃)CH₂CH₂SOCH₃ | H | 0 |
| B-2917 | H | H | H | H | CH₃ | CH₂CH(CH₃)CH₂SOCH₃ | H | 0 |
| B-2918 | H | H | H | H | CH₃ | CH₂CH₂CH(CH₃)SOCH₃ | H | 0 |
| B-2919 | H | H | H | H | CH₃ | CH₂SO₂CH₃ | H | 0 |
| B-2920 | H | H | H | H | CH₃ | CH₂CH₂SO₂CH₃ | H | 0 |
| B-2921 | H | H | H | H | CH₃ | CH₂CH₂CH₂SO₂CH₃ | H | 0 |
| B-2922 | H | H | H | H | CH₃ | CH(CH₃)SO₂CH₃ | H | 0 |
| B-2923 | H | H | H | H | CH₃ | CH₂CH(CH₃)SO₂CH₃ | H | 0 |

TABLE 142

| Compound | R¹ | R² | R³ | R⁴ | R⁵ | R⁶ | R¹⁶ | n |
|---|---|---|---|---|---|---|---|---|
| B-2924 | H | H | H | H | CH₃ | CH(CH₃)CH₂CH₂SO₂CH₃ | H | 0 |
| B-2925 | H | H | H | H | CH₃ | CH₂CH(CH₃)CH₂SO₂CH₃ | H | 0 |
| B-2926 | H | H | H | H | CH₃ | CH₂CH₂CH(CH₃)SO₂CH₃ | H | 0 |
| B-2927 | H | H | H | H | CH₃ | CH₂SCF₃ | H | 0 |
| B-2928 | H | H | H | H | CH₃ | CH₂SCHF₂ | H | 0 |
| B-2929 | H | H | H | H | CH₃ | CH₂SCH₂CF₃ | H | 0 |
| B-2930 | H | H | H | H | CH₃ | CH₂SCH₂CHF₂ | H | 0 |
| B-2931 | H | H | H | H | CH₃ | CH₂SCF₂CF₃ | H | 0 |
| B-2932 | H | H | H | H | CH₃ | CH₂CH₂SCF₃ | H | 0 |
| B-2933 | H | H | H | H | CH₃ | CH₂CH₂SCH₂CF₃ | H | 0 |
| B-2934 | H | H | H | H | CH₃ | CH₂CH₂CH₂SCF₃ | H | 0 |
| B-2935 | H | H | H | H | CH₃ | CH₂CH₂CH₂SCH₂CF₃ | H | 0 |
| B-2936 | H | H | H | H | CH₃ | CH(CH₃)SCF₃ | H | 0 |
| B-2937 | H | H | H | H | CH₃ | CH(CH₃)SCH₂CF₃ | H | 0 |
| B-2938 | H | H | H | H | CH₃ | CH₂CH(CH₃)SCF₃ | H | 0 |
| B-2939 | H | H | H | H | CH₃ | CH₂CH(CH₃)SCH₂CF₃ | H | 0 |
| B-2940 | H | H | H | H | CH₃ | CH(CH₃)CH₂CH₂SCF₃ | H | 0 |
| B-2941 | H | H | H | H | CH₃ | CH(CH₃)CH₂CH₂SCH₂CF₃ | H | 0 |
| B-2942 | H | H | H | H | CH₃ | CH₂CH(CH₃)CH₂SCF₃ | H | 0 |
| B-2943 | H | H | H | H | CH₃ | CH₂CH(CH₃)CH₂SCH₂CF₃ | H | 0 |
| B-2944 | H | H | H | H | CH₃ | CH₂CH₂CH(CH₃)SCF₃ | H | 0 |
| B-2945 | H | H | H | H | CH₃ | CH₂CH₂CH(CH₃)SCH₂CF₃ | H | 0 |
| B-2946 | H | H | H | H | CH₃ | CH₂SOCF₃ | H | 0 |
| B-2947 | H | H | H | H | CH₃ | CH₂CH₂SOCF₃ | H | 0 |
| B-2948 | H | H | H | H | CH₃ | CH₂CH₂CH₂SOCF₃ | H | 0 |
| B-2949 | H | H | H | H | CH₃ | CH(CH₃)SOCF₃ | H | 0 |
| B-2950 | H | H | H | H | CH₃ | CH₂CH(CH₃)SOCF₃ | H | 0 |
| B-2951 | H | H | H | H | CH₃ | CH(CH₃)CH₂CH₂SOCF₃ | H | 0 |
| B-2952 | H | H | H | H | CH₃ | CH₂CH(CH₃)CH₂SOCF₃ | H | 0 |
| B-2953 | H | H | H | H | CH₃ | CH₂CH₂CH(CH₃)SOCF₃ | H | 0 |
| B-2954 | H | H | H | H | CH₃ | CH₂SO₂CF₃ | H | 0 |
| B-2955 | H | H | H | H | CH₃ | CH₂CH₂SO₂CF₃ | H | 0 |
| B-2956 | H | H | H | H | CH₃ | CH₂CH₂CH₂SO₂CF₃ | H | 0 |
| B-2957 | H | H | H | H | CH₃ | CH(CH₃)SO₂CF₃ | H | 0 |
| B-2958 | H | H | H | H | CH₃ | CH₂CH(CH₃)SO₂CF₃ | H | 0 |
| B-2959 | H | H | H | H | CH₃ | CH(CH₃)CH₂CH₂SO₂CF₃ | H | 0 |
| B-2960 | H | H | H | H | CH₃ | CH₂CH(CH₃)CH₂SO₂CF₃ | H | 0 |
| B-2961 | H | H | H | H | CH₃ | CH₂CH₂CH(CH₃)SO₂CF₃ | H | 0 |
| B-2962 | H | H | H | H | CH₃ | CH₂C(=O)CH₃ | H | 0 |
| B-2963 | H | H | H | H | CH₃ | CH₂C(=O)CH₂CH₃ | H | 0 |
| B-2964 | H | H | H | H | CH₃ | CH₂C(=O)C(CH₃)₃ | H | 0 |
| B-2965 | H | H | H | H | CH₃ | CH₂CH₂C(=O)CH₃ | H | 0 |
| B-2966 | H | H | H | H | CH₃ | CH₂CH₂C(=O)C(CH₃)₃ | H | 0 |
| B-2967 | H | H | H | H | CH₃ | CH₂C(=C)CF₃ | H | 0 |
| B-2968 | H | H | H | H | CH₃ | CH₂CH₂C(=O)CF₃ | H | 0 |

TABLE 142-continued

| Compound | R$^1$ | R$^2$ | R$^3$ | R$^4$ | R$^5$ | R$^6$ | R$^{16}$ | n |
|---|---|---|---|---|---|---|---|---|
| B-2969 | H | H | H | H | CH$_3$ | CH$_2$C(=O)OCH$_3$ | H | 0 |
| B-2970 | H | H | H | H | CH$_3$ | CH$_2$C(=O)OCH$_2$CH$_3$ | H | 0 |
| B-2971 | H | H | H | H | CH$_3$ | CH$_2$C(=O)OC(CH$_3$)$_3$ | H | 0 |
| B-2972 | H | H | H | H | CH$_3$ | CH$_2$CH$_2$C(=O)OCH$_3$ | H | 0 |
| B-2973 | H | H | H | H | CH$_3$ | CH$_2$CH$_2$C(=O)OCH$_2$CH$_3$ | H | 0 |
| B-2974 | H | H | H | H | CH$_3$ | CH$_2$CH$_2$C(=O)OC(CH$_3$)$_3$ | H | 0 |
| B-2975 | H | H | H | H | CH$_3$ | CH$_2$C(=O)NH$_2$ | H | 0 |
| B-2976 | H | H | H | H | CH$_3$ | CH$_2$CH$_2$C(=O)NH$_2$ | H | 0 |
| B-2977 | H | H | H | H | CH$_3$ | CH$_2$C(=O)NHCH$_3$ | H | 0 |
| B-2978 | H | H | H | H | CH$_3$ | CH$_2$C(=O)NHCH(CH$_3$)$_2$ | H | 0 |
| B-2979 | H | H | H | H | CH$_3$ | CH$_2$CH$_2$C(=O)NHCH$_3$ | H | 0 |
| B-2980 | H | H | H | H | CH$_3$ | CH$_2$CH$_2$C(=O)NHCH(CH$_3$)$_2$ | H | 0 |
| B-2981 | H | H | H | H | CH$_3$ | CH$_2$C(=O)NHCH$_2$CHF$_2$ | H | 0 |
| B-2982 | H | H | H | H | CH$_3$ | CH$_2$C(=O)NHCH$_2$CF$_3$ | H | 0 |
| B-2983 | H | H | H | H | CH$_3$ | CH$_2$CH$_2$C(=O)NHCH$_2$CHF$_2$ | H | 0 |
| B-2984 | H | H | H | H | CH$_3$ | CH$_2$CH$_2$C(=O)NHCH$_2$CF$_3$ | H | 0 |

TABLE 143

| Compound | R$^1$ | R$^2$ | R$^3$ | R$^4$ | R$^5$ | R$^6$ | R$^{16}$ | n |
|---|---|---|---|---|---|---|---|---|
| B-2985 | H | H | H | H | CH$_3$ | CH$_2$C(=O)N(CH$_3$)$_2$ | H | 0 |
| B-2986 | H | H | H | H | CH$_3$ | CH$_2$C(=O)N(CH$_2$CH$_3$)$_2$ | H | 0 |
| B-2987 | H | H | H | H | CH$_3$ | CH$_2$CH$_2$C(=O)N(CH$_3$)$_2$ | H | 0 |
| B-2988 | H | H | H | H | CH$_3$ | CH$_2$CH$_2$C(=O)N(CH$_2$CH$_3$)$_2$ | H | 0 |
| B-2989 | H | H | H | H | CH$_3$ | CH$_2$CH$_2$OH | H | 0 |
| B-2990 | H | H | H | H | CH$_3$ | CH$_2$CH(OH)CH$_3$ | H | 0 |
| B-2991 | H | H | H | H | CH$_3$ | CH$_2$CH$_2$CH$_2$OH | H | 0 |
| B-2992 | H | H | H | H | CH$_3$ | CH$_2$CH(OH)CH$_2$CH$_3$ | H | 0 |
| B-2993 | H | H | H | H | CH$_3$ | CH$_2$CH(OH)C(CH$_3$)$_3$ | H | 0 |
| B-2994 | H | H | H | H | CH$_3$ | CH$_2$CH$_2$CH(OH)CH$_3$ | H | 0 |
| B-2995 | H | H | H | H | CH$_3$ | CH$_2$CH$_2$CH(OH)C(CH$_3$)$_3$ | H | 0 |
| B-2996 | H | H | H | H | CH$_3$ | CH$_2$C(=NOH)CH$_3$ | H | 0 |
| B-2997 | H | H | H | H | CH$_3$ | CH$_2$C(=NOH)CH$_2$CH$_3$ | H | 0 |
| B-2998 | H | H | H | H | CH$_3$ | CH$_2$C(=NOH)C(CH$_3$)$_3$ | H | 0 |
| B-2999 | H | H | H | H | CH$_3$ | CH$_2$C(=NOCH$_3$)CH$_3$ | H | 0 |
| B-3000 | H | H | H | H | CH$_3$ | CH$_2$C(=NOCH$_3$)CH$_2$CH$_3$ | H | 0 |
| B-3001 | H | H | H | H | CH$_3$ | CH$_2$C(=NOCH$_2$CH$_3$)CH$_3$ | H | 0 |
| B-3002 | H | H | H | H | CH$_3$ | CH$_2$C(=NOCH$_2$CH$_3$)CH$_2$CH$_3$ | H | 0 |
| B-3003 | H | H | H | H | CH$_3$ | CH$_2$C(=NOCH$_2$CF$_3$)CH$_3$ | H | 0 |
| B-3004 | H | H | H | H | CH$_3$ | CH$_2$C(=NOCH$_2$CF$_3$)CH$_2$CH$_3$ | H | 0 |
| B-3005 | H | H | H | H | CH$_3$ | CH$_2$Ph | H | 0 |
| B-3006 | H | H | H | H | CH$_3$ | CH$_2$(2-F)Ph | H | 0 |
| B-3007 | H | H | H | H | CH$_3$ | CH$_2$(3-F)Ph | H | 0 |
| B-3008 | H | H | H | H | CH$_3$ | CH$_2$(4-F)Ph | H | 0 |
| B-3009 | H | H | H | H | CH$_3$ | CH$_2$(2-Cl)Ph | H | 0 |
| B-3010 | H | H | H | H | CH$_3$ | CH$_2$(3-Cl)Ph | H | 0 |
| B-3011 | H | H | H | H | CH$_3$ | CH$_2$(4-Cl)Ph | H | 0 |
| B-3012 | H | H | H | H | CH$_3$ | CH$_2$(2-CF$_3$)Ph | H | 0 |
| B-3013 | H | H | H | H | CH$_3$ | CH$_2$(3-CF$_3$)Ph | H | 0 |
| B-3014 | H | H | H | H | CH$_3$ | CH$_2$(4-CF$_3$)Ph | H | 0 |
| B-3015 | H | H | H | H | CH$_3$ | CH$_2$(naphthalen-1-yl) | H | 0 |
| B-3016 | H | H | H | H | CH$_3$ | CH$_2$(naphthalen-2-yl) | H | 0 |
| B-3017 | H | H | H | H | CH$_3$ | CH$_2$CH$_2$Ph | H | 0 |
| B-3018 | H | H | H | H | CH$_3$ | H | CH$_2$CH$_3$ | 0 |
| B-3019 | H | H | H | H | CH$_3$ | CH$_3$ | CH$_2$CH$_3$ | 0 |
| B-3020 | H | H | H | H | CH$_3$ | CH$_2$CH$_3$ | CH$_2$CH$_3$ | 0 |
| B-3021 | H | H | H | H | CH$_3$ | CH(CH$_3$)$_2$ | CH$_2$CH$_3$ | 0 |
| B-3022 | H | H | H | H | CH$_3$ | CH$_2$CH$_2$CH$_3$ | CH$_2$CH$_3$ | 0 |
| B-3023 | H | H | H | H | CH$_3$ | CH$_2$CH(CH$_3$)$_2$ | CH$_2$CH$_3$ | 0 |
| B-3024 | H | H | H | H | CH$_3$ | CH$_2$C(CH$_3$)$_3$ | CH$_2$CH$_3$ | 0 |
| B-3025 | H | H | H | H | CH$_3$ | CH(CH$_3$)CH$_2$CH$_3$ | CH$_2$CH$_3$ | 0 |
| B-3026 | H | H | H | H | CH$_3$ | CH$_2$(CH$_2$)$_2$CH$_3$ | CH$_2$CH$_3$ | 0 |
| B-3027 | H | H | H | H | CH$_3$ | CH$_2$(CH$_2$)$_3$CH$_3$ | CH$_2$CH$_3$ | 0 |
| B-3028 | H | H | H | H | CH$_3$ | CH$_2$(CH$_2$)$_4$CH$_3$ | CH$_2$CH$_3$ | 0 |
| B-3029 | H | H | H | H | CH$_3$ | CH$_2$(CH$_2$)$_6$CH$_3$ | CH$_2$CH$_3$ | 0 |
| B-3030 | H | H | H | H | CH$_3$ | CH$_2$OCH$_3$ | CH$_2$CH$_3$ | 0 |
| B-3031 | H | H | H | H | CH$_3$ | CH$_2$OCH$_2$CH$_3$ | CH$_2$CH$_3$ | 0 |
| B-3032 | H | H | H | H | CH$_3$ | CH$_2$CH$_2$OCH$_3$ | CH$_2$CH$_3$ | 0 |
| B-3033 | H | H | H | H | CH$_3$ | CH$_2$CH$_2$OCH$_2$CH$_3$ | CH$_2$CH$_3$ | 0 |
| B-3034 | H | H | H | H | CH$_3$ | CF$_3$ | CH$_2$CH$_3$ | 0 |
| B-3035 | H | H | H | H | CH$_3$ | CHF$_2$ | CH$_2$CH$_3$ | 0 |
| B-3036 | H | H | H | H | CH$_3$ | CH$_2$CF$_3$ | CH$_2$CH$_3$ | 0 |
| B-3037 | H | H | H | H | CH$_3$ | CH$_2$CHF$_2$ | CH$_2$CH$_3$ | 0 |
| B-3038 | H | H | H | H | CH$_3$ | CH$_2$CClF$_2$ | CH$_2$CH$_3$ | 0 |

TABLE 143-continued

| Compound | $R^1$ | $R^2$ | $R^3$ | $R^4$ | $R^5$ | $R^6$ | $R^{16}$ | n |
|---|---|---|---|---|---|---|---|---|
| B-3039 | H | H | H | H | $CH_3$ | $CH_2CBrF_2$ | $CH_2CH_3$ | 0 |
| B-3040 | H | H | H | H | $CH_3$ | $CF_2CF_3$ | $CH_2CH_3$ | 0 |
| B-3041 | H | H | H | H | $CH_3$ | $CF_2CHF_2$ | $CH_2CH_3$ | 0 |
| B-3042 | H | H | H | H | $CH_3$ | $CH_2CH_2CF_3$ | $CH_2CH_3$ | 0 |
| B-3043 | H | H | H | H | $CH_3$ | $CH_2CF_2CF_3$ | $CH_2CH_3$ | 0 |
| B-3044 | H | H | H | H | $CH_3$ | $CH_2CF_2CHF_2$ | $CH_2CH_3$ | 0 |
| B-3045 | H | H | H | H | $CH_3$ | $CF_2CHFCF_3$ | $CH_2CH_3$ | 0 |

TABLE 144

| Compound | $R^1$ | $R^2$ | $R^3$ | $R^4$ | $R^5$ | $R^6$ | $R^{16}$ | n |
|---|---|---|---|---|---|---|---|---|
| B-3046 | H | H | H | H | $CH_3$ | $CF_2CF_2CF_3$ | $CH_2CH_3$ | 0 |
| B-3047 | H | H | H | H | $CH_3$ | $CH_2CF_2CF_2CF_3$ | $CH_2CH_3$ | 0 |
| B-3048 | H | H | H | H | $CH_3$ | $CH_2CF_2CHFCF_3$ | $CH_2CH_3$ | 0 |
| B-3049 | H | H | H | H | $CH_3$ | $CH_2CH_2CH_2CF_3$ | $CH_2CH_3$ | 0 |
| B-3050 | H | H | H | H | $CH_3$ | $CH_2CH_2CF_2CF_3$ | $CH_2CH_3$ | 0 |
| B-3051 | H | H | H | H | $CH_3$ | $CF_2CF_2CF_2CF_3$ | $CH_2CH_3$ | 0 |
| B-3052 | H | H | H | H | $CH_3$ | $CH_2CH_2CH(CF_3)_2$ | $CH_2CH_3$ | 0 |
| B-3053 | H | H | H | H | $CH_3$ | $CF_2CF_2CF_2CF_2CF_3$ | $CH_2CH_3$ | 0 |
| B-3054 | H | H | H | H | $CH_3$ | $CH_2CF_2CF_2CF_2CF_3$ | $CH_2CH_3$ | 0 |
| B-3055 | H | H | H | H | $CH_3$ | $CH_2CH_2CH_2CH_2CF_3$ | $CH_2CH_3$ | 0 |
| B-3056 | H | H | H | H | $CH_3$ | $CH_2CF_2CF_2CF_2CHF_2$ | $CH_2CH_3$ | 0 |
| B-3057 | H | H | H | H | $CH_3$ | $CH_2CF_2CF(CF_3)CF_2C(CF_3)_3$ | $CH_2CH_3$ | 0 |
| B-3058 | H | H | H | H | $CH_3$ | $CH_2CH_2CH_2CH_2CH_2CF_3$ | $CH_2CH_3$ | 0 |
| B-3059 | H | H | H | H | $CH_3$ | $CH_2CH_2CH_2CH_2CH_2CH_2CF_3$ | $CH_2CH_3$ | 0 |
| B-3060 | H | H | H | H | $CH_3$ | $CF_2CHFOCH_3$ | $CH_2CH_3$ | 0 |
| B-3061 | H | H | H | H | $CH_3$ | $CF_2CHFOCH_2CH_3$ | $CH_2CH_3$ | 0 |
| B-3062 | H | H | H | H | $CH_3$ | $CH_2CH_2OCH_2CF_3$ | $CH_2CH_3$ | 0 |
| B-3063 | H | H | H | H | $CH_3$ | $CF_2CHFOCF_3$ | $CH_2CH_3$ | 0 |
| B-3064 | H | H | H | H | $CH_3$ | $CF_2CHFOCF_2CF_3$ | $CH_2CH_3$ | 0 |
| B-3065 | H | H | H | H | $CH_3$ | $CF_2CHFOCF_2CF_3$ | $CH_2CH_3$ | 0 |
| B-3066 | H | H | H | H | $CH_3$ | $CH_2CH=CH_2$ | $CH_2CH_3$ | 0 |
| B-3067 | H | H | H | H | $CH_3$ | $CH_2CH=CHCl$ | $CH_2CH_3$ | 0 |
| B-3068 | H | H | H | H | $CH_3$ | $CH_2CH=CCl_2$ | $CH_2CH_3$ | 0 |
| B-3069 | H | H | H | H | $CH_3$ | $CH_2CH_2CF=CF_2$ | $CH_2CH_3$ | 0 |
| B-3070 | H | H | H | H | $CH_3$ | $CH_2CH_2CH=CF_2$ | $CH_2CH_3$ | 0 |
| B-3071 | H | H | H | H | $CH_3$ | $CH_2C≡CH$ | $CH_2CH_3$ | 0 |
| B-3072 | H | H | H | H | $CH_3$ | $CH_2C≡CCH_3$ | $CH_2CH_3$ | 0 |
| B-3073 | H | H | H | H | $CH_3$ | $CH_2C≡Cl$ | $CH_2CH_3$ | 0 |
| B-3074 | H | H | H | H | $CH_3$ | $CH_2C≡CCF_3$ | $CH_2CH_3$ | 0 |
| B-3075 | H | H | H | H | $CH_3$ | cyclobutyl | $CH_2CH_3$ | 0 |
| B-3076 | H | H | H | H | $CH_3$ | cyclopentyl | $CH_2CH_3$ | 0 |
| B-3077 | H | H | H | H | $CH_3$ | cyclohexyl | $CH_2CH_3$ | 0 |
| B-3078 | H | H | H | H | $CH_3$ | 4,4-difluorocyclohexyl | $CH_2CH_3$ | 0 |
| B-3079 | H | H | H | H | $CH_3$ | $CH_2$(cyclopropyl) | $CH_2CH_3$ | 0 |
| B-3080 | H | H | H | H | $CH_3$ | $CH_2$(cyclobutyl) | $CH_2CH_3$ | 0 |
| B-3081 | H | H | H | H | $CH_3$ | $CH_2$(cyclopentyl) | $CH_2CH_3$ | 0 |
| B-3082 | H | H | H | H | $CH_3$ | $CH_2CH_2$(cyclopropyl) | $CH_2CH_3$ | 0 |
| B-3083 | H | H | H | H | $CH_3$ | $CH_2$(2,2-difluorocyclopropyl) | $CH_2CH_3$ | 0 |
| B-3084 | H | H | H | H | $CH_3$ | $CH_2$(2,2-dichlorocyclopropyl) | $CH_2CH_3$ | 0 |
| B-3085 | H | H | H | H | $CH_3$ | $CH_2$(4,4-difluorocyclohexyl) | $CH_2CH_3$ | 0 |
| B-3086 | H | H | H | H | $CH_3$ | $CH_2CH_2$(2,2-difluorocyclopropyl) | $CH_2CH_3$ | 0 |
| B-3087 | H | H | H | H | $CH_3$ | $CH_2CH_2$(2,2-dichlorocyclopropyl) | $CH_2CH_3$ | 0 |
| B-3088 | H | H | H | H | $CH_3$ | $CH_2SCH_3$ | $CH_2CH_3$ | 0 |
| B-3089 | H | H | H | H | $CH_3$ | $CH_2SCH_2CH_3$ | $CH_2CH_3$ | 0 |
| B-3090 | H | H | H | H | $CH_3$ | $CH_2CH_2SCH_3$ | $CH_2CH_3$ | 0 |
| B-3091 | H | H | H | H | $CH_3$ | $CH_2CH_2SCH_2CH_3$ | $CH_2CH_3$ | 0 |
| B-3092 | H | H | H | H | $CH_3$ | $CH_2CH_2CH_2SCH_3$ | $CH_2CH_3$ | 0 |
| B-3093 | H | H | H | H | $CH_3$ | $CH_2CH_2CH_2SCH_2CH_3$ | $CH_2CH_3$ | 0 |
| B-3094 | H | H | H | H | $CH_3$ | $CH(CH_3)SCH_3$ | $CH_2CH_3$ | 0 |
| B-3095 | H | H | H | H | $CH_3$ | $CH(CH_3)SCH_2CH_3$ | $CH_2CH_3$ | 0 |
| B-3096 | H | H | H | H | $CH_3$ | $CH_2CH(CH_3)SCH_3$ | $CH_2CH_3$ | 0 |
| B-3097 | H | H | H | H | $CH_3$ | $CH_2CH(CH_3)SCH_2CH_3$ | $CH_2CH_3$ | 0 |
| B-3098 | H | H | H | H | $CH_3$ | $CH(CH_3)CH_2CH_2SCH_3$ | $CH_2CH_3$ | 0 |
| B-3099 | H | H | H | H | $CH_3$ | $CH(CH_3)CH_2CH_2SCH_2CH_3$ | $CH_2CH_3$ | 0 |
| B-3100 | H | H | H | H | $CH_3$ | $CH_2CH(CH_3)CH_2SCH_3$ | $CH_2CH_3$ | 0 |
| B-3101 | H | H | H | H | $CH_3$ | $CH_2CH(CH_3)CH_2SCH_2CH_3$ | $CH_2CH_3$ | 0 |
| B-3102 | H | H | H | H | $CH_3$ | $CH_2CH_2CH(CH_3)SCH_3$ | $CH_2CH_3$ | 0 |
| B-3103 | H | H | H | H | $CH_3$ | $CH_2CH_2CH(CH_3)SCH_2CH_3$ | $CH_2CH_3$ | 0 |
| B-3104 | H | H | H | H | $CH_3$ | $CH_2SOCH_3$ | $CH_2CH_3$ | 0 |
| B-3105 | H | H | H | H | $CH_3$ | $CH_2CH_2SOCH_3$ | $CH_2CH_3$ | 0 |
| B-3106 | H | H | H | H | $CH_3$ | $CH_2CH_2CH_2SOCH_3$ | $CH_2CH_3$ | 0 |

TABLE 145

| Compound | R¹ | R² | R³ | R⁴ | R⁵ | R⁶ | R¹⁶ | n |
|---|---|---|---|---|---|---|---|---|
| B-3107 | H | H | H | H | CH$_3$ | CH(CH$_3$)SOCH$_3$ | CH$_2$CH$_3$ | 0 |
| B-3108 | H | H | H | H | CH$_3$ | CH$_2$CH(CH$_3$)SOCH$_3$ | CH$_2$CH$_3$ | 0 |
| B-3109 | H | H | H | H | CH$_3$ | CH(CH$_3$)CH$_2$CH$_2$SOCH$_3$ | CH$_2$CH$_3$ | 0 |
| B-3110 | H | H | H | H | CH$_3$ | CH$_2$CH(CH$_3$)CH$_2$SOCH$_3$ | CH$_2$CH$_3$ | 0 |
| B-3111 | H | H | H | H | CH$_3$ | CH$_2$CH$_2$CH(CH$_3$)SOCH$_3$ | CH$_2$CH$_3$ | 0 |
| B-3112 | H | H | H | H | CH$_3$ | CH$_2$SO$_2$CH$_3$ | CH$_2$CH$_3$ | 0 |
| B-3113 | H | H | H | H | CH$_3$ | CH$_2$CH$_2$SO$_2$CH$_3$ | CH$_2$CH$_3$ | 0 |
| B-3114 | H | H | H | H | CH$_3$ | CH$_2$CH$_2$CH$_2$SO$_2$CH$_3$ | CH$_2$CH$_3$ | 0 |
| B-3115 | H | H | H | H | CH$_3$ | CH(CH$_3$)SO$_2$CH$_3$ | CH$_2$CH$_3$ | 0 |
| B-3116 | H | H | H | H | CH$_3$ | CH$_2$CH(CH$_3$)SO$_2$CH$_3$ | CH$_2$CH$_3$ | 0 |
| B-3117 | H | H | H | H | CH$_3$ | CH(CH$_3$)CH$_2$CH$_2$SO$_2$CH$_3$ | CH$_2$CH$_3$ | 0 |
| B-3118 | H | H | H | H | CH$_3$ | CH$_2$CH(CH$_3$)CH$_2$SO$_2$CH$_3$ | CH$_2$CH$_3$ | 0 |
| B-3119 | H | H | H | H | CH$_3$ | CH$_2$CH$_2$CH(CH$_3$)SO$_2$CH$_3$ | CH$_2$CH$_3$ | 0 |
| B-3120 | H | H | H | H | CH$_3$ | CH$_2$SCF$_3$ | CH$_2$CH$_3$ | 0 |
| B-3121 | H | H | H | H | CH$_3$ | CH$_2$SCHF$_2$ | CH$_2$CH$_3$ | 0 |
| B-3122 | H | H | H | H | CH$_3$ | CH$_2$SCH$_2$CF$_3$ | CH$_2$CH$_3$ | 0 |
| B-3123 | H | H | H | H | CH$_3$ | CH$_2$SCH$_2$CHF$_2$ | CH$_2$CH$_3$ | 0 |
| B-3124 | H | H | H | H | CH$_3$ | CH$_2$SCF$_2$CF$_3$ | CH$_2$CH$_3$ | 0 |
| B-3125 | H | H | H | H | CH$_3$ | CH$_2$CH$_2$SCF$_3$ | CH$_2$CH$_3$ | 0 |
| B-3126 | H | H | H | H | CH$_3$ | CH$_2$CH$_2$SCH$_2$CF$_3$ | CH$_2$CH$_3$ | 0 |
| B-3127 | H | H | H | H | CH$_3$ | CH$_2$CH$_2$CH$_2$SCF$_3$ | CH$_2$CH$_3$ | 0 |
| B-3128 | H | H | H | H | CH$_3$ | CH$_2$CH$_2$CH$_2$SCH$_2$CF$_3$ | CH$_2$CH$_3$ | 0 |
| B-3129 | H | H | H | H | CH$_3$ | CH(CH$_3$)SCF$_3$ | CH$_2$CH$_3$ | 0 |
| B-3130 | H | H | H | H | CH$_3$ | CH(CH$_3$)SCH$_2$CF$_3$ | CH$_2$CH$_3$ | 0 |
| B-3131 | H | H | H | H | CH$_3$ | CH$_2$CH(CH$_3$)SCF$_3$ | CH$_2$CH$_3$ | 0 |
| B-3132 | H | H | H | H | CH$_3$ | CH$_2$CH(CH$_3$)SCH$_2$CF$_3$ | CH$_2$CH$_3$ | 0 |
| B-3133 | H | H | H | H | CH$_3$ | CH(CH$_3$)CH$_2$CH$_2$SCF$_3$ | CH$_2$CH$_3$ | 0 |
| B-3134 | H | H | H | H | CH$_3$ | CH(CH$_3$)CH$_2$CH$_2$SCH$_2$CF$_3$ | CH$_2$CH$_3$ | 0 |
| B-3135 | H | H | H | H | CH$_3$ | CH$_2$CH(CH$_3$)CH$_2$SCF$_3$ | CH$_2$CH$_3$ | 0 |
| B-3136 | H | H | H | H | CH$_3$ | CH$_2$CH(CH$_3$)CH$_2$SCH$_2$CF$_3$ | CH$_2$CH$_3$ | 0 |
| B-3137 | H | H | H | H | CH$_3$ | CH$_2$CH$_2$CH(CH$_3$)SCF$_3$ | CH$_2$CH$_3$ | 0 |
| B-3138 | H | H | H | H | CH$_3$ | CH$_2$CH$_2$CH(CH$_3$)SCH$_2$CF$_3$ | CH$_2$CH$_3$ | 0 |
| B-3139 | H | H | H | H | CH$_3$ | CH$_2$SOCF$_3$ | CH$_2$CH$_3$ | 0 |
| B-3140 | H | H | H | H | CH$_3$ | CH$_2$CH$_2$SOCF$_3$ | CH$_2$CH$_3$ | 0 |
| B-3141 | H | H | H | H | CH$_3$ | CH$_2$CH$_2$CH$_2$SOCF$_3$ | CH$_2$CH$_3$ | 0 |
| B-3142 | H | H | H | H | CH$_3$ | CH(CH$_3$)SOCF$_3$ | CH$_2$CH$_3$ | 0 |
| B-3143 | H | H | H | H | CH$_3$ | CH$_2$CH(CH$_3$)SOCF$_3$ | CH$_2$CH$_3$ | 0 |
| B-3144 | H | H | H | H | CH$_3$ | CH(CH$_3$)CH$_2$CH$_2$SOCF$_3$ | CH$_2$CH$_3$ | 0 |
| B-3145 | H | H | H | H | CH$_3$ | CH$_2$CH(CH$_3$)CH$_2$SOCF$_3$ | CH$_2$CH$_3$ | 0 |
| B-3146 | H | H | H | H | CH$_3$ | CH$_2$CH$_2$CH(CH$_3$)SOCF$_3$ | CH$_2$CH$_3$ | 0 |
| B-3147 | H | H | H | H | CH$_3$ | CH$_2$SO$_2$CF$_3$ | CH$_2$CH$_3$ | 0 |
| B-3148 | H | H | H | H | CH$_3$ | CH$_2$CH$_2$SO$_2$CF$_3$ | CH$_2$CH$_3$ | 0 |
| B-3149 | H | H | H | H | CH$_3$ | CH$_2$CH$_2$CH$_2$SO$_2$CF$_3$ | CH$_2$CH$_3$ | 0 |
| B-3150 | H | H | H | H | CH$_3$ | CH(CH$_3$)SO$_2$CF$_3$ | CH$_2$CH$_3$ | 0 |
| B-3151 | H | H | H | H | CH$_3$ | CH$_2$CH(CH$_3$)SO$_2$CF$_3$ | CH$_2$CH$_3$ | 0 |
| B-3152 | H | H | H | H | CH$_3$ | CH(CH$_3$)CH$_2$CH$_2$SO$_2$CF$_3$ | CH$_2$CH$_3$ | 0 |
| B-3153 | H | H | H | H | CH$_3$ | CH$_2$CH(CH$_3$)CH$_2$SO$_2$CF$_3$ | CH$_2$CH$_3$ | 0 |
| B-3154 | H | H | H | H | CH$_3$ | CH$_2$CH$_2$CH(CH$_3$)SO$_2$CF$_3$ | CH$_2$CH$_3$ | 0 |
| B-3155 | H | H | H | H | CH$_3$ | CH$_2$C(=O)CH$_3$ | CH$_2$CH$_3$ | 0 |
| B-3156 | H | H | H | H | CH$_3$ | CH$_2$C(=O)CH$_2$CH$_3$ | CH$_2$CH$_3$ | 0 |
| B-3157 | H | H | H | H | CH$_3$ | CH$_2$C(=O)C(CH$_3$)$_3$ | CH$_2$CH$_3$ | 0 |
| B-3158 | H | H | H | H | CH$_3$ | CH$_2$CH$_2$C(=O)CH$_3$ | CH$_2$CH$_3$ | 0 |
| B-3159 | H | H | H | H | CH$_3$ | CH$_2$CH$_2$C(=O)C(CH$_3$)$_3$ | CH$_2$CH$_3$ | 0 |
| B-3160 | H | H | H | H | CH$_3$ | CH$_2$C(=O)CF$_3$ | CH$_2$CH$_3$ | 0 |
| B-3161 | H | H | H | H | CH$_3$ | CH$_2$CH$_2$C(=O)CF$_3$ | CH$_2$CH$_3$ | 0 |
| B-3162 | H | H | H | H | CH$_3$ | CH$_2$C(=O)OCH$_3$ | CH$_2$CH$_3$ | 0 |
| B-3163 | H | H | H | H | CH$_3$ | CH$_2$C(=O)OCH$_2$CH$_3$ | CH$_2$CH$_3$ | 0 |
| B-3164 | H | H | H | H | CH$_3$ | CH$_2$C(=O)OC(CH$_3$)$_3$ | CH$_2$CH$_3$ | 0 |
| B-3165 | H | H | H | H | CH$_3$ | CH$_2$CH$_2$C(=O)OCH$_3$ | CH$_2$CH$_3$ | 0 |
| B-3166 | H | H | H | H | CH$_3$ | CH$_2$CH$_2$C(=O)OCH$_2$CH$_3$ | CH$_2$CH$_3$ | 0 |
| B-3167 | H | H | H | H | CH$_3$ | CH$_2$CH$_2$C(=O)OC(CH$_3$)$_3$ | CH$_2$CH$_3$ | 0 |

TABLE 146

| Compound | R¹ | R² | R³ | R⁴ | R⁵ | R⁶ | R¹⁶ | n |
|---|---|---|---|---|---|---|---|---|
| B-3168 | H | H | H | H | CH$_3$ | CH$_2$C(=O)NH$_2$ | CH$_2$CH$_3$ | 0 |
| B-3169 | H | H | H | H | CH$_3$ | CH$_2$CH$_2$C(=O)NH$_2$ | CH$_2$CH$_3$ | 0 |
| B-3170 | H | H | H | H | CH$_3$ | CH$_2$C(=O)NHCH$_3$ | CH$_2$CH$_3$ | 0 |
| B-3171 | H | H | H | H | CH$_3$ | CH$_2$C(=O)NHCH(CH$_3$)$_2$ | CH$_2$CH$_3$ | 0 |
| B-3172 | H | H | H | H | CH$_3$ | CH$_2$CH$_2$C(=O)NHCH$_3$ | CH$_2$CH$_3$ | 0 |
| B-3173 | H | H | H | H | CH$_3$ | CH$_2$CH$_2$C(=O)NHCH(CH$_3$)$_2$ | CH$_2$CH$_3$ | 0 |
| B-3174 | H | H | H | H | CH$_3$ | CH$_2$C(=O)NHCH$_2$CHF$_2$ | CH$_2$CH$_3$ | 0 |
| B-3175 | H | H | H | H | CH$_3$ | CH$_2$C(=O)NHCH$_2$CF$_3$ | CH$_2$CH$_3$ | 0 |
| B-3176 | H | H | H | H | CH$_3$ | CH$_2$CH$_2$C(=O)NHCH$_2$CHF$_2$ | CH$_2$CH$_3$ | 0 |

TABLE 146-continued

| Compound | $R^1$ | $R^2$ | $R^3$ | $R^4$ | $R^5$ | $R^6$ | $R^{16}$ | n |
|---|---|---|---|---|---|---|---|---|
| B-3177 | H | H | H | H | CH$_3$ | CH$_2$CH$_2$C(=O)NHCH$_2$CF$_3$ | CH$_2$CH$_3$ | 0 |
| B-3178 | H | H | H | H | CH$_3$ | CH$_2$C(=O)N(CH$_3$)$_2$ | CH$_2$CH$_3$ | 0 |
| B-3179 | H | H | H | H | CH$_3$ | CH$_2$C(=O)N(CH$_2$CH$_3$)$_2$ | CH$_2$CH$_3$ | 0 |
| B-3180 | H | H | H | H | CH$_3$ | CH$_2$CH$_2$C(=O)N(CH$_3$)$_2$ | CH$_2$CH$_3$ | 0 |
| B-3181 | H | H | H | H | CH$_3$ | CH$_2$CH$_2$C(=O)N(CH$_2$CH$_3$)$_2$ | CH$_2$CH$_3$ | 0 |
| B-3182 | H | H | H | H | CH$_3$ | CH$_2$CH$_2$OH | CH$_2$CH$_3$ | 0 |
| B-3183 | H | H | H | H | CH$_3$ | CH$_2$CH(OH)CH$_3$ | CH$_2$CH$_3$ | 0 |
| B-3184 | H | H | H | H | CH$_3$ | CH$_2$CH$_2$CH$_2$OH | CH$_2$CH$_3$ | 0 |
| B-3185 | H | H | H | H | CH$_3$ | CH$_2$CH(OH)CH$_2$CH$_3$ | CH$_2$CH$_3$ | 0 |
| B-3186 | H | H | H | H | CH$_3$ | CH$_2$CH(OH)C(CH$_3$)$_3$ | CH$_2$CH$_3$ | 0 |
| B-3187 | H | H | H | H | CH$_3$ | CH$_2$CH$_2$CH(OH)CH$_3$ | CH$_2$CH$_3$ | 0 |
| B-3188 | H | H | H | H | CH$_3$ | CH$_2$CH$_2$CH(OH)C(CH$_3$)$_3$ | CH$_2$CH$_3$ | 0 |
| B-3189 | H | H | H | H | CH$_3$ | CH$_2$C(=NOH)CH$_3$ | CH$_2$CH$_3$ | 0 |
| B-3190 | H | H | H | H | CH$_3$ | CH$_2$C(=NOH)CH$_2$CH$_3$ | CH$_2$CH$_3$ | 0 |
| B-3191 | H | H | H | H | CH$_3$ | CH$_2$C(=NOH)C(CH$_3$)$_3$ | CH$_2$CH$_3$ | 0 |
| B-3192 | H | H | H | H | CH$_3$ | CH$_2$C(=NOCH$_3$)CH$_3$ | CH$_2$CH$_3$ | 0 |
| B-3193 | H | H | H | H | CH$_3$ | CH$_2$C(=NOCH$_3$)CH$_2$CH$_3$ | CH$_2$CH$_3$ | 0 |
| B-3194 | H | H | H | H | CH$_3$ | CH$_2$C(=NOCH$_2$CH$_3$)CH$_3$ | CH$_2$CH$_3$ | 0 |
| B-3195 | H | H | H | H | CH$_3$ | CH$_2$C(=NOCH$_2$CH$_3$)CH$_2$CH$_3$ | CH$_2$CH$_3$ | 0 |
| B-3196 | H | H | H | H | CH$_3$ | CH$_2$C(=NOCH$_2$CF$_3$)CH$_3$ | CH$_2$CH$_3$ | 0 |
| B-3197 | H | H | H | H | CH$_3$ | CH$_2$C(=NOCH$_2$CF$_3$)CH$_2$CH$_3$ | CH$_2$CH$_3$ | 0 |
| B-3198 | H | H | H | H | CH$_3$ | CH$_2$Ph | CH$_2$CH$_3$ | 0 |
| B-3199 | H | H | H | H | CH$_3$ | CH$_2$(2-F)Ph | CH$_2$CH$_3$ | 0 |
| B-3200 | H | H | H | H | CH$_3$ | CH$_2$(3-F)Ph | CH$_2$CH$_3$ | 0 |
| B-3201 | H | H | H | H | CH$_3$ | CH$_2$(4-F)Ph | CH$_2$CH$_3$ | 0 |
| B-3202 | H | H | H | H | CH$_3$ | CH$_2$(2-Cl)Ph | CH$_2$CH$_3$ | 0 |
| B-3203 | H | H | H | H | CH$_3$ | CH$_2$(3-Cl)Ph | CH$_2$CH$_3$ | 0 |
| B-3204 | H | H | H | H | CH$_3$ | CH$_2$(4-Cl)Ph | CH$_2$CH$_3$ | 0 |
| B-3205 | H | H | H | H | CH$_3$ | CH$_2$(2-CF$_3$)Ph | CH$_2$CH$_3$ | 0 |
| B-3206 | H | H | H | H | CH$_3$ | CH$_2$(3-CF$_3$)Ph | CH$_2$CH$_3$ | 0 |
| B-3207 | H | H | H | H | CH$_3$ | CH$_2$(4-CF$_3$)Ph | CH$_2$CH$_3$ | 0 |
| B-3208 | H | H | H | H | CH$_3$ | CH$_2$(naphthalen-1-yl) | CH$_2$CH$_3$ | 0 |
| B-3209 | H | H | H | H | CH$_3$ | CH$_2$(naphthalen-2-yl) | CH$_2$CH$_3$ | 0 |
| B-3210 | H | H | H | H | CH$_3$ | CH$_2$CH$_2$Ph | CH$_2$CH$_3$ | 0 |
| B-3211 | H | H | H | H | H | H | H | 1 |
| B-3212 | H | H | H | H | H | CH$_3$ | H | 1 |
| B-3213 | H | H | H | H | H | CH$_2$CH$_3$ | H | 1 |
| B-3214 | H | H | H | H | H | CH(CH$_3$)$_2$ | H | 1 |
| B-3215 | H | H | H | H | H | CH$_2$CH$_2$CH$_3$ | H | 1 |
| B-3216 | H | H | H | H | H | CH$_2$CH(CH$_3$)$_2$ | H | 1 |
| B-3217 | H | H | H | H | H | CH$_2$C(CH$_3$)$_3$ | H | 1 |
| B-3218 | H | H | H | H | H | CH(CH$_3$)CH$_2$CH$_3$ | H | 1 |
| B-3219 | H | H | H | H | H | CH$_2$(CH$_2$)$_2$CH$_3$ | H | 1 |
| B-3220 | H | H | H | H | H | CH$_2$(CH$_2$)$_3$CH$_3$ | H | 1 |
| B-3221 | H | H | H | H | H | CF$_3$ | H | 1 |
| B-3222 | H | H | H | H | H | CHF$_2$ | H | 1 |
| B-3223 | H | H | H | H | H | CH$_2$CF$_3$ | H | 1 |
| B-3224 | H | H | H | H | H | CH$_2$CHF$_2$ | H | 1 |
| B-3225 | H | H | H | H | H | CH$_2$CClF$_2$ | H | 1 |
| B-3226 | H | H | H | H | H | CH$_2$CBrF$_2$ | H | 1 |
| B-3227 | H | H | H | H | H | CF$_2$CF$_3$ | H | 1 |
| B-3228 | H | H | H | H | H | CF$_2$CHF$_2$ | H | 1 |

TABLE 147

| Compound | $R^1$ | $R^2$ | $R^3$ | $R^4$ | $R^5$ | $R^6$ | $R^{16}$ | n |
|---|---|---|---|---|---|---|---|---|
| B-3229 | H | H | H | H | H | CH$_2$CH$_2$CF$_3$ | H | 1 |
| B-3230 | H | H | H | H | H | CH$_2$CF$_2$CF$_3$ | H | 1 |
| B-3231 | H | H | H | H | H | CH$_2$CF$_2$CHF$_2$ | H | 1 |
| B-3232 | H | H | H | H | H | CF$_2$CHFCF$_3$ | H | 1 |
| B-3233 | H | H | H | H | H | CF$_2$CF$_2$CF$_3$ | H | 1 |
| B-3234 | H | H | H | H | H | CH$_2$CF$_2$CF$_2$CF$_3$ | H | 1 |
| B-3235 | H | H | H | H | H | CH$_2$CF$_2$CHFCF$_3$ | H | 1 |
| B-3236 | H | H | H | H | H | CH$_2$CH$_2$CH$_2$CF$_3$ | H | 1 |
| B-3237 | H | H | H | H | H | CH$_2$CH$_2$CF$_2$CF$_3$ | H | 1 |
| B-3238 | H | H | H | H | H | CF$_2$CF$_2$CF$_2$CF$_3$ | H | 1 |
| B-3239 | H | H | H | H | H | CH$_2$CH$_2$CH(CF$_3$)$_2$ | H | 1 |
| B-3240 | H | H | H | H | H | CF$_2$CF$_2$CF$_2$CF$_2$CF$_3$ | H | 1 |
| B-3241 | H | H | H | H | H | CH$_2$CF$_2$CF$_2$CF$_2$CF$_3$ | H | 1 |
| B-3242 | H | H | H | H | H | CH$_2$CH$_2$CH$_2$CF$_2$CF$_3$ | H | 1 |
| B-3243 | H | H | H | H | H | CH$_2$CF$_2$CF$_2$CF$_2$CHF$_2$ | H | 1 |
| B-3244 | H | H | H | H | H | CH$_2$CH$_2$CH$_2$CH$_2$CF$_3$ | H | 1 |
| B-3245 | H | H | H | H | H | CH$_2$CH$_2$CH$_2$CH$_2$CH$_2$CF$_3$ | H | 1 |
| B-3246 | H | H | H | H | H | CH$_2$CH$_2$OCH$_2$CF$_3$ | H | 1 |

TABLE 147-continued

| Compound | $R^1$ | $R^2$ | $R^3$ | $R^4$ | $R^5$ | $R^6$ | $R^{16}$ | n |
|---|---|---|---|---|---|---|---|---|
| B-3247 | H | H | H | H | H | $CF_2CHFOCF_3$ | H | 1 |
| B-3248 | H | H | H | H | H | $CF_2CHFOCF_2CF_3$ | H | 1 |
| B-3249 | H | H | H | H | H | $CH_2CH_2CF=CF_2$ | H | 1 |
| B-3250 | H | H | H | H | H | $CH_2CH_2CH=CF_2$ | H | 1 |
| B-3251 | H | H | H | H | H | $CH_2C\equiv CCH_3$ | H | 1 |
| B-3252 | H | H | H | H | H | $CH_2C\equiv Cl$ | H | 1 |
| B-3253 | H | H | H | H | H | $CH_2C\equiv CCF_3$ | H | 1 |
| B-3254 | H | H | H | H | H | $CH_2$(2,2-difluorocyclopropyl) | H | 1 |
| B-3255 | H | H | H | H | H | $CH_2$(2,2-dichlorocyclopropyl) | H | 1 |
| B-3256 | H | H | H | H | H | $CH_2CH_2$(2,2-difluorocyclopropyl) | H | 1 |
| B-3257 | H | H | H | H | H | $CH_2CH_2$(2,2-dichlorocyclopropyl) | H | 1 |
| B-3258 | H | H | H | H | H | $CH_2SCH_3$ | H | 1 |
| B-3259 | H | H | H | H | H | $CH_2SCH_2CH_3$ | H | 1 |
| B-3260 | H | H | H | H | H | $CH_2CH_2SCH_3$ | H | 1 |
| B-3261 | H | H | H | H | H | $CH_2SOCH_3$ | H | 1 |
| B-3262 | H | H | H | H | H | $CH_2CH_2SOCH_3$ | H | 1 |
| B-3263 | H | H | H | H | H | $CH_2SO_2CH_3$ | H | 1 |
| B-3264 | H | H | H | H | H | $CH_2CH_2SO_2CH_3$ | H | 1 |
| B-3265 | H | H | H | H | H | $CH_2SCF_3$ | H | 1 |
| B-3266 | H | H | H | H | H | $CH_2SCHF_2$ | H | 1 |
| B-3267 | H | H | H | H | H | $CH_2SCH_2CF_3$ | H | 1 |
| B-3268 | H | H | H | H | H | $CH_2SCH_2CHF_2$ | H | 1 |
| B-3269 | H | H | H | H | H | $CH_2SCF_2CF_3$ | H | 1 |
| B-3270 | H | H | H | H | H | $CH_2CH_2SCF_3$ | H | 1 |
| B-3271 | H | H | H | H | H | $CH_2CH_2SCH_2CF_3$ | H | 1 |
| B-3272 | H | H | H | H | H | $CH_2CH_2CH_2SCH_2CF_3$ | H | 1 |
| B-3273 | H | H | H | H | H | $CH(CH_3)SCH_2CF_3$ | H | 1 |
| B-3274 | H | H | H | H | H | $CH_2CH(CH_3)SCH_2CF_3$ | H | 1 |
| B-3275 | H | H | H | H | H | $CH(CH_3)CH_2CH_2SCH_2CF_3$ | H | 1 |
| B-3276 | H | H | H | H | H | $CH_2CH(CH_3)CH_2SCH_2CF_3$ | H | 1 |
| B-3277 | H | H | H | H | H | $CH_2CH_2CH(CH_3)SCH_2CF_3$ | H | 1 |
| B-3278 | H | H | H | H | H | $CH_2SOCF_3$ | H | 1 |
| B-3279 | H | H | H | H | H | $CH_2CH_2SOCF_3$ | H | 1 |
| B-3280 | H | H | H | H | H | $CH_2CH_2CH_2SOCF_3$ | H | 1 |
| B-3281 | H | H | H | H | H | $CH_2SO_2CF_3$ | H | 1 |
| B-3282 | H | H | H | H | H | $CH_2CH_2SO_2CF_3$ | H | 1 |
| B-3283 | H | H | H | H | H | $CH_2CH_2CH_2SO_2CF_3$ | H | 1 |
| B-3284 | H | H | H | H | H | $CH_2C(=O)NHCH_2CHF_2$ | H | 1 |
| B-3285 | H | H | H | H | H | $CH_2C(=O)NHCH_2CF_3$ | H | 1 |
| B-3286 | H | H | H | H | H | H | $CH_2CH_3$ | 1 |
| B-3287 | H | H | H | H | H | $CH_3$ | $CH_2CH_3$ | 1 |
| B-3288 | H | H | H | H | H | $CH_2CH_3$ | $CH_2CH_3$ | 1 |
| B-3289 | H | H | H | H | H | $CH(CH_3)_2$ | $CH_2CH_3$ | 1 |

TABLE 148

| Compound | $R^1$ | $R^2$ | $R^3$ | $R^4$ | $R^5$ | $R^6$ | $R^{16}$ | n |
|---|---|---|---|---|---|---|---|---|
| B-3290 | H | H | H | H | H | $CH_2CH_2CH_3$ | $CH_2CH_3$ | 1 |
| B-3291 | H | H | H | H | H | $CH_2CH(CH_3)_2$ | $CH_2CH_3$ | 1 |
| B-3292 | H | H | H | H | H | $CH_2C(CH_3)_3$ | $CH_2CH_3$ | 1 |
| B-3293 | H | H | H | H | H | $CH(CH_3)CH_2CH_3$ | $CH_2CH_3$ | 1 |
| B-3294 | H | H | H | H | H | $CH_2(CH_2)_2CH_3$ | $CH_2CH_3$ | 1 |
| B-3295 | H | H | H | H | H | $CH_2(CH_2)_3CH_3$ | $CH_2CH_3$ | 1 |
| B-3296 | H | H | H | H | H | $CF_3$ | $CH_2CH_3$ | 1 |
| B-3297 | H | H | H | H | H | $CHF_2$ | $CH_2CH_3$ | 1 |
| B-3298 | H | H | H | H | H | $CH_2CF_3$ | $CH_2CH_3$ | 1 |
| B-3299 | H | H | H | H | H | $CH_2CHF_2$ | $CH_2CH_3$ | 1 |
| B-3300 | H | H | H | H | H | $CH_2CClF_2$ | $CH_2CH_3$ | 1 |
| B-3301 | H | H | H | H | H | $CH_2CBrF_2$ | $CH_2CH_3$ | 1 |
| B-3302 | H | H | H | H | H | $CF_2CF_3$ | $CH_2CH_3$ | 1 |
| B-3303 | H | H | H | H | H | $CF_2CHF_2$ | $CH_2CH_3$ | 1 |
| B-3304 | H | H | H | H | H | $CH_2CH_2CF_3$ | $CH_2CH_3$ | 1 |
| B-3305 | H | H | H | H | H | $CH_2CF_2CF_3$ | $CH_2CH_3$ | 1 |
| B-3306 | H | H | H | H | H | $CH_2CF_2CHF_2$ | $CH_2CH_3$ | 1 |
| B-3307 | H | H | H | H | H | $CF_2CHFCF_3$ | $CH_2CH_3$ | 1 |
| B-3308 | H | H | H | H | H | $CF_2CF_2CF_3$ | $CH_2CH_3$ | 1 |
| B-3309 | H | H | H | H | H | $CH_2CF_2CF_2CF_3$ | $CH_2CH_3$ | 1 |
| B-3310 | H | H | H | H | H | $CH_2CF_2CHFCF_3$ | $CH_2CH_3$ | 1 |

TABLE 148-continued

| Compound | $R^1$ | $R^2$ | $R^3$ | $R^4$ | $R^5$ | $R^6$ | $R^{16}$ | n |
|---|---|---|---|---|---|---|---|---|
| B-3311 | H | H | H | H | H | $CH_2CH_2CH_2CF_3$ | $CH_2CH_3$ | 1 |
| B-3312 | H | H | H | H | H | $CH_2CH_2CF_2CF_3$ | $CH_2CH_3$ | 1 |
| B-3313 | H | H | H | H | H | $CF_2CF_2CF_2CF_3$ | $CH_2CH_3$ | 1 |
| B-3314 | H | H | H | H | H | $CH_2CH_2CH(CF_3)_2$ | $CH_2CH_3$ | 1 |
| B-3315 | H | H | H | H | H | $CF_2CF_2CF_2CF_2CF_3$ | $CH_2CH_3$ | 1 |
| B-3316 | H | H | H | H | H | $CH_2CF_2CF_2CF_2CF_3$ | $CH_2CH_3$ | 1 |
| B-3317 | H | H | H | H | H | $CH_2CH_2CH_2CH_2CF_3$ | $CH_2CH_3$ | 1 |
| B-3318 | H | H | H | H | H | $CH_2CF_2CF_2CF_2CHF_2$ | $CH_2CH_3$ | 1 |
| B-3319 | H | H | H | H | H | $CH_2CH_2CH_2CH_2CH_2CF_3$ | $CH_2CH_3$ | 1 |
| B-3320 | H | H | H | H | H | $CH_2CH_2CH_2CH_2CH_2CH_2CF_3$ | $CH_2CH_3$ | 1 |
| B-3321 | H | H | H | H | H | $CH_2CH_2OCH_2CF_3$ | $CH_2CH_3$ | 1 |
| B-3322 | H | H | H | H | H | $CF_2CHFOCF_3$ | $CH_2CH_3$ | 1 |
| B-3323 | H | H | H | H | H | $CF_2CHFOCF_2CF_3$ | $CH_2CH_3$ | 1 |
| B-3324 | H | H | H | H | H | $CH_2CH_2CF=CF_2$ | $CH_2CH_3$ | 1 |
| B-3325 | H | H | H | H | H | $CH_2CH_2CH=CF_2$ | $CH_2CH_3$ | 1 |
| B-3326 | H | H | H | H | H | $CH_2C\equiv CCH_3$ | $CH_2CH_3$ | 1 |
| B-3327 | H | H | H | H | H | $CH_2C\equiv Cl$ | $CH_2CH_3$ | 1 |
| B-3328 | H | H | H | H | H | $CH_2C\equiv CCF_3$ | $CH_2CH_3$ | 1 |
| B-3329 | H | H | H | H | H | $CH_2(2,2\text{-difluorocyclopropyl})$ | $CH_2CH_3$ | 1 |
| B-3330 | H | H | H | H | H | $CH_2(2,2\text{-dichlorocyclopropyl})$ | $CH_2CH_3$ | 1 |
| B-3331 | H | H | H | H | H | $CH_2CH_2(2,2\text{-difluorocyclopropyl})$ | $CH_2CH_3$ | 1 |
| B-3332 | H | H | H | H | H | $CH_2CH_2(2,2\text{-dichlorocyclopropyl})$ | $CH_2CH_3$ | 1 |
| B-3333 | H | H | H | H | H | $CH_2SCH_3$ | $CH_2CH_3$ | 1 |
| B-3334 | H | H | H | H | H | $CH_2SCH_2CH_3$ | $CH_2CH_3$ | 1 |
| B-3335 | H | H | H | H | H | $CH_2CH_2SCH_3$ | $CH_2CH_3$ | 1 |
| B-3336 | H | H | H | H | H | $CH_2SOCH_3$ | $CH_2CH_3$ | 1 |
| B-3337 | H | H | H | H | H | $CH_2CH_2SOCH_3$ | $CH_2CH_3$ | 1 |
| B-3338 | H | H | H | H | H | $CH_2SO_2CH_3$ | $CH_2CH_3$ | 1 |
| B-3339 | H | H | H | H | H | $CH_2CH_2SO_2CH_3$ | $CH_2CH_3$ | 1 |
| B-3340 | H | H | H | H | H | $CH_2SCF_3$ | $CH_2CH_3$ | 1 |
| B-3341 | H | H | H | H | H | $CH_2SCHF_2$ | $CH_2CH_3$ | 1 |
| B-3342 | H | H | H | H | H | $CH_2SCH_2CF_3$ | $CH_2CH_3$ | 1 |
| B-3343 | H | H | H | H | H | $CH_2SCH_2CHF_2$ | $CH_2CH_3$ | 1 |
| B-3344 | H | H | H | H | H | $CH_2SCF_2CF_3$ | $CH_2CH_3$ | 1 |
| B-3345 | H | H | H | H | H | $CH_2CH_2SCF_3$ | $CH_2CH_3$ | 1 |
| B-3346 | H | H | H | H | H | $CH-CH_2SCH_2CF_3$ | $CH_2CH_3$ | 1 |
| B-3347 | H | H | H | H | H | $CH_2CH_2CH_2SCH_2CF_3$ | $CH_2CH_3$ | 1 |
| B-3348 | H | H | H | H | H | $CH(CH_3)SCH_2CF_3$ | $CH_2CH_3$ | 1 |
| B-3349 | H | H | H | H | H | $CH_2CH(CH_3)SCH_2CF_3$ | $CH_2CH_3$ | 1 |
| B-3350 | H | H | H | H | H | $CH(CH_3)CH_2CH_2SCH_2CF_3$ | $CH_2CH_3$ | 1 |

TABLE 149

| Compound | $R^1$ | $R^2$ | $R^3$ | $R^4$ | $R^5$ | $R^6$ | $R^{16}$ | n |
|---|---|---|---|---|---|---|---|---|
| B-3351 | H | H | H | H | H | $CH_2CH(CH_3)CH_2SCH_2CF_3$ | $CH_2CH_3$ | 1 |
| B-3352 | H | H | H | H | H | $CH_2CH_2CH(CH_3)SCH_2CF_3$ | $CH_2CH_3$ | 1 |
| B-3353 | H | H | H | H | H | $CH_2SOCF_3$ | $CH_2CH_3$ | 1 |
| B-3354 | H | H | H | H | H | $CH_2CH_2SOCF_3$ | $CH_2CH_3$ | 1 |
| B-3355 | H | H | H | H | H | $CH_2CH_2CH_2SOCF_3$ | $CH_2CH_3$ | 1 |
| B-3356 | H | H | H | H | H | $CH_2SO_2CF_3$ | $CH_2CH_3$ | 1 |
| B-3357 | H | H | H | H | H | $CH_2CH_2SO_2CF_3$ | $CH_2CH_3$ | 1 |
| B-3358 | H | H | H | H | H | $CH_2CH_2CH_2SO_2CF_3$ | $CH_2CH_3$ | 1 |
| B-3359 | H | H | H | H | H | $CH_2C(=O)NHCH_2CHF_2$ | $CH_2CH_3$ | 1 |
| B-3360 | H | H | H | H | H | $CH_2C(=O)NHCH_2CF_3$ | $CH_2CH_3$ | 1 |
| B-3361 | H | H | H | H | H | $CH_2CH_2CF_2CF_2CF_2CF_3$ | $CH_2CH_3$ | 0 |

On the other hand, the present compound represented by general formula [I] or [II] can be produced in accordance with, but not limited to, the production methods shown below. Hereinafter, for example, "compound represented by general formula [I]" is synonymous to "compound represented by formula [I]" and "compound [I]".

<Production Method 1>

A compound represented by general formula [V] among the present compounds can be produced, for example, in accordance with the following method.

[Chemical formula 3]

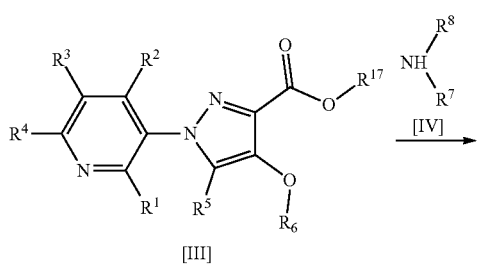

-continued

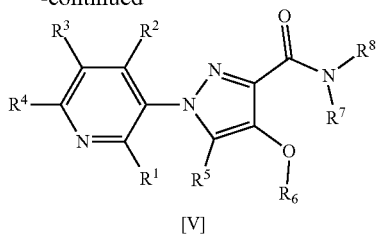

[V]

(wherein, $R^{17}$ represents a $C_1$-$C_6$ alkyl group, and $R^1$, $R^2$, $R^3$, $R^4$, $R^5$, $R^6$, $R^7$, and $R^8$ are as defined above.)

That is, the compound represented by general formula [V] can be produced by reacting the compound represented by general formula [III] and the compound represented by general formula [IV] in an appropriate solvent in the presence or absence of an appropriate base.

The use amount of compound [IV] used in the present reaction may be appropriately selected from the range of typically 1 to 500 mol, and is preferably 1.0 to 300 mol, relative to 1 mol of compound [III].

Examples of the solvent that can be used in the present reaction include ethers such as diethylether, tetrahydrofuran, methyltert-butylether, or 1,4-dioxane; aromatic hydrocarbons such as benzene, toluene, xylene, or chlorobenzene; halogenated hydrocarbons such as dichloromethane, chloroform, or 1,2-dichloroethane; aprotic polar solvents such as N,N-dimethylformamide, N,N-dimethylacetamide, N-methyl-2-pyrrolidone, dimethyl sulfoxide, or sulfolane; alcohols such as methanol, ethanol, or 2-propanol; nitriles such as acetonitrile or propionitrile; esters such as ethyl acetate or ethyl propionate; aliphatic hydrocarbons such as pentane, hexane, cyclohexane, or heptane; pyridines such as pyridine or picoline; water, or mixed solvents thereof. The use amount of the solvent is 0.1 to 500 liters, preferably 0.2 to 50 liters relative to 1 mol of compound [III].

Examples of the base that can be used in the present reaction include inorganic bases including: hydroxides of alkali metal such as sodium hydroxide or potassium hydroxide; hydroxides of alkali earth metal such as calcium hydroxide or magnesium hydroxide; carbonates of alkali metal such as sodium carbonate or potassium carbonate; bicarbonates of alkali metal such as sodium hydrogen carbonate or potassium hydrogen carbonate; or organic bases including: metal hydrides such as sodium hydride or potassium hydride; metal salts of alcohol such as sodium methoxide, sodium ethoxide, or potassium tert-butoxide; or triethylamine, N,N-dimethylaniline, pyridine, 4-N,N-dimethylaminopyridine, 1,8-diazacyclo[5.4.0]-7-undecene, and so on. The use amount of the base may be appropriately selected from the range of 0 to 5 mol, and is preferably 0 to 1.2 mol, relative to 1 mol of compound [II].

The reaction temperature of the present reaction may be selected from any range of temperature typically from −30° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, compound [V] can be isolated by conducting an operation of pouring the reaction mixture into water, and extracting with an organic solvent followed concentration or the like. The isolated compound [V] can be further purified by column chromatography, recrystallization, or the like as necessary.

<Production Method 2>

A compound represented by general formula [VI] among the present compounds can be produced, for example, in accordance with the following method.

[Chemical formula 4]

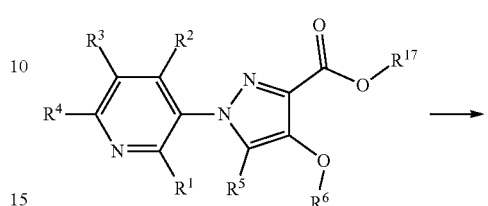

[III]

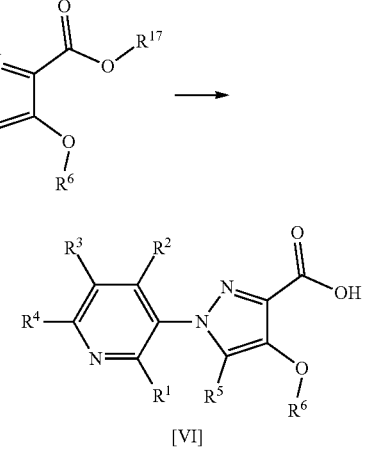

[VI]

(wherein, $R^1$, $R^2$, $R^3$, $R^4$, $R^5$, $R^6$, and $R^{17}$ are as defined above.)

That is, the compound represented by general formula [VI] can be produced by hydrolysis of compound [III] in an appropriate solvent in the presence of an appropriate base or appropriate acid.

Examples of the base that can be used in the present reaction include inorganic bases including hydroxides of alkali metal such as sodium hydroxide, potassium hydroxide, lithium hydroxide, or barium hydroxide; carbonates of alkali metal such as sodium carbonate or potassium carbonate; bicarbonates of alkali metal such as sodium hydrogen carbonate or potassium hydrogen carbonate. The use amount of the base may be appropriately selected from the range of 0.1 to 50 mol, and is preferably 0.5 to 20 mol, relative to 1 mol of compound [III].

Examples of the acid that can be used in the present reaction include inorganic acids such as hydrochloric acid, hydrobromic acid, or sulfuric acid; or carboxylic acids such as acetic acid or trifluoroacetic acid. The use amount of the acid may be appropriately selected from the range of 1 to 1000 mol, and is preferably 1 to 100 mol, relative to 1 mol of compound [III].

Examples of the solvent that can be used in the present reaction include ethers such as diethyl ether, tetrahydrofuran, methyl tert-butyl ether, or 1,4-dioxane; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; alcohols such as methanol, ethanol, or 2-propanol; nitriles such as acetonitrile or propionitrile; ketones such as acetone or methylethylketone; water, or mixed solvents thereof. The use amount of the solvent is 0.1 to 500 liters, preferably 0.3 to 30 liters relative to 1 mol of compound [III].

The reaction temperature of the present reaction may be selected from any range of temperature typically from −30° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, compound [VI] can be isolated by conducting an operation of pouring the reaction mixture into water and neutralizing the reaction mixture, and then collecting the precipitated solid by filtration or extracting with an organic solvent followed by concentration or the like operation. The isolated compound [VI] can be further purified by column chromatography, recrystallization, or the like as necessary.

<Production Method 3>

A compound represented by general formula [V] among the present compounds can also be produced, for example, in accordance with the following method.

[Chemical formula 5]

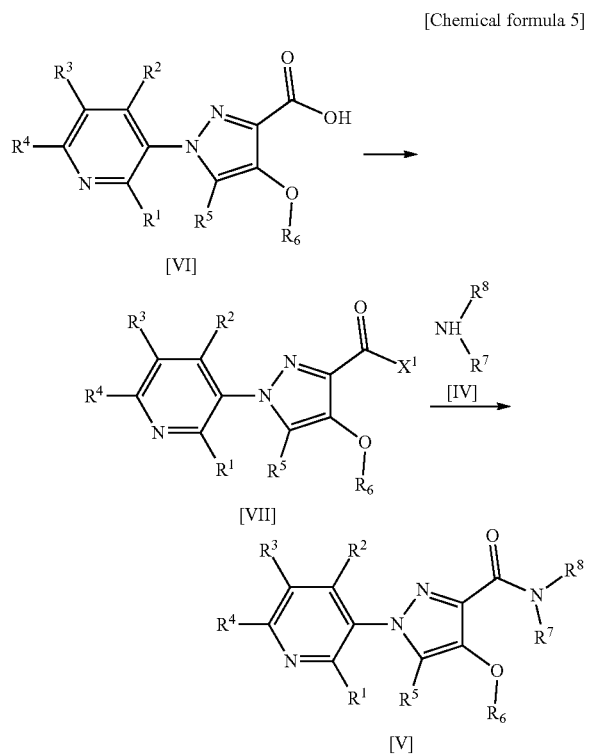

[V]

(wherein, $X^1$ represents a halogen atom, and $R^1$, $R^2$, $R^3$, $R^4$, $R^5$, $R^6$, $R^7$, and $R^8$ are as defined above.)

That is, the compound represented by general formula [V] can be produced by (step 1) making compound [VI] into compound [VII] by using an acid halogenating agent in an appropriate solvent in the presence or absence of an appropriate catalyst, and then (step 2) reacting with compound [IV] in an appropriate solvent in the presence or absence of an appropriate base.

(Step 1)

Examples of the acid halogenating agent that can be used in the present reaction include thionyl chloride, oxalyl chloride, or phosphoryl chloride. The use amount of the acid halogenating agent may be appropriately selected from the range of 0.1 to 30 mol, and is preferably 0.5 to 6 mol, relative to 1 mol of compound [VI].

Examples of the acid catalyst that can be used in the present reaction include N,N-dimethylformamide. The use amount of the catalyst may be appropriately selected from the range of 0.01 to 1 mol, and is preferably 0.01 to 0.1 mol, relative to 1 mol of compound [VI].

Examples of the solvent that can be used in the present reaction include ethers such as diethylether, tetrahydrofuran, or 1,4-dioxane; aromatic hydrocarbons such as benzene, toluene, xylene, or chlorobenzene; halogenated hydrocarbons such as dichloromethane, chloroform, or 1,2-dichloroethane; nitriles such as acetonitrile or propionitrile; esters such as ethyl acetate, butyl acetate, or ethyl propionate; aliphatic hydrocarbons such as pentane, hexane, cyclohexane, or heptane; or mixed solvents thereof. The use amount of the solvent is 0.1 to 100 liters, preferably 0.3 to 10 liters relative to 1 mol of compound [VI].

The reaction temperature of the present reaction may be selected from any range of temperature typically from −30° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, compound [VII] can be isolated by conducting concentration or the like operation.

(Step 2)

The use amount of compound [IV] used in the present reaction may be appropriately selected from the range of typically 1 to 500 mol, and is preferably 1.0 to 300 mol, relative to 1 mol of compound [VI].

The base, solvent, reaction temperature, and reaction time that can be used in the present reaction are as described in the Production method 1

After end of the reaction, compound [V] can be isolated by conducting an operation of pouring the reaction mixture into water, and then collecting the precipitated solid by filtration or extracting with an organic solvent followed by concentration or the like. The isolated compound [V] can be further purified by column chromatography, recrystallization, or the like as necessary.

<Production Method 4>

A compound represented by general formula [V] among the present compounds can also be produced, for example, in accordance with the following method.

[Chemical formula 6]

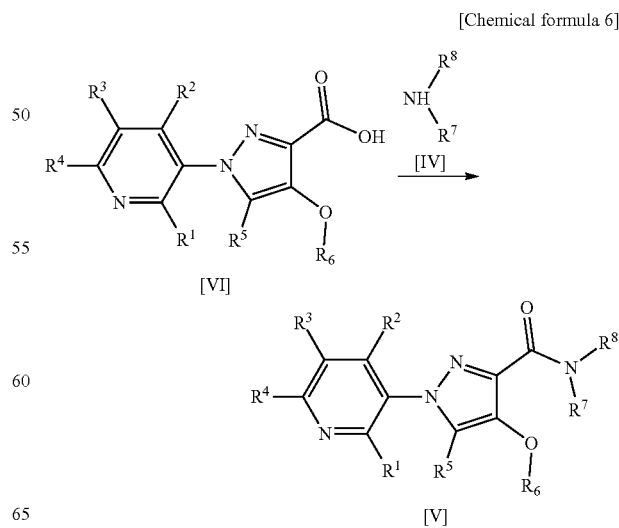

(wherein, $R^1$, $R^2$, $R^3$, $R^4$, $R^5$, $R^6$, $R^7$, and $R^8$ are as defined above.)

That is, the compound represented by general formula [V] can be produced by reacting compound [VI] and compound [IV] in an appropriate solvent in the presence or absence of an appropriate condensing agent and an appropriate base.

The use amount of compound [IV] used in the present reaction may be appropriately selected from the range of 1 to 3 mol, and is preferably 1.0 to 1.2 mol, relative to 1 mol of compound [VI].

Examples of the condensing agent that can be used in the present reaction include 1-ethyl-3-(3-dimethylaminopropyl) carbodiimide hydrochloride, 1-ethyl-3-(3-dimethylaminopropyl)carbodiimide, N,N'-dicyclohexylcarbodiimide, N,N'-diisopropylcarbodiimide, N,N'-carbonyldiimidazole, 4-(4,6-dimethoxy-1,3,5-triazine-2-yl)-4-methylmorpholinium chloride, 1H-benzotriazole-1-yloxytris(dimethylamino) phosphonium hexafluorophosphate, {{[(1-cyano-2-ethoxy-2-oxoethylidene)amino]oxy}-4-morpholinomethylene} dimethylammonium hexafluorophosphate, or O-(7-azabenzotriazole-1-yl)-N,N,N',N'-tetramethyluronium hexafluorofluorophosphate. The use amount of the condensing agent may be appropriately selected from the range of 1 to 3 mol, and is preferably 1.0 to 1.2 mol, relative to 1 mol of compound [VI].

When a base is used in the present reaction, examples of the base that can be used include organic bases such as triethylamine, 4-methylmorpholine, diisopropylethylamine, 1,8-diazabicyclo[5.4.0]-7-undecene, pyridine, 4-N,N-dimethylaminopyridine, or 2,6-lutidine. The use amount of the base may be appropriately selected from the range of 0 to 5 mol, and is preferably 0.1 to 2.2 mol, relative to 1 mol of compound [VI].

Examples of the solvent that can be used in the present reaction include halogenated hydrocarbons such as dichloromethane, chloroform, or 1,2-dichloroethane; hydrocarbons such as hexane or heptane; esters such as ethyl acetate; nitriles such as acetonitrile or propionitrile; aprotic polar solvents such as N,N-dimethylformamide, N,N-dimethylacetamide, N-methyl-2-pyrrolidone, dimethyl sulfoxide, or sulfolane; ethers such as diethylether, cyclopentylmethylether, tetrahydrofuran, 2-methyltetrahydrofuran, or 1,4-dioxane; or mixed solvents thereof. The use amount of the solvent is 0.1 to 100 liters, preferably 0.3 to 50 liters relative to 1 mol of compound [VI].

The present reaction can be conducted in the presence of a catalyst as necessary, and examples of the catalyst include 4-(N,N-dimethyl)aminopyridine, or 4-hydroxybenzotriazole. The use amount of the catalyst may be appropriately selected from the range of 0.001 to 1 mol, and is preferably 0.01 to 0.1 mol, relative to 1 mol of compound [VI].

The reaction temperature of the present reaction may be selected from any range of temperature from −20° C. to a reflux temperature in a reaction system, and is preferably in the range of 0° C. to 80° C.

The reaction time of the present reaction is typically 1 minute to 48 hours although it differs depending on the reaction temperature, the reaction substrate, the reaction amount, and the like.

After end of the reaction, compound [V] can be isolated by conducting an operation of pouring the reaction mixture into water, and extracting with an organic solvent followed concentration or the like. The isolated compound [V] can be further purified by column chromatography, recrystallization, or the like as necessary.

<Production Method 5>

A compound represented by general formula [IX] among the present compounds can be produced, for example, by using a compound represented by general formula [VIII] in accordance with the following method.

[Chemical formula 7]

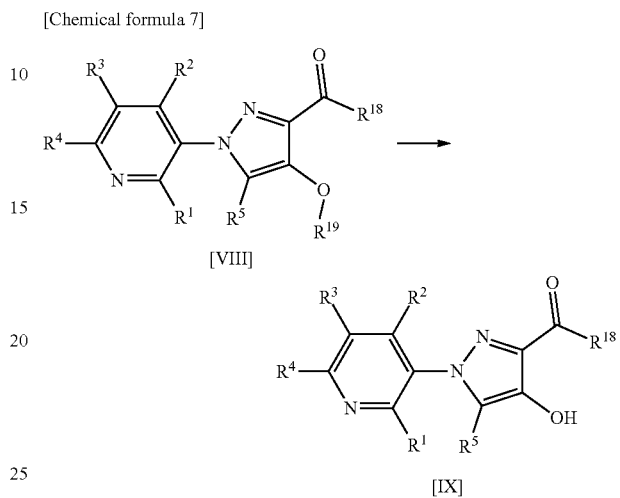

(wherein, $R^{18}$ represents a group $OR^{17}$ or a group $NR^7R^8$, $R^{19}$ represents a benzyl group that is unsubstituted or substituted with $R^9$, and $R^1$, $R^2$, $R^3$, $R^4$, $R^5$, and $R^9$ are as defined above.)

That is, the compound represented by general formula [IX] can be produced by hydrogenolysis reaction of a compound [VIII] in a hydrogen gas atmosphere, in an appropriate solvent in the presence of an appropriate catalyst.

Examples of the catalyst that is used in the present reaction include platinum, Raney nickel, platinum black, palladium-carbon, palladium black, palladium hydroxide-carbon, and platinum oxide. The use amount of the catalyst may be appropriately selected from the range of 0.01 to 1 mol, and is preferably 0.01 to 0.1 mol, relative to 1 mol of compound [VIII].

Examples of the solvent that can be used in the present reaction include ethers such as diethylether, tetrahydrofuran, or 1,4-dioxane; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; aliphatic hydrocarbons such as pentane, hexane, cyclohexane, or heptane; ketones such as acetone, or 2-butanone; esters such as ethyl acetate, butyl acetate, or ethyl propionate; water, acetic acid, or mixed solvents thereof. The use amount of the solvent is 0.1 to 100 liters, preferably 0.3 to 30 liters relative to 1 mol of compound [VIII].

The reaction temperature of the present reaction may be selected from any range of temperature typically from 0° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, compound [IX] can be isolated by conducting an operation of pouring the reaction mixture into water, and extracting with an organic solvent followed concentration or the like. Alternatively, compound [IX] can also be isolated by concentrating the solvent after filtering insoluble matters from the reaction mixture. The isolated compound [IX] can be further purified by column chromatography, recrystallization, or the like as necessary.

<Production Method 6>

A compound represented by general formula [XII] among the present compounds can be produced, for example, by using a compound represented by general formula [IX] in accordance with the following method.

[Chemical formula 8]

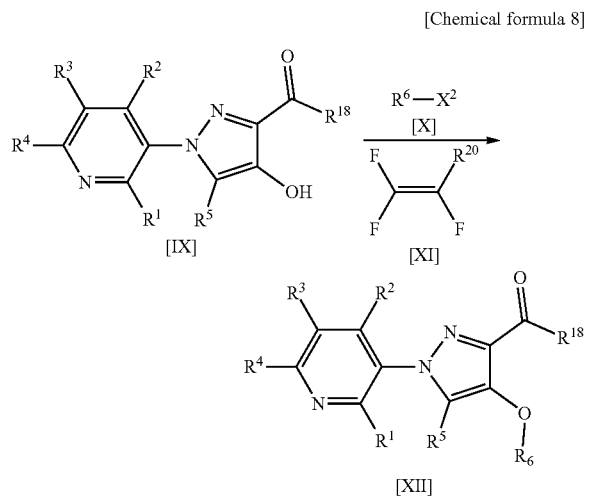

(wherein, $R^{20}$ represents a fluorine atom, $C_1$-$C_6$ alkoxy group, $C_1$-$C_6$ haloalkyl group, or $C_1$-$C_6$ haloalkoxy group, $R^1$, $R^2$, $R^3$, $R^4$, $R^5$, $R^6$, and $R^{18}$ are as defined above, $X^2$ represents a halogen atom, $C_1$-$C_6$ alkylsulfonyloxy group, trifluoromethanesulfonyloxy group, nonafluorobutylsulfonyloxy group, phenylsulfonyloxy group, 4-toluenesulfonyloxy group, $C_1$-$C_6$ alkylsulfonyl group, phenylsulfonyl group, or 4-toluenesulfonyl group.)

That is, the compound represented by general formula [XII] can be produced by reacting compound [IX] and compound [X] or compound [XI] in an appropriate solvent in the presence or absence of an appropriate base.

The use amount of compound [X] or compound [XI] used in the present reaction may be appropriately selected from the range of 1 to 5 mol, and is preferably 1.0 to 1.2 mol, relative to 1 mol of compound [IX].

Examples of the solvent that can be used in the present reaction include ethers such as diethylether, tetrahydrofuran, or 1,4-dioxane; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; nitriles such as acetonitrile, or propionitrile; aliphatic hydrocarbons such as pentane, hexane, cyclohexane, or heptane; pyridines such as pyridine, or picoline; tertiary amines such as triethylamine, or tributylamine; water, or mixed solvents thereof. The use amount of the solvent is 0.1 to 300 liters, preferably 0.3 to 50 liters relative to 1 mol of compound [IX].

Examples of the base that can be used in the present reaction include inorganic bases including: hydroxides of alkali metal such as sodium hydroxide or potassium hydroxide; hydroxides of alkali earth metal such as calcium hydroxide or magnesium hydroxide; carbonates of alkali metal such as sodium carbonate or potassium carbonate; bicarbonates of alkali metal such as sodium hydrogen carbonate or potassium hydrogen carbonate; or organic bases including: metal hydrides such as sodium hydride or potassium hydride; metal salts of alcohol such as sodium methoxide, sodium ethoxide, or potassium tert-butoxide; or triethylamine, N,N-dimethylaniline, pyridine, 4-N,N-dimethylaminopyridine, 1,8-diazacyclo[5.4.0]-7-undecene, and so on. The use amount of the base may be appropriately selected from the range of 1 to 5 mol, and is preferably 1.0 to 1.2 mol, relative to 1 mol of compound [IX]. The organic bases such as triethylamine or pyridine can also be used as the solvent.

The reaction temperature of the present reaction may be selected from any range of temperature typically from −70° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, compound [XII] can be isolated by conducting an operation of pouring the reaction mixture into water, and extracting with an organic solvent followed concentration or the like. The isolated compound [XII] can be further purified by column chromatography, recrystallization, or the like as necessary.

<Production Method 7>

A compound represented by general formula [XII] among the present compounds can be produced, for example, by using a compound represented by general formula [IX] in accordance with the following method.

[Chemical formula 9]

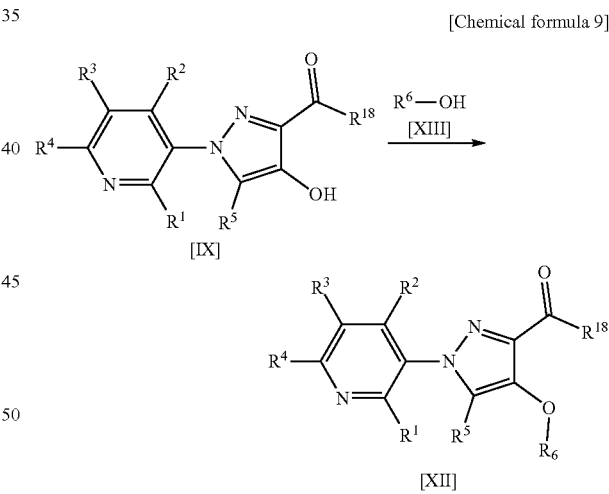

(wherein, $R^1$, $R^2$, $R^3$, $R^4$, $R^5$, $R^6$, and $R^{18}$ are as defined above.)

That is, the compound represented by general formula [XII] can be produced by reacting compound [IX] and compound [XIII] in an appropriate solvent in the presence of trisubstituted phosphine and an azodicarboxylic acid derivative or in the presence of a phosphorane reagent.

The use amount of compound [XIII] used in the present reaction may be appropriately selected from the range of 1.0 to 5.0 mol, and is preferably 1.0 to 2.0 mol, relative to 1 mol of compound [IX].

Examples of the solvent that can be used in the present reaction include ethers such as diethylether, tetrahydrofuran, or 1,4-dioxane; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; nitriles such as acetonitrile, or propionitrile; halogenated hydrocarbons such as dichloromethane, chloroform, or 1,2-dichloroethane; aliphatic hydrocarbons such as pentane, hexane, cyclohexane, or heptane; ketones such as acetone, methylethylketone, or cyclohexane; water, or mixed solvents thereof. The use amount of the solvent is 0.1 to 300 liters, preferably 0.3 to 50 liters relative to 1 mol of compound [IX].

Examples of the trisubstituted phosphine that can be used in the present reaction include triphenylphosphine, tributylphosphine, or trimethylphosphine. The use amount of the trisubstituted phosphine may be appropriately selected from the range of 1.0 to 5.0 mol, and is preferably 1.0 to 3.0 mol, relative to 1 mol of compound [IX].

Examples of the azodicarboxylic acid derivative that can be used in the present reaction include diethyl azodicarboxylate, diisopropyl azodicarboxylate, dimethoxyethyl azodicarboxylate, or N,N,N',N',-tetramethyl azodicarboxylic amide. The use amount of the azodicarboxylic acid derivative may be appropriately selected from the range of 1.0 to 5.0 mol, and is preferably 1.0 to 2.0 mol, relative to 1 mol of compound [IX].

Examples of the phosphorane reagent that can be used in the present reaction include cyanomethylenetrimethylphosphorane, or cyanomethylenetributylphosphorane. The use amount of the phosphorane may be appropriately selected from the range of 1.0 to 5.0 mol, and is preferably 1.0 to 2.0 mol, relative to 1 mol of compound [IX]. The reaction temperature of the present reaction may be selected from any range of temperature typically from −30° C. to a reflux temperature in a reaction system, and is preferably in the range of 0° C. to 150° C.

The reaction time of the present reaction is typically 10 minutes to 24 hours although it differs depending on the reaction temperature, reaction substrate, reaction amount and so on.

After end of the reaction, compound [XII] can be isolated by conducting an operation of pouring the reaction mixture into water, and extracting with an organic solvent followed concentration or the like. Compound [XII] can also be isolated by concentrating the solvent from the reaction mixture. The isolated compound [XII] can be further purified by column chromatography, recrystallization, or the like as necessary.

<Production Method 8>

A compound represented by general formula [V] among the present compounds can be produced, for example, by using a compound represented by general formula [XIV] in accordance with the following method.

[Chemical formula 10]

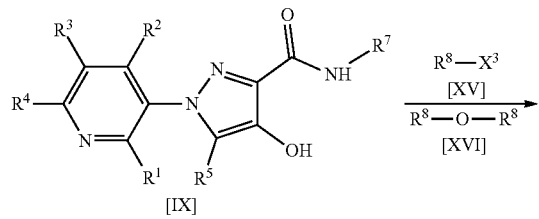

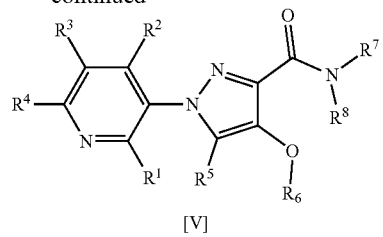

-continued

[V]

(wherein, $X^3$ represents a halogen atom, $C_1$-$C_6$ alkylsulfonyloxy group, trifluoromethanesulfonyloxy group, nonafluorobutylsulfonyloxy group, phenylsulfonyloxy group, 4-toluenesulfonyloxy group, $C_1$-$C_6$ alkylsulfonyl group, phenylsulfonyl group, or 4-toluenesulfonyl group, $R^1$, $R^2$, $R^3$, $R^4$, $R^5$, $R^6$, $R^7$, and $R^8$ are as defined above.) That is, the compound represented by general formula [V] can be produced by reacting compound [XIV] and compound [XV] or compound [XVI] in an appropriate solvent in the presence or absence of an appropriate base.

The use amount of compound [XV] or compound [XVI] used in the present reaction may be appropriately selected from the range of 1 to 10 mol, and is preferably 1.0 to 5.0 mol, relative to 1 mol of compound [XIV].

Examples of the solvent that can be used in the present reaction include ethers such as diethylether, tetrahydrofuran, or 1,4-dioxane; aromatic hydrocarbons such as benzene, toluene, xylene, or chlorobenzene; aprotic polar solvents such as N,N-dimethylformamide, N,N-dimethylacetamide, N-methyl-2-pyrrolidone, dimethyl sulfoxide, or sulfolane; alcohols such as methanol, ethanol, 2-propanol, or methyl cellosolve; nitriles such as acetonitrile, or propionitrile; aliphatic hydrocarbons such as pentane, hexane, cyclohexane, or heptane; pyridines such as pyridine, or picoline; water, or mixed solvents thereof. The use amount of the solvent is 0.1 to 300 liters, preferably 0.3 to 50 liters relative to 1 mol of compound [XIV].

Examples of the base that can be used in the present reaction include inorganic bases including: hydroxides of alkali metal such as sodium hydroxide or potassium hydroxide; hydroxides of alkali earth metal such as calcium hydroxide or magnesium hydroxide; carbonates of alkali metal such as sodium carbonate or potassium carbonate; bicarbonates of alkali metal such as sodium hydrogen carbonate or potassium hydrogen carbonate; or organic bases including: metal hydrides such as sodium hydride or potassium hydride; metal salts of alcohol such as sodium methoxide, sodium ethoxide, or potassium tert-butoxide; or triethylamine, N,N-dimethylaniline, pyridine, 4-N,N-dimethylaminopyridine, 1,8-diazacyclo[5.4.0]-7-undecene, and so on. The use amount of the base may be appropriately selected from the range of 1 to 10 mol, and is preferably 1 to 6 mol, relative to 1 mol of compound [XIV]. The organic bases such as triethylamine or pyridine can also be used as the solvent.

The present reaction can be conducted in the presence of a catalyst as necessary, and examples of the catalyst include pyridine, 4-(N,N-dimethyl)aminopyridine, or 4-pyrrolidinopyridine. The use amount of the catalyst may be appropriately selected from the range of 0.001 to 1 mol, and is preferably 0.01 to 0.1 mol, relative to 1 mol of compound [XIV].

The reaction temperature of the present reaction may be selected from any range of temperature typically from −70°

C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, compound [V] can be isolated by conducting an operation of pouring the reaction mixture into water, and extracting with an organic solvent followed concentration or the like. The isolated compound [V] can be further purified by column chromatography, recrystallization, or the like as necessary.

<Production Method 9>

A compound represented by general formula [XVII] among the present compounds can be produced, for example, by using a compound represented by general formula [V] in accordance with the following method.

[Chemical formula 11]

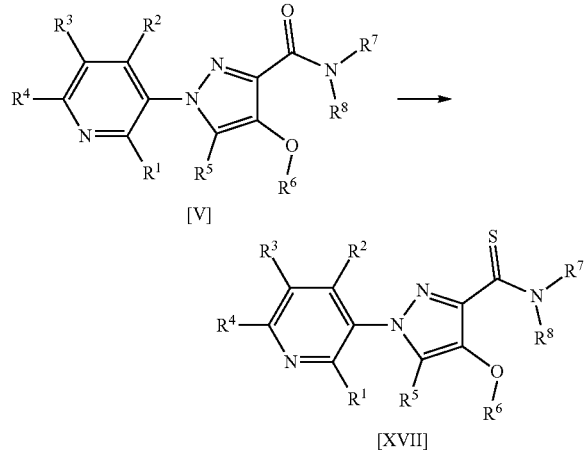

[V]

[XVII]

(wherein, $R^1$, $R^2$, $R^3$, $R^4$, $R^5$, $R^6$, $R^7$, and $R^8$ are as defined above.) That is, the compound represented by general formula [XVII] can be produced by reacting compound [V] and an appropriate sulfidizing agent.

Examples of the solvent that can be used in the present reaction include ethers such as diethylether, tetrahydrofuran, or 1,4-dioxane; aromatic hydrocarbons such as benzene, toluene, xylene, or chlorobenzene; aprotic polar solvents such as dimethylsulfoxide, or sulfolane, halogenated hydrocarbons such as dichloromethane, chloroform, or 1,2-dichloroethane; aliphatic hydrocarbons such as pentane, hexane, cyclohexane, or heptane; water or mixed solvents thereof. The use amount of the solvent is 0.1 to 300 liters, preferably 0.3 to 50 liters relative to 1 mol of compound [V].

Examples of the sulfidizing agent that can be used in the present reaction include phosphorus pentasulfide, and a Lawesson's reagent. The use amount of the sulfidizing agent may be appropriately selected from the range of 0.5 to 30 mol, and is preferably 0.5 to 5 mol, relative to 1 mol of compound [V].

The reaction temperature of the present reaction may be selected from any range of temperature typically from −70° C. to a reflux temperature in a reaction system, and is preferably in the range of 0° C. to 150° C.

The reaction time of the present reaction is typically 10 minutes to 24 hours although it differs depending on the reaction temperature, the reaction substrate, the reaction amount, and the like.

After end of the reaction, compound [XVII] can be isolated by conducting an operation of pouring the reaction mixture into water, and extracting with an organic solvent followed concentration or the like. Alternatively, compound [XVII] can also be isolated by concentrating the solvent of the reaction mixture. The isolated compound [XVII] can be further purified by column chromatography, recrystallization, or the like as necessary.

<Production Method 10>

A compound represented by general formula [XIX] among the present compounds can be produced, for example, by using a compound represented by general formula [XVIII] in accordance with the following method.

[Chemical formula 12]

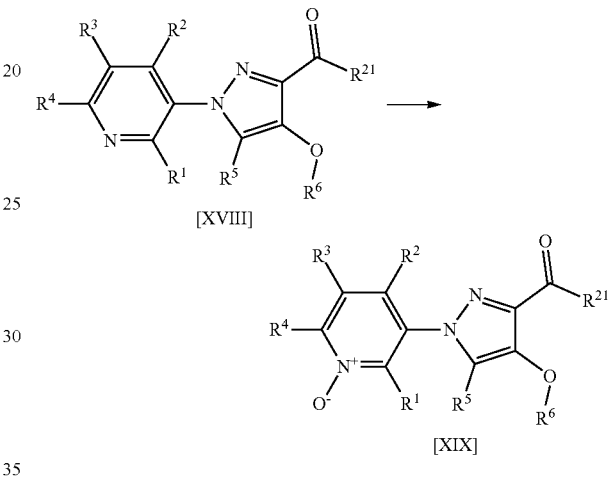

[XVIII]

[XIX]

($R^{21}$ represents a hydroxy group, group $OR^{17}$, or group $NR^7R^8$, and wherein $R^1$, $R^2$, $R^3$, $R^4$, $R^5$, and $R^6$ are as defined above.) That is, the compound represented by general formula [XIX] can be produced by reacting compound [XVIII] and an appropriate oxidizing agent in an appropriate solvent in the presence or absence of a catalyst.

Examples of the solvent that can be used in the present reaction include halogenated hydrocarbons such as dichloromethane, chloroform, 1,2-dichloroethane, carbon tetrachloride, chlorobenzene, or dichlorobenzene; ethers such as 1,4-dioxane, tetrahydrofuran, 1,2-dimethoxyethane, or diethylether; amides such as N,N-dimethylacetamide, N,N-dimethylformamide, or N-methyl-2-pyrrolidinone; alcohols such as methanol, ethanol, propanol, isopropanol, butanol, or tert-butanol; ketones such as acetone or 2-butanone; nitriles such as acetonitrile or propionitrile; acetic acid, water, or mixtures thereof. The use amount of the solvent is 0.1 to 500 liters, preferably 0.3 to 200 liters relative to 1 mol of compound [XVIII].

Examples of the oxidizing agent include organic peroxides such as m-chloroperbenzoic acid, performic acid, or peracetic acid; and inorganic peroxides such as hydrogen peroxide, potassium permanganate, OXONE (registered tradename available from E. I. Du Pont de Nemours and Company, product containing potassium peroxymonosulfate), or sodium periodate. The use amount of the oxidizing agent is 0.5 to 3 mol, relative to 1 mol of compound [XVIII].

Examples of the catalyst that can be used in the present reaction include sodium tungstate. The use amount of the catalyst is 0.01 to 0.5 mol, relative to 1 mol of compound [XVIII].

The reaction temperature of the present reaction may be selected from any range of temperature typically from −30° C. to a reflux temperature in a reaction system, and is preferably in the range of −10° C. to 100° C.

The reaction time of the present reaction is typically 10 minutes to 48 hours although it differs depending on the reaction temperature, the reaction substrate, the reaction amount, and the like.

After end of the reaction, compound [XIX] can be isolated by conducting an operation of pouring the reaction mixture into water, and extracting with an organic solvent followed concentration or the like. Alternatively, compound [XIX] can also be isolated by concentrating the solvent of the reaction mixture. The isolated compound [XIX] can be further purified by column chromatography, recrystallization, or the like as necessary.

<Method for Producing Intermediate>

A compound represented by general formula [XXIII] can be produced, for example, by using a compound represented by general formula [XX] in accordance with the following method.

[Chemical formula 13]

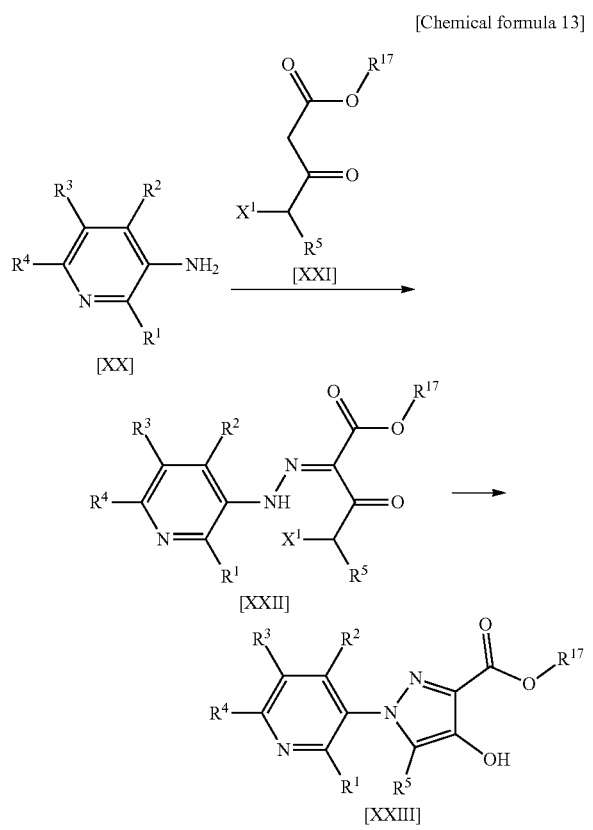

(wherein, $R^1$, $R^2$, $R^3$, $R^4$, $R^5$, $R^{17}$, and $X^1$ are as defined above.)

That is, the compound represented by general formula [XXIII] can be obtained by cyclization reaction after obtaining compound [XXII] by Japp-klingemann reaction between compound [XX] and compound [XXI]. The compound represented by general formula [XXIII] can be produced by a method described in WO 2012/028332 A, WO 2014/114649 A, WO 2016/027790 A, WO 2016/166250 A, or U.S. Pat. No. 5,055,482, or produced in accordance with such a method.

The present harmful organism control agent contains the pyrazole-3-carboxylic acid amide derivative or an agriculturally acceptable salt thereof represented by general formula [I] of the present invention, as an active ingredient. The present harmful organism control agent is representatively an insecticide and a miticide.

The present harmful organism control agent can contain an additive component (carrier) that is typically used in a pesticide formulation, as necessary. Also the pesticide composition can contain an additive component (carrier) that is typically used in a pesticide formulation.

Examples of the additive component include a carrier such as a solid carrier or a liquid carrier, a surfactant, a binder or a tackifier, a thickener, a coloring agent, a spreader, a sticker, an antifreezing agent, an anticaking agent, a disintegrating agent, and a stabilizing agent, and besides the above, an antiseptic, a plant piece, or the like may be added to the additive component as necessary. These additive components may be used singly or in combination of two or more kinds.

Hereinafter, the aforementioned additive components are described.

Examples of the solid carrier include mineral carriers such as pyrophyllite clay, kaolin clay, silica clay, talc, diatomite, zeolite, bentonite, Japanese acid clay, activated clay, attapulgus clay, vermiculite, pearlite, pumice, white carbon (synthetic silicic acid, synthetic silicate, or the like), or titanium dioxide; vegetal carriers such as woody powder, corn haulm, walnut shell, fruit stone, chaff, sawdust, bran, soybean meal, powdered cellulose, starch, dextrin, or saccgarudes; inorganic salt carriers such as calcium carbonate, ammonium sulfate, sodium sulfate, or potassium chloride; and polymeric carriers such as polyethylene, polypropylene, polyvinyl chloride, polyvinyl acetate, ethylene-vinyl acetate copolymer, or urea-aldehyde resin.

Examples of the liquid carrier include monohydric alcohols such as methanol, ethanol, propanol, isopropanol, butanol, or cyclohexanol; polyhydric alcohols such as ethylene glycol, diethylene glycol, propylene glycol, hexylene glycol, polyethylene glycol, polypropylene glycol, or glycerin; polyhydric alcohol derivatives such as polypropylene glycol ether; ketones such as acetone, methylethyl ketone, methylisobutyl ketone, diisobutyl ketone, cyclohexanone, or isophoron; ethers such as ethyl ether, dioxane, Cellosolve, dipropyl ether, or tetrahydrofuran; aliphatic hydrocarbons such as normal paraffin, naphthene, isoparaffin, kerosene, or mineral oil; aromatic hydrocarbons such as toluene, $C_9$-$C_{10}$ alkylbenzene, xylene, solvent naphtha, alkyl naphthalene, or high boiling point aromatic hydrocarbons; halogenated hydrocarbons such as 1,2-dichloroethane, chloroform, or carbon tetrachloride; esters such as ethyl acetate, diisopropyl phthalate, dibutyl phthalate, dioctyl phthalate, or dimethyl adipate; lactones such as γ-butyrolactone; amides such as N,N-dimethylformamide, N,N-diethylformamide, N,N-dimethylacetamide, or N-alkylpyrrolidinone; nitriles such as acetonitrile; sulfur compounds such as dimethyl sulfoxide; vegetable oils such as soybean oil, rapeseed oil, cottonseed oil, coconut oil, or castor oil; and water.

Although not particularly limited, the surfactant preferably gelates or shows swelling property in water, and examples of the surfactant include nonionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkylphenyl ether, polyoxyethylene dialkylphenyl ether, polyoxyethylene alkylphenyl ether formalin condensate, polyoxyethylene polyoxypropylene block polymer, alkylpolyoxyethylene polypropylene block polymer ether, polyoxyethylene alkyl amine, polyoxyethylene fatty acid amide, polyoxyethylene fatty acid bisphenyl ether, polyalkylene benzyl phenyl ether, polyoxyalkylene styryl phenyl ether, acetylene diol, polyoxyalkylene-added acetylene diol, polyoxyethylene ether silicone, ester silicone, fluorine surfactant, polyoxyethylene castor oil, or polyoxyethylene hardened castor oil; anionic surfactants such as alkyl sulfates, polyoxyethylene alkyl ether sulfates, polyoxyethylene alkyl phenyl ether sulfates, polyoxyethylene styryl phenyl ether sulfate, alkyl benzenesulfonates, lignin sulfonate, alkyl sulfosuccinates, naphthalene sulfonate, alkylnaphthalene sulfonates, salts of formalin condensate of naphthalene sulfonate, fatty acid salts, polycarboxylates, N-methyl-fatty acid Sarcosinates, resinates, polyoxyethylene alkyl ether phosphates, or polyoxyethylene alkyl phenylether phosphates; cationic surfactants such as alkyl amine salts such as lauryl amine hydrochloride, stearyl amine hydrochloride, oleyl amine hydrochloride, stearyl amine acetate, stearyl aminopropylamine acetate, alkyl trimethyl ammonium chlorides, or alkyl dimethylbenzarconium chloride; and amphoteric surfactants including a betaine type such as dialkyl diaminoethyl betaine, or alkyl dimethylbenzyl betaine, and an amino acid type such as dialkylaminoethyl glycin, or alkyl dimethylbenzyl glycin.

Examples of the binder or the tackifier include carboxymethylcelullose or a salt thereof, dextrin, soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of 6000 to 20000, polyethylene oxide having an average molecular weight of 100000 to 5000000, and naturally-occurring phospholipid (for example, Cephalin acid, lecithin, or the like).

Examples of the thickener include water-soluble polymers such as xanthan gum, guar gum, carboxymethylcelullose, polyvinylpyrrolidone, carboxyvinyl polymer, acrylic polymer, starch derivatives, or polysaccharides; and inorganic fine powder such as high purity bentonite or white carbon.

Examples of the coloring agent include inorganic pigments such as iron oxide, titanium oxide, or Prussian blue; and organic dyes such as an alizarin dye, an azo dye, or a metal phthalocyanine dye.

Examples of the spreader include a silicone surfactant, cellulose powder, dextrin, processed starch, a polyaminocarboxylic acid chelate compound, a cross-linked polyvinylpyrrolidone, malic acid and styrenes, methacrylic acid copolymer, a half ester of a polymer of polyhydric alcohol and dicarboxylic acid anhydride, and a water-soluble salt of polystyrene sulfonic acid.

Examples of the sticker include various surfactants such as sodium dialkyl sulfosuccinate, polyoxyethylene alkyl ether, polyoxyethylene alkylphenyl ether, or polyoxyethylene fatty acid ester; paraffin, terpene, polyamide resin, polyacrylate, polyoxyethylene, wax, polyvinylalkyl ether, an alkylphenol formalin condensate, and a synthetic resin emulsion.

Examples of the antifreezing agent include polyhydric alcohols such as ethylene glycol, diethylene glycol, propylene glycol, or glycerin.

Examples of the anticaking agent include polysaccharides such as starch, alginic acid, mannose, or galactose; polyvinylpyrrolidone, white carbon, ester gum, and petroleum resin.

Examples of the disintegrating agent include sodium tripolyphosphate, sodium hexametaphosphate, a stearic metal salt, cellulose powder, dextrin, copolymer of methacrylic ester, polyvinylpyrrolidone, polyaminocarboxylic chelate compound, styrene sulfonate-isobutylene-maleic anhydride copolymer, and starch-polyacrylonitrile graft copolymer.

Examples of the stabilizing agent include a desiccant such as zeolite, calcined lime, or magnesium oxide; an antioxidant based on phenol, amine, sulfur, phosphoric acid, or the like; an ultraviolet absorber based on salicylic acid, benzophenone, or the like.

In the present harmful organism control agent, when the additive component is contained, the content thereof is selected typically in a range of 5 to 95%, preferably in the range of 20 to 90% on the mass basis in the case of a carrier such as a solid carrier or a liquid carrier, typically in a range of 0.1% to 30%, preferably in a range of 0.5 to 10% in the case of a surfactant, and typically in a range of 0.1 to 30%, preferably in a range of 0.5 to 10% in the case of other additive.

The present harmful organism control agent is used while it is prepared into any formulation including dusts, dusts and granules, granules, water-dispersible powders, water-soluble powders, water-dispersible granules, tablets, Jumbos, emulsifiable concentrates, oils, solutions, flowable concentrates, emulsions, microemulsions, suspoemulsions, ultra-low volume formulations, microcapsules, smoking agents, aerosols, baiting agents, and pastes.

In actual use of the formulation, the formulation can be used per se or after dilution with a diluent such as water in a predetermined concentration. Application of various formulations containing the present compound, and dilution products thereof can be conducted by a method ordinarily used, such as dispersion (e.g., spraying, misting, atomizing, powder dispersion, granule dispersion, on-water-surface dispersion, or inbox dispersion), in-soil application (e.g., mixing or drenching), on-surface application (e.g., coating, dust coating, or covering), seed treatment (e.g., smearing or dressing treatment), immersion, poison bait, smoking, and the like. It is also possible to mix the above-mentioned active ingredient with a livestock feed in order to prevent the infestation and growth of pests, particularly harmful insects in the excreta of the livestock.

A method for controlling a harmful organism of the present invention can be conducted by using an active ingredient amount of the compound represented by general formula [I] of the present invention or a salt thereof in the above-mentioned application method described above.

The mixing proportion (% by mass) of the active ingredient in the present harmful organism control agent is appropriately selected as needed. For example, the mixing proportion may be appropriately selected typically in a range of 0.01 to 20%, preferably 0.05 to 10% for dusts, dusts and granules, microgranules, or the like; typically in a range of 0.1 to 30%, preferably 0.5 to 20% for granules or the like; typically in a range of 1 to 70%, preferably 5 to 50% for water-dispersible powders, water-dispersible granules, or the like; typically in a range of 1 to 95%, preferably 10 to 80% for water-soluble powders, solutions, or the like; typically in a range of 5 to 90%, preferably 10 to 80% for emulsifiable concentrates or the like; typically in a range of 1 to 50%, preferably 5 to 30% for oils or the like; typically in a range of 5 to 60%, preferably 10 to 50% for flowable concentrates or the like; typically in a range of 5 to 70%, preferably 10 to 60% for emulsions, microemulsions, suspoemulsions, or the like; typically in a range of 1 to 80%, preferably 5 to 50% for tablets, baiting agents, pastes, or the like; typically in a range of 0.1 to 50%, preferably 1 to 30% for smoking agents or the like; and typically in a range of 0.05 to 20%, preferably 0.1 to 10% for aerosols or the like.

The formulation is sprayed after dilution in an appropriate concentration, or applied directly.

When present harmful organism control agent is used after dilution with a diluent, the concentration of the active ingredient is generally 0.1 to 5000 ppm. When the formulation is used per se, the application amount thereof per unit area is 0.1 to 5000 g per 1 ha in terms of the active ingredient compound; however, the application amount is not restricted thereto.

It goes without saying that the present harmful organism control agent is sufficiently effective when the present compound is used alone as an active ingredient. However, the present harmful organism control agent may be mixed or used in combination, as necessary, with other fertilizers and agricultural chemicals such as insecticide, miticide, nematicide, synergist, fungicide, antiviral agent, attractant, herbicide, plant growth-controlling agent, and the like. In this case, a more excellent effect can be exhibited.

Below are shown examples of known insecticides, miticides, nematicides, and synergist compounds, which may be mixed or used in combination. Insecticide active ingredients: acrinathrin, azadirachtin, azamethiphos, acynonapyr, azinphos-ethyl, azinphos-methyl, acequinocyl, acetamiprid, acetoprole, acephate, azocyclotin, abamectin, afidopyropen, afoxolaner, amidoflumet, amitraz, alanycarb, aldicarb, aldoxycarb, allethrin [including d-cis-trans-body, and d-trans-body], isazophos, isamidofos, isocarbophos, isoxathion, isofenphos-methyl, isoprocarb, epsilon-metofluthrin, epsilon-momfluorothrin, ivermectin, imicyafos, imidacloprid, imiprothrin, indoxacarb, esfenvalerate, ethiofencarb, ethion, ethiprole, ethylene dibromide, etoxazole, etofenprox, ethoprophos, etrimfos, emamectin, emamectin benzoate, endosulfan, empenthrin, oxazosulfyl, oxamyl, oxydemeton-methyl, oxydeprofos, omethoate, cadusafos, kappa-tefluthrin, kappa-bifenthrin, karanjin, cartap, carbaryl, carbosulfan, carbofuran, gamma-BHC, xylylcarb, quinalphos, kinoprene, chinomethionat, coumaphos, cryolite, clothianidin, clofentezine, chromafenozide, chlorantraniliprole, chlorethoxyfos, chlordane, chloropicrin, chlorpyrifos, chlorpyrifos-methyl, chlorfenapyr, chlorfenvinphos, chlorfluazuron, chlormephos, chloroprallethrin, cyazypyr, cyanophos, diafenthiuron, diamidafos, cyantraniliprole, dienochlor, cyenopyrafen, dioxabenzofos, diofenolan, cyclaniliprole, cycloxaprid, dicrotophos, dichlofenthion, cycloprothrin, dichlorvos, dicloromezotiaz, dicofol, dicyclanil, disulfoton, dinotefuran, dinobuton, cyhalodiamide, cyhalothrin [including gamma-body, and lambda-body], cyphenothrin [including (1R)-trans-body], cyfluthrin) [including beta-body], diflubenzuron, cyflumetofen, diflovidazin, cyhexatin, cypermethrin [including alpha-body, beta-body, theta-body, and zeta-body], dimethyl-2,2,2-trichloro-1-hydroxyethyl phosphate (DEP), dimethylvinphos, dimethoate, dimefluthrin, silafluofen, cyromazine, spinetoram, spinosad, spirodiclofen, spirotetramat, spiropidion, spiromesifen, sulcofuron-sodium, sulfluramid, sulfoxaflor, sulfotep, diazinon, thiacloprid, thiamethoxam, tioxazafen, thiodicarb, thiocyclam, thiosultap, thionazin, thiofanox, thiometon, tyclopyrazoflor, tetrachlorantraniliprole, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, tralomethrin, transfluthrin, triazamate, triazophos, trichlorfon, triflumuron, triflumezopyrim, trimethacarb, tolfenpyrad, naled, nicotine, nitenpyram, nemadectin, novaluron, noviflumuron, *Verticillium* lecanii, hydroprene, *Bacillus spha-ericus, Bacillus subtillis, Bacillus thuringiensis*, insect toxin produced by *Bacillus thuringiensis, Bacillus thuringiensis* subsp. Aizawai, *Bacillus thuringiensis* subsp. *Israelensis, Bacillus thuringiensis* subsp. Kurstaki, *Bacillus thuringiensis* subsp. Tenebrionis, *Bacillus popilliae*, Pasteuriapenetrans spore, vamidothion, parathion, parathion-methyl, halfenprox, halofenozide, bioallethrin, bioallethrin S-cyclopentenyl, bioresmethrin, bis-(2-chloro-1-methylethyl)ether (DCIP), bistrifluron, hydramethylnon, bifenazate, bifenthrin, pyflubumide, piperonyl butoxide, pymetrozine, pyraclofos, pyrafluprole, pyridaphenthion, pyridaben, pyridalyl, pyrifluquinazon, pyriprole, pyriproxyfen, pirimicarb, pyrimidifen, pyriminostrobin, pirimiphos-methyl, pyrethrine, famphur, fipronil, fenazaquin, fenamiphos, fenitrothion, fenoxycarb, fenothiocarb, phenothrin [including (1R)-trans-body], fenobucarb, fenthion, phenthoate, fenvalerate, fenpyroximate, fenbutatin oxide, fenpropathrin, fonofos, sulfuryl fluoride, butocarboxim, butoxycarboxim, buprofezin, furathiocarb, prallethrin, fluacrypyrim, fluazaindolizine, fluazuron, fluensulfone, fluopyram, sodium fluoroacetate, fluxametamide, flucycloxuron, flucythrinate, flusulfamide, fluthrin, fluvalinate [including tau-body], flupyradifurone, flupyrazofos, flupyrimin, flufiprole, flufenerim, flufenoxystrobin, flufenoxuron, fluhexafon, flubendiamide, flumethrin, fluralaner, flurimfen, prothiofos, protrifenbute, flonicamid, propaphos, propargite, profenofos, broflanilide, profluthrin, propetamphos, propoxur, flometoquin, bromopropylate, hexythiazox, hexaflumuron, Pacilimyces *tenuipes, Paecilomyces* fumosoroceus, heptafluthrin, heptenophos, permethrin, benclothiaz, benzpyrimoxan, bensultap, benzoximate, bendiocarb, benfuracarb, *Beauveria tenella, Beauveria bassiana, Beauveria brongniartii*, phoxim, phosalone, fosthiazate, fosthietan, phosphamidon, phosmet, polynactins, formetanate, phorate, malathion, milbemectin, mecarbam, mesulfenfos, methomyl, metaldehyde, metaflumizone, methamidophos, metham, methiocarb, methidathion, methyl isothiocyanate, methyl bromide, methoxychlor, methoxyfenozide, methothrin, metofluthrin, methoprene, metolcarb, mevinphos, meperfluthrin, Monacrosporium phymatophagum, monocrotophos, momfluorothrin, litlure-A, litlure-B, aluminium phosphide, zinc phosphide, phosphine, lufenuron, rescalure, resmethrin, lepimectin, rotenone, nuclear polyhedrosis virus silkworm-embedded body, fenbutatin oxide, calcium cyanide, organotins, nicotine-sulfate, (Z)-11-tetradecenyl=acetate, (Z)-11-hexadecenal, (Z)— 11-hexadecenyl=acetate, (Z)-9,12-tetradecadienyl=acetate, (Z)-9-tetradecene-1-ol, (Z,E)-9,11-tetradecadienyl=acetate, (Z,E)-9,12-tetradecadienyl=acetate, 1,1,1-trichloro-2,2-bis(4-chlorophenyl)ethane (DDT), 1,3-dichloropropene(1,3-dichloropropene), 2,4-dichloro-5-{2-[4-(trifluoromethyl)phenyl]ethoxy}phenyl 2,2,2-trifluoroethyl sulfoxide (Chemical name, CAS registry number: 1472050-04-6), 2,4-dichloro-5-{2-[4-(trifluoromethyl)phenyl]ethoxy}phenyl 2,2,2-trifluoroethyl sulfoxide (Chemical name, CAS registry number: 1472052-11-1), 2,4-dimethyl-5-[6-(trifluoromethylthio)hexyloxy]phenyl-2,2,2-trifluoroethyl sulfoxide (Chemical name, CAS registry number: 1472050-34-2), 2-{2-fluoro-4-methyl-5-[(2,2,2-trifluoroethyl)sulfinyl]phenoxy}-5-(trifluoromethyl)pyridine (Chemical name, CAS registry number: 1448758-62-0), 3-chloro-2-{2-fluoro-4-methyl-5-[(2,2,2-trifluoroethyl)sulfinyl]phenoxy}-5-(trifluoromethyl)pyridine (Chemical name, CAS registry number: 1448761-28-1), 4,6-dinitro-o-cresol (DNOC), 4-fluoro-2-methyl-5-(5,5-dimethylhexyloxy]phenyl-2,2,2-trifluoroethyl sulfoxide (Chemical name, CAS registry number: 1472047-71-4), Bt protein (CrylAb, CrylAc, CrylFa, Cry2Ab, mCry3A, Cry3Ab, Cry3Bb, Cry34/35Ab1), CL900167 (code number), NA-85 (code number), NI-30 (code number), O,O-diethyl-O-[4-(dimethylsulfamoyl)phenyl]-phosphorothioate (DSP), O-ethyl-O-4-(nitrophenyl)phenylphosphonothioate (EPN), RU15525 (code number), XMC(XMC), Z-13-icosen-10-one, ZXI8901 (code number).

Next, examples of known bactericides or disease controller compounds that can be mixed or used in combination are shown below.

Bactericide active ingredients: azaconazole, acibenzolar-S-methyl, azoxystrobin, anilazine, amisulbrom, aminopyrifen, ametoctradin, aldimorph, isotianil, isopyrazam, isofetamid, isoflucypram, isoprothiolane, ipconazole, ipflufenoquin, ipfentrifluconazole, iprodione, iprovalicarb, iprobenfos, imazalil, iminoctadine-albesilate, iminoctadine-triacetate, imibenconazole, inpyrfluxam, imprimatin A, imprimatin B, edifenphos, etaconazole, ethaboxam, ethirimol, ethoxyquin, etridiazole, enestroburin, enoxastrobin, epoxiconazole, organic oils, oxadixyl, oxazinylazole, oxathiapiprolin, oxycarboxin, oxine-copper, oxytetracycline, oxpoconazole-fumarate, oxolinic acid, copper dioctanoate, octhilinone, ofurace, orysastrobin, o-phenylphenol, kasugamycin, captafol, carpropamid, carbendazim, carboxin, carvone, quinoxyfen, quinofumelin, chinomethionat, captan, quinconazole, quintozene, guazatine, cufraneb, coumethoxystrobin, coumoxystrobin, kresoxim-methyl, clozylacon, chlozolinate, chlorothalonil, chloroneb, cyazofamid, diethofencarb, diclocymet, dichlofluanid, dichlobentiazox, diclomezine, dicloran, dichlorophen, dithianon, diniconazole, diniconazole-M, zineb, dinocap, dipymetitrone, diphenylamine, difenoconazole, cyflufenamid, diflumetorim, cyproconazole, cyprodinil, simeconazole, dimethirimol, dimethyl disulfide, dimethomorph, cymoxanil, dimoxystrobin, *Pseudomonas rhodesiae* HAI-0804, ziram, silthiofam, streptomycin, spiroxamine, sedaxane, zoxamide, solatenol, dazomet, *Talaromyces flavus*, tiadinil, thiabendazole, thiram, thiophanate, thiophanate-methyl, thifluzamide, thiram, tecnazene, tecloftalam, tetraconazole, debacarb, tebuconazole, tebufloquin, terbinafine, dodine, dodemorph, triadimenol, triadimefon, triazoxide, trichlamide, triclopyricarb, *Trichoderma* atroviride, tricyclazole, triticonazole, tridemorph, triflumizole, trifloxystrobin, triforine, tolylfluanid, tolclofos-methyl, tolnifanide, tolprocarb, nabam, natamycin, naftifine, nitrapyrin, nitrothal-isopropyl, nuarimol, copper nonyl phenol sulphonate, *Bacillus subtilis*) (strain: QST 713, validamycin, valifenalate, picarbutrazox, bixafen, picoxystrobin, pydiflumetofen, bitertanol, binapacryl, hinokitiol, biphenyl, piperalin, hymexazol, pyraoxystrobin, pyraclostrobin, pyraziflumid, pyrazophos, pyrapropoyne, pyrametostrobin, pyriofenone, pyrisoxazole, pyridachlometyl, pyrifenox, pyributicarb, pyribencarb, pyrimethanil, pyroquilon, vinclozolin, ferbam, famoxadone, phenazine oxide, fenamidone, fenaminstrobin, fenarimol, fenoxanil, ferimzone, fenpiclonil, fenpicoxamid, fenpyrazamine, fenbuconazole, fenfuram, fenpropidin, fenpropimorph, fenhexamid, folpet, phthalide, bupirimate, fuberidazole, blasticidin-S, furametpyr, furalaxyl, furancarboxylic acid, fluazinam, fluindapyr, fluoxastrobin, fluopicolide, fluopimomide, fluopyram, fluoroimide, fluxapyroxad, fluquinconazole, furconazole, furconazole-cis, fludioxonil, flusilazole, flusulfamide, flutianil, flutolanil, flutriafol, flufenoxystrobin, flumetover, flumorph, proquinazid, prochloraz, procymidone, prothiocarb, prothioconazole, bronopol, propamocarb-hydrochloride, propiconazole, propineb, probenazole, bromuconazole, flometoquin, florylpicoxamid, hexaconazole, benalaxyl, benalaxyl-M, benodanil, benomyl, pefurazoate, penconazole, pencycuron, benzovindiflupyr, benthiazole, benthiavalicarb-isopropyl, penthiopyrad, penflufen, boscalid, fosetyl (alminium, calcium, sodium), polyoxin, polycarbamate, Bordeaux mixture, mancopper, mancozeb, mandipropamid, mandestrobin, maneb, myclobutanil, mineral oils, mildiomycin, methasulfocarb, metam, metalaxyl, metalaxyl-M, metiram, metyltetraprole, metconazole, metominostrobin, metrafenone, mepanipyrim, mefentrifluconazole, meptyldinocap, mepronil, iodocarb, laminarin, *Rhizobium vitis*, phosphorous acid and salts, copper oxychloride, silver, cuprous oxide, copper hydroxide, potassium bicarbonate, sodium bicarbonate, sulfur, oxyquinoline sulfate, copper sulfate, (3,4-dichloroisothiazole-5-yl)methyl 4-(tert-butyl)benzoic ester (Chemical name, CAS registry number: 1231214-23-5), BAF-045 (code number), BAG-010 (code number), UK-2A (code number), dodecylbenzenesulfonic acid bisethylenediamine copper [II] salt (DBEDC), MIF-1002 (code number), NF-180 (code number), triphenyltin acetate (TPTA), triphenyltin chloride (TPTC), triphenyltin hydroxide (TPTH), avirulent *Erwinia carotovora*.

Next, examples of known herbicides or plant growth regulator compounds that can be mixed or used in combination are shown below.

Herbicide active ingredients: ioxynil, aclonifen, acrolein, azafenidin, acifluorfen (including a salt with sodium or the like), azimsulfuron, asulam, acetochlor, atrazine, anilofos, amicarbazone, amidosulfuron, amitrole, aminocyclopyrachlor, aminopyralid, amiprofos-methyl, ametryn, alachlor, alloxydim, ancymidol, isouron, isoxachlortole, isoxaflutole, isoxaben, isodecylalkoholethoxylat, isoproturon, ipfencarbazone, imazaquin, imazapic (including a salt with amine or the like), imazapyr (including a salt of isopropylamine or the like), imazamethabenz-methyl, imazamox, imazethapyr, imazosulfuron, indaziflam, indanofan, eglinazine-ethyl, esprocarb, ethametsulfuron-methyl, ethalfluralin, ethidimuron, ethoxysulfuron, ethoxyfen-ethyl, ethofumesate, etobenzanid, endothal-disodium, oxadiazon, oxadiargyl, oxaziclomefone, oxasulfuron, oxyfluorfen, oryzalin, orthosulfamuron, orbencarb, oleic acid, cafenstrole, carfentrazone-ethyl, karbutilate, carbetamide, quizalofop, quizalofop-ethyl, quizalofop-P-ethyl, quizalofop-P-tefuryl, quinoclamine, quinclorac, quinmerac, cumyluron, clacyfos, glyphosate (including a salt of sodium, potassium, amine, propylamine, isopropylamine, dimethylamine, trimesium, or the like), glufosinate (including a salt of amine, sodium, or the like), glufosinate-P, glufosinate-P-sodium, clethodim, clodinafop-propargyl, clopyralid, clomazone, chlomethoxyfen, clomeprop, cloransulam-methyl, chloramben, chloridazon, chlorimuron-ethyl, chlorsulfuron, chlorthal-dimethyl, chlorthiamid, chlorphthalim, chlorflurenol-methyl, chlorpropham, chlorbromuron, chloroxuron, chlorotoluron, ketospiradox (including a salt of sodium, calcium, ammonia, or the like), saflufenacil, sarmentine, cyanazine, cyanamide, diuron, diethatyl-ethyl, dicamba (including a salt of amine, diethylamine, isopropylamine, diglycolamine, sodium, lithium, or the like), cycloate, cycloxydim, diclosulam, cyclosulfamuron, cyclopyranil, cyclopyrimorate, dichlobenil, diclofop-P-methyl, diclofop-methyl, dichlorprop, dichlorprop-P, diquat, dithiopyr, siduron, dinitramine, cinidon-ethyl, cinosulfuron, dinoseb, dinoterb, cyhalofop-butyl, diphenamid, difenzoquat, diflufenican, diflufenzopyr, simazine, dimethachlor, dimethametryn, dimethenamid, dimethenamid-P, simetryn, dimepiperate, dimefuron, cinmethylin, swep, sulcotrione, sulfentrazone, sulfosate, sulfosulfuron, sulfometuron-methyl, sethoxydim, terbacil, daimuron, thaxtomin A, dalapon, thiazopyr, tiafenacil, thiencarbazone (including sodium salt, methyl ester, or the like), tiocarbazil, thiobencarb, thidiazimin, thidiazuron, thifensulfuron-methyl, desmedipham, desmetryne, thenylchlor, tebutam, tebuthiuron, tepraloxydim, tefuryltrione, terbuthylazine, terbutryn, terbumeton, tembotrione, topramezone, tralkoxydim, triaziflam, triasulfuron, triafamone, tri-allate, trietazine, triclopyr, triclopyr-butotyl, tritosulfuron, trifludimoxazin, triflusulfuron-methyl, trifluralin, trifloxysulfuron-sodium, tribenuron-methyl, tolpyralate, naptalam (including a salt with sodium or the like), naproanilide, napropamide, napropamide-M, nicosulfuron, neburon, norflurazon, vemolate, paraquat dichloride, halauxifen-benzyl, halauxifen-methyl, haloxyfop, haloxyfop-P, haloxyfop-etotyl, halosafen, halosulfuron-methyl, picloram, picolinafen, bicyclopyrone, bispyribac-sodium, pinoxaden, bifenox, piperophos, pyraclonil, pyrasulfotole, pyrazoxyfen, pyrazosulfuron-ethyl, pyrazolynate, bilanafos, pyraflufen-ethyl, pyridafol, pyrithiobac-sodium, pyridate, pyriftalid, pyributicarb, pyribenzoxim, pyrimisulfan, pyriminobac-methyl, pyroxasulfone, pyroxsulam, phenisopham, fenuron, fenoxasulfone, fenoxaprop (including methyl, ethyl, isopropylester), fenoxaprop-P (including methyl, ethyl, isopropyl ester), fenquinotrione, fenthiaprop-ethyl, fentrazamide, phenmedipham, foramsulfuron, butachlor, butafenacil, butamifos, butylate, butenachlor, butralin, butroxydim, flazasulfuron, flamprop (including methyl, ethyl, isopropyl ester), flamprop-M (including methyl, ethyl, isopropyl ester), primisulfuron-methyl, fluazifop-butyl, fluazifop-P-butyl, fluazolate, fluometuron, fluoroglycofen-ethyl, flucarbazone-sodium, fluchloralin, flucetosulfuron, fluthiacet-methyl, flupyrsulfuron-methyl (including a salt of sodium, calcium, ammonia, or the like), flufenacet, flufenpyr-ethyl, flupropanate, flupoxame, flumioxazin, flumiclorac-pentyl, flumetsulam, fluridone, flurtamone, fluroxypyr (including an ester such as butomethyl or meptyl, a salt of sodium, calcium, ammonia, or the like), flurochloridone, pretilachlor, procarbazone-sodium, prodiamine, prosulfuron, prosulfocarb, propaquizafop, propachlor, propazine, propanil, propyzamide, propisochlor, propyrisulfuron, propham, profluazol, prohexadione-calcium, propoxycarbazone, propoxycarbazone-sodium, profoxydim, bromacil, brompyrazon, prometryn, prometon, bromoxynil (including an ester of butyric acid, octanoic acid, heptanoic acid, or the like), bromofenoxim, bromobutide, florasulam, florpyrauxifen, florpyrauxifen-benzyl, hexazinone, pethoxamid, benazolin, penoxsulam, heptamaloxyloglucan, beflubutamid, pebulate, pelargonic acid, bencarbazone, pendimethalin, benzfendizone, bensulide, bensulfuron-methyl, benzobicyclon, benzofenap, bentazone, pentanochlor, pentoxazone, benfluralin, benfuresate, fosamine, fomesafen, foramsulfuron, forchlorfenuron, mecoprop (including a salt of sodium, potassium, isopropylamine, triethanolamine, dimethylamine, or the like), mecoprop-P-potassium, mesosulfuron (including an ester of methyl or the like), mesotrione, metazachlor, metazosulfuron, methabenzthiazuron, metamitron, metamifop, metam, disodium methanearsonate (DSMA), methiozolin, methyldymuron, metoxuron, metosulam, metsulfuron-methyl, metobromuron, metobenzuron, metolachlor, metribuzin, mepiquat chloride, mefenacet, monosulfuron (including methyl, ethyl, isopropylester), monolinuron, molinate, iodosulfuron, iodosulfulon-methyl-sodium, iofensulfuron, iofensulfuron-sodium, lactofen, lancotrione, linuron, rimsulfuron, lenacil, 2,2,2-trichloroacetic acid (TCA) (including a salt of sodium, calcium, ammonia, or the like), 2,3,6-trichlorobenzoic acid (2,3,6-TBA), 2,4,5-trichlorophenoxyacetic acid (2,4,5-T), 2,4-dichlorophenoxyacetic acid (2,4-D) (including a salt of amine, diethylamine, triethanolamine, isopropylamine, sodium, lithium, or the like), 2-amino-3-chloro-1,4-naphthoquinone (ACN), 2-methyl-4-chlorophenoxyacetic acid (MCPA) (including a sodium salt, ethyl ester, or the like), 2-methyl-4-chlorophenoxyacetic acid (MCPB) (including a sodium salt, ethyl ester, or the like), 4-(2,4-dichlorophenoxy)butyric acid (2,4-DB), 4,6-dinitro-O-cresol (DNOC) (including a salt of amine, sodium, or the like), AE-F-150944 (code number), F9600 (code number), IR-6396 (code number), MCPA-thioethyl, SYP-298 (code number), SYP-300 (code number), S-ethyldipropylthiocarbamate (EPTC), S-metolachlor, S-9750 (code number), MSMA, HW-02 (code number).

Plant growth regulators: 1-naphthylacetamide, 1-methylcyclopropene, 2,6-diisopropylnaphthalene, 4-oxo-4-(2-phenylethyl)aminobutyric acid (Chemical name, CAS registry number: 1083-55-2), 4-chlorophenoxyacetic acid (4-CPA), n-decanol, aviglycine, ancymidol, abscisic acid, inabenfide, indole acetic acid, indole butyric acid, uniconazole, uniconazole-P, Ecolyst, ethychlozate, ethephon, epocholeone, oxine-sulfate, carvone, calcium formate, cloxyfonac, cloxyfonac-potassium, cloprop, chlormequat, choline, cytokinins, cyclanilide, dikegulac, gibberellin acid, dimethipin, sintofen, daminozide, thidiazuron, triacontanol, trinexapac-ethyl, paclobutrazol, paraffin, flumetralin, flurprimidol, flurenol, prohydrojasmon, prohexadione-calcium, heptamaloxyloglucan, benzylaminopurine, forchlorfenuron, maleic hydrazide, mepiquat chloride, mefluidide, calcium peroxide.

Next, examples of known phytotoxicity alleviating compounds that can be mixed or used in combination are shown below.

Isoxadifen, isoxadifen-ethyl, oxabetrinil, cloquintcet-mexyl, dietholate, cyometrinil, dichlormid, dicyclonone, cyprosulfamide, 1,8-Naphthalic Anhydride, fenchlorazole-O-ethyl, fenclorim, furilazole, fluxofenim, flurazole, benoxacor, mephenate, mefenpyr, mefenpyr-ethyl, mefenpyr-diethyl, lower alkyl-substituted benzoic acid, 2,2-dichloro-N-(1,3-dioxane-2-ylmethyl)-N-(2-propenyl)acetamide (PPG-1292), 2-dichloromethyl-2-methyl-1,3-dioxane (MG-191), 3-dichloroacetyl-2,2,5-trimethyl-1,3-oxazolidine (R-29148), 4-dichloroacetyl-1-oxa-4-azaspiro[4.5]decane (AD-67), MON4660 (code number), metcamifen, N1,N2-diallyl-N2-dichloroacetyl glycineamide (DKA-24), TI-35 (code number).

The present harmful organism control agent configured as described above exhibits excellent controlling effect on Orthoptera pests, Thysanoptera pests, Hemiptera pests, Coleoptera pests, Diptera pests, Lepidoptera pests, Hymenoptera pests, Collembola pests, Thysanura pests, Blattodea pests, Isoptera pests, Psocoptera pests, Mallophage pests, Anoplura pests, plant parasitic Acari, plant parasitic nematoda, plant parasitic mollusks, and other harmful organisms such as harmful animals, uncomfortable animals, sanitary insects, and parasites. As such harmful organisms, the following organism species can be exemplified.

Examples of the Orthopteran pests include Ruspolia lineosa or the like of Tettigoniidae, *Teleogryllus emma, Truljalia hibinonis*, or the like of Gryllidae, *Gryllotalpa orientalis* or the like of Gryllotalpidae, *Oxya hyla* intricate, *Locusta migratoria, Melanoplus sanguinipes, Melanoplus differentialis, Melanoplus femurrubrum*, or the like of Acrididae, *Atractomorpha lata* of Pyrgomorphidae, *Euscyrtus japonicus* of Eneopteridae, and *Xya japonicus* or the like of Tridactylidae.

Examples of the Thysanoptera pests include *Frankliniella intonsa, Frankliniella occidentalis, Scirtothrips dorsalis, Thrips palmi, Thrips tabaci, Thrips setosus, Heliothrips haemorrhoidalis, Stenchaetothrips biformis*, or the like of Thripidae, and *Ponticulothrips diospyrosi, Liothrips wasabiae, Haplothrips aculeatus*, or the like of Phlaeothripidaes.

Examples of the Hemipteran pests include *Mogannia minuta* or the like of Cicadidae, *Aphrophora intermedia* or the like of Aphrophoridae, *Machaerotypus sibiricus* or the like of Membracidae, *Arboridia apicalis, Empoasca onukii, Nephotettix cincticeps, Nephotettix malayanus, Nephotettix virescens, Nephotettix nigropictus, Recilia dorsalis*, Okura Leafhopper (*Amrasca biguttula*), Mango Leafhopper (*Idioscopus nitidulus, Idioscopus clypealis, Amritodus atkinsoni*), *Empoasca fabae*, or the like of Cicadellidae, *Pentastiridius apicalis* or the like of Cixiidae, *Laodelphax striatellus, Nilaparvata lugens, Sogatella furcifera*, or the like of Delphacidae, *Nisia nervosa* or the like of Meenoplidae, *Kamendaka saccharivora* or the like of Derbidae, *Achilus flammeus* or the like of Cixidia, *Orosanga japonicus* or the like of Ricaniidae, *Mimophantia maritima* or the like of Flatidae, *Cacopsylla pyrisuga, Diaphorina citri*, or the like of Psyllidae, *Calophya mangiferae* or the like of Calophyidae, *Daktulosphaira vitifoliae* or the like of Phylloxeridae, *Adelges laricis, Adelges tsugae*, or the like of Adelgidae, *Acyrthosiphon pisum, Aphis gossypii, Aphis spiraecola, Lipaphis erysimi, Brevicoryne brassicae, Myzuspersicae, Schizaphis graminum, Rhopalosiphum padi, Toxoptera aurautii, Aulacorthum solani, Macrosiphum euphorbiae, Nasonovia ribisnigri, Sitobion avenae, Aphis glycines*, or the like of Aphydidae, *Aleurocanthus camelliae, Aleurocanthus spiniferus, Bemisia tabaci, Bemisia argentifolii, Trialeurodes vaporariorum*, or the like of Aleyrodidae, *Drosicha corpulenta, Icerya purchasi*, or the like of Margarodidae, *Dysmicoccus brevipes, Planococcus citri, Pseudococcus comstocki*, or the like of Pseudococcidae, *Ceroplastes ceriferus, Ceroplastes rubens*, or the like of Coccidae, *Aclerda takahashii* or the like of Aclerdidae, *Aonidiella aurantii, Diaspidiotus pemiciosus, Pseudaulacaspis pentagoa, Unaspis yanonensis*, or the like of Diaspididae, *Lygus lineolaris, Trigonotylus caelestialium, Apolygus lucorum, Nesidiocoris tenuis, Halticus bractatus*, or the like of Miridae, *Stephanitis pyrioides, Stephanitis nashi*, or the like of Tingidae, *Eurydema rugosum, Eysarcoris lewisi, Eysarcoris aeneus, Lagynotomus elongatus, Nezara viridula, Plautia crossota, Nezara antennata, Eushistus heros*, or the like of Pentatomidae, *Megacopta cribraria* or the like of Plataspidae, *Urochela luteovoria* or the like of Urostylididae, *Cavelerius saccharivorus* or the like of Lygaeidae, *Malcus japonicus* or the like of Malcidae, *Dysdercus cingulatus* or the like of Pyrrhocoridae, *Leptocorisa acuta, Leptocorisa chinensis*, or the like of Alydidae, *Anacanthocoris striicomis* or the like of Coreidae, *Rhopalus maculatus* or the like of Rhopalidae, and *Cimex lectularis* or the like of Cimicidae.

Examples of the Coleoptera pests include *Anomara cuprea, Anomara rufocuprea, Popilliaj aponica, Oxycetonia jucunda, Anomala geniculata, Oryctes rhinoceros, Heptophylla picea*, or the like of Scarabaeidae, *Agriotes ogurae, Agriotes lineatus, Agriotes obscurus, Melanotus okinawensis, Melanotus fortnumi*, or the like of Elateridae, *Anthrenus verbasci* or the like of Dermestidae, *Heterobostrychus hamatipennis* or the like of Bostrychidae, *Stegobium paniceum* or the like of Anobiidae, *Pitinus clavipes* or the like of Ptinidae, *Tenebroides mauritanicus* or the like of Trogossitidae, *Necrobia rufipes* of Cleridae, *Carpophilus hemipterus, Meligethes aeneus*, or the like of Nitidulidae, *Ahasverus advena* or the like of Silvanidae, *Cryptolestes ferrugineus* or the like of Laemophloeidae, *Epilachna varivestis, Henosepilachna vigintioctopunctata* or the like of Coccinellidae, *Tenebrio molitor, Tribolium castaneum*, or the like of Tenebrionidae, *Epicauta gorhami* or the like of Meloidae, *Anoplophora glabripennis, Xylotrechus pyrrhoderus, Monochamus alternatus, Dectes texanus*, or the like of Cerambycidae, *Callosobruchus chinensis* or the like of Bruchidae, *Leptinotarsa decemlineata, Diabrotica virgifera virgifera, Diabrotica barberi, Diabrotica undecimpunctata howardi, Aulacophora femoralis, Phaedon brassicae, Cassida nebulosa, Oulema oryzae, Epilachna varivestis, Phyllotreta striolata, Demotina fasciculata, Psylliodes chrysocephala, Cerotoma trifurcate, Colaspis brunnea, Colaspis crinnicornis, Odontota homi, Chaetocnema pulicaria*, or the like of Chrysomelidae, *Cylas formicarius* or the like of Brentidae, *Hypera postica, Listroderes costirostris, Euscepes postfasciatus, Curculio sikkimensis*, or the like of Curculionidae, *Echinocnemus bipunctatus, Lissorhoptrus oryzophilus, Oryzophagus oryzae*, or the like of Erirhinidae, *Sitophilus zeamais, Sphenophrus venatus*, or the like of Dryophthoridae, *Tomicus piniperda* or the like of Scolytidae, *Crossotarsus niponicus* or the like of Platypodidae, and *Lyctus brunneus* or the like of Lyctidae.

Examples of the Diptera include *Tipula aino* or the like of Tipulidae, *Plecia nearctica* or the like of Bibionidae, *Exechia shiitakevora* or the like of Mycetophidae, *Pnyxiascabiei, Bradysia agrestis*, or the like of Sciaridae, *Asphondylia yushimai, Mayetiola destructor, Dasineura oxycoccana*, or the like of Cecidomyiidae, *Aedes aegypti, Culex pipiens pallens*, or the like of Culicidae, *Simulium takahashii* or the like of Simuliidae, *Chironomus oryzae* or the like of Chironomidae, *Chrysops suavis, Tabanus trigonus*, or the like of Tabanidae, *Eumerus strigatus* or the like of Syrphidae, *Bactrocera dorsalis, Euphranta japonica, Ceratitis capitata*, or the like of Tephritidae, *Liriomyza trifolii, Liriomyza sativae, Agromyza oryzae, Liriomyza bryoniae, Chromatomyia horticola, Liriomyza chinensis, Liriomyza trifolii*, or the like of Agromyzidae, *Meromyza nigriventris* or the like of Chloropidae, *Drosophila suzukii, Drosophila melanogaster*, or the like of Drosophilidae, *Hydrellia griseola* or the like of Ephydridae, *Hippobosca equina* or the like of Hippoboscidae, *Parallelpmma sasakawae* or the like of Scatophagidae, *Delia antiqua, Delia platura*, or the like of Anthomyiidae, *Fannia canicularis* or the like of Fanniidae, *Musca domestica, Stomoxys calcitrans* or the like of Muscidae, *Sarcophaga peregrina* or the like of Sarcophagidae, *Gasterophilus intestinalis* or the like of Gasterophilidae, *Hypoderma lineatum* or the like of Hypodermatidae, and *Oestrus ovis* or the like of Oestridae.

Examples of the Lepidoptera include *Endoclita excrescens* or the like of Hepialidae, *Antispila ampelopsia* or the like of Heliozelidae, *Zeuzera leuconotum, Cossus insularis*, or the like of Cossidae, *Archips fuscocupreanus, Adoxophyes orana fasciata, Grapholita molesta, Homona magnanima, Leguminivora glycinivorella, Cydia pomonella, Lobesia botrana*, or the like of Tortricidae, *Eupoecilia ambiguella* or the like of Cochylidae, *Bambalina* sp., *Eumeta minuscula*, or the like of Psychidae, *Nemapogon granella, Tinea translucens*, or the like of Tineidae, *Bucculatrix pyrivorella* or the like of Bucculatricidae, *Lyonetia clerkella, Lyonetiaprunifoliella malinella*, or the like of Lyonetiidae, *Caloptilia theivora, Phyllonorycter ringoniella*, or the like of Gracilariidae, *Phyllocnistis citrella* or the like of Phyllocnistidae, *Acrolepiopsis sapporensis* or the like of Acrolepiidae, *Plutella xylostella* of Plutellidae, *Yponomeuta orientalis*, or the like of Yponomeutidae, *Argyresthia conjugella* or the like of Argyresthidae, *Nokona regalis, Synanthedin hector* or the like of Sesidae, *Phthorimaea operculella, Sitotroga cerealella, Pectinophora gossypiella, Tuta absoluta*, or the like of Gelechiidae, *Carposina sasakii* or the like of Carposinidae, *Illiberis pruni* or the like of Zygaenidae, *Monema flavescens* or the like of Limacodidae, *Ancylolomia japonica, Chilo suppressalis, Cnaphalocrocis medinalis, Ostrinia fumacalis, Hellulla undalis, Conogethes punctiferlis, Diaphania indica, Parapediasia teterrella, Ostrinia nubilalis*, or the like of Crambidae, *Diatraea saccharalis, Cadra cautella, Galleria mellonella*, or the like of Pyralidae, *Nippoptilia vitis* or the like of Pterophoridae, *Papilio xuthus* or the like of Papilionidae, *Pieris rapae* or the like of Pieridae, *Parnara guttata* or the like of Hesperiidae, *Ascotis selenaria* or the like of Geometridae, *Dendrolimus spectabilis, Malacosoma neustrium testaceum*, or the like of Lasiocampidae, *Agrius convolvuli* or the like of Sphingidae, *Ama pseudoconspersa, Orygia recens approximans, Lymantria dispar*, or the like of Lymantriidae, *Hyphantria cunea* or the like of Arctiidae, and *Agrotis ipsilon, Agrotis segetum, Autographa nigrisigna, Helicoverpa armigera, Helicoverpa zea, Heliothis virescens, Spodoptera exigua, Spodoptera litura, Chrysodeix includens, Spodoptera frugiperda, Nephelodes minians*, or the like of Noctuidae.

Examples of the Hymenoptera pests include *Arge pagana* or the like of Argidae, *Apethymus kuri, Athalia rosae ruficomis*, or the like of Tenthredinidae, *Dryocosmus kuriphilus*, or the like of Cynipidae, *Vespa simillima xanthoptera* or the like of Vespidae, *Solenopsis invicta, Linepithema humile*, or the like of Formicidae, and *Megachile nipponica* or the like of Megachilidae.

Examples of the Collembola pests include *Bourletiella hortensis* or the like of Sminthuridae.

Examples of the Thysanura pests include *Lepisma saccharina, Ctenolepisma villosa*, or the like of Lepismatidae.

Examples of the Blattodea pests include *Periplaneta americana* of Blattidae, and *Blattella germanica* or the like of Blattellidae.

Examples of the Isoptera pests include *Incisitermes minor* or the like of Kalotermitidae, *Coptotermes formosanus* or the like of Rhinotermitidae, and *Odontotermes formosanus* or the like of Termitidae.

Examples of the Psocoptera pests include *Trogium pulsatorium* or the like of Trogiidae, and *Liposcelis corrodens* or the like of Liposcelididae.

Examples of the Dermaptera pests include *Labodura riparia* or the like of Labiduridae.

Examples of the Mallophaga pests include *Lipeurus caponis* or the like of Menoponidae, and *Damalinia bovis* or the like of Trichodectidae.

Examples of the Anoplura pests include *Haematopinus suis* or the like of Haematopinidae, *Pediculus humanus* or the like of Pediculine, *Linognathus setosus* or the like of Linognathidae, and *Pthirus pubis* or the like of Pthiridae Examples of the Acari pests include *Penthaleus major* or the like of Eupodidae, *Phytonemus pallidus, Polyphagotarsonemus latus*, or the like of Tarsonemidae, one species of *Siteroptes* sp. or the like of Pyemotidae, *Brevipalpus lewisi* or the like of Tenuipalpidae, *Tuckerella pavoniformis* or the like of Tuckerellidae, *Eotetrany chusboreus, Panonychus citri, Panonychus ulmi, Tetranychus urticae, Tetranychus kanzawai*, or the like of Tetranychidae, *Trisetacus pini* or the like of Nalepellidae, *Aculops pelekassi, Epitrimerus pyri, Phyllocoptruta oleivora, Aculops lycopersici*, or the like of Eriophyidae, *Diptacus crenatae* or the like of Diptilomiopida, *Aleuroglyphus ovatus, Tyrophagus putrescentiae*, or *Rhizoglyphus robini* of Acaridae, *Omithonyssus sylvialum* or the like of Macronyssidae, *Varroaj acobsoni* or the like of Varroidae, *Dermanyssus gallinae* or the like of Dermanyssidae, *Omithonyssus sylvialum* or the like of Macronyssidae, *Boophilus microplus, Rhipicephalus sanguineus, Haemaph-* *ysalis longicornis*, or the like of Ixodidae, and *Sarcoptes scabiei* or the like of Sarcoptidae.

Examples of the plant parasitic nematoda, include *Xiphinema index* or the like of Longidoridae, *Paratrichodorus minor* or the like of Trichodoridae, one species of Rhabditidae (*Rhabditella* sp.) or the like, one species of Tylenchidae (*Aglenchus* sp.) or the like, one species of Tylodoridae (*Cephalenchus* sp.) or the like, *Nothotylenchus acris, Ditylenchus* destructor, or the like of Anguinidae, *Rotylenchulus reniformis, Helicotylenchus dihystera*, or the like of Hoplolaimidae, *Paratylenchus curvitatus* or the like of Paratylenchidae, *Meloidogyne incognita, Meloidogyne hapla*, or the like of Meloidogynidae, *Globodera rostochiensis, Globodera pallida, Heterodera glycines*, or the like of Heteroderidae, *Tylenchorhynchus claytoni* or the like of Telotylenchidae, one species of Psilenchidae (*Psilenchus* sp.) or the like, one species of Criconematidae (*Criconemoides* sp.) or the like, *Tylenchulus semipenetrans* or the like of Tylenchulidae, *Sphaeronema camelliae* or the like of Sphaeronematidae, *Sphaeronema camelliae, Radopholus citrophilus, Radopholus similis, Nacobbus aberrans, Pratylenchus penetrans, Pratylenchus coffeae*, or the like of Pratylenchidae, *Iotonchium ungulatum* or the like of Iotonchiidae, *Aphelenchus avenae* or the like of Aphelenchidae, *Aphelenchoides besseyi, Aphelenchoides fragariae*, or the like of Aphelenchoididae, and *Bursaphelenchus xylophilus* or the like of Palasitaphelenchidae.

Examples of the plant parasitic mollusks include *Pomacea canaliculata* or the like of Pilidae, *Leavicaulis alte* or the like of Veronicellidae, *Achatina fulica* or the like of Achatinidae, *Meghimatium bilineatum* or the like of Philomycidae, *Succinealauta* or the like of Succineidae, *Discus pauper* or the like of Didcidae, *Zonitoides yessoensis* or the like of Zonitidae, *Limax flavus, Lehmannia valentiana, Deroceras reticulatum*, or the like of Limacidae, *Parakaliella harimensis* or the like of Helicarionidae, and *Acusta despecta sieboldiana, Bradybaena similaris*, or the like of Bradybaenidae.

Examples of other harmful organisms such as harmful animals, uncomfortable animals, sanitary insects, livestock insects, and parasites include *Procambarus clarkii* or the like of Decapoda Astacidae, *Armadillidium vulgare* or the like of Isopoda Porcellionidae, *Armadillidium vulgare* or the like of Armadillidiidae, Chilopoda pests such as *Scutigeromorpha Sutigeridae, Scolopendra subspinipes*, or the like, Diplopoda pests such as *Oxidus gracilis, Theridiidae hasseltii* or the like of Araneae *Latrodectus hasseltii, Chiracanthium japonicum*, or the like of Clubionidae, *Androctonus crassicauda* or the like of Scorpiones, roundworm endoparasites such as *Ascaris lumbricoides* or the like, *Syphacia* sp. or the like, and *Wuchereria bancrofti* or the like, and flatworm endoparasites such as *Distomum* sp., *Paragonimus westermanii, Metagonimus yokokawai, Schistosoma japonicum, Taenia solium, Taeniarhynchus saginatus, Echinococcus* sp., or *Diphyllobothrium latum*.

The present harmful organism control agent exhibits a controlling effect also on the harmful organisms and the like exemplified above that have acquired the resistance to existing harmful organism control agents. Furthermore, the present harmful organism control agent can be applied to plants that have acquired characteristics such as pest tolerance, disease tolerance, herbicide tolerance, or the like by gene recombination, artificial mating, or the like.

Next, the production methods, formulation methods and applications of the present compound will be described in detail by way of Examples. However, the present invention is in no way restricted by these Examples. The melting point which is a physical property value of the present compound was determined by a MP-500V micro melting point measuring apparatus available from Yanaco. The refractive index was determined by using an Abbe refractometer available from ATAGO CO., LTD. $^1$H NMR spectrum was determined by using JNM-LA400 (400 MHz), JNM-LA300 (300 MHz) or JNM-ECS300 (300 MHz) available from JEOL Ltd. and tetramethylsilane (TMS) as the internal standard. A high resolution mass spectrum (HRMS) was measured by using Q Exactive Focus Hybrid Quadrupole-Orbitrap LC-MS/MS System (ESI, positive mode) available from Thermo Fisher Scientific.

Methods for producing production intermediates of the present compound are also described.

EXAMPLES

Example 1

Production of 4-(2,2,3,3,3-pentafluoropropoxy)-1-(pyridine-3-yl)-1H-pyrazole-3-carboxamide (Present Compound Number: A-0044)

1) Ethyl 4-(2,2,3,3,3-pentafluoropropoxy)-1-(pyridine-3-yl)-1H-pyrazole-3-carboxylate (Present Compound Number: B-0298)

Ethyl 4-hydroxy-1-(pyridine-3-yl)-1H-pyrazole-3-carboxylate (2.5 g, 10.7 mmol) synthesized by the method described in Reference examples 1 and 2 of WO 2016/027790 A, 2,2,3,3,3-pentafluoropropyl nonafluorobutanesulfonate (4.7 g, 10.9 mmol) and potassium carbonate, anhydrous (1.6 g, 11.6 mmol) were sequentially added at room temperature to dimethyl sulfoxide (50 mL) and further stirred for 3 hours. The reaction solution was poured into saturated brine, and extracted with ethyl acetate. The obtained organic layer was dried over anhydrous magnesium sulfate, and then the solvent was distilled off under reduced pressure. The residue was purified by silica gel column chromatography, to give ethyl 4-(2,2,3,3,3-pentafluoropropoxy)-1-(pyridine-3-yl)-1H-pyrazole-3-carboxylate (3.3 g, yield: 84%).

$^1$H-NMR data (400 MHz, CDCl$_3$/TMS δ (ppm)): 1.45 (3H, t), 4.47 (2H, q), 4.54 (2H, t), 7.45 (1H, dd), 7.81 (1H, s), 8.11 (1H, d), 8.63 (1H, d), 8.96 (1H, d)

2) 4-(2,2,3,3,3-pentafluoropropoxy)-1-(pyridine-3-yl)-1H-pyrazole-3-carboxamide (Present Compound Number: A-0044)

Ethyl 4-(2,2,3,3,3-pentafluoropropoxy)-1-(pyridine-3-yl)-1H-pyrazole-3-carboxylate (1.2 g, 3.3 mmol) was dissolved in methanol (100 mL), and aqueous ammonia (content: 28%, 50 mL) was further added and stirred at room temperature for 12 hours. The solvent of the reaction solution was distilled off under reduced pressure, and the residue was purified by silica gel column chromatography to give 4-(2,2,3,3,3-pentafluoropropoxy)-1-(pyridine-3-yl)-1H-pyrazole-3-carboxamide (0.8 g, yield: 72%).

$^1$H-NMR data (400 MHz, CDCl$_3$/TMS δ (ppm)): 4.68 (2H, t), 5.95 (1H, br), 6.81 (1H, br), 7.45 (1H, dd), 7.91 (1H, s), 8.06 (1H, d), 8.63 (1H, d), 8.97 (1H, d)

Example 2

Production of 4-benzyloxy-1-(pyridine-3-yl)-1H-pyrazole-3-carboxamide (Present Compound Number: A-0240)

1) Ethyl 4-benzyloxy-1-(pyridine-3-yl)-1H-pyrazole-3-carboxylate (Present Compound Number: B-0494)

In a solution of ethyl 4-hydroxy-1-(pyridine-3-yl)-1H-pyrazole-3-carboxylate (7.5 g, 32.2 mmol) in N,N-dimethylformamide (150 mL), sodium hydride (content 60%, 1.5 g, 37.5 mmol) was added little by little at room temperature, and stirred for about 30 minutes. To this reaction solution, benzyl bromide (5.5 g, 32.2 mmol) was added at room temperature, and allowed to react for 1 hour. The reaction solution was poured into saturated brine, and extracted with ethyl acetate. The obtained organic layer was dried over anhydrous magnesium sulfate, and then the solvent was distilled off under reduced pressure. The obtained solid was washed with hexane, to give ethyl 4-benzyloxy-1-(pyridine-3-yl)-1H-pyrazole-3-carboxylate (8.1 g, yield: 78%).

$^1$H-NMR data (400 MHz, CDCl$_3$/TMS δ (ppm)): 1.44 (3H, t), 4.47 (2H, q), 5.15 (2H, s), 7.32-7.48 (6H, m), 7.56 (1H, s), 8.09 (1H, d), 8.58 (1H, d), 8.89 (1H, d)

2) 4-benzyloxy-1-(pyridine-3-yl)-1H-pyrazole-3-carboxamide (Present Compound Number: A-0240)

Ethyl 4-benzyloxy-1-(pyridine-3-yl)-1H-pyrazole-3-carboxylate (7.5 g, 23.2 mmol) was dissolved in ethanol (200 mL), and potassium hydroxide (10.0 g, 178.2 mmol) and water (20 mL) were added at room temperature, and stirred for 1 hour. The solvent of the reaction solution was distilled off under reduced pressure, and 6 N hydrochloric acid was added to the residue, and the precipitated solid was collected by filtration, and dried to give crude 4-benzyloxy-1-(pyridine-3-yl)-1H-pyrazole-3-carboxylic acid. The obtained 4-benzyloxy-1-(pyridine-3-yl)-1H-pyrazole-3-carboxylic acid was dissolved in dichloromethane (200 mL), and oxalyl chloride (10 g, 78.8 mmol) and N,N-dimethylformamide (catalytic amount) were added, and allowed to react at room temperature for 13 hours. The solution was distilled off under reduced pressure, and the residue was dissolved in ethyl acetate (50 mL). The solution was added to a mixed solution of ethyl acetate (200 mL) and aqueous ammonia (content: 28%, 50 mL) at 0° C., and then stirred at room temperature for 1 hour. The solvent in the reaction solution was distilled off under reduced pressure, and the residue was extracted with ethyl acetate and dried over anhydrous magnesium sulfate, and then the solvent was distilled off. The obtained solid was washed with hexane, to give 4-benzyloxy-1-(pyridine-3-yl)-1H-pyrazole-3-carboxamide (5.5 g, yield: 81%).

$^1$H-NMR data (400 MHz, CDCl$_3$/TMS δ (ppm)): 6.04 (1H, br), 6.95 (1H, br), 7.36-7.47 (6H, m), 7.63 (1H, s), 8.11 (1H, d), 8.57 (1H, d), 8.90 (1H, d)

Example 3

Production of 1-(pyridine-3-yl)-4-[1,1,2-trifluoro-2-(trifluoromethoxy)ethoxy]-1H-pyrazole-3-carboxamide (Present Compound Number: A-0071)

1) 4-hydroxy-1-(pyridine-3-yl)-1H-pyrazole-3-carboxamide (Present Compound Number: A-0001)

In ethanol (100 mL), 4-benzyloxy-1-(pyridine-3-yl)-1H-pyrazole-3-carboxamide (1.5 g, 5.1 mmol) was dissolved, and palladium activated carbon (content: 10%, 0.5 g) was added, and hydrogen (120 mL) was introduced over 2 hours. The reaction solution was filtered, and the solvent was distilled off under reduced pressure. The residue was washed with hexane to give 4-hydroxy-1-(pyridine-3-yl)-1H-pyrazole-3-carboxamide (0.55 g, yield: 53%).

$^1$H-NMR data (400 MHz, DMSO-d6/TMS δ (ppm)): 7.56 (1H, dd), 7.62 (1H, br), 7.69 (1H, br), 8.21 (1H, s), 8.24 (1H, d), 8.54 (1H, d), 9.13 (1H, d), 9.35 (1H, br)

2) 1-(pyridine-3-yl)-4-[1,1,2-trifluoro-2-(trifluoromethoxy)ethoxy]-1H-pyrazole-3-carboxamide (Present Compound Number: A-0071)

In a mixed solvent of N,N-dimethylformamide (100 mL) and triethylamine (20 mL), 4-hydroxy-1-(pyridine-3-yl)-1H-pyrazole-3-carboxamide (0.9 g, 4.4 mmoL) was added. In the reaction solution, (trifluoromethyl)(trifluorovinyl) ether (2 g, 12.0 mmoL) was introduced at 50° C. over about 30 minutes, and further stirred for 30 minutes. After end of the reaction, the solvent was distilled off under reduced pressure. The residue was purified by silica gel column chromatography to give 1-(pyridine-3-yl)-4-[1,1,2-trifluoro-2-(trifluoromethoxy)ethoxy]-1H-pyrazole-3-carboxamide (0.8 g, yield: 49%).

$^1$H-NMR data (400 MHz, CDCl$_3$/TMS δ (ppm)): 5.77 (1H, br), 6.17 (1H, d), 6.72 (1H, br), 7.48 (1H, dd), 8.05 (1H, s), 8.06 (1H, d), 8.67 (1H, d), 9.01 (1H, d)

Example 4

Production of 4-(3,3-dimethylbutoxy)-1-(pyridine-3-yl)-1H-pyrazole-3-carboxamide (Present Compound Number: A-0017)

1) Ethyl 4-(3,3-dimethylbutoxy)-1-(pyridine-3-yl)-1H-pyrazole-3-carboxylate (Present Compound Number: B-0271)

Ethyl 4-hydroxy-1-(pyridine-3-yl)-1H-pyrazole-3-carboxylate (1.0 g, 4.3 mmoL), 3,3-dimethylbutanol (0.53 g, 5.2 mmoL) and triphenylphosphine (1.4 g, 5.2 mmoL) were dissolved in THF (50 mL), and diisopropyl azodicarboxylate (1.1 g, 5.2 mmoL) was added under cooling on ice, and stirred overnight at room temperature. After end of the reaction, the solvent was distilled off under reduced pressure, and the residue was purified by silica gel column chromatography to give ethyl 4-(3,3-dimethylbutoxy)-1-(pyridine-3-yl)-1H-pyrazole-3-carboxylate (1.27 g, yield: 93%).

$^1$H-NMR data (300 MHz, CDCl$_3$/TMS δ (ppm)): 1.02 (9H, s), 1.42 (3H, t), 1.82 (2H, t), 4.07 (2H, t), 4.44 (2H, q), 7.43 (1H, dd), 7.62 (1H, s), 8.15 (1H, d), 8.59 (1H, d), 8.96 (1H, d)

2) 4-(3,3-dimethylbutoxy)-1-(pyridine-3-yl)-1H-pyrazole-3-carboxylic acid (Present Compound Number: B-0017)

Ethyl 4-(3,3-dimethylbutoxy)-1-(pyridine-3-yl)-1H-pyrazole-3-carboxylate (1.1 g, 3.4 mmoL) was dissolved in ethanol (30 mL), and a mixed solution of sodium hydroxide (0.33 g, 8.4 mmoL) and water (20 mL) was added at room temperature, and stirred for 1 hour. The solvent of the reaction solution was distilled off under reduced pressure, and the residue was added with 6 N hydrochloric acid, and extracted with ethyl acetate, and washed with saturated brine. After drying over anhydrous magnesium sulfate, the solvent was distilled off, to give 4-(3,3-dimethylbutoxy)-1-(pyridine-3-yl)-1H-pyrazole-3-carboxylic acid (0.73 g, yield: 74%).

$^1$H-NMR data (300 MHz, CDCl$_3$/TMS δ (ppm)): 1.03 (9H, s), 1.85 (2H, t), 4.15 (2H, t), 7.49 (1H, dd), 7.71 (1H, s), 8.23 (1H, d), 8.64 (1H, d), 9.04 (1H, d)

3) 4-(3,3-dimethylbutoxy)-1-(pyridine-3-yl)-1H-pyrazole-3-carboxamide (Present Compound Number: A-0017)

In dichloromethane (15 mL), 4-(3,3-dimethylbutoxy)-1-(pyridine-3-yl)-1H-pyrazole-3-carboxylic acid (0.65 g, 2.3 mmoL) was dissolved, and oxalyl chloride (1 mL) and N,N-dimethylformamide (catalytic amount) were added, and heated under reflux at 40° C. for 1 hour. The solution was distilled off under reduced pressure, and the residue was suspended in THF (20 mL). After adding the solution to a mixed solution of THF (15 mL) and aqueous ammonia (content: 28%, 20 mL) under cooling on ice, the solution was stirred for 30 minutes under cooling on ice. The solvent of the reaction solution was distilled off under reduced pressure, and the residue was washed sequentially with water and hexane, and the obtained solid was dried, to give 4-(3,3-dimethylbutoxy)-1-(pyridine-3-yl)-1H-pyrazole-3-carboxamide (0.45 g, yield: 69%).

$^1$H-NMR data (300 MHz, CDCl$_3$/TMS δ (ppm)): 1.02 (9H, s), 1.83 (2H, t), 4.14 (2H, t), 5.73 (1H, br), 6.95 (1H, br), 7.42 (1H, dd), 7.67 (1H, s), 8.18 (1H, d), 8.58 (1H, d), 8.96 (1H, d)

Example 5

Production of N-isobutyryl-1-(pyridine-3-yl)-4-[1,1,2-trifluoro-2-(trifluoromethoxy)ethoxy]-1H-pyrazole-3-carboxamide (Present Compound Number: A-2403)

In THF (10 mL), 1-(pyridine-3-yl)-4-[1,1,2-trifluoro-2-(trifluoromethoxy)ethoxy]-1H-pyrazole-3-carboxamide (0.40 g, 1.1 mmoL) was dissolved, and sodium hydride (content: 55%, 57 mg, 1.3 mmoL) was added under cooling on ice, and stirred for 30 minutes, and then isobutyric chloride (0.13 g, 1.2 mmoL) was added and stirred overnight at room temperature. Further, sodium hydride (content: 55%, 0.20 g, 4.6 mmoL) and isobutyric chloride (0.40 g, 3.8 mmoL) were added at room temperature, and stirred at 40° C. for 3 hours. After end of the reaction, 6 N hydrochloric acid was added so that the pH was 1 to 2, and then the solvent was distilled off under reduced pressure, and the residue was purified by silica gel chromatography, to give N-isobutyryl-1-(pyridine-3-yl)-4-[1,1,2-trifluoro-2-(trifluoromethoxy)ethoxy]-1H-pyrazole-3-carboxamide (0.21 g, yield: 44%).

$^1$H-NMR data (400 MHz, CDCl$_3$/TMS δ (ppm)): 1.26 (6H, d), 3.56 (1H, sext), 6.14 (1H, dt), 7.52 (1H, dd), 8.05-8.10 (2H, m), 8.71 (1H, dd), 9.00 (1H, d), 9.13 (1H, br)

Example 6

Production of 1-(pyridine-3-yl)-4-[1,1,2-trifluoro-2-(trifluoromethoxy)ethoxy]-1H-pyrazole-3-carbonitrile In dichloromethane (20 mL), 1-(pyridine-3-yl)-4-[1,1,2-trifluoro-2-(trifluoromethoxy)ethoxy]-1H-pyrazole-3-carboxamide (0.80 g, 2.2 mmoL) and triethylamine (0.66 g, 6.5 mmoL) were dissolved, and trifluoroacetic anhydride (0.57 g, 2.7 mmoL) was added under cooling on ice, and then the solution was stirred for 30 minutes, and then trifluoroacetic anhydride (0.10 g, 0.47 mmoL) was further added and stirred at room temperature for 30 minutes. After end of the reaction, the reaction solution was poured into water, and extracted with dichloromethane. The obtained organic layer was dried over anhydrous magnesium sulfate, and then the solvent was distilled off under reduced pressure. The residue was purified by silica gel column chromatography to 1-(pyridine-3-yl)-4-[1,1,2-trifluoro-2-(trifluoromethoxy)ethoxy]-1H-pyrazole-3-carbonitrile (0.72 g, yield: 95%).

$^1$H-NMR data (400 MHz, CDCl$_3$/TMS δ (ppm)): 6.05 (1H, dt), 7.51 (1H, m), 8.06-8.10 (2H, m), 8.71 (1H, dd), 8.98 (1H, d)

Example 7

Production of 1-(pyridine-3-yl)-4-[1,1,2-trifluoro-2-(trifluoromethoxy)ethoxy]-1H-pyrazole-3-carbothioamide (Present Compound Number: A-5436)

In 1,4-dioxane (10 mL), 1-(pyridine-3-yl)-4-[1,1,2-trifluoro-2-(trifluoromethoxy)ethoxy]-1H-pyrazole-3-carboxamide (0.60 g, 1.6 mmoL) was dissolved, and Lawesson's reagent (0.52 g, 1.3 mmoL) was added and stirred at 80° C. for 1 hour. After end of the reaction, the solvent was distilled off under reduced pressure, and the residue was purified by silica gel column chromatography to give 1-(pyridine-3-yl)-4-[1,1,2-trifluoro-2-(trifluoromethoxy)ethoxy]-1H-pyrazole-3-carbothioamide (0.64 g, yield: quantitative).

$^1$H-NMR data (400 MHz, DMSO-d6/TMS δ (ppm)): 7.17 (1H, dt), 7.61 (1H, dd), 8.37 (1H, d), 8.61 (1H, d), 8.96 (1H, s), 9.23 (1H, d), 9.53 (1H, br), 9.88 (1H, br)

Example 8

Production of 3-(3-carbamoyl-4-[1,1,2-trifluoro-2-(trifluoromethoxy)ethoxy]-1H-pyrazole-1-yl)pyridine-1-oxide (Present Compound Number: A-5510)

In chloroform (50 mL), 1-(pyridine-3-yl)-4-[1,1,2-trifluoro-2-(trifluoromethoxy)ethoxy]-1H-pyrazole-3-carboxamide (0.15 g, 0.4 mmoL) was dissolved, and m-chloroperbenzoic acid (content: 60%, 0.25 g, 0.87 mmoL) was added and heated under reflux for 1 hour. After end of the reaction, the solvent was distilled off under reduced pressure, and the residue was purified by silica gel column chromatography to give 3-(3-carbamoyl-4-[1,1,2-trifluoro-2-(trifluoromethoxy)ethoxy]-1H-pyrazole-1-yl)pyridine 1-oxide (0.12 g, yield: 77%).

$^1$H-NMR data (400 MHz, DMSO-d6/TMS δ (ppm)): 7.24 (1H, d), 7.58 (2H, br), 7.93 (2H, br), 8.25 (1H, s), 9.01 (1H, d), 9.05 (1H, d)

Physical property values, including those in the above-described examples, of the present compound [I] synthesized in accordance with the above-described examples are shown in the following Table 150 to Table 155, and physical property values of the present compound [II] are similarly shown in the following Table 156 to Table 159. The compound numbers and the signs in Tables are as defined above.

TABLE 150

| Compound | Physical Property | Value |
|---|---|---|
| A-0001 | Melting Point (° C.) | 233-236 |
| A-0002 | Melting Point (° C.) | 205-208 |
| A-0003 | Melting Point (° C.) | 136-139 |
| A-0005 | Melting Point (° C.) | 245-248 |
| A-0006 | Melting Point (° C.) | 119-122 |
| A-0007 | Melting Point (° C.) | 128-131 |
| A-0008 | Melting Point (° C.) | 156-158 |
| A-0009 | Melting Point (° C.) | 168-170 |
| A-0010 | Melting Point (° C.) | 178-180 |
| A-0011 | Melting Point (° C.) | 119-122 |
| A-0012 | Melting Point (° C.) | 132-133 |
| A-0013 | Melting Point (° C.) | 127-129 |
| A-0014 | Melting Point (° C.) | 130-132 |
| A-0015 | Melting Point (° C.) | 133-135 |
| A-0016 | Melting Point (° C.) | 154-157 |
| A-0017 | Melting Point (° C.) | 144-147 |
| A-0018 | Melting Point (° C.) | 111-112 |
| A-0019 | Melting Point (° C.) | 152-153 |
| A-0020 | Melting Point (° C.) | 102-105 |
| A-0021 | Melting Point (° C.) | 117-120 |
| A-0022 | Melting Point (° C.) | 105-107 |
| A-0028 | Melting Point (° C.) | 111-114 |
| A-0031 | Melting Point (° C.) | 183-186 |
| A-0032 | Melting Point (° C.) | 143-146 |
| A-0034 | Melting Point (° C.) | 130-133 |
| A-0043 | Melting Point (° C.) | 121-124 |
| A-0044 | Melting Point (° C.) | 136-137 |
| A-0045 | Melting Point (° C.) | 139-141 |
| A-0046 | Melting Point (° C.) | 146-147 |
| A-0047 | Melting Point (° C.) | 156-158 |
| A-0050 | Melting Point (° C.) | 137-140 |
| A-0051 | Melting Point (° C.) | 140-142 |
| A-0052 | Melting Point (° C.) | 117-119 |
| A-0056 | Melting Point (° C.) | 83-86 |
| A-0058 | Melting Point (° C.) | 124-127 |
| A-0060 | Melting Point (° C.) | 106-109 |
| A-0061 | Melting Point (° C.) | 142-145 |
| A-0062 | Melting Point (° C.) | 126-128 |
| A-0065 | Melting Point (° C.) | 112-114 |
| A-0067 | Melting Point (° C.) | 127-130 |
| A-0070 | Melting Point (° C.) | 113-115 |
| A-0071 | Melting Point (° C.) | 130-131 |
| A-0072 | Melting Point (° C.) | 147-149 |
| A-0073 | Melting Point (° C.) | 145-147 |
| A-0075 | Melting Point (° C.) | 142-144 |
| A-0076 | Melting Point (° C.) | 151-153 |
| A-0077 | Melting Point (° C.) | 97-100 |
| A-0078 | Melting Point (° C.) | 68-71 |
| A-0080 | Melting Point (° C.) | 169-171 |
| A-0081 | Melting Point (° C.) | 173-176 |
| A-0082 | Melting Point (° C.) | 143-145 |
| A-0083 | Melting Point (° C.) | 92-95 |
| A-0086 | Melting Point (° C.) | 165-168 |

TABLE 151

| Compound | Physical Property | Value |
|---|---|---|
| A-0088 | Melting Point (° C.) | 99-102 |
| A-0089 | Melting Point (° C.) | 173-175 |
| A-0092 | Melting Point (° C.) | 151-154 |
| A-0093 | Melting Point (° C.) | 151-154 |
| A-0094 | Melting Point (° C.) | 147-150 |
| A-0095 | Melting Point (° C.) | 188-191 |
| A-0098 | Melting Point (° C.) | 131-133 |
| A-0100 | Melting Point (° C.) | 90-93 |
| A-0103 | Melting Point (° C.) | 160-163 |
| A-0105 | Melting Point (° C.) | 151-152 |
| A-0106 | Melting Point (° C.) | 65-68 |
| A-0107 | Melting Point (° C.) | 96-97 |
| A-0111 | Refractive Index($n_D^{20}$) | 1.6081 |
| A-0113 | Melting Point (° C.) | 134-135 |
| A-0120 | Melting Point (° C.) | 122-124 |
| A-0121 | Melting Point (° C.) | 140-143 |
| A-0122 | Melting Point (° C.) | 175-177 |

TABLE 151-continued

| Compound | Physical Property | Value |
|---|---|---|
| A-0124 | Melting Point (° C.) | 73-76 |
| A-0125 | Melting Point (° C.) | 67-70 |
| A-0126 | Melting Point (° C.) | 144-147 |
| A-0134 | Melting Point (° C.) | 224-227 |
| A-0135 | Melting Point (° C.) | 164-166 |
| A-0136 | Melting Point (° C.) | 164-166 |
| A-0137 | Melting Point (° C.) | 256-259 |
| A-0138 | Melting Point (° C.) | 184-187 |
| A-0144 | Melting Point (° C.) | 118-121 |
| A-0145 | Melting Point (° C.) | 136-139 |
| A-0151 | Melting Point (° C.) | 101-103 |
| A-0152 | Melting Point (° C.) | 86-89 |
| A-0153 | Melting Point (° C.) | 115-118 |
| A-0165 | Melting Point (° C.) | 96-98 |
| A-0166 | Melting Point (° C.) | 102-104 |
| A-0177 | Melting Point (° C.) | 210-213 |
| A-0186 | Melting Point (° C.) | 170-173 |
| A-0192 | Melting Point (° C.) | 160-163 |
| A-0197 | Melting Point (° C.) | 200-203 |
| A-0199 | Melting Point (° C.) | 180-183 |
| A-0203 | Melting Point (° C.) | 195-198 |
| A-0205 | Melting Point (° C.) | 210-213 |
| A-0211 | Melting Point (° C.) | 172-175 |
| A-0212 | Melting Point (° C.) | 191-194 |
| A-0217 | Melting Point (° C.) | 188-191 |
| A-0221 | Melting Point (° C.) | 120-123 |
| A-0225 | Melting Point (° C.) | 166-168 |
| A-0234 | Melting Point (° C.) | 153-156 |
| A-0240 | Melting Point (° C.) | 162-165 |
| A-0246 | Melting Point (° C.) | 157-160 |
| A-0247 | Melting Point (° C.) | 158-161 |
| A-0248 | Melting Point (° C.) | 147-149 |
| A-0249 | Melting Point (° C.) | 175-178 |
| A-0253 | Melting Point (° C.) | 67-70 |
| A-0254 | Melting Point (° C.) | 149-152 |
| A-0283 | Melting Point (° C.) | 53-56 |

TABLE 152

| Compound | Physical Property | Value |
|---|---|---|
| A-0468 | Melting Point (° C.) | 91-92 |
| A-0658 | Melting Point (° C.) | 99-101 |
| A-0849 | Melting Point (° C.) | 94-97 |
| A-1045 | Melting Point (° C.) | 104-106 |
| A-1106 | Melting Point (° C.) | 57-60 |
| A-1120 | Refractive Index($n_D^{20}$) | 1.5054 |
| A-1302 | Melting Point (° C.) | 83-86 |
| A-1368 | Refractive Index($n_D^{20}$) | 1.4932 |
| A-1429 | Melting Point (° C.) | 78-81 |
| A-1625 | Melting Point (° C.) | 123-125 |
| A-1684 | Melting Point (° C.) | 125-128 |
| A-1882 | Melting Point (° C.) | 125-127 |
| A-1948 | Refractive Index($n_D^{20}$) | 1.5037 |
| A-2014 | Melting Point (° C.) | 92-95 |
| A-2080 | Melting Point (° C.) | 129-131 |
| A-2155 | Melting Point (° C.) | 174-177 |
| A-2164 | Melting Point (° C.) | 190-193 |
| A-2337 | Melting Point (° C.) | 141-143 |
| A-2403 | Refractive Index($n_D^{20}$) | 1.4956 |
| A-2469 | Melting Point (° C.) | 159-162 |
| A-2535 | Refractive Index($n_D^{20}$) | 1.4759 |
| A-2610 | Melting Point (° C.) | 66-69 |
| A-2792 | Melting Point (° C.) | 99-102 |
| A-2858 | Melting Point (° C.) | 111-114 |
| A-2924 | Melting Point (° C.) | 102-105 |
| A-2990 | Melting Point (° C.) | 127-129 |
| A-3056 | Melting Point (° C.) | 142-145 |
| A-3122 | Melting Point (° C.) | 124-126 |
| A-3188 | Melting Point (° C.) | 99-100 |
| A-3254 | Melting Point (° C.) | 135-137 |
| A-3320 | Melting Point (° C.) | 165-167 |
| A-3386 | Refractive Index($n_D^{20}$) | 1.4935 |
| A-3518 | Refractive Index($n_D^{20}$) | 1.4962 |
| A-3584 | Melting Point (° C.) | 145-149 |

TABLE 152-continued

| Compound | Physical Property | Value |
|---|---|---|
| A-3650 | Refractive Index($n_D^{20}$) | 1.5076 |
| A-3716 | Refractive Index($n_D^{20}$) | 1.5279 |
| A-3791 | Refractive Index($n_D^{20}$) | 1.4919 |
| A-3973 | Melting Point (° C.) | 92-95 |
| A-4095 | Melting Point (° C.) | 113-115 |
| A-4257 | Melting Point (° C.) | 173-175 |
| A-4304 | Melting Point (° C.) | 103-104 |
| A-4883 | Melting Point (° C.) | 171-174 |
| A-5436 | Melting Point (° C.) | 155-158 |
| A-5510 | Melting Point (° C.) | 207-210 |

TABLE 153

| Compound | Physical Property | Value |
|---|---|---|
| Methanesulfonate of A-0050 | Melting Point (° C.) | 168-170 |
| Methanesulfonate of A-0071 | Melting Point (° C.) | 137-140 |
| p-toluenespifonate of A-0071 | Melting Point (° C.) | 127-130 |
| Hydrochloride of A-0071 | Melting Point (° C.) | 139-142 |

TABLE 154

| Compound | Physical Property Value ($^1$H-NMR Data, in CDCl$_3$ TMS δ(ppm)) | |
|---|---|---|
| A-0027 | 300 MHz | 1.24(3H, t), 3.60(2H, q), 3.82(2H, t), 4.26 (2H, t), 6.32(1H, br), 7.08(1H, br), 7.43(1H, dd), 7.79 (1H, s),8.18(1H, d), 8.59(1H,d), 8.97(1H,d) |
| A-0209 | 300 MHz | 1.71(3H, d), 3.84-4.01(2H, m), 4.58(1H, q), 5.84(1H, br), 6.84(1H, br), 7.42(1H, br), 7,82 (1H, s), 8.00(1H, d), 8.68(1H, br), 8.99(2H,br) |
| A-1443 | 300 MHz | 4.12(2H, m), 6.11(1H, dt), 7.11(1H, br), 7.49 (1H, dd),8.04-8.08(2H, m), 8.69(1H, dd), 9.00 (1H, d) |
| A-1686 | 400 MHz | 4.41(2H, d), 4.72(2H, t), 7.29(1H, br), 7.52 (1H, dd),7.85(1H, s), 8.03(1H, d), 8.65(1H,d), 8.97(1H,d) |
| A-2139 | 400 MHz | 2.62(3H, s), 5.20(1H, dsext), 7.52(1H, dd), 8.06-8.09(2H, m), 8.71(1H, dd), 8.99(1H, d), 9.21 (1H, br) |
| A-3452 | 400 MHz | 1.82(4H, quin), 2.73(4H, quin), 4.38-4.47 (2H, m),6.18(1H, dt), 7.27(1H, br), 7.45-7.49 (1H, m), 8.02-8.07(2H, m), 8.66(1H, dd), 9.00 (1H, d) |
| A-4038 | 300 MHz | 3.77-3.84(8H, m), 6.05(1H, dt), 7.45(1H, dd), 8.01-8.05(2H, m), 8.64(1H, dd), 8.97(1H, d) |
| A-5658 | 300 MHz | 2.66-2.83(2H, m), 4.42(2H, t), 5,66(1H, br), 6.81(1H, br), 7.45(1H, dd), 7.73(1H, s), 8.13 (1H, m), 8.61(1H, dd), 8.97(1H, d) |

| Compound | Physical Property Value ($^1$H-NMR Data, DMSO-d$_6$ TMS δ(ppm)) | |
|---|---|---|
| A-0004 | 400 MHz | 1.33(6H, d), 4.44(1H, sep), 7.29(1H, br), 7.52 (1H, br), 7.57(1H, dd), 8.30(1H, dd), 8.54 (1H, dd), 8.59(1H, s), 9.16(1H,d) |

TABLE 155

| | Physical Property Value(HRMS, m/z ([M + H])) | | |
|---|---|---|---|
| Compound | Chemical Formula | Calculated Value | Measured Value |
| A-1700 | C$_{14}$H$_{19}$F$_6$N$_5$O$_3$ | 410.0688 | 410.0694 |

TABLE 156

| Compound | Physical Property | Value |
|---|---|---|
| B-0003 | Melting Point (° C.) | 240-243 |
| B-0004 | Melting Point (° C.) | 217-220 |
| B-0006 | Melting Point (° C.) | 199-202 |
| B-0007 | Melting Point (° C.) | 168-170 |
| B-0008 | Melting Point (° C.) | 163-164 |
| B-0009 | Melting Point (° C.) | 144-147 |
| B-0010 | Melting Point (° C.) | 212-215 |
| B-0011 | Melting Point (° C.) | 133-134 |
| B-0013 | Melting Point (° C.) | 162-164 |
| B-0014 | Melting Point (° C.) | 150-153 |
| B-0015 | Melting Point (° C.) | 145-148 |
| B-0016 | Melting Point (° C.) | 150-153 |
| B-0017 | Melting Point (° C.) | 165-168 |
| B-0019 | Melting Point (° C.) | 176-178 |
| B-0020 | Melting Point (° C.) | 157-158 |
| B-0021 | Melting Point (° C.) | 151-154 |
| B-0022 | Melting Point (° C.) | 147-150 |
| B-0043 | Melting Point (° C.) | 177-180 |
| B-0045 | Melting Point (° C.) | 165-168 |
| B-0046 | Melting Point (° C.) | 207-210 |
| B-0050 | Melting Point (° C.) | 174-176 |
| B-0051 | Melting Point (° C.) | 159-161 |
| B-0052 | Melting Point (° C.) | 170-173 |
| B-0055 | Melting Point (° C.) | 138-141 |
| B-0058 | Melting Point (° C.) | 177-180 |
| B-0062 | Melting Point (° C.) | 171-174 |
| B-0065 | Melting Point (° C.) | 164-167 |
| B-0067 | Melting Point (° C.) | 167-170 |
| B-0068 | Melting Point (° C.) | 201-204 |
| B-0075 | Melting Point (° C.) | 173-175 |
| B-0078 | Melting Point (° C.) | 126-129 |
| B-0080 | Melting Point (° C.) | 225-228 |
| B-0081 | Melting Point (° C.) | 213-215 |
| B-0082 | Melting Point (° C.) | 211-213 |
| B-0083 | Melting Point (° C.) | 200-202 |
| B-0088 | Melting Point (° C.) | 181-183 |
| B-0089 | Melting Point (° C.) | 168-171 |
| B-0093 | Melting Point (° C.) | 210-213 |
| B-0094 | Melting Point (° C.) | 193-196 |
| B-0095 | Melting Point (° C.) | 215-217 |
| B-0098 | Melting Point (° C.) | 166-169 |
| B-0100 | Melting Point (° C.) | 153-155 |
| B-0103 | Melting Point (° C.) | 182-185 |
| B-0105 | Melting Point (° C.) | 175-178 |
| B-0120 | Melting Point (° C.) | 131-133 |
| B-0121 | Melting Point (° C.) | 179-181 |
| B-0136 | Melting Point (° C.) | 136-139 |
| B-0137 | Melting Point (° C.) | 166-168 |
| B-0151 | Melting Point (° C.) | 182-185 |
| B-0152 | Melting Point (° C.) | 166-169 |
| B-0153 | Melting Point (° C.) | 142-144 |
| B-0165 | Melting Point (° C.) | 120-123 |
| B-0166 | Melting Point (° C.) | 145-147 |

TABLE 157

| Compound | Physical Property | Value |
|---|---|---|
| B-0192 | Melting Point (° C.) | 248-249 |
| B-0246 | Melting Point (° C.) | 250-253 |
| B-0247 | Melting Point (° C.) | 230-233 |
| B-0248 | Melting Point (° C.) | 207-209 |
| B-0249 | Melting Point (° C.) | 200-203 |
| B-0253 | Melting Point (° C.) | 189-192 |
| B-0254 | Melting Point (° C.) | 218-221 |
| B-0255 | Melting Point (° C.) | 130-131 |
| B-0256 | Melting Point (° C.) | 130-133 |
| B-0257 | Melting Point (° C.) | 104-106 |
| B-0258 | Refractive Index($n_D^{20}$) | 1.5569 |
| B-0259 | Refractive Index($n_D^{20}$) | 1.5322 |
| B-0260 | Melting Point (° C.) | 95-96 |
| B-0261 | Melting Point (° C.) | 105-107 |
| B-0263 | Melting Point (° C.) | 59-62 |
| B-0264 | Melting Point (° C.) | 87-90 |
| B-0265 | Melting Point (° C.) | 122-125 |
| B-0266 | Melting Point (° C.) | 90-91 |
| B-0267 | Melting Point (° C.) | 92-95 |
| B-0268 | Refractive Index($n_D^{20}$) | 1.551 |
| B-0269 | Melting Point (° C.) | 80-82 |
| B-0271 | Melting Point (° C.) | 91-92 |
| B-0272 | Melting Point (° C.) | 57-60 |
| B-0273 | Melting Point (° C.) | 61-63 |
| B-0274 | Melting Point (° C.) | 51-53 |
| B-0275 | Melting Point (° C.) | 50-52 |
| B-0276 | Melting Point (° C.) | 47-50 |
| B-0281 | Melting Point (° C.) | 73-74 |
| B-0282 | Melting Point (° C.) | 41-43 |
| B-0285 | Melting Point (° C.) | 94-97 |
| B-0286 | Melting Point (° C.) | 103-104 |
| B-0298 | Melting Point (° C.) | 101-102 |
| B-0299 | Melting Point (° C.) | 125-127 |
| B-0300 | Melting Point (° C.) | 73-76 |
| B-0304 | Melting Point (° C.) | 103-104 |
| B-0305 | Melting Point (° C.) | 124-126 |
| B-0306 | Melting Point (° C.) | 117-120 |
| B-0310 | Melting Point (° C.) | 96-99 |
| B-0312 | Melting Point (° C.) | 97-99 |
| B-0314 | Melting Point (° C.) | 63-65 |
| B-0316 | Melting Point (° C.) | 110-112 |
| B-0319 | Melting Point (° C.) | 104-107 |
| B-0321 | Melting Point (° C.) | 80-83 |
| B-0324 | Melting Point (° C.) | 94-97 |
| B-0325 | Melting Point (° C.) | 85-87 |
| B-0329 | Melting Point (° C.) | 97-100 |
| B-0330 | Melting Point (° C.) | 126-128 |
| B-0332 | Melting Point (° C.) | 108-110 |
| B-0334 | Melting Point (° C.) | 122-124 |
| B-0335 | Melting Point (° C.) | 107-109 |
| B-0336 | Refractive Index($n_D^{20}$) | 1.5509 |
| B-0340 | Melting Point (° C.) | 124-127 |
| B-0342 | Melting Point (° C.) | 66-68 |

TABLE 158

| Compound | Physical Property | Value |
|---|---|---|
| B-0343 | Melting Point (° C.) | 98-101 |
| B-0346 | Melting Point (° C.) | 103-106 |
| B-0347 | Melting Point (° C.) | 105-106 |
| B-0348 | Melting Point (° C.) | 96-98 |
| B-0349 | Melting Point (° C.) | 118-120 |
| B-0352 | Melting Point (° C.) | 95-96 |
| B-0354 | Melting Point (° C.) | 88-90 |
| B-0357 | Melting Point (° C.) | 98-101 |
| B-0359 | Melting Point (° C.) | 123-125 |
| B-0360 | Melting Point (° C.) | 102-103 |
| B-0361 | Melting Point (° C.) | 86-87 |
| B-0367 | Melting Point (° C.) | 65-66 |
| B-0374 | Melting Point (° C.) | 55-58 |
| B-0375 | Refractive Index($n_D^{20}$) | 1.5681 |
| B-0376 | Melting Point (° C.) | 143-146 |
| B-0378 | Melting Point (° C.) | 114-116 |
| B-0379 | Melting Point (° C.) | 118-119 |
| B-0380 | Melting Point (° C.) | 80-82 |
| B-0390 | Melting Point (° C.) | 115-117 |
| B-0405 | Melting Point (° C.) | 110-113 |
| B-0406 | Melting Point (° C.) | 97-99 |
| B-0407 | Melting Point (° C.) | 91-94 |
| B-0419 | Melting Point (° C.) | 63-66 |
| B-0420 | Melting Point (° C.) | 57-60 |
| B-0438 | Melting Point (° C.) | 136-138 |
| B-0446 | Melting Point (° C.) | 90-92 |
| B-0463 | Melting Point (° C.) | 158-161 |
| B-0465 | Melting Point (° C.) | 97-100 |
| B-0471 | Melting Point (° C.) | 103-106 |
| B-0475 | Melting Point (° C.) | 138-141 |
| B-0494 | Melting Point (° C.) | 129-130 |
| B-0500 | Melting Point (° C.) | 153-156 |
| B-0501 | Melting Point (° C.) | 93-95 |
| B-0502 | Melting Point (° C.) | 165-167 |

TABLE 158-continued

| Compound | Physical Property Value | |
|---|---|---|
| B-0503 | Melting Point (° C.) | 160-162 |
| B-0504 | Melting Point (° C.) | 159-161 |
| B-0507 | Refractive Index($n_D^{20}$) | 1.5858 |
| B-0508 | Melting Point (° C.) | 115-117 |
| B-0891 | Melting Point (° C.) | 90-93 |
| B-1088 | Melting Point (° C.) | 121-122 |
| B-1133 | Melting Point (° C.) | 53-54 |
| B-1474 | Melting Point (° C.) | 129-131 |
| B-1667 | Melting Point (° C.) | 141-143 |
| B-2107 | Melting Point (° C.) | 196-199 |
| B-2246 | Melting Point (° C.) | 122-124 |
| B-2300 | Melting Point (° C.) | 108-109 |

TABLE 159

| Compound | Physical Property Value ($^1$H-NMR Data, in CDCl$_3$ TMS δ(ppm)) | |
|---|---|---|
| B-0262 | 300 MHz | 1.02(3H, t), 1.37-1,45(6H, m), 1.66-1.84 (2H, m),4.08-4.18(1H, m), 4.40-4.49(2H, m), 7.42(1H, dd), 7.62(1H, s), 8.11-8.15(1H, m), 8.59(1H, dd), 8.95(1H,d) |
| B-0270 | 300 MHz | 0.93-1.03(6H, m), 1.40-1.82(9H, m), 3.92-3.99 (1H,m), 4.42(2H, q), 7,39-7.44(1H, m), 7.58 (1H, s), 8.11-8.15(1H, m), 8.58(1H, dd), 8.94 (1H, d) |
| B-0297 | 300 MHz | 1.43(3H, t), 2.64-2.77(2H, m), 4.26(2H, t), 4.45(2H,q), 7.44(1H, dd), 7.70(1H, s), 8.11-8.15(1H, m), 8.61(1H, d), 8.96(1H, d) |
| B-0337 | 300 MHz | 0.65-0.81(4H, m), 1.22-1.30(1H, m), 1.41 (3H, t), 4.44(2H, q), 4.70(2H, d), 7.42(1H, dd), 7.78(1H, s), 8.10-8.15(1H, m), 8.59(1H, dd), 8,94(1H, d) |
| B-0702 | 400 MHz | 1.41(3H, t), 4.51(2H, t), 7.37(1H, br), 7.46 (1H, s),7.70(1H, d), 8,86(1H, s), 8.92(1H, d) |
| B-0727 | 400 MHz | 1.40(3H, t), 4.49(2H, q), 4.63(1H, t), 7,60 (1H, s),7.74(1H, d), 8.90(1H, s), 8.92(1H, d) |
| B-3247 | 400 MHz | 7.29(1H, dt), 7.59(1H, dd), 7.89(1H, dd), 8.27(1H, d),8.91(1H, t), 9.04(1H, s), 13.52 (1H, br) |
| B-3322 | 300 MHz | 1.41(3H, t), 4.45(2H, q), 6.04(1H, dt), 7.41 (1H, dd),7.68(1H, dd), 7.98(1H, s), 8.21 (1H, d), 8.76(1H, t) |
| B-3361 | 300 MHz | 1.43(3H, t), 2.65-2.82(2H, m), 4.34(2H, t), 4,45(2H, q), 7.44(1H, dd), 7.71(1H, s), 8.11-8.15(1H, m), 8.62(1H, dd), 8.96(1H, d) |

Next, formulation examples of the harmful organism control agent of the present invention using the pyrazole-3-carboxylic acid amide derivative of the present invention produced in the manner as described above, or an agriculturally acceptable salt thereof will be specifically described. It is to be noted that the compound, the kinds and the mixing ratios of additives are not limited to this, but may be changed in a wide range. In the following description, "part" means a part by mass.

(Formulation Example 1) Emulsion

| | |
|---|---|
| Compounds described in Table 1 to Table 93, and Table 150 to Table 155 | 10 parts |
| cyclohexanone | 30 parts |
| Polyoxyethylene alkyl aryl ether | 11 parts |
| Sodium alkylbenzenesulfonate | 4 parts |
| Methylnaphthalene | 45 parts |

These ingredients were uniformly dissolved to give an emulsifiable concentrate.

(Formulation Example 2) Water-Dispersible Powder

| | |
|---|---|
| Compounds described in Table 1 to Table 93, and Table 150 to Table 155 | 10 parts |
| Sodium salt of naphthalene sulfonic acid formalin condensate | 0.5 parts |
| Polyoxyethylene alkyl aryl ether | 0.5 parts |
| Diatomaceous earth | 24 parts |
| Clay | 65 parts |

These ingredients were uniformly mixed and ground to give a water-dispersible powder.

(Formulation Example 3) Dust

| | |
|---|---|
| Compounds described in Table 1 to Table 93, and Table 150 to Table 155 | 2 parts |
| Diatomaceous earth | 5 parts |
| Clay | 93 parts |

These ingredients were uniformly mixed and ground to give a dust.

(Formulation Example 4) Granule

| | |
|---|---|
| Compounds described in Table 1 to Table 93, and Table 150 to Table 155 | 5 parts |
| Sodium salt of lauryl alcohol sulfate | 2 parts |
| Sodium ligninsulfonate | 5 parts |
| Carboxymethylcellulose | 2 parts |
| Clay | 86 parts |

These ingredients were uniformly mixed and ground. To this mixture, water in an amount corresponding to 20 parts was added and kneaded, and processed into 14 to 32 mesh granules by using an extruding granulator, and then dried to give granules.

(Formulation Example 5) Flowable Concentrate

| | |
|---|---|
| Compounds described in Table 1 to Table 93, and Table 150 to Table 155 | 20 parts |
| Polyoxyethylene styrenated phenyl ether sulfate | 4 parts |
| Ethylene glycol | 7 parts |
| Silicone AF-118N (available from Asahi Kasei Corporation) | 0.02 parts |
| Water | 68.98 parts |

These ingredients were mixed with a high-speed stirrer for 30 minutes, and then ground with a wet grinder to give a flowable concentrate.

(Formulation Example 6) Water-Dispersible Granule

| | |
|---|---|
| Compounds described in Table 1 to Table 93, and Table 150 to Table 155 | 10 parts |
| Sodium ligninsulfonate | 5 parts |
| Polyoxyethylene alkyl aryl ether | 1 part |

-continued

| | |
|---|---|
| Sodium polycarboxylate | 3 parts |
| White carbon | 5 parts |
| Pregelatinized starch | 1 part |
| Calcium carbonate | 65 parts |
| Water | 10 parts |

These ingredients were mixed and kneaded and extrusion granulated. The obtained granules were dried by a fluidized-bed dryer, to give a water-dispersible granule.

Next, the effect exerted by the harmful organism control agent of the present invention will be described by way of test examples.

(Test Example 1) *Plutella xylostella* Killing Test

The water-dispersible powder prepared in accordance with Manufacturing example 2 was diluted in water so that the concentration of the active ingredient was 500 ppm. A cabbage leaf was dipped in this liquid agent, and air-dried, and then put into a plastic cup. Ten second instar larvae of *Plutella xylostella* were released in the cup, and the cup was lidded. Then, the cup was placed in a thermostatic chamber at 25° C., and the number of dead insects was examined after 6 days, and the percentage of dead insects was determined by the calculation formula of numerical formula 1. The test was conducted singly.

Percentage of Dead Insects(%) = [Numerical formula 1]

$$\left(-\frac{\text{Number of Live Insects}}{\text{Number of tested Insects}}\right) \times 100$$

The compounds showing a percentage of dead insects of 50% or more in this test are as follows.

A-0001, A-0006, A-0008A, A-0009, A-0010, A-0015, A-0015, A-0028, A-0067, A-0082, A-0083, A-0098, A-0100, A-0111, A-0120, A-0125, A-0144, A-0145, A-0165, A-0177, A-0197, A-0203, A-0211, A-0212, A-0225, A-0234, A-0246, A-0247, A-0248, A-0254, A-0283, A-1106, A-1120, A-1302, A-1368, A-1429, A-1443, A-1684, A-1948, A-2014, A-2164, A-2337, A-2403, A-2469, A-2535, A-2610, A-2858, A-2924, A-2990, A-3056, A-3188, A-3254, A-3320, A-3386, A-3452, A-3518, A-3584, A-3650, A-3716, A-3791, A-3973, A-4257, B-0006, B-0009, B-0010, B-0013, B-0014, B-0015, B-0016, B-0017, B-0043, B-0050, B-0051, B-0068, B-0083, B-0093, B-0098, B-0100, B-0137, B-0246, B-0247, B-0253, B-0254, B-0263, B-0264, B-0267, B-0269, B-0270, B-0271, B-0275, B-0285, B-0286, B-0332, B-0336, B-0337, B-0347, B-0354, B-0357, B-0360, B-0374, B-0375, B-0376, B-0379, B-0405, B-0438, B-0446, B-0465, B-0500, B-0503, B-0507, B-0508, B-0727, B-01088, B-01474, B-02300

(Test Example 2) *Helicoverpa armigera* Killing Test

The water-dispersible powder prepared in accordance with Manufacturing example 2 was diluted in water so that the concentration of the active ingredient was 500 ppm. A cabbage leaf was dipped in this liquid agent, and air-dried, and then put into a plastic cup. Five newly hatched larvae of *Helicoverpa armigera* were released in the cup, and the cup was lidded. Then, the cup was placed in a thermostatic chamber at 25° C., and the number of dead insects was examined after 6 days, and the percentage of dead insects was determined by the calculation formula of numerical formula 1. The test was conducted in duplicate.

The compounds showing a percentage of dead insects of 50% or more in this test are as follows.

A-0004, A-0006, A-0018, A-0043, A-0045, A-0052, A-0058, A-0061, A-0062, A-0065, A-0067, A-0073, A-0145, A-0151, A-0186, A-0246, A-1106, A-1429, A-1443, A-1625, A-3122, A-3254, A-3320, A-3791, A-3973, A-4257, A-4304, A-5436, B-0004, B-0006, B-0016, B-0043, B-0045, B-0056, B-0065, B-0067, B-0088, B-0089, B-0095, B-0153, B-0165, B-0192, B-0246, B-0256, B-0276, B-02786, B-0297, B-0299, B-0300, B-0312, B-0316, B-0319, B-0321, B-0334, B-0340, B-0348, B-0349, B-0360, B-0405, B-0407, B-0471, B-0475, B-0500, B-0508, B-0891, B-1133, B-1667, B-2300

(Test Example 3) *Aphis gossypii* Killing Test

The water-dispersible powder prepared in accordance with Formulation example 2 was diluted in water so that the concentration of the active ingredient was 500 ppm. A nursery plant of cucumber preliminarily inoculated with nymphs of *Aphis gossypii* was dipped in this liquid agent, and air-dried. The nursery plant of cucumber after the treatment was placed in a thermostatic chamber at 25° C., and the number of live insects was counted after 3 days, and the percentage of dead insects was determined by the calculation formula of numerical formula 1. The test was conducted singly.

The compounds showing a percentage of dead insects of 50% or more in this test are as follows.

A-0001, A-0002, A-0003, A-0004, A-0005, A-0006, A-0007, A-0008, A-0009, A-0010, A-0011, A-0012, A-0013, A-0014, A-0015, A-0017, A-0018, A-0019, A-0020, A-0027, A-0028, A-0031, A-00, A-0034, A-0043, A-0044, A-0045, A-0046, A-0047, A-0050, A-0051, A-0052, A-0053, A-0056, A-0058, A-0060, A-0061, A-0062, A-0065, A-0067, A-0070, A-0071, A-0072, A-0073, A-0075, A-0076, A-0077, A-0078, A-0080, A-0081, A-0083, A-0086, A-0088, A-0092, A-0093, A-0094, A-0098, A-0100, A-0103, A-0105, A-0106, A-0111, A-0113, A-0122, A-0151, A-0152, A-0153, A-0165, A-0186, A-0221, A-0225, A-0234, A-0240, A-0249, A-0253, A-0254, A-0283, A-0468, A-0658, A-0849, A-1045, A-1106, A-1120, A-1302, A-1368, A-1429, A-1443, A-1625, A-1684, A-1686, A-1700, A-1882, A-1948, A-2014, A-2080, A-2155, A-2164, A-2337, A-2403, A-2469, A-2535, A-2610, A-2792, A-2858, A-2924, A-2990, A-3056, A-3122, A-3188, A-3254, A-3320, A-3386, A-3452, A-3518, A-3584, A-3650, A-3716, A-3791, A-3973, A-4095, A-4304, A-5436, A-5510

(Test Example 4) *Nilaparvata lugens* Killing Activity Test

The water-dispersible powder prepared in accordance with Formulation example 2 was diluted in water so that the concentration of the active ingredient was 500 ppm. Paddy was dipped in this liquid agent, and then put into a plastic cup. Ten second instar larvae of *Nilaparvata lugens* were released in the plastic cup, and the cup was lidded, and placed in a thermostatic chamber at 25° C. After 6 days, the number of live insects was counted, and the percentage of dead insects was determined by the calculation formula of numerical formula 1. The test was conducted singly.

The compounds showing a percentage of dead insects of 50% or more in this test are as follows.

A-0002, A-0003, A-0004, A-0005, A-0006, A-0007, A-0009, A-0010, A-0011, A-0013, A-0015, A-0016, A-0017, A-0018, A-0019, A-0020, A-0021, A-0022, A-27, A-0028,

A-0032, A-0034, A-0043, A-0045, A-0046, A-0047, A-0051, A-0052, A-0056, A-0058, A-0060, A-0062, A-0067, A-0070, A-0071, A-0073, A-0075, A-0076, A-0078, A-0080, A-0081, A-0081, A-0082, A-0083, A-0089, A-0092, A-0093, A-0094, A-0095, A-0098, A-0100, A-0103, A-0105, A-0113, A-0120, A-0121, A-01222, A-0125, A-0126, A-0135, A-0136, A-0137, A-0144, A-0145, A-0151, A-0153, A-0165, A-0166, A-0177, A-0186, A-0209, A-0211, A-0217, A-0221, A-0234, A-0246, A-0247, A-0248, A-0249, A-0253, A-0254, A-0283, A-0468, A-0658, A-1045, A-1106, A-1120, A-1368, A-1443, A-1625, A-1684, A-1700, A-1882, A-1948, A-2014, A-2080, A-2155, A-2164, A-2337, A-2403, A-2469, A-2990, A-3056, A-3122, A-3188, A-3320, A-3386, A-3452, A-3518, A-3584, A-3650, A-3973, A-4095, A-4257, A-5436, A-5510, B-0004, B-0009, B-0010, B-0011, B-0015, B-0016, B-0017, B-0021, B-0022, B-0045, B-0046, B-0058, B-0062, B-0067, B-0075, B-0081, B-0082, B-0083, B-0093, B-0100, B-0105, B-0121, B-0151, B-0257, B-0258, B-0259, B-0260, B-0262, B-0263, B-0264, B-0265, B-0268, B-0269, B-0270, B-0271, B-0273, B-0274, B-0275, B-0276, B-0285, B-0286, B-0297, B-0299, B-0300, B-0305, B-0306, B-0312, B-0314, B-0316, B-0329, B-0332, B-0336, B-0337, B-0342, B-0352, B-0354, B-0357, B-0359, B-0361, B-0367, B-0374, B-0375, B-0378, B-0379, B-0380, B-0390, B-0405, B-0407, B-0419, B-0420, B-0463, B-0465, B-0507, B-0727, B-1133

INDUSTRIAL APPLICABILITY

The present invention provides a novel compound having excellent insecticide activity, and is useful in pesticide fields and agricultural fields, and has industrial applicability.

The invention claimed is:

1. A pyrazole-3-carboxylic acid amide derivative represented by general formula [I] or an agriculturally acceptable salt thereof:

[Chemical formula 1]

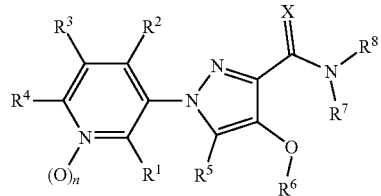

wherein, n represents an integer of 0 or 1,

X represents an oxygen atom, $R^1$, $R^3$, $R_4$, and $R^5$ each independently represents a hydrogen atom or a halogen atom, $R^2$ represents a hydrogen atom, $R^6$ represents a $C_1$-$C_{12}$ haloalkyl group, $C_1$-$C_6$ alkoxy $C_1$-$C_6$ haloalkyl group, $C_1$-$C_6$ haloalkoxy $C_1$-$C_6$ alkyl group, $C_1$-$C_6$ haloalkoxy $C_1$-$C_6$ haloalkyl group, $R^7$ represents a hydrogen atom, $R^8$ represents a hydrogen atom.

2. A pesticide composition containing the pyrazole-3-carboxylic acid amide derivative or an agriculturally acceptable salt thereof according to claim 1.

3. A pesticide composition according to claim 2, wherein the pesticide composition further contains a surfactant.

4. A pyrazole-3-carboxlyic acid amide derivative or an agriculturally acceptable salt thereof according to claim 1, wherein $R^6$ represents a $C_1$-$C_6$ haloalkoxy $C_1$-$C_6$ haloalkyl group.

5. A pyrazole-3-carboxlyic acid amide derivative or an agriculturally acceptable salt thereof according to claim 1, wherein $R^6$ represents a 1,1,2-trifluoro-2-(trifluoromethoxy) ethyl group.

* * * * *